United States Patent
Iwasa et al.

(10) Patent No.: US 9,920,046 B2
(45) Date of Patent: Mar. 20, 2018

(54) OXIME-SUBSTITUTED AMIDE COMPOUND AND PEST CONTROL AGENT

(71) Applicant: NISSAN CHEMICAL INDUSTRIES, LTD., Chiyoda-ku (JP)

(72) Inventors: Motoyoshi Iwasa, Funabashi (JP); Keisuke Tsuji, Funabashi (JP); Mitsutaka Tomizawa, Funabashi (JP); Takeshi Mita, Funabashi (JP); Hidehito Kuwahara, Shiraoka (JP); Miho Asahi, Shiraoka (JP); Hotaka Imanaka, Shiraoka (JP)

(73) Assignee: Nissan Chemical Industries, Ltd., Chiyoda-ku (JP)

( * ) Notice: Subject to any disclaimer, the term of this patent is extended or adjusted under 35 U.S.C. 154(b) by 0 days.

(21) Appl. No.: 15/207,764

(22) Filed: Jul. 12, 2016

(65) Prior Publication Data

US 2016/0318919 A1   Nov. 3, 2016

Related U.S. Application Data

(63) Continuation of application No. 14/414,173, filed as application No. PCT/JP2013/069207 on Jul. 12, 2013, now Pat. No. 9,434,684.

(30) Foreign Application Priority Data

Jul. 12, 2012 (JP) .................. 2012-156398
Feb. 4, 2013 (JP) .................. 2013-019666
May 16, 2013 (JP) .................. 2013-103989

(51) Int. Cl.
*C07D 405/12* (2006.01)
*C07D 409/12* (2006.01)
(Continued)

(52) U.S. Cl.
CPC ........... *C07D 417/12* (2013.01); *A01N 37/18* (2013.01); *A01N 37/20* (2013.01); *A01N 37/34* (2013.01);
(Continued)

(58) Field of Classification Search
CPC .. C07D 417/12; C07D 213/42; C07D 213/53; C07D 213/61; C07D 213/65;
(Continued)

(56) References Cited

U.S. PATENT DOCUMENTS 6,403,600 B1   6/2002   Maurer et al.
6,864,289 B1   3/2005   Tohnishi et al.
(Continued)

FOREIGN PATENT DOCUMENTS

EP   1 256 569 A1   11/2002
EP   1 428 817 A1   6/2004
(Continued)

OTHER PUBLICATIONS

Shinzo Kagabu, "Discovery of Imidacloprid and Further Developments from Strategic Molecular Designs" Journal of Agricultural and Food Chemistry, vol. 59 (7), 2011, pp. 2887-2896.
(Continued)

*Primary Examiner* — Daniel R Carcanague
(74) *Attorney, Agent, or Firm* — Oblon, McClelland, Maier & Neustadt, L.L.P.

(57) ABSTRACT

To provide a novel pesticide, especially a fungicide and a nematocide.
An oxime-substituted amide compound represented by the formula (I) or its salt, and a pesticide containing it:

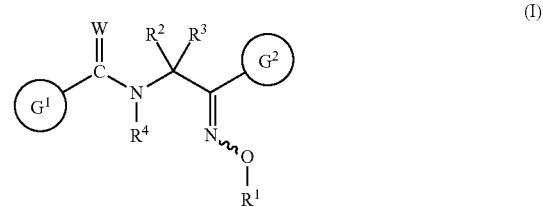

wherein $G^1$ is a structure represented by $G^1$-1 or the like, $G^2$ is a structure represented by $G^2$-2 or the like:

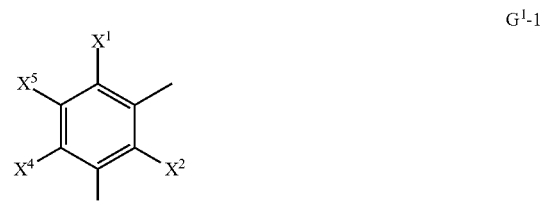

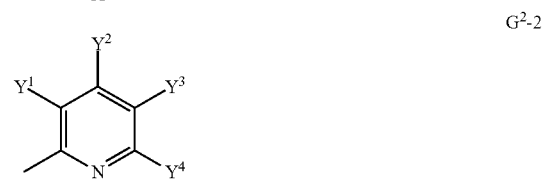

W is an oxygen atom or the like, $X^1$ is a halogen atom, methyl, trifluoromethyl or the like, each of $X^2$, $X^3$, $X^4$ and $X^5$ is independently a hydrogen atom, a halogen atom or the like, each of $Y^1$ and $Y^3$ is independently a halogen atom, cyano, methyl, trifluoromethyl, $C_2$-$C_6$ alkynyl or the like, each of $Y^2$ and $Y^4$ is independently a hydrogen atom, a halogen atom or the like, $R^1$ is $C_1$-$C_6$ alkyl, $C_1$-$C_4$ haloalkyl, ($C_1$-$C_4$)alkyl substituted with $R^{18}$, $C_3$-$C_6$ cycloalkyl, $C_3$-$C_6$ alkenyl or the like, each of $R^2$ and $R^3$ is independently a
(Continued)

hydrogen atom, methyl or the like, $R^4$ is a hydrogen atom or the like, $R^{18}$ is $C_3$-$C_6$ cycloalkyl, phenyl, phenyl substituted with $(Z)_m$ or the like, Z is a halogen atom or the like, and m is an integer of 1, 2 or 3.

12 Claims, No Drawings

(51) Int. Cl.

| | | |
|---|---|---|
| C07D 333/38 | (2006.01) | |
| C07D 213/65 | (2006.01) | |
| C07D 213/53 | (2006.01) | |
| C07D 417/12 | (2006.01) | |
| A01N 43/10 | (2006.01) | |
| A01N 43/40 | (2006.01) | |
| C07D 213/82 | (2006.01) | |
| C07D 407/12 | (2006.01) | |
| C07C 251/48 | (2006.01) | |
| C07C 251/52 | (2006.01) | |
| C07D 213/42 | (2006.01) | |
| C07D 213/61 | (2006.01) | |
| A01N 37/20 | (2006.01) | |
| A01N 43/56 | (2006.01) | |
| A01N 43/60 | (2006.01) | |
| A01N 43/713 | (2006.01) | |
| A01N 43/76 | (2006.01) | |
| A01N 43/78 | (2006.01) | |
| A01N 43/80 | (2006.01) | |
| A01N 43/84 | (2006.01) | |
| A01N 47/12 | (2006.01) | |
| A01N 37/18 | (2006.01) | |
| A01N 37/34 | (2006.01) | |
| A01N 41/10 | (2006.01) | |
| A01N 41/12 | (2006.01) | |
| A01N 55/00 | (2006.01) | |
| C07C 255/64 | (2006.01) | |
| C07C 317/32 | (2006.01) | |
| C07C 321/28 | (2006.01) | |
| C07D 241/24 | (2006.01) | |
| C07D 401/12 | (2006.01) | |
| C07D 413/12 | (2006.01) | |
| C07F 7/08 | (2006.01) | |

(52) U.S. Cl.
CPC ............ *A01N 41/10* (2013.01); *A01N 41/12* (2013.01); *A01N 43/10* (2013.01); *A01N 43/40* (2013.01); *A01N 43/56* (2013.01); *A01N 43/60* (2013.01); *A01N 43/713* (2013.01); *A01N 43/76* (2013.01); *A01N 43/78* (2013.01); *A01N 43/80* (2013.01); *A01N 43/84* (2013.01); *A01N 47/12* (2013.01); *A01N 55/00* (2013.01); *C07C 251/48* (2013.01); *C07C 251/52* (2013.01); *C07C 255/64* (2013.01); *C07C 317/32* (2013.01); *C07C 321/28* (2013.01); *C07D 213/42* (2013.01); *C07D 213/53* (2013.01); *C07D 213/61* (2013.01); *C07D 213/65* (2013.01); *C07D 213/82* (2013.01); *C07D 241/24* (2013.01); *C07D 333/38* (2013.01); *C07D 401/12* (2013.01); *C07D 405/12* (2013.01); *C07D 407/12* (2013.01); *C07D 409/12* (2013.01); *C07D 413/12* (2013.01); *C07F 7/0814* (2013.01)

(58) Field of Classification Search
CPC .. C07D 213/82; C07D 241/24; C07D 333/38; C07D 401/12; C07D 405/12; C07D 407/12; C07D 409/12; C07D 413/12
USPC ...................................................... 546/268.1
See application file for complete search history.

(56) References Cited

U.S. PATENT DOCUMENTS

| | | | |
|---|---|---|---|
| 9,434,684 B2* | 9/2016 | Iwasa | .................... A01N 37/20 |
| 2003/0153464 A1 | 8/2003 | Nakamura et al. | |
| 2004/0254237 A1 | 12/2004 | Nakamura et al. | |
| 2008/0318779 A1 | 12/2008 | Nakamura et al. | |
| 2009/0163545 A1 | 6/2009 | Goldfarb | |
| 2010/0093707 A1 | 4/2010 | Nakamura et al. | |
| 2010/0261675 A1 | 10/2010 | Nakamura et al. | |
| 2010/0261735 A1 | 10/2010 | Nakamura et al. | |
| 2012/0157476 A1 | 6/2012 | Hebeisen et al. | |

FOREIGN PATENT DOCUMENTS

| | | | |
|---|---|---|---|
| JP | 2001-158764 | | 6/2001 |
| JP | 2002-523397 | | 7/2002 |
| JP | 2004-35439 | | 2/2004 |
| JP | 2007210924 | * | 8/2007 |
| JP | 2013-82699 A | | 5/2013 |
| WO | 01/21576 | | 3/2001 |
| WO | 01/55136 | | 8/2001 |
| WO | WO 2006/016708 A1 | | 2/2006 |
| WO | WO 2008/081011 A1 | | 7/2008 |
| WO | 2009/127722 | | 10/2009 |
| WO | 2011/151369 | | 12/2011 |
| WO | 2011/151370 | | 12/2011 |
| WO | 2012/080144 | | 6/2012 |

OTHER PUBLICATIONS

International Search Report dated Sep. 24, 2013, in PCT/JP2013/069207, filed Jul. 12, 2013.
Chemical Abstracts STN Registry database record for RN 343374-29-8 entered on Jun. 26, 2001.
Extended European Search Report dated Dec. 15, 2015 in Patent Application 13816560.0.

* cited by examiner

OXIME-SUBSTITUTED AMIDE COMPOUND AND PEST CONTROL AGENT

This is a continuation of U.S. application Ser. No. 14/414,173, filed Jan. 12, 2015, which is the National Stage of International application no. PCT/JP2013/069207, filed Jul. 12, 2013, which claimed priority to Japanese patent application no. 2012-156398, filed Jul. 12, 2012; Japanese patent application no. 2013-019666, filed Feb. 4, 2013, and Japanese patent application no. 2013-103989, filed May 16, 2013, of which all of the disclosures are incorporated herein by reference in their entireties.

TECHNICAL FIELD

The present invention relates to a novel oxime-substituted amide compound or its salt, and a pesticidal composition containing the compound as an active ingredient.

BACKGROUND ART

Heretofore, with respect to oxime-substituted amide compounds, N-[2-(methoxyimino)-2-phenylethyl]-4-(trifluoromethyl)nicotinamide and 3-iodo-$N^2$-[2-(methoxyimino)-2-phenylethyl]-$N^1$-[2-methyl-4-[1,2,2,2-tetrafluoro-1-(trifluoromethyl)ethyl]phenyl]phthalic acid diamide are known to have insecticidal activity (for example, Patent Documents 1 and 2).

Further, 2-chloro-N-[2-(4-chlorophenyl)-2-(methoxyimino)ethyl]benzamide, N-[2-(4-chlorophenyl)-2-(methoxyimino)ethyl]-2,4-dichlorobenzamide and the like are known to alter the lifespan of eukaryotic organisms (Patent Document 3).

Further, certain pyrazole-4-carboxamide derivatives are known to have fungicidal activity (for example, Patent Documents 4 to 7).

However, the oxime-substituted amide compound of the present invention is not disclosed at all, and its usefulness as a pesticide has not been known.

PRIOR ART DOCUMENTS

Patent Documents

Patent Document 1: JP-A-2004-035439
Patent Document 2: WO2001/021576
Patent Document 3: U.S. Patent Application Publication No. 2009/0163545
Patent Document 4: WO2001-055136
Patent Document 5: WO2009-127722
Patent Document 6: WO2011-151369
Patent Document 7: WO2011-151370

DISCLOSURE OF INVENTION

Technical Problem

Infection or parasitism of pests such as pathogens and parasites causes, in a case where the hosts are plants such as grain, fruits, vegetables or ornamental plants, a decrease in the quality of agricultural crops and a remarkable decrease in the yield, and in some cases, serious damages such as death of the plants, and inflicts heavy economic losses not only on the producers but also on the consumers. Thus, to effectively control such pests is a very important object to achieve efficient and stable production of agricultural crops. Further, in a case where the hosts are animals such as companion creatures/pets or livestock/poultry, to effectively control such pests is an important object also for the purpose of maintaining health of the target animals and further, in a case where the target animals are livestock or poultry, for the purpose of stably producing safe food or high quality general merchandise such as wool, feathers or leathers. From such a viewpoint, heretofore, development of pesticides targeted at pathogens or parasites has advanced, and various effective pesticides have been put into practical use.

However, recently, control of pests with conventional pesticides has become difficult in more and more cases, as pathogens or parasites acquire resistance to them over many years of their use. Problems of the high toxicity of some conventional pesticides and of the disturbance of the ecosystem by some conventional pesticides which remain in the environment for a long period are becoming apparent. Under these circumstances, development of novel pesticides not only having excellent pesticidal activity on pathogens and parasites but also having high pesticidal properties such as low toxicity and low persistence and of an effective controlling method is always expected.

Solution to Problem

The present inventors have conducted extensive studies to achieve the above object and as a result, found that a novel oxime-substituted amide compound represented by the following formula (I) is a very useful compound which is excellent in pesticidal activities, especially in antifungal and nematicidal activities, and has little harmful effect on non-target organisms such as plants, mammals, fishes, useful insects and natural enemies, and accomplished the present invention.

That is, the present invention relates to an oxime-substituted amide compound represented by the formula (I), or its N-oxide or salt:

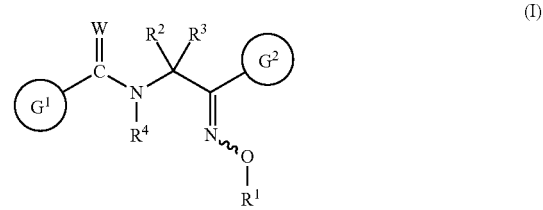

wherein $G^1$ is a structure represented by any one of $G^1$-1 to $G^1$-51:

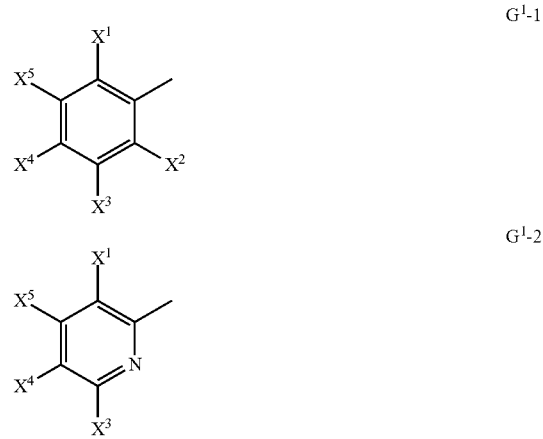

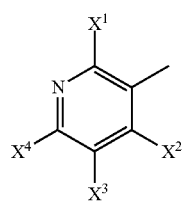 G¹-3
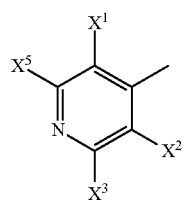 G¹-4
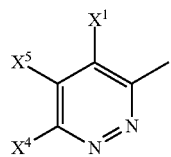 G¹-5
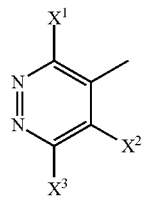 G¹-6
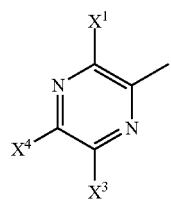 G¹-7
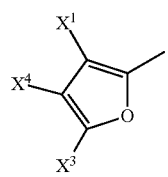 G¹-8
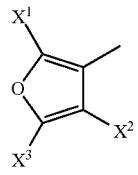 G¹-9
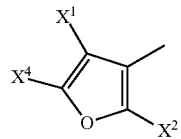 G¹-10
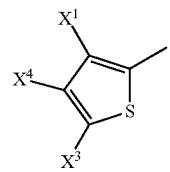 G¹-11
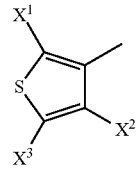 G¹-12
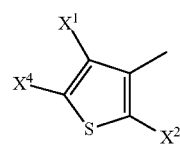 G¹-13
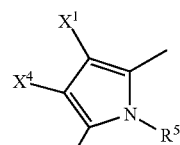 G¹-14
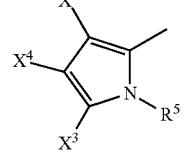 G¹-15
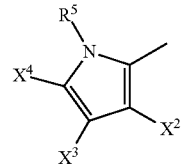 G¹-16
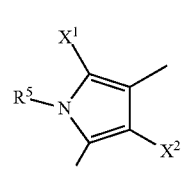 G¹-17
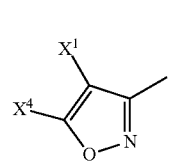 G¹-18
G¹-19

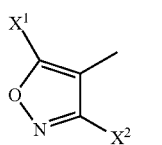 G¹-20
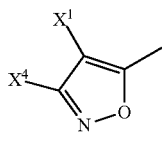 G¹-21
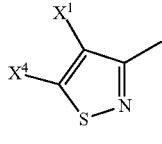 G¹-22
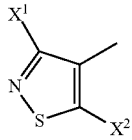 G¹-23
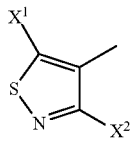 G¹-24
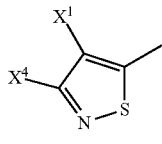 G¹-25
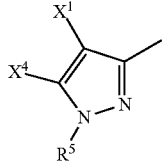 G¹-26
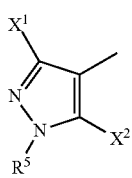 G¹-27
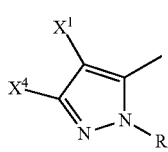 G¹-28
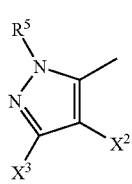 G¹-29
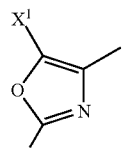 G¹-30
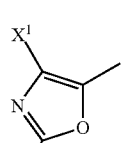 G¹-31
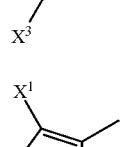 G¹-32
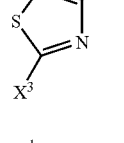 G¹-33
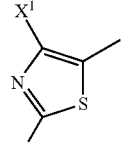 G¹-34
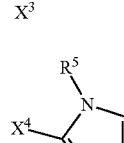 G¹-35
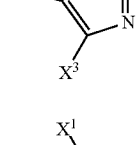 G¹-36
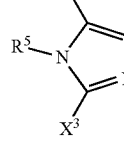 G¹-37
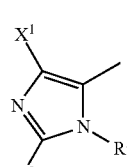 G¹-38

-continued
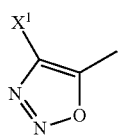 G¹-39
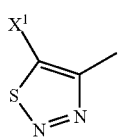 G¹-40
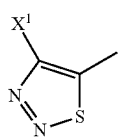 G¹-41
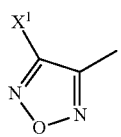 G¹-42
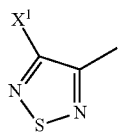 G¹-43
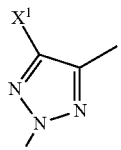 G¹-44
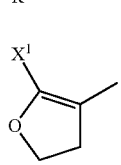 G¹-45
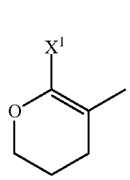 G¹-46
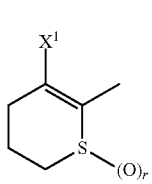 G¹-47
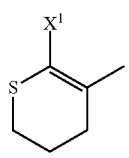 G¹-48
-continued
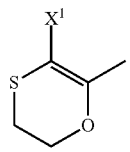 G¹-49
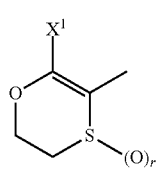 G¹-50
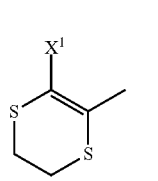 G¹-51
$G^2$ is a structure represented by any one of $G^2$-1 to $G^2$-19:
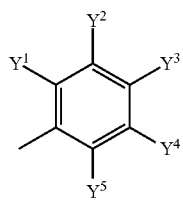 G²-1
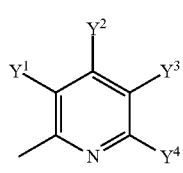 G²-2
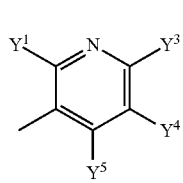 G²-3
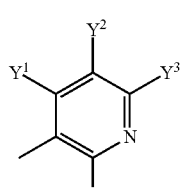 G²-4
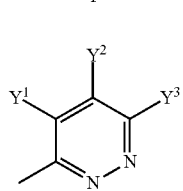 G²-5

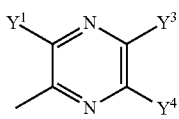 G²-6

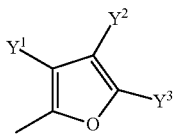 G²-7

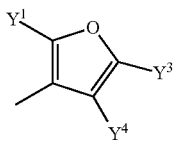 G²-8

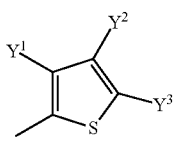 G²-9

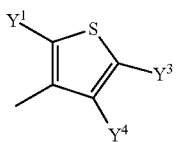 G²-10

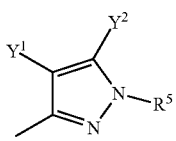 G²-11

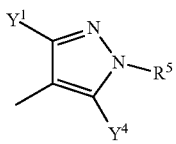 G²-12

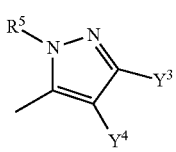 G²-13

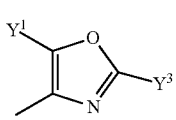 G²-14

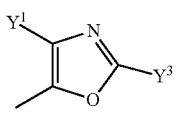 G²-15

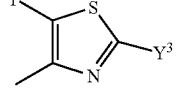 G²-16

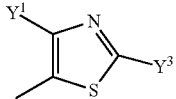 G²-17

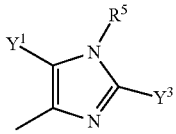 G²-18

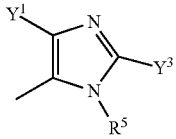 G²-19

W is an oxygen atom or a sulfur atom, $X^1$ is a halogen atom, cyano, nitro, —SF$_5$, C$_1$-C$_6$ alkyl, (C$_1$-C$_6$)alkyl optionally substituted with R$^6$, C$_3$-C$_8$ cycloalkyl, C$_3$-C$_8$ halocycloalkyl, C$_2$-C$_6$ alkenyl, C$_2$-C$_6$ haloalkenyl, C$_2$-C$_6$ alkynyl, C$_2$-C$_6$ haloalkynyl, —OR$^7$, —S(O)$_r$R$^7$, —N(R$^9$)R$^8$, —C(O)NH$_2$, —C(S)NH$_2$, tri(C$_1$-C$_6$ alkyl)silyl, phenyl, phenyl substituted with (Z)$_m$ or D-3, each of $X^2$, $X^3$, $X^4$ and $X^5$ is independently a hydrogen atom, a halogen atom, cyano, nitro, C$_1$-C$_6$ alkyl, (C$_1$-C$_6$) alkyl optionally substituted with R$^6$, C$_3$-C$_8$ cycloalkyl, C$_3$-C$_8$ halocycloalkyl, C$_2$-C$_6$ alkenyl, C$_2$-C$_6$ haloalkenyl, C$_2$-C$_6$ alkynyl, C$_2$-C$_6$ haloalkynyl, —OH, —OR$^7$, —SH, —S(O)$_r$R$^7$, —N(R$^9$)R$^8$, C$_1$-C$_6$ alkylcarbonyl, C$_1$-C$_6$ alkoxycarbonyl, —C(O)NH$_2$, —C(S)NH$_2$, phenyl, phenyl substituted with (Z)$_m$, D-2 or D-32, provided that when G$_1$ is a structure represented by G$^1$-27 and $X^1$ is dihalomethyl, $X^2$ is a hydrogen atom, each of $Y^1$ and $Y^3$ is independently a hydrogen atom, a halogen atom, cyano, nitro, —SCN, —SF$_5$, C$_1$-C$_8$ alkyl, (C$_1$-C$_6$)alkyl optionally substituted with R$^6$, C$_3$-C$_{10}$ cycloalkyl, (C$_3$-C$_{10}$)cycloalkyl optionally substituted with R$^6$, E-1 to E-22, C$_2$-C$_6$ alkenyl, (C$_2$-C$_6$)alkenyl optionally substituted with R$^6$, C$_5$-C$_{10}$ cycloalkenyl, C$_5$-C$_{10}$ halocycloalkenyl, C$_2$-C$_6$ alkynyl, (C$_2$-C$_6$)alkynyl optionally substituted with R$^6$, —OH, —OR$^7$, —OS(O)$_2$R$^7$, —SH, —S(O)$_r$R$^7$, —N(R$^9$)R$^8$, —N=C(R$^{9a}$)R$^{8a}$, —C(O)R$^{10}$, —C(R$^{10}$)=NOH, —C(R$^{10}$)=NOR$^{11}$, M-3, M-13, M-30, —C(O)OH, —C(O)OR$^{11}$, —C(O)SR$^{11}$, —C(O)N(R$^{13}$)R$^{12}$, M-7, M-17, M-23, M-26, —C(S)OR$^{11}$, —C(S)SR$^{11}$, —C(S)N(R$^{13}$)R$^{12}$, M-9, M-19, M-23, M-24, M-28, M-25, M-29, —S(O)$_2$OR$^{11}$, —S(O)$_2$N(R$^{13}$)R$^{12}$, —Si(R$^{14a}$)(R$^{14b}$)R$^{14}$, phenyl, phenyl substituted with (Z)$_m$, or D-1 to D-38, each of $Y^2$, $Y^4$ and $Y^5$ is independently a hydrogen atom, a halogen atom, cyano, nitro, —SCN, —SF$_5$, C$_1$-C$_6$ alkyl, (C$_1$-C$_6$)alkyl optionally substituted with R$^6$, C$_3$-C$_8$ cycloalkyl, C$_3$-C$_8$ halocycloalkyl, —OH, —OR$^7$, —SH, —S(O)$_r$R$^7$, —NH$_2$, C$_1$-C$_6$ alkylamino, di(C$_1$-C$_6$ alkyl) amino, C$_2$-C$_6$ alkenyl, C$_2$-C$_6$ haloalkenyl, C$_2$-C$_6$ alkynyl, C$_2$-C$_6$ haloalkynyl, C$_1$-C$_6$ alkoxycarbonyl, —C(O)NH$_2$ or —C(S)NH$_2$, or, $Y^1$, $Y^2$, $Y^3$ and $Y^4$ represent that $Y^1$ or $Y^3$ and $Y^2$, or $Y^3$ and $Y^4$, together form —CH$_2$CH$_2$CH$_2$—, —CH$_2$CH$_2$O—, —CH$_2$OCH$_2$—, —OCH$_2$O—, —CH$_2$CH$_2$CH$_2$—, —CH$_2$CH$_2$S—, —CH$_2$SCH$_2$—, —SCH$_2$S—, —CH$_2$CH$_2$N(R$^5$)—, —CH$_2$N(R$^5$)CH$_2$—, —CH$_2$CH$_2$CH$_2$CH$_2$—, —CH$_2$CH$_2$CH$_2$O—, —CH$_2$CH$_2$OCH$_2$—, —CH$_2$OCH$_2$O—, —OCH$_2$CH$_2$O—, —OCH$_2$CH$_2$S—, —SCH$_2$CH$_2$S—, —CH$_2$CH=CH—, —N(R$^5$)N=CH—, —OCH$_2$CH=CH—, —CH=CHCH=CH—, —CH=CHCH=N—, —CH=CHN=CH—, —CH=NCH=N— or —N=CHCH=N— to form a 5-membered ring or a 6-membered ring together with the carbon atoms attached to Y$^1$, Y$^2$, Y$^3$ and Y$^4$, wherein hydrogen atoms on the respective ring-constituting carbon atoms may optionally be substituted with a halogen atom, cyano, nitro, C$_1$-C$_4$ alkyl or C$_1$-C$_4$ haloalkyl, and further, when G$^1$ is a structure represented by G$^1$-1, G$^1$-9, G$^1$-10, G$^1$-12, G$^1$-13, G$^1$-16 to G$^1$-20, G$^1$-22 to G$^1$-24, G$^1$-26, G$^1$-27, G$^1$-30, G$^1$-32, G$^1$-35, G$^1$-38, G$^1$-40 or G$^1$-42 to G$^1$-50, Y$^1$ and Y$^2$, Y$^2$ and Y$^3$, or Y$^3$ and Y$^4$, together may form —OCH=CH—, —SCH=CH—, —N(R$^5$)CH=CH—, —OCH=N—, —SCH=N— or —N(R$^5$)CH=N— to form a 5-membered ring together with the carbon atoms attached to Y$^1$, Y$^2$, Y$^3$ and Y$^4$, wherein hydrogen atoms on the respective ring-constituting carbon atoms may optionally be substituted with a halogen atom, cyano, nitro, C$_1$-C$_4$ alkyl or C$_1$-C$_4$ haloalkyl, D-1 to D-38 are aromatic heterocyclic rings represented by the following structural formulae, respectively:

D-1

D-2

D-3

D-4

D-5

D-6

D-7

D-8

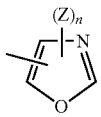

D-9

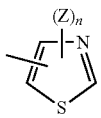

D-10

D-11

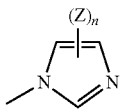

D-12

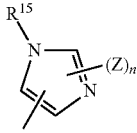

D-13

D-14

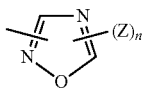

D-15

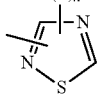

D-16

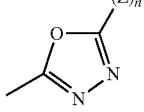

D-17

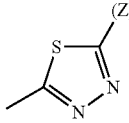

D-18

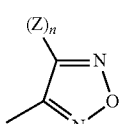

D-19

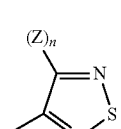

D-20

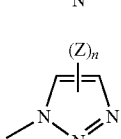

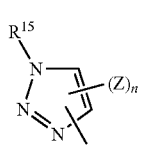
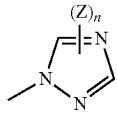
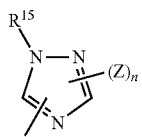
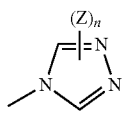
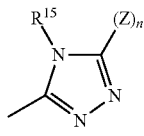
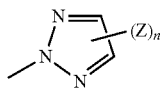
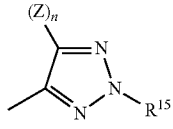
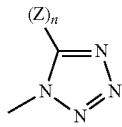
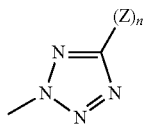
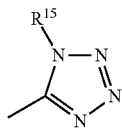
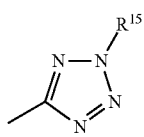
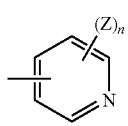
D-21
D-22
D-23
D-24
D-25
D-26
D-27
D-28
D-29
D-30
D-31
D-32
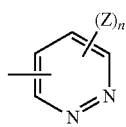
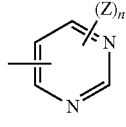
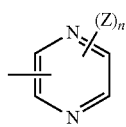
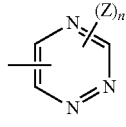
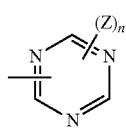
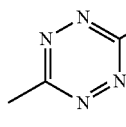
D-33
D-34
D-35
D-36
D-37
D-38
E-1 to E-22 are saturated heterocyclic rings represented by the following structural formulae, respectively:
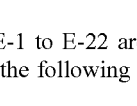
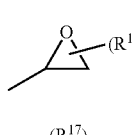
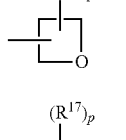
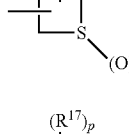
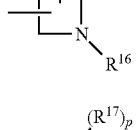
E-1
E-2
E-3
E-4
E-5

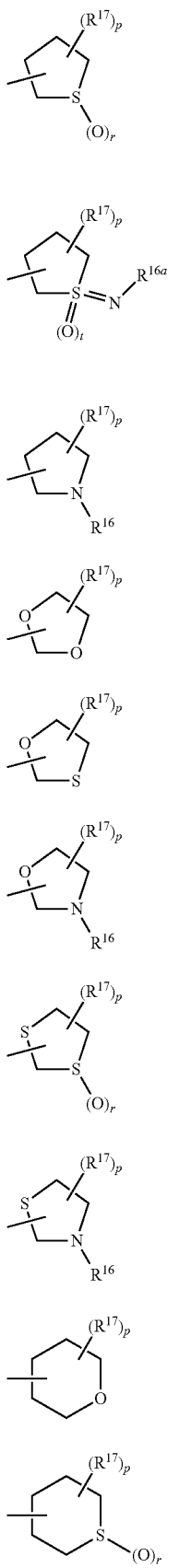
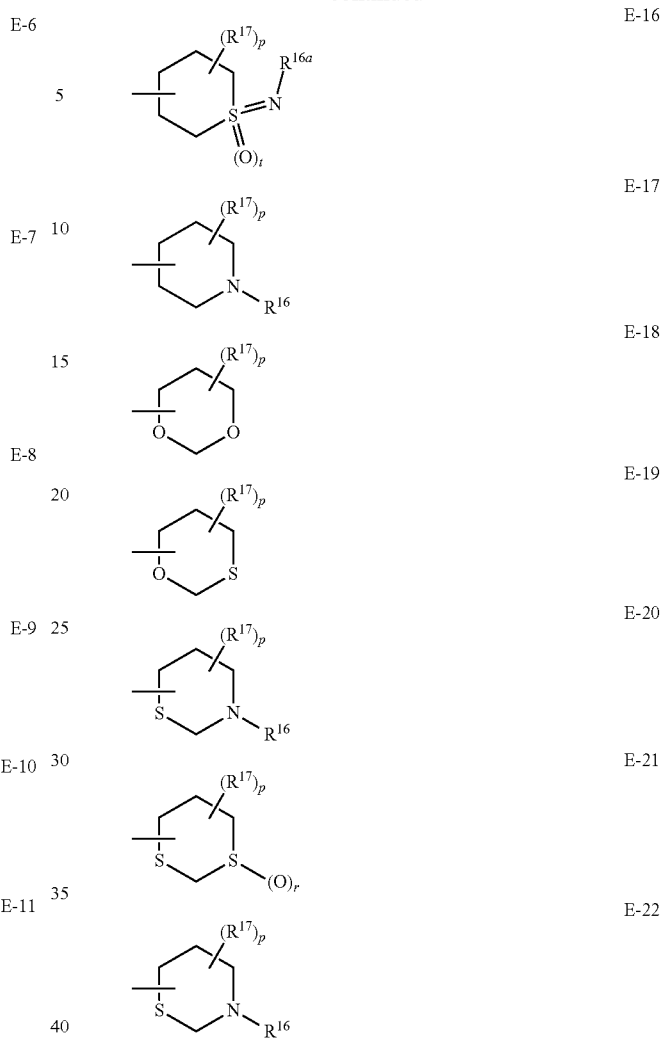

Z is a halogen atom, cyano, nitro, $C_1$-$C_4$ alkyl, $C_1$-$C_4$ haloalkyl, $C_1$-$C_4$ alkoxy($C_1$-$C_4$)alkyl, $C_1$-$C_4$ haloalkoxy($C_1$-$C_4$)alkyl, $C_1$-$C_4$ alkylthio($C_1$-$C_4$)alkyl, $C_1$-$C_4$ haloalkylthio($C_1$-$C_4$)alkyl, $C_1$-$C_4$ alkylsulfinyl($C_1$-$C_4$)alkyl, $C_1$-$C_4$ haloalkylsulfinyl($C_1$-$C_4$)alkyl, $C_1$-$C_4$ alkylsulfonyl($C_1$-$C_4$)alkyl, $C_1$-$C_4$ haloalkylsulfonyl($C_1$-$C_4$)alkyl, $C_3$-$C_6$ cycloalkyl, $C_3$-$C_6$ halocycloalkyl, —OH, $C_1$-$C_4$ alkoxy, $C_1$-$C_4$ haloalkoxy, $C_1$-$C_4$ alkylsulfonyloxy, $C_1$-$C_4$ haloalkylsulfonyloxy, $C_1$-$C_4$ alkylthio, $C_1$-$C_4$ haloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, —$NH_2$, $C_1$-$C_4$ alkylamino, di($C_1$-$C_4$ alkyl)amino, $C_1$-$C_4$ alkoxycarbonyl, $C_1$-$C_4$ haloalkoxycarbonyl, —C(O)$NH_2$, $C_1$-$C_4$ alkylaminocarbonyl, di($C_1$-$C_4$ alkyl)aminocarbonyl, —C(S)$NH_2$, —S(O)$_2NH_2$ or phenyl, when m or n is an integer of at least 2, the respective Z's may be identical with or different from one another, and when there are two neighboring Z's, the two neighboring Z's may form —$CH_2CH_2CH_2$—, —$CH_2CH_2O$—, —$CH_2OCH_2$—, —$OCH_2O$—, —$CH_2CH_2S$—, —$CH_2SCH_2$—, —$CH_2CH_2CH_2CH_2$—, —$CH_2CH_2CH_2O$—, —$CH_2CH_2OCH_2$—, —$CH_2OCH_2O$—, —$OCH_2CH_2O$—, —$CH_2CH_2S$—, —$OCH_2CH_2S$— or —CH═CH—CH═CH— to form a 5-membered ring or a 6-membered ring together with the carbon atoms attached to the two Z's, wherein hydrogen atoms on the respective ring-constituting carbon atoms may optionally be substituted with a halogen atom, a cyano group, a nitro group, a methyl group, a trifluoromethyl group, a methoxy group or a methylthio group, $R^1$ is $C_1$-$C_8$ alkyl, $(C_1$-$C_8)$alkyl optionally substituted with $R^{18}$, $C_3$-$C_{10}$ cycloalkyl, $C_3$-$C_{10}$ halocycloalkyl, E-2 to E-8, E-14 to E-18, E-21, $C_3$-$C_6$ alkenyl, $C_3$-$C_6$ haloalkenyl, $C_5$-$C_{10}$ cycloalkenyl, $C_5$-$C_{10}$ halocycloalkenyl, $C_3$-$C_6$ alkynyl, $C_3$-$C_6$ haloalkynyl, phenyl($C_3$-$C_6$)alkynyl, phenyl or phenyl substituted with $(Z)_m$, $R^2$ is a hydrogen atom, cyano, $C_1$-$C_6$ alkyl, $C_1$-$C_6$ haloalkyl, $C_1$-$C_4$ alkoxy($C_1$-$C_4$)alkyl, $C_1$-$C_4$ alkylthio($C_1$-$C_4$)alkyl, $C_1$-$C_4$ alkylsulfinyl($C_1$-$C_4$)alkyl, $C_1$-$C_4$ alkylsulfonyl($C_1$-$C_4$)alkyl, $C_3$-$C_6$ cycloalkyl or phenyl, or may form the after-mentioned ring together with $R^3$, provided that when $G^1$ is a structure represented by $G^1$-1, $X^1$ is a chlorine atom, $X^2$, $X^3$ and $X^5$ are hydrogen atoms, $X^4$ is a hydrogen atom or a chlorine atom, $G^2$ is a structure represented by $G^2$-1, $Y^3$ is a chlorine atom, and $Y^1$, $Y^2$, $Y^4$ and $Y^5$ are hydrogen atoms, $R^2$ is cyano, $C_1$-$C_6$ alkyl, $C_1$-$C_6$ haloalkyl, $C_1$-$C_4$ alkoxy($C_1$-$C_4$)alkyl, $C_1$-$C_4$ alkylthio($C_1$-$C_4$)alkyl, $C_1$-$C_4$ alkylsulfinyl($C_1$-$C_4$)alkyl, $C_1$-$C_4$ alkylsulfonyl($C_1$-$C_4$)alkyl, $C_3$-$C_6$ cycloalkyl or phenyl, $R^3$ is a hydrogen atom or $C_1$-$C_6$ alkyl, or $R^3$ may form, together with $R^2$, a $C_2$-$C_5$ alkylene chain to form a 3- to 6-membered ring together with the carbon atom attached to $R^2$ and $R^3$, wherein the alkylene chain may contain an oxygen atom, sulfur atom or nitrogen atom, and may optionally be substituted with a $C_1$-$C_4$ alkyl group, a —CHO group, a $C_1$-$C_4$ alkylcarbonyl group, a $C_1$-$C_4$ alkoxycarbonyl group, a $C_1$-$C_4$ alkylaminocarbonyl group, a $C_1$-$C_4$ haloalkylaminocarbonyl group, a di($C_1$-$C_4$ alkyl)aminocarbonyl group or a phenyl group, $R^4$ is a hydrogen atom, cyano, nitro, $C_1$-$C_6$ alkyl, $(C_1$-$C_6)$ alkyl optionally substituted with $R^{19}$, $C_3$-$C_8$ cycloalkyl, $C_3$-$C_6$ alkenyl, $C_3$-$C_6$ haloalkenyl, $C_5$-$C_{10}$ cycloalkenyl, $C_5$-$C_{10}$ halocycloalkenyl, $C_3$-$C_6$ alkynyl, $C_3$-$C_6$ haloalkynyl, —C(O)$R^{20}$, —C(O)O$R^{21}$, —C(O)S$R^{21}$, —C(O)N($R^{23}$)$R^{22}$, —C(O)C(O)O$R^{21}$, —C(S)O$R^{21}$, —C(S)S$R^{21}$, —C(S)N($R^{23}$)$R^{22}$, —OH, —O$R^{21}$, —S$R^{21}$, —N($R^{25}$)$R^{24}$, —N=C($R^{25a}$)$R^{24a}$, —S(O)$_2R^{21}$, —S(O)$_2$N($R^{23}$)$R^{22}$ or —SN($R^{27}$)$R^{26}$, $R^5$ is a hydrogen atom, $C_1$-$C_6$ alkyl, $C_1$-$C_6$ haloalkyl, $C_3$-$C_6$ cycloalkyl($C_1$-$C_4$)alkyl, $C_3$-$C_6$ cycloalkyl, $C_2$-$C_6$ alkenyl, $C_2$-$C_6$ haloalkenyl, $C_2$-$C_6$ alkynyl or $C_2$-$C_6$ haloalkynyl, $R^6$ is a halogen atom, cyano, nitro, $C_3$-$C_8$ cycloalkyl, $C_3$-$C_8$ halocycloalkyl, hydroxy($C_3$-$C_8$)cycloalkyl, $C_1$-$C_6$ alkoxy($C_3$-$C_8$)cycloalkyl, $C_3$-$C_6$ alkenyl, $C_3$-$C_8$ cycloalkenyl, E-1 to E-22, —OH, —O$R^7$, —SH, —S(O)$_r$$R^7$, —N($R^9$)$R^8$, —C($R^{10}$)=NOH, —C($R^{10}$)=NO$R^{11}$, —C(O)O$R^{11}$, —C(O)N($R^{13}$)$R^{12}$, —Si($R^{14a}$)($R^{14b}$)$R^{14}$, phenyl, phenyl substituted with $(Z)_m$ or D-1 to D-38, $R^7$ is $C_1$-$C_6$ alkyl, $(C_1$-$C_6)$ alkyl optionally substituted with $R^{28}$, $C_3$-$C_8$ cycloalkyl, $(C_3$-$C_8)$cycloalkyl optionally substituted with $R^{28}$, E-2 to E-8, E-14 to E-18, E-21, $C_2$-$C_6$ alkenyl, $(C_2$-$C_6)$alkenyl optionally substituted with $R^{28}$, $C_5$-$C_{10}$ cycloalkenyl, $C_5$-$C_{10}$ halocycloalkenyl, $C_3$-$C_6$ alkynyl, $(C_3$-$C_6)$alkynyl optionally substituted with $R^{28}$, $C_1$-$C_6$ alkylcarbonyl, $C_1$-$C_6$ alkoxycarbonyl, phenyl, phenyl substituted with $(Z)_m$, D-1, D-2, D-4 to D-6, D-8 to D-10, D-12 to D-19, D-21, D-23, D-25, D-27 or D-30 to D-38, $R^8$ is a hydrogen atom, $C_1$-$C_6$ alkyl, $(C_1$-$C_6)$alkyl optionally substituted with $R^{28}$, $C_3$-$C_8$ cycloalkyl, $C_3$-$C_8$ halocycloalkyl, $C_3$-$C_6$ alkenyl, $C_3$-$C_6$ haloalkenyl, $C_3$-$C_6$ alkynyl, $C_3$-$C_6$ haloalkynyl, —C(O)$R^{10}$, —C(O)C(O)$R^{11}$, —C(O)O$R^{11}$, —C(O)C(O)O$R^{11}$, —C(O)S$R^{11}$, —C(O)N($R^{13}$)$R^{12}$, —C(S)O$R^{11}$, —C(S)S$R^{11}$, —C(S)N($R^{13}$)$R^{12}$, —OH, —S(O)$_2R^{11}$ or —S(O)$_2$N($R^{13}$)$R^{12}$, or may form the after-mentioned ring together with $R^9$, $R^9$ is a hydrogen atom, $C_1$-$C_6$ alkyl, $(C_1$-$C_6)$alkyl optionally substituted with $R^{28}$, $C_3$-$C_8$ cycloalkyl, $C_3$-$C_6$ alkenyl, $C_3$-$C_6$ haloalkenyl, $C_3$-$C_6$ alkynyl, $C_3$-$C_6$ haloalkynyl, —CHO, $C_1$-$C_6$ alkylcarbonyl, $C_1$-$C_6$ haloalkylcarbonyl or $C_1$-$C_6$ alkoxycarbonyl, or $R^9$ may form, together with $R^8$, a $C_2$-$C_6$ alkylene chain to form a 3- to 7-membered ring together with the nitrogen atom attached to $R^8$ and $R^9$, wherein the alkylene chain may contain an oxygen atom, sulfur atom or nitrogen atom, and may optionally be substituted with a halogen atom, a $C_1$-$C_4$ alkyl group, a $C_1$-$C_4$ haloalkyl group, an oxo group or a thioxo group, $R^{8a}$ is $C_1$-$C_6$ alkyl, $C_1$-$C_6$ alkoxy, $C_1$-$C_6$ haloalkoxy, $C_3$-$C_6$ alkenyloxy, phenoxy or phenoxy substituted with $(Z)_m$, or may form the after-mentioned ring together with $R^{9a}$, $R^{9a}$ is a hydrogen atom, $C_1$-$C_6$ alkyl, $C_1$-$C_6$ haloalkyl, $C_3$-$C_6$ alkenyl, phenyl or phenyl substituted with $(Z)_m$, or $R^{9a}$ may form, together with $R^{8a}$, a $C_4$-$C_6$ alkylene chain to form a 5- to 7-membered ring together with the carbon atom attached to $R^{8a}$ and $R^{9a}$, wherein the alkylene chain may contain an oxygen atom or sulfur atom, $R^{10}$ is a hydrogen atom, $C_1$-$C_6$ alkyl, $(C_1$-$C_6)$alkyl optionally substituted with $R^{28}$, $C_3$-$C_8$ cycloalkyl, $C_3$-$C_8$ halocycloalkyl, $C_2$-$C_6$ alkenyl, $C_2$-$C_6$ haloalkenyl, $C_5$-$C_{10}$ cycloalkenyl, $C_5$-$C_{10}$ halocycloalkenyl, $C_2$-$C_6$ alkynyl, $C_2$-$C_6$ haloalkynyl, phenyl, phenyl substituted with $(Z)_m$, or D-1 to D-38, $R^{11}$ is $C_1$-$C_6$ alkyl, $(C_1$-$C_6)$alkyl optionally substituted with $R^{28}$, $C_3$-$C_8$ cycloalkyl, $C_3$-$C_8$ halocycloalkyl, $C_3$-$C_6$ alkenyl, $C_3$-$C_6$ haloalkenyl, $C_5$-$C_{10}$ cycloalkenyl, $C_5$-$C_{10}$ halocycloalkenyl, $C_3$-$C_6$ alkynyl, $C_3$-$C_6$ haloalkynyl, phenyl, phenyl substituted with $(Z)_m$, D-1, D-2, D-4 to D-6, D-8 to D-10, D-12 to D-19, D-21, D-23, D-25, D-27 or D-30 to D-38, $R^{12}$ is a hydrogen atom, $C_1$-$C_6$ alkyl, $(C_1$-$C_6)$alkyl optionally substituted with $R^{28}$, $C_3$-$C_8$ cycloalkyl, $C_3$-$C_8$ halocycloalkyl, $C_2$-$C_6$ alkenyl, $C_2$-$C_6$ haloalkenyl, $C_3$-$C_6$ alkynyl, $C_3$-$C_6$ haloalkynyl, $C_1$-$C_6$ alkylcarbonyl, $C_1$-$C_6$ haloalkylcarbonyl, phenylcarbonyl, $C_1$-$C_6$ alkoxycarbonyl, phenyl, phenyl substituted with $(Z)_m$, D-1 to D-25 or D-27 to D-38, or may form the after-mentioned ring together with $R^{13}$, $R^{13}$ is a hydrogen atom, $C_1$-$C_6$ alkyl, $C_1$-$C_6$ haloalkyl, $C_3$-$C_6$ cycloalkyl($C_1$-$C_4$)alkyl, $C_1$-$C_4$ alkoxy($C_1$-$C_4$)alkyl, $C_1$-$C_4$ alkylthio($C_1$-$C_4$)alkyl, $C_1$-$C_4$ alkylsulfonyl($C_1$-$C_4$)alkyl, cyano($C_1$-$C_4$)alkyl, $C_3$-$C_6$ alkenyl or $C_3$-$C_6$ alkynyl, or $R^{13}$ may form, together with $R^{12}$, a $C_2$-$C_6$ alkylene chain to form a 3- to 7-membered ring together with the nitrogen atom attached to $R^{12}$ and $R^{13}$, wherein the alkylene chain may contain an oxygen atom, sulfur atom or nitrogen atom, and may optionally be substituted with a halogen atom, a $C_1$-$C_4$ alkyl group, a $C_1$-$C_4$ alkoxy group, a —CHO group, a $C_1$-$C_4$ alkylcarbonyl group or a $C_1$-$C_4$ alkoxycarbonyl group, $R^{14}$ is $C_1$-$C_6$ alkyl, $C_1$-$C_6$ haloalkyl, $C_1$-$C_6$ alkoxy, phenyl or phenyl substituted with $(Z)_m$, each of $R^{14a}$ and $R^{14b}$ is independently $C_1$-$C_6$ alkyl, $C_1$-$C_6$ haloalkyl or $C_1$-$C_6$ alkoxy, $R^{15}$ is a hydrogen atom, cyano, $C_1$-$C_6$ alkyl, $C_1$-$C_6$ haloalkyl, $C_3$-$C_6$ cycloalkyl($C_1$-$C_4$)alkyl, hydroxy($C_1$-$C_4$) alkyl, $C_1$-$C_4$ alkoxy($C_1$-$C_4$)alkyl, $C_1$-$C_4$ haloalkoxy($C_1$-$C_4$) alkyl, $C_1$-$C_4$ alkylthio($C_1$-$C_4$)alkyl, $C_1$-$C_4$ haloalkylthio($C_1$-$C_4$)alkyl, $C_1$-$C_4$ alkylamino($C_1$-$C_4$)alkyl, di($C_1$-$C_4$ alkyl)amino($C_1$-$C_4$)alkyl, cyano($C_1$-$C_4$)alkyl, $C_1$-$C_4$ alkoxycarbonyl($C_1$-$C_4$)alkyl, $C_1$-$C_4$ haloalkoxycarbonyl ($C_1$-$C_4$)alkyl, phenyl($C_1$-$C_4$)alkyl, phenyl($C_1$-$C_4$)alkyl substituted with $(Z)_m$, $C_3$-$C_6$ cycloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkylcarbonyl, phenylcarbonyl, phenylcarbonyl substituted with $(Z)_m$, $C_1$-$C_6$ alkoxycarbonyl, $C_1$-$C_6$ haloalkoxycarbonyl, di($C_1$-$C_6$ alkyl)aminocarbonyl, $C_1$-$C_6$ alkylsulfonyl, phenylsulfonyl, phenylsulfonyl substituted with $(Z)_m$, di($C_1$-$C_6$ alkyl)aminosulfonyl, phenyl, phenyl substituted with $(Z)_m$, or $C_1$-$C_6$ alkoxy, and further, when $R^{15}$ and Z are neighboring, the neighboring $R^{15}$ and Z may form —$CH_2CH_2CH_2CH_2$—, —CH=CH—CH=CH—, —N=CH—CH=CH—, —CH=N—CH=CH—, —CH=CH—N=CH— or —CH=CH—CH=N— to form a 6-membered ring together with the atoms respectively attached to $R^{15}$ and Z, wherein hydrogen atoms on the respective ring-constituting carbon atoms may optionally be substituted with a halogen atom, a methyl group or a trifluoromethyl group, $R^{16}$ is a hydrogen atom, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ alkenyl, $C_3$-$C_6$ haloalkenyl, $C_3$-$C_6$ alkynyl, $C_3$-$C_6$ haloalkynyl, —C(O)$R^{10}$, —C(O)C(O)$R^{11}$, —C(O)O$R^{11}$, —C(O)C(O)O$R^{11}$, —C(O)S$R^{11}$, —C(O)N($R^{13}$)$R^{12}$, —C(S)O$R^{11}$, —C(S)S$R^1$, —C(S)N($R^{13}$)$R^{12}$, —S(O)$_2R^{11}$, —S(O)$_2$N($R^{13}$)$R^{12}$, phenyl, phenyl substituted with $(Z)_m$ or D-3, $R^{16a}$ is a hydrogen atom, cyano, nitro, $C_1$-$C_6$ alkyl, $C_1$-$C_6$ haloalkyl, $C_1$-$C_6$ alkylcarbonyl, $C_1$-$C_6$ haloalkylcarbonyl, $C_1$-$C_6$ alkoxycarbonyl, $C_1$-$C_6$ haloalkoxycarbonyl, $C_1$-$C_6$ alkylsulfonyl or $C_1$-$C_6$ haloalkylsulfonyl, $R^{17}$ is a halogen atom, cyano, $C_1$-$C_6$ alkyl, $C_1$-$C_6$ haloalkyl, hydroxy($C_1$-$C_4$)alkyl, $C_1$-$C_4$ alkoxy($C_1$-$C_4$) alkyl, $C_1$-$C_4$ alkoxycarbonyl($C_1$-$C_4$)alkyl, $C_1$-$C_6$ alkoxy, $C_1$-$C_6$ alkylthio, $C_1$-$C_6$ alkylamino, di($C_1$-$C_6$ alkyl)amino, $C_1$-$C_6$ alkoxycarbonyl, phenyl or phenyl substituted with $(Z)_m$, when p is an integer of at least 2, the respective $R^{17}$'s may be identical with or different from one another, and further, when two $R^{17}$'s are on the same carbon atom, the two $R^{17}$'s together may form $C_1$-$C_4$ alkylidene, oxo, thioxo, imino, $C_1$-$C_4$ alkylimino or $C_1$-$C_4$ alkoxyimino, $R^{18}$ is a halogen atom, cyano, nitro, $C_3$-$C_{10}$ cycloalkyl, $C_3$-$C_{10}$ halocycloalkyl, E-1 to E-22, $C_5$-$C_{10}$ cycloalkenyl, $C_5$-$C_{10}$ halocycloalkenyl, —O$R^{29}$, —N($R^{30}$)$R^{29}$, —SH, —S(O)$_rR^{31}$, —S(O)$_r$($R^{31}$)=N$R^{16a}$, —C(O)$R^{32}$, —C($R^{32}$)=NOH, —C($R^{32}$)=NO$R^{33}$, —C(O)OH, —C(O)O$R^{33}$, —C(O)S$R^{33}$, —C(O)N($R^{35}$)$R^{34}$, —C(O)C(O)O$R^{33}$, —C(S)O$R^{33}$, —C(S)S$R^{33}$, —C(S)N($R^{35}$)$R^{34}$, —S(O)$_2$OH, —S(O)$_2$O$R^{33}$, —S(O)$_2$N($R^{35}$)$R^{34}$, —Si($R^{14a}$)($R^{14b}$)$R^{14}$, M-1 to M-30, phenyl, phenyl substituted with $(Z)_m$ or D-1 to D-38, M-1 to M-30 are partial saturated heterocyclic rings represented by the following structural formulae, respectively:

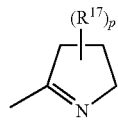

M-1

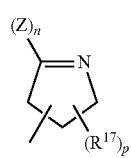

M-2

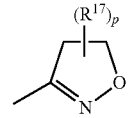

M-3

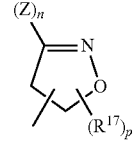

M-4

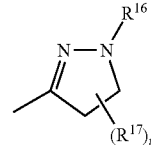

M-5

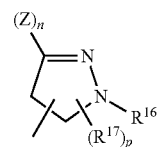

M-6

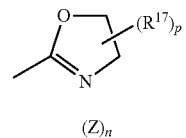

M-7

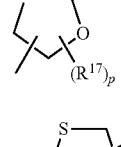

M-8

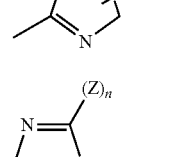

M-9

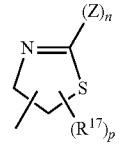

M-10

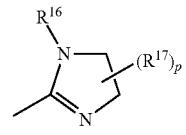

M-11

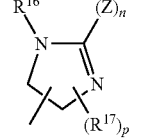

M-12

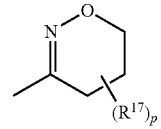

M-13

-continued

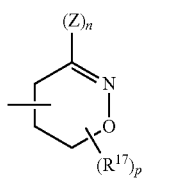
M-14

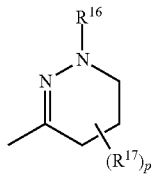
M-15

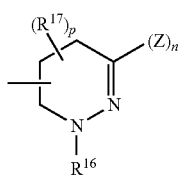
M-16

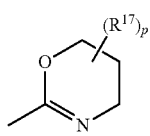
M-17

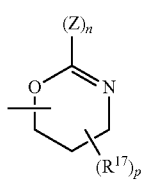
M-18

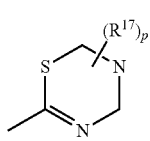
M-19

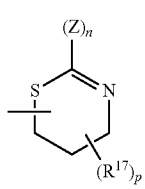
M-20

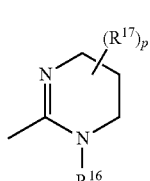
M-21

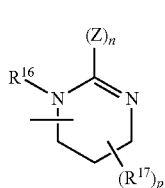
M-22

-continued

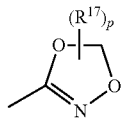
M-23

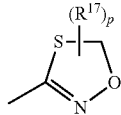
M-24

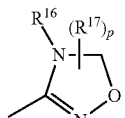
M-25

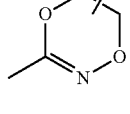
M-26

M-27

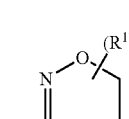
M-28

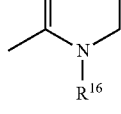
M-29

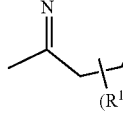
M-30

$R^{19}$ is a halogen atom, cyano, nitro, $C_3$-$C_8$ cycloalkyl, E-5, E-6, E-14, E-15, $C_5$-$C_{10}$ cycloalkenyl, —$OR^{36}$, —$S(O)_rR^{37}$, —$C(R^{32})$=NOH, —$C(R^{32})$=$NOR^{33}$, M-3, —$C(O)OR^{33}$, —$C(O)SR^{33}$, —$C(O)NH_2$, M-7, M-17, —$C(O)C(O)OR^{33}$, —$C(S)OR^{33}$, —$C(S)SR^{33}$, —$C(S)NH_2$, M-9, M-19, —$S(O)_2N(R^{35})R^{34}$ or —$Si(R^{14a})(R^{14b})R^{14}$, $R^{20}$ is a hydrogen atom, $C_1$-$C_6$ alkyl, ($C_1$-$C_6$)alkyl optionally substituted with $R^{28}$, $C_3$-$C_8$ cycloalkyl, $C_3$-$C_8$ halocycloalkyl, $C_2$-$C_6$ alkenyl, $C_2$-$C_6$ haloalkenyl, $C_5$-$C_{10}$ cycloalkenyl, $C_5$-$C_{10}$ halocycloalkenyl, $C_2$-$C_6$ alkynyl or $C_2$-$C_6$ haloalkynyl, $R^{21}$ is $C_1$-$C_6$ alkyl, ($C_1$-$C_6$)alkyl optionally substituted with $R^{28}$, $C_3$-$C_8$ cycloalkyl, $C_3$-$C_8$ halocycloalkyl, $C_3$-$C_6$ alkenyl, $C_3$-$C_6$ haloalkenyl, $C_5$-$C_{10}$ cycloalkenyl, $C_5$-$C_{10}$ halocycloalkenyl, $C_3$-$C_6$ alkynyl or $C_3$-$C_6$ haloalkynyl, $R^{22}$ is a hydrogen atom, $C_1$-$C_6$ alkyl, ($C_1$-$C_6$)alkyl optionally substituted with $R^{28}$, $C_3$-$C_8$ cycloalkyl, $C_3$-$C_8$ halocycloalkyl, $C_2$-$C_6$ alkenyl, $C_2$-$C_6$ haloalkenyl, $C_3$-$C_6$ alkynyl, $C_3$-$C_6$ haloalkynyl, $C_1$-$C_6$ alkylcarbonyl, $C_1$-$C_6$ haloalkylcarbonyl, phenylcarbonyl, $C_1$-$C_6$ alkoxycarbonyl, phenyl, phenyl substituted with $(Z)_m$, D-1 to D-25 or D-27 to D-38, or may form the after-mentioned ring together with $R^{23}$, $R^{23}$ is a hydrogen atom, $C_1$-$C_6$ alkyl, $C_1$-$C_6$ haloalkyl, $C_3$-$C_6$ cycloalkyl($C_1$-$C_4$)alkyl, $C_1$-$C_4$ alkoxy($C_1$-$C_4$)alkyl, $C_1$-$C_4$ alkylthio($C_1$-$C_4$)alkyl, $C_1$-$C_4$ alkylsulfonyl($C_1$-$C_4$) alkyl, cyano($C_1$-$C_4$)alkyl, $C_3$-$C_6$ alkenyl or $C_3$-$C_6$ alkynyl, or $R^{23}$ may form, together with $R^{22}$, a $C_2$-$C_6$ alkylene chain to form a 3- to 7-membered ring together with the nitrogen atom attached to $R^{22}$ and $R^{23}$, wherein the alkylene chain may contain an oxygen atom, sulfur atom or nitrogen atom, and may optionally be substituted with a halogen atom, a $C_1$-$C_4$ alkyl group, a $C_1$-$C_4$ alkoxy group, a —CHO group, a $C_1$-$C_4$ alkylcarbonyl group or a $C_1$-$C_4$ alkoxycarbonyl group, $R^{24}$ is a hydrogen atom, $C_1$-$C_6$ alkyl, $C_1$-$C_6$ haloalkyl, $C_3$-$C_8$ cycloalkyl, $C_3$-$C_8$ halocycloalkyl, $C_3$-$C_8$ alkenyl, $C_3$-$C_6$ haloalkenyl, $C_3$-$C_6$ alkynyl, $C_3$-$C_6$ haloalkynyl, —S(O)$_2$R$^{33}$ or —S(O)$_2$N(R$^{35}$)R$^{34}$, or may form the after-mentioned ring together with $R^{25}$, $R^{25}$ is a hydrogen atom, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl or $C_3$-$C_6$ haloalkynyl, or $R^{25}$ may form, together with $R^{24}$, a $C_4$-$C_5$ alkylene chain to form a 5- to 6-membered ring together with the nitrogen atom attached to $R^{24}$ and $R^{25}$, wherein the alkylene chain may contain an oxygen atom, sulfur atom or nitrogen atom, and may optionally be substituted with a halogen atom, a $C_1$-$C_4$ alkyl group, a $C_1$-$C_4$ haloalkyl group, a $C_1$-$C_4$ alkoxy group, a —CHO group, a $C_1$-$C_4$ alkylcarbonyl group, a $C_1$-$C_4$ alkoxycarbonyl group, an oxo group or a thioxo group, $R^{24a}$ is a hydrogen atom, $C_1$-$C_6$ alkyl, $C_1$-$C_6$ haloalkyl, $C_3$-$C_8$ cycloalkyl, phenyl or phenyl substituted with $(Z)_m$, or may form the after-mentioned ring together with $R^{25a}$, $R^{25a}$ is a hydrogen atom, $C_1$-$C_6$ alkyl, $C_1$-$C_6$ alkoxy, $C_1$-$C_6$ alkylthio or di($C_1$-$C_6$ alkyl)amino, or $R^{25a}$ may form, together with $R^{24a}$, a $C_3$-$C_5$ alkylene chain to form a 4- to 6-membered ring together with the carbon atom attached to $R^{24a}$ and $R^{25a}$, wherein the alkylene chain may contain an oxygen atom, sulfur atom or nitrogen atom, and may optionally be substituted with a halogen atom, a $C_1$-$C_4$ alkyl group, a $C_1$-$C_4$ haloalkyl group, a —CHO group, a $C_1$-$C_4$ alkylcarbonyl group or a $C_1$-$C_4$ alkoxycarbonyl group, $R^{26}$ is $C_1$-$C_{12}$ alkyl, $C_1$-$C_{12}$ haloalkyl, $C_1$-$C_{12}$ alkoxy($C_1$-$C_{12}$)alkyl, cyano($C_1$-$C_{12}$)alkyl, $C_1$-$C_{12}$ alkoxycarbonyl($C_1$-$C_{12}$)alkyl, phenyl($C_1$-$C_4$)alkyl, phenyl($C_1$-$C_4$)alkyl substituted with $(Z)_m$, $C_3$-$C_{12}$ alkenyl, $C_3$-$C_{12}$ haloalkenyl, $C_3$-$C_{12}$ alkynyl, $C_3$-$C_{12}$ haloalkynyl, $C_1$-$C_{12}$ alkylcarbonyl, $C_1$-$C_{12}$ alkoxycarbonyl, —C(O)ON=C(CH$_3$)SCH$_3$, —C(O)ON=C(SCH$_3$)C(O)N(CH$_3$)$_2$, phenyl or phenyl substituted with $(Z)_m$, or may form the after-mentioned ring together with $R^{27}$, $R^{27}$ is $C_1$-$C_{12}$ alkyl, $C_1$-$C_{12}$ haloalkyl, $C_1$-$C_{12}$ alkoxy($C_1$-$C_{12}$ alkyl), cyano($C_1$-$C_{12}$) alkyl, $C_1$-$C_{12}$ alkoxycarbonyl($C_1$-$C_{12}$)alkyl, phenyl($C_1$-$C_4$)alkyl, phenyl($C_1$-$C_4$)alkyl substituted with $(Z)_m$, $C_3$-$C_{12}$ alkenyl, $C_3$-$C_{12}$ haloalkenyl, $C_3$-$C_{12}$ alkynyl, $C_3$-$C_{12}$ haloalkynyl, phenyl or phenyl substituted with $(Z)_m$, or $R^{27}$ may form, together with $R^{26}$, a $C_4$-$C_7$ alkylene chain to form a 5- to 8-membered ring together with the nitrogen atom attached to $R^{26}$ and $R^{27}$, wherein the alkylene chain may contain an oxygen atom or sulfur atom, and may optionally be substituted with a $C_1$-$C_4$ alkyl group or a $C_1$-$C_4$ alkoxy group, $R^{28}$ is a halogen atom, cyano, nitro, $C_3$-$C_8$ cycloalkyl, $C_3$-$C_8$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, di($C_1$-$C_6$ alkyl)amino, $C_1$-$C_6$ alkoxycarbonyl, $C_1$-$C_6$ haloalkoxycarbonyl, —C(O)NH$_2$, $C_1$-$C_6$ alkylaminocarbonyl, di($C_1$-$C_6$ alkyl)aminocarbonyl, —C(S)NH$_2$, phenyl, phenyl substituted with $(Z)_m$, or D-1 to D-38, $R^{29}$ is a hydrogen atom, $C_1$-$C_8$ alkyl, ($C_1$-$C_8$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_3$-$C_8$ alkenyl, ($C_3$-$C_8$)alkenyl optionally substituted with $R^{38}$, $C_3$-$C_8$ alkynyl, ($C_3$—$C_8$)alkynyl optionally substituted with $R^{38}$, —C(O)R$^{39}$, —C(O)C(O) R$^{40}$, —C(O)OR$^{40}$, —C(O)C(O)OR$^{40}$, —C(O)SR$^{40}$, —C(O)N(R$^{42}$)R$^{41}$, —C(S)R$^{39}$, —C(S)OR$^{40}$, —C(S)SR$^{40}$, —C(S)N(R$^{42}$)R$^{41}$, —S(O)$_2$R$^{40}$, —S(O)$_2$N(R$^{42}$)R$^{41}$, —Si(R$^{14a}$)(R$^{14b}$)R$^{14}$, —P(O)(OR$^{43}$)$_2$, —P(S)(OR$^{43}$)$_2$, phenyl, phenyl substituted with $(Z)_m$, D-1, D-2, D-4 to D-6, D-8 to D-10, D-12 to D-19, D-21, D-23, D-25, D-27 or D-30 to D-38, or may form the after-mentioned ring together with $R^{30}$, $R^{30}$ is a hydrogen atom, $C_1$-$C_6$ alkyl, $C_1$-$C_6$ haloalkyl, $C_3$-$C_4$ cycloalkyl($C_1$-$C_4$)alkyl, $C_1$-$C_4$ alkoxy($C_1$-$C_4$)alkyl, $C_1$-$C_4$ alkylthio($C_1$-$C_4$)alkyl, cyano($C_1$-$C_4$)alkyl, $C_3$-$C_6$ cycloalkyl, $C_3$-$C_6$ alkenyl, $C_3$-$C_6$ alkynyl, $C_1$-$C_6$ haloalkylcarbonyl, $C_1$-$C_6$ alkoxycarbonyl, $C_1$-$C_6$ alkoxy, $C_1$-$C_6$ alkylsulfonyl, phenyl or phenyl substituted with $(Z)_m$, or $R^{30}$ may form, together with $R^{29}$, a $C_2$-$C_6$ alkylene chain to form a 3- to 7-membered ring together with the nitrogen atom attached to $R^{29}$ and $R^{30}$, wherein the alkylene chain may contain an oxygen atom, sulfur atom or nitrogen atom, and may optionally be substituted with a halogen atom, a $C_1$-$C_4$ alkyl group, a $C_1$-$C_4$ haloalkyl group, a $C_1$-$C_4$ alkoxy group, a —CHO group, a $C_1$-$C_4$ alkylcarbonyl group, a $C_1$-$C_4$ alkoxycarbonyl group, a phenyl group, a phenyl group substituted with $(Z)_m$, an oxo group or a thioxo group, $R^{31}$ is $C_1$-$C_8$ alkyl, ($C_1$-$C_5$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_3$-$C_8$ alkenyl, ($C_3$-$C_8$)alkenyl optionally substituted with $R^{38}$, $C_3$-$C_8$ alkynyl, ($C_3$-$C_8$)alkynyl optionally substituted with $R^{38}$, —C(O)R$^{39}$, —C(O)C(O)R$^{40}$, —C(O)OR$^{40}$, —C(O)C(O)OR$^{40}$, —C(O)SR$^{40}$, —C(O)N(R$^{42}$)R$^{41}$, —C(S)R$^{39}$, —C(S)OR$^{40}$, —C(S)SR$^{40}$, —C(S)N(R$^{42}$)R$^{41}$, —SH, $C_1$-$C_6$ alkylthio, $C_1$-$C_6$ haloalkylthio, phenylthio, phenylthio substituted with $(Z)_m$, —P(O)(OR$^{43}$)$_2$, —P(S)(OR$^{43}$)$_2$, phenyl, phenyl substituted with $(Z)_m$, D-9, D-10, D-12, D-14 to D-17, D-30 or D-32 to D-35, $R^{32}$ is a hydrogen atom, $C_1$-$C_6$ alkyl, $C_1$-$C_6$ haloalkyl, $C_3$-$C_6$ cycloalkyl($C_1$-$C_4$)alkyl, $C_1$-$C_6$ alkoxy($C_1$-$C_4$)alkyl, $C_1$-$C_6$ haloalkoxy($C_1$-$C_4$)alkyl, $C_1$-$C_6$ alkylthio($C_1$-$C_4$) alkyl, $C_1$-$C_6$ haloalkylthio($C_1$-$C_4$)alkyl, $C_1$-$C_6$ alkylsulfonyl($C_1$-$C_4$)alkyl, $C_1$-$C_6$ haloalkylsulfonyl($C_1$-$C_4$)alkyl, phenyl($C_1$-$C_4$)alkyl, phenyl($C_1$-$C_4$)alkyl substituted with $(Z)_m$, $C_3$-$C_6$ cycloalkyl, phenyl or phenyl substituted with $(Z)_m$, $R^{33}$ is $C_1$-$C_6$ alkyl, ($C_1$-$C_6$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_2$-$C_6$ alkenyl, ($C_2$-$C_6$)alkenyl optionally substituted with $R^{38}$, $C_3$-$C_6$ alkynyl, ($C_3$-$C_6$)alkynyl optionally substituted with $R^{38}$, phenyl, phenyl substituted with $(Z)_m$, D-1, D-2, D-4 to D-6, D-8 to D-10, D-12 to D-19, D-21, D-23, D-25, D-27 or D-30 to D-38, $R^{34}$ is a hydrogen atom, $C_1$-$C_6$ alkyl, ($C_1$-$C_6$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_2$-$C_6$ alkenyl, ($C_2$-$C_6$)alkenyl optionally substituted with $R^{38}$, $C_3$-$C_8$ alkynyl, ($C_3$-$C_6$)alkynyl optionally substituted with $R^{38}$, phenyl, phenyl substituted with $(Z)_m$, D-1 to D25 or D-27 to D-38, or may form the after-mentioned ring together with $R^{35}$, $R^{35}$ is a hydrogen atom, $C_1$-$C_6$ alkyl, ($C_1$-$C_6$)alkyl optionally substituted with $R^{38}$, $C_3$-$C_6$ alkenyl, $C_3$-$C_6$ haloalkenyl, $C_3$-$C_6$ alkynyl, $C_3$-$C_6$ haloalkynyl, phenyl or phenyl substituted with $(Z)_m$, or $R^{35}$ may form, together with $R^{34}$, a $C_2$-$C_5$ alkylene chain to form a 3- to 6-membered ring together with the nitrogen atom attached to $R^{34}$ and $R^{35}$, wherein the alkylene chain may contain an oxygen atom, sulfur atom or nitrogen atom, and may optionally be substituted with a halogen atom, a $C_1$-$C_4$ alkyl group, a $C_1$-$C_4$ alkoxy group, a —CHO group, a $C_1$-$C_4$ alkylcarbonyl group, a $C_1$-$C_4$ alkoxycarbonyl group, a phenyl group, a phenyl group substituted with $(Z)_m$ or an oxo group, $R^{36}$ is a hydrogen atom, $C_1$-$C_8$ alkyl, ($C_1$-$C_5$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_3$-$C_8$ alkenyl, ($C_3$-$C_8$)alkenyl optionally substituted with $R^{38}$, $C_3$-$C_8$ alkynyl, ($C_3$-$C_8$)alkynyl optionally substituted with $R^{38}$, —C(O)$R^{39}$, —C(O)C(O)$R^{40}$, —C(O)O$R^{40}$, —C(O)C(O)O$R^{40}$, —C(O)S$R^{40}$, —C(O)N($R^{42}$)$R^{41}$, —C(S)$R^{39}$, —C(S)O$R^{40}$, —C(S)S$R^{40}$, —C(S)N($R^{42}$)$R^{41}$, —S(O)$_2$$R^{40}$, —S(O)$_2$N($R^{42}$)$R^{41}$, —Si($R^{14a}$)($R^{14b}$)$R^{14}$, —P(O)(O$R^{43}$)$_2$ or —P(S)(O$R^{43}$)$_2$, $R^{37}$ is $C_1$-$C_8$ alkyl, ($C_1$-$C_8$)alkyl optionally substituted with $R^{38}$, $C_3$-$C_8$ cycloalkyl, ($C_3$-$C_8$)cycloalkyl optionally substituted with $R^{38}$, E-2 to E-6, E-8, E-14 to E-21, $C_3$-$C_8$ alkenyl, ($C_3$-$C_8$)alkenyl optionally substituted with $R^{38}$, $C_3$-$C_8$ alkynyl, ($C_3$-$C_8$)alkynyl optionally substituted with $R^{38}$, —C(O)$R^{39}$, —C(O)C(O)$R^{40}$, —C(O)O$R^{40}$, —C(O)C(O)O$R^{40}$, —C(O)S$R^{40}$, —C(O)N($R^{42}$)$R^{41}$, —C(S)$R^{39}$, —C(S)O$R^{40}$, —C(S)S$R^{40}$, —C(S)N($R^{42}$)$R^{41}$, —SH, $C_1$-$C_6$ alkylthio, $C_1$-$C_6$ haloalkylthio, phenylthio, phenylthio substituted with $(Z)_m$, —P(O)(O$R^{43}$)$_2$ or —P(S)(O$R^{43}$)$_2$, $R^{38}$ is a halogen atom, cyano, nitro, $C_3$-$C_8$ cycloalkyl, $C_3$-$C_8$ halocycloalkyl, E-5, E-6, E-9, E-10, E-12, E-14, E-15, E-18, E-19, E-21, —OH, —O$R^{40}$, —OC(O)$R^{39}$, —OC(O)O$R^{40}$, —OC(O)N($R^{42}$)$R^{41}$, —OC(S)N($R^{42}$)$R^{41}$, —SH, —S(O)$_r$$R^{40}$, —SC(O)$R^{39}$, —SC(O)O$R^{40}$, —SC(O)N($R^{42}$)$R^{41}$, —SC(S)N($R^{42}$)$R^{41}$, —N($R^{42}$)$R^{41}$, —N($R^{42}$)C(O)$R^{39}$, —N($R^{42}$)C(O)O$R^{40}$, N($R^{42}$)C(O)S$R^{40}$, —N($R^{42}$)C(O)N($R^{42}$)$R^{41}$, —N($R^{42}$)C(S)N($R^{42}$)$R^{41}$, —N($R^{42}$)S(O)$_2$$R^{40}$, —C(O)$R^{39}$, —C(O)OH, —C(O)O$R^{40}$, —C(O)S$R^{40}$, —C(O)N($R^{42}$)$R^{41}$, —C(O)C(O)O$R^{40}$, —C(S)S$R^{40}$, —C(S)N($R^{42}$)$R^{41}$, —Si($R^{14a}$)($R^{14b}$)$R^{14}$, —P(O)(O$R^{43}$)$_2$, —P(S)(O$R^{43}$)$_2$, —P(phenyl)$_2$, —P(O)(phenyl)$_2$, phenyl, phenyl substituted with $(Z)_m$, or D-1 to D-38, $R^{39}$ is a hydrogen atom, $C_1$-$C_6$ alkyl, $C_1$-$C_6$ haloalkyl, ($C_1$-$C_4$)alkyl optionally substituted with $R^{44}$, $C_3$-$C_6$ cycloalkyl, $C_3$-$C_6$ halocycloalkyl, E-5, E-6, E-14, E-15, $C_2$-$C_8$ alkenyl, $C_2$-$C_8$ haloalkenyl, $C_5$-$C_{10}$ cycloalkenyl, $C_5$-$C_{10}$ halocycloalkenyl, $C_2$-$C_8$ alkynyl, $C_2$-$C_8$ haloalkynyl, phenyl, phenyl substituted with $(Z)_m$, or D-1 to D-38, $R^{40}$ is $C_1$-$C_6$ alkyl, $C_1$-$C_6$ haloalkyl, ($C_1$-$C_4$)alkyl optionally substituted with $R^{44}$, $C_3$-$C_6$ cycloalkyl, E-5, E-6, $C_2$-$C_8$ alkenyl, $C_2$-$C_8$ haloalkenyl, $C_3$-$C_8$ alkynyl or phenyl, $R^{41}$ is a hydrogen atom, $C_1$-$C_6$ alkyl, $C_1$-$C_6$ haloalkyl, ($C_1$-$C_4$)alkyl optionally substituted with $R^{44}$, $C_3$-$C_6$ cycloalkyl, E-5, E-6, E-14, $C_2$-$C_8$ alkenyl, $C_2$-$C_8$ haloalkenyl, $C_3$-$C_8$ alkynyl, phenyl, phenyl substituted with $(Z)_m$, D-1 to D-25 or D-27 to D-38, or may form the after-mentioned ring together with $R^{42}$, $R^{42}$ is a hydrogen atom, $C_1$-$C_6$ alkyl, $C_1$-$C_6$ haloalkyl, $C_3$-$C_8$ cycloalkyl, $C_3$-$C_6$ alkenyl or $C_3$-$C_6$ alkynyl, or $R^{42}$ may form, together with $R^{41}$, a $C_2$-$C_5$ alkylene chain to form a 3- to 6-membered ring together with the nitrogen atom attached to $R^{41}$ and $R^{42}$, wherein the alkylene chain may contain an oxygen atom, sulfur atom or nitrogen atom, and may optionally be substituted with a halogen atom, a $C_1$-$C_4$ alkyl group, a $C_1$-$C_4$ alkoxy group, a —CHO group, a $C_1$-$C_4$ alkylcarbonyl group, a $C_1$-$C_4$ alkoxycarbonyl group, a phenyl group or a phenyl group substituted with $(Z)_m$, $R^{43}$ is $C_1$-$C_6$ alkyl or $C_1$-$C_6$ haloalkyl, $R^{44}$ is cyano, $C_3$-$C_6$ cycloalkyl, $C_3$-$C_6$ halocycloalkyl, E-5, E-6, E-14, E-15, $C_1$-$C_4$ alkoxy, $C_1$-$C_4$ haloalkoxy, phenoxy, phenoxy substituted with $(Z)_m$, $C_1$-$C_4$ alkylthio, $C_1$-$C_4$ haloalkylthio, phenylthio, phenylthio substituted with $(Z)_m$, $C_1$-$C_4$ alkylsulfonyl, $C_1$-$C_4$ haloalkylsulfonyl, phenylsulfonyl, phenylsulfonyl substituted with $(Z)_m$, —N($R^{46}$)$R^{45}$, $C_1$-$C_4$ alkylcarbonyl, $C_1$-$C_4$ haloalkylcarbonyl, $C_1$-$C_4$ alkoxycarbonyl, $C_1$-$C_4$ alkylaminocarbonyl, di($C_1$-$C_4$ alkyl)aminocarbonyl, tri($C_1$-$C_4$ alkyl)silyl, phenyl, phenyl substituted with $(Z)_m$, or D-1 to D-38, $R^{45}$ is a hydrogen atom, $C_1$-$C_4$ alkyl, $C_1$-$C_4$ alkylcarbonyl, $C_1$-$C_4$ haloalkylcarbonyl, $C_1$-$C_4$ alkoxycarbonyl, phenylcarbonyl or phenylcarbonyl substituted with $(Z)_m$, $R^{46}$ is a hydrogen atom or $C_1$-$C_4$ alkyl, m is an integer of 1, 2, 3, 4 or 5, n is an integer of 0, 1, 2, 3 or 4, p is an integer of 0, 1, 2, 3, 4, 5, 6, 7, 8 or 9, r is an integer of 0, 1 or 2, and t is an integer of 0 or 1.

Further, the present invention relates to all stereoisomers thereof, its intermediate, and a pesticide containing it as an active ingredient.

Advantageous Effects of Invention

The compound of the present invention represented by the formula (I) and the pesticide containing the compound as an active ingredient have excellent controlling effect on pests, especially fungi and nematodes in agricultural fields or zootechnical/hygienic fields, and have sufficient controlling effect on pests which have acquired resistance to conventional pesticides. Further, they have little harmful effect on non-target organisms such as plants, mammals, fishes, useful insects and natural enemies, show low persistence and are environmentally friendly.

Thus, the present invention can provide useful novel pesticides.

DESCRIPTION OF EMBODIMENT(S)

The oxime-substituted amide compounds of the present invention represented by the formula (I) can have geometrical isomers such as E-isomers and Z-isomers, and the present invention covers both E-isomers and Z-isomers and mixtures containing them in any ratios. The compounds of the present invention can have optically active isomers due to the presence of one or more asymmetric carbon atoms depending on the types of substituents in them, and the present invention covers any optically active isomers and any racemates.

As a halogen atom herein, a fluorine atom, a chlorine atom, a bromine atom or an iodine atom may be mentioned. Herein, the expression "halo" also means such a halogen atom.

In the specific description of the substituents herein, the expression "n-" denotes "normal", "i-" "iso", "s-" "secondary", "tert-" "tertiary", and "Ph" "phenyl".

The expression "$C_a$-$C_b$ alkyl" herein means a linear or branched hydrocarbon group containing from a to b carbon atoms such as a methyl group, an ethyl group, a n-propyl group, an i-propyl group, a n-butyl group, an i-butyl group, a s-butyl group, a tert-butyl group, a pentyl group, a 1-ethylpropyl group, a 2,2-dimethylpropyl group or a hexyl group, and those within the designated carbon number range are selected.

The expression "$C_a$-$C_b$ haloalkyl" herein means a linear or branched hydrocarbon group containing from a to b carbon atoms in which hydrogen atom(s) on carbon atom(s) are optionally substituted with halogen atom(s) which may be identical with or different from one another if two or more halogen atoms are present, such as a fluoromethyl group, a chloromethyl group, a bromomethyl group, an iodomethyl group, a difluoromethyl group, a dichloromethyl group, a trifluoromethyl group, a chlorodifluoromethyl group, a trichloromethyl group, a bromodifluoromethyl group, a 1-fluoroethyl group, a 2-fluoroethyl group, a 2-chloroethyl group, a 2-bromoethyl group, a 2,2-difluoroethyl group, a 2,2,2-trifluoroethyl group, a 2-chloro-2,2-difluoroethyl group, a 2,2,2-trichloroethyl group, a 2-bromo-2,2-difluoroethyl group, a 1,1,2,2-tetrafluoroethyl group, a 2-chloro-1,1,2-trifluoroethyl group, a pentafluoroethyl group, a 2,2-difluoropropyl group, a 3,3,3-trifluoropropyl group, a 3-bromo-3,3-difluoropropyl group, a 2,2,3,3-tetrafluoropropyl group, a 2,2,3,3,3-pentafluoropropyl group, a 1,1,2,3,3,3-hexafluoropropyl group, a heptafluoropropyl group, a 2,2,2-trifluoro-1-(methyl)ethyl group, a 2,2,2-trifluoro-1-(trifluoromethyl)ethyl group, a 1,2,2,2-tetrafluoro-1-(trifluoromethyl)ethyl group, a 2,2,3,4,4,4-hexafluorobutyl group, a 2,2,3,3,4,4,4-heptafluorobutyl group or a nonafluorobutyl group, and those within the designated carbon number range are selected.

The expression "$C_a$-$C_b$ cycloalkyl" herein means a cyclic hydrocarbon group containing from a to b carbon atoms in the form of a 3- to 10-membered monocyclic or polycyclic ring which may optionally be substituted with an alkyl group as long as the number of carbon atoms does not exceed the designated carbon number range, such as a cyclopropyl group, a 1-methylcyclopropyl group, a 2-methylcyclopropyl group, a 2,2-dimethylcyclopropyl group, a cyclobutyl group, a cyclopentyl group or a cyclohexyl group, and those within the designated carbon number range are selected.

The expression "$C_a$-$C_b$ halocycloalkyl" herein means a cyclic hydrocarbon group containing from a to b carbon atoms in the form of a 3- to 10-membered monocyclic or polycyclic ring which may optionally be substituted with an alkyl group as long as the number of carbon atoms does not exceed the designated carbon number range, in which hydrogen atom(s) on carbon atom(s) in a ring moiety and/or in a side chain are optionally substituted with halogen atom(s) which may be identical with or different from one another if two or more halogen atoms are present, such as a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group or a 2,2,3,3-tetrafluorocyclobutyl group, and those within the designated carbon atom range are selected.

The expression "$C_a$-$C_b$ alkenyl" herein means a linear or branched unsaturated hydrocarbon group containing from a to b carbon atoms and having one or more double bonds in the molecule such as a vinyl group, a 1-propenyl group, a 2-propenyl group, a 1-methylethenyl group, a 1-butenyl group, a 2-butenyl group, a 1-methyl-1-propenyl group, a 2-methyl-1-propenyl group, a 2-methyl-2-propenyl group or a 3-methyl-2-butenyl group, and those within the designated carbon atom range are selected.

The expression "$C_a$-$C_b$ haloalkenyl" herein means a linear or branched unsaturated hydrocarbon group containing from a to b carbon atoms and having one or more double bonds in the molecule, in which hydrogen atom(s) on carbon atom(s) are optionally substituted with halogen atom(s) which may be identical with or different from one another if two or more halogen atoms are present, such as a 2-fluorovinyl group, a 2-chlorovinyl group, a 1,2-dichlorovinyl group, a 2,2-dichlorovinyl group, a 2-fluoro-2-propenyl group, a 2-chloro-2-propenyl group, a 3-chloro-2-propenyl group, a 3,3-difluoro-2-propenyl group, a 2,3-dichloro-2-propenyl group, a 3,3-dichloro-2-propenyl group, a 2,3,3-trifluoro-2-propenyl group, a 2,3,3-trichloro-2-propenyl group, a 1-(trifluoromethyl)ethenyl group, a 4,4-difluoro-3-butenyl group, a 3,4,4-trifluoro-3-butenyl group, a 2,4,4,4-tetrafluoro-2-butenyl group or a 3-chloro-4,4,4-trifluoro-2-butenyl group, and those within the designated carbon atom range are selected.

The expression "$C_a$-$C_b$ cycloalkenyl" herein means a cyclic unsaturated hydrocarbon group containing from a to b carbon atoms and containing one or more endo- or exo-double bonds in the form of a 3- to 10-membered monocyclic or polycyclic ring which may optionally be substituted with an alkyl group as long as the number of carbon atoms does not exceed the designated carbon number range, such as a 1-cyclopentenyl group, a 2-cyclopentenyl group, a 1-cyclohexenyl group, a 2-cyclohexenyl group or a bicyclo[2.2.1]-5-hepten-2-yl group, and those within the designated carbon atom range are selected.

The expression "$C_a$-$C_b$ halocycloalkenyl" herein means a cyclic unsaturated hydrocarbon group containing from a to b carbon atoms and containing one or more endo- or exo-double bonds in the form of a 3- to 10-membered monocyclic or polycyclic ring which may optionally be substituted with an alkyl group as long as the number of carbon atoms does not exceed the designated carbon number range, in which hydrogen atom(s) on carbon atom(s) in the ring moiety and/or in the side chain are optionally substituted with halogen atom(s) which may be identical with or different from one another if two or more halogen atoms are present, such as a 2-fluoro-1-cyclopentenyl group, a 2-chloro-1-cyclopentenyl group, a 3-chloro-2-cyclopentenyl group or a 2-fluoro-1-cyclohexenyl group, and those within the designated carbon atom range are selected.

The expression "$C_a$-$C_b$ alkylidene" herein means a linear or branched hydrocarbon group containing from a to b carbon atoms which attaches by a double bond, such as a methylidene group, an ethylidene group, a propylidene group or a 1-methylethylidene group, and those within the designated carbon number range are selected.

The expression "$C_a$-$C_b$ alkynyl" herein means a linear or branched unsaturated hydrocarbon group containing from a to b carbon atoms and having one or more triple bonds in the molecule such as an ethynyl group, a 1-propynyl group, a 2-propynyl group, a 1-butynyl group, a 2-butynyl group, a 3-butynyl group, a 1-methyl-2-propynyl group, a 2-pentynyl group or a 3-hexynyl group, and those within the designated carbon atom range are selected.

The expression "$C_a$-$C_b$ haloalkynyl" herein means a linear or branched unsaturated hydrocarbon group containing from a to b carbon atoms and having one or more triple bonds in the molecule, in which hydrogen atom(s) on carbon atom(s) are optionally substituted with halogen atom(s) which may be identical with or different from one another if two or more halogen atoms are present, such as a 2-chloroethynyl group, a 2-bromoethynyl group, a 2-iodoethynyl group, a 3-chloro-2-propynyl group or a 3-bromo-2-propynyl group or a 3-iodo-2-propynyl group, and those within the designated carbon number range are selected.

The expression "$C_a$-$C_b$ alkoxy" herein means an alkyl-O— group in which the alkyl is a previously mentioned alkyl group containing from a to b carbon atoms, such as a methoxy group, an ethoxy group, a n-propyloxy group, an i-propyloxy group, a n-butyloxy group, an i-butyloxy group, a s-butyloxy group, a tert-butyloxy group, a pentyloxy group or a hexyloxy group, and those within the designated carbon atom range are selected.

The expression "$C_a$-$C_b$ haloalkoxy" herein means a haloalkyl-O— group in which the haloalkyl is a previously mentioned haloalkyl group containing from a to b carbon atoms, such as a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2,-tetrafluoroethoxy group, a 2-chloro-1,1,2-trifluoroethoxy group or a 1,1,2,3,3,3-hexafluoropropyloxy group, and those within the designated carbon atom range are selected.

The expression "$C_a$-$C_b$ alkenyloxy" herein means an alkenyl-O— group in which the alkenyl is a previously mentioned alkenyl group containing from a to b carbon atoms, such as a 2-propenyloxy group, a 2-butenyloxy group, a 2-methyl-2-propenyloxy group or a 3-methyl-2-butenyloxy group, and those within the designated carbon atom range are selected.

The expression "$C_a$-$C_b$ alkylthio" herein means an alkyl-S— group in which the alkyl is a previously mentioned alkyl group containing from a to b carbon atoms, such as a methylthio group, an ethylthio group, a n-propylthio group, an i-propylthio group, a n-butylthio group, an i-butylthio group, a s-butylthio group or a tert-butylthio group, and those within the designated carbon atom range are selected.

The expression "$C_a$-$C_b$ haloalkylthio" herein means a haloalkyl-S— group in which the haloalkyl is a previously mentioned haloalkyl group containing from a to b carbon atoms, such as a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 1,1,2,3,3,3-hexafluoropropylthio group, a heptafluoropropylthio group, a 1,2,2,2-tetrafluoro-1-(trifluoromethyl)ethylthio group or a nonafluorobutylthio group, and those within the designated carbon atom range are selected.

The expression "$C_a$-$C_b$ alkylsulfinyl" herein means an alkyl-S(O)— group in which the alkyl is a previously mentioned alkyl group containing from a to b carbon atoms, such as a methylsulfinyl group, an ethylsulfinyl group, a n-propylsulfinyl group, an i-propylsulfinyl group, a n-butylsulfinyl group, an i-butylsulfinyl group, a s-butylsulfinyl group or a tert-butylsulfinyl group, and those within the designated carbon atom range are selected.

The expression "$C_a$-$C_b$ haloalkylsulfinyl" herein means a haloalkyl-S(O)— group in which the haloalkyl is a previously mentioned haloalkyl group containing from a to b carbon atoms, such as a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group or a nonafluorobutylsulfinyl group, and those within the designated carbon atom range are selected.

The expression "$C_a$-$C_b$ alkylsulfonyl" herein means an alkyl-S(O)$_2$— group in which the alkyl is a previously mentioned alkyl group containing from a to b carbon atoms, such as a methylsulfonyl group, an ethylsulfonyl group, a n-propylsulfonyl group, an i-propylsulfonyl group, a n-butylsulfonyl group, an i-butylsulfonyl group, a s-butylsulfonyl group or a tert-butylsulfonyl group, and those within the designated carbon atom range are selected.

The expression "$C_a$-$C_b$ haloalkylsulfonyl" herein means a haloalkyl-S(O)$_2$— group in which the haloalkyl is a previously mentioned haloalkyl group containing from a to b carbon atoms, such as a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group or a 2-chloro-1,1,2-trifluoroethylsulfonyl group, and those within the designated carbon atom range are selected.

The expression "$C_a$-$C_b$ alkylamino" herein means an amino group in which either hydrogen atom is replaced by a previously mentioned alkyl group containing from a to b carbon atoms, such as a methylamino group, an ethylamino group, a n-propylamino group, an i-propylamino group, a n-butylamino group, an i-butylamino group or a tert-butylamino group, and those within the designated carbon atom range are selected.

The expression "di($C_a$-$C_b$ alkyl)amino" herein means an amino group in which both hydrogen atoms are replaced by previously mentioned alkyl groups containing from a to b carbon atoms which may be identical with or different from each other, such as a dimethylamino group, an ethyl(methyl)amino group, a diethylamino group, a di(n-propyl)amino group or a di(n-butyl)amino group, and those within the designated carbon atom range are selected.

The expression "$C_a$-$C_b$ alkylimino" herein means an alkyl-N=group in which the alkyl is a previously mentioned alkyl group containing from a to b carbon atoms, such as a methylimino group, an ethylimino group, a n-propylimino group, an i-propylimino group, a n-butylimino group, an i-butylimino group or a s-butylimino group, and those within the designated carbon atom range are selected.

The expression "$C_a$-$C_b$ alkoxyimino" herein means an alkoxy-N=group in which the alkoxy is a previously mentioned alkoxy group containing from a to b carbon atoms, such as a methoxyimino group, an ethoxyimino group, a n-propyloxyimino group, an i-propyloxyimino group or a n-butyloxyimino group, and those within the designated carbon atom range are selected.

The expression "$C_a$-$C_b$ alkylcarbonyl" herein means an alkyl-C(O)— group in which the alkyl is a previously mentioned alkyl group containing from a to b carbon atoms, such as an acetyl group, a propionyl group, a butyryl group, an isobutyryl group, a valeryl group, an isovaleryl group, a 2-methylbutanoyl group or a pivaloyl group, and those within the designated carbon atom range are selected.

The expression "$C_a$-$C_b$ haloalkylcarbonyl" herein means a haloalkyl-C(O)— group in which the haloalkyl is a previously mentioned haloalkyl group containing from a to b carbon atoms, such as a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a pentafluoropropionyl group, a heptafluorobutanoyl group or a 3-chloro-2,2-dimethylpropanoyl group, and those within the designated carbon atom range are selected.

The expression "$C_a$-$C_b$ cycloalkylcarbonyl" herein means a cycloalkyl-C(O)— group in which the cycloalkyl is a previously mentioned cycloalkyl group containing from a to b carbon atoms, such as a cyclopropylcarbonyl group, a cyclobutylcarbonyl group, a cyclopentylcarbonyl group, a 2,2-dimethylcyclopropylcarbonyl group or a cyclohexylcarbonyl group, and those within the designated carbon atom range are selected.

The expression "$C_a$-$C_b$ alkoxycarbonyl" herein means an alkyl-O—C(O)— group in which the alkyl is a previously mentioned alkyl group containing from a to b carbon atoms, such as a methoxycarbonyl group, an ethoxycarbonyl group, a n-propyloxycarbonyl group, an i-propyloxycarbonyl group, a n-butoxycarbonyl group, an i-butoxycarbonyl group or a tert-butoxycarbonyl group, and those within the designated carbon atom range are selected.

The expression "$C_a$-$C_b$ haloalkoxycarbonyl" herein means a haloalkyl-O—C(O)— group in which the haloalkyl is a previously mentioned haloalkyl group containing from a to b carbon atoms, such as a chloromethoxycarbonyl group, a 2-chloroethoxycarbonyl group, a 2,2-difluoroethoxycarbonyl group, a 2,2,2-trifluoroethoxycarbonyl group or a 2,2,2-trichloroethoxycarbonyl group, and those within the designated carbon atom range are selected.

The expression "$C_a$-$C_b$ alkylaminocarbonyl" herein means a carbamoyl group in which either hydrogen atom is replaced by a previously mentioned alkyl group containing from a to b carbon atoms, such as a methylcarbamoyl group, an ethylcarbamoyl group, a n-propylcarbamoyl group, an i-propylcarbamoyl group, a n-butylcarbamoyl group, an i-butylcarbamoyl group, a s-butylcarbamoyl group or a tert-butylcarbamoyl group, and those within the designated carbon atom range are selected.

The expression "$C_a$-$C_b$ haloalkylaminocarbonyl" herein means a carbamoyl group in which either hydrogen atom is replaced by a previously mentioned haloalkyl group containing from a to b carbon atoms, such as a 2-fluoroethylcarbamoyl group, a 2-chloroethylcarbamoyl group, a 2,2-difluoroethylcarbamoyl group or a 2,2,2-trifluoroethylcarbamoyl group, and those within the designated carbon atom range are selected.

The expression "di($C_a$-$C_b$ alkyl)aminocarbonyl" herein means a carbamoyl group in which both hydrogen atoms are replaced by previously mentioned alkyl groups containing from a to b carbon atoms which may be identical with or different from each other, such as an N,N-dimethylcarbamoyl group, an N-ethyl-N-methylcarbamoyl group, an N,N-diethylcarbamoyl group, an N,N-di(n-propyl)carbamoyl group or an N,N-di(n-butyl)carbamoyl group, and those within the designated carbon atom range are selected.

The expression "di($C_a$-$C_b$ alkyl)aminosulfonyl" herein means a sulfamoyl group in which both hydrogen atoms are replaced by previously mentioned alkyl groups containing from a to b carbon atoms which may be identical with or different from each other, such as an N,N-dimethylsulfamoyl group, an N-ethyl-N-methylsulfamoyl group, an N,N-diethylsulfamoyl group, an N,N-di(n-propyl)sulfamoyl group or an N,N-di(n-butyl)sulfamoyl group, and those within the designated carbon atom range are selected.

The expression "tri($C_a$-$C_b$ alkyl)silyl" herein means a silyl group replaced by previously mentioned alkyl groups containing from a to b carbon atoms which may be identical with or different from one another, such as a trimethylsilyl group, a triethylsilyl group, a tri(n-propyl)silyl group, an ethyldimethylsilyl group, a n-propyldimethylsilyl group, a n-butyldimethylsilyl group, an i-butyldimethylsilyl group or a tert-butyldimethylsilyl group, and those within the designated carbon atom range are selected.

The expression "$C_a$-$C_b$ alkylsulfonyloxy" herein means an alkylsulfonyl-O— group in which the alkylsulfonyl is a previously mentioned alkylsulfonyl group containing from a to b carbon atoms, such as a methylsulfonyloxy group, an ethylsulfonyloxy group, a n-propylsulfonyloxy group or an i-propylsulfonyloxy group, and those within the designated carbon atom range are selected.

The expression "$C_a$-$C_b$ haloalkylsulfonyloxy" herein means a haloalkylsulfonyl-O-group in which the haloalkylsulfonyl is a previously mentioned haloalkylsulfonyl group containing from a to b carbon atoms, such as a difluoromethylsulfonyloxy group, a trifluoromethylsulfonyloxy group, a chlorodifluoromethylsulfonyloxy group or a bromodifluoromethylsulfonyloxy group, and those within the designated carbon atom range are selected.

The expression such as "$C_a$-$C_b$ cycloalkyl($C_d$-$C_e$)alkyl", "hydroxy($C_d$-$C_e$)alkyl", "$C_a$-$C_b$ alkoxy($C_d$-$C_e$)alkyl", "$C_a$-$C_b$ haloalkoxy($C_d$-$C_e$)alkyl", "$C_a$-$C_b$ alkylthio($C_d$-$C_e$)alkyl", "$C_a$-$C_b$ haloalkylthio($C_d$-$C_e$)alkyl", "$C_a$-$C_b$ alkylsulfinyl($C_d$-$C_e$)alkyl", "$C_a$-$C_b$ haloalkylsulfinyl($C_d$-$C_e$)alkyl", "$C_a$-$C_b$ alkylsulfonyl($C_d$-$C_e$)alkyl", "$C_a$-$C_b$ haloalkylsulfonyl($C_d$-$C_e$)alkyl", "$C_a$-$C_b$ alkylamino($C_d$-$C_e$)alkyl", "di($C_a$-$C_b$ alkyl)amino($C_d$-$C_e$)alkyl", "cyano($C_d$-$C_e$)alkyl", "$C_a$-$C_b$ alkoxycarbonyl($C_d$-$C_e$)alkyl", "$C_a$-$C_b$ haloalkoxycarbonyl($C_d$-$C_e$)alkyl", "phenyl($C_d$-$C_e$)alkyl" or "phenyl($C_d$-$C_e$) alkyl substituted with $(Z)_m$" herein means a previously mentioned alkyl group containing from d to e carbon atoms in which hydrogen atom(s) on carbon atom(s) are optionally substituted with previously mentioned optional $C_a$-$C_b$ cycloalkyl group, $C_a$-$C_b$ alkoxy group, $C_a$-$C_b$ haloalkoxy group, $C_a$-$C_b$ alkylthio group, $C_a$-$C_b$ haloalkylthio group, $C_a$-$C_b$ alkylsulfinyl group, $C_a$-$C_b$ haloalkylsulfinyl group, $C_a$-$C_b$ alkylsulfonyl group, $C_a$-$C_b$ haloalkylsulfonyl group, $C_a$-$C_b$ alkylamino group, di($C_a$-$C_b$ alkyl)amino group, $C_a$-$C_b$ alkoxycarbonyl group, $C_a$-$C_b$ haloalkoxycarbonyl group, hydroxy group, cyano group, phenyl group or phenyl group substituted with $(Z)_m$, and those within the designated carbon atom range are selected.

The expression such as "hydroxy($C_d$-$C_e$)cycloalkyl" or "$C_a$-$C_b$ alkoxy($C_d$-$C_e$)cycloalkyl" herein means a previously mentioned cycloalkyl group containing from d to e carbon atoms in which hydrogen atom(s) on carbon atom(s) are optionally substituted with previously mentioned optional $C_a$-$C_b$ alkoxy group(s) or hydroxy group(s), and those within the designated carbon atom range are selected.

The expression "phenyl($C_a$-$C_b$)alkynyl" herein means a previously mentioned alkynyl group containing from a to b carbon atoms in which hydrogen atom(s) on carbon atom(s) are optionally substituted with phenyl group(s), and those within the designated carbon atom range are selected.

The expression such as "($C_a$-$C_b$) alkyl optionally substituted with $R^6$", "($C_a$-$C_b$) alkyl optionally substituted with $R^{18}$", "($C_a$-$C_b$) alkyl optionally substituted with $R^{19}$", "($C_a$-$C_b$) alkyl optionally substituted with $R^{28}$", "($C_a$-$C_b$) alkyl optionally substituted with $R^{38}$" or "($C_a$-$C_b$) alkyl optionally substituted with $R^{44}$" herein means a previously mentioned alkyl group containing from a to b carbon atoms in which hydrogen atom(s) on carbon atom(s) are optionally substituted with optional $R^6$, $R^{18}$, $R^{19}$, $R^{28}$, $R^{38}$ or $R^{44}$, and those within the designated carbon atom range are selected. When there are two or more $R^6$'s, $R^{18}$'s, $R^{19}$'s, $R^{28}$'S, $R^{38}$'S or $R^{44}$'S on a ($C_a$-$C_b$) alkyl group, each $R^6$, $R^{18}$, $R^{19}$, $R^{28}$, $R^{38}$ or $R^{44}$ may be identical with or different from one another.

The expression such as "$(C_a-C_b)$ cycloalkyl optionally substituted with $R^6$", "$(C_a-C_b)$ cycloalkyl optionally substituted with $R^{28}$" or "$(C_a-C_b)$ cycloalkyl optionally substituted with $R^{38}$" herein means a previously mentioned cycloalkyl group containing from a to b carbon atoms in which hydrogen atom(s) on carbon atom(s) in the ring moiety and/or in the side chain are optionally substituted with optional $R^6$, $R^{28}$ or $R^{38}$, and those within the designated carbon atom range are selected. When there are two or more $R^6$'s, $R^{28}$'s or $R^{38}$'s on a $(C_a-C_b)$ cycloalkyl group, each $R^6$, $R^{28}$ or $R^{38}$ may be identical with or different from one another.

The expression such as "$(C_a-C_b)$ alkenyl optionally substituted with $R^6$", "$(C_a-C_b)$ alkenyl optionally substituted with $R^{28}$" or "$(C_a-C_b)$ alkenyl optionally substituted with $R^{38}$" herein means a previously mentioned alkenyl group containing from a to b carbon atoms in which hydrogen atom(s) on carbon atom(s) are optionally substituted with optional $R^6$, $R^{28}$ or $R^{38}$, and those within the designated carbon atom range are selected. When there are two or more $R^6$'s, $R^{28}$'s or $R^{38}$'s on a $(C_a-C_b)$ alkenyl group, each $R^6$, $R^{28}$ or $R^{38}$ may be identical with or different from one another.

The expression such as "$(C_a-C_b)$ alkynyl optionally substituted with $R^6$", "$(C_a-C_b)$ alkynyl optionally substituted with $R^{28}$" or "$(C_a-C_b)$ alkynyl optionally substituted with $R^{38}$" herein means a previously mentioned alkynyl group containing from a to b carbon atoms in which hydrogen atom(s) on carbon atom(s) are optionally substituted with optional $R^6$, $R^{28}$ or $R^{38}$, and those within the designated carbon atom range are selected. When there are two or more $R^6$'s, $R^{28}$'s or $R^{38}$'s on a $(C_a-C_b)$ alkynyl group, each $R^6$, $R^{28}$ or $R^{38}$ may be identical with or different from one another.

The expression "$R^3$ may form, together with $R^2$, a $C_2-C_5$ alkylene chain to form a 3- to 6-membered ring together with the carbon atom attached to $R^2$ and $R^3$, wherein the alkylene chain may contain an oxygen atom, sulfur atom or nitrogen atom" is specifically exemplified by a cyclopropane ring, a cyclobutane ring, a cyclopentane ring, a tetrahydrofuran ring, a tetrahydrothiophene ring, a pyrrolidine ring, a cyclohexane ring, a tetrahydropyran ring, a tetrahydrothiopyran ring, a piperidine ring, a cycloheptane ring, an oxepane ring, a thiepane ring, an azepane ring or the like, and those within the designated carbon atom range are selected.

The expression such as "$R^9$ may form, together with $R^8$, a $C_2-C_6$ alkylene chain to form a 3- to 7-membered ring together with the nitrogen atom attached to $R^8$ and $R^9$, wherein the alkylene chain may contain an oxygen atom, sulfur atom or nitrogen atom, and may optionally be substituted with an oxo group or a thioxo group", "$R^{25}$ and $R^{24}$ together may form a $C_4-C_5$ alkylene chain to form a 5- to 6-membered ring together with the nitrogen atom attached to $R^{24}$ and $R^{25}$, wherein the alkylene chain may contain an oxygen atom, sulfur atom or nitrogen atom, and may optionally be substituted with an oxo group or a thioxo group", "$R^{30}$ may form, together with $R^{29}$, a $C_2-C_6$ alkylene chain to form a 3- to 7-membered ring together with the nitrogen atom attached to $R^{29}$ and $R^{30}$ wherein the alkylene chain may contain an oxygen atom, sulfur atom or nitrogen atom, and may optionally be substituted with an oxo group or a thioxo group" or "$R^{35}$ may form, together with $R^{34}$, a $C_2-C_5$ alkylene chain to form a 3- to 6-membered ring together with the nitrogen atom attached to $R^{34}$ and $R^{35}$, wherein the alkylene chain may contain an oxygen atom, sulfur atom or nitrogen atom, and may optionally be substituted with an oxo group" is specifically exemplified by aziridine, azetidine, azetidin-2-one, pyrrolidine, pyrrolidin-2-one, oxazolidine, oxazolidin-2-one, oxazolidine-2-thione, thiazolidine, thiazolidin-2-one, thiazolidine-2-thione, imidazolidine, imidazolidin-2-one, imidazolidine-2-thione, piperidine, piperidin-2-one, piperidine-2-thione, 2H-3,4,5,6-tetrahydro-1,3-oxazin-2-one, 2H-3,4,5,6-tetrahydro-1,3-oxazine-2-thione, morpholine, 2H-3,4,5,6-tetrahydro-1,3-thiazin-2-one, 2H-3,4,5,6-tetrahydro-1,3-thiazine-2-thione, thiomorpholine, thiomorpholine-1-oxide, thiomorpholine-1,1-dioxide, perhydropyrimidin-2-one, piperazine, homopiperidine, homopiperidin-2-one, heptamethyleneimine or the like, and those within the designated carbon atom range are selected.

The expression such as "$R^{13}$ may form, together with $R^{12}$, a $C_2-C_6$ alkylene chain to form a 3- to 7-membered ring together with the nitrogen atom attached to $R^{12}$ and $R^{13}$ wherein the alkylene chain may contain an oxygen atom, sulfur atom or nitrogen atom", "$R^{23}$ may form, together with $R^{22}$, a $C_2-C_6$ alkylene chain to form a 3- to 7-membered ring together with the nitrogen atom attached to $R^{22}$ and $R^{23}$, wherein the alkylene chain may contain an oxygen atom, sulfur atom or nitrogen atom", "$R^{27}$ may form, together with $R^{26}$, a $C_4-C_7$ alkylene chain to form a 5- to 8-membered ring together with the nitrogen atom attached to $R^{26}$ and $R^{27}$, wherein the alkylene chain may contain an oxygen atom or sulfur atom" or "$R^{42}$ may form, together with $R^{41}$, a $C_2-C_5$ alkylene chain to form a 3- to 6-membered ring together with the nitrogen atom attached to $R^{41}$ and $R^{42}$, wherein the alkylene chain may contain an oxygen atom, sulfur atom or nitrogen atom" is specifically exemplified by aziridine, azetidine, pyrrolidine, oxazolidine, thiazolidine, imidazolidine, piperidine, morpholine, thiomorpholine, thiomorpholine-1-oxide, thiomorpholine-1,1-dioxide, piperazine, homopiperidine, heptamethyleneimine or the like, and those within the designated carbon atom range are selected.

The expression such as "$R^{9a}$ may form, together with $R^{8a}$, a $C_4-C_6$ alkylene chain to form a 5- to 7-membered ring together with the carbon atom attached to $R^{8a}$ and $R^{9a}$ wherein the alkylene chain may contain an oxygen atom or sulfur atom" or "$R^{25a}$ may form, together with $R^{24a}$, a $C_3-C_5$ alkylene chain to form a 4- to 6-membered ring together with the carbon atom attached to $R^{24a}$ and $R^{25a}$, wherein the alkylene chain may contain an oxygen atom, sulfur atom or nitrogen atom" is specifically exemplified by cyclopentylidene, tetrahydrofuran-3-ylidene, tetrahydrothiophen-3-ylidene, cyclohexylidene, tetrahydropyran-3-ylidene, tetrahydropyran-4-ylidene, tetrahydrothiopyran-3-ylidene, tetrahydrothiopyran-4-ylidene or the like, and those within the designated carbon atom range are selected.

As the preferred range of the substituent represented by $G^1$ in the compounds which fall within the present invention, the following sets may, for example, be mentioned.

$G^1$-I: $G^1$-1 [wherein $X^1$ is a bromine atom, an iodine atom, methyl, difluoromethyl or trifluoromethyl, and $X^2$, $X^3$, $X^4$ and $X^5$ are hydrogen atoms].

$G^1$-II: $G^1$-1 [wherein $X^1$ is a chlorine atom, and $X^2$, $X^3$, $X^4$ and $X^5$ are hydrogen atoms].

$G^1$-III: $G^1$-2 [wherein $X^1$ is a halogen atom, methyl or trifluoromethyl, and $X^3$, $X^4$ and $X^5$ are hydrogen atoms].

$G^1$-IV: $G^1$-3 [wherein $X^1$ is a halogen atom or trifluoromethyl, and $X^2$, $X^3$ and $X^4$ are hydrogen atoms].

$G^1$-V: $G^1$-7 [wherein $X^1$ is trifluoromethyl, and $X^3$ and $X^4$ are hydrogen atoms].

$G^1$-VI: $G^1$-11 [wherein $X^1$ is a halogen atom, methyl or trifluoromethyl, and $X^3$ and $X^4$ are hydrogen atoms].

$G^1$-VII: $G^1$-12 [wherein $X^1$ is a halogen atom or trifluoromethyl, and $X^2$ and $X^3$ are hydrogen atoms].

G¹-VIII: G¹-16 [wherein $X^1$ is trifluoromethyl, $X^2$ and $X^4$ are hydrogen atoms, and $R^5$ is methyl].

G¹-IX: G¹-27 [wherein $X^1$ is difluoromethyl or trifluoromethyl, $X^2$ is a hydrogen atom, and $R^5$ is methyl].

G¹-X: G¹-33 [wherein $X^1$ is difluoromethyl or trifluoromethyl, and $X^3$ is methyl].

G¹-XI: G¹-1 [wherein $X^1$ is nitro, and $X^2$, $X^3$, $X^4$ and $X^5$ are hydrogen atoms].

G¹-XII: G¹-1 [wherein $X^1$ is trifluoromethyl, $X^2$ and $X^3$ are hydrogen atoms, $X^4$ is a halogen atom, and $X^5$ is a hydrogen atom].

G¹-XIII: G¹-9 [wherein $X^1$ is methyl or trifluoromethyl, $X^2$ is a hydrogen atom, and $X^3$ is methyl].

G¹-XIV: G¹-27 [wherein $X^1$ is a halogen atom or trifluoromethyl, $X^2$ is a halogen atom, and $R^5$ is methyl].

G¹-XV: G¹-32 [wherein $X^1$ and $X^3$ are methyl].

G¹-XVI: G¹-50 [wherein $X^1$ is trifluoromethyl, and r is 0].

G¹-XVII: G¹-1 [wherein $X^1$ is a fluorine atom, cyano, $C_1$-$C_4$ alkoxy, $C_1$-$C_4$ haloalkoxy, $C_1$-$C_4$ alkylthio or phenyl, and $X^2$, $X^3$, $X^4$ and $X^5$ are hydrogen atoms].

G¹-XVIII: G¹-1 [wherein $X^1$ is a halogen atom, methyl or trifluoromethyl, $X^2$ is a hydrogen atom or a halogen atom, $X^3$ and $X^4$ are hydrogen atoms, and $X^5$ is a hydrogen atom or a halogen atom].

G¹-XIX: G¹-2 [wherein $X^1$ is a halogen atom, $X^3$ is a hydrogen atom, $X^4$ is trifluoromethyl, and $X^5$ is a hydrogen atom].

G¹-XX: G¹-4 [wherein $X^1$ is trifluoromethyl, and $X^2$, $X^3$ and $X^5$ are hydrogen atoms].

G¹-XXI: G¹-8 [wherein $X^1$ is a halogen atom or methyl, and $X^3$ and $X^4$ are hydrogen atoms].

G¹-XXII: G¹-9 [wherein $X^1$ is trifluoromethyl, $X^2$ is a hydrogen atom, and $X^3$ is phenyl].

G¹-XXIII: G¹-13 [wherein $X^1$ is a halogen atom, and $X^2$ and $X^4$ are hydrogen atoms].

G¹-XXIV: G¹-20 [wherein $X^1$ is trifluoromethyl, and $X^2$ is a hydrogen atom].

G¹-XXV: G¹-30 [wherein $X^1$ is trifluoromethyl, and $X^3$ is methyl].

G¹-XXVI: G¹-33 [wherein $X^1$ and $X^3$ are trifluoromethyl].

G¹-XXVII: G¹-44 [wherein $X^1$ is trifluoromethyl, and $R^5$ is $C_1$-$C_4$ alkyl].

G¹-XXVIII: G¹-1 [wherein $X^1$ is $C_1$-$C_4$ alkyl, $C_1$-$C_4$ haloalkyl, $C_3$-$C_6$ cycloalkyl, $C_1$-$C_4$ haloalkylthio, —$NH_2$ or D-3, $X^2$, $X^3$, $X^4$ and $X^5$ are hydrogen atoms, and n is 0].

G¹-XXIX: G¹-2 [wherein $X^1$ is difluoromethyl, and $X^3$, $X^4$ and $X^5$ are hydrogen atoms].

G¹-XXX: G¹-3 [wherein $X^1$ is methyl, and $X^2$, $X^3$ and $X^4$ are hydrogen atoms].

G¹-XXXI: G¹-5 [wherein $X^1$ is trifluoromethyl, and $X^4$ and $X^5$ are hydrogen atoms].

G¹-XXXII: G¹-7 [wherein $X^1$ is a halogen atom or methyl, and $X^3$ and $X^4$ are hydrogen atoms].

G¹-XXXIII: G¹-8 [wherein $X^1$ is trifluoromethyl, and $X^3$ and $X^4$ are hydrogen atoms].

G¹-XXXIV: G¹-9 and G¹-12 [wherein $X^1$ is difluoromethyl, and $X^2$ and $X^3$ are hydrogen atoms].

G¹-XXXV: G¹-10 and G¹-13 [wherein $X^1$ is difluoromethyl or trifluoromethyl, and $X^2$ and $X^4$ are hydrogen atoms].

G¹-XXXVI: G¹-11 [wherein $X^1$ is difluoromethyl, and $X^3$ and $X^4$ are hydrogen atoms].

G¹-XXXVII: G¹-16 [wherein $X^1$ is difluoromethyl or trifluoromethyl, $X^2$ and $X^4$ are hydrogen atoms, and $R^5$ is $C_1$-$C_4$ alkyl].

G¹-XXXVIII: G¹-19 and G¹-23 [wherein $X^1$ is difluoromethyl or trifluoromethyl, and $X^2$ is a hydrogen atom].

G¹-XXXIX: G¹-27 [wherein $X^1$ is a halogen atom, $C_1$-$C_4$ alkyl, $C_2$-$C_4$ haloalkyl or $C_1$-$C_4$ alkoxy, $X^2$ is a hydrogen atom, a fluorine atom or a chlorine atom, and $R^5$ is $C_1$-$C_4$ alkyl].

G¹-XL: G¹-27 [wherein $X^1$ is $C_1$-$C_4$ alkyl or $C_1$-$C_4$ haloalkyl, $X^2$ is a hydrogen atom, and $R^5$ is $C_1$-$C_4$ alkyl, $C_1$-$C_4$ haloalkyl or $C_3$-$C_6$ cycloalkyl].

G¹-XLI: G¹-31 [wherein $X^1$ is trifluoromethyl, and $X^3$ is a halogen atom or methyl].

G¹-XLII: G¹-32 [wherein $X^1$ is a halogen atom, difluoromethyl or trifluoromethyl, and $X^3$ is a hydrogen atom or methyl].

G¹-XLIII: G¹-33 [wherein $X^1$ is a halogen atom, methyl, difluoromethyl or trifluoromethyl, and $X^3$ is a hydrogen atom, a halogen atom, $C_1$-$C_4$ alkyl, $C_1$-$C_4$ haloalkyl, $C_3$-$C_6$ cycloalkyl, $C_1$-$C_4$ alkoxy or —$NH_2$].

G¹-XLIV: G¹-41 and G¹-43 [wherein $X^1$ is trifluoromethyl].

G¹-XLV: G¹-45, G¹-46, G¹-49 and G¹-51 [wherein $X^1$ is methyl or trifluoromethyl].

G¹-XLVI: G¹-50 [wherein $X^1$ is methyl or trifluoromethyl, and r is an integer of from 0 to 2].

Among them, as the scope of the substituent represented by G¹, more preferred are G¹-I to G¹-XVI, G¹-XXIX, G¹-XXX, G¹-XXXII to G¹-XXXVII and G¹-XLII, particularly preferred are G¹-I to G¹-X.

As the preferred range of the substituent represented by G² in the compounds which fall within the present invention, the following sets may, for example, be mentioned.

G²-I: G²-1 [wherein $Y^1$ is a halogen atom, $Y^2$ is a hydrogen atom, $Y^3$ is a halogen atom or methyl, and $Y^4$ and $Y^5$ are hydrogen atoms].

G²-II: G²-2 [wherein $Y^1$ is a halogen atom, $Y^2$ is a hydrogen atom or a halogen atom, $Y^3$ is a halogen atom, cyano, trifluoromethyl, $C_1$-$C_4$ haloalkoxy, —$C(R^{10})$=$NOR^{11}$, $C_2$-$C_6$ alkynyl, cyclopropylethynyl, trimethylsilylethynyl or phenylethynyl, $Y^4$ is a hydrogen atom or a halogen atom, $R^{10}$ is methyl, and $R^{11}$ is methyl or ethyl].

G²-III: G²-1 [wherein $Y^1$ and $Y^2$ are hydrogen atoms, $Y^3$ is a halogen atom or methyl, and $Y^4$ and $Y^5$ are hydrogen atoms].

G²-IV: G²-1 [wherein $Y^1$ is a hydrogen atom, $Y^2$ and $Y^3$ together may form —CH=CHCH=CH— to form a 6-membered ring together with the carbon atoms attached to $Y^2$ and $Y^3$, and $Y^4$ and $Y^5$ are hydrogen atoms].

G²-V: G²-1 [wherein $Y^1$ is a halogen atom, methyl, trifluoromethyl or methoxy, $Y^2$ is a hydrogen atom or a halogen atom, $Y^3$ is a hydrogen atom, a halogen atom, methyl, trifluoromethyl, $C_1$-$C_4$ alkoxy, —$C(R^{10})$=$NOR^{11}$, $C_2$-$C_4$ alkenyl, phenyl or D-7, $Y^4$ is a hydrogen atom or a halogen atom, $Y^5$ is a hydrogen atom or a halogen atom, Z is trifluoromethyl, $R^{10}$ is methyl, $R^{11}$ is methyl or ethyl, and n is 1].

G²-VI: G²-2 [wherein $Y^1$ is a halogen atom, $Y^2$ is a hydrogen atom, $Y^3$ is methyl, $C_1$-$C_4$ alkoxy, $C_2$-$C_4$ alkenyl, ($C_2$-$C_6$)alkynyl substituted with $R^6$, D-3 or D-7, $Y^4$ is a hydrogen atom, $R^6$ is a halogen atom, $C_3$-$C_6$ cycloalkyl, —OH, trimethylsilyl or phenyl, and n is 0].

G²-VII: G²-2 [wherein $Y^1$ is a halogen atom, $Y^2$ is cyano, $Y^3$ is a halogen atom, and $Y^4$ is a hydrogen atom].

G²-VIII: G²-6 [wherein $Y^1$ and $Y^3$ are halogen atoms, and $Y^4$ is a hydrogen atom].

G²-IX: G²-9 [wherein $Y^1$ is a halogen atom, $Y^2$ is a hydrogen atom or a halogen atom, and $Y^3$ is a halogen atom].

G²-X: G²-10 [wherein $Y^1$ is a halogen atom, $Y^3$ is a hydrogen atom or a halogen atom, and $Y^4$ is a hydrogen atom].

G²-XI: G²-1 [wherein $Y^1$ and $Y^2$ are hydrogen atoms, $Y^3$ is $C_2$-$C_4$ alkyl, $C_1$-$C_4$ haloalkyl, $C_1$-$C_4$ haloalkoxy, phenoxy or phenyl, and $Y^4$ and $Y^5$ are hydrogen atoms].

G²-XII: G²-1 [wherein $Y^1$ is a hydrogen atom, $Y^2$ is a halogen atom or $C_1$-$C_4$ alkoxy, $Y^3$ is a hydrogen atom or a halogen atom, $Y^4$ is a hydrogen atom, a halogen atom or trifluoromethyl, and $Y^5$ is a hydrogen atom].

G²-XIII: G²-1 [wherein $Y^1$ is a halogen atom, E-9 or —C($R^{10}$)=N$OR^{11}$, $Y^2$ is a hydrogen atom, or $Y^2$ may form, together with $Y^1$, —CH=CHCH=CH— to form a 6-membered ring together with the carbon atoms attached to $Y^1$ and $Y^2$, $Y^3$ is a hydrogen atom, a halogen atom, cyano, $C_1$-$C_4$ alkylthio, $C_1$-$C_4$ alkylsulfinyl, $C_1$-$C_4$ alkylsulfonyl, —C(O)$R^{10}$, M-7, phenyl substituted with $(Z)_m$, D-3 or D-7, $Y^4$ is a hydrogen atom or trifluoromethyl, $Y^5$ is a hydrogen atom, Z is trifluoromethoxy, $R^{10}$ is a hydrogen atom or $C_1$-$C_4$ alkyl, $R^{11}$ is $C_1$-$C_4$ alkyl, $R^{17}$ is methyl, m is 1, n is 0, and p is an integer of from 0 to 2.

G²-XIV: G²-2 [wherein $Y^1$ is a hydrogen atom, a halogen atom, trifluoromethyl or methoxy, $Y^2$ is a hydrogen atom, $Y^3$ is a halogen atom, $C_1$-$C_4$ haloalkyl, $C_1$-$C_4$ alkoxymethyl, —$OR^7$ or D-22, $Y^4$ is a hydrogen atom or methoxy, $R^7$ is phenyl or phenyl substituted with $(Z)_m$, Z is a halogen atom, m is 1, and n is 0].

G²-XV: G²-3 [wherein $Y^1$ is a halogen atom, each of $Y^3$ and $Y^4$ is independently a hydrogen atom or a halogen atom, and $Y^5$ is a hydrogen atom].

G²-XVI: G²-11 [wherein $Y^1$ is a halogen atom, $Y^2$ is $C_1$-$C_4$ alkoxy, and $R^5$ is methyl].

G²-XVII: G²-12 [wherein $Y^1$ is trifluoromethyl, $Y^4$ is a hydrogen atom, and $R^5$ is methyl].

G²-XVIII: G²-17 [wherein $Y^1$ and $Y^3$ are halogen atoms].

G²-XIX: G²-1 [wherein $Y^1$ is a hydrogen atom, $Y^2$ is a hydrogen atom, a halogen atom, methyl, trifluoromethyl, $C_1$-$C_4$ alkoxy, $C_1$-$C_4$ haloalkoxy or phenoxy, $Y^3$ is a hydrogen atom, a halogen atom, cyano, nitro, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy or $C_1$-$C_4$ haloalkylthio, or $Y^3$ may form, together with $Y^2$, —OCH$_2$O—, —OCH$_2$CH$_2$O— or —CH=CHCH=CH— to form a 5-membered ring or a 6-membered ring together with the carbon atoms attached to $Y^2$ and $Y^3$, wherein hydrogen atoms on the respective ring-constituting carbon atoms may optionally be substituted with a halogen atom or methyl, $Y^4$ is a hydrogen atom, a halogen atom, methyl or trifluoromethyl, and $Y^5$ is a hydrogen atom].

G²-XX: G²-1 [wherein $Y^1$ is a halogen atom, methyl or trifluoromethyl, $Y^2$ is a hydrogen atom, $Y^3$ is cyano, nitro, —$OR^7$, —S(O)$_r$$R^7$, —C($R^{10}$)=N$OR^{11}$, —C(O)NH$_2$, —C(S)NH$_2$, $C_2$-$C_6$ alkynyl or ($C_2$-$C_6$)alkynyl substituted with $R^6$, $Y^4$ and $Y^5$ are hydrogen atoms, $R^6$ is a halogen atom, $C_3$-$C_6$ cycloalkyl, —OH, $C_1$-$C_3$ alkoxy, $C_1$-$C_3$ alkylthio, $C_1$-$C_3$ alkylsulfinyl, $C_1$-$C_3$ alkylsulfonyl or —Si($R^{14a}$)($R^{14b}$)$R^{14}$, $R^7$ is $C_1$-$C_4$ haloalkyl, $C_2$-$C_4$ haloalkenyl, $C_3$-$C_4$ haloalkynyl, phenyl or phenyl substituted with $(Z)_m$, $R^{10}$ is a hydrogen atom or $C_1$-$C_4$ alkyl, $R^{11}$ is $C_1$-$C_4$ alkyl, $R^{14}$ is $C_1$-$C_4$ alkyl or phenyl, each of $R^{14a}$ and $R^{14b}$ is independently $C_1$-$C_4$ alkyl, Z is a halogen atom, m is 1, and r is an integer of from 0 to 2].

G²-XXI: G²-1 [wherein $Y^1$ is a halogen atom, $C_1$-$C_4$ alkyl, $C_1$-$C_4$ haloalkyl, $C_1$-$C_4$ alkoxymethyl, $C_1$-$C_4$ alkoxy, $C_1$-$C_4$ haloalkoxy, phenoxy or $C_1$-$C_4$ alkylthio, $Y^2$ is a hydrogen atom, methyl or methoxy, or $Y^2$ may form, together with $Y^1$, —OCH$_2$O— or —OCH$_2$CH$_2$O—, to form a 5-membered ring or a 6-membered ring together with the carbon atoms attached to $Y^1$ and $Y^2$, wherein hydrogen atoms on the respective ring-constituting carbon atoms may optionally be substituted with a halogen atom or methyl, $Y^3$ is a hydrogen atom, a halogen atom, cyano, nitro, methyl or trifluoromethyl, or $Y^3$ may form, together with $Y^2$, —OCH$_2$O— or —OCH$_2$CH$_2$O— to form a 5-membered ring or a 6-membered ring together with the carbon atoms attached to $Y^2$ and $Y^3$, wherein hydrogen atoms on the respective ring-constituting carbon atoms may optionally be substituted with a halogen atom or methyl, and $Y^4$ and $Y^5$ are hydrogen atoms].

G²-XXII: G²-1 [wherein $Y^1$ is a halogen atom, methyl or methoxy, $Y^2$ is a hydrogen atom, $Y^3$ is a hydrogen atom, a halogen atom, methyl or trifluoromethyl, $Y^4$ is a halogen atom, methyl or methoxy, or $Y^4$ may form, together with $Y^3$, —OCH$_2$O— or —OCH$_2$CH$_2$O—, to form a 5-membered ring or a 6-membered ring together with the carbon atoms attached to $Y^3$ and $Y^4$, wherein hydrogen atoms on the respective ring-constituting carbon atoms may optionally be substituted with a halogen atom or methyl, and $Y^5$ is a hydrogen atom].

G²-XXIII: G²-1 [wherein $Y^1$ is a halogen atom, methyl or trifluoromethyl, $Y^2$ is a hydrogen atom or a halogen atom, $Y^3$ is a hydrogen atom, a halogen atom, $C_1$-$C_4$ alkyl, trifluoromethyl or methoxy, $Y^4$ is a hydrogen atom, and $Y^5$ is a halogen atom or methyl].

G²-XXIV: G²-2 [wherein $Y^1$ is cyano, nitro, difluoromethoxy, trifluoromethoxy or methylthio, $Y^2$ is a hydrogen atom, $Y^3$ is a halogen atom, $C_1$-$C_4$ alkyl or trifluoromethyl, and $Y^4$ is a hydrogen atom].

G²-XXV: G²-2 [wherein $Y^1$ is a halogen atom, methyl or trifluoromethyl, $Y^2$ is cyano, methyl, $C_1$-$C_4$ alkoxy, $C_1$-$C_4$ haloalkoxy or $C_1$-$C_4$ alkylthio, $Y^3$ is a halogen atom, methyl or trifluoromethyl, and $Y^4$ is a hydrogen atom].

G²-XXVI: G²-2 [wherein $Y^1$ is a halogen atom, methyl or trifluoromethyl, $Y^2$ is a hydrogen atom, $Y^3$ is a halogen atom, cyano, nitro, methyl, difluoromethyl, trifluoromethyl, $C_1$-$C_4$ alkoxy, $C_1$-$C_4$ haloalkoxy, $C_1$-$C_4$ alkylthio, —N($R^9$)$R^8$, —C($R^{10}$)=N$OR^{11}$, M-3, —C(O)NH$_2$, —C(S)NH$_2$, —SO$_2$N(CH$_3$)$_2$, $C_2$-$C_6$ alkynyl, ($C_2$-$C_6$)alkynyl substituted with $R^6$, D-11, D-28 or D-29, $Y^4$ is a hydrogen atom, $R^6$ is a halogen atom, $C_3$-$C_6$ cycloalkyl, hydroxy($C_3$-$C_6$)cycloalkyl, $C_3$-$C_4$ alkenyl, $C_5$-$C_6$ cycloalkenyl, —OH, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, —Si($R^{14a}$)($R^{14b}$)$R^{14}$, phenyl, phenyl substituted with $(Z)_m$, D-1, D-2, D-4, D-12 or D-32, $R^8$ and $R^9$ together may form a $C_4$-$C_5$ alkylene chain to form a 5- to 6-membered ring together with the nitrogen atom attached to $R^8$ and $R^9$, wherein the alkylene chain may contain an oxygen atom or sulfur atom, $R^{10}$ is a hydrogen atom or $C_1$-$C_4$ alkyl, $R^{11}$ is $C_1$-$C_4$ alkyl, $R^{14}$ is $C_1$-$C_4$ alkyl or phenyl, each of $R^{14a}$ and $R^{14b}$ is independently a $C_1$-$C_4$ alkyl, $R^{17}$ is $C_1$-$C_4$ alkyl, Z is a halogen atom or $C_1$-$C_4$ alkyl, m is an integer of 1 or 2, n is 0, and p is an integer of from 0 to 2].

G²-XXVII: G²-3 [wherein $Y^1$ is a halogen atom or methyl, $Y^3$ is a halogen atom, methyl, trifluoromethyl or methoxy, $Y^4$ is a halogen atom or cyano, and $Y^5$ is a hydrogen atom].

G²-XXVIII: G²-4 [wherein $Y^1$ is a halogen atom or methyl, $Y^2$ is a hydrogen atom, $Y^3$ is a halogen atom or methoxy, and $Y^5$ is a hydrogen atom].

G²-XXIX: G²-5 [wherein $Y^1$ is a halogen atom, methyl, difluoromethyl or trifluoromethyl, $Y^2$ is a hydrogen atom, and $Y^3$ is a halogen atom, methyl, trifluoromethyl or methoxy].

G²-XXX: G²-6 [wherein each of $Y^1$ and $Y^3$ is independently a halogen atom or methyl, and $Y^4$ is a hydrogen atom or methyl].

G²-XXXI: G²-7 [wherein Y¹, Y² and Y³ are halogen atoms].

G²-XXXII: G²-9 [wherein Y¹ is a halogen atom or methyl, Y² is a hydrogen atom, a halogen atom or methyl, Y³ is a halogen atom, or Y³ may form, together with Y², —CH=CHCH=CH— to form a 6-membered ring together with the carbon atoms attached to Y² and Y³, wherein hydrogen atoms on the respective ring-constituting carbon atoms may optionally be substituted with a halogen atom].

G²-XXXIII: G²-10 [wherein Y¹ is methyl, Y³ is a hydrogen atom, a halogen atom or methyl, and Y⁴ is a hydrogen atom].

G²-XXXIV: G²-10 [wherein Y¹ is a hydrogen atom or a halogen atom, Y³ is a halogen atom, Y⁴ is a halogen atom, or Y⁴ may form, together with Y³, —CH₂CH₂CH₂CH₂— or —CH=CHCH=CH— to form a 6-membered ring together with the carbon atoms attached to Y³ and Y⁴, wherein hydrogen atoms on the respective ring-constituting carbon atoms may optionally be substituted with a halogen atom].

G²-XXXV: G²-14 [wherein Y¹ is methyl, and Y³ is trifluoromethyl].

G²-XXXVI: G²-16 and G²-17 [wherein Y¹ is methyl, and Y³ is a halogen atom or trifluoromethyl].

Among them, as the scope of the substituent represented by G², more preferred are G²-1 to G²-X, G²-XX, G²-XXVIII, G²-XXIX and G²-XXX, particularly preferred are G²-1 and G²-II.

In the compounds which fall within the present invention, the substituent represented by W may be an oxygen atom or a sulfur atom, and W is preferably an oxygen atom.

As the preferred range of the substituent represented by R¹ in the compounds which fall within the present invention, the following sets may, for example, be mentioned.

R¹-I: $C_1$-$C_6$ alkyl, ($C_1$-$C_4$)alkyl substituted with $R^{18}$ [wherein $R^{18}$ is $C_3$-$C_6$ cycloalkyl or trimethylsilyl], $C_3$-$C_6$ cycloalkyl, $C_3$-$C_6$ alkenyl and $C_3$-$C_6$ alkynyl.

R¹-II: $C_1$-$C_4$ haloalkyl, ($C_1$-$C_4$)alkyl substituted with $R^{18}$ [wherein $R^{18}$ is phenyl, phenyl substituted with $(Z)_m$ or D-32, Z is a halogen atom, cyano, nitro, methyl, trifluoromethyl or trifluoromethoxy, when m is an integer of at least 2, the respective Z's may be identical with or different from one another, m is an integer of from 1 to 3, and n is 1], and $C_3$-$C_4$ haloalkenyl.

R¹-III: ($C_1$-$C_4$)alkyl substituted with $R^{18}$ [wherein $R^{18}$ is cyano, E-5, $C_1$-$C_4$ alkoxy, $C_1$-$C_4$ alkylthio, —$C(R^{32})$=$NOR^{33}$, D-5 or D-10, $R^{32}$ is methyl, $R^{33}$ is methyl or ethyl, Z is a halogen atom or methyl, n is an integer of 0 or 1, and p is 0], and phenyl.

R¹-IV: ($C_1$-$C_4$)alkyl substituted with $R^{18}$ [wherein $R^{18}$ is phenyl substituted with $(Z)_m$ or D-32, Z is a halogen atom, $C_1$-$C_4$ alkyl, methoxy, trifluoromethylthio or phenyl, when m and n are 2, the two Z's may be identical with or different from each other, and when there are two neighboring Z's, the two neighboring Z's may form —CH=CH—CH=CH— to form a 6-membered ring together with the carbon atoms attached to the Z's, m is an integer of 1 or 2, and n is an integer of from 0 to 2].

R¹-V: ($C_1$-$C_4$)alkyl substituted with $R^{18}$ [wherein $R^{18}$ is E-9, —$C(R^{32})$=$NOR^{33}$, M-4, $C_1$-$C_4$ alkoxycarbonyl, $C_1$-$C_4$ haloalkylaminocarbonyl or D-1, $R^{32}$ is a hydrogen atom or $C_1$-$C_4$ alkyl, $R^{33}$ is $C_1$-$C_4$ alkyl, Z is methyl or trifluoromethyl, n is 1, and p is 0], E-2 [wherein p is 0] and E-14 [wherein p is 0].

R¹-VI: $C_3$-$C_6$ halocycloalkyl and $C_3$-$C_4$ haloalkynyl.

R¹-VII: E-3 [wherein p is 0, and r is an integer of from 0 to 2], E-4 [wherein $R^{16}$ is —$C(O)R^{10}$ or —$C(O)OR^{11}$, $R^{10}$ is a hydrogen atom, $C_1$-$C_4$ alkyl or cyclopropyl, $R^{11}$ is $C_1$-$C_4$ alkyl or $C_1$-$C_4$ haloalkyl, and p is 0], E-5 [wherein p is 0], E-6 [wherein p is 0, and r is an integer of from 0 to 2], E-8 [wherein $R^{16}$ is —$C(O)R^{10}$ or —$C(O)OR^{11}$, $R^{10}$ is a hydrogen atom, $C_1$-$C_4$ alkyl or cyclopropyl, $R^{11}$ is $C_1$-$C_4$ alkyl or $C_1$-$C_4$ haloalkyl, and p is 0], E-15 [wherein p is 0, and r is an integer of from 0 to 2], and E-17 [wherein $R^{16}$ is —$C(O)R^{10}$ or —$C(O)OR^{11}$, $R^{10}$ is a hydrogen atom, $C_1$-$C_4$ alkyl or cyclopropyl, $R^{11}$ is $C_1$-$C_4$ alkyl or $C_1$-$C_4$ haloalkyl, and p is 0].

R¹-VIII: ($C_1$-$C_4$)alkyl optionally substituted with $R^{18}$ [wherein $R^{18}$ is a halogen atom, $C_3$-$C_6$ halocycloalkyl, $C_1$-$C_4$ alkoxy, $C_1$-$C_4$ haloalkoxy or $C_1$-$C_4$ alkylthio].

R¹-IX: ($C_1$-$C_4$)alkyl optionally substituted with $R^{18}$ [wherein $R^{18}$ is a halogen atom, E-2 to E-4, E-6, E-8, M-3, —$C(R^{32})$=$NOR^{33}$, —$C(O)NH_2$ or —$C(S)NH_2$, $R^{16}$ is —$C(O)R^{10}$ or —$C(O)OR^{11}$, $R^{10}$ is a hydrogen atom, $C_1$-$C_4$ alkyl or cyclopropyl, $R^{11}$ is $C_1$-$C_4$ alkyl or $C_1$-$C_4$ haloalkyl, $R^{17}$ is $C_1$-$C_4$ alkyl, $R^{32}$ is a hydrogen atom or methyl, $R^{33}$ is $C_1$-$C_4$ alkyl or $C_1$-$C_4$ haloalkyl, p is an integer of from 0 to 2, and r is an integer of from 0 to 2].

R¹-X: ($C_1$-$C_4$)alkyl optionally substituted with $R^{18}$ [wherein $R^{18}$ is a halogen atom, phenyl substituted with $(Z)_m$, D-2, D-4, D-6, D-8, D-9, D-12, D-14, D-15 or D-17, $R^{15}$ is methyl, Z is a halogen atom, methyl, ethyl, trifluoromethyl, difluoromethoxy, methylthio, methylsulfinyl, methylsulfonyl, trifluoromethylsulfinyl or trifluoromethylsulfony, when m and n are 2, the respective Z's may be identical with or different from each other, m is an integer of 1 or 2, and n is an integer of from 0 to 2].

Among them, as the scope of the substituent represented by R¹, more preferred are R¹-I to R¹-IV, particularly preferred are R¹-I and R¹-II.

As the preferred range of the substituent represented by R² in the compounds which fall within the present invention, the following sets may, for example, be mentioned.

R²-I: A hydrogen atom.
R²-II: Methyl
R²-III Ethyl.
R²-IV: $C_3$-$C_4$ alkyl and phenyl.
R²-V: Fluoromethyl and trifluoromethyl.
R²-VI: Methoxymethyl, methylthiomethyl, methylsulfinylmethyl and methylsulfonylmethyl.
R²-VII: Cyclopropyl and cyclobutyl.

Among them, as the scope of the substituted represented by R², more preferred are R²-I to R²-III and R²-V, particularly preferred are R²-I and R²-II.

As the scope of the substituent represented by R³ in the compounds which fall within the present invention, the following sets may, for example, be mentioned.

R³-1: A hydrogen atom.
R³-II: Methyl.
R³-III: R³ forms a cyclopropyl ring together with R².
R³-IV: R³ forms, together with R², a $C_3$-$C_5$ alkylene chain to form a 4- to 6-membered ring together with the carbon atom attached to R² and R³.
R³-V: $C_2$-$C_4$ alkyl.
R³-VI: R³ form, together with R², a $C_2$-$C_5$ alkylene chain to form a 3- to 6-membered ring together with the carbon atom attached to R² and R³, wherein the alkylene chain contains an oxygen atom or sulfur atom.

Among them, as the scope of the substituent represented by R³, more preferred are R³-I to R³-III, and particularly preferred is R³-I.

As the scope of the substituent represented by R⁴ in the compounds which fall within the present invention, the following sets may, for example, be mentioned.

R⁴-I: A hydrogen atom.
R⁴-II: $C_1$-$C_4$ alkylcarbonyl.
R⁴-III: $C_1$-$C_4$ alkoxycarbonyl.
R⁴-IV: $C_1$-$C_4$ haloalkylthio.
R⁴-V: $C_1$-$C_4$ alkyl, ($C_1$-$C_2$)alkyl substituted with $R^{19}$ [wherein $R^{19}$ is cyano or $C_1$-$C_4$ alkoxy], cyclopropyl, allyl and propargyl.
R⁴-VI: $C_3$-$C_6$ cycloalkyl, $C_2$-$C_4$ alkenyl and $C_2$-$C_4$ alkynyl.
R⁴-VII: ($C_1$-$C_2$)alkyl substituted with $R^{19}$ [wherein $R^{19}$ is —$OR^{36}$, —C(O)$NH_2$ or —C(S)$NH_2$, $R^{36}$ is $C_2$-$C_4$ haloalkyl, $C_1$-$C_4$ alkylcarbonyl, $C_3$-$C_6$ cycloalkylcarbonyl or $C_1$-$C_4$ alkoxycarbonyl].
R⁴-VIII: —C(O)$R^{20}$ [wherein $R^{20}$ is $C_1$-$C_4$ alkoxymethyl, $C_1$-$C_4$ alkylthiomethyl, $C_1$-$C_4$ alkylsulfonylmethyl, $C_3$-$C_4$ cycloalkyl or $C_2$-$C_4$ alkenyl].
R⁴-IX: —C(O)$OR^{21}$ [wherein $R^{21}$ is $C_1$-$C_4$ haloalkyl, $C_1$-$C_4$ alkoxy($C_1$-$C_2$)alkyl, allyl or propargyl].
R⁴-X: $C_1$-$C_4$ alkoxy.

Among them, as the scope of the substituent represented by $R^4$, more preferred are R⁴-I to R⁴-IV, particularly preferred is R⁴-I.

The sets indicating the preferred range of each substituent in the compounds which fall within the present invention may be combined arbitrarily to indicate the preferred range of the compounds of the present invention.

The preferred range of $G^1$, $G^2$, $R^1$ and $R^2$ of the compound represented by the formula (I) may be combined, for example, as shown in Table 1. The combinations shown in Table 1 merely exemplify the present invention, and the compound of the present invention represented by the formula (I) is by no means restricted thereto.

TABLE 1

| $G^1$ | $R^2$ | $G^2$ | $R^1$ |
|---|---|---|---|
| $G^1$-I | $R^2$-I | $G^2$-I | $R^1$-I |
| $G^1$-I | $R^2$-II | $G^2$-I | $R^1$-I |
| $G^1$-I | $R^2$-III | $G^2$-I | $R^1$-I |
| $G^1$-I | $R^2$-V | $G^2$-I | $R^1$-I |
| $G^1$-I | $R^2$-VI | $G^2$-I | $R^1$-I |
| $G^1$-I | $R^2$-VII | $G^2$-I | $R^1$-I |
| $G^1$-I | $R^2$-II | $G^2$-I | $R^1$-II |
| $G^1$-I | $R^2$-V | $G^2$-I | $R^1$-II |
| $G^1$-I | $R^2$-II | $G^2$-I | $R^1$-III |
| $G^1$-I | $R^2$-II | $G^2$-I | $R^1$-V |
| $G^1$-I | $R^2$-I | $G^2$-II | $R^1$-I |
| $G^1$-I | $R^2$-II | $G^2$-II | $R^1$-I |
| $G^1$-I | $R^2$-III | $G^2$-II | $R^1$-I |
| $G^1$-I | $R^2$-IV | $G^2$-II | $R^1$-I |
| $G^1$-I | $R^2$-V | $G^2$-II | $R^1$-I |
| $G^1$-I | $R^2$-VI | $G^2$-II | $R^1$-I |
| $G^1$-I | $R^2$-VII | $G^2$-II | $R^1$-I |
| $G^1$-I | $R^2$-I | $G^2$-II | $R^1$-II |
| $G^1$-I | $R^2$-II | $G^2$-II | $R^1$-II |
| $G^1$-I | $R^2$-V | $G^2$-II | $R^1$-II |
| $G^1$-I | $R^2$-I | $G^2$-II | $R^1$-III |
| $G^1$-I | $R^2$-I | $G^2$-II | $R^1$-IV |
| $G^1$-I | $R^2$-I | $G^2$-II | $R^1$-V |
| $G^1$-I | $R^2$-I | $G^2$-II | $R^1$-VI |
| $G^1$-I | $R^2$-II | $G^2$-II | $R^1$-VI |
| $G^1$-I | $R^2$-I | $G^2$-II | $R^1$-VII |
| $G^1$-I | $R^2$-I | $G^2$-II | $R^1$-VIII |
| $G^1$-I | $R^2$-II | $G^2$-II | $R^1$-VIII |
| $G^1$-I | $R^2$-I | $G^2$-II | $R^1$-IX |
| $G^1$-I | $R^2$-I | $G^2$-II | $R^1$-X |
| $G^1$-I | $R^2$-II | $G^2$-III | $R^1$-I |
| $G^1$-I | $R^2$-II | $G^2$-III | $R^1$-II |
| $G^1$-I | $R^2$-II | $G^2$-IV | $R^1$-I |
| $G^1$-I | $R^2$-II | $G^2$-IV | $R^1$-II |
| $G^1$-I | $R^2$-II | $G^2$-V | $R^1$-I |
| $G^1$-I | $R^2$-II | $G^2$-V | $R^1$-II |
| $G^1$-I | $R^2$-I | $G^2$-VI | $R^1$-I |
| $G^1$-I | $R^2$-II | $G^2$-VI | $R^1$-I |
| $G^1$-I | $R^2$-I | $G^2$-VI | $R^1$-II |
| $G^1$-I | $R^2$-II | $G^2$-VI | $R^1$-II |
| $G^1$-I | $R^2$-I | $G^2$-VII | $R^1$-I |
| $G^1$-I | $R^2$-I | $G^2$-VII | $R^1$-II |
| $G^1$-I | $R^2$-I | $G^2$-VIII | $R^1$-I |
| $G^1$-I | $R^2$-II | $G^2$-VIII | $R^1$-I |
| $G^1$-I | $R^2$-I | $G^2$-VIII | $R^1$-II |
| $G^1$-I | $R^2$-II | $G^2$-VIII | $R^1$-II |
| $G^1$-I | $R^2$-I | $G^2$-IX | $R^1$-I |
| $G^1$-I | $R^2$-II | $G^2$-IX | $R^1$-I |
| $G^1$-I | $R^2$-I | $G^2$-IX | $R^1$-II |
| $G^1$-I | $R^2$-II | $G^2$-IX | $R^1$-II |
| $G^1$-I | $R^2$-II | $G^2$-X | $R^1$-I |
| $G^1$-I | $R^2$-II | $G^2$-X | $R^1$-II |
| $G^1$-I | $R^2$-II | $G^2$-XI | $R^1$-I |
| $G^1$-I | $R^2$-II | $G^2$-XI | $R^1$-II |
| $G^1$-I | $R^2$-II | $G^2$-XII | $R^1$-I |
| $G^1$-I | $R^2$-II | $G^2$-XII | $R^1$-II |
| $G^1$-I | $R^2$-II | $G^2$-XIII | $R^1$-I |
| $G^1$-I | $R^2$-I | $G^2$-XIV | $R^1$-I |
| $G^1$-I | $R^2$-I | $G^2$-XV | $R^1$-I |
| $G^1$-I | $R^2$-II | $G^2$-XV | $R^1$-I |
| $G^1$-I | $R^2$-I | $G^2$-XV | $R^1$-II |
| $G^1$-I | $R^2$-II | $G^2$-XVI | $R^1$-I |
| $G^1$-I | $R^2$-II | $G^2$-XVII | $R^1$-I |
| $G^1$-I | $R^2$-I | $G^2$-XVIII | $R^1$-I |
| $G^1$-I | $R^2$-II | $G^2$-XIX | $R^1$-I |
| $G^1$-I | $R^2$-II | $G^2$-XX | $R^1$-I |
| $G^1$-I | $R^2$-II | $G^2$-XXI | $R^1$-I |
| $G^1$-I | $R^2$-II | $G^2$-XXII | $R^1$-I |
| $G^1$-I | $R^2$-II | $G^2$-XXIII | $R^1$-I |
| $G^1$-I | $R^2$-I | $G^2$-XXIV | $R^1$-I |
| $G^1$-I | $R^2$-I | $G^2$-XXV | $R^1$-I |
| $G^1$-I | $R^2$-I | $G^2$-XXVI | $R^1$-I |
| $G^1$-I | $R^2$-II | $G^2$-XXVI | $R^1$-I |
| $G^1$-I | $R^2$-I | $G^2$-XXVI | $R^1$-II |
| $G^1$-I | $R^2$-II | $G^2$-XXVI | $R^1$-II |
| $G^1$-I | $R^2$-I | $G^2$-XXVII | $R^1$-I |
| $G^1$-I | $R^2$-II | $G^2$-XXVII | $R^1$-I |
| $G^1$-I | $R^2$-I | $G^2$-XXVIII | $R^1$-I |
| $G^1$-I | $R^2$-II | $G^2$-XXVIII | $R^1$-I |
| $G^1$-I | $R^2$-I | $G^2$-XXIX | $R^1$-I |
| $G^1$-I | $R^2$-II | $G^2$-XXIX | $R^1$-I |
| $G^1$-I | $R^2$-I | $G^2$-XXIX | $R^1$-II |
| $G^1$-I | $R^2$-II | $G^2$-XXIX | $R^1$-II |
| $G^1$-I | $R^2$-I | $G^2$-XXX | $R^1$-I |
| $G^1$-I | $R^2$-II | $G^2$-XXX | $R^1$-I |
| $G^1$-I | $R^2$-I | $G^2$-XXX | $R^1$-II |
| $G^1$-I | $R^2$-II | $G^2$-XXX | $R^1$-II |
| $G^1$-I | $R^2$-I | $G^2$-XXXI | $R^1$-I |
| $G^1$-I | $R^2$-I | $G^2$-XXXII | $R^1$-I |
| $G^1$-I | $R^2$-II | $G^2$-XXXII | $R^1$-I |
| $G^1$-I | $R^2$-I | $G^2$-XXXIII | $R^1$-I |
| $G^1$-I | $R^2$-II | $G^2$-XXXIII | $R^1$-I |
| $G^1$-I | $R^2$-I | $G^2$-XXXIV | $R^1$-I |
| $G^1$-I | $R^2$-II | $G^2$-XXXIV | $R^1$-I |
| $G^1$-I | $R^2$-I | $G^2$-XXXV | $R^1$-I |
| $G^1$-I | $R^2$-I | $G^2$-XXXVI | $R^1$-I |
| $G^1$-II | $R^2$-I | $G^2$-II | $R^1$-I |
| $G^1$-II | $R^2$-II | $G^2$-II | $R^1$-I |
| $G^1$-II | $R^2$-I | $G^2$-II | $R^1$-II |
| $G^1$-II | $R^2$-II | $G^2$-II | $R^1$-II |
| $G^1$-II | $R^2$-I | $G^2$-XXVI | $R^1$-I |
| $G^1$-III | $R^2$-II | $G^2$-I | $R^1$-I |
| $G^1$-III | $R^2$-II | $G^2$-I | $R^1$-II |
| $G^1$-III | $R^2$-I | $G^2$-II | $R^1$-I |
| $G^1$-III | $R^2$-II | $G^2$-II | $R^1$-I |
| $G^1$-III | $R^2$-I | $G^2$-II | $R^1$-II |
| $G^1$-III | $R^2$-II | $G^2$-II | $R^1$-II |
| $G^1$-III | $R^2$-I | $G^2$-VI | $R^1$-I |
| $G^1$-III | $R^2$-I | $G^2$-VI | $R^1$-II |
| $G^1$-III | $R^2$-I | $G^2$-IX | $R^1$-I |
| $G^1$-III | $R^2$-II | $G^2$-IX | $R^1$-II |
| $G^1$-III | $R^2$-II | $G^2$-XX | $R^1$-I |
| $G^1$-III | $R^2$-I | $G^2$-XXVI | $R^1$-I |
| $G^1$-IV | $R^2$-I | $G^2$-I | $R^1$-I |
| $G^1$-IV | $R^2$-II | $G^2$-I | $R^1$-I |

TABLE 1-continued

| G¹ | R² | G² | R¹ |
|---|---|---|---|
| G¹-IV | R²-II | G²-I | R¹-II |
| G¹-IV | R²-II | G²-II | R¹-I |
| G¹-IV | R²-I | G²-II | R¹-II |
| G¹-IV | R²-II | G²-II | R¹-II |
| G¹-IV | R²-I | G²-VI | R¹-I |
| G¹-IV | R²-I | G²-VI | R¹-II |
| G¹-IV | R²-II | G²-IX | R¹-I |
| G¹-IV | R²-II | G²-IX | R¹-II |
| G¹-IV | R²-II | G²-XX | R¹-I |
| G¹-IV | R²-I | G²-XXVI | R¹-I |
| G¹-V | R²-II | G²-I | R¹-I |
| G¹-V | R²-II | G²-I | R¹-II |
| G¹-V | R²-I | G²-II | R¹-I |
| G¹-V | R²-II | G²-II | R¹-I |
| G¹-V | R²-I | G²-II | R¹-II |
| G¹-V | R²-II | G²-II | R¹-II |
| G¹-V | R²-I | G²-VI | R¹-I |
| G¹-V | R²-I | G²-VI | R¹-II |
| G¹-V | R²-II | G²-IX | R¹-I |
| G¹-V | R²-II | G²-IX | R¹-II |
| G¹-V | R²-II | G²-XX | R¹-I |
| G¹-V | R²-I | G²-XXVI | R¹-I |
| G¹-VI | R²-I | G²-I | R¹-I |
| G¹-VI | R²-II | G²-I | R¹-I |
| G¹-VI | R²-II | G²-I | R¹-II |
| G¹-VI | R²-I | G²-II | R¹-I |
| G¹-VI | R²-II | G²-II | R¹-I |
| G¹-VI | R²-I | G²-II | R¹-II |
| G¹-VI | R²-II | G²-II | R¹-II |
| G¹-VI | R²-I | G²-III | R¹-I |
| G¹-VI | R²-II | G²-III | R¹-II |
| G¹-VI | R²-I | G²-VI | R¹-I |
| G¹-VI | R²-I | G²-VI | R¹-II |
| G¹-VI | R²-II | G²-IX | R¹-I |
| G¹-VI | R²-II | G²-IX | R¹-II |
| G¹-VI | R²-I | G²-XXVI | R¹-I |
| G¹-VII | R²-II | G²-I | R¹-I |
| G¹-VII | R²-II | G²-I | R¹-II |
| G¹-VII | R²-I | G²-II | R¹-I |
| G¹-VII | R²-II | G²-II | R¹-I |
| G¹-VII | R²-I | G²-II | R¹-II |
| G¹-VII | R²-II | G²-II | R¹-II |
| G¹-VII | R²-I | G²-VI | R¹-I |
| G¹-VII | R²-I | G²-VI | R¹-II |
| G¹-VII | R²-II | G²-IX | R¹-I |
| G¹-VII | R²-II | G²-IX | R¹-II |
| G¹-VII | R²-I | G²-XXVI | R¹-I |
| G¹-VIII | R²-II | G²-I | R¹-I |
| G¹-VIII | R²-II | G²-I | R¹-II |
| G¹-VIII | R²-I | G²-II | R¹-I |
| G¹-VIII | R²-II | G²-II | R¹-I |
| G¹-VIII | R²-I | G²-II | R¹-II |
| G¹-VIII | R²-II | G²-II | R¹-II |
| G¹-VIII | R²-I | G²-VI | R¹-I |
| G¹-VIII | R²-I | G²-VI | R¹-II |
| G¹-VIII | R²-II | G²-IX | R¹-I |
| G¹-VIII | R²-II | G²-IX | R¹-II |
| G¹-VIII | R²-II | G²-XX | R¹-I |
| G¹-VIII | R²-I | G²-XXVI | R¹-I |
| G¹-IX | R²-I | G²-I | R¹-I |
| G¹-IX | R²-II | G²-I | R¹-I |
| G¹-IX | R²-II | G²-I | R¹-II |
| G¹-IX | R²-I | G²-II | R¹-I |
| G¹-IX | R²-II | G²-II | R¹-I |
| G¹-IX | R²-I | G²-II | R¹-II |
| G¹-IX | R²-II | G²-II | R¹-II |
| G¹-IX | R²-I | G²-VI | R¹-I |
| G¹-IX | R²-I | G²-VI | R¹-II |
| G¹-IX | R²-II | G²-IX | R¹-I |
| G¹-IX | R²-II | G²-IX | R¹-II |
| G¹-IX | R²-II | G²-XX | R¹-I |
| G¹-IX | R²-I | G²-XXVI | R¹-I |
| G¹-X | R²-II | G²-I | R¹-I |
| G¹-X | R²-II | G²-I | R¹-II |
| G¹-X | R²-I | G²-II | R¹-I |
| G¹-X | R²-II | G²-II | R¹-I |
| G¹-X | R²-I | G²-II | R¹-II |
| G¹-X | R²-II | G²-II | R¹-II |
| G¹-X | R²-I | G²-VI | R¹-I |
| G¹-X | R²-I | G²-VI | R¹-II |
| G¹-X | R²-II | G²-IX | R¹-I |
| G¹-X | R²-II | G²-IX | R¹-II |
| G¹-X | R²-II | G²-XX | R¹-I |
| G¹-X | R²-I | G²-XXVI | R¹-I |
| G¹-XI | R²-I | G²-II | R¹-I |
| G¹-XI | R²-I | G²-II | R¹-II |
| G¹-XII | R²-I | G²-II | R¹-I |
| G¹-XIII | R²-II | G²-I | R¹-I |
| G¹-XIII | R²-I | G²-II | R¹-I |
| G¹-XIII | R²-II | G²-II | R¹-I |
| G¹-XIV | R²-I | G²-II | R¹-I |
| G¹-XV | R²-I | G²-II | R¹-I |
| G¹-XVI | R²-II | G²-I | R¹-I |
| G¹-XVI | R²-I | G²-II | R¹-I |
| G¹-XVII | R²-I | G²-II | R¹-I |
| G¹-XVIII | R²-I | G²-II | R¹-I |
| G¹-XVIII | R²-II | G²-III | R¹-I |
| G¹-XVIII | R²-II | G²-III | R¹-II |
| G¹-XIX | R²-I | G²-II | R¹-I |
| G¹-XX | R²-I | G²-II | R¹-I |
| G¹-XXI | R²-I | G²-II | R¹-I |
| G¹-XXII | R²-I | G²-II | R¹-I |
| G¹-XXIII | R²-II | G²-I | R¹-I |
| G¹-XXIII | R²-II | G²-I | R¹-II |
| G¹-XXIII | R²-I | G²-II | R¹-I |
| G¹-XXIII | R²-II | G²-II | R¹-I |
| G¹-XXIII | R²-I | G²-II | R¹-II |
| G¹-XXIII | R²-II | G²-II | R¹-II |
| G¹-XXIV | R²-I | G²-II | R¹-I |
| G¹-XXV | R²-II | G²-II | R¹-I |
| G¹-XXVI | R²-I | G²-II | R¹-I |
| G¹-XXVII | R²-II | G²-I | R¹-I |
| G¹-XXVII | R²-I | G²-II | R¹-I |
| G¹-XXVIII | R²-I | G²-II | R¹-I |
| G¹-XXIX | R²-II | G²-I | R¹-I |
| G¹-XXIX | R²-II | G²-I | R¹-II |
| G¹-XXIX | R²-I | G²-II | R¹-I |
| G¹-XXIX | R²-II | G²-II | R¹-I |
| G¹-XXIX | R²-I | G²-II | R¹-II |
| G¹-XXIX | R²-II | G²-II | R¹-II |
| G¹-XXIX | R²-I | G²-VI | R¹-I |
| G¹-XXIX | R²-I | G²-VI | R¹-II |
| G¹-XXIX | R²-II | G²-IX | R¹-I |
| G¹-XXIX | R²-II | G²-IX | R¹-II |
| G¹-XXX | R²-II | G²-I | R¹-I |
| G¹-XXX | R²-II | G²-I | R¹-II |
| G¹-XXX | R²-I | G²-II | R¹-I |
| G¹-XXX | R²-II | G²-II | R¹-I |
| G¹-XXX | R²-I | G²-II | R¹-II |
| G¹-XXX | R²-II | G²-II | R¹-II |
| G¹-XXXI | R²-I | G²-II | R¹-I |
| G¹-XXXII | R²-II | G²-I | R¹-I |
| G¹-XXXII | R²-II | G²-I | R¹-II |
| G¹-XXXII | R²-I | G²-II | R¹-I |
| G¹-XXXII | R²-II | G²-II | R¹-I |
| G¹-XXXII | R²-I | G²-II | R¹-II |
| G¹-XXXII | R²-II | G²-II | R¹-II |
| G¹-XXXIII | R²-II | G²-I | R¹-I |
| G¹-XXXIII | R²-II | G²-I | R¹-II |
| G¹-XXXIII | R²-I | G²-II | R¹-I |
| G¹-XXXIII | R²-II | G²-II | R¹-I |
| G¹-XXXIII | R²-I | G²-II | R¹-II |
| G¹-XXXIII | R²-II | G²-II | R¹-II |
| G¹-XXXIV | R²-II | G²-I | R¹-I |
| G¹-XXXIV | R²-II | G²-I | R¹-II |
| G¹-XXXIV | R²-I | G²-II | R¹-I |
| G¹-XXXIV | R²-II | G²-II | R¹-I |
| G¹-XXXIV | R²-I | G²-II | R¹-II |
| G¹-XXXIV | R²-II | G²-II | R¹-II |
| G¹-XXXV | R²-II | G²-I | R¹-I |
| G¹-XXXV | R²-II | G²-I | R¹-II |
| G¹-XXXV | R²-I | G²-II | R¹-I |
| G¹-XXXV | R²-II | G²-II | R¹-I |
| G¹-XXXV | R²-I | G²-II | R¹-II |
| G¹-XXXV | R²-II | G²-II | R¹-II |

TABLE 1-continued

| G¹ | R² | G² | R¹ |
|---|---|---|---|
| G¹-XXXVI | R²-II | G²-I | R¹-I |
| G¹-XXXVI | R²-II | G²-I | R¹-II |
| G¹-XXXVI | R²-I | G²-II | R¹-I |
| G¹-XXXVI | R²-II | G²-II | R¹-I |
| G¹-XXXVI | R²-I | G²-II | R¹-II |
| G¹-XXXVI | R²-II | G²-II | R¹-II |
| G¹-XXXVII | R²-II | G²-I | R¹-I |
| G¹-XXXVII | R²-II | G²-I | R¹-II |
| G¹-XXXVII | R²-I | G²-II | R¹-I |
| G¹-XXXVII | R²-II | G²-II | R¹-I |
| G¹-XXXVII | R²-I | G²-II | R¹-II |
| G¹-XXXVII | R²-II | G²-II | R¹-II |
| G¹-XXXVIII | R²-I | G²-II | R¹-I |
| G¹-XXXIX | R²-I | G²-II | R¹-I |
| G¹-XL | R²-I | G²-II | R¹-I |
| G¹-XLI | R²-II | G²-I | R¹-I |
| G¹-XLI | R²-I | G²-II | R¹-I |
| G¹-XLII | R²-II | G²-I | R¹-I |
| G¹-XLII | R²-II | G²-I | R¹-II |
| G¹-XLII | R²-I | G²-II | R¹-I |
| G¹-XLII | R²-II | G²-II | R¹-I |
| G¹-XLII | R²-I | G²-II | R¹-II |
| G¹-XLII | R²-II | G²-II | R¹-II |
| G¹-XLIII | R²-II | G²-I | R¹-I |
| G¹-XLIII | R²-I | G²-II | R¹-I |
| G¹-XLIII | R²-II | G²-II | R¹-I |
| G¹-XLIV | R²-I | G²-II | R¹-I |
| G¹-XLV | R²-I | G²-II | R¹-I |
| G¹-XLVI | R²-I | G²-II | R¹-I |

Some of the compounds of the present invention represented by the formula (I) can be converted, by ordinary methods, to acid addition salts with hydrogen halides such as hydrofluoric acid, hydrochloric acid, hydrobromic acid and hydroiodic acid, with inorganic acids such as nitric acid, sulfuric acid, phosphoric acid, chloric acid and perchloric acid, with sulfonic acids such as methanesulfonic acid, ethanesulfonic acid, trifluoromethanesulfonic acid, benzenesulfonic acid and p-toluenesulfonic acid, with carboxylic acids such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid, with amino acids such as glutamic acid and aspartic acid.

Some of the compounds of the present invention represented by the formula (I) can be converted, by ordinary methods, to metal salts with alkali metals such as lithium, sodium and potassium, with alkaline earth metals such as calcium, barium and magnesium, with metals such as aluminum.

The pesticides herein mean fungicides and parasiticides for controlling harmful pathogens and parasites which infect/parasitize plants or animals.

Plants herein mean grain, fruits and vegetables, cultivated as food for human, feed crop for livestock and poultry, ornamental plants of which appearances are enjoyed, or Tracheophyta such as planting of parks, streets and the like, and specifically, the following plants may, for example, be mentioned, but the present invention is not restricted thereto.

Plants of the order Pinales belonging to the family Pinaceae such as Japanese Red Pine (*Pinus densiflora*), Scots Pine (*Pinus sylvestris*), Japanese Black Pine (*Pinus thunbergii*), etc.

Plants of the group Magnoliids belonging to the family Piperaceae such as pepper (*Piper nigrum*), etc., the family Lauraceae such as Avocado (*Persea americana*), etc.

Plants of the group monocots belonging to the family Araceae such as Konjac (*Amorphophallus konjac*), Eddoe (*Colocasia esculenta*), etc., the family Dioscoreaceae such as Chinese yam (*Dioscorea batatas*), Japanese yam (*Dioscorea japonica*), etc., the family Alliaceae such as Leek (*Allium ampeloprasum* var. *porrum*), Onion (*Allium cepa*), Rakkyo (*Allium chinense*), Welsh onion (*Allium fistulosum*), Garlic (*Allium sativum*), Chives (*Allium schoenoprasum*), Chive (*Allium schoenoprasum* var. *foliosum*), Oriental garlic (*Allium tuberosum*), Scallion (*Allium×wakegi*), etc., the family Asparagaceae such as Asparagus (*Asparagus officinalis*), etc., the family Arecaceae subfamily Arecoideae such as Coconut palm (*Cocos nucifera*), Oil palm (*Elaeis quineensis*), etc., the family Arecaceae the subfamily Coryphoideae such as Date palm (*Phoenix dactylifera*), etc., the family Bromeliaceae such as Pineapple (*Ananas comosus*), etc., the family Poaceae subfamily Ehrhartoideae such as Rice (*Oryza sativa*), etc., the family Poaceae subfamily Pooideae such as Bent grass (*Agrostis* spp.), Blue grass (*Poa* spp.), Barley (*Hordeum vulgare*), Wheat (*Triticum aestivum, T. durum*), Rye (*Secale cereale*), etc., the family Poaceae subfamily Chloridoideae such as Bermuda grass (*Cynodon dactylon*), Grass (*Zoysia* spp.), etc., the family Poaceae subfamily Panicoideae such as Sugarcane (*Saccharum officinarum*), Sorgum (*Sorghum bicolor*), Corn (*Zea mays*), etc., the family Musaceae such as Banana (*Musa* spp.), etc., the family Zingiberaceae such as Myoga (*Zingiber mioga*), Ginger (*Zingiber officinale*), etc.

Plants of the group eudicots belonging to the family Nelumbonaceae such as Lotus root (*Nelumbo nucifera*), etc., the family Fabaceae such as Peanut (*Arachis hypogaea*), Chickpea (*Cicer arietinum*), Lentil (*Lens culinaris*), Pea (*Pisum sativum*), Broad bean (*Vicia faba*), Soybean (*Glycine max*), Common bean (*Phaseolus vulgaris*), Adzuki bean (*Vigna angularis*), Cowpea (*Vigna unguiculata*), etc., the family Cannabaceae such as Hop (*Humulus lupulus*), etc., the family Moraceae such as Fig Tree (*Ficus carica*), Mulberry (*Morus* spp.), etc., the family Rhamnaceae such as Common jujube (*Ziziphus jujuba*), etc., the family Rosaceae subfamily Rosoideae such as Strawberry (*Fragaria*), Rose (*Rosa* spp.), etc., the family Rosaceae subfamily Maloideae such as Japanese loguat (*Eriobotrya japonica*), Apple (*Malus pumila*), European Pear (*Pyrus communis*), Nashi Pear (*Pyrus pyrifolia* var. *culta*), etc., the family Rosaceae subfamily Prunoideae such as Peach (*Amygdalus persica*), Apricot (*Prunus armeniaca*), Cherry (*Prunus avium*), Prune (*Prunus domestica*), Almond (*Prunus dulcis*), Japanese Apricot (*Prunus mume*), Japanese Plum (*Prunus salicina*), *Cerasus speciosa, Cerasus×yedoensis* 'Somei-yoshino', etc., the family Cucurbitaceae such as Winter melon (*Benincasa hispida*), Watermelon (*Citrullus lanatus*), Bottle gourd (*Lagenaria siceraria* var. *hispida*), Luffa (*Luffa cylindrica*), Pumpkin (*Cucurbita* spp.), Zucchini (*Cucurbita pepo*), Bitter melon (*Momordica charantia* var. *pavel*), Muskmelon (*Cucumis melo*), Oriental pickling melon (*Cucumis melo* var. *conomon*), Oriental melon (*Cucumis melo* var. *makuwa*), Cucumber (*Cucumis sativus*), etc., the family Fagaceae such as Japanese Chestnut (*Castanea crenata*), etc., the family Juglandaceae such as Walnut (*Juglans* spp.), etc., the family Anacardiaceae such as Cashew (*Anacardium occidentale*), Mango (*Mangifera indica*), Pistachio (*Pistacia vera*), etc., the family Rutaceae subfamily Rutoideae such as Japanese pepper (*Zanthoxylum piperitum*), etc., the family Rutaceae subfamily Aurantioideae such as Bitter orange (*Citrus aurantium*), Lime (*Citrus aurantifolia*), Hassaku orange (*Citrus hassaku*), Yuzu (*Citrus junos*), Lemon (*Citrus limon*), Natsumikan (*Citrus natsudaidai*), Grapefruit (*Citrus×paradisi*), Orange (*Citrus sinensis*), Kabosu (*Citrus*

*sphaerocarpa*), Sudachi (*Citrus sudachi*), Mandarin Orange (*Citrus tangerina*), Satsuma (*Citrus unshiu*), Kumquat (*Fortunella* spp.), etc., the family Brassicaceae such as Horseradish (*Armoracia rusticana*), Mustard (*Brassica juncea*), Takana (*Brassica juncea* var. *integrifolia*), Rapeseed (*Brassica napus*), Cauliflower (*Brassica oleracea* var. *botrytis*), Cabbage (*Brassica oleracea* var. *capitata*), Brussels sprout (*Brassica oleracea* var. *gemmifera*), Broccoli (*Brassica oleracea* var. *italica*), Green pak choi (*Brassica rapa* var. *chinensis*), Nozawana (*Brassica rapa* var. *hakabura*), Napa cabbage (*Brassica rapa* var. *nippo-oleifera*), Potherb Mustard (*Brassica rapa* var. *nipposinica*), Napa cabbage (*Brassica rapa* var. *pekinensis*), Turnip leaf (*Brassica rapa* var. *perviridis*), Turnip (*Brassica rapa* var. *rapa*), Garden rocket (*Eruca vesicaria*), Daikon (*Raphanus sativus* var. *longipinnatus*), Wasabi (*Wasabia japonica*), etc., the family Caricaceae such as Papaya (*Carica papaya*), etc., the family Malvaceae such as Okra (*Abelmoschus esculentus*), Cotton plant (*Gossypium* spp.), Cacao (*Theobroma cacao*), etc., the family Vitaceae such as Grape (*Vitis* spp.), etc., the family Amaranthaceae such as Sugar beet (*Beta vulgaris* ssp. *vulgaris* var. *altissima*), Table beet (*Beta vulgaris* ssp. *vulgaris* var. *vulgaris*), Spinach (*Spinacia oleracea*), etc., the family Polygonaceae such as Buckwheat (*Fagopyrum esculentum*), etc., the family Ebenaceae such as Kaki Persimmon (*Diospyros kaki*), etc., the family Theaceae scuh as Tea plant (*Camellia sinensis*), etc., the family Actinidiaceae such as Kiwifruit (*Actinidia deliciosa, A. chinensis*), etc., the family Ericaceae such as Blueberry (*Vaccinium* spp.), Cranberry (*Vaccinium* spp.), etc., the family Rubiaceae such as Coffee plants (*Coffea* spp.), etc., the family Lamiaceae such as Lemon balm (*Melissa officinalis*), Mint (*Mentha* spp.), Basil (*Ocimum basilicum*), Shiso (*Perilla frutescens* var. *crispa*), *Perilla frutescens* var. *frutescens*, Common Sage (*Salvia officinalis*), Thyme (*Thymus* spp.), etc., the family Pedaliaceae such as Sesame (*Sesamum indicum*), etc., the family Oleaceae such as Olive (*Olea europaea*), etc. the family Convolvulaceae such as Sweet potato (*Ipomoea batatas*), etc., the family Solanaceae such as Tomato (*Solanum lycopersicum*), Eggplant (*Solanum melongena*), Potato (*Solanum tuberosum*), Chili pepper (*Capsicum annuum*), Bell pepper (*Capsicum annuum* var. '*grossum*'), Tobacco (*Nicotiana tabacum*), etc., the family Apiaceae such as Celery (*Apium graveolens* var. *dulce*), Coriander (*Coriandrum sativum*), Japanese honeywort (*Cryptotaenia Canadensis* subsp. *japonica*), Carrot (*Daucus carota* subsp. *sativus*), Parsley (*Petroselium crispum*), Italian parsley (*Petroselinum neapolitanum*), etc., the family Araliaceae such as Udo (*Aralia cordata*), *Aralia elata*, etc., the family Asteraceae subfamily Carduoideae such as Artichoke (*Cynara scolymus*), etc., the family Asteraceae subfamily Asteraceae such as Chicory (*Cichorium intybus*), Lettuce (*Lactuca sativa*), etc., the family Asteraceae subfamily Asteraceae such as Florists' daisy (*Dendranthema grandiflorum*), Crown daisy (*Glebionis coronaria*), Sunflower (*Helianthus annuus*), Fuki (*Petasites japonicus*), Burdock (*Arctium lappa*), etc.

Animals herein mean human, companion creatures/pets, livestock/poultry, and vertebrate such as research/laboratory animals, and specifically, the following animals may, for example, be mentioned, but the present invention is not restricted thereto.

Animals of the class Mammalia belonging to the family Cebidae such as Tufted capuchin (*Cebus apella*), etc., the family Cercopithecidae such as Crab-eating macaque (*Macaca fascicularis*), Rhesus macaque (*Macaca* mulatta), etc., the family Hominidae such as Chimpanzee (*Pan troglodytes*), Human (*Homo sapiens*), etc., the family Leporidae such as European rabbit (*Oryctolagus cuniculus*), etc., the family Chinchillidae such as Long-tailed chinchilla (*Chinchilla lanigera*), etc., the family Caviidae such as Guinea pig (*Cavia porcellus*), etc., the family Cricetidae such as Golden hamster (*Mesocricetus auratus*), Djungarian hamster (*Phodopus sungorus*), Chinese hamster (*Cricetulus griseus*), etc., the family Muridae such as Mongolian gerbil (*Meriones unguiculatus*), House mouse (*Mus musculus*), Black rat (*Rattus rattus*), etc., the family Sciuridae such as Chipmunk (*Tamias sibiricus*), etc., the family Camelidae such as Dromedary (*Camelus dromedarius*), Bactrian camel (*Camelus bactrianus*), Alpaca (*Vicugna pacos*), Llama (*Lama glama*), etc., the family Suidae such as Pig (*Susscrofa domesticus*), etc., the family Cervidae such as Reindeer (*Rangifer tarandus*), Red deer (*Cervus elaphus*), etc., the family Bovidae such as Yak (*Bos grunniens*), Cattle (*Bos taurus*), Water buffalo (Bubalus arnee), Goat (*Capra hircus*), Sheep (*Ovis aries*), etc., the family Felidae such as Cat (*Felis silvestris catus*), etc., the family Canidae such as Dog (*Canis lupus familiaris*), Red fox (*Vulpes vulpes*), etc., the family Mustelidae such as European mink (*Mustela lutreola*), American mink (*Mustela vison*), Ferret (*Mustela putorius furo*), etc., the family Equidae such as Donkey (*Equus asinus*), Horse (*Equus caballus*), etc., the family Macropodidae such as Red kangaroo (*Macropus rufus*), etc.

Animals of the class Aves belonging to the family Struthionidae such as Ostrich (*Struthio camelus*), etc., the family Rheidae such as American rhea (*Rhea americana*), etc., the family Dromaiidae such as Emu (*Dromaius novaehollandiae*), etc., the family Phasianidae such as Ptarmigan (*Lagopus muta*), Wild turkey (*Meleagris gallopavo*), Japanese quail (*Coturnix japonica*), Chicken (*Gallus gallus domesticus*), Common pheasant (*Phasianus colchicus*), Golden pheasant (*Chrysolophus pictus*), Indian peafowl (*Pavo cristatus*), etc., the family Numididae such as Helmeted guineafowl (*Numida meleagris*), etc., the family Anatidae such as Mallard (*Anas platyrhynchos*), Domesticated duck (*Anas platyrhynchos* var. *domesticus*), Spot-billed duck (*Anas poecilorhyncha*), Greylag goose (*Anser anser*), Swan goose (*Anser cygnoides*), Whooper swan (*Cygnus cygnus*), Mute swan (*Cygnus olor*), etc., the family Columbidae such as Rock dove (*Columba livia*), Oriental turtle dove (*Streptopelia orientalis*), European turtle dove (*Streptopelia turtur*), etc., the family Cacatuidae such as Sulphur-crested cockatoo (*Cacatua galerita*), Galah (*Eolophus roseicapilla*), Cockatiel (*Nymphicus hollandicus*), etc., the family Psittacidae such as Rosy-faced lovebird (*Agapornis roseicollis*), Blue-and-yellow macaw (*Ara ararauna*), Scarlet Macaw (*Ara macao*), Budgerigar (*Melopsittacus undulatus*), African grey parrot (*Psittacus erithacus*), etc., the family Sturnidae such as Common hill myna (*Gracula religiosa*), etc., the family Estrildidae such as Red avadavat (*Amandava amandava*), Zebra finch (*Taeniopygia guttata*), Bengalese finch (*Lonchura striata* var. *domestica*), Java sparrow (*Padda oryzivora*), etc., the family Fringillidae such as Domestic canary (*Serinus canaria domestica*), European goldfinch (*Carduelis carduelis*), etc.

Animals of the class Reptilia belonging to the family Chamaeleonidae such as Veiled chameleon (*Chamaeleo calyptratus*), etc., the family Iguanidae such as Green iguana (*Iguana iguana*), Carolina anole (*Anolis carolinensis*), etc., the family Varanidae such as Nile monitor (*Varanus niloticus*), Water monitor (*Varanus salvator*), etc., the family Scincidae such as Solomon islands skink (*Corucia zebrata*), etc., the family Colubridae such as Beauty rat snake (*Elaphe taeniura*), etc., the family Boidae such as *Boa* constrictor (*Boa constrictor*), etc., the family Pythonidae such as Indian python (*Python molurus*), Reticulated python (*Python reticulatus*), etc., the family Chelydridae such as Common snapping turtle (*Chelydra serpentina*), etc., the family Emydidae such as Diamondback terrapin (*Malaclemys terrapin*), Pond slider (*Trachemys scripta*), etc., the family Geoemydidae such as Japanese pond turtle (*Mauremys japonica*), etc., the family Testudinidae such as Central Asian tortoise (*Agrionemys horsfieldii*), etc., the family Trionychidae such as Soft-shelled turtle (*Pelodiscus sinensis*), etc., the family Alligatoridae such as American alligator (*Alligator mississippiensis*), Black caiman (*Melanosuchus niger*), etc., the family Crocodylidae such as Siamese crocodile (*Crocodylus siamensis*), etc.

Animals of the class Actinopterygii belonging to the family Cyprinidae such as Carp (*Cyprinus carpio*), Goldfish (*Carassius auratus auratus*), Zebrafish (*Danio rerio*), etc., the family Cobitidae such as Kuhli loach (*Pangio kuhlii*), etc., the family Characidae such as Red piranha (*Pygocentrus nattereri*), Neon tetra (*Paracheirodon innesi*), etc., the family Salmonidae such as Maraena whitefish (*Coregonus lavaretus maraena*), Coho salmon (*Oncorhynchus kisutsh*), Rainbow trout (*Oncorhynchus mykiss*), Chinook salmon (*Oncorhynchus tshawytscha*), Atlantic salmon (*Salmo salar*), Brown trout (*Salmo trutta*), etc., the family Percichthyidae such as Spotted sea bass (*Lateolabrax maculatus*), etc., the family Serranidae such as Sea goldie (*Pseudanthias squamipinnis*), Longtooth grouper (*Epinephelus bruneus*), Convict grouper (*Epinephelus septemfasciatus*), etc., the family Centrarchidae such as Bluegill (*Lepomis macrochirus*), etc., the family Carangidae such as White trevally (*Pseudocaranx dentex*), Greater amberjack (*Seriola dumerili*), Japanese amberjack (*Seriola quinqueradiata*), etc., the family Sparidae such as Red sea bream (*Paqrus maior*), etc., the family Cichlidae such as Nile tilapia (*Oreochromis niloticus*), Angelfish (*Pterophyllum scalare*), etc., the family Scombridae such as Pacific bluefin tuna (*Thunnus orientalis*), etc., the family Tetraodontidae such as Japanese pufferfish (*Takifugu rubripes*), etc.

Pathogens herein mean microorganisms which cause plant diseases and animal infections, and specifically, the following microorganisms may, for example, be mentioned, but the present invention is not restricted thereto.

Fungi of the phylum Ascomycota, such as *Taphrina* spp. (e.g. *Taphrina deformans, T. pruni*, etc.), *Pneumocystis* spp., *Geotrichum* spp., *Candida* spp. (e.g. *Candida albicans, C. sorbosa*, etc.), *Pichia* spp. (e.g. *Pichia kluyveri*, etc.), *Geotrichum* spp., *Capnodium* spp., *Fumago* spp., *Hypocapnodium* spp., *Cercospora* spp. (e.g. *Cercospora apii, C. asparagi, C. beticola, C. capsici, C. carotae, C. kaki, C. kikuchii, C. zonata*, etc.), *Cercosporidium* spp., *Cladosporium* spp. (e.g. *Cladosporium colocasiae, C. cucumerinum, C. variabile*, etc.), *Davidiella* spp., *Didymosporium* spp., *Heterosporium* spp. (e.g. *Heterosporium allii*, etc.), *Mycosphaerella* spp. (e.g. *Mycosphaerella arachidis, M. berkeleyi, M. cerasella, M. fijiensis, M. fragariae, M. graminicola, M. nawae, M. pinodes, M. pomi, M. zingiberis*, etc.), *Mycovellosiella* spp. (e.g. *Mycovellosiella fulva, M. nattrassii*, etc.), *Paracercospora* spp. (e.g. *Paracercospora egenula*, etc.), *Phaeoisariopsis* spp., *Phaeoramularia* spp., *Pseudocercospora* spp. (e.g. *Pseudocercospora abelmoschi, P. fuligena, P. vitis*, etc.), *Pseudocercosporella* spp. (e.g. *Pseudocercosporella capsellae*, etc.), *Ramichloridium* spp., *Ramularia* spp., *Septogloeum* spp., *Septoria* spp. (e.g. *Septoria albopunctata, S. apiicola, S. chrysanthemella, S. helianthi, S. obesa*, etc.), *Sphaerulina* spp., *Aureobasidium* spp., *Kabatiella* spp., *Plowrightia* spp., *Stigmina* spp., *Elsi-*

*noe* spp. (e.g. *Elsinoe ampelina, E. araliae, E. fawcettii*, etc.), *Sphaceloma* spp. (e.g. *Sphaceloma caricae*, etc.), *Ascochyta* spp. (e.g. *Ascochyta pisi*, etc.), *Corynespora* spp. (e.g. *Corynespora cassiicola*, etc.), *Leptosphaeria* spp. (e.g. *Leptosphaeria coniothyrium, L. maculans*, etc.), *Saccharicola* spp., *Phaeosphaeria* spp., *Ophiosphaerella* spp., *Setophoma* spp., *Helminthosporium* spp., *Alternaria* spp. (e.g. *Alternaria alternata, A. brassicae, A. brassicicola, A. citri, A. dauci, A. helianthi, A. japonica, A. kikuchiana, A. mali, A. panax, A. porri, A. radicina, A. solani*, etc.), *Bipolaris* spp. (e.g. *Bipolaris sorghicola*, etc.), *Cochliobolus* spp. (e.g. *Cochliobolus heterostrophus, C. lunatus, C. miyabeanus*, etc.), *Curvularia* spp. (e.g. *Curvularia geniculata, C. verruculosa*, etc.), *Drechslera* spp., *Pleospora* spp. (e.g. *Pleospora herbarum*, etc.), *Pyrenophora* spp. (e.g. *Pyrenophora graminea, P. teres*, etc.), *Setosphaeria* spp. (e.g. *Setosphaeria turcica*, etc.), *Stemphylium* spp. (e.g. *Stemphylium botryosum, S. lycopersici, S. solani, S. vesicarium*, etc.), *Fusicladium* spp., *Venturia* spp. (e.g. *Venturia carpophila, V. Inaequalis, V. nashicola, V. pirina*, etc.), *Didymella* spp. (e.g. *Didymella bryoniae, D. fabae*, etc.), *Hendersonia* spp., *Phoma* spp. (e.g. *Phoma erratica* var. *mikan, P. exigua* var. *exigua, P. wasabiae*, etc.), *Pyrenochaeta* spp. (e.g. *Pyrenochaeta lycopersici*, etc.), *Stagonospora* spp. (e.g. *Stagonospora sacchari*, etc.), *Botryosphaeria* spp. (e.g. *Botryosphaeria berengeriana f.* sp. *piricola, B. dothidea*, etc.), *Dothiorella* spp., *Fusicoccum* spp., *Guignardia* spp., *Lasiodiplodia* spp. (e.g. *Lasiodiplodia theobromae*, etc.), *Macrophoma* spp., *Macrophomina* spp., *Neofusicoccum* spp., *Phyllosticta* spp. (e.g. *Phyllosticta zingiberis*, etc.), *Schizothyrium* spp. (e.g. *Schizothyrium pomi*, etc.), *Acrospermum* spp., *Leptosphaerulina* spp., *Aspergillus* spp., *Penicillium* spp. (e.g. *Penicillium digitatum, P. italicum, P. sclerotigenum*, etc.), *Microsporum* spp., *Trichophyton* spp. (e.g. *Trichophyton mentagrophytes, T. rubrum*, etc.), *Histoplasma* spp., *Blumeria* spp. (e.g. *Blumeria graminis f.* sp. *hordei, B. g. f.* sp. *tritici*, etc.), *Erysiphe* spp. (e.g. *Erysiphe betae, E. cichoracearum, E. c.* var. *cichoracearum, E. heraclei, E. pisi*, etc.), *Golovinomyces* spp. (e.g. *Golovinomyces cichoracearum* var. *latisporus*, etc.), *Leveillula* spp. (e.g. *Leveillula taurica*, etc.), *Microsphaera* spp., *Oidium* spp. (e.g. *Oidium neolycopersici*, etc.), *Phyllactinia* spp. (e.g. *Phyllactinia kakicola, P. mali, P. moricola*, etc.), *Podosphaera* spp. (e.g. *Podosphaera fusca, P. leucotricha, P. pannosa, P. tridactyla* var. *tridactyla, P. xanthii*, etc.), *Sphaerotheca* spp. (e.g. *Sphaerotheca aphanis* var. *aphanis, S. fuliginea*, etc.), *Uncinula* spp. (e.g. *Uncinula necator, U. n.* var. *necator*, etc.), *Uncinuliella* spp. (e.g. *Uncinuliella simulans* var. *simulans, U. s.* var. *tandae*, etc.), *Blumeriella* spp. (e.g. *Blumeriella iaapii*, etc.), *Cylindrosporium* spp., *Diplocarpon* spp. (e.g. *Diplocarpon mali, D. mespili, D. rosae*, etc.), *Gloeosporium* spp. (e.g. *Gloeosporium minus*, etc.), *Marssonina* spp., *Tapesia* spp. (e.g. *Tapesia acuformis, T. yallundae*, etc.), *Lachnum* spp., *Scleromitrula* spp., *Botryotinia* spp. (e.g. *Botryotinia fuckeliana*, etc.), *Botrytis* spp. (e.g. *Botrytis allii, B. byssoidea, B. cinerea, B. elliptica, B. fabae, B. squamosa*, etc.), *Ciborinia* spp., *Grovesinia* spp., *Monilia mumecola, Monilinia* spp. (e.g. *Monilinia fructicola, M. fructigena, M. laxa, M. mali, M. vaccinii-corymbosi*, etc.), *Sclerotinia* spp. (e.g. *Sclerotinia borealis, S. homoeocarpa, S. minor, S. sclerotiorum*, etc.), *Valdensia* spp. (e.g. *Valdensia heterodoxa*, etc.),

*Claviceps* spp. (e.g. *Claviceps sorghi, C. sorghicola*, etc.), *Epichloe* spp., *Ephelis japonica, Villosiclava virens, Hypomyces* spp. (e.g. *Hypomyces solani f.* sp. *mori, H. s. f.* sp. *pisi*, etc.), *Trichoderma* spp. (e.g. *Trichoderma viride*, etc.), *Calonectria* spp. (e.g. *Calonectria ilicicola*, etc.), *Cande-*

*lospora* spp., *Cylindrocarpon* spp., *Cylindrocladium* spp., *Fusarium* spp. (e.g. *Fusarium arthrosporioides, F. crookwellense, F. culmorum, F. cuneirostrum, F. oxysporum, F. o. f.* sp. *adzukicola, F. o. f.* sp. *allii, F. o. f.* sp. *asparagi, F. o. f.* sp. *batatas, F. o. f.* sp. *cepae, F. o. f.* sp. *colocasiae, F. o. f.* sp. *conglutinans, F. o. f.* sp. *cubense, F. o. f.* sp. *cucumerinum, F. o. f.* sp. *fabae, F. o. f.* sp. *fragariae, F. o. f.* sp. *lactucae, F. o. f.* sp. *lagenariae, F. o. f.* sp. *lycopersici, F. o. f.* sp. *melongenae, F. o. f.* sp. *melonis, F. o. f.* sp. *nelumbinicola, F. o. f.* sp. *niveum, F. o. f.* sp. *radicis-lycopersici, F. o. f.* sp. *raphani, F. o. f.* sp. *spinaciae, F. sporotrichioides, F. solani, F. s. f.* sp. *cucurbitae, F. s. f.* sp. *eumartii, F. s. f.* sp. *pisi, F. s. f.* sp. *radicicola*, etc.), *Gibberella* spp. (e.g. *Gibberella avenacea, G. baccata, G. fujikuroi, G. zeae*, etc.), *Haematonectria* spp., *Nectria* spp., *Ophionectria* spp., *Caldariomyces* spp., *Myrothecium* spp., *Trichothecium* spp., *Verticillium* spp. (e.g. *Verticillium albo-atrum, V. dahliae, V. longisporum*, etc.), *Ceratocystis* spp. (e.g. *Ceratocystis fiсicola, C. fimbriata*, etc.), *Thielaviopsis* spp. (e.g. *Thielaviopsis basicola*, etc.), *Adiscisо* spp., *Monochaetia* spp., *Pestalotia* spp. (e.g. *Pestalotia eriobotrifolia*, etc.), *Pestalotiopsis* spp. (e.g. *Pestalotiopsis funerea, P. longiseta, P. neglecta, P. theae*, etc.), *Physalospora* spp., *Nemania* spp., *Nodulisporium* spp., *Rosellinia* spp. (e.g. *Rosellinia necatrix*, etc.), *Monographella* spp. (e.g. *Monographella nivalis*, etc.), *Ophiostoma* spp., *Cryphonectria* spp. (e.g. *Cryphonectria parasitica*, etc.), *Diaporthe* spp. (e.g. *Diaporthe citri, D. kyushuensis, D. nomurai, D. tanakae*, etc.), *Diaporthopsis* spp., *Phomopsis* spp. (e.g. *Phomopsis asparagi, P. fukushii, P. obscurans, P. vexans*, etc.),

*Cryptosporella* spp., *Discula* spp. (e.g. *Discula theae-sinensis*, etc.), *Gnomonia* spp., *Coniella* spp., *Coryneum* spp., *Greeneria* spp., *Melanconis* spp., *Cytospora* spp., *Leucostoma* spp., *Valsa* spp. (e.g. *Valsa ceratosperma*, etc.), *Tubakia* spp., *Monosporascus* spp., *Clasterosporium* spp., *Gaeumannomyces* spp. (e.g. *Gaeumannomyces graminis*, etc.), *Magnaporthe* spp. (e.g. *Magnaporthe risea*, etc.), *Pyricularia* spp. (e.g. *Pyricularia zingiberis*, etc.), *Monilochaetes infuscans, Colletotrichum* spp. (e.g. *Colletotrichum acutatum, C. capsici, C. cereale, C. destructivum, C. fragariae, C. lindemuthianum, C. nigrum, C. orbiculare, C. spinaciae*, etc.), *Glomerella* spp. (e.g. *Glomerella cingulata*, etc.), *Khuskia oryzae, Phyllachora* spp. (e.g. *Phyllachora pomigena*, etc.), *Ellisembia* spp., *Briosia* spp., *Cephalosporium* spp. (e.g. *Cephalosporium gramineum*, etc.), *Epicoccum* spp., *Gloeocercospora sorghi, Mycocentrospora* spp., *Peltaster* spp. (e.g. *Peltaster fructicola*, etc.), *Phaeocytostroma* spp., *Phialophora* spp. (e.g. *Phialophora grecata*, etc.), *Pseudophloeosporella dioscoreae, Pseudoseptoria* spp., *Rhynchosporium* spp. (e.g. *Rhynchosporium secalis*, etc.), *Sarocladium* spp., *Coleophoma* spp., *Helicoceras oryzae*, etc. Fungi of the phylum Basidiomycota, such as *Septobasidium* spp. (e.g. *Septobasidium bogoriense, S. tanakae*, etc.), *Helicobasidium* spp. (e.g. *Helicobasidium longisporum*, etc.), *Coleosporium* spp. (e.g. *Coleosporium plectranthi*, etc.), *Cronartium* spp., *Phakopsora* spp. (e.g. *Phakopsora artemisiae, P. nishidana, P. pachyrhizi*, etc.), *Physopella* spp. (e.g. *Physopella ampelopsidis*, etc.), *Kuehneola* spp. (e.g. *Kuehneola japonica*, etc.), *Phragmidium* spp. (e.g. *Phragmidium fusiforme, P. mucronatum, P. rosaemultiflorae*, etc.), *Gymnosporangium* spp. (e.g. *Gymnosporangium asiaticum, G. yamadae*, etc.), *Puccinia* spp. (e.g. *Puccinia allii, P. brachypodii* var. *poae-nemoralis, P. coronata, P. c.* var. *coronata, P. cynodontis, P. graminis, P. g.* subsp. *graminicola, P. hordei, P. horiana, P. kuehnii, P. melanocephala, P. recondita, P. striiformis* var. *striiformis, P. tanaceti* var. *tanaceti, P. tokyensis, P. zoysiae*, etc.), *Uromyces* spp. (e.g. *Uromyces phaseoli* var. *azukicola, U. p.* var. *phaseoli, Uromyces viciae-fabae* var. *viciae-fabae*, etc.), *Naohidemyces vaccinii, Nyssopsora* spp., *Leucotelium* spp., *Tranzschelia* spp. (e.g. *Tranzschelia discolor*, etc.), *Aecidium* spp., *Blastospora* spp. (e.g. *Blastospora smilacis*, etc.), *Uredo* spp., *Sphacelotheca* spp., *Urocystis* spp., *Sporisorium* spp. (e.g. *Sporisorium scitamineum*, etc.), *Ustilago* spp. (e.g. *Ustilago maydis, U. nuda*, etc.), *Entyloma* spp., *Exobasidium* spp. (e.g. *Exobasidium reticulatum, E. vexans*, etc.), *Microstroma* spp., *Tilletia* spp. (e.g. *Tilletia caries, T. controversa, T. laevis*, etc.), *Itersonilia* spp. (e.g. *Itersonilia perplexans*, etc.), *Cryptococcus* spp., *Bovista* spp. (e.g. *Bovista dermoxantha*, etc.), *Lycoperdon* spp. (e.g. *Lycoperdon curtisii, L. perlatum*, etc.), *Conocybe* spp. (e.g. *Conocybe apala*, etc.), *Marasmius* spp. (e.g. *Marasmius oreades*, etc.), *Armillaria* spp., *Helotium* spp., *Lepista* spp. (e.g. *Lepista subnuda*, etc.), *Sclerotium* spp. (e.g. *Sclerotium cepivorum*, etc.), *Typhula* spp. (e.g. *Typhula incarnata, T. ishikariensis* var. *ishikariensis*, etc.), *Athelia* spp. (e.g. *Athelia rolfsii*, etc.), *Ceratobasidium* spp. (e.g. *Ceratobasidium cornigerum*, etc.), *Ceratorhiza* spp., *Rhizoctonia* spp. (e.g. *Rhizoctonia solani*, etc.), *Thanatephorus* spp. (e.g. *Thanatephorus cucumeris*, etc.), *Laetisaria* spp., *Waitea* spp., *Fomitiporia* spp., *Ganoderma* spp., *Chondrostereum purpureum, Phanerochaete* spp., etc.

Fungi of the phylum Chitridiomycota such as *Olpidium* spp., etc.

Fungi of the phylum Blastocladiomycota such as *Physoderma* spp., etc.

Fungi of the phylum Mucoromycotina such as *Choanephora* spp., *Choanephoroidea cucurbitae, Mucor* spp. (e.g. *Mucor fragilis*, etc.), *Rhizopus* spp. (e.g. *Rhizopus arrhizus, R. chinensis, R. oryzae, R. stolonifer* var. *stolonifer*, etc.), etc.

Protists of the phylum Cercozoa such as *Plasmodiophora* spp. (e.g. *Plasmodiophora brassicae*, etc.), *Spongospora subterranea f.* sp. *subterranea*, etc.

Microorganisms of the phylum Heterokontophyta class Oomycetes such as *Aphanomyces* spp. (e.g. *Aphanomyces cochlioides, A. raphani*, etc.), *Albugo* spp. (e.g. *Albugo macrospora, A. wasabiae*, etc.), *Bremia* spp. (e.g. *Bremia lactucae*, etc.), *Hyaloperonospora* spp., *Peronosclerospora* spp., *Peronospora* spp. (e.g. *Peronospora alliariae-wasabi, P. chrysanthemi-coronarii, P. destructor, P. farinosa f.* sp. *spinaciae, P. manshurica, P. parasitica, P. sparsa*, etc.), *Plasmopara* spp. (e.g. *Plasmopara halstedii, P. nivea, P. viticola*, etc.), *Pseudoperonospora* spp. (e.g. *Pseudoperonospora cubensis*, etc.), *Sclerophthora* spp., *Phytophthora* spp. (e.g. *Phytophthora cactorum, P. capsici, P. citricola, P. citrophthora, P. cryptogea, P. fragariae, P. infestans, P. melonis, P. nicotianae, P. palmivora, P. porri, P. soiae, P. syringae, P. vignae f.* sp. *adzukicola*, etc.), *Pythium* spp. (e.g. *Pythium afertile, P. aphanidermatum, P. aperoticum, P. aristosporum, P. arrhenomanes, P. buismaniae, P. debaryanum, P. graminicola, P. horinouchiense, P. irregulare, P. iwayamai, P. myriotylum, P. okanoganense, P. paddicum, P. paroecandrum, P. periplocum, P. spinosum, P. sulcatum, P. sylvaticum, P. ultimum* var. *ultimum, P. vanterpoolii, P. vexans, P. volutum*, etc.), etc.

Gram-positive bacteria of the phylum Actinobacteria such as *Clavibacter* spp. (e.g. *Clavibacter michiganensis* subsp. *michiganensis*, etc.), *Curtobacterium* spp., *Leifsonia* spp. (e.g. *Leifsonia xyli* subsp. *xyli*, etc.), *Streptomyces* spp. (e.g. *Streptomyces ipomoeae*, etc.), etc.

Gram-positive bacteria of the phylum Firmicutes such as *Clostridium* sp., etc.

Gram-positive bacteria of the phylum Tenericutes such as *Phytoplasma*, etc.

Gram-negative bacteria of the phylum Proteobacteria such as *Rhizobium* spp. (e.g. *Rhizobium radiobacter*, etc.), *Acetobacter* spp., *Burkholderia* spp. (e.g. *Burkholderia andropogonis, B. cepacia, B. gladioli, B. glumae, B. plantarii*, etc.), *Acidovorax* spp. (e.g. *Acidovorax avenae* subsp. *avenae, A. a.* subsp. *citrulli, A. konjaci*, etc.), *Herbaspirillum* spp., *Ralstonia* spp. (e.g. *Ralstonia solanacearum*, etc.), *Xanthomonas* spp. (e.g. *Xanthomonas albilineans, X. arboricola pv. pruni, X. axonopodis pv. vitians, X. campestris pv. campestris, X. c. pv. cucurbitae, X. c. pv. glycines, X. c. pv. mangiferaeindicae, X. c. pv. nigromaculans, X. c. pyv. vesicatoria, X. citri* subsp. *citri, X. oryzae pv. oryzae*, etc.), *Pseudomonas* spp. (e.g. *Pseudomonas cichorii, P. fluorescens, P. marginalis, P. m. pyv. marginalis, P. savastanoi pv. glycinea, P. syringae, P. s. pv. actinidiae, P. s. pv. eriobotryae, P. s. py. helianthi, P. s. pv. lachrymans, P. s. pv. maculicola, P. s. pv. mori, P. s. pv. morsprunorum, P. s. pv. spinaciae, P. s. pv. syringae, P. s. pv. theae, P. viridiflava*, etc.), *Rhizobacter* spp., *Brenneria* spp. (e.g. *Brenneria nigrifluens*, etc.), *Dickeya* spp. (e.g. *Dickeya dianthicola, D. zeae*, etc.), *Erwinia* spp. (e.g. *Erwinia amylovora, E. rhapontici*, etc.), *Pantoea* spp., *Pectobacterium* spp. (e.g. *Pectobacterium atrosepticum, P. carotovorum, P. wasabiae*, etc.), etc.

As specific examples the plant diseases and animal infections caused by infection/proliferation of such pathogens, the following plant diseases and animal infections may, for example, be mentioned, but the present invention is not restricted thereto.

Plant diseases:

Leaf curl (*Taphrina deformans*), Plum pockets (*Taphrina pruni*), Leaf spot (*Cercospora asparagi*), Cercospora leaf spot (*Cercospora beticola*), Frogeye leaf spot (*Cercospora capsici*), Angular leaf spot (*Cercospora kaki*), Purple stain (*Cercospora kikuchii*), Brown Leaf spot (*Mycosphaerella arachidis*), Cylindrosporium leaf spot (*Mycosphaerella cerasella, Blumeriella japii*), Speckled leaf blotch (*Mycosphaerella graminicola*), Circular leaf spot (*Mycosphaerella nawae*), Mycosphaerella blight (*Mycosphaerella pinodes*), Leaf spot (*Mycosphaerella zingiberis*), Leaf mold (*Mycovellosiella fulva*), Leaf mold (*Mycovellosiella nattrassii*), Cercospora leaf mold (*Pseudocercospora fuligena*), Isariopsis leaf spot (*Pseudocercospora vitis*), Leaf spot (*Pseudocercosporella capsellae*), Leaf spot (*Septoria chrysanthemella*), Leaf blight (*Septoria obesa*), Anthracnose (*Elsinoe ampelina*), Spot anthracnose (*Elsinoe araliae*), Scab (*Elsinoe fawcettii*), Leaf spot (*Ascochyta pisi*), Corynespora leaf spot (*Corynespora cassiicola*), Stem canker (*Leptosphaeria coniothyrium*), Leaf spot (*Alternaria alternata*), Leaf blight (*Alternaria dauci*), Black spot (*Alternaria kikuchiana*), Alternaria blotch (*Alternaria mali*), Alternaria leaf spot (*Alternaria porri*), Target spot (*Bipolaris sorghicola*), Southern leaf blight (*Cochliobolus heterostrophus*), Brown spot (*Cochliobolus miyabeanus*), Tip blight (*Pleospora herbarum*), Stripe (*Pyrenophora graminea*), Net blotch (*Pyrenophora teres*), Leaf blight (*Setosphaeria turcica*), Northern leaf blight (*Setosphaeria turcica*), Leaf spot (*Stemphylium botryosum*), Scab (*Venturia carpophila*), Scab (*Venturia Inaequalis*), Scab (*Venturia nashicola*), Gummy stem blight (*Didymella bryoniae*), Leaf spot (*Phoma exigua* var. *exigua*), Streak (*Phoma wasabiae*), Ring rot (*Botryosphaeria berengeriana f. sp. piricola*), Soft rot (*Botryosphaeria dothidea, Lasiodiplodia theobromae, Diaporthe* sp.), Common green mold (*Penicillium digitatum*), Blue mold (*Penicillium italicum*), Powdery mildew (*Blumeria graminis f.* sp. *hordei*), Powdery mildew (*Blumeria graminis f.* sp. *tritici*), Powdery mildew (*Erysiphe betae, Leveillula taurica, Oidium* sp., *Podosphaera xanthii*), Powdery mildew (*Erysiphe cichoracearum, Leveillula taurica, Sphaerotheca fuliginea*), Powdery mildew (*Erysiphe heraclei*), Powdery mildew (*Erysiphe pisi*), Powdery mildew (*Leveillula taurica, Oidium neolycopersici, Oidium* sp.), Powdery mildew (*Leveillula taurica*), Powdery mildew (*Oidium* sp., *Podosphaera xanthii*), Powdery mildew (*Oidium* sp.), Powdery mildew (*Phyllactinia kakicola*), Powdery mildew (*Podosphaera fusca*), Powdery mildew (*Podosphaera leucotricha*), Powdery mildew (*Podosphaera pannosa, Uncinuliella simulans* var. *simulans, U. s.* var. *tandae*), Powdery mildew (*Podosphaera xanthii*), Powdery mildew (*Sphaerotheca aphanis* var. *aphanis*), Powdery mildew (*Sphaerotheca fuliginea*), Powdery mildew (*Uncinula necator, U. n.* var. *necator*), Blotch (*Diplocarpon mali*), Black spot (*Diplocarpon rosae*), Gray mold neck rot (*Botrytis allii*), Gray mold, Botrytis blight (*Botrytis cinerea*), Leaf blight (*Botrytis cinerea, B. byssoidea, B. sguamosa*), Chocolate spot (*Botrytis cinerea, B. elliptica, B. fabae*), Brown rot (*Monilinia fructicola, M. fructigena, M. laxa*), Blossom blight (*Monilinia mali*), Dollar spot (*Sclerotinia homoeocarpa*), Cottony rot, *Sclerotinia* rot, Stem rot (*Sclerotinia sclerotiorum*), False smut (*Villosiclava virens*), Root necrosis (*Calonectria ilicicola*), Fusarium blight (*Fusarium crookwellense, F. culmorum, Gibberella avenacea, G. zeae, Mono raphella nivalis*), Fusarium blight (*Fusarium culmorum, Gibberella avenacea, G. zeae*), Dry rot (*Fusarium oxysporum, F. solani f.* sp. *radicicola*), Brown rot (*Fusarium oxysporum, F. solani f.* sp. *pisi, F. s. f.* sp. *radicicola*), Fusarium wilt (*Fusarium oxysporum f.* sp. *adzukicola*), Fusarium basal rot (*Fusarium oxysporum f.* sp. *allii, F. solani f.* sp. *radicicola*), Stem rot (*Fusarium oxysporum f.* sp. *batatas, F. solani*), Dry rot (*Fusarium oxysporum f.* sp. *colocasiae*), Yellows (*Fusarium oxysporum f.* sp. *conglutinans*), Panama disease (*Fusarium oxysporum f.* sp. *cubense*), Fusarium wilt (*Fusarium oxysporum f.* sp. *fragariae*), Root rot (*Fusarium oxysporum f.* sp. *lactucae*), Fusarium wilt (*Fusarium oxysporum f.* sp. *lagenariae, F. o. f.* sp. *niveum*), Fusarium wilt (*Fusarium oxysporum f.* sp. *lycopersici*), Fusarium wilt (*Fusarium oxysporum f.* sp. *melonis*), Yellows (*Fusarium oxysporum f.* sp. *raphani*), Fusarium wilt (*Fusarium oxysporum f.* sp. *spinaciae*), "Bakanae" disease (*Gibberella fujikuroi*), Verticillium black spot (*Verticillium albo-atrum, V. dahliae*), Verticillium wilt (*Verticillium dahliae*), Ceratocystis canker (*Ceratocystis ficicola*), Black rot (*Ceratocystis fimbriata*), Gray blight (*Pestalotiopsis longiseta, P. theae*), Endothia canker (*Cryphonectria parasitica*), Melanose (*Diaporthe citri*), Stem blight (*Phomopsis asparagi*), Phomopsis canker (*Phomopsis fukushii*), Brown spot (*Phomopsis vexans*), Anthracnose (*Discula theae-sinensis*), Valsa canker (*Valsa ceratosperma*), Blast (*Magnaporthe grisea*), Crown rot (*Colletotrichum acutatum, C. fragariae, Glomerella cingulata*), Bitter rot (*Colletotrichum acutatum, Glomerella cinulata*), Anthracnose (*Colletotrichum acutatum, Glomerella cingulata*), Anthracnose (*Colletotrichum acutatum*), Ripe rot (*Colletotrichum acutatum, Glomerella cingulata*), Anthracnose (*Colletotrichum acutatum*), Anthracnose (*Colletotrichum lindemuthianum*), Anthracnose (*Colletotrichum orbiculare*), Anthracnose (*Glomerella cingulata*), Anthracnose (*Glomerella cingulata*), Anthracnose (*Glomerella cingulata*), Brown stem rot (*Phialophora Cregata*), Leaf spot (*Pseudophloeosporella dioscoreae*), Scald (*Rhynchosporium secalis*), Rust (*Phakopsora nishidana*), Rust (*Phakopsora pachyrhizi*), Rust (*Kuehneola japonica, Phragmidium fusiforme, P. mucronatum, P. rosae-multiflorae*), Rust (*Gymnosporangium asiaticum*), Rust (*Gymnosporangium yamadae*), Rust (*Puccinia allii*), Rust (*Puccinia horiana*), Brown rust (*Puccinia recondita*), Rust (*Puccinia tanaceti* var. *tanaceti*), Rust (*Uromyces viciae-fabae* var. *viciae-fabae*), Smut (*Sporisorium scitamineum*), Smut (*Ustilago maydis*), Loose smut (*Ustilago nuda*), Net blister blight (*Exobasidium reticulatum*), Blister blight (*Exobasidium vexans*), Stem rot, Southern blight (*Athelia rolfsii*), Root and stem rot (*Ceratobasidium cornigerum, Rhizoctonia solani*), (*Rhizoctonia solani*), Damping-off (*Rhizoctonia solani*), Damping-off (*Rhizoctonia solani*), Bottom rot (*Rhizoctonia solani*), Brown patch, Large patch (*Rhizoctonia solani*), Sheath blight (*Thanatephorus cucumeris*), Root rot/Leaf blight (*Thanatephorus cucumeris*), Rhizopus rot (*Rhizopus stolonifer* var. *stolonifer*), Clubroot (*Plasmodiophora brassicae*), Aphanomyces root rot (*Aphanomyces cochlioides*), White rust (*Albugo macrospora*), Downy mildew (*Bremia lactucae*), Downy mildew (*Peronospora chrysanthemi-coronarii*), Downy mildew (*Peronospora destructor*), Downy mildew (*Peronospora farinosa f.* sp. *spinaciae*), Downy mildew (*Peronospora manshurica*), Downy mildew (*Peronospora parasitica*), Downy mildew (*Peronospora sparsa*), Downy mildew (*Plasmopara halstedii*), Downy mildew (*Plasmopara nivea*), Downy mildew (*Plasmopara viticola*), Downy mildew (*Pseudoperonospora cubensis*), Phytophthora root rot (*Phytophthora cactorum*), Brown rot (*Phytophthora capsici*), Phytophthora rot (*Phytophthora capsici*), Phytophthora blight (*Phytophthora capsici*), Phytophthora rot (*Phytophthora cryptogea*), Late blight (*Phytophthora infestans*), White powdery rot (*Phytophthora palmivora*), Leaf blight (*Phytophthora porri*), Phytophthora root and stem rot (*Phytophthora soiae*), Phytophthora stem rot (*Phytophthora vignae f.* sp. *adzukicola*), Damping-off (*Pythium aphanidermatum, P. myriotylum, P. paroecandrum, P. ultimum* var. *ultimum*), Root rot (*Pythium aristosporum*), Browning root rot (*Pythium arrhenomanes, P. graminicola*), Damping-off (*Pythium buismaniae, P. myriotylum*), Root rot (*Pythium myriotylum*), Root rot (*Pythium myriotylum, P. ultimum* var. *ultimum*), Brown blotted root rot (*Pythium sulcatum*), Bacterial canker (*Clavibacter michiganensis* subsp. *michiganensis*), Scab (*Streptomyces* spp.), Crown gall (*Rhizobium radiobacter*), Bacterial stripe (*Burkholderia andropogonis*), Soft rot (*Burkholderia cepacia, Pseudomonas marginalis pv. marginalis, Erwinia rhapontici*), Bacterial grain rot (*Burkholderia gladioli, B. glumae*), Bacterial fruit blotch (*Acidovorax avenae* subsp. *citrulli*), Bacterial leaf blight (*Acidovorax koniaci*), Bacterial wilt (*Ralstonia solanacearum*), Bacterial shot hole (*Xanthomonas arboricola pv. pruni, Pseudomonas syringae pv. syringae, Brenneria nigrifluens*), Bacterial leaf spot (*Xanthomonas arboricola pv. pruni*), Bacterial spot (*Xanthomonas axonopodis pv. vitians*), Black rot (*Xanthomonas campestris pv. campestris*), Bacterial pustule (*Xanthomonas campestris pv. glycines*), Bacterial spot (*Xanthomonas campestris pvy. nigromaculans*), Bacterial spot (*Xanthomonas campestris pv. vesicatoria*), Citrus canker (*Xanthomonas citri* subsp. *citri*), (*Pseudomonas cichorii, P. marginalis pv. marginalis, Erwinia* sp.), Bacterial rot (*Pseudomonas cichorii, P. marginalis pv. marginalis, P. viridiflava*), Bacterial blossom blight (*Pseudomonas marginalis pv. marginalis, P. syringae pv. syringae, P. viridiflava*), Bacterial canker (*Pseudomonas syringae pv. actinidiae*), Canker (*Pseudomonas syringae pv. eriobotryae*), Bacterial spot (*Pseudomonas syringae pv. lachrymans*), Bacterial black spot (*Pseudomonas syringae pv. maculicola*), Bacterial canker (*Pseudomonas syringae pv. morsprunorum, Erwinia* sp.), Bacterial shoot blight (*Pseudomonas syringae pv. theae*), Bacterial soft rot (*Dickeya* sp., *Pectobacterium carotovorum*), Fire blight (*Erwinia amylovora*), Soft rot (*Pectobacterium carotovorum*), Bacterial soft rot (*Pectobacterium carotovorum*).

Animal Diseases:

*Pneumocystis* pneumonia (*Pneumocystis jirovecii*), Candidiasis (*Candida albicans*), Aspergillosis (*Aspergillus fumigatus*), Trichophytosis (*Microsporum canis, M. Cypseum, Trichophyton mentagrophytes, T. rubrum, T. tonsurans, T. verrucosum*), Histoplasmosis (*Histoplasma capsulatum*), Cryptococcosis (*Cryptococcus neoformans*).

Parasites herein mean plant-parasitic nematodes parasitizing plants, animal-parasitic nematodes parasitizing animals, Acanthocephala, Platyhelminthes, Protozoa and the like, and specifically, the following parasites may, for example, be mentioned, but the present invention is not restricted thereto.

Nematodes of the order Enoplida such as Giant kidney worm (*Dioctophyma renale*), Thread worms (*Capillaria annulata*), Cropworm (*Capillaria contorta*), Capillary liver worm (*Capillaria hepatica*), Capillaria perforans, Capillaria philippinensis, Capillaria suis, Whipworm (*Trichuris discolor*), Whipworm (*Trichuris ovis*), Pig whipworm (*Trichuris suis*), Human whipworm (*Trichuris trichiura*), Dog whipworm (*Trichuris vulpis*), Pork worm (*Trichinella spiralis*), etc.

Nematodes of the order Rhabditida such as Intestinal threadworm (*Strongyloides papillosus*), Strongyloides planiceps, Pig threadworm (*Strongyloides ransomi*), Threadworm (*Strongyloides stercoralis*), Micronema spp., etc.

Nematodes of the order Strongylida such as Hookworm (*Ancylostoma braziliense*), Dog hookworm (*Ancylostoma caninum*), Old World hookworm (*Ancylostoma duodenale*), Cat hookworm (*Ancylostoma tubaeforme*), The Northern hookworm of dogs (*Uncinaria stenocephala*), Cattle hookworm (*Bunostomum phlebotomum*), Small ruminant hookworm (*Bunostomum trigonocephalum*), New World hookworm (*Necator americanus*), Cyathostomum spp., Cylicocyclus spp., Cylicodontophorus spp., Cylicostephanus spp., Strongylus asini, Strongylus edentatus, Blood worm (*Strongylus eguinus*), Blood worm (*Strongylus vulgaris*), Large-mouthed bowel worm (*Chabertia ovina*), Nodular worm (*Oesophagostomum brevicaudatum*), Nodule worm (*Oesophagostomum columbianum*), Nodule worm (*Oesophagostomum dentatum*), Nodular worm (*Oesophagostomum georgianum*), Nodular worm (*Oesophagostomum maplestonei*), Nodular worm (*Oesophagostomum guadrispinulatum*), Nodular worm (*Oesophagostomum radiatum*), Nodular worm (*Oesophagostomum venulosum*), Syngamus skriabinomorpha, Gapeworm (*Syngamus trachea*), Swine kidney worm (*Stephanurus dentatus*), Cattle bankrupt worm (*Cooperia oncophora*), Red stomach worm (*Hyostrongylus rubidus*), Stomach hair worm (*Trichostrongylus axei*), Trichostrongylus colubriformis, Oriental trichostrongylus (*Trichostrongylus orientalis*), Red stomach worm (*Haemonchus contortus*), Cattle stomach worm (*Mecistocirrus digitatus*), Brown stomach worm (*Ostertagia ostertagi*), Common lungworm (*Dictyocaulus filaria*), Bovine lungworm (*Dictyocaulus viviparus*), Thin-necked intestinal worm (*Nematodirus filicollis*), Swine lungworm (*Metastrongylus elongatus*), Lungworm (*Filaroides hirthi*), Lungworm (*Crenosoma aerophila*), Fox lungworm (*Crenosoma vulpis*), Rat lung worm (*Angiostrongylus cantonensis*), French heartworm (*Angiostrongylus vasorum*), Protostrongylus spp., etc.

Nematodes of the order Aphelenchida such as Rice white tip nematode (*Aphelenchoides besseyi*), Strawberry foliar nematode (*Aphelenchoides fragariae*), Chrysanthemum foliar nematode (*Aphelenchoides ritzemabosi*), Pine wood nematode (*Bursaphelenchus xylophilus*), etc.

Nematodes of the order Tylenchida such as White potato cyst nematode (*Globodera pallida*), Potato cyst nematode (*Globodera rostochiensis*), Cereal cyst nematode (*Heterodera avenae*), Soybean cyst nematode (*Heterodera glycines*), Sugarbeet cyst nematode (*Heterodera schachtii*), Clover cyst nematode (*Heterodera trifolii*), Peanut root-knot nematode (*Meloidogyne arenaria*), Northern root-knot nematode (*Meloidogyne hapla*), Southern root-knot nematode (*Meloidogyne incognita*), Javanese root-knot nematode (*Meloidogyne javanica*), Apple root-knot nematode (*Meloidogyne mali*), Coffee root-lesion nematode (*Pratylenchus coffeae*), (*Pratylenchus drenatus*), Tea root-lesion nematode (*Pratylenchus loosi*), California root-lesion nematode (*Pratylenchus neglectus*), Cobb's root-lesion nematode (*Pratylenchus penetrans*), Walnut root-lesion nematode (*Pratylenchus vulnus*), Citrus burrowing nematode (*Radopholus citrophilus*), Banana burrowing nematode (*Radopholus similis*), etc.

Nematodes of the order Oxyurida such as Pinworm (*Enterobius vermicularis*), Equine pinworm (*Oxyuris equi*), Rabbit pinworm (*Passalurus ambiguus*), etc.

Nematodes of the order Ascaridida such as Pig roundworm (*Ascaris suum*), Horse roundworm (*Parascaris equorum*), Dog roundworm (*Toxascaris leonina*), Dog intestinal roundworm (*Toxocara canis*), Feline roundworm (*Toxocara cati*), Large cattle roundworm (*Toxocara vitulorum*), *Anisakis* spp., *Pseudoterranova* spp., Caecal worm (*Heterakis gallinarum*), Chicken roundworm (*Ascaridia galli*), etc.

Nematodes of the order Spirurida such as Guinea worm (*Dracunculus medinensis*), *Gnathostoma doloresi*, *Gnathostoma hispidum*, *Gnathostoma nipponicum*, Reddish-coloured worm (*Gnathostoma spinigerum*), Dog stomach worm (*Physaloptera canis*), Cat stomach worm (*Physaloptera felidis*, *P. praeputialis*), Feline/canine stomach worm (*Physaloptera rara*), Eye worm (*Thelazia callipaeda*), Bovine eyeworm (*Thelazia rhodesi*), Large mouth stomach worm (*Draschia megastoma*), Equine stomach worm (*Habronema microstoma*), Stomach worm (*Habronema muscae*), Gullet worm (*Gongylonema pulchrum*), Thick stomach worm (*Ascarops strongylina*), *Parafilaria* (*Parafilaria bovicola*), *Parafilaria multipapillosa*, *Stephanofilaria okinawaensis*, Bancroft filarial (*Wuchereria bancrofti*), *Brugia malavi*, Neck threadworm (*Onchocerca cervicalis*), *Onchocerca gibsoni*, Cattle filarial worm (*Onchocerca gutturosa*), *Onchocerca volvulus*, Bovine filarial worm (*Setaria digitata*), Peritoneal worm (*Setaria eguina*), *Setaria labiatopapillosa*, *Setaria marshalli*, Dog heartworm (*Dirofilaria immitis*), African eye worm (*Loa loa*), etc.

Microorganisms of the phylum Acanthocephala such as *Moniliformis moniliformis*, Giant thorny-headed worm (*Macracanthorhynchus hirudinaceus*), etc.

Cestodes of the order Pseudophyllidea such as Fish tapeworm (*Diphyllobothrium latum*), *Diphyllobothrium nihonkaiense*, Manson tapeworm (*Spirometra erinaceieuropaei*), *Diplogonoporus grandis*, etc.

Cestodes of the order Cyclophyllidea such as (*Mesocestoides lineatus*), Chicken tapeworm (*Raillietina cesticillus*), Fowl tapeworm (*Raillietina echinobothrida*), Chicken tapeworm (*Raillietina tetragona*), Canine tapeworm (*Taenia hydatigena*), Canine tapeworm (*Taenia multiceps*), Sheep measles (*Taenia ovis*), Dog tapeworm (*Taenia pisiformis*), Beef tapeworm (*Taenia saginata*), Tapeworm (*Taenia serialis*), Pork tapeworm (*Taenia solium*), Feline tapeworm (*Taenia taeniaeformis*), Hydatid tapeworm (*Echinococcus granulosus*), Small fox tapeworm (*Echinococcus multilocularis*), *Echinococcus oligarthrus*, *Echinococcus vogeli*, Rat tapeworm (*Hymenolepis diminuta*), Dwarf tapeworm (*Hymenolepis nana*), Double-pored dog tapeworm (*Dipylidium caninum*), *Amoebotaenia sphenoides*, *Choanotaenia infundibulum*, *Metroliasthes coturnix*, Equine tapeworm (*Anoplocephala magna*), Cecal tapeworm (*Anoplocephala perfoliata*), Dwarf equine tapeworm (*Paranoplocephala mamillana*), Common tapeworm (*Moniezia benedeni*), Sheep tapeworm (*Moniezia expansa*), *Stilesia* spp., etc.

Trematodes of the order Strigeidida such as *Pharyngostomum cordatum*, Blood fluke (*Schistosoma haematobium*), Blood fluke (*Schistosoma japonicum*), Blood fluke (*Schistosoma mansoni*), etc.

Trematodes of the order Echinostomida such as *Echinostoma cinetorchis*, *Echinostoma hortense*, Giant liver fluke (*Fasciola gigantica*), Common liver fluke (*Fasciola hepatica*), *Fasciolopsis buski*, *Homalogaster paloniae*, etc.

Trematodes of the order Plagiorchiida such as *Dicrocoelium chinensis*, Lancet liver fluke (*Dicrocoelium dendriticum*), African lancet fluke (*Dicrocoelium hospes*), *Eurytrema coelomaticum*, Pancreatic fluke (*Eurytrema pancreaticum*), *Paragonimus miyazakii*, *Paragonimus ohirai*, Lung fluke (*Paragonimus westermani*), etc.

Trematodes of the order Opisthorchiida such as *Amphimerus* spp., Chinese liver fluke (*Clonorchis sinensis*), Cat liver fluke (*Opisthorchis felineus*), Southeast Aasian liver fluke (*Opisthorchis viverrini*), *Pseudamphistomum* spp., *Metorchis* spp., *Parametorchis* spp., Intestinal fluke (*Heterophyes heterophyes*), *Metagonimus yokokawai*, *Pygidiopsis summa*, etc.

Amebas such as *Entamoeba histolytica*, *E. invadens*, etc.

Piroplasmida sporozoa such as *Babesia bigemina*, *Babesia bovis*, *Babesia caballi*, *Babesia canis*, *Babesia felis*, *Babesia gibsoni*, *Babesia ovata*, *Cytauxzoon felis*, *Theileria annulata*, *Theileria mutans*, *Theileria orientalis*, *Theileria parva*, etc.

Haemosporida sporozoa such as *Haemoproteus mansoni*, *Leucocytozoon caulleryi*, *Plasmodium falciparum*, *Plasmodium malariae*, *Plasmodium ovale*, *Plasmodium vivax*, etc.

Eucoccidiorida sporozoa such as *Caryospora* spp., *Eimeria acervulina*, *Eimeria bovis*, *Eimeria brunetti*, *Eimeria maxima*, *Eimeria necatrix*, *Eimeria ovinoidalis*, *Eimeria stiedae*, *Eimeria tenella*, *Isospora canis*, *Isospora felis*, *Isospora suis*, *Tyzzeria alleni*, *Tyzzeria anseris*, *Tyzzeria perniciosa*, *Wenyonella anatis*, *Wenyonella gagari*, *Cryptosporidium canis*, *Cryptosporidium felis*, *Cryptosporidium hominis*, *Cryptosporidium meleagridis*, *Cryptosporidium muris*, *Cryptosporidium parvum*, *Sarcocystis canis*, *Sarcocystis cruzi*, *Sarcocystis felis*, *Sarcocystis hominis*, *Sarcocystis miescheriana*, *Sarcocystis neurona*, *Sarcocystis tenella*, *Sarcocystis ovalis*, *Toxoplasma gondii*, *Hepatozoon canis*, *Hepatozoon felis*, etc.

Vestibuliferida ciliata such as *Balantidium coli*, etc.

Trichomonadida flagellata such as *Histomanas meleagridis*, *Pentatrichomonas hominis*, *Trichomonas tenax*, etc.

Diplomonadida flagellata such as *Giardia intestinalis*, *Giardia muris*, *Hexamita meleagridis*, *Hexamita parva*, etc.

Kinetoplastida flagellata such as *Leishmania donovani*, *Leishmania infantum*, *Leishmania major*, *Leishmania tropica*, *Trypanosoma brucei gambiense*, *Trypanosoma brucei rhodesiense*, *Trypanosoma cruzi*, *Trypanosoma equiperdum*, *Trypanosoma evansi*, etc.

Useful insects herein mean insects useful for human life by utilizing their products, or useful to make agricultural work efficient e.g. by using them for pollination of orchard trees/vegetables, and specifically, Japanese honeybee (*Apis cerana japonica*), Western honey bee (*Apis mellifera*), Bumblebee (*Bombus consobrinus wittenburgi, B. diversus diversus, B. hypocrita hypocrita, B. ignitus, B. terrestris*), Hornfaced bee (*Osmia cornifrons*), Silkworm (*Bombyx mori*) may, for example, be mentioned, but the present invention is not restricted thereto.

Natural enemies herein mean organisms which kill specific organisms particularly specific organisms damaging agricultural crops by predation or parasitism or which inhibit propagation of such organisms, and specifically, the following organisms may, for example, be mentioned, but the present invention is not restricted thereto.

Parasitic wasps belonging to the family Braconidae such as *Dacnusa sasakawai, Dacnusa sibirica, Aphidius colemani, Apanteles glomeratus*, etc., the family Aphelinidae such as *Aphelinus albipodus, Aphelinus asychis, Aphelinus Cossypii, Aphelinus maculatus, Aphelinus varipes, Encarsia formosa, Eretmocerus eremicus, Eretmocerus mundus*, etc., and the family Eulophidae such as *Chrysocharis pentheus, Neochrysocharis formosa, Dilyphus isaea, Hemiptarsenus varicornis*, etc.; Aphidophagous gall midge (*Aphidoletes aphidimyza*); Seven-spot ladybird (*Coccinella septempunctata*); Asian lady beetle (*Harmonia axyridis*); Predatory beetle (*Propylea japonica*); Anthocorid predatory bugs belonging to the family Anthocoridae such as *Orius minutus, Orius nagaii, Orius sauteri*, Minute pirate bug (*Orius strigicollis*), etc.; Predatory mirids belonging to the family Miridae such as *Pilophorus typicus, Nesidiocoris tenuis*, etc.; Predatory thrips belonging to the family Aeolothripidae such as *Franklinothrips vespiformis*, etc.; Green lacewing belonging to the family Chrysopidae such as *Dichochrysa formosanus, Chrysoperla nipponensis*, etc.; Predatory mites belonging to the family Phytoseiidae such as *Neoseiulus californicus, Amblyseius cucumeris, Amblyseius degenerans, Amblyseius swirskii, Phytoseiulus persimilis*, etc.; Wolf spider (*Pardosa pseudoannulata*); Crab spider (*Misumenops tricuspidatus*).

The compounds of the present invention represented by the formula (I) can be produced, for example, by the following processes.

Process A

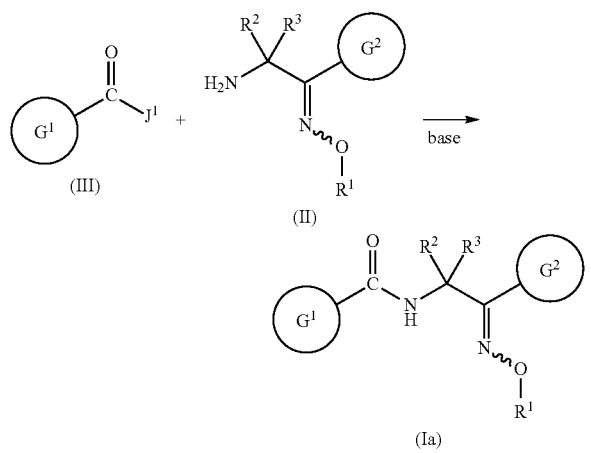

A compound represented by the formula (II) [wherein $G^2$, $R^1$, $R^2$ and $R^3$ are the same as defined above] or its salt (such as a hydrochloride or a hydrobromide) is reacted with a compound represented by the formula (III) [wherein $G^1$ is the same as defined above, and $J^1$ is a chlorine atom, a bromine atom, a $C_1$-$C_4$ alkylcarbonyloxy group (such as a pivaloyloxy group), a $C_1$-$C_4$ alkoxycarbonyloxy group (such as an isobutyloxycarbonyloxy group), an azolyl group (such as an imidazol-1-yl group) or the like], if necessary in a solvent such as benzene, toluene, dichloromethane, chloroform, 1,2-dichloroethane, diethyl ether, tert-butyl methyl ether, tetrahydrofuran, 1,4-dioxane, ethyl acetate, N,N-dimethylformamide, N,N-dimethylacetamide, acetonitrile, water or a mixture of two or more of them in an any ratio, if necessary in the presence of a base such as sodium carbonate, potassium carbonate, sodium hydrogen carbonate, sodium acetate, triethylamine, ethyl diisopropylamine, N-methylmorpholine, pyridine or 4-(dimethylamino)pyridine in an amount of from 1 to 3 equivalents per 1 equivalent of the compound represented by the formula (II), within a temperature range of from 0° C. to the refluxing temperature of the reaction mixture for from 30 minutes to 24 hours, to obtain a compound of the present invention represented by the formula (Ia) [wherein $G^1$, $R^1$, $R^2$ and $R^3$ are the same as defined above] which is a compound of the formula (I) wherein W is an oxygen atom, and $R^4$ is a hydrogen atom.

Some of the compounds represented by the formula (III) used in this process are known compounds, and some of them are commercially available. The rest of them can be synthesized in accordance with known methods disclosed in the literature, for example, by a method in accordance with the method disclosed in J. Med. Chem., 1991, vol. 34, p. 1630, etc., in which a corresponding known carboxylic acid is reacted with a halogenating agent such as thionyl chloride, phosphorus pentachloride or oxalyl chloride, a method in accordance with the method disclosed in Tetrahedron Letters, 2003, vol. 44, p. 4819, J. Med. Chem., 1991, vol. 34, p. 222, etc., in which a corresponding known carboxylic acid is reacted with an organic acid halide such as pivaloyl chloride or isobutyl chloroformate in the presence of a base if necessary, or a method disclosed in J. Org. Chem., 1989, vol. 54, p. 5620, etc., in which a corresponding known carboxylic cid is reacted with carbonyl diimidazole, sulfonyl diimidazole or the like.

Process B

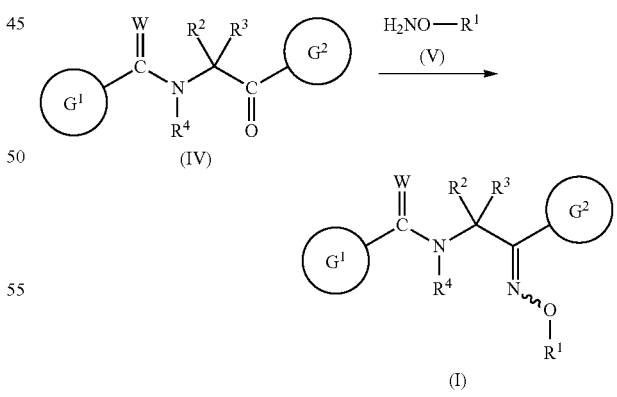

1 Equivalent of a compound represented by the formula (IV) [wherein $G^1$, $G^2$, W, $R^2$, $R^3$ and $R^4$ are the same as defined above] is reacted with from 1 to 3 equivalents of a compound represented by the formula (V) [wherein $R^1$ is the same as defined above] or its salt (such as a hydrochloride or a hydrobromide), if necessary in a solvent such as benzene, toluene, methanol, ethanol, tetrahydrofuran, acetic acid, pyridine, water or a mixture of two or more of them in any ratio, if necessary in the presence of a base such as sodium hydroxide, potassium hydroxide, sodium carbonate, potassium carbonate, sodium hydrogen carbonate, sodium acetate, triethylamine or pyridine in an amount of from 1 to 4 equivalents per 1 equivalent of the compound represented by the formula (IV), or with hydrochloric acid, sulfuric acid or the like as a catalyst in an amount of from 0.1 to 1 equivalent per 1 equivalent of the compound represented by the formula (IV), within a temperature range of from room temperature to the refluxing temperature of the reaction mixture for from 1 to 48 hours to obtain a compound of the present invention represented by the formula (I) [wherein $G^1$, $G^2$, W, $R^1$, $R^2$, $R^3$ and $R^4$ are the same as defined above].

Process C

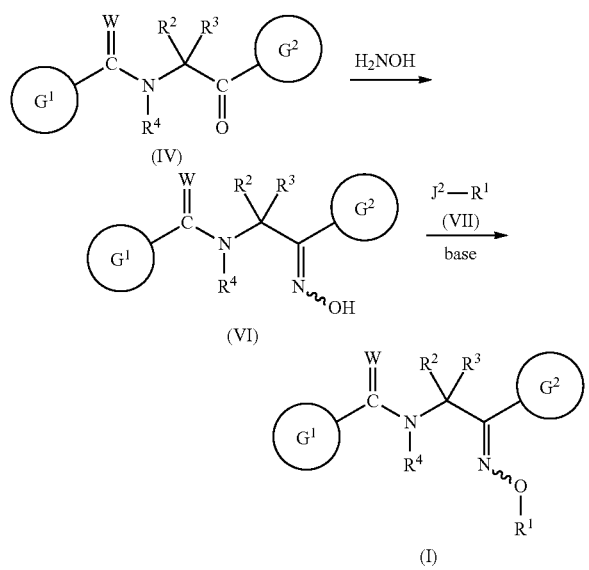

1 Equivalent of a compound represented by the formula (IV) [wherein $G^1$, $G^2$, W, $R^2$, $R^3$ and $R^4$ are the same as defined above] and from 1 to 3 equivalents of hydroxylamine or its salt (such as a hydrochloride or a sulfate) are reacted, if necessary in a solvent such as methanol, ethanol, 1,4-dioxane, acetonitrile, pyridine, water or a mixture of two or more of them in any ratio, if necessary in the presence of a base such as sodium hydroxide, potassium hydroxide, sodium carbonate, potassium carbonate, sodium hydrogen carbonate, sodium acetate, ethyldiisopropylamine or pyridine in an amount of from 1 to 4 equivalents per 1 equivalent of the compound represented by the formula (IV), within a temperature range of from room temperature to the refluxing temperature of the reaction mixture for from 1 to 24 hours to obtain a compound represented by the formula (VI) [wherein $G^1$, $G^2$, W, $R^2$, $R^3$ and $R^4$ are the same as defined above]. 1 Equivalent of the obtained compound represented by the formula (VI) and from 1 to 10 equivalents of a compound represented by the formula (VII) [wherein $R^1$ is the same as defined above, $J^2$ is a chlorine atom, a bromine atom, an iodine atom, a $C_1$-$C_4$ alkylsulfonate group (such as a methanesulfonyloxy group), a $C_1$-$C_4$ haloalkylsulfoante group (such as a trifluoromethanesulfonyloxy group) or the like] are reacted, if necessary in an atmosphere of an inert gas such as nitrogen or argon, if necessary in a solvent such as benzene, toluene, dichloromethane, chloroform, tetrahydrofuran, acetone, acetonitrile, N,N-dimethylformamide, dimethylsulfoxide, water or a mixture of two or more of them in any ratio, if necessary in the presence of a base such as sodium hydride, sodium methoxide, sodium ethoxide, sodium hydroxide, potassium hydroxide, sodium carbonate, potassium carbonate, cesium carbonate or triethylamine in an amount of from 1 to 3 equivalents per 1 equivalent of the compound represented by the formula (VI), if necessary with tetrabutylammonium bromide, potassium iodide or the like as a catalyst in an amount of from 0.01 to 1 equivalent per 1 equivalent of the compound represented by the formula (VI), within a temperature range of from room temperature to the refluxing temperature of the reaction mixture for from 1 to 24 hours to obtain a compound of the present invention represented by the formula (I) [wherein $G^1$, $G^2$, W, $R^1$, $R^2$, $R^3$ and $R^4$ are the same as defined above].

The compounds represented by the formula (VII) used in this process are known compounds, and some of them are commercially available. The rest of them can be synthesized in accordance with known methods disclosed in the literature regarding known compounds.

Process D

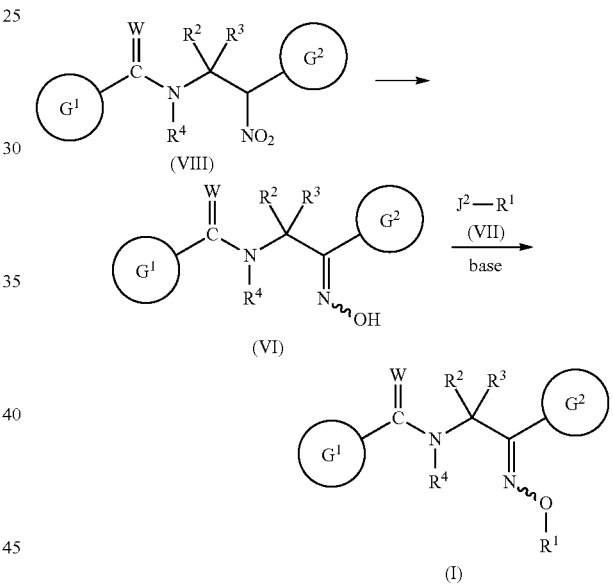

A compound represented by the formula (VIII) [wherein $G^1$, $G^2$, W, $R^2$, $R^3$ and $R^4$ are the same as defined above] is reacted, for example, with sodium nitrite by a method in accordance with J. Org. Chem., 2004, vol. 69, p. 8997, etc., with tin(II) chloride-phenylmercaptan by a method in accordance with Tetrahedron, 1990, vol. 46, p. 587, etc., or with carbon disulfide by a method in accordance with J. Org. Chem., 1983, vol. 48, p. 2766, etc., to obtain a compound represented by the formula (VI) [wherein $G^1$, $G^2$, W, $R^2$, $R^3$ and $R^4$ are the same as defined above].

The compound represented by formula (VI) thus obtained may be reacted with a compound represented by the formula (VII) [wherein $R^1$ and $J^2$ are the same as defined above] in the same manner as in process C to obtain a compound of the present invention represented by the formula (I) [wherein $G^1$, $G^2$, W, $R^1$, $R^2$, $R^3$ and $R^4$ are the same as defined above].

Process E

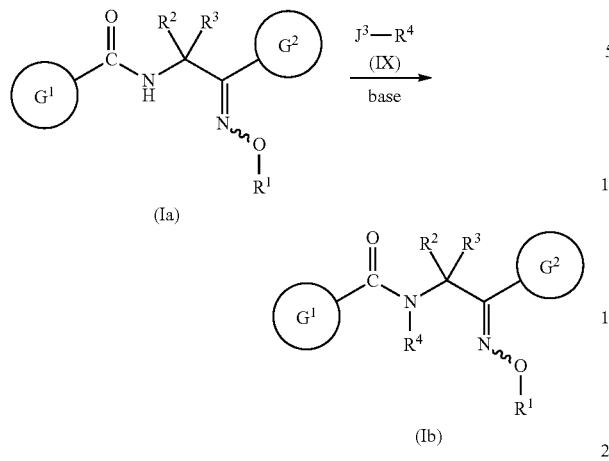

Process F

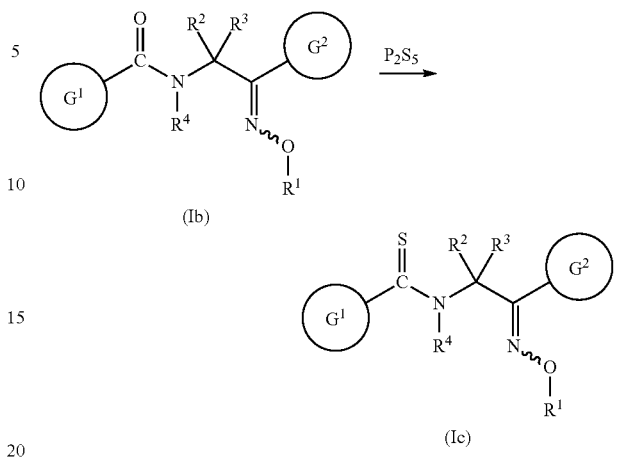

1 Equivalent of a compound of the present invention represented by the formula (Ia) [wherein $G^1$, $G^2$, $R^1$, $R^2$ and $R^3$ are the same as defined above] which is a compound of the formula (I) wherein W is an oxygen atom and $R^4$ is a hydrogen atom, is reacted with from 1 to 10 equivalents of a compound represented by the formula (IX) [wherein $R^4$ is the same as defined above except for a hydrogen atom, and $J^3$ is a favorable leaving group such as a chlorine atom, a bromine atom, an iodine atom, a $C_1$-$C_4$ alkylcarbonyloxy group (such as a pivaloyloxy group), a $C_1$-$C_4$ alkylsulfonate (such as a methanesulfonyloxy group), a $C_1$-$C_4$ haloalkylsulfonate group (such as a trifluoromethanesulfonyloxy group), an arylsulfonate group (such as a benzenesulfonyloxy group or a p-toluenesulfonyloxy group), an azolyl group (such as an imidazol-1-yl group) or the like], if necessary in a polar solvent such as tert-butyl methyl ether, tetrahydrofuran, 1,4-dioxane, acetonitrile or N,N-dimethylformamide, if necessary in the presence of a base such as sodium hydride, potassium tert-butoxide, potassium hydroxide, potassium carbonate, triethylamine or pyridine in an amount of from 1 to 3 equivalents per 1 equivalent of the compound represented by the formula (Ia), within a temperature range of from 0 to 90° C. for from 10 minutes to 24 hours to obtain a compound of the present invention represented by the formula (Ib) [wherein $G^1$, $G^2$, $R^1$, $R^2$ and $R^3$ are the same as defined above, and $R^4$ is the same as defined above except for a hydrogen atom] which is a compound of the formula (I) wherein W is an oxygen atom.

Some of the compounds represented by the formula (IX) used in this process are known compounds, and some of them are commercially available. The rest of them can be synthesized in accordance with known methods disclosed in the literature regarding known compounds, for example, the method disclosed in Chem. Pharm. Bull., 1986, vol. 34, p. 540 and 2001, vol. 49, p. 1102, J. Am. Chem. Soc., 1964, vol. 86, p. 4383, J. Org. Chem., 1983, vol. 48, p. 5280, Org. Synth., 1988, collective vol. 6, p. 101, Synlett, 2005, p. 2847, Synthesis, 1990, p. 1159, JP05/125017, EP0,051,273, GB2,161,802 or the like.

1 Equivalent of a compound of the present invention represented by the formula (Ib) [wherein $G^1$, $G^2$, $R^1$, $R^2$, $R^3$ and $R^4$ are the same as defined above] which is a compound of the formula (I) wherein W is an oxygen atom, and from 1 to 10 equivalents of a sulfidizing agent such as phosphorus pentasulfide, phosphorus pentasulfide-HMDO (hexamethyldisiloxane) or Lawesson's Reagent (2,4-bis(4-methoxyphenyl)-1,3,2,4-dithiadiphosphetane=2,4-disulfide) are reacted, if necessary in a solvent such as benzene, toluene, chlorobenzene, dichloromethane, chloroform, 1,2-dimethoxyethane, tetrahydrofuran, 1,4-dioxane or HMPA, if necessary in the presence of a base such as sodium hydrogen carbonate, triethylamine or pyridine in an amount of from 1 to 4 equivalents per 1 equivalent of the compound represented by the formula (Ib), within a temperature range of from room temperature to the refluxing temperature of the reaction mixture for from 10 minutes to 50 hours, or in pyridine as a base in an amount sufficient as a solvent within a temperature range of from 80° C. to the refluxing temperature of the reaction mixture for from 1 to 3 hours, to obtain a compound of the present invention represented by the formula (Ic) [wherein $G^1$, $G^2$, $R^1$, $R^2$, $R^3$ and $R^4$ are the same as defined above] which is a compound of the formula (I) wherein W is a sulfur atom.

In processes A to F, the reaction mixture after a reaction can be worked up by an ordinary procedure such as direct concentration, a procedure such that the reaction mixture is dissolved in an organic solvent, washed with water and concentrated, or a procedure such that the reaction mixture is poured into ice water, extracted with an organic solvent and concentrated, to obtain the desired oxime-substituted amide compound. If purification is needed, the desired oxime-substituted amide compound may be isolated or purified by an optional purification method such as recrystallization or fractionation by column chromatography, thin layer chromatography or liquid chromatography.

The compound represented by the formula (II) used in process A may be synthesized, for example, by reaction schemes 1 to 3.

Reaction Scheme 1

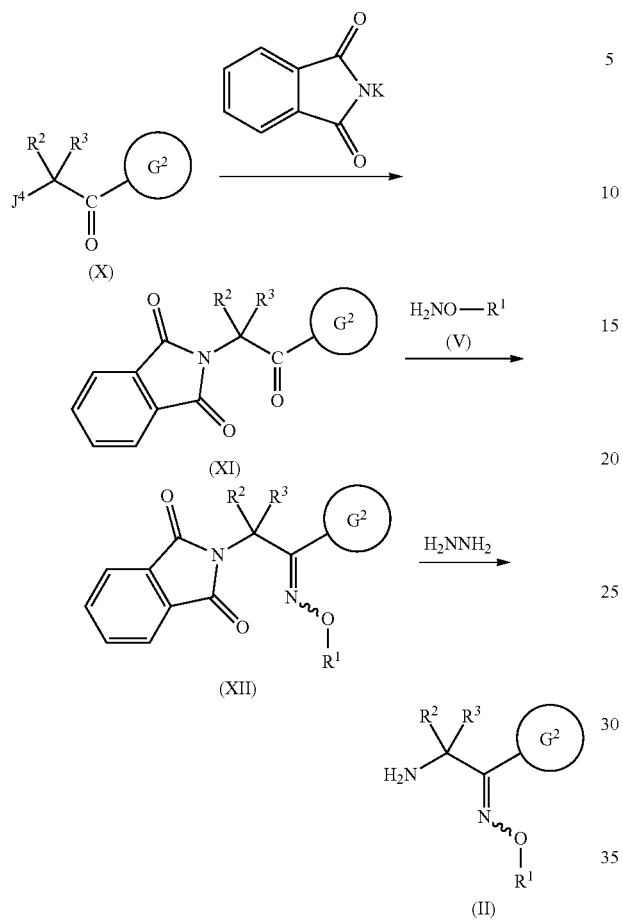

Reaction Scheme 2

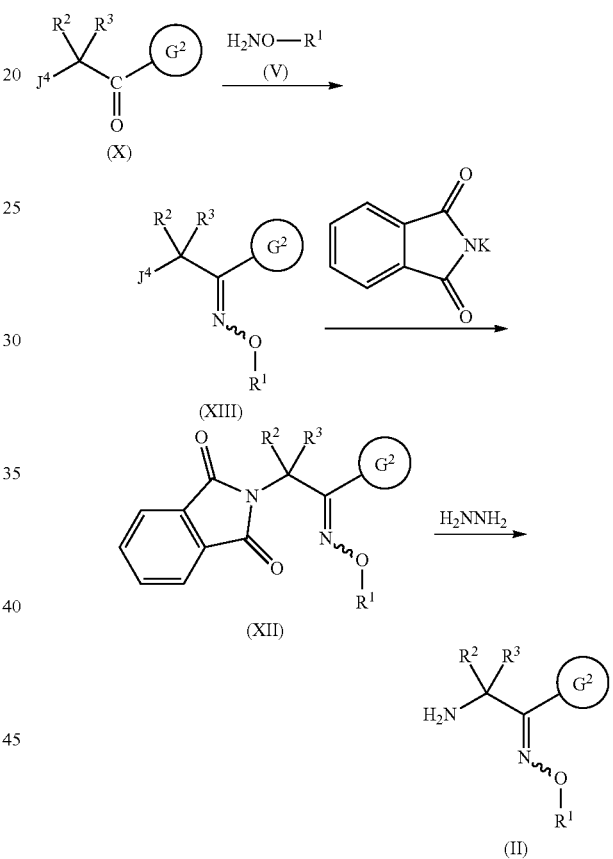

1 Equivalent of a compound represented by the formula (X) [wherein $G^2$, $R^2$ and $R^3$ are the same as defined above, and $J^4$ is a chlorine atom, bromine atom, an iodine atom or the like] and from 1 to 1.5 equivalents of potassium phthalimide are reacted, in a solvent such as toluene, dichloromethane, tetrahydrofuran, 1,4-dioxane, acetone, N,N-dimethylformamide, N,N-dimethylacetamide or dimethylsulfoxide, if necessary in the presence of from 0.1 to 2 equivalents of a base such as sodium carbonate, potassium carbonate or sodium hydrogen carbonate, if necessary with from 0.1 to 1 equivalent of tetrabutylammonium iodide, tributylhexadecylphosphonium bromide, crown ether (18-Crown-6) or the like as a catalyst, within a temperature range of from room temperature to the refluxing temperature of the reaction mixture for from 0.5 to 24 hours to obtain a compound represented by the formula (XI) [wherein $G^2$, $R^2$ and $R^3$ are the same as defined above]. The obtained compound represented by the formula (XI) is reacted with a compound represented by the formula (V) [wherein $R^1$ is the same as defined above] under the same conditions as in process B to obtain a compound represented by the formula (XII) [wherein $G^2$, $R^1$, $R^2$ and $R^3$ are the same as defined above].

Then, the compound represented by the formula (XII) is reacted with hydrazine monohydrate or aqueous hydrazine in an amount of from 1 to 4 equivalents per 1 equivalent of the compound represented by the formula (XII), if necessary in a solvent such as toluene, dichloromethane, chloroform, methanol, ethanol, tetrahydrofuran, 1,4-dioxane, water or a mixture of two or more of them in any ratio, if necessary in an atmosphere of an inert gas such as nitrogen or argon, within a temperature range of from room temperature to the refluxing temperature of the reaction mixture for from 1 to 24 hours to obtain a compound represented by the formula (II) [wherein $G^2$, $R^1$, $R^2$ and $R^3$ are the same as defined above].

Some of the compounds represented by the formula (X) used in this process are known compounds, and some of them are commercially available. The rest of them can be synthesized in accordance with known methods disclosed in the literature regarding known compounds.

A compound represented by the formula (X) [wherein $G^2$, $R^2$, $R^3$ and $J^4$ are the same as defined above] and the compound represented by the formula (V) [wherein $R^1$ is the same as defined above] are reacted under the same conditions as in process B to obtain a compound represented by the formula (XIII) [wherein $G^2$, $R^1$, $R^2$, $R^3$ and $J^4$ are the same as defined above], and the obtained compound represented by the formula (XIII) is reacted with potassium phthalimide in the same manner as in reaction scheme 1 to obtain a compound represented by the formula (XII) [wherein $G^2$, $R^1$, $R^2$ and $R^3$ are the same as defined above].

Then, the compound represented by the formula (XII) is reacted with hydrazine monohydrate or aqueous hydrazine in the same manner as in reaction scheme 1 to obtain a compound represented by the formula (II) [wherein $G^2$, $R^1$, $R^2$, and $R^3$ are the same as defined above].

Reaction Scheme 3

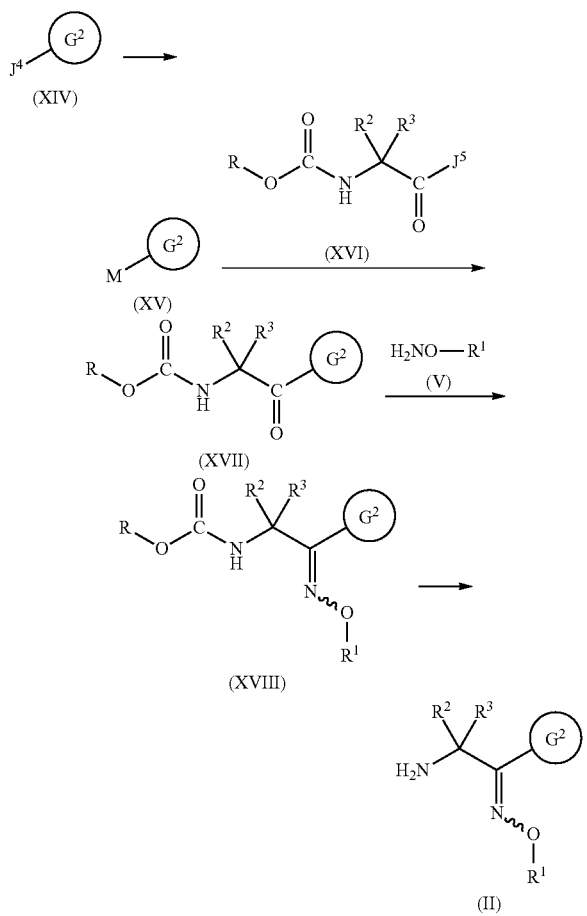

A known compound represented by the formula (XIV) [wherein $G^2$ is the same as defined above, and $J^4$ is a hydrogen atom, a chlorine atom, a bromine atom, an iodine atom or the like] is reacted with an alkyllithium, a Grignard reagent or the like in accordance with a method disclosed in Tetrahedron Lett., 2002, vol. 43, p. 8223 and 2005, vol. 46, p. 8587, J. Org. Chem., 2006, vol. 71, p. 9861, etc., to prepare a compound represented by the formula (XV) [wherein $G^2$ is the same as defined above, and M is Li, MgCl, MgBr, MgI or the like], and the prepared compound represented by the formula (XV) and a compound represented by the formula (XVI) [wherein $R^2$ and $R^3$ are the same as defined above, R is a tert-butyl group, a benzyl group or the like, and $J^5$ is a dimethylamino group, a N-methylmethoxyamino group, a piperidin-1-yl group, a benzotriazol-1-yl group or the like] are reacted to obtain a compound represented by the formula (XVII) [wherein $G^2$, $R^2$, $R^3$ and R are the same as defined above].

Some of the compounds represented by the formula (XVI) are known compounds, and some of them are commercially available. The rest of them can be synthesized in accordance with known methods disclosed in the literature regarding known compounds.

Then, the compound represented by the formula (XVII) and a compound represented by the formula (V) [wherein $R^1$ is the same as defined above] are reacted under the same conditions as in process B to obtain a compound represented by the formula (XVIII) [wherein $G^2$, $R^1$, $R^2$, $R^3$ and R are the same as defined above]. The obtained compound represented by the formula (XVIII) is deprotected under known reaction conditions with respect to the substituent R to obtain a compound represented by the formula (II) [wherein $G^2$, $R^1$ $R^2$, and $R^3$ are the same as defined above] or its salt (such as a hydrochloride, a hydrobromide, a trifluoroacetate or a p-toluenesulfonate).

The compound represented by the formula (IV) used in processes B and C may be synthesized, for example, by reaction scheme 4 or 5.

Reaction Scheme 4

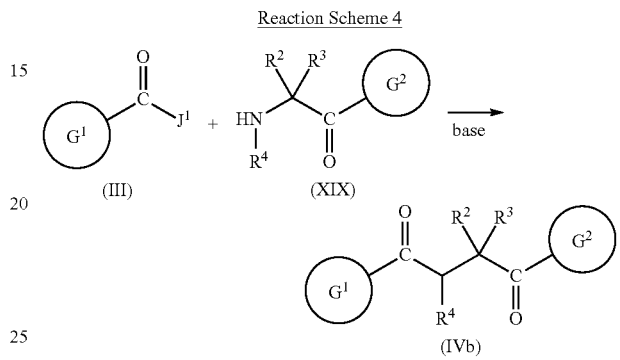

A compound represented by the formula (III) [wherein $G^1$ and $J^1$ are the same as defined above] and a compound represented by the formula (XIX) [wherein $G^2$, $R^2$ and $R^3$ are the same as defined above, and $R^4$ is a hydrogen atom, a $C_1$-$C_6$ alkyl group or the like] or its salt (such as a hydrochloride, a hydrobromide, a trifluoroacetate or a p-toluenesulfonate) are reacted under the same conditions as in process A to obtain a compound represented by the formula (IVb) [wherein $G^1$, $G^2$, $R^2$ and $R^3$ are the same as defined above, and $R^4$ is a hydrogen atom, a $C_1$-$C_6$ alkyl group or the like] which is a compound of the formula (IV) wherein W is an oxygen atom.

Reaction Scheme 5

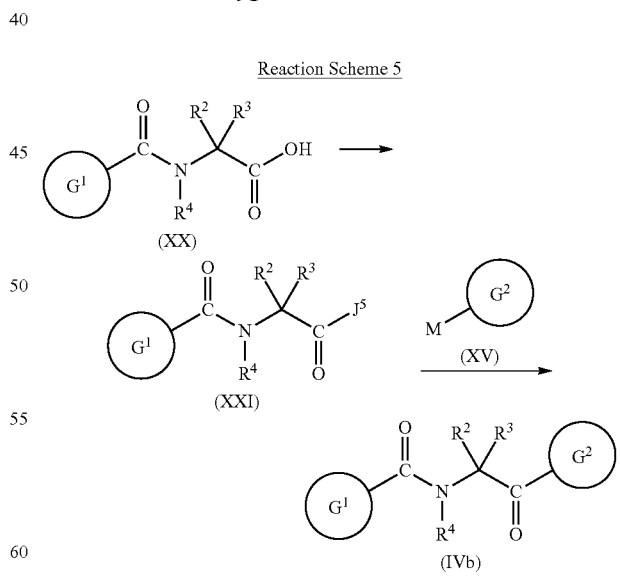

A compound represented by the formula (XX) [wherein $G^1$, $R^2$, $R^3$ and $R^4$ are the same as defined above] is reacted for example by a method disclosed in J. Med. Chem., 2004, vol. 47, p. 6884, Bioorganic & Med. Chem. Lett., 2012, vol. 22, p. 5485, etc. to prepare a compound represented by the formula (XXI) [wherein $G^1$, $R^2$, $R^3$, $R^4$ and $J^5$ are the same as defined above], and the obtained compound represented by the formula (XXI) is reacted with a compound represented by the formula (XV) [wherein $G^2$ and M are the same as defined above] in the same manner as in reaction scheme 3 to obtain a compound represented by the formula (IVb) [wherein $G^1$, $G^2$, $R^2$ and $R^3$ are the same as defined above, and $R^4$ is a hydrogen atom, a $C_1$-$C_6$ alkyl group or the like] which is a compound of the formula (IV) wherein W is an oxygen atom.

Some of the compounds represented by the formula (XX) used in this process are known compounds, and some of them are commercially available. The rest of them can be synthesized in accordance with known methods disclosed in the literature regarding known compounds.

Some of the compounds represented by the formula (V) used in process B are known compounds, and some of them are commercially available. The rest of them can be synthesized, for example, as follows.

Reaction Scheme 6

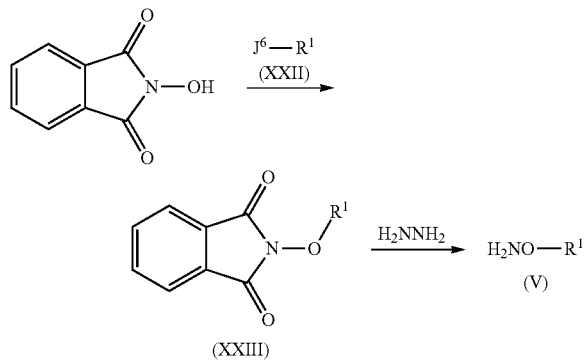

That is, N-hydroxyphthalimide and a compound represented by the formula (XXII) [wherein $R^1$ is the same as defined above, and $J^6$ is a chlorine atom, a bromine atom, an iodine atom or hydroxy group] are reacted, for example, in accordance with a method disclosed in J. Med. Chem., 2008, vol. 51, p. 4601, WO2008/055013, etc. to obtain a compound represented by the formula (XXIII) [wherein $R^1$ is the same as defined above], and the obtained compound represented by the formula (XXIII) is reacted with hydrazine monohydrate or aqueous hydrazine under the same conditions as in reaction scheme 1 to obtain a compound represented by the formula (V) [wherein $R^1$ is the same as defined above].

Some of the compounds represented by the formula (XXII) used in this process are known compounds, and some of them are commercially available. The rest of them can be synthesized in accordance with known methods disclosed in the literature regarding known compounds.

The compound represented by the formula (VIII) used in process D may be synthesized, for example, as follows.

Reaction Scheme 7

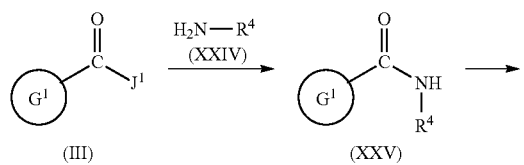

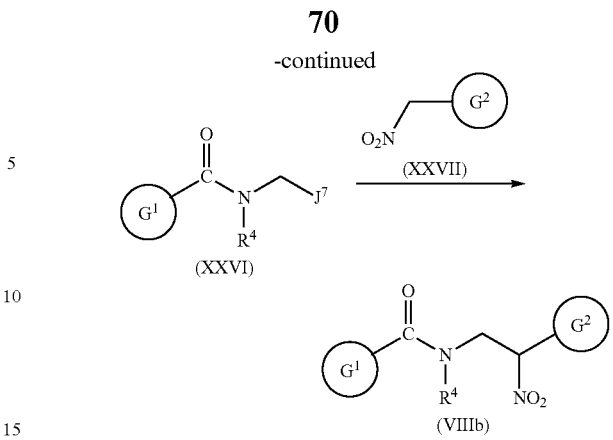

That is, a compound represented by the formula (III) [wherein $G^1$ and $J^1$ are the same as defined above] and a compound represented by the formula (XXIV) [wherein $R^4$ is a hydrogen atom, a $C_1$-$C_6$ alkyl group or the like] or its salt (such as a hydrochloride) are reacted under the same conditions as in process A to obtain a compound represented by the formula (XXV) [wherein $G^1$ is the same as defined above, and $R^4$ is a hydrogen atom, a $C_1$-$C_6$ alkyl group or the like].

The primary amines represented by the formula (XXIV) used in this process are known compounds, and some of them are commercially available. The rest of them can be synthesized in accordance with known methods disclosed in the literature regarding known primary amines.

Then, the obtained compound represented by the formula (XXV) is reacted, for example, in accordance with a method disclosed in WO2007/026965, Tetrahedron Lett., 1994, vol. 35, p. 7107, WO2006/067103, J. Org. Chem., 1987, vol. 52, p. 5475, etc. to obtain a compound represented by the formula (XXVI) [wherein $G^1$ is the same as defined above, $R^4$ is a hydrogen atom, a $C_1$-$C_6$ alkyl group or the like, and $J^7$ is a chlorine atom, a $C_1$-$C_4$ alkylcarbonyloxy group (such as an acetoxy group), a $C_1$-$C_4$ alkylsulfonate group (such as a methanesulfonyloxy group) or an arylsulfonate group (such as a benzenesulfonyloxy group)].

The obtained compound represented by the formula (XXVI) and a compound represented by the formula (XXVII) [wherein $G^2$ is the same as defined above] are reacted, for example, in accordance with a method disclosed in Bull. Chem. Soc. Jpn., 2004, vol. 77, p. 2219, Tetrahedron Lett., 2006, vol. 47, p. 3501, J. Org. Chem., 2004, vol. 69, p. 8997, etc. to obtain a compound represented by the formula (VIIIb) [wherein $G^1$ and $G^2$ are the same as defined above, and $R^4$ is a hydrogen atom, a $C_1$-$C_6$ alkyl group or the like] which is the compound of the formula (VIII) wherein W is an oxygen atom, and $R^2$ and $R^3$ are hydrogen atoms.

The compound represented by the formula (XIX) may be produced by deprotecting a compound represented by the formula (XVII) obtainable by reaction scheme 3 by a known method or may be synthesized, for example, by any of reaction schemes 8 to 11.

Reaction Scheme 8

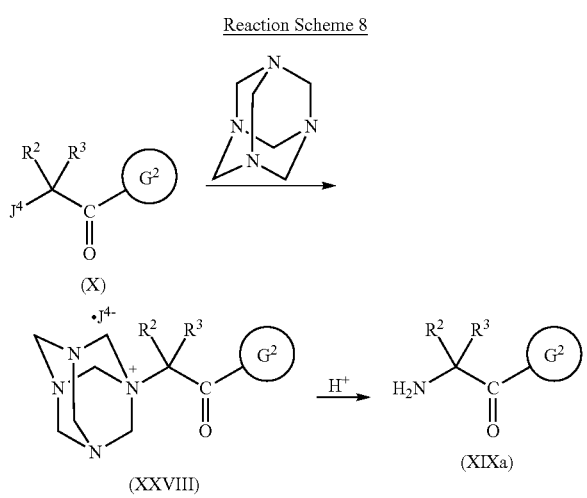

A compound represented by the formula (X) [wherein $G^2$, $R^2$, $R^3$ and $J^4$ are the same as defined above] and hexamethylenetetramine are reacted, for example, in accordance with a method disclosed in J. Heterocyclic Chem., 1987, vol. 24, p. 297 etc., if necessary in a solvent such as toluene, dichloromethane, chloroform, ethanol, diethyl ether, tetrahydrofuran, acetone, ethyl acetate, acetonitrile, water or a mixture of two or more of them in any ratio, if necessary with sodium iodide or the like, within a temperature range of from room temperature to the refluxing temperature of the reaction mixture for from 1 to 24 hours to obtain a quaternary ammonium salt represented by the formula (XXVIII) [wherein $G^2$, $R^2$, $R^3$ and $J^4$ are the same as defined above]. The obtained quaternary ammonium salt represented by the formula (XXVIII) is hydrolyzed in a solvent such as methanol, ethanol, acetonitrile, water or a mixture of two or more of them in any ratio, in the presence of an acid catalyst such as hydrochloric acid or hydrobromic acid within a temperature range of from room temperature to the refluxing temperature of the reaction mixture for from 0.5 to 48 hours to obtain a hydrochloride or hydrobromide of a compound represented by the formula (XIXa) [wherein $G^2$, $R^2$ and $R^3$ are the same as defined above] which is a compound of the formula (XIX) wherein $R^4$ is a hydrogen atom. Further, after completion of the reaction, by neutralization with a base such as sodium hydroxide or potassium hydroxide, a free amine may be isolated.

Reaction Scheme 9

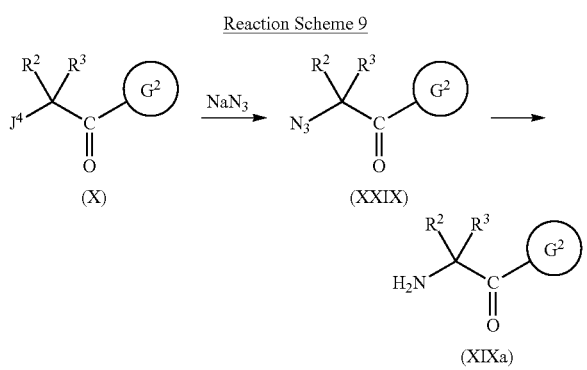

A compound represented by the formula (X) [wherein $G^2$, $R^2$, $R^3$ and $J^4$ are the same as defined above] and sodium azide or lithium azide are reacted, for example, in accordance with a method disclosed in J. Org. Chem., 1986, vol. 51, p. 3374, etc., if necessary in a solvent such as toluene, methanol, tetrahydrofuran, acetone, N,N-dimethylformamide, acetonitrile, dimethylsulfoxide, water or a mixture of two or more of them in any ratio, if necessary with methyl trioctylammonium chloride, potassium iodide or the like as a catalyst, within a temperature range of from 0 to 50° C. for from 0.5 to 18 hours to obtain a compound represented by the formula (XXIX) [wherein $G^2$, $R^2$ and $R^3$ are the same as defined above]. The obtained compound represented by formula (XXIX) is hydrogenated in a solvent such as methanol, ethanol, diethyl ether, water or a mixture of two or more of them in any ratio in the presence of palladium or a platinum catalyst, if necessary with hydrochloric acid or the like, in an atmosphere of hydrogen under 1 to 10 atm at room temperature for from 0.5 to 24 hours; is reacted with a reducing agent such as tin(II) chloride in a solvent such as dichloromethane, methanol, ethanol or ethyl acetate within a temperature range of from room temperature to 60° C. for from 3 to 18 hours; or is reacted with triphenylphosphine and water in a solvent such as tetrahydrofuran, water or a mixture of the two in any ratio within a temperature range of from 0° C. to room temperature for from 0.5 to 24 hours, to obtain a compound (XIXa) [wherein $G^2$, $R^2$ and $R^3$ are the same as defined above] which is a compound of the formula (XIX) wherein $R^4$ is a hydrogen atom. Further, after completion of the reaction if necessary, the compound of the formula (XIXa) may be treated with hydrochloric acid, hydrobromic acid, trifluoroacetic acid, p-toluenesulfonic acid or the like to obtain a salt thereof.

Reaction Scheme 10

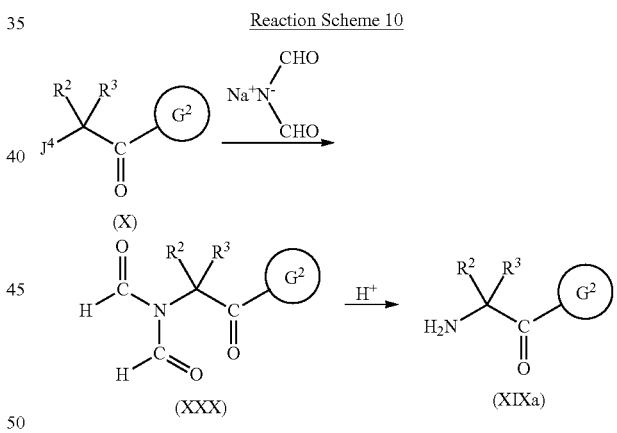

A compound represented by the formula (X) [wherein $G^2$, $R^2$, $R^3$ and $J^4$ are the same as defined above] and diformylimide sodium salt are reacted, for example, in accordance with a method disclosed in Tetrahedron Lett., 1989, vol. 30, p. 5285 etc., in a solvent such as N,N-dimethylformamide or acetonitrile within a temperature range of from room temperature to the refluxing temperature of the reaction mixture for from 2 to 24 hours to obtain a compound represented by the formula (XXX) [wherein $G^2$, $R^2$ and $R^3$ are the same as defined above]. The obtained compound represented by the formula (XXX) is hydrolyzed in a solvent such as methanol, ethanol, 1,4-dioxane, water or a mixture of two or more of them in any ratio with an acid such as hydrochloric acid within a temperature range of from room temperature to the refluxing temperature of the reaction mixture for from 1 to 24 hours to obtain a hydrochloride or the like of a compound represented by the formula (XIXa) [wherein $G^2$, $R^2$ and $R^3$ are the same as defined above] which is a compound of the formula (XIX) wherein $R^4$ is a hydrogen atom. Further, after completion of the reaction, by neutralization with a base such as sodium hydroxide or potassium hydroxide, a free amine may be isolated.

Reaction Scheme 11

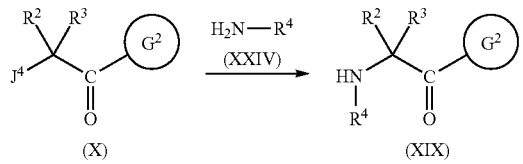

A compound represented by the formula (X) [wherein $G^2$, $R^2$, $R^3$ and $J^4$ are the same as defined above] and an amine represented by the formula (XXIV) [wherein $R^4$ is a hydrogen atom, a $C_1$-$C_6$ alkyl group or the like] or its salt are reacted, if necessary in a solvent such as toluene, dichloromethane, methanol, ethanol, diethyl ether, tetrahydrofuran, 4-methyl-2-pentanone, ethyl acetate, N,N-dimethylformamide, acetonitrile, water or a mixture of two or more of them in any ratio, in an excessive amount of the compound represented by the formula (XXIV) or in the presence of a base such as sodium hydroxide, potassium carbonate, sodium carbonate, sodium hydrogen carbonate, triethylamine or ethyldiisopropylamine, within a temperature range of from 0° C. to the refluxing temperature of the reaction mixture for from 1 to 24 hours to obtain a compound represented by the formula (XIX) [wherein $G^2$, $R^2$ and $R^3$ are the same as defined above, and $R^4$ is a hydrogen atom, a $C_1$-$C_6$ alkyl group or the like].

Some of the compounds represented by the formula (XXVII) are known compounds, and some of them are commercially available. The rest of them may be synthesized, for example, by reaction scheme 12 or 13.

Reaction Scheme 12

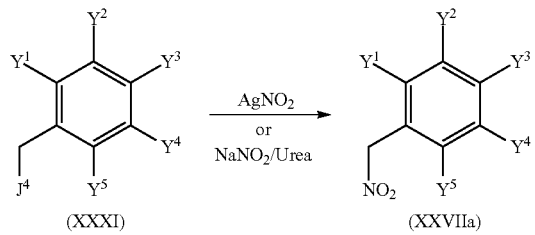

A compound represented by the formula (XXXI) [wherein $Y^1$, $Y^2$, $Y^3$, $Y^4$, $Y^5$ and $J^4$ are the same as defined above] is reacted with silver nitrite in accordance with a known method disclosed in the literature, for example, a method disclosed in J. Org. Chem., 2004, vol. 69, p. 6907, etc., if necessary in a solvent such as benzene, diethyl ether, tert-butyl methyl ether, acetonitrile, water or a mixture of two or more of them in any ratio, within a temperature range of from 0° C. to room temperature for from 30 minutes to 24 hours, or reacted with sodium nitrite-urea, for example, in accordance with a method disclosed in Tetrahedron, 2009, vol. 65, p. 1660, etc., if necessary in a solvent such as N,N-dimethylformamide within a temperature range of from −78° C. to room temperature for from 1 to 6 hours, to obtain a compound represented by the formula (XXVIIa) [wherein $Y^1$, $Y^2$, $Y^3$, $Y^4$ and $Y^5$ are the same as defined above] which is a compound of the formula (XXVII) wherein $G^2$ is $G^2$-1.

The compounds represented by the formula (XXXI) used are known compounds, and some of them are commercially available. The rest of them can be synthesized from known compounds in accordance with known methods disclosed in the literature.

Reaction Scheme 13

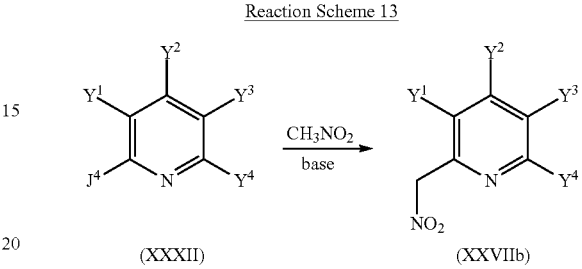

A compound represented by the formula (XXXII) [wherein $Y^1$, $Y^2$, $Y^3$, $Y^4$ and $J^4$ are the same as defined above] and nitromethane are reacted in accordance with a known method disclosed in the literature, for example, a method disclosed in Heterocycles, 1987, vol. 26, p. 3259, WO2004/096772, etc., if necessary in a solvent such as tetrahydrofuran or dimethylsulfoxide, if necessary in the presence of a base such as sodium hydride or potassium tert-butoxide within a temperature range of from 0 to 80° C. for from 1 to 24 hours to obtain a compound of the formula (XXVIIb) [wherein $Y^1$, $Y^2$, $Y^3$ and $Y^4$ are the same as defined above] which is a compound of the formula (XXVII) wherein $G^2$ is $G^2$-2.

The compounds represented by the formula (XXXII) used in this process are known compounds, and some of them are commercially available. The rest of them can be synthesized in accordance with known methods disclosed in the literature regarding known compounds.

In the respective reaction schemes, the compounds after a reaction can be worked up by an ordinary procedure to obtain intermediates to be material compounds in processes A to D.

Further, the respective intermediates produced in such procedure may be used in the next step reaction without isolation nor purification.

As the oxime-substituted amide compounds of the present invention represented by the formula (I) which can be produced by such processes, specifically, the following compounds of a first group and compounds of a second group may, for example, be mentioned. However, the following compounds of a first group and compounds of a second group merely exemplify the present invention, and the oxime-substituted amide compounds of the present invention are by no means restricted thereto.

Further, combinations of substituents in the compounds of the above respective groups are shown in Tables 2 and 3. In the Tables, Et denotes ethyl group, n-Pr and Pr-n denote normal propyl group, i-Pr and Pr-i denote isopropyl group, c-Pr and Pr-c denote cyclopropyl group, n-Bu and Bu-n denote normal butyl group, i-Bu and Bu-i denote isobutyl group, s-Bu and Bu-s denote secondary butyl group, c-Bu and Bu-c denote cyclobutyl group, t-Bu and Bu-t denote tertiary butyl group, Pen denotes pentyl group, c-Pen and Pen-c denote cyclopentyl group, Hex denotes hexyl group, c-Hex and Hex-c denote cyclohexyl group, Ph denotes phenyl group, 1-Naph denotes 1-naphthyl group, and 2-Naph denotes 2-naphthyl group.
Further, in Tables 2 and 3, aromatic heterocyclic rings represented by D-1-1a to D-35-b have the following structures, respectively.
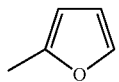
D-1-1a
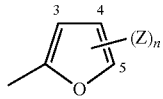
D-1-1b
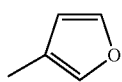
D-1-2a
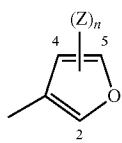
D-1-2b
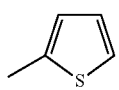
D-2-1a
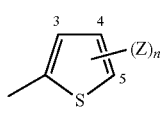
D-2-1b
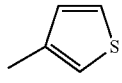
D-2-2a
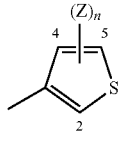
D-2-2b
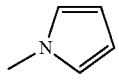
D-3-a
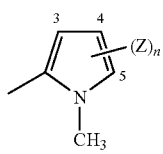
D-4-1b
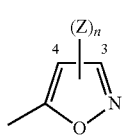
D-5-3b
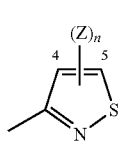
D-6-1b
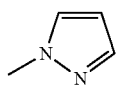
D-7-a
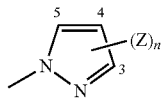
D-7-b
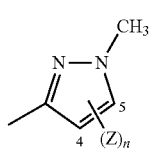
D-8-1b
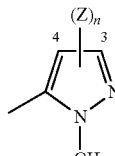
D-8-3b
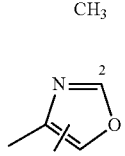
D-9-2b
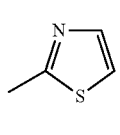
D-10-1a
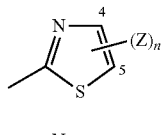
D-10-1b
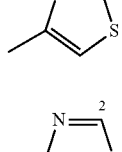
D-10-2a
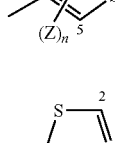
D-10-2b
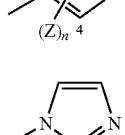
D-10-3b
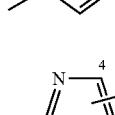
D-11-a
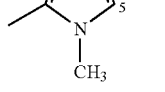
D-12-1b -continued
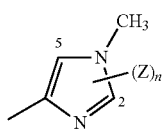 CH3  D-12-2b
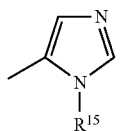  D-12-3a
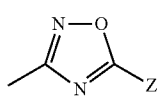  D-14-1b
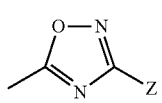  D-14-2b
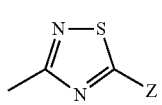  D-15-1b
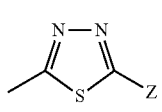  D-17-b
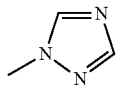  D-22-a
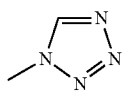  D-28-a
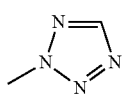  D-29-a
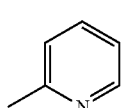  D-32-1a
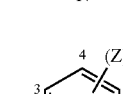  D-32-1b
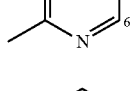  D-32-2a
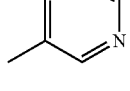  D-32-2b
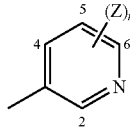  
-continued
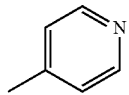  D-32-3a
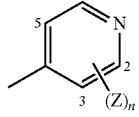  D-32-3b
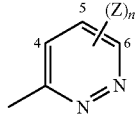  D-33-1b
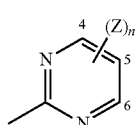  D-34-1b
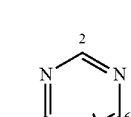  D-34-2b
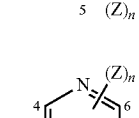  D-34-3b
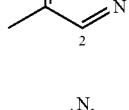  D-35-b
For example, the expression "CH$_2$(D-5-3b)-3-Cl" means a 3-chloroisoxazol-5-ylmethyl group.
In the Tables, aliphatic heterocyclic rings represented by E-2-1a to E-17-3a have the following structures, respectively.
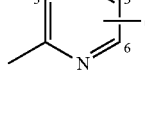  E-2-1a
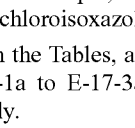  E-2-2a
  E-3-2a
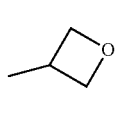  E-3-2b US 9,920,046 B2
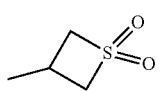 E-3-2c
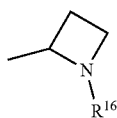 E-4-1a
 E-4-2a
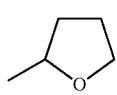 E-5-1a
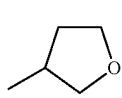 E-5-2a
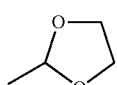 E-9-1a
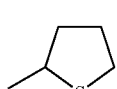 E-6-1a
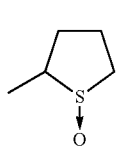 E-6-1b
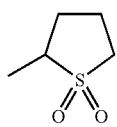 E-6-1c
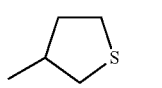 E-6-2a
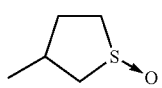 E-6-2b
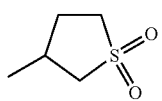 E-6-2c
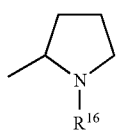 E-8-1a
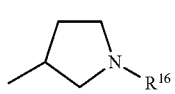 E-8-2a
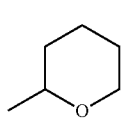 E-14-1a
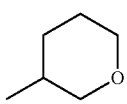 E-14-2a
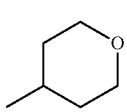 E-14-3a
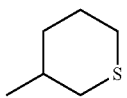 E-15-2a
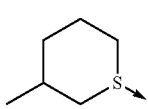 E-15-2b
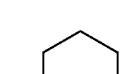 E-15-2c
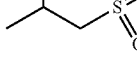 E-15-3a
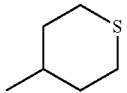 E-15-3b
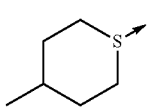 E-15-3c
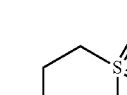 E-17-2a
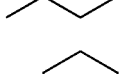 E-17-3a
For example, the expression "CH$_2$(E-4-1a)CHO" means a 1-formylazetidin-2-ylmethyl group.
In the Tables, partial saturated heterocyclic rings represented by M-3-b to M-19-a have the following structures, respectively.
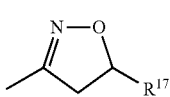 M-3-b
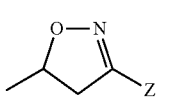 M-4-2a

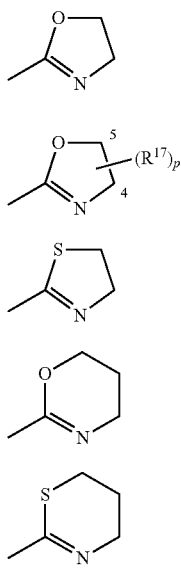
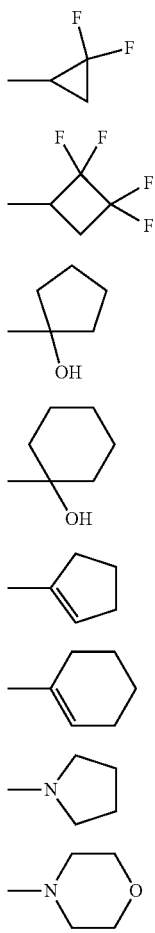
For example, the expression "CH₂(M-4-2a)CH₃" means a 3-methyl-4,5-dihydroisoxazol-5-ylmethyl group.
Further, in the Tables, T-1 to T-9 have the following structures, respectively.
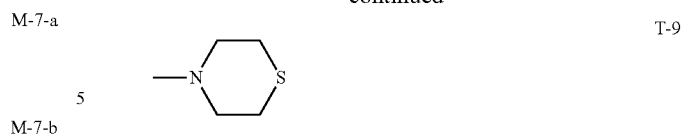
Compounds of First Group ([I]-1 to [I]-68)
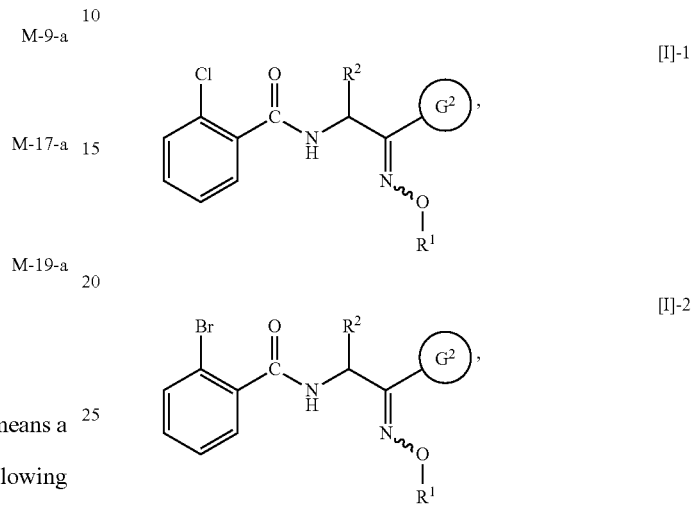

-continued
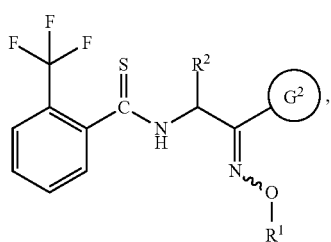
[I]-7
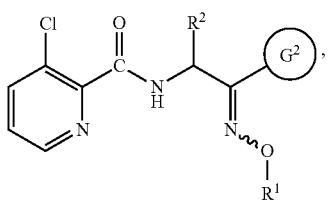
[I]-8
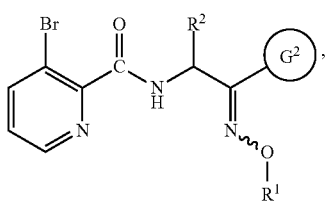
[I]-9
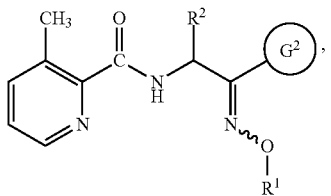
[I]-10
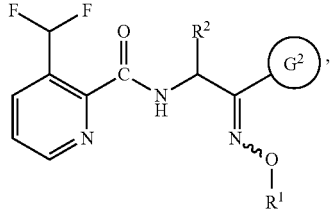
[I]-11
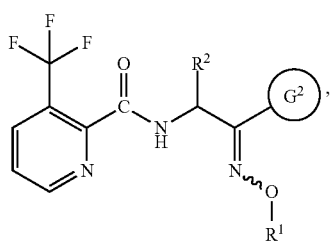
[I]-12
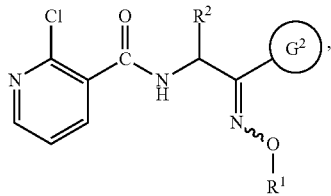
[I]-13
-continued
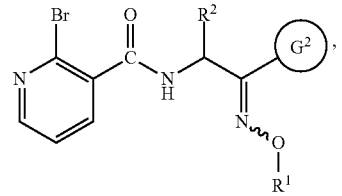
[I]-14
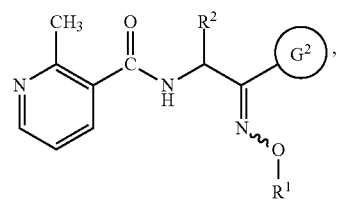
[I]-15
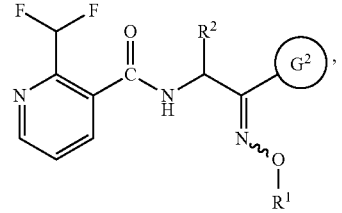
[I]-16
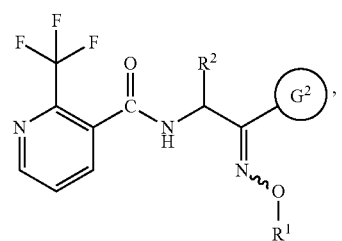
[I]-17
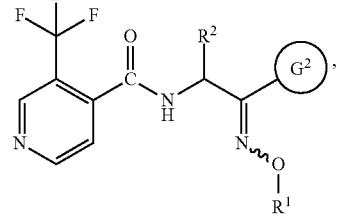
[I]-18
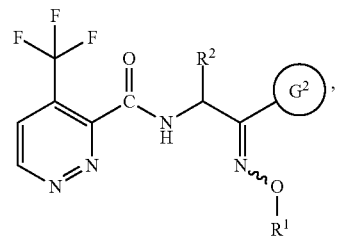
[I]-19
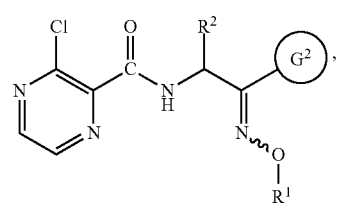
[I]-20

[I]-21
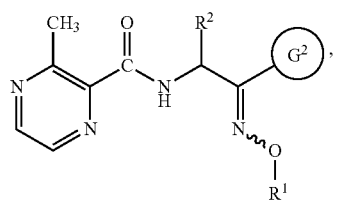
[I]-22
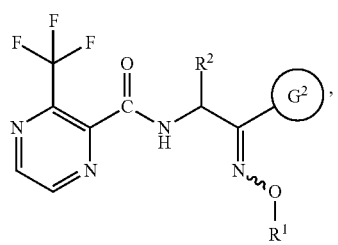
[I]-23
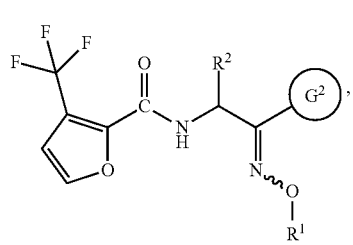
[I]-24
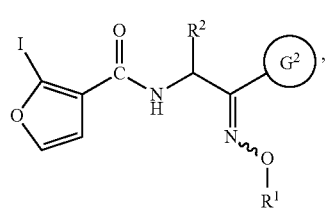
[I]-25
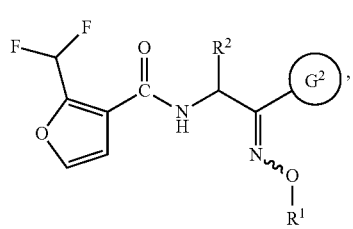
[I]-26
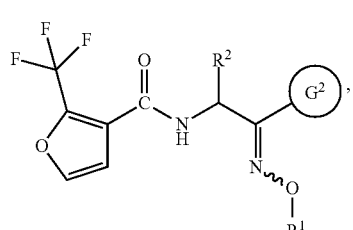
[I]-27
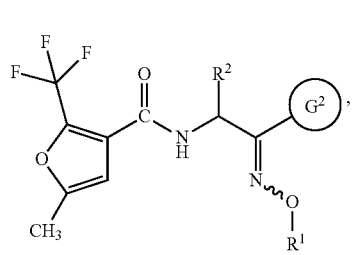
[I]-28
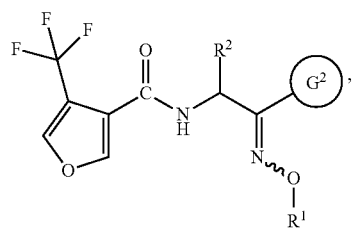
[I]-29
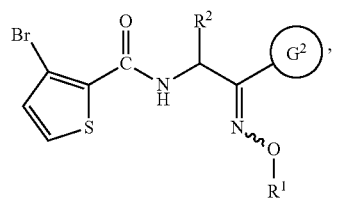
[I]-30
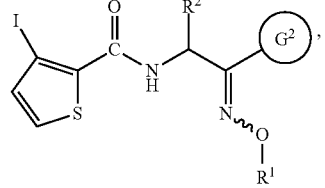
[I]-31
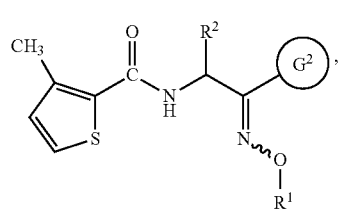
[I]-32
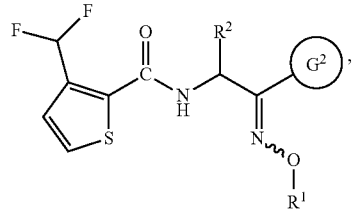
[I]-33
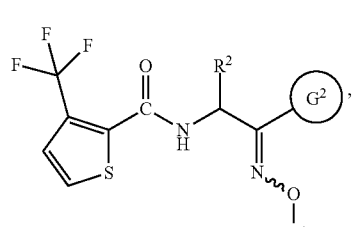
[I]-34
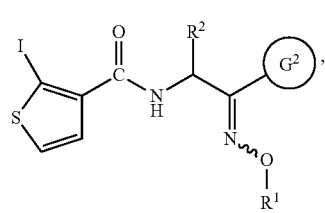

[I]-35
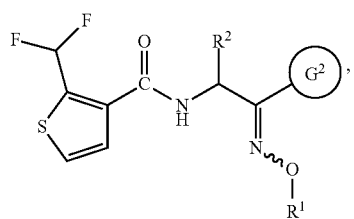
[I]-36
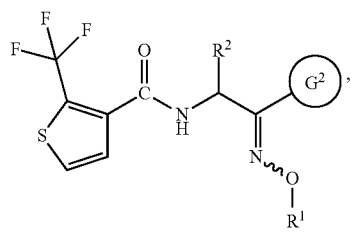
[I]-37
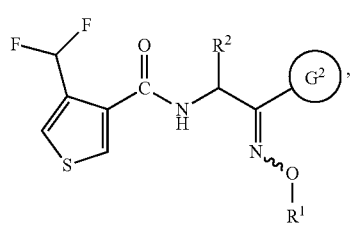
[I]-38
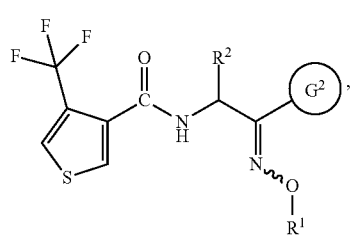
[I]-39
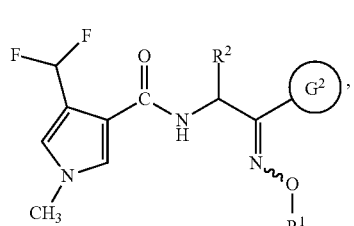
[I]-40
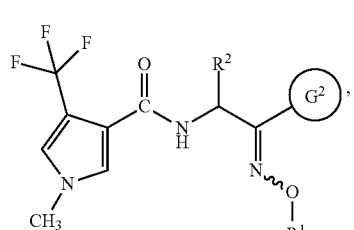
[I]-41
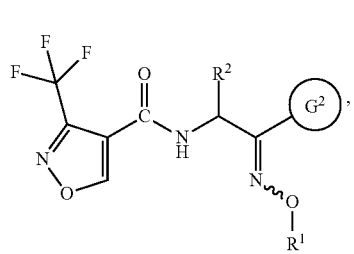
[I]-42
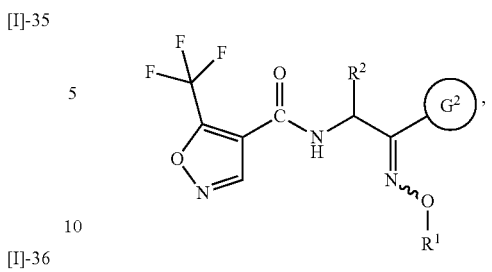
[I]-43
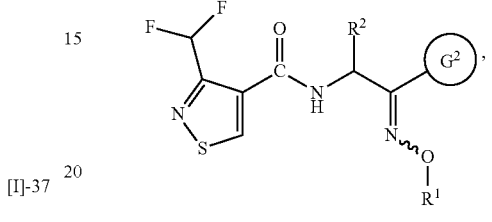
[I]-44
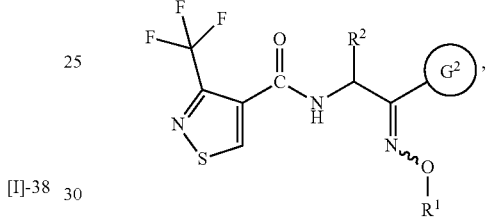
[I]-45
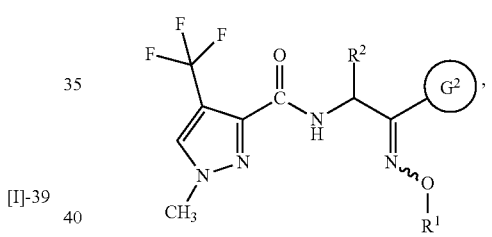
[I]-46
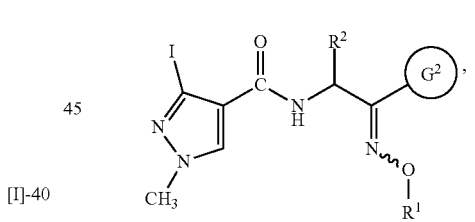
[I]-47
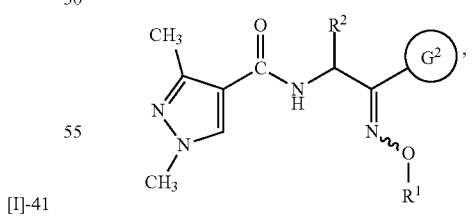
[I]-48
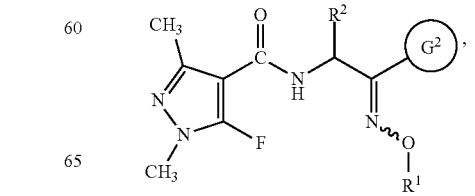

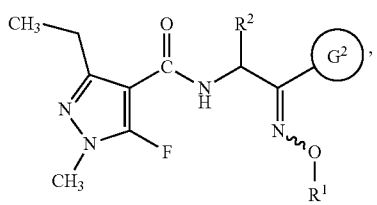
[I]-49
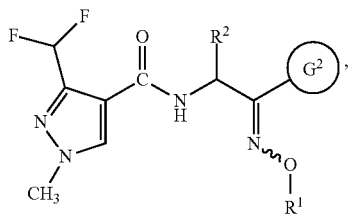
[I]-50
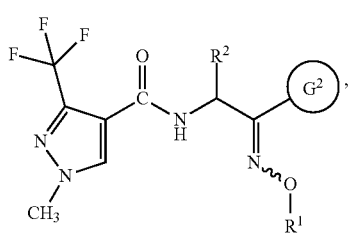
[I]-51
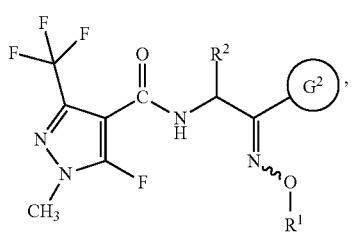
[I]-52
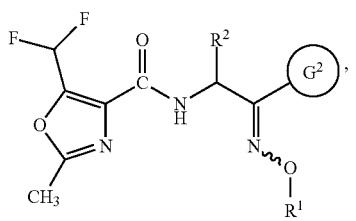
[I]-53
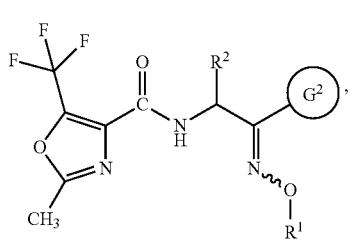
[I]-54
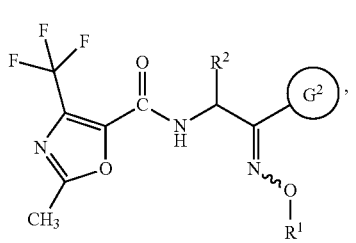
[I]-55
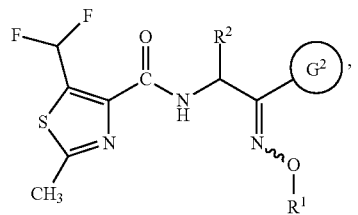
[I]-56
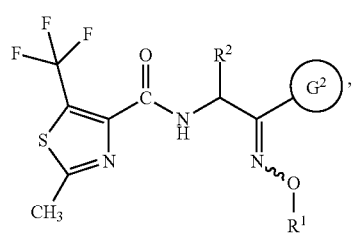
[I]-57
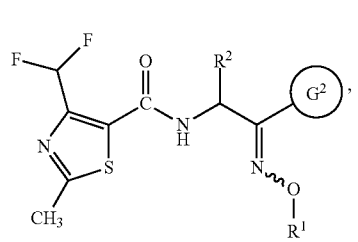
[I]-58
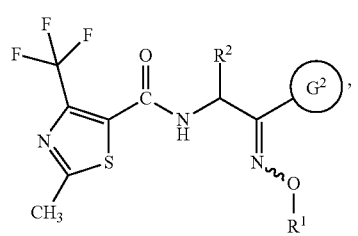
[I]-59
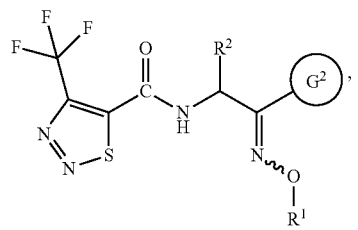
[I]-60
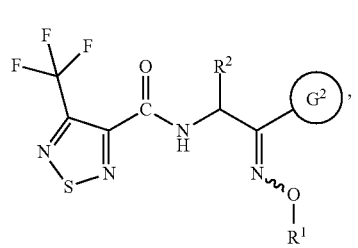
[I]-61
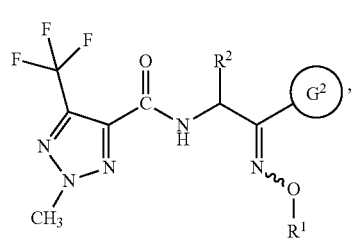
[I]-62

[I]-63 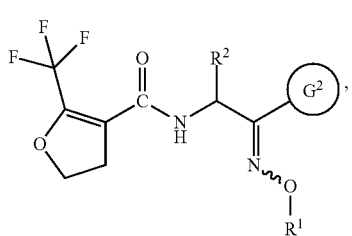

[I]-64 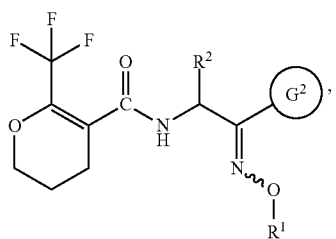

[I]-65 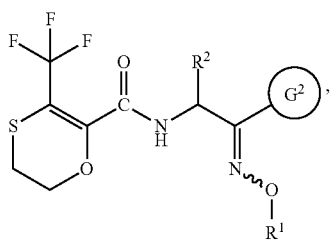

[I]-66 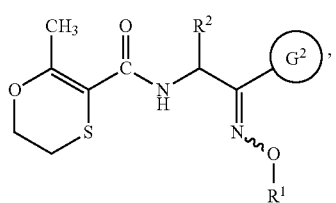

[I]-67 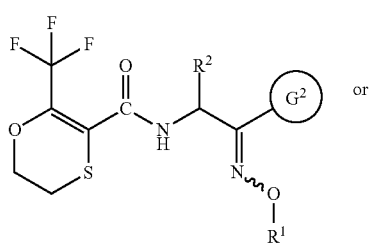 or

[I]-68 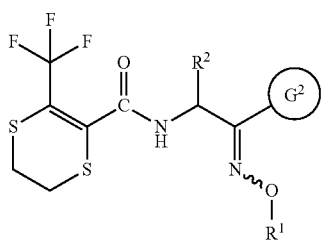

G²-1 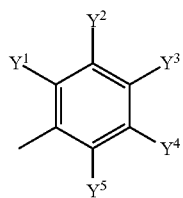

G²-2 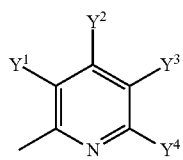

G²-3 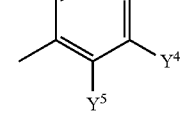

G²-4 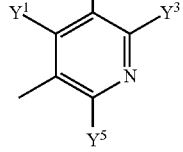

G²-6 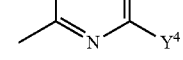

G²-7 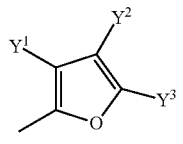

G²-8

G²-9 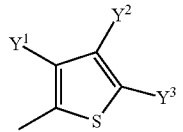

G²-10 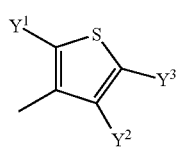

Combinations of substituents in the compounds of the above first group are shown in Table 2. In Table 2, the expression (R) or (S) in the column substituent $R^2$ means that the proportion of the R isomer or the S isomer is at least 90% in a mixture ratio of optical isomers due to the carbon atom attached to $R^2$.

The expressions G²-1 to G²-10 in the column substituent G² mean the following specific structures, respectively.

The expression "-" in the columns substituents $Y^2$, $Y^4$ and $Y^5$ means that there is no corresponding substituent present.

The expression (E) or (Z) in the column substituent $R^1$ means that the proportion of the E-isomer or the Z-isomer is at least 90% in a mixture ratio of oxime geometrical isomers attached to the substituent $R^1$.

TABLE 2

| R² | G² | Y¹ | Y² | Y³ | Y⁴ | Y⁵ | R¹ |
|---|---|---|---|---|---|---|---|
| CH₃ | G²-1 | H | H | H | H | H | CH₃ |
| CH₃ | G²-1 | H | H | F | H | H | CH₃ |
| CH₃ | G²-1 | H | H | Cl | H | H | CH₃ |
| CH₃ | G²-1 | H | H | CH₃ | H | H | CH₃ |
| CH₃ | G²-1 | H | H | Et | H | H | CH₃ |
| CH₃ | G²-1 | H | H | i-Pr | H | H | CH₃ |
| CH₃ | G²-1 | H | H | c-Hex | H | H | CH₃ |
| CH₃ | G²-1 | H | H | OCHF₂ | H | H | CH₃ |
| CH₃ | G²-1 | H | H | NO₂ | H | H | CH₃ |
| CH₃ | G²-1 | H | H | CN | H | H | CH₃ |
| CH₃ | G²-1 | H | F | F | H | H | CH₃ |
| CH₃ | G²-1 | H | F | Cl | H | H | CH₃ |
| CH₃ | G²-1 | H | Cl | H | H | H | CH₃ |
| CH₃ | G²-1 | H | Cl | H | Cl | H | CH₃ |
| CH₃ | G²-1 | H | Cl | F | H | H | CH₃ |
| CH₃ | G²-1 | H | Cl | Br | H | H | CH₃ |
| CH₃ | G²-1 | H | Cl | CH₃ | H | H | CH₃ |
| CH₃ | G²-1 | H | Cl | CH₃ | CH₃ | H | CH₃ |
| CH₃ | G²-1 | H | Br | H | H | H | CH₃ |
| CH₃ | G²-1 | H | Br | Cl | H | H | CH₃ |
| CH₃ | G²-1 | H | Br | Br | H | H | CH₃ |
| CH₃ | G²-1 | H | Br | OCF₃ | H | H | CH₃ |
| CH₃ | G²-1 | H | CH₃ | H | H | H | CH₃ |
| CH₃ | G²-1 | H | CH₃ | Cl | H | H | CH₃ |
| CH₃ | G²-1 | H | CH₃ | Br | H | H | CH₃ |
| CH₃ | G²-1 | H | CH₃ | CH₃ | H | H | CH₃ |
| CH₃ | G²-1 | H | CH₃ | OCH₃ | H | H | CH₃ |
| CH₃ | G²-1 | H | CH₃ | OCF₃ | H | H | CH₃ |
| CH₃ | G²-1 | H | CF₃ | H | H | H | CH₃ |
| CH₃ | G²-1 | H | CF₃ | Cl | H | H | CH₃ |
| CH₃ | G²-1 | H | OCH₃ | H | H | H | CH₃ |
| CH₃ | G²-1 | H | OCH₃ | Cl | H | H | CH₃ |
| CH₃ | G²-1 | H | OCHF₂ | H | H | H | CH₃ |
| CH₃ | G²-1 | H | OCF₃ | H | H | H | CH₃ |
| CH₃ | G²-1 | H | OPh | H | H | H | CH₃ |
| CH₃ | G²-1 | H | OPh | F | H | H | CH₃ |
| CH₃ | G²-1 | H | —OCH₂O— | | H | H | CH₃ |
| CH₃ | G²-1 | H | —OCF₂O— | | H | H | CH₃ |
| CH₃ | G²-1 | H | —OCF₂CF₂O— | | H | H | CH₃ |
| CH₃ | G²-1 | H | —CH=CHC(CH₃)=CH— | | H | H | CH₃ |
| CH₃ | G²-1 | F | H | H | H | H | CH₃ |
| CH₃ | G²-1 | F | H | H | H | F | CH₃ |
| CH₃ | G²-1 | F | H | F | H | H | CH₃ |
| CH₃ | G²-1 | F | H | F | H | F | CH₃ |
| CH₃ | G²-1 | F | H | F | F | H | CH₃ |
| CH₃ | G²-1 | F | H | Cl | H | H | CH₃ |
| CH₃ | G²-1 | F | H | Cl | H | H | CH₃(E) |
| CH₃ | G²-1 | F | H | Cl | H | H | CH₃(Z) |
| CH₃(S) | G²-1 | F | H | Cl | H | H | CH₃ |
| CH₃(S) | G²-1 | F | H | Cl | H | H | CH₃(E) |
| CH₃(S) | G²-1 | F | H | Cl | H | H | CH₃(Z) |
| CH₃ | G²-1 | F | H | Cl | F | H | CH₃ |
| CH₃ | G²-1 | F | H | Cl | Cl | H | CH₃ |
| CH₃ | G²-1 | F | H | Br | H | H | CH₃ |
| CH₃ | G²-1 | F | H | Br | F | H | CH₃ |
| CH₃ | G²-1 | Cl | H | H | H | H | CH₃ |
| CH₃ | G²-1 | Cl | H | H | H | F | CH₃ |
| CH₃ | G²-1 | Cl | H | H | H | Cl | CH₃ |
| H | G²-1 | Cl | H | F | H | H | CH₃ |
| CH₃ | G²-1 | Cl | H | F | H | H | CH₃ |
| CH₃ | G²-1 | Cl | H | F | H | H | CH₃(E) |
| CH₃ | G²-1 | Cl | H | F | H | H | CH₃(Z) |
| CH₃(S) | G²-1 | Cl | H | F | H | H | CH₃ |
| CH₃(S) | G²-1 | Cl | H | F | H | H | CH₃(E) |
| CH₃(S) | G²-1 | Cl | H | F | H | H | CH₃(Z) |
| CH₃ | G²-1 | Cl | H | F | F | H | CH₃ |
| H | G²-1 | Cl | H | Cl | H | H | CH₃ |
| H | G²-1 | Cl | H | Cl | H | H | CH₃(Z) |
| CH₃ | G²-1 | Cl | H | Cl | H | H | CH₃ |
| CH₃ | G²-1 | Cl | H | Cl | H | H | CH₃(E) |
| CH₃ | G²-1 | Cl | H | Cl | H | H | CH₃(Z) |
| CH₃(R) | G²-1 | Cl | H | Cl | H | H | CH₃ |
| CH₃(R) | G²-1 | Cl | H | Cl | H | H | CH₃(E) |
| CH₃(R) | G²-1 | Cl | H | Cl | H | H | CH₃(Z) |
| CH₃(S) | G²-1 | Cl | H | Cl | H | H | CH₃ |

TABLE 2-continued

| $R^2$ | $G^2$ | $Y^1$ | $Y^2$ | $Y^3$ | $Y^4$ | $Y^5$ | $R^1$ |
|---|---|---|---|---|---|---|---|
| $CH_3(S)$ | $G^2$-1 | Cl | H | Cl | H | H | $CH_3(E)$ |
| $CH_3(S)$ | $G^2$-1 | Cl | H | Cl | H | H | $CH_3(Z)$ |
| $CH_3$ | $G^2$-1 | Cl | H | Cl | H | Cl | $CH_3$ |
| $CH_3$ | $G^2$-1 | Cl | H | Cl | F | H | $CH_3$ |
| $CH_3$ | $G^2$-1 | Cl | H | Cl | Cl | H | $CH_3$ |
| $CH_3$ | $G^2$-1 | Cl | H | Br | H | H | $CH_3$ |
| $CH_3$ | $G^2$-1 | Cl | H | Br | H | H | $CH_3(E)$ |
| $CH_3(S)$ | $G^2$-1 | Cl | H | Br | H | H | $CH_3$ |
| $CH_3(S)$ | $G^2$-1 | Cl | H | Br | H | H | $CH_3(E)$ |
| $CH_3$ | $G^2$-1 | Cl | H | Br | H | Cl | $CH_3$ |
| $CH_3$ | $G^2$-1 | Cl | H | I | H | Cl | $CH_3$ |
| $CH_3$ | $G^2$-1 | Cl | H | $CH_3$ | H | H | $CH_3$ |
| $CH_3$ | $G^2$-1 | Cl | H | $CH_3$ | H | H | $CH_3(E)$ |
| $CH_3(S)$ | $G^2$-1 | Cl | H | $CH_3$ | H | H | $CH_3$ |
| $CH_3(S)$ | $G^2$-1 | Cl | H | $CH_3$ | H | H | $CH_3(E)$ |
| $CH_3$ | $G^2$-1 | Cl | H | $CH_3$ | H | Cl | $CH_3$ |
| $CH_3$ | $G^2$-1 | Cl | H | $CF_3$ | H | H | $CH_3$ |
| $CH_3$ | $G^2$-1 | Cl | H | $CF_3$ | H | H | $CH_3(E)$ |
| $CH_3(S)$ | $G^2$-1 | Cl | H | $CF_3$ | H | H | $CH_3$ |
| $CH_3(S)$ | $G^2$-1 | Cl | H | $CF_3$ | H | H | $CH_3(E)$ |
| $CH_3$ | $G^2$-1 | Cl | H | $CF_3$ | H | Cl | $CH_3$ |
| $CH_3$ | $G^2$-1 | Cl | H | $OCH_3$ | H | H | $CH_3$ |
| $CH_3$ | $G^2$-1 | Cl | H | $OCH_3$ | H | Cl | $CH_3$ |
| $CH_3$ | $G^2$-1 | Cl | H | $OCHF_2$ | H | H | $CH_3$ |
| $CH_3$ | $G^2$-1 | Cl | H | $OCH_2CH{=}CCl_2$ | H | H | $CH_3$ |
| $CH_3$ | $G^2$-1 | Cl | H | OPh | H | H | $CH_3$ |
| $CH_3$ | $G^2$-1 | Cl | H | O(Ph-3-F) | H | H | $CH_3$ |
| $CH_3$ | $G^2$-1 | Cl | H | O(Ph-4-F) | H | H | $CH_3$ |
| $CH_3$ | $G^2$-1 | Cl | H | $SCH_3$ | H | H | $CH_3$ |
| $CH_3$ | $G^2$-1 | Cl | H | $S(O)CH_3$ | H | H | $CH_3$ |
| $CH_3$ | $G^2$-1 | Cl | H | $SO_2CH_3$ | H | H | $CH_3$ |
| $CH_3$ | $G^2$-1 | Cl | H | $SCF_3$ | H | H | $CH_3$ |
| $CH_3$ | $G^2$-1 | Cl | H | $CH{=}NOCH_3$ | H | H | $CH_3$ |
| $CH_3$ | $G^2$-1 | Cl | H | $CH{=}NOEt$ | H | H | $CH_3$ |
| $CH_3$ | $G^2$-1 | Cl | H | $C(CH_3){=}NOCH_3$ | H | H | $CH_3$ |
| $CH_3$ | $G^2$-1 | Cl | H | $C(CH_3){=}NOEt$ | H | H | $CH_3$ |
| $CH_3$ | $G^2$-1 | Cl | H | $C(Et){=}NOCH_3$ | H | H | $CH_3$ |
| $CH_3$ | $G^2$-1 | Cl | H | $C(Et){=}NOEt$ | H | H | $CH_3$ |
| $CH_3$ | $G^2$-1 | Cl | H | CN | H | H | $CH_3$ |
| $CH_3$ | $G^2$-1 | Cl | H | $C(O)NH_2$ | H | H | $CH_3$ |
| $CH_3$ | $G^2$-1 | Cl | H | $C(S)NH_2$ | H | H | $CH_3$ |
| $CH_3$ | $G^2$-1 | Cl | H | $CH{=}CH_2$ | H | H | $CH_3$ |
| $CH_3$ | $G^2$-1 | Cl | H | C≡CH | H | H | $CH_3$ |
| $CH_3$ | $G^2$-1 | Cl | H | C≡CH | H | H | $CH_3(E)$ |
| $CH_3(S)$ | $G^2$-1 | Cl | H | C≡CH | H | H | $CH_3$ |
| $CH_3(S)$ | $G^2$-1 | Cl | H | C≡CH | H | H | $CH_3(E)$ |
| $CH_3$ | $G^2$-1 | Cl | H | C≡$CCH_3$ | H | H | $CH_3$ |
| $CH_3$ | $G^2$-1 | Cl | H | C≡$CCH_3$ | H | H | $CH_3(E)$ |
| $CH_3$ | $G^2$-1 | Cl | H | C≡CEt | H | H | $CH_3$ |
| $CH_3$ | $G^2$-1 | Cl | H | C≡CPr-n | H | H | $CH_3$ |
| $CH_3$ | $G^2$-1 | Cl | H | C≡CPr-c | H | H | $CH_3$ |
| $CH_3$ | $G^2$-1 | Cl | H | C≡CPr-c | H | H | $CH_3(E)$ |
| $CH_3$ | $G^2$-1 | Cl | H | C≡CBu-n | H | H | $CH_3$ |
| $CH_3$ | $G^2$-1 | Cl | H | C≡CBu-t | H | H | $CH_3$ |
| $CH_3$ | $G^2$-1 | Cl | H | C≡CBu-t | H | H | $CH_3(E)$ |
| $CH_3(S)$ | $G^2$-1 | Cl | H | C≡CBu-t | H | H | $CH_3$ |
| $CH_3(S)$ | $G^2$-1 | Cl | H | C≡CBu-t | H | H | $CH_3(E)$ |
| $CH_3$ | $G^2$-1 | Cl | H | C≡CPen-c | H | H | $CH_3$ |
| $CH_3$ | $G^2$-1 | Cl | H | C≡CPen-c | H | H | $CH_3(E)$ |
| $CH_3$ | $G^2$-1 | Cl | H | C≡CCl | H | H | $CH_3$ |
| $CH_3$ | $G^2$-1 | Cl | H | C≡CBr | H | H | $CH_3$ |
| $CH_3$ | $G^2$-1 | Cl | H | C≡CI | H | H | $CH_3$ |
| $CH_3$ | $G^2$-1 | Cl | H | C≡$CC(CH_3)_2OH$ | H | H | $CH_3$ |
| $CH_3$ | $G^2$-1 | Cl | H | C≡$CC(CH_3)_2OH$ | H | H | $CH_3(E)$ |
| $CH_3$ | $G^2$-1 | Cl | H | C≡$CC(CH_3)_2OCH_3$ | H | H | $CH_3$ |
| $CH_3$ | $G^2$-1 | Cl | H | C≡$CC(CH_3)_2OCH_3$ | H | H | $CH_3(E)$ |
| $CH_3$ | $G^2$-1 | Cl | H | C≡$CSi(CH_3)_3$ | H | H | $CH_3$ |
| $CH_3$ | $G^2$-1 | Cl | H | C≡$CSi(CH_3)_3$ | H | H | $CH_3(E)$ |
| $CH_3(S)$ | $G^2$-1 | Cl | H | C≡$CSi(CH_3)_3$ | H | H | $CH_3$ |
| $CH_3(S)$ | $G^2$-1 | Cl | H | C≡$CSi(CH_3)_3$ | H | H | $CH_3(E)$ |
| $CH_3$ | $G^2$-1 | Cl | H | C≡CPh | H | H | $CH_3$ |
| $CH_3$ | $G^2$-1 | Cl | H | C≡CPh | H | H | $CH_3(E)$ |
| $CH_3(S)$ | $G^2$-1 | Cl | H | C≡CPh | H | H | $CH_3$ |
| $CH_3(S)$ | $G^2$-1 | Cl | H | C≡CPh | H | H | $CH_3(E)$ |
| $CH_3$ | $G^2$-1 | Cl | H | Ph | H | H | $CH_3$ |
| $CH_3$ | $G^2$-1 | Cl | H | Ph-4-$OCF_3$ | H | H | $CH_3$ |
| $CH_3$ | $G^2$-1 | Cl | —$OCH_2O$— | | H | H | $CH_3$ |
| $CH_3$ | $G^2$-1 | Cl | Cl | H | H | H | $CH_3$ |

TABLE 2-continued

| R² | G² | Y¹ | Y² | Y³ | Y⁴ | Y⁵ | R¹ |
|---|---|---|---|---|---|---|---|
| CH₃ | G²-1 | Cl | Cl | H | H | Cl | CH₃ |
| CH₃ | G²-1 | Cl | Cl | Cl | H | H | CH₃ |
| CH₃ | G²-1 | Cl | | —OCF₂O— | H | H | CH₃ |
| CH₃ | G²-1 | Br | H | H | OCH₃ | H | CH₃ |
| CH₃ | G²-1 | Br | H | F | H | H | CH₃ |
| CH₃ | G²-1 | Br | H | F | F | H | CH₃ |
| CH₃ | G²-1 | Br | H | Cl | H | Br | CH₃ |
| CH₃ | G²-1 | Br | H | I | H | Br | CH₃ |
| CH₃ | G²-1 | Br | H | Et | H | Br | CH₃ |
| CH₃ | G²-1 | Br | H | CF₃ | H | H | CH₃ |
| CH₃ | G²-1 | Br | H | CF₃ | H | Br | CH₃ |
| CH₃ | G²-1 | CH₃ | H | H | H | H | CH₃ |
| CH₃ | G²-1 | CH₃ | H | H | H | Cl | CH₃ |
| CH₃ | G²-1 | CH₃ | H | H | H | CH₃ | CH₃ |
| CH₃ | G²-1 | CH₃ | H | H | CH₃ | H | CH₃ |
| CH₃ | G²-1 | CH₃ | H | F | H | H | CH₃ |
| CH₃ | G²-1 | CH₃ | H | Cl | H | Cl | CH₃ |
| CH₃ | G²-1 | CH₃ | H | Br | H | H | CH₃ |
| CH₃ | G²-1 | CH₃ | H | CH₃ | H | Cl | CH₃ |
| CH₃ | G²-1 | CH₃ | H | CH₃ | H | CH₃ | CH₃ |
| CH₃ | G²-1 | CH₃ | H | CF₃ | H | H | CH₃ |
| CH₃ | G²-1 | CH₃ | H | OCH₃ | H | H | CH₃ |
| CH₃ | G²-1 | CH₃ | H | OPr-i | H | H | CH₃ |
| CH₃ | G²-1 | CH₃ | H | OCHF₂ | H | H | CH₃ |
| CH₃ | G²-1 | CH₃ | H | —OCH₂O— | | H | CH₃ |
| CH₃ | G²-1 | CH₃ | H | —OCF₂O— | | H | CH₃ |
| CH₃ | G²-1 | CH₃ | Cl | H | H | H | CH₃ |
| CH₃ | G²-1 | CH₃ | Cl | Cl | H | H | CH₃ |
| CH₃ | G²-1 | CH₃ | CH₃ | Cl | H | H | CH₃ |
| CH₃ | G²-1 | CH₃ | —OCH₂O— | | H | H | CH₃ |
| CH₃ | G²-1 | CH₃ | —OCF₂O— | | H | H | CH₃ |
| CH₃ | G²-1 | CH₃ | —OCF₂CF₂O— | | H | H | CH₃ |
| CH₃ | G²-1 | CF₃ | H | H | H | H | CH₃ |
| CH₃ | G²-1 | CF₃ | H | H | H | Cl | CH₃ |
| CH₃ | G²-1 | CF₃ | H | CF₃ | H | H | CH₃ |
| CH₃ | G²-1 | CH₂OCH₃ | H | H | H | H | CH₃ |
| CH₃ | G²-1 | OCH₃ | H | H | H | H | CH₃ |
| CH₃ | G²-1 | OCH₃ | H | H | Br | H | CH₃ |
| CH₃ | G²-1 | OCH₃ | H | H | OCH₃ | H | CH₃ |
| CH₃ | G²-1 | OCH₃ | OCH₃ | H | H | H | CH₃ |
| CH₃ | G²-1 | OPh | H | H | H | H | CH₃ |
| CH₃ | G²-1 | | —OCH₂O— | H | H | H | CH₃ |
| CH₃ | G²-1 | | —OCF₂O— | H | H | H | CH₃ |
| H | G²-2 | H | H | CF₃ | H | — | CH₃ |
| H | G²-2 | F | H | Cl | H | — | CH₃ |
| H | G²-2 | F | H | Cl | H | — | CH₃(Z) |
| CH₃ | G²-2 | F | H | Cl | H | — | CH₃(Z) |
| CH₃(S) | G²-2 | F | H | Cl | H | — | CH₃(Z) |
| H | G²-2 | F | H | Br | H | — | CH₃ |
| H | G²-2 | F | H | Br | H | — | CH₃(Z) |
| CH₃ | G²-2 | F | H | Br | H | — | CH₃(Z) |
| CH₃(S) | G²-2 | F | H | Br | H | — | CH₃(Z) |
| H | G²-2 | F | H | CF₃ | H | — | CH₃ |
| H | G²-2 | F | H | CF₃ | H | — | CH₃(Z) |
| H | G²-2 | Cl | H | H | H | — | CH₃(Z) |
| H | G²-2 | Cl | H | F | H | — | CH₃ |
| H | G²-2 | Cl | H | F | H | — | CH₃(Z) |
| CH₃ | G²-2 | Cl | H | F | H | — | CH₃(Z) |
| CH₃(S) | G²-2 | Cl | H | F | H | — | CH₃(Z) |
| H | G²-2 | Cl | H | Cl | H | — | CH₃ |
| H | G²-2 | Cl | H | Cl | H | — | CH₃(E) |
| H | G²-2 | Cl | H | Cl | H | — | CH₃(Z) |
| CH₃ | G²-2 | Cl | H | Cl | H | — | CH₃ |
| CH₃ | G²-2 | Cl | H | Cl | H | — | CH₃(E) |
| CH₃ | G²-2 | Cl | H | Cl | H | — | CH₃(Z) |
| CH₃(R) | G²-2 | Cl | H | Cl | H | — | CH₃ |
| CH₃(R) | G²-2 | Cl | H | Cl | H | — | CH₃(E) |
| CH₃(R) | G²-2 | Cl | H | Cl | H | — | CH₃(Z) |
| CH₃(S) | G²-2 | Cl | H | Cl | H | — | CH₃ |
| CH₃(S) | G²-2 | Cl | H | Cl | H | — | CH₃(E) |
| CH₃(S) | G²-2 | Cl | H | Cl | H | — | CH₃(Z) |
| Et | G²-2 | Cl | H | Cl | H | — | CH₃ |
| n-Pr | G²-2 | Cl | H | Cl | H | — | CH₃ |
| i-Pr | G²-2 | Cl | H | Cl | H | — | CH₃ |
| c-Pr | G²-2 | Cl | H | Cl | H | — | CH₃ |
| CH₂F | G²-2 | Cl | H | Cl | H | — | CH₃ |
| CF₃ | G²-2 | Cl | H | Cl | H | — | CH₃ |
| CH₂OCH₃ | G²-2 | Cl | H | Cl | H | — | CH₃ |

TABLE 2-continued

| R² | G² | Y¹ | Y² | Y³ | Y⁴ | Y⁵ | R¹ |
|---|---|---|---|---|---|---|---|
| CH₂SCH₃ | G²-2 | Cl | H | Cl | H | — | CH₃ |
| Ph | G²-2 | Cl | H | Cl | H | — | CH₃(Z) |
| H | G²-2 | Cl | H | Cl | F | — | CH₃ |
| H | G²-2 | Cl | H | Cl | F | — | CH₃(Z) |
| CH₃ | G²-2 | Cl | H | Cl | F | — | CH₃ |
| CH₃ | G²-2 | Cl | H | Cl | F | — | CH₃(Z) |
| CH₃(S) | G²-2 | Cl | H | Cl | F | — | CH₃ |
| CH₃(S) | G²-2 | Cl | H | Cl | F | — | CH₃(Z) |
| H | G²-2 | Cl | H | Cl | Cl | — | CH₃ |
| H | G²-2 | Cl | H | Cl | Cl | — | CH₃(Z) |
| H | G²-2 | Cl | H | Br | H | — | CH₃ |
| H | G²-2 | Cl | H | Br | H | — | CH₃(E) |
| H | G²-2 | Cl | H | Br | H | — | CH₃(Z) |
| CH₃ | G²-2 | Cl | H | Br | H | — | CH₃ |
| CH₃ | G²-2 | Cl | H | Br | H | — | CH₃(Z) |
| CH₃(S) | G²-2 | Cl | H | Br | H | — | CH₃ |
| CH₃(S) | G²-2 | Cl | H | Br | H | — | CH₃(Z) |
| H | G²-2 | Cl | H | CF₃ | H | — | CH₃ |
| H | G²-2 | Cl | H | CF₃ | H | — | CH₃(Z) |
| CH₃ | G²-2 | Cl | H | CF₃ | H | — | CH₃ |
| CH₃ | G²-2 | Cl | H | CF₃ | H | — | CH₃(Z) |
| CH₃(R) | G²-2 | Cl | H | CF₃ | H | — | CH₃ |
| CH₃(R) | G²-2 | Cl | H | CF₃ | H | — | CH₃(Z) |
| CH₃(S) | G²-2 | Cl | H | CF₃ | H | — | CH₃ |
| CH₃(S) | G²-2 | Cl | H | CF₃ | H | — | CH₃(Z) |
| H | G²-2 | Cl | H | OCH₃ | H | — | CH₃ |
| H | G²-2 | Cl | H | OCHF₂ | H | — | CH₃ |
| H | G²-2 | Cl | H | OCF₃ | H | — | CH₃ |
| H | G²-2 | Cl | H | O(Ph-4-Cl) | H | — | CH₃ |
| H | G²-2 | Cl | H | CH=NOCH₃ | H | — | CH₃ |
| H | G²-2 | Cl | H | CH=NOEt | H | — | CH₃ |
| H | G²-2 | Cl | H | C(CH₃)=NOCH₃ | H | — | CH₃ |
| CH₃ | G²-2 | Cl | H | C(CH₃)=NOCH₃ | H | — | CH₃ |
| CH₃(S) | G²-2 | Cl | H | C(CH₃)=NOCH₃ | H | — | CH₃ |
| H | G²-2 | Cl | H | C(CH₃)=NOEt | H | — | CH₃ |
| H | G²-2 | Cl | H | C(Et)=NOCH₃ | H | — | CH₃ |
| H | G²-2 | Cl | H | C≡CH | H | — | CH₃ |
| H | G²-2 | Cl | H | C≡CH | H | — | CH₃(Z) |
| H | G²-2 | Cl | H | C≡CCH₃ | H | — | CH₃ |
| H | G²-2 | Cl | H | C≡CCH₃ | H | — | CH₃(Z) |
| H | G²-2 | Cl | H | C≡CEt | H | — | CH₃ |
| H | G²-2 | Cl | H | C≡CPr-n | H | — | CH₃ |
| H | G²-2 | Cl | H | C≡CPr-c | H | — | CH₃ |
| H | G²-2 | Cl | H | C≡CPr-c | H | — | CH₃(Z) |
| CH₃ | G²-2 | Cl | H | C≡CPr-c | H | — | CH₃ |
| CH₃ | G²-2 | Cl | H | C≡CPr-c | H | — | CH₃(Z) |
| CH₃(S) | G²-2 | Cl | H | C≡CPr-c | H | — | CH₃ |
| CH₃(S) | G²-2 | Cl | H | C≡CPr-c | H | — | CH₃(Z) |
| H | G²-2 | Cl | H | C≡CBu-n | H | — | CH₃ |
| H | G²-2 | Cl | H | C≡CBu-t | H | — | CH₃ |
| H | G²-2 | Cl | H | C≡CBu-t | H | — | CH₃(Z) |
| CH₃ | G²-2 | Cl | H | C≡CBu-t | H | — | CH₃ |
| CH₃ | G²-2 | Cl | H | C≡CBu-t | H | — | CH₃(Z) |
| CH₃(S) | G²-2 | Cl | H | C≡CBu-t | H | — | CH₃ |
| CH₃(S) | G²-2 | Cl | H | C≡CBu-t | H | — | CH₃(Z) |
| H | G²-2 | Cl | H | C≡CPen-c | H | — | CH₃ |
| H | G²-2 | Cl | H | C≡CPen-c | H | — | CH₃(Z) |
| H | G²-2 | Cl | H | C≡CCl | H | — | CH₃ |
| H | G²-2 | Cl | H | C≡CBr | H | — | CH₃ |
| H | G²-2 | Cl | H | C≡CI | H | — | CH₃ |
| H | G²-2 | Cl | H | C≡CC(CH₃)₂OH | H | — | CH₃ |
| H | G²-2 | Cl | H | C≡CC(CH₃)₂OH | H | — | CH₃(Z) |
| H | G²-2 | Cl | H | C≡CC(CH₃)₂OCH₃ | H | — | CH₃ |
| H | G²-2 | Cl | H | C≡CC(CH₃)₂OCH₃ | H | — | CH₃(Z) |
| H | G²-2 | Cl | H | C≡CSi(CH₃)₃ | H | — | CH₃ |
| H | G²-2 | Cl | H | C≡CSi(CH₃)₃ | H | — | CH₃(Z) |
| H | G²-2 | Cl | H | C≡CPh | H | — | CH₃ |
| H | G²-2 | Cl | H | C≡CPh | H | — | CH₃(Z) |
| H | G²-2 | Cl | F | Cl | H | — | CH₃ |
| H | G²-2 | Cl | F | Cl | H | — | CH₃(Z) |
| CH₃ | G²-2 | Cl | F | Cl | H | — | CH₃(Z) |
| CH₃(S) | G²-2 | Cl | F | Cl | H | — | CH₃(Z) |
| H | G²-2 | Cl | Cl | Cl | H | — | CH₃ |
| H | G²-2 | Cl | Cl | Cl | H | — | CH₃(Z) |
| CH₃ | G²-2 | Cl | Cl | Cl | H | — | CH₃(Z) |
| CH₃(S) | G²-2 | Cl | Cl | Cl | H | — | CH₃(Z) |
| H | G²-2 | Br | H | F | H | — | CH₃ |
| H | G²-2 | Br | H | F | H | — | CH₃(Z) |

TABLE 2-continued

| R² | G² | Y¹ | Y² | Y³ | Y⁴ | Y⁵ | R¹ |
|---|---|---|---|---|---|---|---|
| H | G²-2 | Br | H | Cl | H | — | CH₃ |
| H | G²-2 | Br | H | Cl | H | — | CH₃(Z) |
| CH₃ | G²-2 | Br | H | Cl | H | — | CH₃(Z) |
| CH₃(S) | G²-2 | Br | H | Cl | H | — | CH₃(Z) |
| H | G²-2 | Br | H | Br | H | — | CH₃ |
| H | G²-2 | Br | H | Br | H | — | CH₃(Z) |
| CH₃ | G²-2 | Br | H | Br | H | — | CH₃ |
| CH₃ | G²-2 | Br | H | Br | H | — | CH₃(Z) |
| CH₃(S) | G²-2 | Br | H | Br | H | — | CH₃ |
| CH₃(S) | G²-2 | Br | H | Br | H | — | CH₃(Z) |
| H | G²-2 | Br | H | CF₃ | H | — | CH₃ |
| H | G²-2 | Br | H | CF₃ | H | — | CH₃(Z) |
| H | G²-2 | OCH₃ | H | Cl | H | — | CH₃ |
| H | G²-3 | Cl | — | Cl | H | H | CH₃ |
| CH₃ | G²-3 | Cl | — | Cl | H | H | CH₃ |
| H | G²-4 | Cl | H | Cl | — | H | CH₃ |
| CH₃ | G²-4 | Cl | H | Cl | — | H | CH₃ |
| H | G²-4 | Cl | H | CF₃ | — | H | CH₃ |
| H | G²-4 | Cl | H | C≡CPr-c | — | H | CH₃ |
| CH₃ | G²-4 | Cl | H | C≡CPr-c | — | H | CH₃ |
| H | G²-4 | Cl | H | C≡CBu-t | — | H | CH₃ |
| CH₃ | G²-4 | Cl | H | C≡CBu-t | — | H | CH₃ |
| H | G²-6 | Cl | — | Cl | H | — | CH₃ |
| CH₃ | G²-6 | Cl | — | Cl | H | — | CH₃ |
| H | G²-7 | Cl | H | Br | — | — | CH₃ |
| CH₃ | G²-7 | Cl | H | Br | — | — | CH₃ |
| H | G²-7 | Cl | H | C≡CPr-c | — | — | CH₃ |
| CH₃ | G²-7 | Cl | H | C≡CPr-c | — | — | CH₃ |
| H | G²-7 | Cl | H | C≡CBu-t | — | — | CH₃ |
| CH₃ | G²-7 | Cl | H | C≡CBu-t | — | — | CH₃ |
| H | G²-7 | Cl | Cl | Cl | — | — | CH₃ |
| CH₃ | G²-8 | CH₃ | — | CH₃ | H | — | CH₃ |
| H | G²-9 | F | H | Br | — | — | CH₃ |
| CH₃ | G²-9 | Cl | H | Cl | — | — | CH₃ |
| CH₃ | G²-9 | Cl | H | Cl | — | — | CH₃(Z) |
| CH₃(S) | G²-9 | Cl | H | Cl | — | — | CH₃ |
| CH₃(S) | G²-9 | Cl | H | Cl | — | — | CH₃(Z) |
| H | G²-9 | Cl | H | Br | — | — | CH₃ |
| CH₃ | G²-9 | Cl | H | Br | — | — | CH₃ |
| CH₃ | G²-9 | Cl | H | Br | — | — | CH₃(Z) |
| CH₃(S) | G²-9 | Cl | H | Br | — | — | CH₃ |
| CH₃(S) | G²-9 | Cl | H | Br | — | — | CH₃(Z) |
| CH₃ | G²-9 | Cl | H | C≡CH | — | — | CH₃ |
| CH₃ | G²-9 | Cl | H | C≡CH | — | — | CH₃(Z) |
| CH₃(S) | G²-9 | Cl | H | C≡CH | — | — | CH₃ |
| CH₃(S) | G²-9 | Cl | H | C≡CH | — | — | CH₃(Z) |
| CH₃ | G²-9 | Cl | H | C≡CCH₃ | — | — | CH₃ |
| CH₃ | G²-9 | Cl | H | C≡CCH₃ | — | — | CH₃(Z) |
| CH₃ | G²-9 | Cl | H | C≡CEt | — | — | CH₃ |
| CH₃ | G²-9 | Cl | H | C≡CPr-n | — | — | CH₃ |
| CH₃ | G²-9 | Cl | H | C≡CPr-c | — | — | CH₃ |
| CH₃ | G²-9 | Cl | H | C≡CPr-c | — | — | CH₃(Z) |
| CH₃ | G²-9 | Cl | H | C≡CBu-n | — | — | CH₃ |
| CH₃ | G²-9 | Cl | H | C≡CBu-t | — | — | CH₃ |
| CH₃ | G²-9 | Cl | H | C≡CBu-t | — | — | CH₃(Z) |
| CH₃(S) | G²-9 | Cl | H | C≡CBu-t | — | — | CH₃ |
| CH₃(S) | G²-9 | Cl | H | C≡CBu-t | — | — | CH₃(Z) |
| CH₃ | G²-9 | Cl | H | C≡CPen-c | — | — | CH₃ |
| CH₃ | G²-9 | Cl | H | C≡CPen-c | — | — | CH₃(Z) |
| CH₃ | G²-9 | Cl | H | C≡CCl | — | — | CH₃ |
| CH₃ | G²-9 | Cl | H | C≡CBr | — | — | CH₃ |
| CH₃ | G²-9 | Cl | H | C≡CI | — | — | CH₃ |
| CH₃ | G²-9 | Cl | H | C≡CC(CH₃)₂OH | — | — | CH₃ |
| CH₃ | G²-9 | Cl | H | C≡CC(CH₃)₂OH | — | — | CH₃(Z) |
| CH₃ | G²-9 | Cl | H | C≡CC(CH₃)₂OCH₃ | — | — | CH₃ |
| CH₃ | G²-9 | Cl | H | C≡CC(CH₃)₂OCH₃ | — | — | CH₃(Z) |
| CH₃ | G²-9 | Cl | H | C≡CSi(CH₃)₃ | — | — | CH₃ |
| CH₃ | G²-9 | Cl | H | C≡CSi(CH₃)₃ | — | — | CH₃(Z) |
| CH₃(S) | G²-9 | Cl | H | C≡CSi(CH₃)₃ | — | — | CH₃ |
| CH₃(S) | G²-9 | Cl | H | C≡CSi(CH₃)₃ | — | — | CH₃(Z) |
| CH₃ | G²-9 | Cl | H | C≡CPh | — | — | CH₃ |
| CH₃ | G²-9 | Cl | H | C≡CPh | — | — | CH₃(Z) |
| CH₃(S) | G²-9 | Cl | H | C≡CPh | — | — | CH₃ |
| CH₃(S) | G²-9 | Cl | H | C≡CPh | — | — | CH₃(Z) |
| H | G²-9 | Cl | Cl | Cl | — | — | CH₃ |
| CH₃ | G²-9 | Cl | Cl | Cl | — | — | CH₃ |
| CH₃ | G²-9 | Cl | Cl | Cl | — | — | CH₃(Z) |
| CH₃(S) | G²-9 | Cl | Cl | Cl | — | — | CH₃ |

TABLE 2-continued

| R² | G² | Y¹ | Y² | Y³ | Y⁴ | Y⁵ | R¹ |
|---|---|---|---|---|---|---|---|
| CH₃(S) | G²-9 | Cl | Cl | Cl | — | — | CH₃(Z) |
| CH₃ | G²-9 | Cl | —CH=CHCCl=CH— | | — | — | CH₃ |
| CH₃ | G²-9 | Cl | —CH=CClCH=CH— | | — | — | CH₃ |
| CH₃ | G²-9 | Cl | —CH=CBrCH=CH— | | — | — | CH₃ |
| H | G²-9 | Br | H | Br | — | — | CH₃ |
| H | G²-9 | Br | Br | Br | — | — | CH₃ |
| H | G²-9 | Br | CH₃ | Br | — | — | CH₃ |
| H | G²-9 | CH₃ | H | Cl | — | — | CH₃ |
| H | G²-9 | CH₃ | H | Br | — | — | CH₃ |
| H | G²-9 | CH₃ | Br | Br | — | — | CH₃ |
| CH₃ | G²-10 | H | — | Cl | Cl | — | CH₃ |
| CH₃ | G²-10 | H | — | —CH=CHCH=CH— | | — | CH₃ |
| H | G²-10 | Cl | — | Cl | H | — | CH₃ |
| CH₃ | G²-10 | Cl | — | Cl | H | — | CH₃ |
| CH₃ | G²-10 | Cl | — | Cl | Cl | — | CH₃ |
| CH₃ | G²-10 | Br | — | Cl | Cl | — | CH₃ |
| H | G²-10 | Br | — | Br | H | — | CH₃ |
| CH₃ | G²-10 | Br | — | Br | H | — | CH₃ |
| H | G²-10 | CH₃ | — | Cl | H | — | CH₃ |
| CH₃ | G²-10 | CH₃ | — | Cl | H | — | CH₃ |
| H | G²-10 | CH₃ | — | Br | H | — | CH₃ |
| CH₃ | G²-10 | CH₃ | — | CH₃ | H | — | CH₃ |
| CH₃ | G²-1 | H | H | Br | H | H | Et |
| CH₃ | G²-1 | H | H | I | H | H | Et |
| CH₃ | G²-1 | H | H | t-Bu | H | H | Et |
| CH₃ | G²-1 | H | H | CF₃ | H | H | Et |
| CH₃ | G²-1 | H | H | OCF₃ | H | H | Et |
| CH₃ | G²-1 | H | H | OPh | H | H | Et |
| CH₃ | G²-1 | H | H | Ph | H | H | Et |
| CH₃ | G²-1 | H | F | F | F | H | Et |
| CH₃ | G²-1 | H | Cl | Cl | H | H | Et |
| CH₃ | G²-1 | H | Br | H | CF₃ | H | Et |
| CH₃ | G²-1 | H | OPr-i | H | H | H | Et |
| CH₃ | G²-1 | H | —CH=CHCH=CH— | | H | H | Et |
| CH₃ | G²-1 | F | H | F | H | H | Et |
| CH₃ | G²-1 | F | H | Cl | H | H | Et |
| CH₃ | G²-1 | F | H | Cl | H | H | Et(E) |
| CH₃(S) | G²-1 | F | H | Cl | H | H | Et |
| CH₃(S) | G²-1 | F | H | Cl | H | H | Et(E) |
| CH₃ | G²-1 | F | H | Br | H | H | Et |
| CH₃ | G²-1 | F | H | Br | F | H | Et |
| CH₃ | G²-1 | F | H | CF₃ | H | H | Et |
| CH₃ | G²-1 | Cl | H | H | F | H | Et |
| CH₃ | G²-1 | Cl | H | H | Cl | H | Et |
| CH₃ | G²-1 | Cl | H | H | CF₃ | H | Et |
| CH₃ | G²-1 | Cl | H | F | H | H | Et |
| CH₃ | G²-1 | Cl | H | F | H | H | Et(E) |
| CH₃(S) | G²-1 | Cl | H | F | H | H | Et |
| CH₃(S) | G²-1 | Cl | H | F | H | H | Et(E) |
| CH₃ | G²-1 | Cl | H | Cl | H | H | Et |
| CH₃ | G²-1 | Cl | H | Cl | H | H | Et(E) |
| CH₃(S) | G²-1 | Cl | H | Cl | H | H | Et |
| CH₃(S) | G²-1 | Cl | H | Cl | H | H | Et(E) |
| CH₃ | G²-1 | Cl | H | Br | H | H | Et |
| CH₃ | G²-1 | Cl | H | CH₃ | H | H | Et |
| CH₃ | G²-1 | Cl | H | CH₃ | H | H | Et(E) |
| CH₃(S) | G²-1 | Cl | H | CH₃ | H | H | Et |
| CH₃(S) | G²-1 | Cl | H | CH₃ | H | H | Et(E) |
| CH₃ | G²-1 | Cl | H | CF₃ | H | H | Et |
| CH₃ | G²-1 | Cl | H | OCH₃ | H | H | Et |
| CH₃ | G²-1 | Cl | H | SCH₃ | H | H | Et |
| CH₃ | G²-1 | Cl | H | S(O)CH₃ | H | H | Et |
| CH₃ | G²-1 | Cl | H | SO₂CH₃ | H | H | Et |
| CH₃ | G²-1 | Cl | H | C(O)CH₃ | H | H | Et |
| CH₃ | G²-1 | Cl | H | C(CH₃)=NOCH₃ | H | H | Et |
| CH₃ | G²-1 | Cl | H | CN | H | H | Et |
| CH₃ | G²-1 | Cl | H | (M-7-b)-4,4-(CH₃)₂ | H | H | Et |
| CH₃ | G²-1 | Cl | H | CH=CH₂ | H | H | Et |
| CH₃ | G²-1 | Cl | H | Ph | H | H | Et |
| CH₃ | G²-1 | Cl | H | Ph-4-OCF₃ | H | H | Et |
| CH₃ | G²-1 | Cl | H | D-3-a | H | H | Et |
| CH₃ | G²-1 | Cl | H | D-7-a | H | H | Et |
| CH₃ | G²-1 | Cl | H | (D-7-b)-3-CF₃ | H | H | Et |
| CH₃ | G²-1 | Cl | F | H | H | H | Et |
| CH₃ | G²-1 | Br | H | F | H | H | Et |
| CH₃ | G²-1 | Br | H | F | F | H | Et |
| CH₃ | G²-1 | CH₃ | H | Cl | H | H | Et |
| CH₃ | G²-1 | CH₃ | H | CH₃ | H | H | Et |

TABLE 2-continued

| R² | G² | Y¹ | Y² | Y³ | Y⁴ | Y⁵ | R¹ |
|---|---|---|---|---|---|---|---|
| CH₃ | G²-1 | CF₃ | H | Cl | H | H | Et |
| CH₃ | G²-1 | OCH₃ | H | Cl | H | H | Et |
| CH₃ | G²-1 | CH=NOEt | H | Cl | H | H | Et |
| CH₃ | G²-1 | E-9-1a | H | Cl | H | H | Et |
| CH₃ | G²-1 | —CH=CHCH=CH— | | Br | H | H | Et |
| H | G²-2 | F | H | Cl | H | — | Et |
| H | G²-2 | F | H | Cl | H | — | Et(Z) |
| CH₃ | G²-2 | F | H | Cl | H | — | Et(Z) |
| CH₃(S) | G²-2 | F | H | Cl | H | — | Et(Z) |
| H | G²-2 | F | H | Br | H | — | Et |
| H | G²-2 | F | H | Br | H | — | Et(Z) |
| CH₃ | G²-2 | F | H | Br | H | — | Et(Z) |
| CH₃(S) | G²-2 | F | H | Br | H | — | Et(Z) |
| H | G²-2 | F | H | CF₃ | H | — | Et |
| H | G²-2 | F | H | CF₃ | H | — | Et(Z) |
| H | G²-2 | Cl | H | F | H | — | Et |
| H | G²-2 | Cl | H | F | H | — | Et(Z) |
| CH₃ | G²-2 | Cl | H | F | H | — | Et(Z) |
| CH₃(S) | G²-2 | Cl | H | F | H | — | Et(Z) |
| H | G²-2 | Cl | H | Cl | H | — | Et |
| H | G²-2 | Cl | H | Cl | H | — | Et(E) |
| H | G²-2 | Cl | H | Cl | H | — | Et(Z) |
| CH₃ | G²-2 | Cl | H | Cl | H | — | Et |
| CH₃ | G²-2 | Cl | H | Cl | H | — | Et(E) |
| CH₃ | G²-2 | Cl | H | Cl | H | — | Et(Z) |
| CH₃(S) | G²-2 | Cl | H | Cl | H | — | Et |
| CH₃(S) | G²-2 | Cl | H | Cl | H | — | Et(E) |
| CH₃(S) | G²-2 | Cl | H | Cl | H | — | Et(Z) |
| H | G²-2 | Cl | H | Cl | F | — | Et |
| H | G²-2 | Cl | H | Cl | F | — | Et(E) |
| H | G²-2 | Cl | H | Cl | F | — | Et(Z) |
| CH₃ | G²-2 | Cl | H | Cl | F | — | Et |
| CH₃ | G²-2 | Cl | H | Cl | F | — | Et(Z) |
| CH₃(S) | G²-2 | Cl | H | Cl | F | — | Et |
| CH₃(S) | G²-2 | Cl | H | Cl | F | — | Et(Z) |
| t-Bu | G²-2 | Cl | H | Cl | H | — | Et |
| H | G²-2 | Cl | H | Cl | Cl | — | Et |
| H | G²-2 | Cl | H | Cl | Cl | — | Et(Z) |
| H | G²-2 | Cl | H | Br | H | — | Et |
| H | G²-2 | Cl | H | Br | H | — | Et(E) |
| H | G²-2 | Cl | H | Br | H | — | Et(Z) |
| CH₃ | G²-2 | Cl | H | Br | H | — | Et |
| CH₃ | G²-2 | Cl | H | Br | H | — | Et(Z) |
| CH₃(S) | G²-2 | Cl | H | Br | H | — | Et |
| CH₃(S) | G²-2 | Cl | H | Br | H | — | Et(Z) |
| H | G²-2 | Cl | H | CF₃ | H | — | Et |
| H | G²-2 | Cl | H | CF₃ | H | — | Et(E) |
| H | G²-2 | Cl | H | CF₃ | H | — | Et(Z) |
| CH₃ | G²-2 | Cl | H | CF₃ | H | — | Et |
| CH₃ | G²-2 | Cl | H | CF₃ | H | — | Et(Z) |
| CH₃(S) | G²-2 | Cl | H | CF₃ | H | — | Et |
| CH₃(S) | G²-2 | Cl | H | CF₃ | H | — | Et(Z) |
| H | G²-2 | Cl | H | CH=NOCH₃ | H | — | Et |
| H | G²-2 | Cl | H | CH=NOEt | H | — | Et |
| H | G²-2 | Cl | H | C(CH₃)=NOCH₃ | H | — | Et |
| CH₃ | G²-2 | Cl | H | C(CH₃)=NOCH₃ | H | — | Et |
| CH₃(S) | G²-2 | Cl | H | C(CH₃)=NOCH₃ | H | — | Et |
| H | G²-2 | Cl | H | C(CH₃)=NOEt | H | — | Et |
| H | G²-2 | Cl | H | C(Et)=NOCH₃ | H | — | Et |
| H | G²-2 | Cl | H | C≡CH | H | — | Et |
| H | G²-2 | Cl | H | C≡CH | H | — | Et(Z) |
| H | G²-2 | Cl | H | C≡CCH₃ | H | — | Et |
| H | G²-2 | Cl | H | C≡CCH₃ | H | — | Et(Z) |
| H | G²-2 | Cl | H | C≡CEt | H | — | Et |
| H | G²-2 | Cl | H | C≡CPr-n | H | — | Et |
| H | G²-2 | Cl | H | C≡CPr-c | H | — | Et |
| H | G²-2 | Cl | H | C≡CPr-c | H | — | Et(Z) |
| CH₃ | G²-2 | Cl | H | C≡CPr-c | H | — | Et |
| CH₃ | G²-2 | Cl | H | C≡CPr-c | H | — | Et(Z) |
| CH₃(S) | G²-2 | Cl | H | C≡CPr-c | H | — | Et |
| CH₃(S) | G²-2 | Cl | H | C≡CPr-c | H | — | Et(Z) |
| H | G²-2 | Cl | H | C≡CBu-n | H | — | Et |
| H | G²-2 | Cl | H | C≡CBu-t | H | — | Et |
| H | G²-2 | Cl | H | C≡CBu-t | H | — | Et(Z) |
| CH₃ | G²-2 | Cl | H | C≡CBu-t | H | — | Et |
| CH₃ | G²-2 | Cl | H | C≡CBu-t | H | — | Et(Z) |
| CH₃(S) | G²-2 | Cl | H | C≡CBu-t | H | — | Et |
| CH₃(S) | G²-2 | Cl | H | C≡CBu-t | H | — | Et(Z) |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CPen-c | H | — | Et |
| H | G²-2 | Cl | H | C≡CPen-c | H | — | Et(Z) |
| H | G²-2 | Cl | H | C≡CCl | H | — | Et |
| H | G²-2 | Cl | H | C≡CBr | H | — | Et |
| H | G²-2 | Cl | H | C≡CI | H | — | Et |
| H | G²-2 | Cl | H | C≡CC(CH₃)₂OH | H | — | Et |
| H | G²-2 | Cl | H | C≡CC(CH₃)₂OH | H | — | Et(Z) |
| H | G²-2 | Cl | H | C≡CC(CH₃)₂OCH₃ | H | — | Et |
| H | G²-2 | Cl | H | C≡CC(CH₃)₂OCH₃ | H | — | Et(Z) |
| H | G²-2 | Cl | H | C≡CSi(CH₃)₃ | H | — | Et |
| H | G²-2 | Cl | H | C≡CSi(CH₃)₃ | H | — | Et(Z) |
| H | G²-2 | Cl | H | C≡CPh | H | — | Et |
| H | G²-2 | Cl | H | C≡CPh | H | — | Et(Z) |
| H | G²-2 | Cl | H | CN | H | — | Et |
| H | G²-2 | Cl | F | Cl | H | — | Et |
| H | G²-2 | Cl | F | Cl | H | — | Et(Z) |
| CH₃ | G²-2 | Cl | F | Cl | H | — | Et(Z) |
| CH₃(S) | G²-2 | Cl | F | Cl | H | — | Et(Z) |
| H | G²-2 | Cl | Cl | Cl | H | — | Et |
| H | G²-2 | Cl | Cl | Cl | H | — | Et(Z) |
| CH₃ | G²-2 | Cl | Cl | Cl | H | — | Et(Z) |
| CH₃(S) | G²-2 | Cl | Cl | Cl | H | — | Et(Z) |
| H | G²-2 | Br | H | F | H | — | Et |
| H | G²-2 | Br | H | F | H | — | Et(Z) |
| H | G²-2 | Br | H | Cl | H | — | Et |
| H | G²-2 | Br | H | Cl | H | — | Et(Z) |
| CH₃ | G²-2 | Br | H | Cl | H | — | Et(Z) |
| CH₃(S) | G²-2 | Br | H | Cl | H | — | Et(Z) |
| H | G²-2 | Br | H | Br | H | — | Et |
| H | G²-2 | Br | H | Br | H | — | Et(Z) |
| CH₃ | G²-2 | Br | H | Br | H | — | Et |
| CH₃ | G²-2 | Br | H | Br | H | — | Et(Z) |
| CH₃(S) | G²-2 | Br | H | Br | H | — | Et |
| CH₃(S) | G²-2 | Br | H | Br | H | — | Et(Z) |
| H | G²-2 | Br | H | CF₃ | H | — | Et |
| H | G²-2 | Br | H | CF₃ | H | — | Et(Z) |
| H | G²-3 | Cl | — | H | Cl | H | Et |
| H | G²-4 | Cl | H | Cl | — | H | Et |
| CH₃ | G²-4 | Cl | H | Cl | — | H | Et |
| H | G²-4 | Cl | H | CF₃ | — | H | Et |
| H | G²-6 | Cl | — | Cl | H | — | Et |
| CH₃ | G²-6 | Cl | — | Cl | H | — | Et |
| H | G²-7 | Cl | H | Br | — | — | Et |
| CH₃ | G²-7 | Cl | H | Br | — | — | Et |
| H | G²-7 | Cl | Cl | Cl | — | — | Et |
| CH₃ | G²-9 | Cl | H | Cl | — | — | Et |
| CH₃ | G²-9 | Cl | H | Cl | — | — | Et(Z) |
| CH₃ | G²-9 | Cl | H | Br | — | — | Et |
| CH₃ | G²-9 | Cl | H | Br | — | — | Et(Z) |
| CH₃ | G²-9 | Cl | H | C≡CPr-c | — | — | Et |
| CH₃ | G²-9 | Cl | H | C≡CPr-c | — | — | Et(Z) |
| CH₃ | G²-9 | Cl | H | C≡CBu-t | — | — | Et |
| CH₃ | G²-9 | Cl | H | C≡CBu-t | — | — | Et(Z) |
| H | G²-9 | Cl | Cl | Cl | — | — | Et |
| CH₃ | G²-9 | Cl | Cl | Cl | — | — | Et |
| CH₃ | G²-9 | Cl | Cl | Cl | — | — | Et(Z) |
| CH₃ | G²-10 | Cl | — | H | H | — | Et |
| CH₃ | G²-10 | Cl | — | Cl | H | — | Et |
| CH₃ | G²-1 | Cl | H | F | H | H | n-Pr |
| CH₃ | G²-1 | Cl | H | F | H | H | n-Pr(E) |
| CH₃(S) | G²-1 | Cl | H | F | H | H | n-Pr |
| CH₃(S) | G²-1 | Cl | H | F | H | H | n-Pr(E) |
| H | G²-2 | F | H | Cl | H | — | n-Pr |
| H | G²-2 | F | H | Cl | H | — | n-Pr(Z) |
| CH₃ | G²-2 | F | H | Cl | H | — | n-Pr(Z) |
| CH₃(S) | G²-2 | F | H | Cl | H | — | n-Pr(Z) |
| H | G²-2 | F | H | Br | H | — | n-Pr |
| H | G²-2 | F | H | Br | H | — | n-Pr(Z) |
| CH₃ | G²-2 | F | H | Br | H | — | n-Pr(Z) |
| CH₃(S) | G²-2 | F | H | Br | H | — | n-Pr(Z) |
| H | G²-2 | F | H | CF₃ | H | — | n-Pr |
| H | G²-2 | F | H | CF₃ | H | — | n-Pr(Z) |
| H | G²-2 | Cl | H | F | H | — | n-Pr |
| H | G²-2 | Cl | H | F | H | — | n-Pr(Z) |
| CH₃ | G²-2 | Cl | H | F | H | — | n-Pr(Z) |
| CH₃(S) | G²-2 | Cl | H | F | H | — | n-Pr(Z) |
| H | G²-2 | Cl | H | Cl | H | — | n-Pr |
| H | G²-2 | Cl | H | Cl | H | — | n-Pr(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | Cl | H | — | n-Pr |
| CH₃ | G²-2 | Cl | H | Cl | H | — | n-Pr(Z) |
| CH₃(S) | G²-2 | Cl | H | Cl | H | — | n-Pr |
| CH₃(S) | G²-2 | Cl | H | Cl | H | — | n-Pr(Z) |
| H | G²-2 | Cl | H | Cl | F | — | n-Pr |
| H | G²-2 | Cl | H | Cl | F | — | n-Pr(Z) |
| CH₃ | G²-2 | Cl | H | Cl | F | — | n-Pr |
| CH₃ | G²-2 | Cl | H | Cl | F | — | n-Pr(Z) |
| CH₃(S) | G²-2 | Cl | H | Cl | F | — | n-Pr |
| CH₃(S) | G²-2 | Cl | H | Cl | F | — | n-Pr(Z) |
| H | G²-2 | Cl | H | Cl | Cl | — | n-Pr |
| H | G²-2 | Cl | H | Cl | Cl | — | n-Pr(Z) |
| H | G²-2 | Cl | H | Br | H | — | n-Pr |
| H | G²-2 | Cl | H | Br | H | — | n-Pr(Z) |
| CH₃ | G²-2 | Cl | H | Br | H | — | n-Pr |
| CH₃ | G²-2 | Cl | H | Br | H | — | n-Pr(Z) |
| CH₃(S) | G²-2 | Cl | H | Br | H | — | n-Pr |
| CH₃(S) | G²-2 | Cl | H | Br | H | — | n-Pr(Z) |
| H | G²-2 | Cl | H | CF₃ | H | — | n-Pr |
| H | G²-2 | Cl | H | CF₃ | H | — | n-Pr(E) |
| H | G²-2 | Cl | H | CF₃ | H | — | n-Pr(Z) |
| CH₃ | G²-2 | Cl | H | CF₃ | H | — | n-Pr |
| CH₃ | G²-2 | Cl | H | CF₃ | H | — | n-Pr(Z) |
| CH₃(S) | G²-2 | Cl | H | CF₃ | H | — | n-Pr |
| CH₃(S) | G²-2 | Cl | H | CF₃ | H | — | n-Pr(Z) |
| H | G²-2 | Cl | H | CH=NOCH₃ | H | — | n-Pr |
| H | G²-2 | Cl | H | CH=NOEt | H | — | n-Pr |
| H | G²-2 | Cl | H | C(CH₃)=NOCH₃ | H | — | n-Pr |
| CH₃ | G²-2 | Cl | H | C(CH₃)=NOCH₃ | H | — | n-Pr |
| CH₃(S) | G²-2 | Cl | H | C(CH₃)=NOCH₃ | H | — | n-Pr |
| H | G²-2 | Cl | H | C(CH₃)=NOEt | H | — | n-Pr |
| H | G²-2 | Cl | H | C(Et)=NOCH₃ | H | — | n-Pr |
| H | G²-2 | Cl | H | C≡CH | H | — | n-Pr |
| H | G²-2 | Cl | H | C≡CH | H | — | n-Pr(Z) |
| H | G²-2 | Cl | H | C≡CCH₃ | H | — | n-Pr |
| H | G²-2 | Cl | H | C≡CCH₃ | H | — | n-Pr(Z) |
| H | G²-2 | Cl | H | C≡CEt | H | — | n-Pr |
| H | G²-2 | Cl | H | C≡CPr-n | H | — | n-Pr |
| H | G²-2 | Cl | H | C≡CPr-c | H | — | n-Pr |
| H | G²-2 | Cl | H | C≡CPr-c | H | — | n-Pr(Z) |
| CH₃ | G²-2 | Cl | H | C≡CPr-c | H | — | n-Pr |
| CH₃ | G²-2 | Cl | H | C≡CPr-c | H | — | n-Pr(Z) |
| CH₃(S) | G²-2 | Cl | H | C≡CPr-c | H | — | n-Pr |
| CH₃(S) | G²-2 | Cl | H | C≡CPr-c | H | — | n-Pr(Z) |
| H | G²-2 | Cl | H | C≡CBu-n | H | — | n-Pr |
| H | G²-2 | Cl | H | C≡CBu-t | H | — | n-Pr |
| H | G²-2 | Cl | H | C≡CBu-t | H | — | n-Pr(Z) |
| CH₃ | G²-2 | Cl | H | C≡CBu-t | H | — | n-Pr |
| CH₃ | G²-2 | Cl | H | C≡CBu-t | H | — | n-Pr(Z) |
| CH₃(S) | G²-2 | Cl | H | C≡CBu-t | H | — | n-Pr |
| CH₃(S) | G²-2 | Cl | H | C≡CBu-t | H | — | n-Pr(Z) |
| H | G²-2 | Cl | H | C≡CPen-c | H | — | n-Pr |
| H | G²-2 | Cl | H | C≡CPen-c | H | — | n-Pr(Z) |
| H | G²-2 | Cl | H | C≡CCl | H | — | n-Pr |
| H | G²-2 | Cl | H | C≡CBr | H | — | n-Pr |
| H | G²-2 | Cl | H | C≡CI | H | — | n-Pr |
| H | G²-2 | Cl | H | C≡CC(CH₃)₂OH | H | — | n-Pr |
| H | G²-2 | Cl | H | C≡CC(CH₃)₂OH | H | — | n-Pr(Z) |
| H | G²-2 | Cl | H | C≡CC(CH₃)₂OCH₃ | H | — | n-Pr |
| H | G²-2 | Cl | H | C≡CC(CH₃)₂OCH₃ | H | — | n-Pr(Z) |
| H | G²-2 | Cl | H | C≡CSi(CH₃)₃ | H | — | n-Pr |
| H | G²-2 | Cl | H | C≡CSi(CH₃)₃ | H | — | n-Pr(Z) |
| H | G²-2 | Cl | H | C≡CPh | H | — | n-Pr |
| H | G²-2 | Cl | H | C≡CPh | H | — | n-Pr(Z) |
| H | G²-2 | Cl | F | Cl | H | — | n-Pr |
| H | G²-2 | Cl | F | Cl | H | — | n-Pr(Z) |
| CH₃ | G²-2 | Cl | F | Cl | H | — | n-Pr(Z) |
| CH₃(S) | G²-2 | Cl | F | Cl | H | — | n-Pr(Z) |
| H | G²-2 | Cl | Cl | Cl | H | — | n-Pr |
| H | G²-2 | Cl | Cl | Cl | H | — | n-Pr(Z) |
| CH₃ | G²-2 | Cl | Cl | Cl | H | — | n-Pr(Z) |
| CH₃(S) | G²-2 | Cl | Cl | Cl | H | — | n-Pr(Z) |
| H | G²-2 | Br | H | F | H | — | n-Pr |
| H | G²-2 | Br | H | F | H | — | n-Pr(Z) |
| H | G²-2 | Br | H | Cl | H | — | n-Pr |
| H | G²-2 | Br | H | Cl | H | — | n-Pr(Z) |
| CH₃ | G²-2 | Br | H | Cl | H | — | n-Pr(Z) |
| CH₃(S) | G²-2 | Br | H | Cl | H | — | n-Pr(Z) |

TABLE 2-continued

| R² | G² | Y¹ | Y² | Y³ | Y⁴ | Y⁵ | R¹ |
|---|---|---|---|---|---|---|---|
| H | G²-2 | Br | H | Br | H | — | n-Pr |
| H | G²-2 | Br | H | Br | H | — | n-Pr(Z) |
| CH₃ | G²-2 | Br | H | Br | H | — | n-Pr |
| CH₃ | G²-2 | Br | H | Br | H | — | n-Pr(Z) |
| CH₃(S) | G²-2 | Br | H | Br | H | — | n-Pr |
| CH₃(S) | G²-2 | Br | H | Br | H | — | n-Pr(Z) |
| H | G²-2 | Br | H | CF₃ | H | — | n-Pr |
| H | G²-2 | Br | H | CF₃ | H | — | n-Pr(Z) |
| H | G²-6 | Cl | — | Cl | H | — | n-Pr |
| CH₃ | G²-6 | Cl | — | Cl | H | — | n-Pr |
| CH₃ | G²-9 | Cl | H | Cl | — | — | n-Pr |
| CH₃ | G²-9 | Cl | H | Cl | — | — | n-Pr(Z) |
| CH₃ | G²-9 | Cl | H | Br | — | — | n-Pr |
| CH₃ | G²-9 | Cl | H | Br | — | — | n-Pr(Z) |
| CH₃ | G²-9 | Cl | H | C≡CPr-c | — | — | n-Pr |
| CH₃ | G²-9 | Cl | H | C≡CPr-c | — | — | n-Pr(Z) |
| CH₃ | G²-9 | Cl | H | C≡CBu-t | — | — | n-Pr |
| CH₃ | G²-9 | Cl | H | C≡CBu-t | — | — | n-Pr(Z) |
| H | G²-9 | Cl | Cl | Cl | — | — | n-Pr |
| CH₃ | G²-9 | Cl | Cl | Cl | — | — | n-Pr |
| CH₃ | G²-9 | Cl | Cl | Cl | — | — | n-Pr(Z) |
| CH₃ | G²-1 | H | H | Ph | H | H | i-Pr |
| CH₃ | G²-1 | F | H | Cl | H | H | i-Pr |
| CH₃ | G²-1 | F | H | Cl | H | H | i-Pr(E) |
| CH₃(S) | G²-1 | F | H | Cl | H | H | i-Pr |
| CH₃(S) | G²-1 | F | H | Cl | H | H | i-Pr(E) |
| CH₃ | G²-1 | F | H | Br | H | H | i-Pr |
| CH₃ | G²-1 | Cl | H | F | H | H | i-Pr |
| CH₃ | G²-1 | Cl | H | F | H | H | i-Pr(E) |
| CH₃(S) | G²-1 | Cl | H | F | H | H | i-Pr |
| CH₃(S) | G²-1 | Cl | H | F | H | H | i-Pr(E) |
| H | G²-1 | Cl | H | Cl | H | H | i-Pr |
| CH₃ | G²-1 | Cl | H | Cl | H | H | i-Pr |
| CH₃ | G²-1 | Cl | H | Cl | H | H | i-Pr(E) |
| CH₃(S) | G²-1 | Cl | H | Cl | H | H | i-Pr |
| CH₃(S) | G²-1 | Cl | H | Cl | H | H | i-Pr(E) |
| CH₃ | G²-1 | Cl | H | Br | H | H | i-Pr |
| CH₃ | G²-1 | Cl | H | CH₃ | H | H | i-Pr |
| CH₃ | G²-1 | Cl | H | CH₃ | H | H | i-Pr(E) |
| CH₃(S) | G²-1 | Cl | H | CH₃ | H | H | i-Pr |
| CH₃(S) | G²-1 | Cl | H | CH₃ | H | H | i-Pr(E) |
| CH₃ | G²-1 | CH₃ | H | OPr-i | H | H | i-Pr |
| H | G²-2 | H | H | CF₃ | H | — | i-Pr |
| H | G²-2 | F | H | F | H | — | i-Pr |
| H | G²-2 | F | H | Cl | H | — | i-Pr |
| H | G²-2 | F | H | Cl | H | — | i-Pr(Z) |
| CH₃ | G²-2 | F | H | Cl | H | — | i-Pr |
| CH₃ | G²-2 | F | H | Cl | H | — | i-Pr(Z) |
| CH₃(S) | G²-2 | F | H | Cl | H | — | i-Pr |
| CH₃(S) | G²-2 | F | H | Cl | H | — | i-Pr(Z) |
| H | G²-2 | F | H | Cl | F | — | i-Pr |
| H | G²-2 | F | H | Cl | F | — | i-Pr(Z) |
| H | G²-2 | F | H | Br | H | — | i-Pr |
| H | G²-2 | F | H | Br | H | — | i-Pr(Z) |
| CH₃ | G²-2 | F | H | Br | H | — | i-Pr(Z) |
| CH₃(S) | G²-2 | F | H | Br | H | — | i-Pr(Z) |
| H | G²-2 | F | H | I | H | — | i-Pr |
| H | G²-2 | F | H | CH₃ | H | — | i-Pr |
| H | G²-2 | F | H | CF₃ | H | — | i-Pr |
| H | G²-2 | F | H | CF₃ | H | — | i-Pr(Z) |
| H | G²-2 | F | H | OCH₂CF₃ | H | — | i-Pr |
| H | G²-2 | F | H | NO₂ | H | — | i-Pr |
| H | G²-2 | F | H | T-7 | H | — | i-Pr |
| H | G²-2 | F | H | T-8 | H | — | i-Pr |
| H | G²-2 | F | H | T-9 | H | — | i-Pr |
| H | G²-2 | F | H | CN | H | — | i-Pr |
| H | G²-2 | F | H | D-3-a | H | — | i-Pr |
| H | G²-2 | Cl | H | H | H | — | i-Pr(Z) |
| H | G²-2 | Cl | H | F | H | — | i-Pr |
| H | G²-2 | Cl | H | F | H | — | i-Pr(Z) |
| CH₃ | G²-2 | Cl | H | F | H | — | i-Pr |
| CH₃ | G²-2 | Cl | H | F | H | — | i-Pr(Z) |
| CH₃(S) | G²-2 | Cl | H | F | H | — | i-Pr |
| CH₃(S) | G²-2 | Cl | H | F | H | — | i-Pr(Z) |
| H | G²-2 | Cl | H | Cl | H | — | i-Pr |
| H | G²-2 | Cl | H | Cl | H | — | i-Pr(E) |
| H | G²-2 | Cl | H | Cl | H | — | i-Pr(Z) |
| CH₃ | G²-2 | Cl | H | Cl | H | — | i-Pr |

TABLE 2-continued

| $R^2$ | $G^2$ | $Y^1$ | $Y^2$ | $Y^3$ | $Y^4$ | $Y^5$ | $R^1$ |
|---|---|---|---|---|---|---|---|
| CH₃ | G²-2 | Cl | H | Cl | H | — | i-Pr(E) |
| CH₃ | G²-2 | Cl | H | Cl | H | — | i-Pr(Z) |
| CH₃(R) | G²-2 | Cl | H | Cl | H | — | i-Pr |
| CH₃(R) | G²-2 | Cl | H | Cl | H | — | i-Pr(E) |
| CH₃(R) | G²-2 | Cl | H | Cl | H | — | i-Pr(Z) |
| CH₃(S) | G²-2 | Cl | H | Cl | H | — | i-Pr |
| CH₃(S) | G²-2 | Cl | H | Cl | H | — | i-Pr(E) |
| CH₃(S) | G²-2 | Cl | H | Cl | H | — | i-Pr(Z) |
| CH₂F | G²-2 | Cl | H | Cl | H | — | i-Pr |
| H | G²-2 | Cl | H | Cl | F | — | i-Pr |
| H | G²-2 | Cl | H | Cl | F | — | i-Pr(Z) |
| CH₃ | G²-2 | Cl | H | Cl | F | — | i-Pr |
| CH₃ | G²-2 | Cl | H | Cl | F | — | i-Pr(Z) |
| CH₃(S) | G²-2 | Cl | H | Cl | F | — | i-Pr |
| CH₃(S) | G²-2 | Cl | H | Cl | F | — | i-Pr(Z) |
| H | G²-2 | Cl | H | Cl | Cl | — | i-Pr |
| H | G²-2 | Cl | H | Cl | Cl | — | i-Pr(Z) |
| H | G²-2 | Cl | H | Cl | OCH₃ | — | i-Pr |
| H | G²-2 | Cl | H | Br | H | — | i-Pr |
| H | G²-2 | Cl | H | Br | H | — | i-Pr(Z) |
| CH₃ | G²-2 | Cl | H | Br | H | — | i-Pr |
| CH₃ | G²-2 | Cl | H | Br | H | — | i-Pr(Z) |
| CH₃(S) | G²-2 | Cl | H | Br | H | — | i-Pr |
| CH₃(S) | G²-2 | Cl | H | Br | H | — | i-Pr(Z) |
| H | G²-2 | Cl | H | CH₃ | H | — | i-Pr |
| H | G²-2 | Cl | H | CH₃ | H | — | i-Pr(Z) |
| CH₃ | G²-2 | Cl | H | CH₃ | H | — | i-Pr(Z) |
| CH₃(S) | G²-2 | Cl | H | CH₃ | H | — | i-Pr(Z) |
| H | G²-2 | Cl | H | CHF₂ | H | — | i-Pr |
| H | G²-2 | Cl | H | CHF₂ | H | — | i-Pr(Z) |
| CH₃ | G²-2 | Cl | H | CHF₂ | H | — | i-Pr(Z) |
| CH₃(S) | G²-2 | Cl | H | CHF₂ | H | — | i-Pr(Z) |
| H | G²-2 | Cl | H | CF₃ | H | — | i-Pr |
| H | G²-2 | Cl | H | CF₃ | H | — | i-Pr(E) |
| H | G²-2 | Cl | H | CF₃ | H | — | i-Pr(Z) |
| CH₃ | G²-2 | Cl | H | CF₃ | H | — | i-Pr |
| CH₃ | G²-2 | Cl | H | CF₃ | H | — | i-Pr(Z) |
| CH₃(R) | G²-2 | Cl | H | CF₃ | H | — | i-Pr |
| CH₃(R) | G²-2 | Cl | H | CF₃ | H | — | i-Pr(Z) |
| CH₃(S) | G²-2 | Cl | H | CF₃ | H | — | i-Pr |
| CH₃(S) | G²-2 | Cl | H | CF₃ | H | — | i-Pr(Z) |
| H | G²-2 | Cl | H | CH₂OCH₃ | H | — | i-Pr |
| H | G²-2 | Cl | H | OCH₃ | H | — | i-Pr |
| H | G²-2 | Cl | H | OCHF₂ | H | — | i-Pr |
| H | G²-2 | Cl | H | OCF₃ | H | — | i-Pr |
| H | G²-2 | Cl | H | OCF₂Cl | H | — | i-Pr |
| H | G²-2 | Cl | H | OCF₂Br | H | — | i-Pr |
| H | G²-2 | Cl | H | O(Ph-4-Cl) | H | — | i-Pr(Z) |
| H | G²-2 | Cl | H | SCH₃ | H | — | i-Pr |
| H | G²-2 | Cl | H | NO₂ | H | — | i-Pr |
| H | G²-2 | Cl | H | CH=NOCH₃ | H | — | i-Pr |
| H | G²-2 | Cl | H | CH=NOEt | H | — | i-Pr |
| CH₃ | G²-2 | Cl | H | CH=NOEt | H | — | i-Pr |
| CH₃(S) | G²-2 | Cl | H | CH=NOEt | H | — | i-Pr |
| H | G²-2 | Cl | H | C(CH₃)=NOCH₃ | H | — | i-Pr |
| CH₃ | G²-2 | Cl | H | C(CH₃)=NOCH₃ | H | — | i-Pr |
| CH₃(S) | G²-2 | Cl | H | C(CH₃)=NOCH₃ | H | — | i-Pr |
| H | G²-2 | Cl | H | C(CH₃)=NOEt | H | — | i-Pr |
| CH₃ | G²-2 | Cl | H | C(CH₃)=NOEt | H | — | i-Pr |
| CH₃(S) | G²-2 | Cl | H | C(CH₃)=NOEt | H | — | i-Pr |
| H | G²-2 | Cl | H | C(Et)=NOCH₃ | H | — | i-Pr |
| CH₃ | G²-2 | Cl | H | C(Et)=NOCH₃ | H | — | i-Pr |
| CH₃(S) | G²-2 | Cl | H | C(Et)=NOCH₃ | H | — | i-Pr |
| H | G²-2 | Cl | H | C(Et)=NOEt | H | — | i-Pr |
| H | G²-2 | Cl | H | (M-3-b)CH₃ | H | — | i-Pr |
| H | G²-2 | Cl | H | CN | H | — | i-Pr |
| H | G²-2 | Cl | H | CN | H | — | i-Pr(Z) |
| CH₃ | G²-2 | Cl | H | CN | H | — | i-Pr(Z) |
| CH₃(S) | G²-2 | Cl | H | CN | H | — | i-Pr(Z) |
| H | G²-2 | Cl | H | C(O)NH₂ | H | — | i-Pr |
| H | G²-2 | Cl | H | C(S)NH₂ | H | — | i-Pr |
| H | G²-2 | Cl | H | M-7-a | H | — | i-Pr |
| H | G²-2 | Cl | H | M-9-a | H | — | i-Pr |
| H | G²-2 | Cl | H | M-17-a | H | — | i-Pr |
| H | G²-2 | Cl | H | M-19-a | H | — | i-Pr |
| H | G²-2 | Cl | H | CH=CH₂ | H | — | i-Pr |
| H | G²-2 | Cl | H | C≡CH | H | — | i-Pr |
| H | G²-2 | Cl | H | C≡CH | H | — | i-Pr(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | C≡CH | H | — | i-Pr |
| CH₃ | G²-2 | Cl | H | C≡CH | H | — | i-Pr(Z) |
| CH₃(S) | G²-2 | Cl | H | C≡CH | H | — | i-Pr |
| CH₃(S) | G²-2 | Cl | H | C≡CH | H | — | i-Pr(Z) |
| H | G²-2 | Cl | H | C≡CCH₃ | H | — | i-Pr |
| H | G²-2 | Cl | H | C≡CCH₃ | H | — | i-Pr(Z) |
| H | G²-2 | Cl | H | C≡CEt | H | — | i-Pr |
| H | G²-2 | Cl | H | C≡CPr-n | H | — | i-Pr |
| H | G²-2 | Cl | H | C≡CPr-i | H | — | i-Pr |
| H | G²-2 | Cl | H | C≡CPr-c | H | — | i-Pr(Z) |
| CH₃ | G²-2 | Cl | H | C≡CPr-c | H | — | i-Pr |
| CH₃ | G²-2 | Cl | H | C≡CPr-c | H | — | i-Pr(Z) |
| CH₃(S) | G²-2 | Cl | H | C≡CPr-c | H | — | i-Pr |
| CH₃(S) | G²-2 | Cl | H | C≡CPr-c | H | — | i-Pr(Z) |
| H | G²-2 | Cl | H | C≡CBu-n | H | — | i-Pr |
| H | G²-2 | Cl | H | C≡CBu-i | H | — | i-Pr |
| H | G²-2 | Cl | H | C≡CBu-s | H | — | i-Pr |
| H | G²-2 | Cl | H | C≡CBu-t | H | — | i-Pr |
| H | G²-2 | Cl | H | C≡CBu-t | H | — | i-Pr(Z) |
| CH₃ | G²-2 | Cl | H | C≡CBu-t | H | — | i-Pr |
| CH₃ | G²-2 | Cl | H | C≡CBu-t | H | — | i-Pr(Z) |
| CH₃(S) | G²-2 | Cl | H | C≡CBu-t | H | — | i-Pr |
| CH₃(S) | G²-2 | Cl | H | C≡CBu-t | H | — | i-Pr(Z) |
| H | G²-2 | Cl | H | C≡CPen-c | H | — | i-Pr |
| H | G²-2 | Cl | H | C≡CPen-c | H | — | i-Pr(Z) |
| H | G²-2 | Cl | H | C≡CCl | H | — | i-Pr |
| H | G²-2 | Cl | H | C≡CBr | H | — | i-Pr |
| H | G²-2 | Cl | H | C≡CI | H | — | i-Pr |
| H | G²-2 | Cl | H | C≡CC(CH₃)₂F | H | — | i-Pr |
| H | G²-2 | Cl | H | C≡CC(CH₃)₂Cl | H | — | i-Pr |
| H | G²-2 | Cl | H | C≡CC(CH₃)₂Cl | H | — | i-Pr(Z) |
| H | G²-2 | Cl | H | C≡CC(CH₃)₂Br | H | — | i-Pr |
| H | G²-2 | Cl | H | C≡CCH₂OCH₃ | H | — | i-Pr |
| H | G²-2 | Cl | H | C≡CC(CH₃)₂OH | H | — | i-Pr |
| H | G²-2 | Cl | H | C≡CC(CH₃)₂OH | H | — | i-Pr(Z) |
| H | G²-2 | Cl | H | C≡CC(CH₃)₂OCH₃ | H | — | i-Pr |
| H | G²-2 | Cl | H | C≡CC(CH₃)₂OCH₃ | H | — | i-Pr(Z) |
| H | G²-2 | Cl | H | C≡CC(CH₃)₂OEt | H | — | i-Pr |
| H | G²-2 | Cl | H | C≡CC(CH₃)₂OEt | H | — | i-Pr(Z) |
| H | G²-2 | Cl | H | C≡C(T-3) | H | — | i-Pr |
| H | G²-2 | Cl | H | C≡C(T-4) | H | — | i-Pr |
| H | G²-2 | Cl | H | C≡CCH₂SCH₃ | H | — | i-Pr |
| H | G²-2 | Cl | H | C≡CCH₂S(O)CH₃ | H | — | i-Pr |
| H | G²-2 | Cl | H | C≡CCH₂SO₂CH₃ | H | — | i-Pr |
| H | G²-2 | Cl | H | C≡CC(CH₃)₂SEt | H | — | i-Pr |
| H | G²-2 | Cl | H | C≡CC(CH₃)₂SEt | H | — | i-Pr(Z) |
| H | G²-2 | Cl | H | C≡CSi(CH₃)₃ | H | — | i-Pr |
| H | G²-2 | Cl | H | C≡CSi(CH₃)₃ | H | — | i-Pr(Z) |
| H | G²-2 | Cl | H | C≡C(T-5) | H | — | i-Pr |
| H | G²-2 | Cl | H | C≡C(T-6) | H | — | i-Pr |
| H | G²-2 | Cl | H | C≡CPh | H | — | i-Pr |
| H | G²-2 | Cl | H | C≡CPh | H | — | i-Pr(Z) |
| H | G²-2 | Cl | H | C≡C(Ph-2-F) | H | — | i-Pr |
| H | G²-2 | Cl | H | C≡C(Ph-3-F) | H | — | i-Pr |
| H | G²-2 | Cl | H | C≡C(Ph-4-F) | H | — | i-Pr |
| H | G²-2 | Cl | H | C≡C(Ph-2-Cl) | H | — | i-Pr |
| H | G²-2 | Cl | H | C≡C(Ph-3-Cl) | H | — | i-Pr |
| H | G²-2 | Cl | H | C≡C(Ph-4-Cl) | H | — | i-Pr |
| H | G²-2 | Cl | H | C≡C(Ph-2-CH₃) | H | — | i-Pr |
| H | G²-2 | Cl | H | C≡C(Ph-3-CH₃) | H | — | i-Pr |
| H | G²-2 | Cl | H | C≡C(Ph-4-CH₃) | H | — | i-Pr |
| H | G²-2 | Cl | H | C≡C(Ph-4-Bu-t) | H | — | i-Pr |
| H | G²-2 | Cl | H | C≡C(Ph-2-CF₃) | H | — | i-Pr |
| H | G²-2 | Cl | H | C≡C(Ph-3-CF₃) | H | — | i-Pr |
| H | G²-2 | Cl | H | C≡C(Ph-4-CF₃) | H | — | i-Pr |
| H | G²-2 | Cl | H | C≡C(Ph-2-OCH₃) | H | — | i-Pr |
| H | G²-2 | Cl | H | C≡C(Ph-3-OCH₃) | H | — | i-Pr |
| H | G²-2 | Cl | H | C≡C(Ph-4-OCH₃) | H | — | i-Pr |
| H | G²-2 | Cl | H | C≡C(Ph-4-OCF₃) | H | — | i-Pr |
| H | G²-2 | Cl | H | C≡C(Ph-4-NO₂) | H | — | i-Pr |
| H | G²-2 | Cl | H | C≡C(Ph-4-CN) | H | — | i-Pr |
| H | G²-2 | Cl | H | C≡C(Ph-2,4-F₂) | H | — | i-Pr |
| H | G²-2 | Cl | H | C≡C(Ph-3,4-F₂) | H | — | i-Pr |
| H | G²-2 | Cl | H | C≡C(Ph-3,5-F₂) | H | — | i-Pr |
| H | G²-2 | Cl | H | C≡C(1-Naph) | H | — | i-Pr |
| H | G²-2 | Cl | H | C≡C(D-2-2a) | H | — | i-Pr |
| H | G²-2 | Cl | H | C≡C(D-12-3a)CH₃ | H | — | i-Pr |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡C(D-32-1a) | H | — | i-Pr |
| H | G²-2 | Cl | H | C≡C(D-32-2a) | H | — | i-Pr |
| H | G²-2 | Cl | H | C≡C(D-32-3a) | H | — | i-Pr |
| H | G²-2 | Cl | H | Ph-4-F | H | — | i-Pr |
| H | G²-2 | Cl | H | D-3-a | H | — | i-Pr |
| H | G²-2 | Cl | H | D-3-a | H | — | i-Pr(Z) |
| H | G²-2 | Cl | H | D-7-a | H | — | i-Pr |
| H | G²-2 | Cl | H | D-11-a | H | — | i-Pr |
| H | G²-2 | Cl | H | D-22-a | H | — | i-Pr |
| H | G²-2 | Cl | H | D-28-a | H | — | i-Pr |
| H | G²-2 | Cl | H | D-29-a | H | — | i-Pr |
| H | G²-2 | Cl | F | Cl | H | — | i-Pr |
| H | G²-2 | Cl | F | Cl | H | — | i-Pr(Z) |
| CH₃ | G²-2 | Cl | F | Cl | H | — | i-Pr |
| CH₃ | G²-2 | Cl | F | Cl | H | — | i-Pr(Z) |
| CH₃(S) | G²-2 | Cl | F | Cl | H | — | i-Pr |
| CH₃(S) | G²-2 | Cl | F | Cl | H | — | i-Pr(Z) |
| H | G²-2 | Cl | Cl | Cl | H | — | i-Pr |
| H | G²-2 | Cl | Cl | Cl | H | — | i-Pr(Z) |
| CH₃ | G²-2 | Cl | Cl | Cl | H | — | i-Pr |
| CH₃ | G²-2 | Cl | Cl | Cl | H | — | i-Pr(Z) |
| CH₃(S) | G²-2 | Cl | Cl | Cl | H | — | i-Pr |
| CH₃(S) | G²-2 | Cl | Cl | Cl | H | — | i-Pr(Z) |
| H | G²-2 | Cl | Br | Cl | H | — | i-Pr |
| H | G²-2 | Cl | Br | Cl | H | — | i-Pr(Z) |
| H | G²-2 | Cl | I | Cl | H | — | i-Pr |
| H | G²-2 | Cl | CH₃ | Cl | H | — | i-Pr |
| H | G²-2 | Cl | CH₃ | Cl | H | — | i-Pr(Z) |
| H | G²-2 | Cl | CH₂OCH₃ | Cl | H | — | i-Pr |
| H | G²-2 | Cl | CH₂SCH₃ | Cl | H | — | i-Pr |
| H | G²-2 | Cl | CH₂SO₂CH₃ | Cl | H | — | i-Pr |
| H | G²-2 | Cl | OCH₃ | Cl | H | — | i-Pr |
| H | G²-2 | Cl | SCH₃ | Cl | H | — | i-Pr |
| H | G²-2 | Cl | SO₂CH₃ | Cl | H | — | i-Pr |
| H | G²-2 | Cl | CN | Cl | H | — | i-Pr |
| H | G²-2 | Cl | CN | Cl | H | — | i-Pr(Z) |
| H | G²-2 | Cl | C(O)OCH₃ | Cl | H | — | i-Pr |
| H | G²-2 | Br | H | F | H | — | i-Pr |
| H | G²-2 | Br | H | F | H | — | i-Pr(Z) |
| CH₃ | G²-2 | Br | H | F | H | — | i-Pr(Z) |
| CH₃(S) | G²-2 | Br | H | F | H | — | i-Pr(Z) |
| H | G²-2 | Br | H | Cl | H | — | i-Pr |
| H | G²-2 | Br | H | Cl | H | — | i-Pr(Z) |
| CH₃ | G²-2 | Br | H | Cl | H | — | i-Pr |
| CH₃ | G²-2 | Br | H | Cl | H | — | i-Pr(Z) |
| CH₃(S) | G²-2 | Br | H | Cl | H | — | i-Pr |
| CH₃(S) | G²-2 | Br | H | Cl | H | — | i-Pr(Z) |
| H | G²-2 | Br | H | Br | H | — | i-Pr |
| H | G²-2 | Br | H | Br | H | — | i-Pr(Z) |
| CH₃ | G²-2 | Br | H | Br | H | — | i-Pr |
| CH₃ | G²-2 | Br | H | Br | H | — | i-Pr(Z) |
| CH₃(S) | G²-2 | Br | H | Br | H | — | i-Pr |
| CH₃(S) | G²-2 | Br | H | Br | H | — | i-Pr(Z) |
| H | G²-2 | Br | H | CH₃ | H | — | i-Pr |
| H | G²-2 | Br | H | CF₃ | H | — | i-Pr |
| H | G²-2 | Br | H | CF₃ | H | — | i-Pr(Z) |
| H | G₂-2 | Br | H | OCH₃ | H | — | i-Pr |
| H | G²-2 | Br | H | OCHF₂ | H | — | i-Pr |
| H | G²-2 | Br | H | NO₂ | H | — | i-Pr |
| H | G²-2 | Br | H | CN | H | — | i-Pr |
| H | G²-2 | Br | H | C(O)NH₂ | H | — | i-Pr |
| H | G²-2 | Br | H | C(S)NH₂ | H | — | i-Pr |
| H | G²-2 | Br | H | SO₂N(CH₃)₂ | H | — | i-Pr |
| H | G²-2 | Br | CH₃ | Br | H | — | i-Pr |
| H | G²-2 | I | H | CF₃ | H | — | i-Pr |
| H | G²-2 | CH₃ | H | F | H | — | i-Pr |
| H | G²-2 | CH₃ | H | F | H | — | i-Pr(Z) |
| H | G²-2 | CH₃ | H | Cl | H | — | i-Pr |
| H | G²-2 | CH₃ | H | Cl | H | — | i-Pr(Z) |
| H | G²-2 | CH₃ | H | Br | H | — | i-Pr |
| H | G²-2 | CH₃ | H | I | H | — | i-Pr |
| H | G²-2 | CH₃ | H | CH₃ | H | — | i-Pr |
| CH₃ | G²-2 | CH₃ | H | CH₃ | H | — | i-Pr |
| H | G²-2 | CH₃ | H | CF₃ | H | — | i-Pr |
| H | G²-2 | CH₃ | H | OCH₃ | H | — | i-Pr |
| H | G²-2 | CH₃ | H | OCH₂CF₃ | H | — | i-Pr |
| H | G²-2 | CH₃ | H | NO₂ | H | — | i-Pr |
| H | G²-2 | CH₃ | H | CN | H | — | i-Pr |

TABLE 2-continued

| R² | G² | Y¹ | Y² | Y³ | Y⁴ | Y⁵ | R¹ |
|---|---|---|---|---|---|---|---|
| H | G²-2 | CH₃ | H | C(O)NH₂ | H | — | i-Pr |
| H | G²-2 | CH₃ | H | C(S)NH₂ | H | — | i-Pr |
| H | G²-2 | CF₃ | H | Br | H | — | i-Pr |
| H | G²-2 | CF₃ | H | CH₃ | H | — | i-Pr |
| H | G²-2 | CF₃ | H | CF₃ | H | — | i-Pr |
| H | G²-2 | CF₃ | H | NO₂ | H | — | i-Pr |
| H | G²-2 | CF₃ | H | CN | H | — | i-Pr |
| H | G²-2 | CF₃ | H | D-3-a | H | — | i-Pr |
| H | G²-2 | OCH₃ | H | Cl | H | — | i-Pr |
| H | G²-2 | OCH₃ | H | Br | H | — | i-Pr |
| H | G²-2 | OCHF₂ | H | Cl | H | — | i-Pr |
| H | G²-2 | OCHF₂ | H | Br | H | — | i-Pr |
| H | G²-2 | SCH₃ | H | Br | H | — | i-Pr |
| H | G²-2 | NO₂ | H | Cl | H | — | i-Pr |
| H | G²-2 | NO₂ | H | Br | H | — | i-Pr |
| H | G²-2 | NO₂ | H | CF₃ | H | — | i-Pr |
| H | G²-2 | CN | H | Cl | H | — | i-Pr |
| H | G²-2 | CN | H | Br | H | — | i-Pr |
| H | G²-2 | CN | H | CH₃ | H | — | i-Pr |
| H | G²-2 | CN | H | Et | H | — | i-Pr |
| H | G²-2 | CN | H | CF₃ | H | — | i-Pr |
| H | G²-3 | F | — | F | F | H | i-Pr |
| H | G²-3 | Cl | — | H | Cl | H | i-Pr |
| H | G²-3 | Cl | — | Cl | H | H | i-Pr |
| CH₃ | G²-3 | Cl | — | Cl | H | H | i-Pr |
| H | G²-3 | Cl | — | Cl | F | H | i-Pr |
| H | G²-3 | Cl | — | CF₃ | H | H | i-Pr |
| H | G²-3 | Br | — | Br | H | H | i-Pr |
| CH₃ | G²-3 | CH₃ | — | Cl | H | H | i-Pr |
| H | G²-3 | CH₃ | — | Cl | CN | H | i-Pr |
| H | G²-3 | CH₃ | — | CF₃ | H | H | i-Pr |
| H | G²-4 | Cl | H | Cl | — | H | i-Pr |
| CH₃ | G²-4 | Cl | H | Cl | — | H | i-Pr |
| H | G²-4 | Cl | H | CF₃ | — | H | i-Pr |
| H | G²-4 | Cl | H | C≡CPr-c | — | H | i-Pr |
| CH₃ | G²-4 | Cl | H | C≡CPr-c | — | H | i-Pr |
| H | G²-4 | Cl | H | C≡CBu-t | — | H | i-Pr |
| CH₃ | G²-4 | Cl | H | C≡CBu-t | — | H | i-Pr |
| CH₃ | G²-4 | CH₃ | H | Cl | — | H | i-Pr |
| H | G²-6 | Cl | — | Cl | H | — | i-Pr |
| CH₃ | G²-6 | Cl | — | Cl | H | — | i-Pr |
| H | G²-6 | CH₃ | — | Cl | H | — | i-Pr |
| H | G²-6 | CH₃ | — | Cl | CH₃ | — | i-Pr |
| H | G²-6 | CH₃ | — | CH₃ | H | — | i-Pr |
| H | G²-6 | CH₃ | — | C≡CPr-c | H | — | i-Pr |
| H | G²-6 | CH₃ | — | C≡CBu-t | H | — | i-Pr |
| H | G²-7 | Cl | H | Br | — | — | i-Pr |
| CH₃ | G²-7 | Cl | H | Br | — | — | i-Pr |
| H | G²-7 | Cl | H | C≡CPr-c | — | — | i-Pr |
| CH₃ | G²-7 | Cl | H | C≡CPr-c | — | — | i-Pr |
| H | G²-7 | Cl | H | C≡CBu-t | — | — | i-Pr |
| CH₃ | G²-7 | Cl | H | C≡CBu-t | — | — | i-Pr |
| H | G²-7 | Cl | Cl | Cl | — | — | i-Pr |
| CH₃ | G²-9 | Cl | H | Cl | — | — | i-Pr |
| CH₃ | G²-9 | Cl | H | Cl | — | — | i-Pr(Z) |
| CH₃ | G²-9 | Cl | H | Br | — | — | i-Pr |
| CH₃ | G²-9 | Cl | H | Br | — | — | i-Pr(Z) |
| CH₃ | G²-9 | Cl | H | C≡CPr-c | — | — | i-Pr |
| CH₃ | G²-9 | Cl | H | C≡CPr-c | — | — | i-Pr(Z) |
| CH₃ | G²-9 | Cl | H | C≡CBu-t | — | — | i-Pr |
| CH₃ | G²-9 | Cl | H | C≡CBu-t | — | — | i-Pr(Z) |
| H | G²-9 | Cl | Cl | Cl | — | — | i-Pr |
| CH₃ | G²-9 | Cl | Cl | Cl | — | — | i-Pr |
| CH₃ | G²-9 | Cl | Cl | Cl | — | — | i-Pr(Z) |
| H | G²-2 | Cl | H | Cl | H | — | c-Pr |
| H | G²-2 | Cl | H | CF₃ | H | — | c-Pr |
| H | G²-2 | F | H | Cl | H | — | n-Bu |
| H | G²-2 | F | H | Cl | H | — | n-Bu(Z) |
| H | G²-2 | Cl | H | F | H | — | n-Bu |
| H | G²-2 | Cl | H | F | H | — | n-Bu(Z) |
| H | G²-2 | Cl | H | Cl | H | — | n-Bu |
| H | G²-2 | Cl | H | Cl | H | — | n-Bu(Z) |
| CH₃ | G²-2 | Cl | H | Cl | H | — | n-Bu |
| CH₃ | G²-2 | Cl | H | Cl | H | — | n-Bu(Z) |
| CH₃(S) | G²-2 | Cl | H | Cl | H | — | n-Bu |
| CH₃(S) | G²-2 | Cl | H | Cl | H | — | n-Bu(Z) |
| H | G²-2 | Cl | H | Cl | F | — | n-Bu |
| H | G²-2 | Cl | H | Cl | F | — | n-Bu(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | Cl | F | — | n-Bu(Z) |
| CH₃(S) | G²-2 | Cl | H | Cl | F | — | n-Bu(Z) |
| H | G²-2 | Cl | H | Br | H | — | n-Bu |
| H | G²-2 | Cl | H | Br | H | — | n-Bu(Z) |
| CH₃ | G²-2 | Cl | H | Br | H | — | n-Bu(Z) |
| CH₃(S) | G²-2 | Cl | H | Br | H | — | n-Bu(Z) |
| H | G²-2 | Cl | H | CF₃ | H | — | n-Bu |
| H | G²-2 | Cl | H | CF₃ | H | — | n-Bu(Z) |
| CH₃ | G²-2 | Cl | H | CF₃ | H | — | n-Bu(Z) |
| CH₃(S) | G²-2 | Cl | H | CF₃ | H | — | n-Bu(Z) |
| H | G²-2 | Cl | H | C≡CH | H | — | n-Bu |
| H | G²-2 | Cl | H | C≡CH | H | — | n-Bu(Z) |
| H | G²-2 | Cl | H | C≡CCH₃ | H | — | n-Bu |
| H | G²-2 | Cl | H | C≡CCH₃ | H | — | n-Bu(Z) |
| H | G²-2 | Cl | H | C≡CEt | H | — | n-Bu |
| H | G²-2 | Cl | H | C≡CPr-n | H | — | n-Bu |
| H | G²-2 | Cl | H | C≡CPr-c | H | — | n-Bu |
| H | G²-2 | Cl | H | C≡CPr-c | H | — | n-Bu(Z) |
| CH₃ | G²-2 | Cl | H | C≡CPr-c | H | — | n-Bu |
| CH₃ | G²-2 | Cl | H | C≡CPr-c | H | — | n-Bu(Z) |
| CH₃(S) | G²-2 | Cl | H | C≡CPr-c | H | — | n-Bu |
| CH₃(S) | G²-2 | Cl | H | C≡CPr-c | H | — | n-Bu(Z) |
| H | G²-2 | Cl | H | C≡CBu-n | H | — | n-Bu |
| H | G²-2 | Cl | H | C≡CBu-t | H | — | n-Bu |
| H | G²-2 | Cl | H | C≡CBu-t | H | — | n-Bu(Z) |
| CH₃ | G²-2 | Cl | H | C≡CBu-t | H | — | n-Bu(Z) |
| CH₃(S) | G²-2 | Cl | H | C≡CBu-t | H | — | n-Bu(Z) |
| H | G²-2 | Cl | H | C≡CPen-c | H | — | n-Bu |
| H | G²-2 | Cl | H | C≡CPen-c | H | — | n-Bu(Z) |
| H | G²-2 | Cl | H | C≡CCl | H | — | n-Bu |
| H | G²-2 | Cl | H | C≡CBr | H | — | n-Bu |
| H | G²-2 | Cl | H | C≡CI | H | — | n-Bu |
| H | G²-2 | Cl | H | C≡CC(CH₃)₂OH | H | — | n-Bu |
| H | G²-2 | Cl | H | C≡CC(CH₃)₂OH | H | — | n-Bu(Z) |
| H | G²-2 | Cl | H | C≡CC(CH₃)₂OCH₃ | H | — | n-Bu |
| H | G²-2 | Cl | H | C≡CC(CH₃)₂OCH₃ | H | — | n-Bu(Z) |
| H | G²-2 | Cl | H | C≡CSi(CH₃)₃ | H | — | n-Bu |
| H | G²-2 | Cl | H | C≡CSi(CH₃)₃ | H | — | n-Bu(Z) |
| H | G²-2 | Cl | H | C≡CPh | H | — | n-Bu |
| H | G²-2 | Cl | H | C≡CPh | H | — | n-Bu(Z) |
| H | G²-2 | Cl | F | Cl | H | — | n-Bu |
| H | G²-2 | Cl | F | Cl | H | — | n-Bu(Z) |
| H | G²-2 | Cl | Cl | Cl | H | — | n-Bu |
| H | G²-2 | Cl | Cl | Cl | H | — | n-Bu(Z) |
| H | G²-2 | Br | H | Cl | H | — | n-Bu |
| H | G²-2 | Br | H | Cl | H | — | n-Bu(Z) |
| H | G²-2 | Br | H | Br | H | — | n-Bu |
| H | G²-2 | Br | H | Br | H | — | n-Bu(Z) |
| CH₃ | G²-2 | Br | H | Br | H | — | n-Bu(Z) |
| CH₃(S) | G²-2 | Br | H | Br | H | — | n-Bu(Z) |
| H | G²-2 | F | H | Cl | H | — | i-Bu |
| H | G²-2 | F | H | Cl | H | — | i-Bu(Z) |
| H | G²-2 | Cl | H | F | H | — | i-Bu |
| H | G²-2 | Cl | H | F | H | — | i-Bu(Z) |
| H | G²-2 | Cl | H | Cl | H | — | i-Bu |
| H | G²-2 | Cl | H | Cl | H | — | i-Bu(Z) |
| CH₃ | G²-2 | Cl | H | Cl | H | — | i-Bu |
| CH₃ | G²-2 | Cl | H | Cl | H | — | i-Bu(Z) |
| CH₃(S) | G²-2 | Cl | H | Cl | H | — | i-Bu |
| CH₃(S) | G²-2 | Cl | H | Cl | H | — | i-Bu(Z) |
| H | G²-2 | Cl | H | Cl | F | — | i-Bu |
| H | G²-2 | Cl | H | Cl | F | — | i-Bu(Z) |
| CH₃ | G²-2 | Cl | H | Cl | F | — | i-Bu(Z) |
| CH₃(S) | G²-2 | Cl | H | Cl | F | — | i-Bu(Z) |
| H | G²-2 | Cl | H | Br | H | — | i-Bu |
| H | G²-2 | Cl | H | Br | H | — | i-Bu(Z) |
| CH₃ | G²-2 | Cl | H | Br | H | — | i-Bu(Z) |
| CH₃(S) | G²-2 | Cl | H | Br | H | — | i-Bu(Z) |
| H | G²-2 | Cl | H | CF₃ | H | — | i-Bu |
| H | G²-2 | Cl | H | CF₃ | H | — | i-Bu(Z) |
| CH₃ | G²-2 | Cl | H | CF₃ | H | — | i-Bu(Z) |
| CH₃(S) | G²-2 | Cl | H | CF₃ | H | — | i-Bu(Z) |
| H | G²-2 | Cl | H | C≡CH | H | — | i-Bu |
| H | G²-2 | Cl | H | C≡CH | H | — | i-Bu(Z) |
| H | G²-2 | Cl | H | C≡CPr-c | H | — | i-Bu |
| H | G²-2 | Cl | H | C≡CPr-c | H | — | i-Bu(Z) |
| H | G²-2 | Cl | H | C≡CBu-t | H | — | i-Bu |
| H | G²-2 | Cl | H | C≡CBu-t | H | — | i-Bu(Z) |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CC(CH₃)₂OCH₃ | H | — | i-Bu |
| H | G²-2 | Cl | H | C≡CC(CH₃)₂OCH₃ | H | — | i-Bu(Z) |
| H | G²-2 | Cl | H | C≡CSi(CH₃)₃ | H | — | i-Bu |
| H | G²-2 | Cl | H | C≡CSi(CH₃)₃ | H | — | i-Bu(Z) |
| H | G²-2 | Cl | H | C≡CPh | H | — | i-Bu |
| H | G²-2 | Cl | H | C≡CPh | H | — | i-Bu(Z) |
| H | G²-2 | Cl | F | Cl | H | — | i-Bu |
| H | G²-2 | Cl | F | Cl | H | — | i-Bu(Z) |
| H | G²-2 | Cl | Cl | Cl | H | — | i-Bu |
| H | G²-2 | Cl | Cl | Cl | H | — | i-Bu(Z) |
| H | G²-2 | Br | H | Cl | H | — | i-Bu |
| H | G²-2 | Br | H | Cl | H | — | i-Bu(Z) |
| H | G²-2 | Br | H | Br | H | — | i-Bu |
| H | G²-2 | Br | H | Br | H | — | i-Bu(Z) |
| CH₃ | G²-2 | Br | H | Br | H | — | i-Bu(Z) |
| CH₃(S) | G²-2 | Br | H | Br | H | — | i-Bu(Z) |
| CH₃ | G²-1 | H | H | CF₃ | H | H | CH₂Pr-c |
| CH₃ | G²-1 | H | H | OCF₃ | H | H | CH₂Pr-c |
| CH₃ | G²-1 | H | H | Ph | H | H | CH₂Pr-c |
| CH₃ | G²-1 | H | F | F | F | H | CH₂Pr-c |
| CH₃ | G²-1 | H | Cl | Cl | H | H | CH₂Pr-c |
| CH₃ | G²-1 | F | H | F | H | H | CH₂Pr-c |
| CH₃ | G²-1 | F | H | F | H | F | CH₂Pr-c |
| CH₃ | G²-1 | F | H | Br | H | H | CH₂Pr-c |
| CH₃ | G²-1 | Cl | H | F | H | H | CH₂Pr-c |
| CH₃ | G²-1 | Cl | H | F | H | H | CH₂Pr-c(E) |
| CH₃(S) | G²-1 | Cl | H | F | H | H | CH₂Pr-c |
| CH₃(S) | G²-1 | Cl | H | F | H | H | CH₂Pr-c(E) |
| CH₃ | G²-1 | Cl | H | Br | H | H | CH₂Pr-c |
| H | G²-2 | F | H | Cl | H | — | CH₂Pr-c |
| H | G²-2 | F | H | Cl | H | — | CH₂Pr-c(Z) |
| CH₃ | G²-2 | F | H | Cl | H | — | CH₂Pr-c(Z) |
| CH₃(S) | G²-2 | F | H | Cl | H | — | CH₂Pr-c(Z) |
| H | G²-2 | F | H | Br | H | — | CH₂Pr-c |
| H | G²-2 | F | H | Br | H | — | CH₂Pr-c(Z) |
| CH₃ | G²-2 | F | H | Br | H | — | CH₂Pr-c(Z) |
| CH₃(S) | G²-2 | F | H | Br | H | — | CH₂Pr-c(Z) |
| H | G²-2 | F | H | CF₃ | H | — | CH₂Pr-c |
| H | G²-2 | F | H | CF₃ | H | — | CH₂Pr-c(Z) |
| H | G²-2 | Cl | H | F | H | — | CH₂Pr-c |
| H | G²-2 | Cl | H | F | H | — | CH₂Pr-c(Z) |
| CH₃ | G²-2 | Cl | H | F | H | — | CH₂Pr-c(Z) |
| CH₃(S) | G²-2 | Cl | H | F | H | — | CH₂Pr-c(Z) |
| H | G²-2 | Cl | H | Cl | H | — | CH₂Pr-c |
| H | G²-2 | Cl | H | Cl | H | — | CH₂Pr-c(Z) |
| CH₃ | G²-2 | Cl | H | Cl | H | — | CH₂Pr-c |
| CH₃ | G²-2 | Cl | H | Cl | H | — | CH₂Pr-c(Z) |
| CH₃(S) | G²-2 | Cl | H | Cl | H | — | CH₂Pr-c |
| CH₃(S) | G²-2 | Cl | H | Cl | H | — | CH₂Pr-c(Z) |
| H | G²-2 | Cl | H | Cl | F | — | CH₂Pr-c |
| H | G²-2 | Cl | H | Cl | F | — | CH₂Pr-c(Z) |
| CH₃ | G²-2 | Cl | H | Cl | F | — | CH₂Pr-c |
| CH₃ | G²-2 | Cl | H | Cl | F | — | CH₂Pr-c(Z) |
| CH₃(S) | G²-2 | Cl | H | Cl | F | — | CH₂Pr-c |
| CH₃(S) | G²-2 | Cl | H | Cl | F | — | CH₂Pr-c(Z) |
| H | G²-2 | Cl | H | Cl | Cl | — | CH₂Pr-c |
| H | G²-2 | Cl | H | Cl | Cl | — | CH₂Pr-c(Z) |
| H | G²-2 | Cl | H | Br | H | — | CH₂Pr-c |
| H | G²-2 | Cl | H | Br | H | — | CH₂Pr-c(Z) |
| CH₃ | G²-2 | Cl | H | Br | H | — | CH₂Pr-c |
| CH₃ | G²-2 | Cl | H | Br | H | — | CH₂Pr-c(Z) |
| CH₃(S) | G²-2 | Cl | H | Br | H | — | CH₂Pr-c |
| CH₃(S) | G²-2 | Cl | H | Br | H | — | CH₂Pr-c(Z) |
| H | G²-2 | Cl | H | CF₃ | H | — | CH₂Pr-c |
| H | G²-2 | Cl | H | CF₃ | H | — | CH₂Pr-c(E) |
| H | G²-2 | Cl | H | CF₃ | H | — | CH₂Pr-c(Z) |
| CH₃ | G²-2 | Cl | H | CF₃ | H | — | CH₂Pr-c |
| CH₃ | G²-2 | Cl | H | CF₃ | H | — | CH₂Pr-c(Z) |
| CH₃(S) | G²-2 | Cl | H | CF₃ | H | — | CH₂Pr-c |
| CH₃(S) | G²-2 | Cl | H | CF₃ | H | — | CH₂Pr-c(Z) |
| H | G²-2 | Cl | H | CH=NOCH₃ | H | — | CH₂Pr-c |
| H | G²-2 | Cl | H | CH=NOEt | H | — | CH₂Pr-c |
| H | G²-2 | Cl | H | C(CH₃)=NOCH₃ | H | — | CH₂Pr-c |
| CH₃ | G²-2 | Cl | H | C(CH₃)=NOCH₃ | H | — | CH₂Pr-c |
| CH₃(S) | G²-2 | Cl | H | C(CH₃)=NOCH₃ | H | — | CH₂Pr-c |
| H | G²-2 | Cl | H | C(CH₃)=NOEt | H | — | CH₂Pr-c |
| H | G²-2 | Cl | H | C(Et)=NOCH₃ | H | — | CH₂Pr-c |
| H | G²-2 | Cl | H | C≡CH | H | — | CH₂Pr-c |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CH | H | — | CH₂Pr-c(Z) |
| H | G²-2 | Cl | H | C≡CCH₃ | H | — | CH₂Pr-c |
| H | G²-2 | Cl | H | C≡CCH₃ | H | — | CH₂Pr-c(Z) |
| H | G²-2 | Cl | H | C≡CEt | H | — | CH₂Pr-c |
| H | G²-2 | Cl | H | C≡CPr-n | H | — | CH₂Pr-c |
| H | G²-2 | Cl | H | C≡CPr-c | H | — | CH₂Pr-c |
| H | G²-2 | Cl | H | C≡CPr-c | H | — | CH₂Pr-c(Z) |
| CH₃ | G²-2 | Cl | H | C≡CPr-c | H | — | CH₂Pr-c |
| CH₃ | G²-2 | Cl | H | C≡CPr-c | H | — | CH₂Pr-c(Z) |
| CH₃(S) | G²-2 | Cl | H | C≡CPr-c | H | — | CH₂Pr-c |
| CH₃(S) | G²-2 | Cl | H | C≡CPr-c | H | — | CH₂Pr-c(Z) |
| H | G²-2 | Cl | H | C≡CBu-n | H | — | CH₂Pr-c |
| H | G²-2 | Cl | H | C≡CBu-t | H | — | CH₂Pr-c |
| H | G²-2 | Cl | H | C≡CBu-t | H | — | CH₂Pr-c(Z) |
| CH₃ | G²-2 | Cl | H | C≡CBu-t | H | — | CH₂Pr-c |
| CH₃ | G²-2 | Cl | H | C≡CBu-t | H | — | CH₂Pr-c(Z) |
| CH₃(S) | G²-2 | Cl | H | C≡CBu-t | H | — | CH₂Pr-c |
| CH₃(S) | G²-2 | Cl | H | C≡CBu-t | H | — | CH₂Pr-c(Z) |
| H | G²-2 | Cl | H | C≡CPen-c | H | — | CH₂Pr-c |
| H | G²-2 | Cl | H | C≡CPen-c | H | — | CH₂Pr-c(Z) |
| H | G²-2 | Cl | H | C≡CCl | H | — | CH₂Pr-c |
| H | G²-2 | Cl | H | C≡CBr | H | — | CH₂Pr-c |
| H | G²-2 | Cl | H | C≡CI | H | — | CH₂Pr-c |
| H | G²-2 | Cl | H | C≡CC(CH₃)₂OH | H | — | CH₂Pr-c |
| H | G²-2 | Cl | H | C≡CC(CH₃)₂OH | H | — | CH₂Pr-c(Z) |
| H | G²-2 | Cl | H | C≡CC(CH₃)₂OCH₃ | H | — | CH₂Pr-c |
| H | G²-2 | Cl | H | C≡CC(CH₃)₂OCH₃ | H | — | CH₂Pr-c(Z) |
| H | G²-2 | Cl | H | C≡CSi(CH₃)₃ | H | — | CH₂Pr-c |
| H | G²-2 | Cl | H | C≡CSi(CH₃)₃ | H | — | CH₂Pr-c(Z) |
| H | G²-2 | Cl | H | C≡CPh | H | — | CH₂Pr-c |
| H | G²-2 | Cl | H | C≡CPh | H | — | CH₂Pr-c(Z) |
| H | G²-2 | Cl | H | CN | H | — | CH₂Pr-c |
| H | G²-2 | Cl | F | Cl | H | — | CH₂Pr-c |
| H | G²-2 | Cl | F | Cl | H | — | CH₂Pr-c(Z) |
| CH₃ | G²-2 | Cl | F | Cl | H | — | CH₂Pr-c(Z) |
| CH₃(S) | G²-2 | Cl | F | Cl | H | — | CH₂Pr-c(Z) |
| H | G²-2 | Cl | Cl | Cl | H | — | CH₂Pr-c |
| H | G²-2 | Cl | Cl | Cl | H | — | CH₂Pr-c(Z) |
| CH₃ | G²-2 | Cl | Cl | Cl | H | — | CH₂Pr-c(Z) |
| CH₃(S) | G²-2 | Cl | Cl | Cl | H | — | CH₂Pr-c(Z) |
| H | G²-2 | Br | H | F | H | — | CH₂Pr-c |
| H | G²-2 | Br | H | F | H | — | CH₂Pr-c(Z) |
| H | G²-2 | Br | H | Cl | H | — | CH₂Pr-c |
| H | G²-2 | Br | H | Cl | H | — | CH₂Pr-c(Z) |
| CH₃ | G²-2 | Br | H | Cl | H | — | CH₂Pr-c(Z) |
| CH₃(S) | G²-2 | Br | H | Cl | H | — | CH₂Pr-c(Z) |
| H | G²-2 | Br | H | Br | H | — | CH₂Pr-c |
| H | G²-2 | Br | H | Br | H | — | CH₂Pr-c(Z) |
| CH₃ | G²-2 | Br | H | Br | H | — | CH₂Pr-c |
| CH₃ | G²-2 | Br | H | Br | H | — | CH₂Pr-c(Z) |
| CH₃(S) | G²-2 | Br | H | Br | H | — | CH₂Pr-c |
| CH₃(S) | G²-2 | Br | H | Br | H | — | CH₂Pr-c(Z) |
| H | G²-2 | Br | H | CF₃ | H | — | CH₂Pr-c |
| H | G²-2 | Br | H | CF₃ | H | — | CH₂Pr-c(Z) |
| H | G²-6 | Cl | — | Cl | H | — | CH₂Pr-c |
| CH₃ | G²-6 | Cl | — | Cl | H | — | CH₂Pr-c |
| CH₃ | G²-9 | Cl | H | Cl | — | — | CH₂Pr-c |
| CH₃ | G²-9 | Cl | H | Cl | — | — | CH₂Pr-c(Z) |
| CH₃ | G²-9 | Cl | H | Br | — | — | CH₂Pr-c |
| CH₃ | G²-9 | Cl | H | Br | — | — | CH₂Pr-c(Z) |
| CH₃ | G²-9 | Cl | H | C≡CPr-c | — | — | CH₂Pr-c |
| CH₃ | G²-9 | Cl | H | C≡CPr-c | — | — | CH₂Pr-c(Z) |
| CH₃ | G²-9 | Cl | H | C≡CBu-t | — | — | CH₂Pr-c |
| CH₃ | G²-9 | Cl | H | C≡CBu-t | — | — | CH₂Pr-c(Z) |
| CH₃ | G²-9 | Cl | Cl | Cl | — | — | CH₂Pr-c |
| CH₃ | G²-9 | Cl | Cl | Cl | — | — | CH₂Pr-c(Z) |
| CH₃ | G²-1 | Cl | H | F | H | H | s-Bu |
| CH₃ | G²-1 | Cl | H | F | H | H | s-Bu(E) |
| CH₃(S) | G²-1 | Cl | H | F | H | H | s-Bu |
| CH₃(S) | G²-1 | Cl | H | F | H | H | s-Bu(E) |
| H | G²-2 | F | H | Cl | H | — | s-Bu |
| H | G²-2 | F | H | Cl | H | — | s-Bu(Z) |
| CH₃ | G²-2 | F | H | Cl | H | — | s-Bu(Z) |
| CH₃(S) | G²-2 | F | H | Cl | H | — | s-Bu(Z) |
| H | G²-2 | F | H | Br | H | — | s-Bu |
| H | G²-2 | F | H | Br | H | — | s-Bu(Z) |
| CH₃ | G²-2 | F | H | Br | H | — | s-Bu(Z) |
| CH₃(S) | G²-2 | F | H | Br | H | — | s-Bu(Z) |

TABLE 2-continued

| R² | G² | Y¹ | Y² | Y³ | Y⁴ | Y⁵ | R¹ |
|---|---|---|---|---|---|---|---|
| H | G²-2 | F | H | CF₃ | H | — | s-Bu |
| H | G²-2 | F | H | CF₃ | H | — | s-Bu(Z) |
| H | G²-2 | Cl | H | F | H | — | s-Bu |
| H | G²-2 | Cl | H | F | H | — | s-Bu(Z) |
| CH₃ | G²-2 | Cl | H | F | H | — | s-Bu(Z) |
| CH₃(S) | G²-2 | Cl | H | F | H | — | s-Bu(Z) |
| H | G²-2 | Cl | H | Cl | H | — | s-Bu |
| H | G²-2 | Cl | H | Cl | H | — | s-Bu(E) |
| H | G²-2 | Cl | H | Cl | H | — | s-Bu(Z) |
| CH₃ | G²-2 | Cl | H | Cl | H | — | s-Bu |
| CH₃ | G²-2 | Cl | H | Cl | H | — | s-Bu(Z) |
| CH₃(S) | G²-2 | Cl | H | Cl | H | — | s-Bu |
| CH₃(S) | G²-2 | Cl | H | Cl | H | — | s-Bu(Z) |
| H | G²-2 | Cl | H | Cl | F | — | s-Bu |
| H | G²-2 | Cl | H | Cl | F | — | s-Bu(Z) |
| CH₃ | G²-2 | Cl | H | Cl | F | — | s-Bu |
| CH₃ | G²-2 | Cl | H | Cl | F | — | s-Bu(Z) |
| CH₃(S) | G²-2 | Cl | H | Cl | F | — | s-Bu |
| CH₃(S) | G²-2 | Cl | H | Cl | F | — | s-Bu(Z) |
| H | G²-2 | Cl | H | Cl | Cl | — | s-Bu |
| H | G²-2 | Cl | H | Cl | Cl | — | s-Bu(Z) |
| H | G²-2 | Cl | H | Br | H | — | s-Bu |
| H | G²-2 | Cl | H | Br | H | — | s-Bu(Z) |
| CH₃ | G²-2 | Cl | H | Br | H | — | s-Bu |
| CH₃ | G²-2 | Cl | H | Br | H | — | s-Bu(Z) |
| CH₃(S) | G²-2 | Cl | H | Br | H | — | s-Bu |
| CH₃(S) | G²-2 | Cl | H | Br | H | — | s-Bu(Z) |
| H | G²-2 | Cl | H | CF₃ | H | — | s-Bu |
| H | G²-2 | Cl | H | CF₃ | H | — | s-Bu(Z) |
| CH₃ | G²-2 | Cl | H | CF₃ | H | — | s-Bu |
| CH₃ | G²-2 | Cl | H | CF₃ | H | — | s-Bu(Z) |
| CH₃(S) | G²-2 | Cl | H | CF₃ | H | — | s-Bu |
| CH₃(S) | G²-2 | Cl | H | CF₃ | H | — | s-Bu(Z) |
| H | G²-2 | Cl | H | CH=NOCH₃ | H | — | s-Bu |
| H | G²-2 | Cl | H | CH=NOEt | H | — | s-Bu |
| H | G²-2 | Cl | H | C(CH₃)=NOCH₃ | H | — | s-Bu |
| CH₃ | G²-2 | Cl | H | C(CH₃)=NOCH₃ | H | — | s-Bu |
| CH₃(S) | G²-2 | Cl | H | C(CH₃)=NOCH₃ | H | — | s-Bu |
| H | G²-2 | Cl | H | C(CH₃)=NOEt | H | — | s-Bu |
| H | G²-2 | Cl | H | C(Et)=NOCH₃ | H | — | s-Bu |
| H | G²-2 | Cl | H | C≡CH | H | — | s-Bu |
| H | G²-2 | Cl | H | C≡CH | H | — | s-Bu(Z) |
| H | G²-2 | Cl | H | C≡CCH₃ | H | — | s-Bu |
| H | G²-2 | Cl | H | C≡CCH₃ | H | — | s-Bu(Z) |
| H | G²-2 | Cl | H | C≡CEt | H | — | s-Bu |
| H | G²-2 | Cl | H | C≡CPr-n | H | — | s-Bu |
| H | G²-2 | Cl | H | C≡CPr-c | H | — | s-Bu |
| H | G²-2 | Cl | H | C≡CPr-c | H | — | s-Bu(Z) |
| CH₃ | G²-2 | Cl | H | C≡CPr-c | H | — | s-Bu |
| CH₃ | G²-2 | Cl | H | C≡CPr-c | H | — | s-Bu(Z) |
| CH₃(S) | G²-2 | Cl | H | C≡CPr-c | H | — | s-Bu |
| CH₃(S) | G²-2 | Cl | H | C≡CPr-c | H | — | s-Bu(Z) |
| H | G²-2 | Cl | H | C≡CBu-n | H | — | s-Bu |
| H | G²-2 | Cl | H | C≡CBu-t | H | — | s-Bu |
| H | G²-2 | Cl | H | C≡CBu-t | H | — | s-Bu(Z) |
| CH₃ | G²-2 | Cl | H | C≡CBu-t | H | — | s-Bu |
| CH₃ | G²-2 | Cl | H | C≡CBu-t | H | — | s-Bu(Z) |
| CH₃(S) | G²-2 | Cl | H | C≡CBu-t | H | — | s-Bu |
| CH₃(S) | G²-2 | Cl | H | C≡CBu-t | H | — | s-Bu(Z) |
| H | G²-2 | Cl | H | C≡CPen-c | H | — | s-Bu |
| H | G²-2 | Cl | H | C≡CPen-c | H | — | s-Bu(Z) |
| H | G²-2 | Cl | H | C≡CCl | H | — | s-Bu |
| H | G²-2 | Cl | H | C≡CBr | H | — | s-Bu |
| H | G²-2 | Cl | H | C≡CI | H | — | s-Bu |
| H | G²-2 | Cl | H | C≡CC(CH₃)₂OH | H | — | s-Bu |
| H | G²-2 | Cl | H | C≡CC(CH₃)₂OH | H | — | s-Bu(Z) |
| H | G²-2 | Cl | H | C≡CC(CH₃)₂OCH₃ | H | — | s-Bu |
| H | G²-2 | Cl | H | C≡CC(CH₃)₂OCH₃ | H | — | s-Bu(Z) |
| H | G²-2 | Cl | H | C≡CSi(CH₃)₃ | H | — | s-Bu |
| H | G²-2 | Cl | H | C≡CSi(CH₃)₃ | H | — | s-Bu(Z) |
| H | G²-2 | Cl | H | C≡CPh | H | — | s-Bu |
| H | G²-2 | Cl | H | C≡CPh | H | — | s-Bu(Z) |
| H | G²-2 | Cl | F | Cl | H | — | s-Bu |
| H | G²-2 | Cl | F | Cl | H | — | s-Bu(Z) |
| CH₃ | G²-2 | Cl | F | Cl | H | — | s-Bu(Z) |
| CH₃(S) | G²-2 | Cl | F | Cl | H | — | s-Bu(Z) |
| H | G²-2 | Cl | Cl | Cl | H | — | s-Bu |
| H | G²-2 | Cl | Cl | Cl | H | — | s-Bu(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Cl | Cl | Cl | H | — | s-Bu(Z) |
| CH₃(S) | G²-2 | Cl | Cl | Cl | H | — | s-Bu(Z) |
| H | G²-2 | Br | H | Cl | H | — | s-Bu |
| H | G²-2 | Br | H | Cl | H | — | s-Bu(Z) |
| CH₃ | G²-2 | Br | H | Cl | H | — | s-Bu(Z) |
| CH₃(S) | G²-2 | Br | H | Cl | H | — | s-Bu(Z) |
| H | G²-2 | Br | H | Br | H | — | s-Bu |
| H | G²-2 | Br | H | Br | H | — | s-Bu(Z) |
| CH₃ | G²-2 | Br | H | Br | H | — | s-Bu |
| CH₃ | G²-2 | Br | H | Br | H | — | s-Bu(Z) |
| CH₃(S) | G²-2 | Br | H | Br | H | — | s-Bu |
| CH₃(S) | G²-2 | Br | H | Br | H | — | s-Bu(Z) |
| H | G²-2 | Br | H | CF₃ | H | — | s-Bu |
| H | G²-2 | Br | H | CF₃ | H | — | s-Bu(Z) |
| H | G²-6 | Cl | — | Cl | H | — | s-Bu |
| CH₃ | G²-6 | Cl | — | Cl | H | — | s-Bu |
| CH₃ | G²-9 | Cl | H | Cl | — | — | s-Bu |
| CH₃ | G²-9 | Cl | H | Cl | — | — | s-Bu(Z) |
| CH₃ | G²-9 | Cl | H | Br | — | — | s-Bu |
| CH₃ | G²-9 | Cl | H | Br | — | — | s-Bu(Z) |
| CH₃ | G²-9 | Cl | H | C≡CPr-c | — | — | s-Bu |
| CH₃ | G²-9 | Cl | H | C≡CPr-c | — | — | s-Bu(Z) |
| CH₃ | G²-9 | Cl | H | C≡CBu-t | — | — | s-Bu |
| CH₃ | G²-9 | Cl | H | C≡CBu-t | — | — | s-Bu(Z) |
| CH₃ | G²-9 | Cl | Cl | Cl | — | — | s-Bu |
| CH₃ | G²-9 | Cl | Cl | Cl | — | — | s-Bu(Z) |
| H | G²-2 | Cl | H | Cl | H | — | c-Bu |
| H | G²-2 | Cl | H | Cl | H | — | c-Bu(Z) |
| CH₃ | G²-2 | Cl | H | Cl | H | — | c-Bu(Z) |
| CH₃(S) | G²-2 | Cl | H | Cl | H | — | c-Bu(Z) |
| H | G²-2 | Cl | H | Cl | F | — | c-Bu |
| H | G²-2 | Cl | H | Cl | F | — | c-Bu(Z) |
| H | G²-2 | Cl | H | Br | H | — | c-Bu |
| H | G²-2 | Cl | H | Br | H | — | c-Bu(Z) |
| CH₃ | G²-2 | Cl | H | Br | H | — | c-Bu(Z) |
| CH₃(S) | G²-2 | Cl | H | Br | H | — | c-Bu(Z) |
| H | G²-2 | Cl | H | CF₃ | H | — | c-Bu |
| H | G²-2 | Cl | H | CF₃ | H | — | c-Bu(Z) |
| CH₃ | G²-2 | Cl | H | CF₃ | H | — | c-Bu(Z) |
| CH₃(S) | G²-2 | Cl | H | CF₃ | H | — | c-Bu(Z) |
| H | G²-2 | Cl | H | C≡CPr-c | H | — | c-Bu |
| H | G²-2 | Cl | H | C≡CPr-c | H | — | c-Bu(Z) |
| H | G²-2 | Cl | H | C≡CBu-t | H | — | c-Bu |
| H | G²-2 | Cl | H | C≡CBu-t | H | — | c-Bu(Z) |
| H | G²-2 | Cl | H | C≡CC(CH₃)₂OCH₃ | H | — | c-Bu |
| H | G²-2 | Cl | H | C≡CC(CH₃)₂OCH₃ | H | — | c-Bu(Z) |
| H | G²-2 | Cl | H | C≡CSi(CH₃)₃ | H | — | c-Bu |
| H | G²-2 | Cl | H | C≡CSi(CH₃)₃ | H | — | c-Bu(Z) |
| H | G²-2 | Cl | H | C≡CPh | H | — | c-Bu |
| H | G²-2 | Cl | H | C≡CPh | H | — | c-Bu(Z) |
| H | G²-2 | Cl | F | Cl | H | — | c-Bu |
| H | G²-2 | Cl | F | Cl | H | — | c-Bu(Z) |
| H | G²-2 | Br | H | Cl | H | — | c-Bu |
| H | G²-2 | Br | H | Cl | H | — | c-Bu(Z) |
| H | G²-2 | Br | H | Br | H | — | c-Bu |
| H | G²-2 | Br | H | Br | H | — | c-Bu(Z) |
| CH₃ | G²-1 | Cl | H | F | H | H | t-Bu |
| CH₃ | G²-1 | Cl | H | F | H | H | t-Bu(E) |
| CH₃(S) | G²-1 | Cl | H | F | H | H | t-Bu |
| CH₃(S) | G²-1 | Cl | H | F | H | H | t-Bu(E) |
| H | G²-2 | F | H | Cl | H | — | t-Bu |
| H | G²-2 | F | H | Cl | H | — | t-Bu(Z) |
| CH₃ | G²-2 | F | H | Cl | H | — | t-Bu(Z) |
| CH₃(S) | G²-2 | F | H | Cl | H | — | t-Bu(Z) |
| H | G²-2 | F | H | Br | H | — | t-Bu |
| H | G²-2 | F | H | Br | H | — | t-Bu(Z) |
| CH₃ | G²-2 | F | H | Br | H | — | t-Bu(Z) |
| CH₃(S) | G²-2 | F | H | Br | H | — | t-Bu(Z) |
| H | G²-2 | F | H | CF₃ | H | — | t-Bu |
| H | G²-2 | F | H | CF₃ | H | — | t-Bu(Z) |
| H | G²-2 | Cl | H | F | H | — | t-Bu |
| H | G²-2 | Cl | H | F | H | — | t-Bu(Z) |
| CH₃ | G²-2 | Cl | H | F | H | — | t-Bu(Z) |
| CH₃(S) | G²-2 | Cl | H | F | H | — | t-Bu(Z) |
| H | G²-2 | Cl | H | Cl | H | — | t-Bu |
| H | G²-2 | Cl | H | Cl | H | — | t-Bu(E) |
| H | G²-2 | Cl | H | Cl | H | — | t-Bu(Z) |
| CH₃ | G²-2 | Cl | H | Cl | H | — | t-Bu |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | Cl | H | — | t-Bu(Z) |
| CH₃(S) | G²-2 | Cl | H | Cl | H | — | t-Bu |
| CH₃(S) | G²-2 | Cl | H | Cl | H | — | t-Bu(Z) |
| H | G²-2 | Cl | H | Cl | F | — | t-Bu |
| H | G²-2 | Cl | H | Cl | F | — | t-Bu(Z) |
| CH₃ | G²-2 | Cl | H | Cl | F | — | t-Bu |
| CH₃ | G²-2 | Cl | H | Cl | F | — | t-Bu(Z) |
| CH₃(S) | G²-2 | Cl | H | Cl | F | — | t-Bu |
| CH₃(S) | G²-2 | Cl | H | Cl | F | — | t-Bu(Z) |
| H | G²-2 | Cl | H | Cl | Cl | — | t-Bu |
| H | G²-2 | Cl | H | Cl | Cl | — | t-Bu(Z) |
| H | G²-2 | Cl | H | Br | H | — | t-Bu |
| H | G²-2 | Cl | H | Br | H | — | t-Bu(Z) |
| CH₃ | G²-2 | Cl | H | Br | H | — | t-Bu |
| CH₃ | G²-2 | Cl | H | Br | H | — | t-Bu(Z) |
| CH₃(S) | G²-2 | Cl | H | Br | H | — | t-Bu |
| CH₃(S) | G²-2 | Cl | H | Br | H | — | t-Bu(Z) |
| H | G²-2 | Cl | H | CF₃ | H | — | t-Bu |
| H | G²-2 | Cl | H | CF₃ | H | — | t-Bu(Z) |
| CH₃ | G²-2 | Cl | H | CF₃ | H | — | t-Bu |
| CH₃ | G²-2 | Cl | H | CF₃ | H | — | t-Bu(Z) |
| CH₃(S) | G²-2 | Cl | H | CF₃ | H | — | t-Bu |
| CH₃(S) | G²-2 | Cl | H | CF₃ | H | — | t-Bu(Z) |
| H | G²-2 | Cl | H | CH=NOCH₃ | H | — | t-Bu |
| H | G²-2 | Cl | H | CH=NOEt | H | — | t-Bu |
| H | G²-2 | Cl | H | C(CH₃)=NOCH₃ | H | — | t-Bu |
| CH₃ | G²-2 | Cl | H | C(CH₃)=NOCH₃ | H | — | t-Bu |
| CH₃(S) | G²-2 | Cl | H | C(CH₃)=NOCH₃ | H | — | t-Bu |
| H | G²-2 | Cl | H | C(CH₃)=NOEt | H | — | t-Bu |
| H | G²-2 | Cl | H | C(Et)=NOCH₃ | H | — | t-Bu |
| H | G²-2 | Cl | H | C≡CH | H | — | t-Bu |
| H | G²-2 | Cl | H | C≡CH | H | — | t-Bu(Z) |
| H | G²-2 | Cl | H | C≡CCH₃ | H | — | t-Bu |
| H | G²-2 | Cl | H | C≡CCH₃ | H | — | t-Bu(Z) |
| H | G²-2 | Cl | H | C≡CEt | H | — | t-Bu |
| H | G²-2 | Cl | H | C≡CPr-n | H | — | t-Bu |
| H | G²-2 | Cl | H | C≡CPr-c | H | — | t-Bu |
| H | G²-2 | Cl | H | C≡CPr-c | H | — | t-Bu(Z) |
| CH₃ | G²-2 | Cl | H | C≡CPr-c | H | — | t-Bu |
| CH₃ | G²-2 | Cl | H | C≡CPr-c | H | — | t-Bu(Z) |
| CH₃(S) | G²-2 | Cl | H | C≡CPr-c | H | — | t-Bu |
| CH₃(S) | G²-2 | Cl | H | C≡CPr-c | H | — | t-Bu(Z) |
| H | G²-2 | Cl | H | C≡CBu-n | H | — | t-Bu |
| H | G²-2 | Cl | H | C≡CBu-t | H | — | t-Bu |
| H | G²-2 | Cl | H | C≡CBu-t | H | — | t-Bu(Z) |
| CH₃ | G²-2 | Cl | H | C≡CBu-t | H | — | t-Bu |
| CH₃ | G²-2 | Cl | H | C≡CBu-t | H | — | t-Bu(Z) |
| CH₃(S) | G²-2 | Cl | H | C≡CBu-t | H | — | t-Bu |
| CH₃(S) | G²-2 | Cl | H | C≡CBu-t | H | — | t-Bu(Z) |
| H | G²-2 | Cl | H | C≡CPen-c | H | — | t-Bu |
| H | G²-2 | Cl | H | C≡CPen-c | H | — | t-Bu(Z) |
| H | G²-2 | Cl | H | C≡CCl | H | — | t-Bu |
| H | G²-2 | Cl | H | C≡CBr | H | — | t-Bu |
| H | G²-2 | Cl | H | C≡CI | H | — | t-Bu |
| H | G²-2 | Cl | H | C≡CC(CH₃)₂OH | H | — | t-Bu |
| H | G²-2 | Cl | H | C≡CC(CH₃)₂OH | H | — | t-Bu(Z) |
| H | G²-2 | Cl | H | C≡CC(CH₃)₂OCH₃ | H | — | t-Bu |
| H | G²-2 | Cl | H | C≡CC(CH₃)₂OCH₃ | H | — | t-Bu(Z) |
| H | G²-2 | Cl | H | C≡CSi(CH₃)₃ | H | — | t-Bu |
| H | G²-2 | Cl | H | C≡CSi(CH₃)₃ | H | — | t-Bu(Z) |
| H | G²-2 | Cl | H | C≡CPh | H | — | t-Bu |
| H | G²-2 | Cl | H | C≡CPh | H | — | t-Bu(Z) |
| H | G²-2 | Cl | F | Cl | H | — | t-Bu |
| H | G²-2 | Cl | F | Cl | H | — | t-Bu(Z) |
| CH₃ | G²-2 | Cl | F | Cl | H | — | t-Bu(Z) |
| CH₃(S) | G²-2 | Cl | F | Cl | H | — | t-Bu(Z) |
| H | G²-2 | Cl | Cl | Cl | H | — | t-Bu |
| H | G²-2 | Cl | Cl | Cl | H | — | t-Bu(Z) |
| CH₃ | G²-2 | Cl | Cl | Cl | H | — | t-Bu(Z) |
| CH₃(S) | G²-2 | Cl | Cl | Cl | H | — | t-Bu(Z) |
| H | G²-2 | Br | H | F | H | — | t-Bu |
| H | G²-2 | Br | H | F | H | — | t-Bu(Z) |
| H | G²-2 | Br | H | Cl | H | — | t-Bu |
| H | G²-2 | Br | H | Cl | H | — | t-Bu(Z) |
| CH₃ | G²-2 | Br | H | Cl | H | — | t-Bu(Z) |
| CH₃(S) | G²-2 | Br | H | Cl | H | — | t-Bu(Z) |
| H | G²-2 | Br | H | Br | H | — | t-Bu |
| H | G²-2 | Br | H | Br | H | — | t-Bu(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Br | H | Br | H | — | t-Bu |
| CH₃ | G²-2 | Br | H | Br | H | — | t-Bu(Z) |
| CH₃(S) | G²-2 | Br | H | Br | H | — | t-Bu |
| CH₃(S) | G²-2 | Br | H | Br | H | — | t-Bu(Z) |
| H | G²-2 | Br | H | CF₃ | H | — | t-Bu |
| H | G²-2 | Br | H | CF₃ | H | — | t-Bu(Z) |
| H | G²-6 | Cl | — | Cl | H | — | t-Bu |
| CH₃ | G²-6 | Cl | — | Cl | H | — | t-Bu |
| CH₃ | G²-9 | Cl | H | Cl | — | — | t-Bu |
| CH₃ | G²-9 | Cl | H | Cl | — | — | t-Bu(Z) |
| CH₃ | G²-9 | Cl | H | Br | — | — | t-Bu |
| CH₃ | G²-9 | Cl | H | Br | — | — | t-Bu(Z) |
| CH₃ | G²-9 | Cl | H | C≡CPr-c | — | — | t-Bu |
| CH₃ | G²-9 | Cl | H | C≡CPr-c | — | — | t-Bu(Z) |
| CH₃ | G²-9 | Cl | H | C≡CBu-t | — | — | t-Bu |
| CH₃ | G²-9 | Cl | H | C≡CBu-t | — | — | t-Bu(Z) |
| CH₃ | G²-9 | Cl | Cl | Cl | — | — | t-Bu |
| CH₃ | G²-9 | Cl | Cl | Cl | — | — | t-Bu(Z) |
| H | G²-2 | Cl | H | Cl | H | — | Pen |
| H | G²-2 | Cl | H | Cl | H | — | Pen(Z) |
| CH₃ | G²-2 | Cl | H | Cl | H | — | Pen(Z) |
| CH₃(S) | G²-2 | Cl | H | Cl | H | — | Pen(Z) |
| H | G²-2 | Cl | H | Cl | F | — | Pen |
| H | G²-2 | Cl | H | Cl | F | — | Pen(Z) |
| H | G²-2 | Cl | H | Br | H | — | Pen |
| H | G²-2 | Cl | H | Br | H | — | Pen(Z) |
| CH₃ | G²-2 | Cl | H | Br | H | — | Pen(Z) |
| CH₃(S) | G²-2 | Cl | H | Br | H | — | Pen(Z) |
| H | G²-2 | Cl | H | CF₃ | H | — | Pen |
| H | G²-2 | Cl | H | CF₃ | H | — | Pen(Z) |
| CH₃ | G²-2 | Cl | H | CF₃ | H | — | Pen(Z) |
| CH₃(S) | G²-2 | Cl | H | CF₃ | H | — | Pen(Z) |
| H | G²-2 | Cl | H | C≡CPr-c | H | — | Pen |
| H | G²-2 | Cl | H | C≡CPr-c | H | — | Pen(Z) |
| H | G²-2 | Cl | H | C≡CBu-t | H | — | Pen |
| H | G²-2 | Cl | H | C≡CBu-t | H | — | Pen(Z) |
| H | G²-2 | Cl | H | C≡CC(CH₃)₂OCH₃ | H | — | Pen |
| H | G²-2 | Cl | H | C≡CC(CH₃)₂OCH₃ | H | — | Pen(Z) |
| H | G²-2 | Cl | H | C≡CSi(CH₃)₃ | H | — | Pen |
| H | G²-2 | Cl | H | C≡CSi(CH₃)₃ | H | — | Pen(Z) |
| H | G²-2 | Cl | H | C≡CPh | H | — | Pen |
| H | G²-2 | Cl | H | C≡CPh | H | — | Pen(Z) |
| H | G²-2 | Cl | F | Cl | H | — | Pen |
| H | G²-2 | Cl | F | Cl | H | — | Pen(Z) |
| H | G²-2 | Br | H | Cl | H | — | Pen |
| H | G²-2 | Br | H | Cl | H | — | Pen(Z) |
| H | G²-2 | Br | H | Br | H | — | Pen |
| H | G²-2 | Br | H | Br | H | — | Pen(Z) |
| H | G²-2 | Cl | H | Cl | H | — | CH₂Bu-c |
| H | G²-2 | Cl | H | Cl | H | — | CH₂Bu-c(Z) |
| H | G²-2 | Cl | H | CF₃ | H | — | CH₂Bu-c |
| H | G²-2 | Cl | H | CF₃ | H | — | CH₂Bu-c(Z) |
| H | G²-2 | Cl | H | Cl | H | — | CH(CH₃)Pr-i |
| H | G²-2 | F | H | Cl | H | — | CH(Et)₂ |
| H | G²-2 | F | H | Cl | H | — | CH(Et)₂(Z) |
| H | G²-2 | Cl | H | F | H | — | CH(Et)₂ |
| H | G²-2 | Cl | H | F | H | — | CH(Et)₂(Z) |
| H | G²-2 | Cl | H | Cl | H | — | CH(Et)₂ |
| H | G²-2 | Cl | H | Cl | H | — | CH(Et)₂(Z) |
| CH₃ | G²-2 | Cl | H | Cl | H | — | CH(Et)₂ |
| CH₃ | G²-2 | Cl | H | Cl | H | — | CH(Et)₂(Z) |
| CH₃(S) | G²-2 | Cl | H | Cl | H | — | CH(Et)₂ |
| CH₃(S) | G²-2 | Cl | H | Cl | H | — | CH(Et)₂(Z) |
| H | G²-2 | Cl | H | Cl | F | — | CH(Et)₂ |
| H | G²-2 | Cl | H | Cl | F | — | CH(Et)₂(Z) |
| CH₃ | G²-2 | Cl | H | Cl | F | — | CH(Et)₂(Z) |
| CH₃(S) | G²-2 | Cl | H | Cl | F | — | CH(Et)₂(Z) |
| H | G²-2 | Cl | H | Br | H | — | CH(Et)₂ |
| H | G²-2 | Cl | H | Br | H | — | CH(Et)₂(Z) |
| CH₃ | G²-2 | Cl | H | Br | H | — | CH(Et)₂(Z) |
| CH₃(S) | G²-2 | Cl | H | Br | H | — | CH(Et)₂(Z) |
| H | G²-2 | Cl | H | CF₃ | H | — | CH(Et)₂ |
| H | G²-2 | Cl | H | CF₃ | H | — | CH(Et)₂(Z) |
| CH₃ | G²-2 | Cl | H | CF₃ | H | — | CH(Et)₂(Z) |
| CH₃(S) | G²-2 | Cl | H | CF₃ | H | — | CH(Et)₂(Z) |
| H | G²-2 | Cl | H | C≡CH | H | — | CH(Et)₂ |
| H | G²-2 | Cl | H | C≡CH | H | — | CH(Et)₂(Z) |
| H | G²-2 | Cl | H | C≡CPr-c | H | — | CH(Et)₂ |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CPr-c | H | — | CH(Et)₂(Z) |
| H | G²-2 | Cl | H | C≡CBu-t | H | — | CH(Et)₂ |
| H | G²-2 | Cl | H | C≡CBu-t | H | — | CH(Et)₂(Z) |
| H | G²-2 | Cl | H | C≡CC(CH₃)₂OCH₃ | H | — | CH(Et)₂ |
| H | G²-2 | Cl | H | C≡CC(CH₃)₂OCH₃ | H | — | CH(Et)₂(Z) |
| H | G²-2 | Cl | H | C≡CSi(CH₃)₃ | H | — | CH(Et)₂ |
| H | G²-2 | Cl | H | C≡CSi(CH₃)₃ | H | — | CH(Et)₂(Z) |
| H | G²-2 | Cl | H | C≡CPh | H | — | CH(Et)₂ |
| H | G²-2 | Cl | H | C≡CPh | H | — | CH(Et)₂(Z) |
| H | G²-2 | Cl | F | Cl | H | — | CH(Et)₂ |
| H | G²-2 | Cl | F | Cl | H | — | CH(Et)₂(Z) |
| H | G²-2 | Cl | Cl | Cl | H | — | CH(Et)₂ |
| H | G²-2 | Cl | Cl | Cl | H | — | CH(Et)₂(Z) |
| H | G²-2 | Br | H | Cl | H | — | CH(Et)₂ |
| H | G²-2 | Br | H | Cl | H | — | CH(Et)₂(Z) |
| H | G²-2 | Br | H | Br | H | — | CH(Et)₂ |
| H | G²-2 | Br | H | Br | H | — | CH(Et)₂(Z) |
| CH₃ | G²-2 | Br | H | Br | H | — | CH(Et)₂(Z) |
| CH₃(S) | G²-2 | Br | H | Br | H | — | CH(Et)₂(Z) |
| H | G²-2 | Cl | H | Cl | H | — | CH(CH₃)Pr-c |
| H | G²-2 | Cl | H | Cl | H | — | CH(CH₃)Pr-c(Z) |
| H | G²-2 | Cl | H | CF₃ | H | — | CH(CH₃)Pr-c |
| H | G²-2 | Cl | H | CF₃ | H | — | CH(CH₃)Pr-c(Z) |
| H | G²-2 | F | H | Cl | H | — | c-Pen |
| H | G²-2 | F | H | Cl | H | — | c-Pen(Z) |
| H | G²-2 | Cl | H | F | H | — | c-Pen |
| H | G²-2 | Cl | H | F | H | — | c-Pen(Z) |
| H | G²-2 | Cl | H | Cl | H | — | c-Pen |
| H | G²-2 | Cl | H | Cl | H | — | c-Pen(Z) |
| CH₃ | G²-2 | Cl | H | Cl | H | — | c-Pen |
| CH₃ | G²-2 | Cl | H | Cl | H | — | c-Pen(Z) |
| CH₃(S) | G²-2 | Cl | H | Cl | H | — | c-Pen |
| CH₃(S) | G²-2 | Cl | H | Cl | H | — | c-Pen(Z) |
| H | G²-2 | Cl | H | Cl | F | — | c-Pen |
| H | G²-2 | Cl | H | Cl | F | — | c-Pen(Z) |
| CH₃ | G²-2 | Cl | H | Cl | F | — | c-Pen(Z) |
| CH₃(S) | G²-2 | Cl | H | Cl | F | — | c-Pen(Z) |
| H | G²-2 | Cl | H | Br | H | — | c-Pen |
| H | G²-2 | Cl | H | Br | H | — | c-Pen(Z) |
| CH₃ | G²-2 | Cl | H | Br | H | — | c-Pen(Z) |
| CH₃(S) | G²-2 | Cl | H | Br | H | — | c-Pen(Z) |
| H | G²-2 | Cl | H | CF₃ | H | — | c-Pen |
| H | G²-2 | Cl | H | CF₃ | H | — | c-Pen(Z) |
| CH₃ | G²-2 | Cl | H | CF₃ | H | — | c-Pen(Z) |
| CH₃(S) | G²-2 | Cl | H | CF₃ | H | — | c-Pen(Z) |
| H | G²-2 | Cl | H | C≡CH | H | — | c-Pen |
| H | G²-2 | Cl | H | C≡CH | H | — | c-Pen(Z) |
| H | G²-2 | Cl | H | C≡CPr-c | H | — | c-Pen |
| H | G²-2 | Cl | H | C≡CPr-c | H | — | c-Pen(Z) |
| H | G²-2 | Cl | H | C≡CBu-t | H | — | c-Pen |
| H | G²-2 | Cl | H | C≡CBu-t | H | — | c-Pen(Z) |
| H | G²-2 | Cl | H | C≡CC(CH₃)₂OCH₃ | H | — | c-Pen |
| H | G²-2 | Cl | H | C≡CC(CH₃)₂OCH₃ | H | — | c-Pen(Z) |
| H | G²-2 | Cl | H | C≡CSi(CH₃)₃ | H | — | c-Pen |
| H | G²-2 | Cl | H | C≡CSi(CH₃)₃ | H | — | c-Pen(Z) |
| H | G²-2 | Cl | H | C≡CPh | H | — | c-Pen |
| H | G²-2 | Cl | H | C≡CPh | H | — | c-Pen(Z) |
| H | G²-2 | Cl | F | Cl | H | — | c-Pen |
| H | G²-2 | Cl | F | Cl | H | — | c-Pen(Z) |
| H | G²-2 | Cl | Cl | Cl | H | — | c-Pen |
| H | G²-2 | Cl | Cl | Cl | H | — | c-Pen(Z) |
| H | G²-2 | Br | H | Cl | H | — | c-Pen |
| H | G²-2 | Br | H | Cl | H | — | c-Pen(Z) |
| H | G²-2 | Br | H | Br | H | — | c-Pen |
| H | G²-2 | Br | H | Br | H | — | c-Pen(Z) |
| CH₃ | G²-2 | Br | H | Br | H | — | c-Pen(Z) |
| CH₃(S) | G²-2 | Br | H | Br | H | — | c-Pen(Z) |
| H | G²-3 | Cl | — | H | Cl | H | c-Pen |
| H | G²-2 | Cl | H | Cl | H | — | Hex |
| H | G²-2 | Cl | H | Cl | H | — | Hex(Z) |
| H | G²-2 | Cl | H | CF₃ | H | — | Hex |
| H | G²-2 | Cl | H | CF₃ | H | — | Hex(Z) |
| H | G²-2 | Cl | H | Cl | H | — | CH₂Pen-c |
| H | G²-2 | Cl | H | Cl | H | — | CH₂Pen-c(Z) |
| H | G²-2 | Cl | H | CF₃ | H | — | CH₂Pen-c |
| H | G²-2 | Cl | H | CF₃ | H | — | CH₂Pen-c(Z) |
| H | G²-2 | Cl | H | Cl | H | — | c-Hex |
| H | G²-2 | Cl | H | Cl | H | — | c-Hex(Z) |

TABLE 2-continued

| R² | G² | Y¹ | Y² | Y³ | Y⁴ | Y⁵ | R¹ |
|---|---|---|---|---|---|---|---|
| H | G²-2 | Cl | H | CF₃ | H | — | c-Hex |
| H | G²-2 | Cl | H | CF₃ | H | — | c-Hex(Z) |
| H | G²-2 | Cl | H | Cl | H | — | CH₂Hex-c |
| H | G²-2 | Cl | H | Cl | H | — | CH₂Hex-c(Z) |
| CH₃ | G²-2 | Cl | H | Cl | H | — | CH₂Hex-c(Z) |
| CH₃(S) | G²-2 | Cl | H | Cl | H | — | CH₂Hex-c(Z) |
| H | G²-2 | Cl | H | Cl | F | — | CH₂Hex-c |
| H | G²-2 | Cl | H | Cl | F | — | CH₂Hex-c(Z) |
| H | G²-2 | Cl | H | Br | H | — | CH₂Hex-c |
| H | G²-2 | Cl | H | Br | H | — | CH₂Hex-c(Z) |
| CH₃ | G²-2 | Cl | H | Br | H | — | CH₂Hex-c(Z) |
| CH₃(S) | G²-2 | Cl | H | Br | H | — | CH₂Hex-c(Z) |
| H | G²-2 | Cl | H | CF₃ | H | — | CH₂Hex-c |
| H | G²-2 | Cl | H | CF₃ | H | — | CH₂Hex-c(Z) |
| CH₃ | G²-2 | Cl | H | CF₃ | H | — | CH₂Hex-c(Z) |
| CH₃(S) | G²-2 | Cl | H | CF₃ | H | — | CH₂Hex-c(Z) |
| H | G²-2 | Cl | H | C≡CPr-c | H | — | CH₂Hex-c |
| H | G²-2 | Cl | H | C≡CPr-c | H | — | CH₂Hex-c(Z) |
| H | G²-2 | Cl | H | C≡CBu-t | H | — | CH₂Hex-c |
| H | G²-2 | Cl | H | C≡CBu-t | H | — | CH₂Hex-c(Z) |
| H | G²-2 | Cl | H | C≡CC(CH₃)₂OCH₃ | H | — | CH₂Hex-c |
| H | G²-2 | Cl | H | C≡CC(CH₃)₂OCH₃ | H | — | CH₂Hex-c(Z) |
| H | G²-2 | Cl | H | C≡CSi(CH₃)₃ | H | — | CH₂Hex-c |
| H | G²-2 | Cl | H | C≡CSi(CH₃)₃ | H | — | CH₂Hex-c(Z) |
| H | G²-2 | Cl | H | C≡CPh | H | — | CH₂Hex-c |
| H | G²-2 | Cl | H | C≡CPh | H | — | CH₂Hex-c(Z) |
| H | G²-2 | Cl | F | Cl | H | — | CH₂Hex-c |
| H | G²-2 | Cl | F | Cl | H | — | CH₂Hex-c(Z) |
| H | G²-2 | Br | H | Cl | H | — | CH₂Hex-c |
| H | G²-2 | Br | H | Cl | H | — | CH₂Hex-c(Z) |
| H | G²-2 | Br | H | Br | H | — | CH₂Hex-c |
| H | G²-2 | Br | H | Br | H | — | CH₂Hex-c(Z) |
| H | G²-2 | Cl | H | Cl | H | — | CH₂CH₂Cl |
| H | G²-2 | Cl | H | Cl | H | — | CH₂CH₂Cl(Z) |
| H | G²-2 | Cl | H | CF₃ | H | — | CH₂CH₂Cl |
| H | G²-2 | Cl | H | CF₃ | H | — | CH₂CH₂Cl(Z) |
| CH₃ | G²-1 | Cl | H | F | H | H | CH₂CHF₂ |
| CH₃ | G²-1 | Cl | H | F | H | H | CH₂CHF₂(E) |
| CH₃(S) | G²-1 | Cl | H | F | H | H | CH₂CHF₂ |
| CH₃(S) | G²-1 | Cl | H | F | H | H | CH₂CHF₂(E) |
| H | G²-2 | F | H | Cl | H | — | CH₂CHF₂ |
| H | G²-2 | F | H | Cl | H | — | CH₂CHF₂(Z) |
| CH₃ | G²-2 | F | H | Cl | H | — | CH₂CHF₂(Z) |
| CH₃(S) | G²-2 | F | H | Cl | H | — | CH₂CHF₂(Z) |
| H | G²-2 | F | H | Br | H | — | CH₂CHF₂ |
| H | G²-2 | F | H | Br | H | — | CH₂CHF₂(Z) |
| CH₃ | G²-2 | F | H | Br | H | — | CH₂CHF₂(Z) |
| CH₃(S) | G²-2 | F | H | Br | H | — | CH₂CHF₂(Z) |
| H | G²-2 | F | H | CF₃ | H | — | CH₂CHF₂ |
| H | G²-2 | F | H | CF₃ | H | — | CH₂CHF₂(Z) |
| H | G²-2 | Cl | H | F | H | — | CH₂CHF₂ |
| H | G²-2 | Cl | H | F | H | — | CH₂CHF₂(Z) |
| CH₃ | G²-2 | Cl | H | F | H | — | CH₂CHF₂(Z) |
| CH₃(S) | G²-2 | Cl | H | F | H | — | CH₂CHF₂(Z) |
| H | G²-2 | Cl | H | Cl | H | — | CH₂CHF₂ |
| H | G²-2 | Cl | H | Cl | H | — | CH₂CHF₂(Z) |
| CH₃ | G²-2 | Cl | H | Cl | H | — | CH₂CHF₂ |
| CH₃ | G²-2 | Cl | H | Cl | H | — | CH₂CHF₂(Z) |
| CH₃(S) | G²-2 | Cl | H | Cl | H | — | CH₂CHF₂ |
| CH₃(S) | G²-2 | Cl | H | Cl | H | — | CH₂CHF₂(Z) |
| H | G²-2 | Cl | H | Cl | F | — | CH₂CHF₂ |
| H | G²-2 | Cl | H | Cl | F | — | CH₂CHF₂(Z) |
| CH₃ | G²-2 | Cl | H | Cl | F | — | CH₂CHF₂ |
| CH₃ | G²-2 | Cl | H | Cl | F | — | CH₂CHF₂(Z) |
| CH₃(S) | G²-2 | Cl | H | Cl | F | — | CH₂CHF₂ |
| CH₃(S) | G²-2 | Cl | H | Cl | F | — | CH₂CHF₂(Z) |
| H | G²-2 | Cl | H | Cl | Cl | — | CH₂CHF₂ |
| H | G²-2 | Cl | H | Cl | Cl | — | CH₂CHF₂(Z) |
| H | G²-2 | Cl | H | Br | H | — | CH₂CHF₂ |
| H | G²-2 | Cl | H | Br | H | — | CH₂CHF₂(Z) |
| CH₃ | G²-2 | Cl | H | Br | H | — | CH₂CHF₂ |
| CH₃ | G²-2 | Cl | H | Br | H | — | CH₂CHF₂(Z) |
| CH₃(S) | G²-2 | Cl | H | Br | H | — | CH₂CHF₂ |
| CH₃(S) | G²-2 | Cl | H | Br | H | — | CH₂CHF₂(Z) |
| H | G²-2 | Cl | H | CF₃ | H | — | CH₂CHF₂ |
| H | G²-2 | Cl | H | CF₃ | H | — | CH₂CHF₂(E) |
| H | G²-2 | Cl | H | CF₃ | H | — | CH₂CHF₂(Z) |
| CH₃ | G²-2 | Cl | H | CF₃ | H | — | CH₂CHF₂ |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | CF₃ | H | — | CH₂CHF₂(Z) |
| CH₃(S) | G²-2 | Cl | H | CF₃ | H | — | CH₂CHF₂ |
| CH₃(S) | G²-2 | Cl | H | CF₃ | H | — | CH₂CHF₂(Z) |
| H | G²-2 | Cl | H | CH=NOCH₃ | H | — | CH₂CHF₂ |
| H | G²-2 | Cl | H | CH=NOEt | H | — | CH₂CHF₂ |
| H | G²-2 | Cl | H | C(CH₃)=NOCH₃ | H | — | CH₂CHF₂ |
| CH₃ | G²-2 | Cl | H | C(CH₃)=NOCH₃ | H | — | CH₂CHF₂ |
| CH₃(S) | G²-2 | Cl | H | C(CH₃)=NOCH₃ | H | — | CH₂CHF₂ |
| H | G²-2 | Cl | H | C(CH₃)=NOEt | H | — | CH₂CHF₂ |
| H | G²-2 | Cl | H | C(Et)=NOCH₃ | H | — | CH₂CHF₂ |
| H | G²-2 | Cl | H | C≡CH | H | — | CH₂CHF₂ |
| H | G²-2 | Cl | H | C≡CH | H | — | CH₂CHF₂(Z) |
| H | G²-2 | Cl | H | C≡CCH₃ | H | — | CH₂CHF₂ |
| H | G²-2 | Cl | H | C≡CCH₃ | H | — | CH₂CHF₂(Z) |
| H | G²-2 | Cl | H | C≡CEt | H | — | CH₂CHF₂ |
| H | G²-2 | Cl | H | C≡CPr-n | H | — | CH₂CHF₂ |
| H | G²-2 | Cl | H | C≡CPr-c | H | — | CH₂CHF₂ |
| H | G²-2 | Cl | H | C≡CPr-c | H | — | CH₂CHF₂(Z) |
| CH₃ | G²-2 | Cl | H | C≡CPr-c | H | — | CH₂CHF₂ |
| CH₃ | G²-2 | Cl | H | C≡CPr-c | H | — | CH₂CHF₂(Z) |
| CH₃(S) | G²-2 | Cl | H | C≡CPr-c | H | — | CH₂CHF₂ |
| CH₃(S) | G²-2 | Cl | H | C≡CPr-c | H | — | CH₂CHF₂(Z) |
| H | G²-2 | Cl | H | C≡CBu-n | H | — | CH₂CHF₂ |
| H | G²-2 | Cl | H | C≡CBu-t | H | — | CH₂CHF₂ |
| H | G²-2 | Cl | H | C≡CBu-t | H | — | CH₂CHF₂(Z) |
| CH₃ | G²-2 | Cl | H | C≡CBu-t | H | — | CH₂CHF₂ |
| CH₃ | G²-2 | Cl | H | C≡CBu-t | H | — | CH₂CHF₂(Z) |
| CH₃(S) | G²-2 | Cl | H | C≡CBu-t | H | — | CH₂CHF₂ |
| CH₃(S) | G²-2 | Cl | H | C≡CBu-t | H | — | CH₂CHF₂(Z) |
| H | G²-2 | Cl | H | C≡CPen-c | H | — | CH₂CHF₂ |
| H | G²-2 | Cl | H | C≡CPen-c | H | — | CH₂CHF₂(Z) |
| H | G²-2 | Cl | H | C≡CCl | H | — | CH₂CHF₂ |
| H | G²-2 | Cl | H | C≡CBr | H | — | CH₂CHF₂ |
| H | G²-2 | Cl | H | C≡CI | H | — | CH₂CHF₂ |
| H | G²-2 | Cl | H | C≡CC(CH₃)₂OH | H | — | CH₂CHF₂ |
| H | G²-2 | Cl | H | C≡CC(CH₃)₂OH | H | — | CH₂CHF₂(Z) |
| H | G²-2 | Cl | H | C≡CC(CH₃)₂OCH₃ | H | — | CH₂CHF₂ |
| H | G²-2 | Cl | H | C≡CC(CH₃)₂OCH₃ | H | — | CH₂CHF₂(Z) |
| H | G²-2 | Cl | H | C≡CSi(CH₃)₃ | H | — | CH₂CHF₂ |
| H | G²-2 | Cl | H | C≡CSi(CH₃)₃ | H | — | CH₂CHF₂(Z) |
| H | G²-2 | Cl | H | C≡CPh | H | — | CH₂CHF₂ |
| H | G²-2 | Cl | H | C≡CPh | H | — | CH₂CHF₂(Z) |
| H | G²-2 | Cl | F | Cl | H | — | CH₂CHF₂ |
| H | G²-2 | Cl | F | Cl | H | — | CH₂CHF₂(Z) |
| CH₃ | G²-2 | Cl | F | Cl | H | — | CH₂CHF₂(Z) |
| CH₃(S) | G²-2 | Cl | F | Cl | H | — | CH₂CHF₂(Z) |
| H | G²-2 | Cl | Cl | Cl | H | — | CH₂CHF₂ |
| H | G²-2 | Cl | Cl | Cl | H | — | CH₂CHF₂(Z) |
| CH₃ | G²-2 | Cl | Cl | Cl | H | — | CH₂CHF₂(Z) |
| CH₃(S) | G²-2 | Cl | Cl | Cl | H | — | CH₂CHF₂(Z) |
| H | G²-2 | Br | H | F | H | — | CH₂CHF₂ |
| H | G²-2 | Br | H | F | H | — | CH₂CHF₂(Z) |
| H | G²-2 | Br | H | Cl | H | — | CH₂CHF₂ |
| H | G²-2 | Br | H | Cl | H | — | CH₂CHF₂(Z) |
| CH₃ | G²-2 | Br | H | Cl | H | — | CH₂CHF₂(Z) |
| CH₃(S) | G²-2 | Br | H | Cl | H | — | CH₂CHF₂(Z) |
| H | G²-2 | Br | H | Br | H | — | CH₂CHF₂ |
| H | G²-2 | Br | H | Br | H | — | CH₂CHF₂(Z) |
| CH₃ | G²-2 | Br | H | Br | H | — | CH₂CHF₂ |
| CH₃ | G²-2 | Br | H | Br | H | — | CH₂CHF₂(Z) |
| CH₃(S) | G²-2 | Br | H | Br | H | — | CH₂CHF₂ |
| CH₃(S) | G²-2 | Br | H | Br | H | — | CH₂CHF₂(Z) |
| H | G²-2 | Br | H | CF₃ | H | — | CH₂CHF₂ |
| H | G²-2 | Br | H | CF₃ | H | — | CH₂CHF₂(Z) |
| H | G²-6 | Cl | — | Cl | H | — | CH₂CHF₂ |
| CH₃ | G²-6 | Cl | — | Cl | H | — | CH₂CHF₂ |
| CH₃ | G²-9 | Cl | H | Cl | — | — | CH₂CHF₂ |
| CH₃ | G²-9 | Cl | H | Cl | — | — | CH₂CHF₂(Z) |
| CH₃ | G²-9 | Cl | H | Br | — | — | CH₂CHF₂ |
| CH₃ | G²-9 | Cl | H | Br | — | — | CH₂CHF₂(Z) |
| CH₃ | G²-9 | Cl | H | C≡CPr-c | — | — | CH₂CHF₂ |
| CH₃ | G²-9 | Cl | H | C≡CPr-c | — | — | CH₂CHF₂(Z) |
| CH₃ | G²-9 | Cl | H | C≡CBu-t | — | — | CH₂CHF₂ |
| CH₃ | G²-9 | Cl | H | C≡CBu-t | — | — | CH₂CHF₂(Z) |
| CH₃ | G²-9 | Cl | Cl | Cl | — | — | CH₂CHF₂ |
| CH₃ | G²-9 | Cl | Cl | Cl | — | — | CH₂CHF₂(Z) |
| CH₃ | G²-1 | H | H | CF₃ | H | H | CH₂CF₃ |
| CH₃ | G²-1 | H | H | OPh | H | H | CH₂CF₃ |

TABLE 2-continued

| R² | G² | Y¹ | Y² | Y³ | Y⁴ | Y⁵ | R¹ |
|---|---|---|---|---|---|---|---|
| CH₃ | G²-1 | H | H | Ph | H | H | CH₂CF₃ |
| CH₃ | G²-1 | H | F | F | F | H | CH₂CF₃ |
| CH₃ | G²-1 | H | \multicolumn{2}{c}{—CH═CHCH═CH—} | | H | CH₂CF₃ |
| CH₃ | G²-1 | F | H | Br | H | H | CH₂CF₃ |
| CH₃ | G²-1 | Cl | H | F | H | H | CH₂CF₃ |
| CH₃ | G²-1 | Cl | H | F | H | H | CH₂CF₃(E) |
| CH₃(S) | G²-1 | Cl | H | F | H | H | CH₂CF₃ |
| CH₃(S) | G²-1 | Cl | H | F | H | H | CH₂CF₃(E) |
| CH₃ | G²-1 | Cl | H | Cl | H | H | CH₂CF₃ |
| CH₃ | G²-1 | Cl | H | Br | H | H | CH₂CF₃ |
| H | G²-2 | F | H | Cl | H | — | CH₂CF₃ |
| H | G²-2 | F | H | Cl | H | — | CH₂CF₃(Z) |
| CH₃ | G²-2 | F | H | Cl | H | — | CH₂CF₃(Z) |
| CH₃(S) | G²-2 | F | H | Cl | H | — | CH₂CF₃(Z) |
| H | G²-2 | F | H | Br | H | — | CH₂CF₃ |
| H | G²-2 | F | H | Br | H | — | CH₂CF₃(Z) |
| CH₃ | G²-2 | F | H | Br | H | — | CH₂CF₃(Z) |
| CH₃(S) | G²-2 | F | H | Br | H | — | CH₂CF₃(Z) |
| H | G²-2 | F | H | CF₃ | H | — | CH₂CF₃ |
| H | G²-2 | F | H | CF₃ | H | — | CH₂CF₃(Z) |
| H | G²-2 | Cl | H | F | H | — | CH₂CF₃ |
| H | G²-2 | Cl | H | F | H | — | CH₂CF₃(Z) |
| CH₃ | G²-2 | Cl | H | F | H | — | CH₂CF₃(Z) |
| CH₃(S) | G²-2 | Cl | H | F | H | — | CH₂CF₃(Z) |
| H | G²-2 | Cl | H | Cl | H | — | CH₂CF₃ |
| H | G²-2 | Cl | H | Cl | H | — | CH₂CF₃(E) |
| H | G²-2 | Cl | H | Cl | H | — | CH₂CF₃(Z) |
| CH₃ | G²-2 | Cl | H | Cl | H | — | CH₂CF₃ |
| CH₃ | G²-2 | Cl | H | Cl | H | — | CH₂CF₃(Z) |
| CH₃(S) | G²-2 | Cl | H | Cl | H | — | CH₂CF₃ |
| CH₃(S) | G²-2 | Cl | H | Cl | H | — | CH₂CF₃(Z) |
| H | G²-2 | Cl | H | Cl | F | — | CH₂CF₃ |
| H | G²-2 | Cl | H | Cl | F | — | CH₂CF₃(Z) |
| CH₃ | G²-2 | Cl | H | Cl | F | — | CH₂CF₃ |
| CH₃ | G²-2 | Cl | H | Cl | F | — | CH₂CF₃(Z) |
| CH₃(S) | G²-2 | Cl | H | Cl | F | — | CH₂CF₃ |
| CH₃(S) | G²-2 | Cl | H | Cl | F | — | CH₂CF₃(Z) |
| H | G²-2 | Cl | H | Cl | Cl | — | CH₂CF₃ |
| H | G²-2 | Cl | H | Cl | Cl | — | CH₂CF₃(Z) |
| H | G²-2 | Cl | H | Br | H | — | CH₂CF₃ |
| H | G²-2 | Cl | H | Br | H | — | CH₂CF₃(Z) |
| CH₃ | G²-2 | Cl | H | Br | H | — | CH₂CF₃ |
| CH₃ | G²-2 | Cl | H | Br | H | — | CH₂CF₃(Z) |
| CH₃(S) | G²-2 | Cl | H | Br | H | — | CH₂CF₃ |
| CH₃(S) | G²-2 | Cl | H | Br | H | — | CH₂CF₃(Z) |
| H | G²-2 | Cl | H | CF₃ | H | — | CH₂CF₃ |
| H | G²-2 | Cl | H | CF₃ | H | — | CH₂CF₃(Z) |
| CH₃ | G²-2 | Cl | H | CF₃ | H | — | CH₂CF₃ |
| CH₃ | G²-2 | Cl | H | CF₃ | H | — | CH₂CF₃(Z) |
| CH₃(S) | G²-2 | Cl | H | CF₃ | H | — | CH₂CF₃ |
| CH₃(S) | G²-2 | Cl | H | CF₃ | H | — | CH₂CF₃(Z) |
| H | G²-2 | Cl | H | CH═NOCH₃ | H | — | CH₂CF₃ |
| H | G²-2 | Cl | H | CH═NOEt | H | — | CH₂CF₃ |
| H | G²-2 | Cl | H | C(CH₃)═NOCH₃ | H | — | CH₂CF₃ |
| CH₃ | G²-2 | Cl | H | C(CH₃)═NOCH₃ | H | — | CH₂CF₃ |
| CH₃(S) | G²-2 | Cl | H | C(CH₃)═NOCH₃ | H | — | CH₂CF₃ |
| H | G²-2 | Cl | H | C(CH₃)═NOEt | H | — | CH₂CF₃ |
| H | G²-2 | Cl | H | C(Et)═NOCH₃ | H | — | CH₂CF₃ |
| H | G²-2 | Cl | H | C≡CH | H | — | CH₂CF₃ |
| H | G²-2 | Cl | H | C≡CH | H | — | CH₂CF₃(Z) |
| H | G²-2 | Cl | H | C≡CCH₃ | H | — | CH₂CF₃ |
| H | G²-2 | Cl | H | C≡CCH₃ | H | — | CH₂CF₃(Z) |
| H | G²-2 | Cl | H | C≡CEt | H | — | CH₂CF₃ |
| H | G²-2 | Cl | H | C≡CPr-n | H | — | CH₂CF₃ |
| H | G²-2 | Cl | H | C≡CPr-c | H | — | CH₂CF₃ |
| H | G²-2 | Cl | H | C≡CPr-c | H | — | CH₂CF₃(Z) |
| CH₃ | G²-2 | Cl | H | C≡CPr-c | H | — | CH₂CF₃ |
| CH₃ | G²-2 | Cl | H | C≡CPr-c | H | — | CH₂CF₃(Z) |
| CH₃(S) | G²-2 | Cl | H | C≡CPr-c | H | — | CH₂CF₃ |
| CH₃(S) | G²-2 | Cl | H | C≡CPr-c | H | — | CH₂CF₃(Z) |
| H | G²-2 | Cl | H | C≡CBu-n | H | — | CH₂CF₃ |
| H | G²-2 | Cl | H | C≡CBu-t | H | — | CH₂CF₃ |
| H | G²-2 | Cl | H | C≡CBu-t | H | — | CH₂CF₃(Z) |
| CH₃ | G²-2 | Cl | H | C≡CBu-t | H | — | CH₂CF₃ |
| CH₃ | G²-2 | Cl | H | C≡CBu-t | H | — | CH₂CF₃(Z) |
| CH₃(S) | G²-2 | Cl | H | C≡CBu-t | H | — | CH₂CF₃ |
| CH₃(S) | G²-2 | Cl | H | C≡CBu-t | H | — | CH₂CF₃(Z) |
| H | G²-2 | Cl | H | C≡CPen-c | H | — | CH₂CF₃ |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CPen-c | H | — | CH₂CF₃(Z) |
| H | G²-2 | Cl | H | C≡CCl | H | — | CH₂CF₃ |
| H | G²-2 | Cl | H | C≡CBr | H | — | CH₂CF₃ |
| H | G²-2 | Cl | H | C≡CI | H | — | CH₂CF₃ |
| H | G²-2 | Cl | H | C≡CC(CH₃)₂OH | H | — | CH₂CF₃ |
| H | G²-2 | Cl | H | C≡CC(CH₃)₂OH | H | — | CH₂CF₃(Z) |
| H | G²-2 | Cl | H | C≡CC(CH₃)₂OCH₃ | H | — | CH₂CF₃ |
| H | G²-2 | Cl | H | C≡CC(CH₃)₂OCH₃ | H | — | CH₂CF₃(Z) |
| H | G²-2 | Cl | H | C≡CSi(CH₃)₃ | H | — | CH₂CF₃ |
| H | G²-2 | Cl | H | C≡CSi(CH₃)₃ | H | — | CH₂CF₃(Z) |
| H | G²-2 | Cl | H | C≡CPh | H | — | CH₂CF₃ |
| H | G²-2 | Cl | H | C≡CPh | H | — | CH₂CF₃(Z) |
| H | G²-2 | Cl | F | Cl | H | — | CH₂CF₃ |
| H | G²-2 | Cl | F | Cl | H | — | CH₂CF₃(Z) |
| CH₃ | G²-2 | Cl | F | Cl | H | — | CH₂CF₃(Z) |
| CH₃(S) | G²-2 | Cl | F | Cl | H | — | CH₂CF₃(Z) |
| H | G²-2 | Cl | Cl | Cl | H | — | CH₂CF₃ |
| H | G²-2 | Cl | Cl | Cl | H | — | CH₂CF₃(Z) |
| CH₃ | G²-2 | Cl | Cl | Cl | H | — | CH₂CF₃(Z) |
| CH₃(S) | G²-2 | Cl | Cl | Cl | H | — | CH₂CF₃(Z) |
| H | G²-2 | Br | H | F | H | — | CH₂CF₃ |
| H | G²-2 | Br | H | F | H | — | CH₂CF₃(Z) |
| H | G²-2 | Br | H | Cl | H | — | CH₂CF₃ |
| H | G²-2 | Br | H | Cl | H | — | CH₂CF₃(Z) |
| CH₃ | G²-2 | Br | H | Cl | H | — | CH₂CF₃(Z) |
| CH₃(S) | G²-2 | Br | H | Cl | H | — | CH₂CF₃(Z) |
| H | G²-2 | Br | H | Br | H | — | CH₂CF₃ |
| H | G²-2 | Br | H | Br | H | — | CH₂CF₃(Z) |
| CH₃ | G²-2 | Br | H | Br | H | — | CH₂CF₃ |
| CH₃ | G²-2 | Br | H | Br | H | — | CH₂CF₃(Z) |
| CH₃(S) | G²-2 | Br | H | Br | H | — | CH₂CF₃ |
| CH₃(S) | G²-2 | Br | H | Br | H | — | CH₂CF₃(Z) |
| H | G²-2 | Br | H | CF₃ | H | — | CH₂CF₃ |
| H | G²-2 | Br | H | CF₃ | H | — | CH₂CF₃(Z) |
| H | G²-6 | Cl | — | Cl | H | — | CH₂CF₃ |
| CH₃ | G²-6 | Cl | — | Cl | H | — | CH₂CF₃ |
| CH₃ | G²-9 | Cl | H | Cl | — | — | CH₂CF₃ |
| CH₃ | G²-9 | Cl | H | Cl | — | — | CH₂CF₃(Z) |
| CH₃ | G²-9 | Cl | H | Br | — | — | CH₂CF₃ |
| CH₃ | G²-9 | Cl | H | Br | — | — | CH₂CF₃(Z) |
| CH₃ | G²-9 | Cl | H | C≡CPr-c | — | — | CH₂CF₃ |
| CH₃ | G²-9 | Cl | H | C≡CPr-c | — | — | CH₂CF₃(Z) |
| CH₃ | G²-9 | Cl | H | C≡CBu-t | — | — | CH₂CF₃ |
| CH₃ | G²-9 | Cl | H | C≡CBu-t | — | — | CH₂CF₃(Z) |
| CH₃ | G²-9 | Cl | Cl | Cl | — | — | CH₂CF₃ |
| CH₃ | G²-9 | Cl | Cl | Cl | — | — | CH₂CF₃(Z) |
| H | G²-2 | Cl | H | Cl | H | — | CF₂CHF₂ |
| H | G²-2 | Cl | H | Cl | H | — | CF₂CHF₂(Z) |
| H | G²-2 | Cl | H | Cl | H | — | CH₂CF₂Cl |
| H | G²-2 | Cl | H | Cl | H | — | CH₂CF₂Cl(Z) |
| H | G²-2 | Cl | H | CF₃ | H | — | CH₂CF₂Cl |
| H | G²-2 | Cl | H | CF₃ | H | — | CH₂CF₂Cl(Z) |
| H | G²-2 | Cl | H | Cl | H | — | CH₂CF₂CH₃ |
| H | G²-2 | Cl | H | Cl | H | — | CH₂CF₂CH₃(Z) |
| H | G²-2 | Cl | H | CF₃ | H | — | CH₂CF₂CH₃ |
| H | G²-2 | Cl | H | CF₃ | H | — | CH₂CF₂CH₃(Z) |
| H | G²-2 | Cl | H | Cl | H | — | CH₂CH₂CF₃ |
| H | G²-2 | Cl | H | Cl | H | — | CH₂CH₂CF₃(Z) |
| H | G²-2 | Cl | H | CF₃ | H | — | CH₂CH₂CF₃ |
| H | G²-2 | Cl | H | CF₃ | H | — | CH₂CH₂CF₃(Z) |
| H | G²-2 | Cl | H | Cl | H | — | CH(CH₃)CF₃ |
| H | G²-2 | Cl | H | Cl | H | — | CH(CH₃)CF₃(Z) |
| H | G²-2 | Cl | H | CF₃ | H | — | CH(CH₃)CF₃ |
| H | G²-2 | Cl | H | CF₃ | H | — | CH(CH₃)CF₃(Z) |
| H | G²-2 | Cl | H | Cl | H | — | CH₂CF₂CHF₂ |
| H | G²-2 | Cl | H | Cl | H | — | CH₂CF₂CHF₂(Z) |
| H | G²-2 | Cl | H | CF₃ | H | — | CH₂CF₂CHF₂ |
| H | G²-2 | Cl | H | CF₃ | H | — | CH₂CF₂CHF₂(Z) |
| H | G²-2 | Cl | H | Cl | H | — | CH₂CF₂CF₃ |
| H | G²-2 | Cl | H | Cl | H | — | CH₂CF₂CF₃(Z) |
| H | G²-2 | Cl | H | Cl | H | — | CF₂CHFCF₃ |
| H | G²-2 | Cl | H | Cl | H | — | CF₂CHFCF₃(Z) |
| H | G²-2 | Cl | H | Cl | H | — | CH(CF₃)₂ |
| H | G²-2 | Cl | H | Cl | H | — | CH(CF₃)₂(Z) |
| H | G²-2 | Cl | H | Cl | H | — | CH₂(T-1) |
| H | G²-2 | Cl | H | Cl | H | — | CH₂(T-2) |
| H | G²-2 | Cl | H | Cl | H | — | T-2 |
| H | G²-2 | Cl | H | Cl | H | — | CH(CH₃)OEt |

TABLE 2-continued

| R² | G² | Y¹ | Y² | Y³ | Y⁴ | Y⁵ | R¹ |
|---|---|---|---|---|---|---|---|
| H | G²-2 | Cl | H | Cl | H | — | CH(CH₃)OEt(Z) |
| H | G²-2 | Cl | H | CF₃ | H | — | CH(CH₃)OEt |
| H | G²-2 | Cl | H | CF₃ | H | — | CH(CH₃)OEt(Z) |
| H | G²-2 | Cl | H | Cl | H | — | CH(CH₃)OCH₂CF₃ |
| H | G²-2 | Cl | H | CF₃ | H | — | E-5-1a |
| H | G²-2 | Cl | H | Cl | H | — | E-14-1a |
| CH₃ | G²-1 | Cl | H | Cl | H | H | CH₂CH₂OCH₃ |
| CH₃ | G²-1 | Br | H | F | H | H | CH₂CH₂OCH₃ |
| H | G²-2 | Cl | H | Cl | H | — | CH₂CH₂OCH₃ |
| H | G²-2 | Cl | H | CF₃ | H | — | CH₂CH₂OCH₃(Z) |
| H | G²-2 | Cl | H | CF₃ | H | — | CH₂(E-2-1a) |
| H | G²-2 | Cl | H | Cl | H | — | CH₂(E-5-1a) |
| H | G²-2 | Cl | H | Cl | H | — | CH₂(E-9-1a) |
| H | G²-2 | Cl | H | Cl | H | — | E-2-2a |
| H | G²-2 | Cl | H | CF₃ | H | — | E-5-2a |
| H | G²-2 | Cl | H | CF₃ | H | — | E-14-2a |
| H | G²-2 | Cl | H | CF₃ | H | — | CH₂(E-2-2a) |
| H | G²-2 | Cl | H | Cl | H | — | CH₂(E-5-2a) |
| H | G²-2 | Cl | H | CF₃ | H | — | E-14-3a |
| H | G²-2 | Cl | H | Cl | H | — | CH₂CH₂OCH₂CF₃ |
| H | G²-2 | Cl | H | Cl | H | — | CF₂CHFOCF₂CF₂CF₃ |
| H | G²-2 | Cl | H | Cl | H | — | CH₂CH₂SCH₃ |
| H | G²-2 | Cl | H | Cl | H | — | CH₂CH₂SCH₃(Z) |
| H | G²-2 | Cl | H | CF₃ | H | — | CH₂CH₂SCH₃ |
| H | G²-2 | Cl | H | CF₃ | H | — | CH₂CH₂SCH₃(Z) |
| H | G²-2 | Cl | H | CF₃ | H | — | E-3-2a |
| H | G²-2 | Cl | H | CF₃ | H | — | E-3-2b |
| H | G²-2 | Cl | H | CF₃ | H | — | E-3-2c |
| H | G²-2 | Cl | H | CF₃ | H | — | E-6-2a |
| H | G²-2 | Cl | H | CF₃ | H | — | E-6-2b |
| H | G²-2 | Cl | H | CF₃ | H | — | E-6-2c |
| H | G²-2 | Cl | H | CF₃ | H | — | CH₂(E-6-1a) |
| H | G²-2 | Cl | H | CF₃ | H | — | CH₂(E-6-1b) |
| H | G²-2 | Cl | H | CF₃ | H | — | CH₂(E-6-1c) |
| H | G²-2 | Cl | H | CF₃ | H | — | CH₂(E-6-2a) |
| H | G²-2 | Cl | H | CF₃ | H | — | CH₂(E-6-2b) |
| H | G²-2 | Cl | H | CF₃ | H | — | CH₂(E-6-2c) |
| H | G²-2 | Cl | H | CF₃ | H | — | E-15-2a |
| H | G²-2 | Cl | H | CF₃ | H | — | E-15-2b |
| H | G²-2 | Cl | H | CF₃ | H | — | E-15-2c |
| H | G²-2 | Cl | H | CF₃ | H | — | E-15-3a |
| H | G²-2 | Cl | H | CF₃ | H | — | E-15-3b |
| H | G²-2 | Cl | H | CF₃ | H | — | E-15-3c |
| H | G²-2 | Cl | H | CF₃ | H | — | (E-4-2a)CHO |
| H | G²-2 | Cl | H | CF₃ | H | — | (E-4-2a)C(O)CH₃ |
| H | G²-2 | Cl | H | CF₃ | H | — | (E-4-2a)C(O)OCH₃ |
| H | G²-2 | Cl | H | CF₃ | H | — | CH₂(E-4-1a)CHO |
| H | G²-2 | Cl | H | CF₃ | H | — | CH₂(E-4-1a)C(O)CH₃ |
| H | G²-2 | Cl | H | CF₃ | H | — | CH₂(E-4-1a)C(O)OCH₃ |
| H | G²-2 | Cl | H | CF₃ | H | — | CH₂(E-4-2a)CHO |
| H | G²-2 | Cl | H | CF₃ | H | — | CH₂(E-4-2a)C(O)CH₃ |
| H | G²-2 | Cl | H | CF₃ | H | — | CH₂(E-4-2a)C(O)OCH₃ |
| H | G²-2 | Cl | H | CF₃ | H | — | (E-8-2a)CHO |
| H | G²-2 | Cl | H | CF₃ | H | — | (E-8-2a)C(O)CH₃ |
| H | G²-2 | Cl | H | CF₃ | H | — | (E-8-2a)C(O)OCH₃ |
| H | G²-2 | Cl | H | CF₃ | H | — | CH₂(E-8-1a)CHO |
| H | G²-2 | Cl | H | CF₃ | H | — | CH₂(E-8-1a)C(O)CH₃ |
| H | G²-2 | Cl | H | CF₃ | H | — | CH₂(E-8-1a)C(O)OCH₃ |
| H | G²-2 | Cl | H | CF₃ | H | — | CH₂(E-8-2a)CHO |
| H | G²-2 | Cl | H | CF₃ | H | — | CH₂(E-8-2a)C(O)CH₃ |
| H | G²-2 | Cl | H | CF₃ | H | — | CH₂(E-8-2a)C(O)OCH₃ |
| H | G²-2 | Cl | H | CF₃ | H | — | (E-17-2a)CHO |
| H | G²-2 | Cl | H | CF₃ | H | — | (E-17-2a)C(O)CH₃ |
| H | G²-2 | Cl | H | CF₃ | H | — | (E-17-2a)C(O)OCH₃ |
| H | G²-2 | Cl | H | CF₃ | H | — | (E-17-3a)CHO |
| H | G²-2 | Cl | H | CF₃ | H | — | (E-17-3a)C(O)CH₃ |
| H | G²-2 | Cl | H | CF₃ | H | — | (E-17-3a)C(O)OCH₃ |
| H | G²-2 | Cl | H | Cl | H | — | CH₂Si(CH₃)₃ |
| H | G²-2 | Cl | H | Cl | H | — | CH₂Si(CH₃)₃(Z) |
| H | G²-2 | Cl | H | CF₃ | H | — | CH₂Si(CH₃)₃ |
| H | G²-2 | Cl | H | CF₃ | H | — | CH₂Si(CH₃)₃(Z) |
| H | G²-2 | Cl | H | Cl | H | — | CH₂C(CH₃)=NOCH₃ |
| H | G²-2 | Cl | H | CF₃ | H | — | CH₂C(CH₃)=NOCH₃ |
| H | G²-2 | Cl | H | CF₃ | H | — | CH₂(M-3-b)CH₃ |
| H | G²-2 | Cl | H | CF₃ | H | — | CH₂(M-4-2a)CH₃ |
| H | G²-2 | Cl | H | Cl | H | — | CH₂CN |
| H | G²-2 | Cl | H | CF₃ | H | — | CH₂CN |
| H | G²-2 | Cl | H | Cl | H | — | CH(CH₃)CN |

TABLE 2-continued

| $R^2$ | $G^2$ | $Y^1$ | $Y^2$ | $Y^3$ | $Y^4$ | $Y^5$ | $R^1$ |
|---|---|---|---|---|---|---|---|
| H | $G^2$-2 | Cl | H | $CF_3$ | H | — | $CH(CH_3)CN$ |
| H | $G^2$-2 | Cl | H | $CF_3$ | H | — | $CH_2CH_2CN$ |
| H | $G^2$-2 | Cl | H | Cl | H | — | $CH_2C(O)OCH_3$ |
| H | $G^2$-2 | Cl | H | Cl | H | — | $CH_2C(O)OEt$ |
| H | $G^2$-2 | Cl | H | $CF_3$ | H | — | $CH_2C(O)NH_2$ |
| H | $G^2$-2 | Cl | H | $CF_3$ | H | — | $CH_2C(O)NHCH_2CF_3$ |
| H | $G^2$-2 | Cl | H | $CF_3$ | H | — | $CH_2C(S)NH_2$ |
| $CH_3$ | $G^2$-1 | Cl | H | F | H | H | $CH_2CH=CH_2$ |
| $CH_3$ | $G^2$-1 | Cl | H | F | H | H | $CH_2CH=CH_2(E)$ |
| $CH_3(S)$ | $G^2$-1 | Cl | H | F | H | H | $CH_2CH=CH_2$ |
| $CH_3(S)$ | $G^2$-1 | Cl | H | F | H | H | $CH_2CH=CH_2(E)$ |
| H | $G^2$-2 | F | H | Cl | H | — | $CH_2CH=CH_2$ |
| H | $G^2$-2 | F | H | Cl | H | — | $CH_2CH=CH_2(Z)$ |
| $CH_3$ | $G^2$-2 | F | H | Cl | H | — | $CH_2CH=CH_2(Z)$ |
| $CH_3(S)$ | $G^2$-2 | F | H | Cl | H | — | $CH_2CH=CH_2(Z)$ |
| H | $G^2$-2 | F | H | Br | H | — | $CH_2CH=CH_2$ |
| H | $G^2$-2 | F | H | Br | H | — | $CH_2CH=CH_2(Z)$ |
| $CH_3$ | $G^2$-2 | F | H | Br | H | — | $CH_2CH=CH_2(Z)$ |
| $CH_3(S)$ | $G^2$-2 | F | H | Br | H | — | $CH_2CH=CH_2(Z)$ |
| H | $G^2$-2 | F | H | $CF_3$ | H | — | $CH_2CH=CH_2$ |
| H | $G^2$-2 | F | H | $CF_3$ | H | — | $CH_2CH=CH_2(Z)$ |
| H | $G^2$-2 | Cl | H | F | H | — | $CH_2CH=CH_2$ |
| H | $G^2$-2 | Cl | H | F | H | — | $CH_2CH=CH_2(Z)$ |
| $CH_3$ | $G^2$-2 | Cl | H | F | H | — | $CH_2CH=CH_2(Z)$ |
| $CH_3(S)$ | $G^2$-2 | Cl | H | F | H | — | $CH_2CH=CH_2(Z)$ |
| H | $G^2$-2 | Cl | H | Cl | H | — | $CH_2CH=CH_2$ |
| H | $G^2$-2 | Cl | H | Cl | H | — | $CH_2CH=CH_2(Z)$ |
| $CH_3$ | $G^2$-2 | Cl | H | Cl | H | — | $CH_2CH=CH_2$ |
| $CH_3$ | $G^2$-2 | Cl | H | Cl | H | — | $CH_2CH=CH_2(Z)$ |
| $CH_3(S)$ | $G^2$-2 | Cl | H | Cl | H | — | $CH_2CH=CH_2$ |
| $CH_3(S)$ | $G^2$-2 | Cl | H | Cl | H | — | $CH_2CH=CH_2(Z)$ |
| H | $G^2$-2 | Cl | H | Cl | F | — | $CH_2CH=CH_2$ |
| H | $G^2$-2 | Cl | H | Cl | F | — | $CH_2CH=CH_2(Z)$ |
| $CH_3$ | $G^2$-2 | Cl | H | Cl | F | — | $CH_2CH=CH_2$ |
| $CH_3$ | $G^2$-2 | Cl | H | Cl | F | — | $CH_2CH=CH_2(Z)$ |
| $CH_3(S)$ | $G^2$-2 | Cl | H | Cl | F | — | $CH_2CH=CH_2$ |
| $CH_3(S)$ | $G^2$-2 | Cl | H | Cl | F | — | $CH_2CH=CH_2(Z)$ |
| H | $G^2$-2 | Cl | H | Cl | Cl | — | $CH_2CH=CH_2$ |
| H | $G^2$-2 | Cl | H | Cl | Cl | — | $CH_2CH=CH_2(Z)$ |
| H | $G^2$-2 | Cl | H | Br | H | — | $CH_2CH=CH_2$ |
| H | $G^2$-2 | Cl | H | Br | H | — | $CH_2CH=CH_2(Z)$ |
| $CH_3$ | $G^2$-2 | Cl | H | Br | H | — | $CH_2CH=CH_2$ |
| $CH_3$ | $G^2$-2 | Cl | H | Br | H | — | $CH_2CH=CH_2(Z)$ |
| $CH_3(S)$ | $G^2$-2 | Cl | H | Br | H | — | $CH_2CH=CH_2$ |
| $CH_3(S)$ | $G^2$-2 | Cl | H | Br | H | — | $CH_2CH=CH_2(Z)$ |
| H | $G^2$-2 | Cl | H | $CF_3$ | H | — | $CH_2CH=CH_2$ |
| H | $G^2$-2 | Cl | H | $CF_3$ | H | — | $CH_2CH=CH_2(Z)$ |
| $CH_3$ | $G^2$-2 | Cl | H | $CF_3$ | H | — | $CH_2CH=CH_2$ |
| $CH_3$ | $G^2$-2 | Cl | H | $CF_3$ | H | — | $CH_2CH=CH_2(Z)$ |
| $CH_3(S)$ | $G^2$-2 | Cl | H | $CF_3$ | H | — | $CH_2CH=CH_2$ |
| $CH_3(S)$ | $G^2$-2 | Cl | H | $CF_3$ | H | — | $CH_2CH=CH_2(Z)$ |
| H | $G^2$-2 | Cl | H | $CH=NOCH_3$ | H | — | $CH_2CH=CH_2$ |
| H | $G^2$-2 | Cl | H | $CH=NOEt$ | H | — | $CH_2CH=CH_2$ |
| H | $G^2$-2 | Cl | H | $C(CH_3)=NOCH_3$ | H | — | $CH_2CH=CH_2$ |
| $CH_3$ | $G^2$-2 | Cl | H | $C(CH_3)=NOCH_3$ | H | — | $CH_2CH=CH_2$ |
| $CH_3(S)$ | $G^2$-2 | Cl | H | $C(CH_3)=NOCH_3$ | H | — | $CH_2CH=CH_2$ |
| H | $G^2$-2 | Cl | H | $C(CH_3)=NOEt$ | H | — | $CH_2CH=CH_2$ |
| H | $G^2$-2 | Cl | H | $C(Et)=NOCH_3$ | H | — | $CH_2CH=CH_2$ |
| H | $G^2$-2 | Cl | H | C≡CH | H | — | $CH_2CH=CH_2$ |
| H | $G^2$-2 | Cl | H | C≡CH | H | — | $CH_2CH=CH_2(Z)$ |
| H | $G^2$-2 | Cl | H | C≡CPr-c | H | — | $CH_2CH=CH_2$ |
| H | $G^2$-2 | Cl | H | C≡CPr-c | H | — | $CH_2CH=CH_2(Z)$ |
| H | $G^2$-2 | Cl | H | C≡CBu-t | H | — | $CH_2CH=CH_2$ |
| H | $G^2$-2 | Cl | H | C≡CBu-t | H | — | $CH_2CH=CH_2(Z)$ |
| H | $G^2$-2 | Cl | H | $C≡CC(CH_3)_2OCH_3$ | H | — | $CH_2CH=CH_2$ |
| H | $G^2$-2 | Cl | H | $C≡CC(CH_3)_2OCH_3$ | H | — | $CH_2CH=CH_2(Z)$ |
| H | $G^2$-2 | Cl | H | $C≡CSi(CH_3)_3$ | H | — | $CH_2CH=CH_2$ |
| H | $G^2$-2 | Cl | H | $C≡CSi(CH_3)_3$ | H | — | $CH_2CH=CH_2(Z)$ |
| H | $G^2$-2 | Cl | H | C≡CPh | H | — | $CH_2CH=CH_2$ |
| H | $G^2$-2 | Cl | H | C≡CPh | H | — | $CH_2CH=CH_2(Z)$ |
| H | $G^2$-2 | Cl | F | Cl | H | — | $CH_2CH=CH_2$ |
| H | $G^2$-2 | Cl | F | Cl | H | — | $CH_2CH=CH_2(Z)$ |
| $CH_3$ | $G^2$-2 | Cl | F | Cl | H | — | $CH_2CH=CH_2(Z)$ |
| $CH_3(S)$ | $G^2$-2 | Cl | F | Cl | H | — | $CH_2CH=CH_2(Z)$ |
| H | $G^2$-2 | Cl | Cl | Cl | H | — | $CH_2CH=CH_2$ |
| H | $G^2$-2 | Cl | Cl | Cl | H | — | $CH_2CH=CH_2(Z)$ |
| $CH_3$ | $G^2$-2 | Cl | Cl | Cl | H | — | $CH_2CH=CH_2(Z)$ |
| $CH_3(S)$ | $G^2$-2 | Cl | Cl | Cl | H | — | $CH_2CH=CH_2(Z)$ |

TABLE 2-continued

| $R^2$ | $G^2$ | $Y^1$ | $Y^2$ | $Y^3$ | $Y^4$ | $Y^5$ | $R^1$ |
|---|---|---|---|---|---|---|---|
| H | $G^2$-2 | Br | H | F | H | — | $CH_2CH=CH_2$ |
| H | $G^2$-2 | Br | H | F | H | — | $CH_2CH=CH_2(Z)$ |
| H | $G^2$-2 | Br | H | Cl | H | — | $CH_2CH=CH_2$ |
| H | $G^2$-2 | Br | H | Cl | H | — | $CH_2CH=CH_2(Z)$ |
| $CH_3$ | $G^2$-2 | Br | H | Cl | H | — | $CH_2CH=CH_2(Z)$ |
| $CH_3(S)$ | $G^2$-2 | Br | H | Cl | H | — | $CH_2CH=CH_2(Z)$ |
| H | $G^2$-2 | Br | H | Br | H | — | $CH_2CH=CH_2$ |
| H | $G^2$-2 | Br | H | Br | H | — | $CH_2CH=CH_2(Z)$ |
| $CH_3$ | $G^2$-2 | Br | H | Br | H | — | $CH_2CH=CH_2$ |
| $CH_3$ | $G^2$-2 | Br | H | Br | H | — | $CH_2CH=CH_2(Z)$ |
| $CH_3(S)$ | $G^2$-2 | Br | H | Br | H | — | $CH_2CH=CH_2$ |
| $CH_3(S)$ | $G^2$-2 | Br | H | Br | H | — | $CH_2CH=CH_2(Z)$ |
| H | $G^2$-2 | Br | H | $CF_3$ | H | — | $CH_2CH=CH_2$ |
| H | $G^2$-2 | Br | H | $CF_3$ | H | — | $CH_2CH=CH_2(Z)$ |
| H | $G^2$-2 | Cl | H | Cl | H | — | $CH_2C(CH_3)=CH_2$ |
| H | $G^2$-2 | Cl | H | Cl | H | — | $CH_2C(CH_3)=CH_2(Z)$ |
| H | $G^2$-2 | Cl | H | $CF_3$ | H | — | $CH_2C(CH_3)=CH_2$ |
| H | $G^2$-2 | Cl | H | $CF_3$ | H | — | $CH_2C(CH_3)=CH_2(Z)$ |
| $CH_3$ | $G^2$-1 | Cl | H | F | H | H | $CH(CH_3)CH=CH_2$ |
| $CH_3$ | $G^2$-1 | Cl | H | F | H | H | $CH(CH_3)CH=CH_2(E)$ |
| $CH_3(S)$ | $G^2$-1 | Cl | H | F | H | H | $CH(CH_3)CH=CH_2$ |
| $CH_3(S)$ | $G^2$-1 | Cl | H | F | H | H | $CH(CH_3)CH=CH_2(E)$ |
| H | $G^2$-2 | F | H | Cl | H | — | $CH(CH_3)CH=CH_2$ |
| H | $G^2$-2 | F | H | Cl | H | — | $CH(CH_3)CH=CH_2(Z)$ |
| $CH_3$ | $G^2$-2 | F | H | Cl | H | — | $CH(CH_3)CH=CH_2(Z)$ |
| $CH_3(S)$ | $G^2$-2 | F | H | Cl | H | — | $CH(CH_3)CH=CH_2(Z)$ |
| H | $G^2$-2 | F | H | Br | H | — | $CH(CH_3)CH=CH_2$ |
| H | $G^2$-2 | F | H | Br | H | — | $CH(CH_3)CH=CH_2(Z)$ |
| $CH_3$ | $G^2$-2 | F | H | Br | H | — | $CH(CH_3)CH=CH_2(Z)$ |
| $CH_3(S)$ | $G^2$-2 | F | H | Br | H | — | $CH(CH_3)CH=CH_2(Z)$ |
| H | $G^2$-2 | F | H | $CF_3$ | H | — | $CH(CH_3)CH=CH_2$ |
| H | $G^2$-2 | F | H | $CF_3$ | H | — | $CH(CH_3)CH=CH_2(Z)$ |
| H | $G^2$-2 | Cl | H | F | H | — | $CH(CH_3)CH=CH_2$ |
| H | $G^2$-2 | Cl | H | F | H | — | $CH(CH_3)CH=CH_2(Z)$ |
| $CH_3$ | $G^2$-2 | Cl | H | F | H | — | $CH(CH_3)CH=CH_2(Z)$ |
| $CH_3(S)$ | $G^2$-2 | Cl | H | F | H | — | $CH(CH_3)CH=CH_2(Z)$ |
| H | $G^2$-2 | Cl | H | Cl | H | — | $CH(CH_3)CH=CH_2$ |
| H | $G^2$-2 | Cl | H | Cl | H | — | $CH(CH_3)CH=CH_2(Z)$ |
| $CH_3$ | $G^2$-2 | Cl | H | Cl | H | — | $CH(CH_3)CH=CH_2$ |
| $CH_3$ | $G^2$-2 | Cl | H | Cl | H | — | $CH(CH_3)CH=CH_2$ |
| $CH_3(S)$ | $G^2$-2 | Cl | H | Cl | H | — | $CH(CH_3)CH=CH_2$ |
| $CH_3(S)$ | $G^2$-2 | Cl | H | Cl | H | — | $CH(CH_3)CH=CH_2(Z)$ |
| H | $G^2$-2 | Cl | H | Cl | F | — | $CH(CH_3)CH=CH_2$ |
| H | $G^2$-2 | Cl | H | Cl | F | — | $CH(CH_3)CH=CH_2(Z)$ |
| $CH_3$ | $G^2$-2 | Cl | H | Cl | F | — | $CH(CH_3)CH=CH_2$ |
| $CH_3$ | $G^2$-2 | Cl | H | Cl | F | — | $CH(CH_3)CH=CH_2(Z)$ |
| $CH_3(S)$ | $G^2$-2 | Cl | H | Cl | F | — | $CH(CH_3)CH=CH_2$ |
| $CH_3(S)$ | $G^2$-2 | Cl | H | Cl | F | — | $CH(CH_3)CH=CH_2(Z)$ |
| H | $G^2$-2 | Cl | H | Cl | Cl | — | $CH(CH_3)CH=CH_2$ |
| H | $G^2$-2 | Cl | H | Cl | Cl | — | $CH(CH_3)CH=CH_2(Z)$ |
| H | $G^2$-2 | Cl | H | Br | H | — | $CH(CH_3)CH=CH_2$ |
| H | $G^2$-2 | Cl | H | Br | H | — | $CH(CH_3)CH=CH_2(Z)$ |
| $CH_3$ | $G^2$-2 | Cl | H | Br | H | — | $CH(CH_3)CH=CH_2$ |
| $CH_3$ | $G^2$-2 | Cl | H | Br | H | — | $CH(CH_3)CH=CH_2(Z)$ |
| $CH_3(S)$ | $G^2$-2 | Cl | H | Br | H | — | $CH(CH_3)CH=CH_2$ |
| $CH_3(S)$ | $G^2$-2 | Cl | H | Br | H | — | $CH(CH_3)CH=CH_2(Z)$ |
| H | $G^2$-2 | Cl | H | $CF_3$ | H | — | $CH(CH_3)CH=CH_2$ |
| H | $G^2$-2 | Cl | H | $CF_3$ | H | — | $CH(CH_3)CH=CH_2(E)$ |
| H | $G^2$-2 | Cl | H | $CF_3$ | H | — | $CH(CH_3)CH=CH_2(Z)$ |
| $CH_3$ | $G^2$-2 | Cl | H | $CF_3$ | H | — | $CH(CH_3)CH=CH_2$ |
| $CH_3$ | $G^2$-2 | Cl | H | $CF_3$ | H | — | $CH(CH_3)CH=CH_2$ |
| $CH_3(S)$ | $G^2$-2 | Cl | H | $CF_3$ | H | — | $CH(CH_3)CH=CH_2$ |
| $CH_3(S)$ | $G^2$-2 | Cl | H | $CF_3$ | H | — | $CH(CH_3)CH=CH_2(Z)$ |
| H | $G^2$-2 | Cl | H | $CH=NOCH_3$ | H | — | $CH(CH_3)CH=CH_2$ |
| H | $G^2$-2 | Cl | H | $CH=NOEt$ | H | — | $CH(CH_3)CH=CH_2$ |
| H | $G^2$-2 | Cl | H | $C(CH_3)=NOCH_3$ | H | — | $CH(CH_3)CH=CH_2$ |
| $CH_3$ | $G^2$-2 | Cl | H | $C(CH_3)=NOCH_3$ | H | — | $CH(CH_3)CH=CH_2$ |
| $CH_3(S)$ | $G^2$-2 | Cl | H | $C(CH_3)=NOCH_3$ | H | — | $CH(CH_3)CH=CH_2$ |
| H | $G^2$-2 | Cl | H | $C(CH_3)=NOEt$ | H | — | $CH(CH_3)CH=CH_2$ |
| H | $G^2$-2 | Cl | H | $C(Et)=NOCH_3$ | H | — | $CH(CH_3)CH=CH_2$ |
| H | $G^2$-2 | Cl | H | $C\equiv CH$ | H | — | $CH(CH_3)CH=CH_2$ |
| H | $G^2$-2 | Cl | H | $C\equiv CH$ | H | — | $CH(CH_3)CH=CH_2(Z)$ |
| H | $G^2$-2 | Cl | H | $C\equiv CPr$-c | H | — | $CH(CH_3)CH=CH_2$ |
| H | $G^2$-2 | Cl | H | $C\equiv CPr$-c | H | — | $CH(CH_3)CH=CH_2(Z)$ |
| H | $G^2$-2 | Cl | H | $C\equiv CBu$-t | H | — | $CH(CH_3)CH=CH_2$ |
| H | $G^2$-2 | Cl | H | $C\equiv CBu$-t | H | — | $CH(CH_3)CH=CH_2(Z)$ |
| H | $G^2$-2 | Cl | H | $C\equiv CC(CH_3)_2OCH_3$ | H | — | $CH(CH_3)CH=CH_2$ |
| H | $G^2$-2 | Cl | H | $C\equiv CC(CH_3)_2OCH_3$ | H | — | $CH(CH_3)CH=CH_2(Z)$ |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CSi(CH₃)₃ | H | — | CH(CH₃)CH=CH₂ |
| H | G²-2 | Cl | H | C≡CSi(CH₃)₃ | H | — | CH(CH₃)CH=CH₂(Z) |
| H | G²-2 | Cl | H | C≡CPh | H | — | CH(CH₃)CH=CH₂ |
| H | G²-2 | Cl | H | C≡CPh | H | — | CH(CH₃)CH=CH₂(Z) |
| H | G²-2 | Cl | F | Cl | H | — | CH(CH₃)CH=CH₂ |
| H | G²-2 | Cl | F | Cl | H | — | CH(CH₃)CH=CH₂(Z) |
| CH₃ | G²-2 | Cl | F | Cl | H | — | CH(CH₃)CH=CH₂(Z) |
| CH₃(S) | G²-2 | Cl | F | Cl | H | — | CH(CH₃)CH=CH₂(Z) |
| H | G²-2 | Cl | Cl | Cl | H | — | CH(CH₃)CH=CH₂ |
| H | G²-2 | Cl | Cl | Cl | H | — | CH(CH₃)CH=CH₂(Z) |
| CH₃ | G²-2 | Cl | Cl | Cl | H | — | CH(CH₃)CH=CH₂(Z) |
| CH₃(S) | G²-2 | Cl | Cl | Cl | H | — | CH(CH₃)CH=CH₂(Z) |
| H | G²-2 | Br | H | F | H | — | CH(CH₃)CH=CH₂ |
| H | G²-2 | Br | H | F | H | — | CH(CH₃)CH=CH₂(Z) |
| H | G²-2 | Br | H | Cl | H | — | CH(CH₃)CH=CH₂ |
| H | G²-2 | Br | H | Cl | H | — | CH(CH₃)CH=CH₂(Z) |
| CH₃ | G²-2 | Br | H | Cl | H | — | CH(CH₃)CH=CH₂(Z) |
| CH₃(S) | G²-2 | Br | H | Cl | H | — | CH(CH₃)CH=CH₂(Z) |
| H | G²-2 | Br | H | Br | H | — | CH(CH₃)CH=CH₂ |
| H | G²-2 | Br | H | Br | H | — | CH(CH₃)CH=CH₂(Z) |
| CH₃ | G²-2 | Br | H | Br | H | — | CH(CH₃)CH=CH₂ |
| CH₃ | G²-2 | Br | H | Br | H | — | CH(CH₃)CH=CH₂(Z) |
| CH₃(S) | G²-2 | Br | H | Br | H | — | CH(CH₃)CH=CH₂ |
| CH₃(S) | G²-2 | Br | H | Br | H | — | CH(CH₃)CH=CH₂(Z) |
| H | G²-2 | Br | H | CF₃ | H | — | CH(CH₃)CH=CH₂ |
| H | G²-2 | Br | H | CF₃ | H | — | CH(CH₃)CH=CH₂(Z) |
| H | G²-2 | Cl | H | CF₃ | H | — | CH₂CH=C(CH₃)₂ |
| H | G²-2 | Cl | H | Cl | H | — | CH₂CF=CH₂ |
| H | G²-2 | Cl | H | Cl | H | — | CH₂CF=CH₂(Z) |
| H | G²-2 | Cl | H | CF₃ | H | — | CH₂CF=CH₂ |
| H | G²-2 | Cl | H | CF₃ | H | — | CH₂CF=CH₂(Z) |
| H | G²-2 | Cl | H | Cl | H | — | CH₂CCl=CH₂ |
| H | G²-2 | Cl | H | Cl | H | — | CH₂CCl=CH₂(Z) |
| CH₃ | G²-2 | Cl | H | Cl | H | — | CH₂CCl=CH₂(Z) |
| CH₃(S) | G²-2 | Cl | H | Cl | H | — | CH₂CCl=CH₂(Z) |
| H | G²-2 | Cl | H | Cl | F | — | CH₂CCl=CH₂ |
| H | G²-2 | Cl | H | Cl | F | — | CH₂CCl=CH₂(Z) |
| H | G²-2 | Cl | H | Br | H | — | CH₂CCl=CH₂ |
| H | G²-2 | Cl | H | Br | H | — | CH₂CCl=CH₂(Z) |
| CH₃ | G²-2 | Cl | H | Br | H | — | CH₂CCl=CH₂(Z) |
| CH₃(S) | G²-2 | Cl | H | Br | H | — | CH₂CCl=CH₂(Z) |
| H | G²-2 | Cl | H | CF₃ | H | — | CH₂CCl=CH₂ |
| H | G²-2 | Cl | H | CF₃ | H | — | CH₂CCl=CH₂(Z) |
| CH₃ | G²-2 | Cl | H | CF₃ | H | — | CH₂CCl=CH₂(Z) |
| CH₃(S) | G²-2 | Cl | H | CF₃ | H | — | CH₂CCl=CH₂(Z) |
| H | G²-2 | Cl | H | C≡CPr-c | H | — | CH₂CCl=CH₂ |
| H | G²-2 | Cl | H | C≡CPr-c | H | — | CH₂CCl=CH₂(Z) |
| H | G²-2 | Cl | H | C≡CBu-t | H | — | CH₂CCl=CH₂ |
| H | G²-2 | Cl | H | C≡CBu-t | H | — | CH₂CCl=CH₂(Z) |
| H | G²-2 | Cl | H | C≡CC(CH₃)₂OCH₃ | H | — | CH₂CCl=CH₂ |
| H | G²-2 | Cl | H | C≡CC(CH₃)₂OCH₃ | H | — | CH₂CCl=CH₂(Z) |
| H | G²-2 | Cl | H | C≡CSi(CH₃)₃ | H | — | CH₂CCl=CH₂ |
| H | G²-2 | Cl | H | C≡CSi(CH₃)₃ | H | — | CH₂CCl=CH₂(Z) |
| H | G²-2 | Cl | H | C≡CPh | H | — | CH₂CCl=CH₂ |
| H | G²-2 | Cl | H | C≡CPh | H | — | CH₂CCl=CH₂(Z) |
| H | G²-2 | Cl | F | Cl | H | — | CH₂CCl=CH₂ |
| H | G²-2 | Cl | F | Cl | H | — | CH₂CCl=CH₂(Z) |
| H | G²-2 | Br | H | Cl | H | — | CH₂CCl=CH₂ |
| H | G²-2 | Br | H | Cl | H | — | CH₂CCl=CH₂(Z) |
| H | G²-2 | Br | H | Br | H | — | CH₂CCl=CH₂ |
| H | G²-2 | Br | H | Br | H | — | CH₂CCl=CH₂(Z) |
| H | G²-2 | Cl | H | Cl | H | — | CH₂CH=CF₂ |
| H | G²-2 | Cl | H | Cl | H | — | CH₂CH=CF₂(Z) |
| H | G²-2 | Cl | H | CF₃ | H | — | CH₂CH=CF₂ |
| H | G²-2 | Cl | H | CF₃ | H | — | CH₂CH=CF₂(Z) |
| H | G²-2 | Cl | H | Cl | H | — | CH₂CCl=CHCl |
| H | G²-2 | Cl | H | Cl | H | — | CH₂CCl=CHCl(Z) |
| H | G²-2 | Cl | H | CF₃ | H | — | CH₂CCl=CHCl |
| H | G²-2 | Cl | H | CF₃ | H | — | CH₂CCl=CHCl(Z) |
| H | G²-2 | Cl | H | Cl | H | — | CH₂CF=CF₂ |
| H | G²-2 | Cl | H | Cl | H | — | CH₂CF=CF₂(Z) |
| H | G²-2 | Cl | H | CF₃ | H | — | CH₂CF=CF₂ |
| H | G²-2 | Cl | H | CF₃ | H | — | CH₂CF=CF₂(Z) |
| H | G²-2 | Cl | H | Cl | H | — | CH₂CCl=CF₂ |
| H | G²-2 | Cl | H | CF₃ | H | — | CH₂CCl=CF₂ |
| H | G²-2 | Cl | H | Cl | H | — | CH₂CH₂CH=CF₂ |
| H | G²-2 | Cl | H | CF₃ | H | — | CH₂CH₂CH=CF₂ |
| H | G²-2 | Cl | H | Cl | H | — | CH₂CH₂CF=CF₂ |

TABLE 2-continued

| R² | G² | Y¹ | Y² | Y³ | Y⁴ | Y⁵ | R¹ |
|---|---|---|---|---|---|---|---|
| H | G²-2 | Cl | H | CF₃ | H | — | CH₂CH₂CF=CF₂ |
| H | G²-2 | Cl | H | Cl | H | — | CH₂CF=CHCF₃ |
| H | G²-2 | Cl | H | CF₃ | H | — | CH₂CF=CHCF₃ |
| H | G²-2 | Cl | H | Cl | H | — | CH₂C≡CH |
| H | G²-2 | Cl | H | Cl | H | — | CH₂C≡CH(Z) |
| CH₃ | G²-2 | Cl | H | Cl | H | — | CH₂C≡CH(Z) |
| CH₃(S) | G²-2 | Cl | H | Cl | H | — | CH₂C≡CH(Z) |
| H | G²-2 | Cl | H | Cl | F | — | CH₂C≡CH |
| H | G²-2 | Cl | H | Cl | F | — | CH₂C≡CH(Z) |
| H | G²-2 | Cl | H | Br | H | — | CH₂C≡CH |
| H | G²-2 | Cl | H | Br | H | — | CH₂C≡CH(Z) |
| CH₃ | G²-2 | Cl | H | Br | H | — | CH₂C≡CH(Z) |
| CH₃(S) | G²-2 | Cl | H | Br | H | — | CH₂C≡CH(Z) |
| H | G²-2 | Cl | H | CF₃ | H | — | CH₂C≡CH |
| H | G²-2 | Cl | H | CF₃ | H | — | CH₂C≡CH(Z) |
| CH₃ | G²-2 | Cl | H | CF₃ | H | — | CH₂C≡CH(Z) |
| CH₃(S) | G²-2 | Cl | H | CF₃ | H | — | CH₂C≡CH(Z) |
| H | G²-2 | Cl | F | Cl | H | — | CH₂C≡CH |
| H | G²-2 | Cl | F | Cl | H | — | CH₂C≡CH(Z) |
| H | G²-2 | Br | H | Cl | H | — | CH₂C≡CH |
| H | G²-2 | Br | H | Cl | H | — | CH₂C≡CH(Z) |
| H | G²-2 | Br | H | Br | H | — | CH₂C≡CH |
| H | G²-2 | Br | H | Br | H | — | CH₂C≡CH(Z) |
| H | G²-2 | Cl | H | Cl | H | — | CH₂C≡CCH₃ |
| H | G²-2 | Cl | H | CF₃ | H | — | CH₂C≡CCH₃ |
| H | G²-2 | Cl | H | Cl | H | — | CH₂C≡CCl |
| H | G²-2 | Cl | H | CF₃ | H | — | CH₂C≡CCl |
| H | G²-2 | Cl | H | Cl | H | — | CH₂C≡CBr |
| H | G²-2 | Cl | H | CF₃ | H | — | CH₂C≡CBr |
| H | G²-2 | Cl | H | Cl | H | — | CH₂C≡CI |
| H | G²-2 | Cl | H | CF₃ | H | — | CH₂C≡CI |
| H | G²-2 | Cl | H | Cl | H | — | CH₂Ph |
| H | G²-2 | Cl | H | Cl | H | — | CH₂Ph(Z) |
| H | G²-2 | Cl | H | CF₃ | H | — | CH₂Ph |
| H | G²-2 | Cl | H | CF₃ | H | — | CH₂Ph(Z) |
| H | G²-2 | Cl | H | Cl | H | — | CH₂(Ph-2-F) |
| H | G²-2 | Cl | H | Cl | H | — | CH₂(Ph-2-F)(Z) |
| H | G²-2 | Cl | H | CF₃ | H | — | CH₂(Ph-2-F) |
| H | G²-2 | Cl | H | CF₃ | H | — | CH₂(Ph-2-F)(Z) |
| H | G²-2 | Cl | H | Cl | H | — | CH₂(Ph-3-F) |
| H | G²-2 | Cl | H | Cl | H | — | CH₂(Ph-3-F)(Z) |
| CH₃ | G²-2 | Cl | H | Cl | H | — | CH₂(Ph-3-F)(Z) |
| CH₃(S) | G²-2 | Cl | H | Cl | H | — | CH₂(Ph-3-F)(Z) |
| H | G²-2 | Cl | H | Cl | F | — | CH₂(Ph-3-F) |
| H | G²-2 | Cl | H | Cl | F | — | CH₂(Ph-3-F)(Z) |
| H | G²-2 | Cl | H | Br | H | — | CH₂(Ph-3-F) |
| H | G²-2 | Cl | H | Br | H | — | CH₂(Ph-3-F)(Z) |
| CH₃ | G²-2 | Cl | H | Br | H | — | CH₂(Ph-3-F)(Z) |
| CH₃(S) | G²-2 | Cl | H | Br | H | — | CH₂(Ph-3-F)(Z) |
| H | G²-2 | Cl | H | CF₃ | H | — | CH₂(Ph-3-F) |
| H | G²-2 | Cl | H | CF₃ | H | — | CH₂(Ph-3-F)(Z) |
| CH₃ | G²-2 | Cl | H | CF₃ | H | — | CH₂(Ph-3-F)(Z) |
| CH₃(S) | G²-2 | Cl | H | CF₃ | H | — | CH₂(Ph-3-F)(Z) |
| H | G²-2 | Cl | H | C≡CPr-c | H | — | CH₂(Ph-3-F) |
| H | G²-2 | Cl | H | C≡CPr-c | H | — | CH₂(Ph-3-F)(Z) |
| H | G²-2 | Cl | H | C≡CBu-t | H | — | CH₂(Ph-3-F) |
| H | G²-2 | Cl | H | C≡CBu-t | H | — | CH₂(Ph-3-F)(Z) |
| H | G²-2 | Cl | H | C≡CC(CH₃)₂OCH₃ | H | — | CH₂(Ph-3-F) |
| H | G²-2 | Cl | H | C≡CC(CH₃)₂OCH₃ | H | — | CH₂(Ph-3-F)(Z) |
| H | G²-2 | Cl | H | C≡CSi(CH₃)₃ | H | — | CH₂(Ph-3-F) |
| H | G²-2 | Cl | H | C≡CSi(CH₃)₃ | H | — | CH₂(Ph-3-F)(Z) |
| H | G²-2 | Cl | H | C≡CPh | H | — | CH₂(Ph-3-F) |
| H | G²-2 | Cl | H | C≡CPh | H | — | CH₂(Ph-3-F)(Z) |
| H | G²-2 | Cl | F | Cl | H | — | CH₂(Ph-3-F) |
| H | G²-2 | Cl | F | Cl | H | — | CH₂(Ph-3-F)(Z) |
| H | G²-2 | Br | H | Cl | H | — | CH₂(Ph-3-F) |
| H | G²-2 | Br | H | Cl | H | — | CH₂(Ph-3-F)(Z) |
| H | G²-2 | Br | H | Br | H | — | CH₂(Ph-3-F) |
| H | G²-2 | Br | H | Br | H | — | CH₂(Ph-3-F)(Z) |
| H | G²-2 | Cl | H | Cl | H | — | CH₂(Ph-4-F) |
| H | G²-2 | Cl | H | Cl | H | — | CH₂(Ph-4-F)(Z) |
| CH₃ | G²-2 | Cl | H | Cl | H | — | CH₂(Ph-4-F)(Z) |
| CH₃(S) | G²-2 | Cl | H | Cl | H | — | CH₂(Ph-4-F)(Z) |
| H | G²-2 | Cl | H | Cl | F | — | CH₂(Ph-4-F) |
| H | G²-2 | Cl | H | Cl | F | — | CH₂(Ph-4-F)(Z) |
| H | G²-2 | Cl | H | Cl | Cl | — | CH₂(Ph-4-F) |
| H | G²-2 | Cl | H | Br | H | — | CH₂(Ph-4-F) |
| H | G²-2 | Cl | H | Br | H | — | CH₂(Ph-4-F)(Z) |

TABLE 2-continued

| R² | G² | Y¹ | Y² | Y³ | Y⁴ | Y⁵ | R¹ |
|---|---|---|---|---|---|---|---|
| CH₃ | G²-2 | Cl | H | Br | H | — | CH₂(Ph-4-F)(Z) |
| CH₃(S) | G²-2 | Cl | H | Br | H | — | CH₂(Ph-4-F)(Z) |
| H | G²-2 | Cl | H | CF₃ | H | — | CH₂(Ph-4-F) |
| H | G²-2 | Cl | H | CF₃ | H | — | CH₂(Ph-4-F)(Z) |
| CH₃ | G²-2 | Cl | H | CF₃ | H | — | CH₂(Ph-4-F)(Z) |
| CH₃(S) | G²-2 | Cl | H | CF₃ | H | — | CH₂(Ph-4-F)(Z) |
| H | G²-2 | Cl | H | C≡CPr-c | H | — | CH₂(Ph-4-F) |
| H | G²-2 | Cl | H | C≡CPr-c | H | — | CH₂(Ph-4-F)(Z) |
| H | G²-2 | Cl | H | C≡CBu-t | H | — | CH₂(Ph-4-F) |
| H | G²-2 | Cl | H | C≡CBu-t | H | — | CH₂(Ph-4-F)(Z) |
| H | G²-2 | Cl | H | C≡CC(CH₃)₂OCH₃ | H | — | CH₂(Ph-4-F) |
| H | G²-2 | Cl | H | C≡CC(CH₃)₂OCH₃ | H | — | CH₂(Ph-4-F)(Z) |
| H | G²-2 | Cl | H | C≡CSi(CH₃)₃ | H | — | CH₂(Ph-4-F) |
| H | G²-2 | Cl | H | C≡CSi(CH₃)₃ | H | — | CH₂(Ph-4-F)(Z) |
| H | G²-2 | Cl | H | C≡CPh | H | — | CH₂(Ph-4-F) |
| H | G²-2 | Cl | H | C≡CPh | H | — | CH₂(Ph-4-F)(Z) |
| H | G²-2 | Cl | F | Cl | H | — | CH₂(Ph-4-F) |
| H | G²-2 | Cl | F | Cl | H | — | CH₂(Ph-4-F)(Z) |
| H | G²-2 | Br | H | Cl | H | — | CH₂(Ph-4-F) |
| H | G²-2 | Br | H | Cl | H | — | CH₂(Ph-4-F)(Z) |
| H | G²-2 | Br | H | Br | H | — | CH₂(Ph-4-F) |
| H | G²-2 | Br | H | Br | H | — | CH₂(Ph-4-F)(Z) |
| H | G²-2 | Cl | — | H | Cl | H | CH₂(Ph-4-F) |
| H | G²-2 | Cl | H | Cl | H | — | CH₂(Ph-2-Cl) |
| H | G²-2 | Cl | H | CF₃ | H | — | CH₂(Ph-2-Cl) |
| H | G²-2 | Cl | H | Cl | H | — | CH₂(Ph-3-Cl) |
| H | G²-2 | Cl | H | CF₃ | H | — | CH₂(Ph-3-Cl) |
| CH₃ | G²-1 | H | H | F | H | H | CH₂(Ph-4-Cl) |
| CH₃ | G²-1 | Cl | H | Cl | H | H | CH₂(Ph-4-Cl) |
| CH₃ | G²-1 | CH₃ | H | OPr-i | H | H | CH₂(Ph-4-Cl) |
| H | G²-2 | Cl | H | Cl | H | — | CH₂(Ph-4-Cl) |
| H | G²-2 | Cl | H | Cl | H | — | CH₂(Ph-4-Cl)(Z) |
| CH₃ | G²-2 | Cl | H | Cl | H | — | CH₂(Ph-4-Cl)(Z) |
| CH₃(S) | G²-2 | Cl | H | Cl | H | — | CH₂(Ph-4-Cl)(Z) |
| H | G²-2 | Cl | H | Cl | F | — | CH₂(Ph-4-Cl) |
| H | G²-2 | Cl | H | Cl | F | — | CH₂(Ph-4-Cl)(Z) |
| H | G²-2 | Cl | H | Br | H | — | CH₂(Ph-4-Cl) |
| H | G²-2 | Cl | H | Br | H | — | CH₂(Ph-4-Cl)(Z) |
| CH₃ | G²-2 | Cl | H | Br | H | — | CH₂(Ph-4-Cl)(Z) |
| CH₃(S) | G²-2 | Cl | H | Br | H | — | CH₂(Ph-4-Cl)(Z) |
| H | G²-2 | Cl | H | CF₃ | H | — | CH₂(Ph-4-Cl) |
| H | G²-2 | Cl | H | CF₃ | H | — | CH₂(Ph-4-Cl)(Z) |
| CH₃ | G²-2 | Cl | H | CF₃ | H | — | CH₂(Ph-4-Cl)(Z) |
| CH₃(S) | G²-2 | Cl | H | CF₃ | H | — | CH₂(Ph-4-Cl)(Z) |
| H | G²-2 | Cl | H | C≡CPr-c | H | — | CH₂(Ph-4-Cl) |
| H | G²-2 | Cl | H | C≡CPr-c | H | — | CH₂(Ph-4-Cl)(Z) |
| H | G²-2 | Cl | H | C≡CBu-t | H | — | CH₂(Ph-4-Cl) |
| H | G²-2 | Cl | H | C≡CBu-t | H | — | CH₂(Ph-4-Cl)(Z) |
| H | G²-2 | Cl | H | C≡CC(CH₃)₂OCH₃ | H | — | CH₂(Ph-4-Cl) |
| H | G²-2 | Cl | H | C≡CC(CH₃)₂OCH₃ | H | — | CH₂(Ph-4-Cl)(Z) |
| H | G²-2 | Cl | H | C≡CSi(CH₃)₃ | H | — | CH₂(Ph-4-Cl) |
| H | G²-2 | Cl | H | C≡CSi(CH₃)₃ | H | — | CH₂(Ph-4-Cl)(Z) |
| H | G²-2 | Cl | H | C≡CPh | H | — | CH₂(Ph-4-Cl) |
| H | G²-2 | Cl | H | C≡CPh | H | — | CH₂(Ph-4-Cl)(Z) |
| H | G²-2 | Cl | F | Cl | H | — | CH₂(Ph-4-Cl) |
| H | G²-2 | Cl | F | Cl | H | — | CH₂(Ph-4-Cl)(Z) |
| H | G²-2 | Br | H | Cl | H | — | CH₂(Ph-4-Cl) |
| H | G²-2 | Br | H | Cl | H | — | CH₂(Ph-4-Cl)(Z) |
| H | G²-2 | Br | H | Br | H | — | CH₂(Ph-4-Cl) |
| H | G²-2 | Br | H | Br | H | — | CH₂(Ph-4-Cl)(Z) |
| H | G²-2 | Cl | H | CF₃ | H | — | CH₂(Ph-2-CH₃) |
| H | G²-2 | Cl | H | Cl | H | — | CH₂(Ph-3-CH₃) |
| H | G²-2 | Cl | H | Cl | H | — | CH₂(Ph-3-CH₃)(Z) |
| H | G²-2 | Cl | H | CF₃ | H | — | CH₂(Ph-3-CH₃) |
| H | G²-2 | Cl | H | CF₃ | H | — | CH₂(Ph-3-CH₃)(Z) |
| H | G²-2 | Cl | H | CF₃ | H | — | CH₂(Ph-4-CH₃) |
| H | G²-2 | Cl | H | CF₃ | H | — | CH₂(Ph-4-Bu-t) |
| H | G²-2 | Cl | H | CF₃ | H | — | CH₂(Ph-2-CF₃) |
| H | G²-2 | Cl | H | Cl | H | — | CH₂(Ph-3-CF₃) |
| H | G²-2 | Cl | H | Cl | H | — | CH₂(Ph-3-CF₃)(Z) |
| H | G²-2 | Cl | H | CF₃ | H | — | CH₂(Ph-3-CF₃) |
| H | G²-2 | Cl | H | CF₃ | H | — | CH₂(Ph-3-CF₃)(Z) |
| H | G²-2 | Cl | H | Cl | H | — | CH₂(Ph-4-CF₃) |
| H | G²-2 | Cl | H | Cl | H | — | CH₂(Ph-4-CF₃)(Z) |
| H | G²-2 | Cl | H | CF₃ | H | — | CH₂(Ph-4-CF₃) |
| H | G²-2 | Cl | H | CF₃ | H | — | CH₂(Ph-4-CF₃)(Z) |
| H | G²-2 | Cl | H | CF₃ | H | — | CH₂(Ph-3-OCH₃) |
| H | G²-2 | Cl | H | Cl | H | — | CH₂(Ph-4-OCH₃) |

TABLE 2-continued

| R² | G² | Y¹ | Y² | Y³ | Y⁴ | Y⁵ | R¹ |
|---|---|---|---|---|---|---|---|
| H | G²-2 | Cl | H | CF₃ | H | — | CH₂(Ph-4-OCH₃) |
| H | G²-2 | Cl | H | CF₃ | H | — | CH₂(Ph-4-OCHF₂) |
| H | G²-2 | Cl | H | Cl | H | — | CH₂(Ph-2-OCF₃) |
| H | G²-2 | Cl | H | Cl | H | — | CH₂(Ph-2-OCF₃)(Z) |
| H | G²-2 | Cl | H | CF₃ | H | — | CH₂(Ph-2-OCF₃) |
| H | G²-2 | Cl | H | CF₃ | H | — | CH₂(Ph-2-OCF₃)(Z) |
| H | G²-2 | Cl | H | CF₃ | H | — | CH₂(Ph-3-OCF₃) |
| H | G²-2 | Cl | H | CF₃ | H | — | CH₂(Ph-4-OCF₃) |
| H | G²-2 | Cl | H | CF₃ | H | — | CH₂(Ph-4-SCH₃) |
| H | G²-2 | Cl | H | CF₃ | H | — | CH₂[Ph-4-S(O)CH₃] |
| H | G²-2 | Cl | H | CF₃ | H | — | CH₂(Ph-4-SO₂CH₃) |
| H | G²-2 | Cl | H | Cl | H | — | CH₂(Ph-4-SCF₃) |
| H | G²-2 | Cl | H | CF₃ | H | — | CH₂[Ph-4-S(O)CF₃] |
| H | G²-2 | Cl | H | CF₃ | H | — | CH₂(Ph-4-SO₂CF₃) |
| H | G²-2 | Cl | H | Cl | H | — | CH₂(Ph-4-NO₂) |
| H | G²-2 | Cl | H | Cl | H | — | CH₂(Ph-4-NO₂)(Z) |
| H | G²-2 | Cl | H | CF₃ | H | — | CH₂(Ph-4-NO₂) |
| H | G²-2 | Cl | H | CF₃ | H | — | CH₂(Ph-4-NO₂)(Z) |
| H | G²-2 | Cl | H | Cl | H | — | CH₂(Ph-2-CN) |
| H | G²-2 | Cl | H | CF₃ | H | — | CH₂(Ph-2-CN) |
| H | G²-2 | Cl | H | CF₃ | H | — | CH₂(Ph-3-CN) |
| CH₃ | G²-1 | Cl | H | Cl | H | H | CH₂(Ph-4-CN) |
| H | G²-2 | Cl | H | Cl | H | — | CH₂(Ph-4-CN) |
| H | G²-2 | Cl | H | Cl | H | — | CH₂(Ph-4-CN)(Z) |
| CH₃ | G²-2 | Cl | H | Cl | H | — | CH₂(Ph-4-CN)(Z) |
| CH₃(S) | G²-2 | Cl | H | Cl | H | — | CH₂(Ph-4-CN)(Z) |
| H | G²-2 | Cl | H | Cl | F | — | CH₂(Ph-4-CN) |
| H | G²-2 | Cl | H | Cl | F | — | CH₂(Ph-4-CN)(Z) |
| H | G²-2 | Cl | H | Br | H | — | CH₂(Ph-4-CN) |
| H | G²-2 | Cl | H | Br | H | — | CH₂(Ph-4-CN)(Z) |
| CH₃ | G²-2 | Cl | H | Br | H | — | CH₂(Ph-4-CN)(Z) |
| CH₃(S) | G²-2 | Cl | H | Br | H | — | CH₂(Ph-4-CN)(Z) |
| H | G²-2 | Cl | H | CF₃ | H | — | CH₂(Ph-4-CN) |
| H | G²-2 | Cl | H | CF₃ | H | — | CH₂(Ph-4-CN)(Z) |
| CH₃ | G²-2 | Cl | H | CF₃ | H | — | CH₂(Ph-4-CN)(Z) |
| CH₃(S) | G²-2 | Cl | H | CF₃ | H | — | CH₂(Ph-4-CN)(Z) |
| H | G²-2 | Cl | H | C≡CPr-c | H | — | CH₂(Ph-4-CN) |
| H | G²-2 | Cl | H | C≡CPr-c | H | — | CH₂(Ph-4-CN)(Z) |
| H | G²-2 | Cl | H | C≡CBu-t | H | — | CH₂(Ph-4-CN) |
| H | G²-2 | Cl | H | C≡CBu-t | H | — | CH₂(Ph-4-CN)(Z) |
| H | G²-2 | Cl | H | C≡CC(CH₃)₂OCH₃ | H | — | CH₂(Ph-4-CN) |
| H | G²-2 | Cl | H | C≡CC(CH₃)₂OCH₃ | H | — | CH₂(Ph-4-CN)(Z) |
| H | G²-2 | Cl | H | C≡CSi(CH₃)₃ | H | — | CH₂(Ph-4-CN) |
| H | G²-2 | Cl | H | C≡CSi(CH₃)₃ | H | — | CH₂(Ph-4-CN)(Z) |
| H | G²-2 | Cl | H | C≡CPh | H | — | CH₂(Ph-4-CN) |
| H | G²-2 | Cl | H | C≡CPh | H | — | CH₂(Ph-4-CN)(Z) |
| H | G²-2 | Cl | F | Cl | H | — | CH₂(Ph-4-CN) |
| H | G²-2 | Cl | F | Cl | H | — | CH₂(Ph-4-CN)(Z) |
| H | G²-2 | Br | H | Cl | H | — | CH₂(Ph-4-CN) |
| H | G²-2 | Br | H | Cl | H | — | CH₂(Ph-4-CN)(Z) |
| H | G²-2 | Br | H | Br | H | — | CH₂(Ph-4-CN) |
| H | G²-2 | Br | H | Br | H | — | CH₂(Ph-4-CN)(Z) |
| H | G²-2 | Cl | H | CF₃ | H | — | CH₂(Ph-4-Ph) |
| H | G²-2 | Cl | H | CF₃ | H | — | CH₂(Ph-2,4-F₂) |
| H | G²-2 | Cl | H | CF₃ | H | — | CH₂(Ph-2,6-F₂) |
| H | G²-2 | Cl | H | Cl | H | — | CH₂(Ph-3,4-F₂) |
| H | G²-2 | Cl | H | Cl | H | — | CH₂(Ph-3,4-F₂)(Z) |
| CH₃ | G²-2 | Cl | H | Cl | H | — | CH₂(Ph-3,4-F₂)(Z) |
| CH₃(S) | G²-2 | Cl | H | Cl | H | — | CH₂(Ph-3,4-F₂)(Z) |
| H | G²-2 | Cl | H | Cl | F | — | CH₂(Ph-3,4-F₂) |
| H | G²-2 | Cl | H | Cl | F | — | CH₂(Ph-3,4-F₂)(Z) |
| H | G²-2 | Cl | H | Br | H | — | CH₂(Ph-3,4-F₂) |
| H | G²-2 | Cl | H | Br | H | — | CH₂(Ph-3,4-F₂)(Z) |
| CH₃ | G²-2 | Cl | H | Br | H | — | CH₂(Ph-3,4-F₂)(Z) |
| CH₃(S) | G²-2 | Cl | H | Br | H | — | CH₂(Ph-3,4-F₂)(Z) |
| H | G²-2 | Cl | H | CF₃ | H | — | CH₂(Ph-3,4-F₂) |
| H | G²-2 | Cl | H | CF₃ | H | — | CH₂(Ph-3,4-F₂)(Z) |
| CH₃ | G²-2 | Cl | H | CF₃ | H | — | CH₂(Ph-3,4-F₂)(Z) |
| CH₃(S) | G²-2 | Cl | H | CF₃ | H | — | CH₂(Ph-3,4-F₂)(Z) |
| H | G²-2 | Cl | H | C≡CPr-c | H | — | CH₂(Ph-3,4-F₂) |
| H | G²-2 | Cl | H | C≡CPr-c | H | — | CH₂(Ph-3,4-F₂)(Z) |
| H | G²-2 | Cl | H | C≡CBu-t | H | — | CH₂(Ph-3,4-F₂) |
| H | G²-2 | Cl | H | C≡CBu-t | H | — | CH₂(Ph-3,4-F₂)(Z) |
| H | G²-2 | Cl | H | C≡CC(CH₃)₂OCH₃ | H | — | CH₂(Ph-3,4-F₂) |
| H | G²-2 | Cl | H | C≡CC(CH₃)₂OCH₃ | H | — | CH₂(Ph-3,4-F₂)(Z) |
| H | G²-2 | Cl | H | C≡CSi(CH₃)₃ | H | — | CH₂(Ph-3,4-F₂) |
| H | G²-2 | Cl | H | C≡CSi(CH₃)₃ | H | — | CH₂(Ph-3,4-F₂)(Z) |
| H | G²-2 | Cl | H | C≡CPh | H | — | CH₂(Ph-3,4-F₂) |

TABLE 2-continued

| R² | G² | Y¹ | Y² | Y³ | Y⁴ | Y⁵ | R¹ |
|---|---|---|---|---|---|---|---|
| H | G²-2 | Cl | H | C≡CPh | H | — | CH₂(Ph-3,4-F₂)(Z) |
| H | G²-2 | Cl | F | Cl | H | — | CH₂(Ph-3,4-F₂) |
| H | G²-2 | Cl | F | Cl | H | — | CH₂(Ph-3,4-F₂)(Z) |
| H | G²-2 | Br | H | Cl | H | — | CH₂(Ph-3,4-F₂) |
| H | G²-2 | Br | H | Cl | H | — | CH₂(Ph-3,4-F₂)(Z) |
| H | G²-2 | Br | H | Br | H | — | CH₂(Ph-3,4-F₂) |
| H | G²-2 | Br | H | Br | H | — | CH₂(Ph-3,4-F₂)(Z) |
| H | G²-2 | Cl | H | CF₃ | H | — | CH₂(Ph-3,5-F₂) |
| H | G²-2 | Cl | H | Cl | H | — | CH₂(Ph-3-F-4-Cl) |
| H | G²-2 | Cl | H | CF₃ | H | — | CH₂(Ph-3,4-Cl₂) |
| H | G²-2 | Cl | H | Cl | H | — | CH₂(Ph-3-F-4-CF₃) |
| H | G²-2 | Cl | H | Cl | H | — | CH₂(Ph-3-F-4-NO₂) |
| H | G²-2 | Cl | H | Cl | H | — | CH₂(Ph-3-F-4-CN) |
| H | G²-2 | Cl | H | Cl | H | — | CH₂(Ph-2,3,4-F₃) |
| H | G²-2 | Cl | H | Cl | H | — | CH₂(Ph-2,4,5-F₃) |
| H | G²-2 | Cl | H | Cl | H | — | CH₂(Ph-3,4,5-F₃) |
| H | G²-2 | Cl | H | Cl | H | — | CH₂(Ph-3,4,5-F₃)(Z) |
| H | G²-2 | Cl | H | CF₃ | H | — | CH₂(Ph-3,4,5-F₃) |
| H | G²-2 | Cl | H | CF₃ | H | — | CH₂(Ph-3,4,5-F₃)(Z) |
| H | G²-2 | Cl | H | Cl | H | — | CH₂(2-Naph) |
| H | G²-2 | Cl | H | Cl | H | — | CH₂(2-Naph)(Z) |
| H | G²-2 | Cl | H | CF₃ | H | — | CH₂(2-Naph) |
| H | G²-2 | Cl | H | CF₃ | H | — | CH₂(2-Naph)(Z) |
| H | G²-2 | Cl | H | CF₃ | H | — | CH₂(D-1-1b)-4-F |
| H | G²-2 | Cl | H | Cl | H | — | CH₂(D-1-1b)-4-Br |
| H | G²-2 | Cl | H | CF₃ | H | — | CH₂(D-1-1b)-5-F |
| H | G²-2 | Cl | H | CF₃ | H | — | CH₂(D-1-1b)-5-Cl |
| H | G²-2 | Cl | H | Cl | H | — | CH₂(D-1-1b)-5-Br |
| CH₃ | G²-2 | Cl | H | Cl | H | H | CH₂(D-1-1b)-5-CF₃ |
| H | G²-2 | Cl | H | Cl | H | — | CH₂(D-1-1b)-5-CF₃ |
| H | G²-2 | Cl | H | CF₃ | H | — | CH₂(D-1-2b)-5-Cl |
| H | G²-2 | Cl | H | Cl | H | — | CH₂(D-1-2b)-5-Br |
| H | G²-2 | Cl | H | CF₃ | H | — | CH₂(D-2-1b)-4-F |
| H | G²-2 | Cl | H | Cl | H | — | CH₂(D-2-1b)-4-Cl |
| H | G²-2 | Cl | H | CF₃ | H | — | CH₂(D-2-1b)-5-F |
| H | G²-2 | Cl | H | Cl | H | — | CH₂(D-2-1b)-5-Cl |
| H | G²-2 | Cl | H | CF₃ | H | — | CH₂(D-2-2b)-5-F |
| H | G²-2 | Cl | H | Cl | H | — | CH₂(D-2-2b)-5-Cl |
| H | G²-2 | Cl | H | Cl | H | — | CH₂(D-4-1b)-5-Cl |
| H | G²-2 | Cl | H | CF₃ | H | — | CH₂(D-5-3b)-3-Cl |
| H | G²-2 | Cl | H | Cl | H | — | CH₂(D-5-3b)-3-Br |
| H | G²-2 | Cl | H | CF₃ | H | — | CH₂(D-5-3b)-3-CH₃ |
| H | G²-2 | Cl | H | Cl | H | — | CH₂(D-6-1b)-5-Br |
| H | G²-2 | Cl | H | CF₃ | H | — | CH₂(D-8-1b)-5-Cl |
| H | G²-2 | Cl | H | CF₃ | H | — | CH₂(D-8-3b)-3-Cl |
| H | G²-2 | Cl | H | CF₃ | H | — | CH₂(D-9-2b)-2-Cl |
| H | G²-2 | Cl | H | Cl | H | — | CH₂(D-10-1a) |
| H | G²-2 | Cl | H | Cl | H | — | CH₂(D-10-1b)-4-Br |
| H | G²-2 | Cl | H | CF₃ | H | — | CH₂(D-10-1b)-5-F |
| H | G²-2 | Cl | H | CF₃ | H | — | CH₂(D-10-1b)-5-Cl |
| H | G²-2 | Cl | H | Cl | H | — | CH₂(D-10-1b)-5-Br |
| H | G²-2 | Cl | H | Cl | H | — | CH₂(D-10-2a) |
| H | G²-2 | Cl | H | CF₃ | H | — | CH₂(D-10-2b)-2-F |
| H | G²-2 | Cl | H | Cl | H | — | CH₂(D-10-2b)-2-Cl |
| H | G²-2 | Cl | H | Cl | H | — | CH₂(D-10-2b)-2-Br |
| H | G²-2 | Cl | H | Cl | H | — | CH₂(D-10-3b)-2-Cl |
| H | G²-2 | Cl | H | Cl | H | — | CH₂(D-10-3b)-2-Br |
| H | G²-2 | Cl | H | Cl | H | — | CH₂(D-12-1b)-4-Cl |
| H | G²-2 | Cl | H | CF₃ | H | — | CH₂(D-12-1b)-5-Cl |
| H | G²-2 | Cl | H | CF₃ | H | — | CH₂(D-12-2b)-2-Cl |
| H | G²-2 | Cl | H | Cl | H | — | CH₂(D-14-1b)Br |
| H | G²-2 | Cl | H | CF₃ | H | — | CH₂(D-14-2b)Cl |
| H | G²-2 | Cl | H | Cl | H | — | CH₂(D-14-2b)Br |
| H | G²-2 | Cl | H | CF₃ | H | — | CH₂(D-15-1b)Cl |
| H | G²-2 | Cl | H | CF₃ | H | — | CH₂(D-17-b)Cl |
| H | G²-2 | Cl | H | Cl | H | — | CH₂(D-17-b)Br |
| H | G²-2 | Cl | H | CF₃ | H | — | CH₂(D-32-1a) |
| H | G²-2 | Cl | H | CF₃ | H | — | CH₂(D-32-1b)-5-F |
| H | G²-2 | Cl | H | Cl | H | — | CH₂(D-32-1b)-5-Cl |
| H | G²-2 | Cl | H | Cl | H | — | CH₂(D-32-1b)-5-Br |
| H | G²-2 | Cl | H | CF₃ | H | — | CH₂(D-32-2a) |
| CH₃ | G²-1 | H | H | CF₃ | H | H | CH₂(D-32-2b)-6-Cl |
| CH₃ | G²-1 | H | H | OPh | H | H | CH₂(D-32-2b)-6-Cl |
| CH₃ | G²-1 | H | F | F | F | H | CH₂(D-32-2b)-6-Cl |
| CH₃ | G²-1 | H | H | Ph | H | H | CH₂(D-32-2b)-6-Cl |
| CH₃ | G²-1 | H | —CH=CHCH=CH— | | | H | CH₂(D-32-2b)-6-Cl |
| CH₃ | G²-1 | Cl | H | Cl | H | H | CH₂(D-32-2b)-6-Cl |
| CH₃ | G²-1 | Cl | H | Br | H | H | CH₂(D-32-2b)-6-Cl |

TABLE 2-continued

| R² | G² | Y¹ | Y² | Y³ | Y⁴ | Y⁵ | R¹ |
|---|---|---|---|---|---|---|---|
| H | G²-2 | Cl | H | Cl | H | — | CH₂(D-32-2b)-6-Cl |
| H | G²-2 | Cl | H | CF₃ | H | — | CH₂(D-32-2b)-6-Cl |
| H | G²-2 | Cl | H | CF₃ | H | — | CH₂(D-32-3a) |
| CH₃ | G²-1 | Cl | H | Cl | H | H | CH₂(D-32-3b)-2-Cl |
| H | G²-2 | Cl | H | Cl | H | — | CH₂(D-32-3b)-2-Cl |
| H | G²-2 | Cl | H | Cl | H | — | CH₂(D-32-3b)-2-Cl(Z) |
| H | G²-2 | Cl | H | CF₃ | H | — | CH₂(D-32-3b)-2-Cl |
| H | G²-2 | Cl | H | CF₃ | H | — | CH₂(D-32-3b)-2-Cl(Z) |
| H | G²-2 | Cl | H | Cl | H | — | CH₂(D-32-3b)-2,6-Cl₂ |
| H | G²-2 | Cl | H | CF₃ | H | — | CH₂(D-33-1b)-6-Cl |
| H | G²-2 | Cl | H | Cl | H | — | CH₂(D-33-1b)-6-Br |
| H | G²-2 | Cl | H | CF₃ | H | — | CH₂(D-34-1b)-5-Cl |
| H | G²-2 | Cl | H | Cl | H | — | CH₂(D-34-1b)-5-Br |
| H | G²-2 | Cl | H | CF₃ | H | — | CH₂(D-34-2b)-2-Cl |
| H | G²-2 | Cl | H | CF₃ | H | — | CH₂(D-34-2b)-6-Cl |
| H | G²-2 | Cl | H | CF₃ | H | — | CH₂(D-34-3b)-6-Cl |
| H | G²-2 | Cl | H | CF₃ | H | — | CH₂(D-35-b)-5-F |
| H | G²-2 | Cl | H | CF₃ | H | — | CH₂(D-35-b)-5-Cl |
| H | G²-2 | Cl | H | Cl | H | — | CH₂(D-35-b)-5-Br |
| CH₃ | G²-1 | H | Cl | Cl | H | H | CH(CH₃)Ph |
| CH₃ | G²-1 | Cl | H | H | Cl | H | CH(CH₃)Ph |
| H | G²-2 | F | H | Cl | H | — | CH(CH₃)Ph |
| H | G²-2 | F | H | Cl | H | — | CH(CH₃)Ph(Z) |
| H | G²-2 | Cl | H | F | H | — | CH(CH₃)Ph |
| H | G²-2 | Cl | H | F | H | — | CH(CH₃)Ph(Z) |
| H | G²-2 | Cl | H | Cl | H | — | CH(CH₃)Ph |
| H | G²-2 | Cl | H | Cl | H | — | CH(CH₃)Ph(Z) |
| CH₃ | G²-2 | Cl | H | Cl | H | — | CH(CH₃)Ph(Z) |
| CH₃ | G²-2 | Cl | H | Cl | H | — | CH(CH₃)Ph |
| CH₃(S) | G²-2 | Cl | H | Cl | H | — | CH(CH₃)Ph |
| CH₃(S) | G²-2 | Cl | H | Cl | H | — | CH(CH₃)Ph(Z) |
| H | G²-2 | Cl | H | Cl | F | — | CH(CH₃)Ph |
| H | G²-2 | Cl | H | Cl | F | — | CH(CH₃)Ph(Z) |
| CH₃ | G²-2 | Cl | H | Cl | F | — | CH(CH₃)Ph(Z) |
| CH₃(S) | G²-2 | Cl | H | Cl | F | — | CH(CH₃)Ph(Z) |
| H | G²-2 | Cl | H | Br | H | — | CH(CH₃)Ph |
| H | G²-2 | Cl | H | Br | H | — | CH(CH₃)Ph(Z) |
| CH₃ | G²-2 | Cl | H | Br | H | — | CH(CH₃)Ph(Z) |
| CH₃(S) | G²-2 | Cl | H | Br | H | — | CH(CH₃)Ph(Z) |
| H | G²-2 | Cl | H | CF₃ | H | — | CH(CH₃)Ph |
| H | G²-2 | Cl | H | CF₃ | H | — | CH(CH₃)Ph(Z) |
| CH₃ | G²-2 | Cl | H | CF₃ | H | — | CH(CH₃)Ph(Z) |
| CH₃(S) | G²-2 | Cl | H | CF₃ | H | — | CH(CH₃)Ph(Z) |
| H | G²-2 | Cl | H | CN | H | — | CH(CH₃)Ph |
| H | G²-2 | Cl | H | C≡CH | H | — | CH(CH₃)Ph |
| H | G²-2 | Cl | H | C≡CH | H | — | CH(CH₃)Ph(Z) |
| H | G²-2 | Cl | H | C≡CPr-c | H | — | CH(CH₃)Ph |
| H | G²-2 | Cl | H | C≡CPr-c | H | — | CH(CH₃)Ph(Z) |
| H | G²-2 | Cl | H | C≡CBu-t | H | — | CH(CH₃)Ph |
| H | G²-2 | Cl | H | C≡CBu-t | H | — | CH(CH₃)Ph(Z) |
| H | G²-2 | Cl | H | C≡CC(CH₃)₂OCH₃ | H | — | CH(CH₃)Ph |
| H | G²-2 | Cl | H | C≡CC(CH₃)₂OCH₃ | H | — | CH(CH₃)Ph(Z) |
| H | G²-2 | Cl | H | C≡CSi(CH₃)₃ | H | — | CH(CH₃)Ph |
| H | G²-2 | Cl | H | C≡CSi(CH₃)₃ | H | — | CH(CH₃)Ph(Z) |
| H | G²-2 | Cl | H | C≡CPh | H | — | CH(CH₃)Ph |
| H | G²-2 | Cl | H | C≡CPh | H | — | CH(CH₃)Ph(Z) |
| H | G²-2 | Cl | F | Cl | H | — | CH(CH₃)Ph |
| H | G²-2 | Cl | F | Cl | H | — | CH(CH₃)Ph(Z) |
| H | G²-2 | Cl | Cl | Cl | H | — | CH(CH₃)Ph |
| H | G²-2 | Cl | Cl | Cl | H | — | CH(CH₃)Ph(Z) |
| H | G²-2 | Br | H | Cl | H | — | CH(CH₃)Ph |
| H | G²-2 | Br | H | Cl | H | — | CH(CH₃)Ph(Z) |
| H | G²-2 | Br | H | Br | H | — | CH(CH₃)Ph |
| H | G²-2 | Br | H | Br | H | — | CH(CH₃)Ph(Z) |
| CH₃ | G²-2 | Br | H | Br | H | — | CH(CH₃)Ph(Z) |
| CH₃(S) | G²-2 | Br | H | Br | H | — | CH(CH₃)Ph(Z) |
| CH₃ | G²-10 | Cl | — | H | H | — | CH(CH₃)Ph |
| H | G²-2 | Cl | H | Cl | H | — | CH(CH₃)(Ph-2-F) |
| H | G²-2 | Cl | H | Cl | H | — | CH(CH₃)(Ph-2-F)(Z) |
| H | G²-2 | Cl | H | CF₃ | H | — | CH(CH₃)(Ph-2-F) |
| H | G²-2 | Cl | H | CF₃ | H | — | CH(CH₃)(Ph-2-F)(Z) |
| H | G²-2 | Cl | H | Cl | H | — | CH(CH₃)(Ph-3-F) |
| H | G²-2 | Cl | H | Cl | H | — | CH(CH₃)(Ph-3-F)(Z) |
| CH₃ | G²-2 | Cl | H | Cl | H | — | CH(CH₃)(Ph-3-F)(Z) |
| CH₃(S) | G²-2 | Cl | H | Cl | H | — | CH(CH₃)(Ph-3-F)(Z) |
| H | G²-2 | Cl | H | Cl | F | — | CH(CH₃)(Ph-3-F) |
| H | G²-2 | Cl | H | Cl | F | — | CH(CH₃)(Ph-3-F)(Z) |
| H | G²-2 | Cl | H | Cl | Cl | — | CH(CH₃)(Ph-3-F) |

TABLE 2-continued

| R² | G² | Y¹ | Y² | Y³ | Y⁴ | Y⁵ | R¹ |
|---|---|---|---|---|---|---|---|
| H | G²-2 | Cl | H | Br | H | — | CH(CH₃)(Ph-3-F) |
| H | G²-2 | Cl | H | Br | H | — | CH(CH₃)(Ph-3-F)(Z) |
| CH₃ | G²-2 | Cl | H | Br | H | — | CH(CH₃)(Ph-3-F)(Z) |
| CH₃(S) | G²-2 | Cl | H | Br | H | — | CH(CH₃)(Ph-3-F)(Z) |
| H | G²-2 | Cl | H | CF₃ | H | — | CH(CH₃)(Ph-3-F) |
| H | G²-2 | Cl | H | CF₃ | H | — | CH(CH₃)(Ph-3-F)(Z) |
| CH₃ | G²-2 | Cl | H | CF₃ | H | — | CH(CH₃)(Ph-3-F)(Z) |
| CH₃(S) | G²-2 | Cl | H | CF₃ | H | — | CH(CH₃)(Ph-3-F)(Z) |
| H | G²-2 | Cl | H | C≡CPr-c | H | — | CH(CH₃)(Ph-3-F) |
| H | G²-2 | Cl | H | C≡CPr-c | H | — | CH(CH₃)(Ph-3-F)(Z) |
| H | G²-2 | Cl | H | C≡CBu-t | H | — | CH(CH₃)(Ph-3-F) |
| H | G²-2 | Cl | H | C≡CBu-t | H | — | CH(CH₃)(Ph-3-F)(Z) |
| H | G²-2 | Cl | H | C≡CC(CH₃)₂OCH₃ | H | — | CH(CH₃)(Ph-3-F) |
| H | G²-2 | Cl | H | C≡CC(CH₃)₂OCH₃ | H | — | CH(CH₃)(Ph-3-F)(Z) |
| H | G²-2 | Cl | H | C≡CSi(CH₃)₃ | H | — | CH(CH₃)(Ph-3-F) |
| H | G²-2 | Cl | H | C≡CSi(CH₃)₃ | H | — | CH(CH₃)(Ph-3-F)(Z) |
| H | G²-2 | Cl | H | C≡CPh | H | — | CH(CH₃)(Ph-3-F) |
| H | G²-2 | Cl | H | C≡CPh | H | — | CH(CH₃)(Ph-3-F)(Z) |
| H | G²-2 | Cl | F | Cl | H | — | CH(CH₃)(Ph-3-F) |
| H | G²-2 | Cl | F | Cl | H | — | CH(CH₃)(Ph-3-F)(Z) |
| H | G²-2 | Br | H | Cl | H | — | CH(CH₃)(Ph-3-F) |
| H | G²-2 | Br | H | Cl | H | — | CH(CH₃)(Ph-3-F)(Z) |
| H | G²-2 | Br | H | Br | H | — | CH(CH₃)(Ph-3-F) |
| H | G²-2 | Br | H | Br | H | — | CH(CH₃)(Ph-3-F)(Z) |
| H | G²-2 | F | H | Cl | H | — | CH(CH₃)(Ph-4-F) |
| H | G²-2 | F | H | Cl | H | — | CH(CH₃)(Ph-4-F)(Z) |
| H | G²-2 | Cl | H | F | H | — | CH(CH₃)(Ph-4-F) |
| H | G²-2 | Cl | H | F | H | — | CH(CH₃)(Ph-4-F)(Z) |
| H | G²-2 | Cl | H | Cl | H | — | CH(CH₃)(Ph-4-F) |
| H | G²-2 | Cl | H | Cl | H | — | CH(CH₃)(Ph-4-F)(E) |
| H | G²-2 | Cl | H | Cl | H | — | CH(CH₃)(Ph-4-F)(Z) |
| CH₃ | G²-2 | Cl | H | Cl | H | — | CH(CH₃)(Ph-4-F)(Z) |
| CH₃(S) | G²-2 | Cl | H | Cl | H | — | CH(CH₃)(Ph-4-F)(Z) |
| H | G²-2 | Cl | H | Cl | F | — | CH(CH₃)(Ph-4-F) |
| H | G²-2 | Cl | H | Cl | F | — | CH(CH₃)(Ph-4-F)(Z) |
| CH₃ | G²-2 | Cl | H | Cl | F | — | CH(CH₃)(Ph-4-F)(Z) |
| CH₃(S) | G²-2 | Cl | H | Cl | F | — | CH(CH₃)(Ph-4-F)(Z) |
| H | G²-2 | Cl | H | Br | H | — | CH(CH₃)(Ph-4-F) |
| H | G²-2 | Cl | H | Br | H | — | CH(CH₃)(Ph-4-F)(Z) |
| CH₃ | G²-2 | Cl | H | Br | H | — | CH(CH₃)(Ph-4-F)(Z) |
| CH₃(S) | G²-2 | Cl | H | Br | H | — | CH(CH₃)(Ph-4-F)(Z) |
| H | G²-2 | Cl | H | CF₃ | H | — | CH(CH₃)(Ph-4-F) |
| H | G²-2 | Cl | H | CF₃ | H | — | CH(CH₃)(Ph-4-F)(Z) |
| CH₃ | G²-2 | Cl | H | CF₃ | H | — | CH(CH₃)(Ph-4-F)(Z) |
| CH₃(S) | G²-2 | Cl | H | CF₃ | H | — | CH(CH₃)(Ph-4-F)(Z) |
| H | G²-2 | Cl | H | C≡CH | H | — | CH(CH₃)(Ph-4-F) |
| H | G²-2 | Cl | H | C≡CH | H | — | CH(CH₃)(Ph-4-F)(Z) |
| H | G²-2 | Cl | H | C≡CPr-c | H | — | CH(CH₃)(Ph-4-F) |
| H | G²-2 | Cl | H | C≡CPr-c | H | — | CH(CH₃)(Ph-4-F)(Z) |
| H | G²-2 | Cl | H | C≡CBu-t | H | — | CH(CH₃)(Ph-4-F) |
| H | G²-2 | Cl | H | C≡CBu-t | H | — | CH(CH₃)(Ph-4-F)(Z) |
| H | G²-2 | Cl | H | C≡CC(CH₃)₂OCH₃ | H | — | CH(CH₃)(Ph-4-F) |
| H | G²-2 | Cl | H | C≡CC(CH₃)₂OCH₃ | H | — | CH(CH₃)(Ph-4-F)(Z) |
| H | G²-2 | Cl | H | C≡CSi(CH₃)₃ | H | — | CH(CH₃)(Ph-4-F) |
| H | G²-2 | Cl | H | C≡CSi(CH₃)₃ | H | — | CH(CH₃)(Ph-4-F)(Z) |
| H | G²-2 | Cl | H | C≡CPh | H | — | CH(CH₃)(Ph-4-F) |
| H | G²-2 | Cl | H | C≡CPh | H | — | CH(CH₃)(Ph-4-F)(Z) |
| H | G²-2 | Cl | F | Cl | H | — | CH(CH₃)(Ph-4-F) |
| H | G²-2 | Cl | F | Cl | H | — | CH(CH₃)(Ph-4-F)(Z) |
| H | G²-2 | Cl | Cl | Cl | H | — | CH(CH₃)(Ph-4-F) |
| H | G²-2 | Cl | Cl | Cl | H | — | CH(CH₃)(Ph-4-F)(Z) |
| H | G²-2 | Br | H | Cl | H | — | CH(CH₃)(Ph-4-F) |
| H | G²-2 | Br | H | Cl | H | — | CH(CH₃)(Ph-4-F)(Z) |
| H | G²-2 | Br | H | Br | H | — | CH(CH₃)(Ph-4-F) |
| H | G²-2 | Br | H | Br | H | — | CH(CH₃)(Ph-4-F)(Z) |
| CH₃ | G²-2 | Br | H | Br | H | — | CH(CH₃)(Ph-4-F)(Z) |
| CH₃(S) | G²-2 | Br | H | Br | H | — | CH(CH₃)(Ph-4-F)(Z) |
| H | G²-2 | Cl | H | Cl | H | — | CH(CH₃)(D-1-1b)-4-Br |
| H | G²-2 | Cl | H | CF₃ | H | — | CH(CH₃)(D-1-1b)-5-Br |
| H | G²-2 | Cl | H | Cl | H | — | CH(CH₃)(D-2-1b)-4-Br |
| H | G²-2 | Cl | H | Cl | H | — | CH(CH₃)(D-2-1b)-5-Cl |
| H | G²-2 | Cl | H | Cl | H | — | CH(CH₃)(D-2-1b)-5-Br |
| H | G²-2 | Cl | H | CF₃ | H | — | CH(CH₃)(D-5-3b)-3-Cl |
| H | G²-2 | Cl | H | Cl | H | — | CH(CH₃)(D-5-3b)-3-Br |
| H | G²-2 | Cl | H | Cl | H | — | CH(CH₃)(D-10-1b)-4-Br |
| H | G²-2 | Cl | H | Cl | H | — | CH(CH₃)(D-10-1b)-5-Br |
| H | G²-2 | Cl | H | CF₃ | H | — | CH(CH₃)(D-10-2b)-2-Cl |
| H | G²-2 | Cl | H | Cl | H | — | CH(CH₃)(D-10-2b)-2-Br |

TABLE 2-continued

| $R^2$ | $G^2$ | $Y^1$ | $Y^2$ | $Y^3$ | $Y^4$ | $Y^5$ | $R^1$ |
|---|---|---|---|---|---|---|---|
| H | $G^2$-2 | Cl | H | $CF_3$ | H | — | $CH(CH_3)$(D-10-3b)-2-Cl |
| H | $G^2$-2 | Cl | H | Cl | H | — | $CH(CH_3)$(D-10-3b)-2-Br |
| H | $G^2$-2 | Cl | H | $CF_3$ | H | — | $CH(CH_3)$(D-32-1b)-5-F |
| H | $G^2$-2 | Cl | H | Cl | H | — | $CH(CH_3)$(D-32-1b)-5-Cl |
| H | $G^2$-2 | Cl | H | Cl | H | — | $CH(CH_3)$(D-32-1b)-5-Br |
| H | $G^2$-2 | Cl | H | $CF_3$ | H | — | $CH(CH_3)$(D-32-2b)-6-F |
| H | $G^2$-2 | Cl | H | Cl | H | — | $CH(CH_3)$(D-32-2b)-6-Cl |
| H | $G^2$-2 | Cl | H | Cl | H | — | $CH(CH_3)$(D-32-2b)-6-Br |
| H | $G^2$-2 | Cl | H | $CF_3$ | H | — | $CH(CH_3)$(D-32-3b)-2-F |
| H | $G^2$-2 | Cl | H | Cl | H | — | $CH(CH_3)$(D-32-3b)-2-Cl |
| H | $G^2$-2 | Cl | H | Cl | H | — | $CH(CH_3)$(D-32-3b)-2-Br |
| H | $G^2$-2 | Cl | H | $CF_3$ | H | — | $CH(CH_3)$(D-34-1b)-5-F |
| H | $G^2$-2 | Cl | H | Cl | H | — | $CH(CH_3)$(D-34-2b)-2-Cl |
| H | $G^2$-2 | Cl | H | Cl | H | — | $CH(CH_3)$(D-34-2b)-6-Cl |
| H | $G^2$-2 | Cl | H | Cl | H | — | $CH(CH_3)$(D-35-b)-5-Cl |
| H | $G^2$-2 | Cl | H | Cl | H | — | $C(CH_3)_2Ph$ |
| H | $G^2$-2 | Cl | H | Cl | H | — | $CH_2CH_2Ph$ |
| H | $G^2$-2 | Cl | H | $CF_3$ | H | — | $CH_2CH_2Ph$ |
| H | $G^2$-2 | Cl | H | Cl | H | — | Ph |

Compounds of Second Group ([I]-69 to [I]-92)

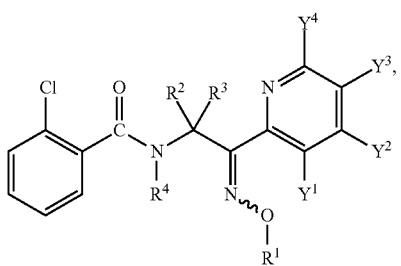

[I]-69

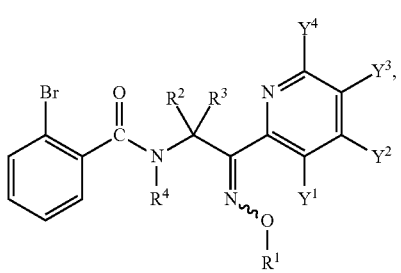

[I]-70

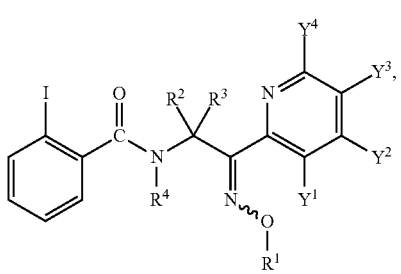

[I]-71

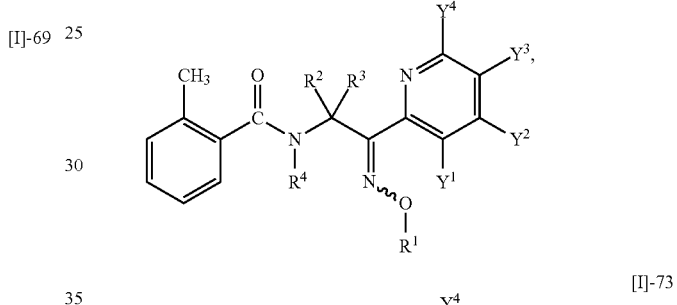

[I]-72

[I]-73

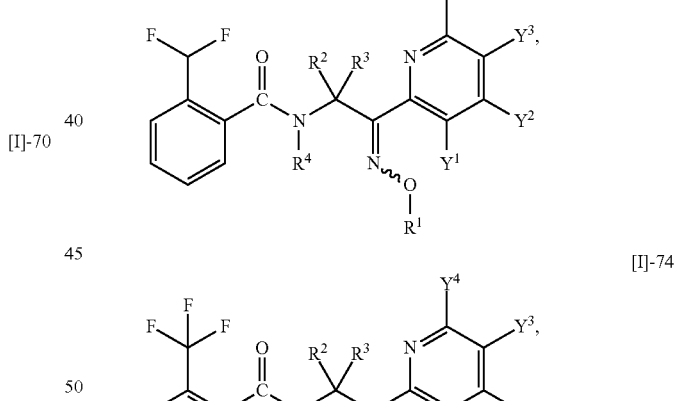

[I]-74

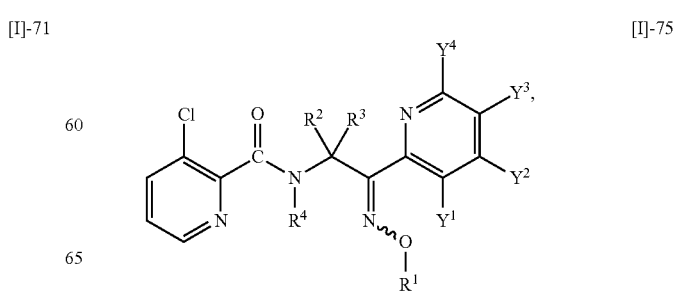

[I]-75

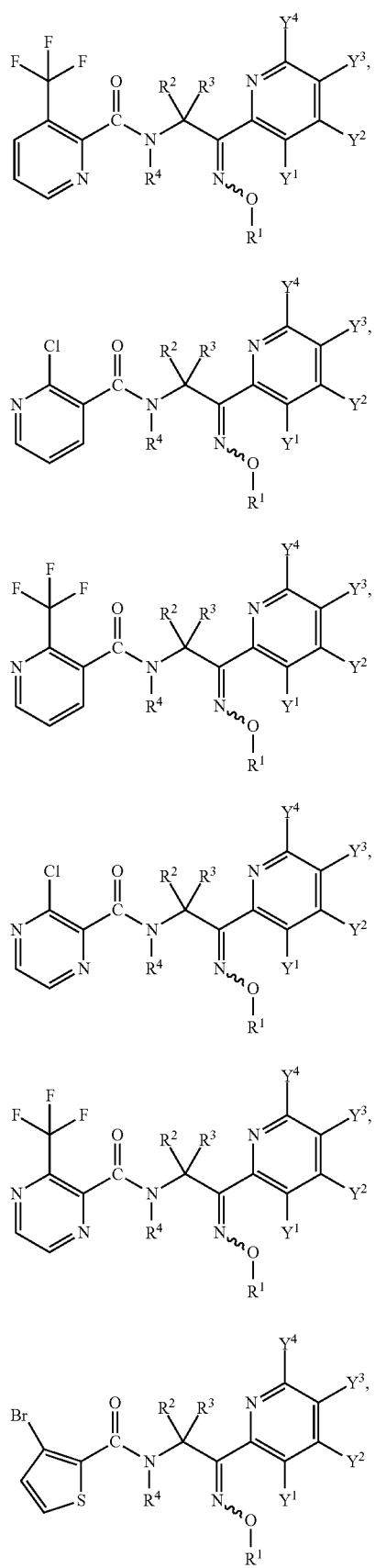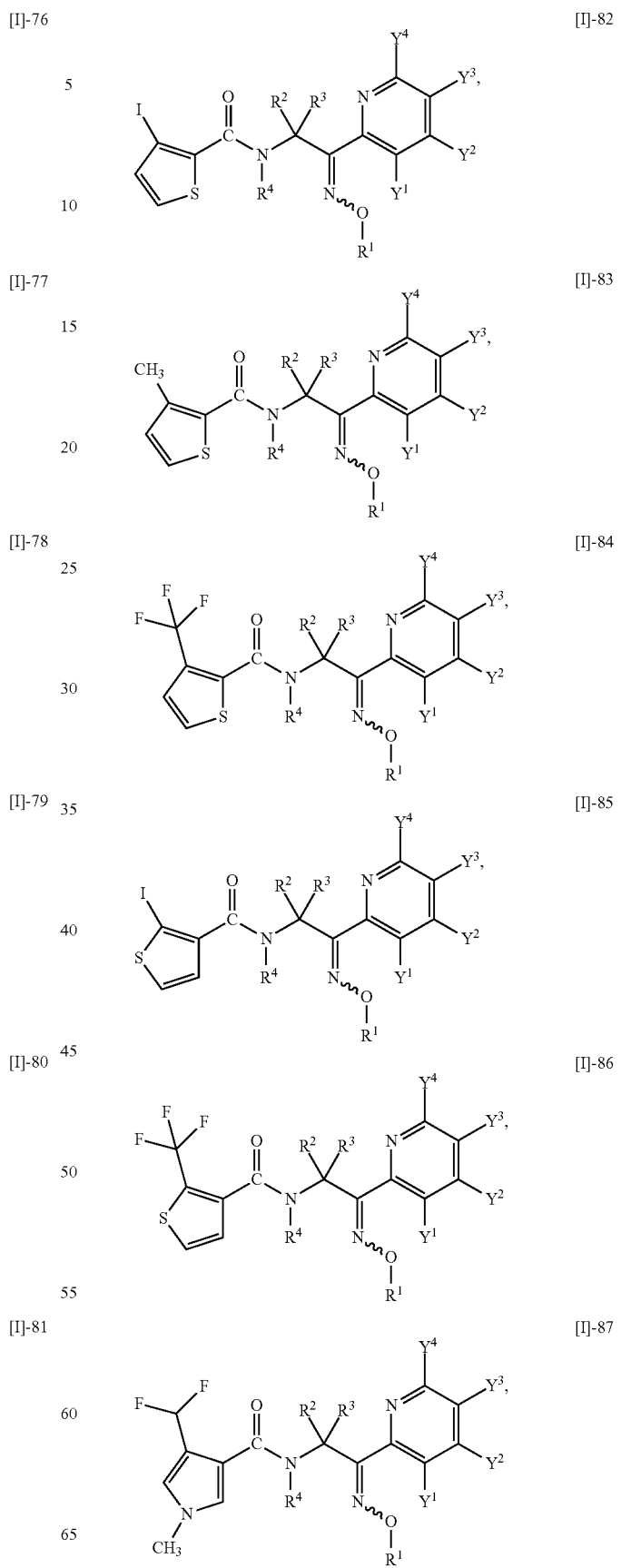

-continued

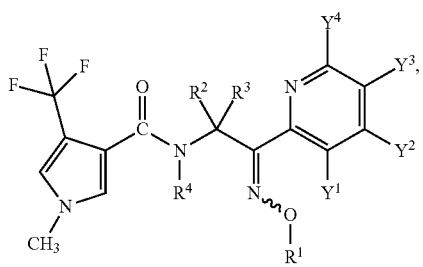
[I]-88

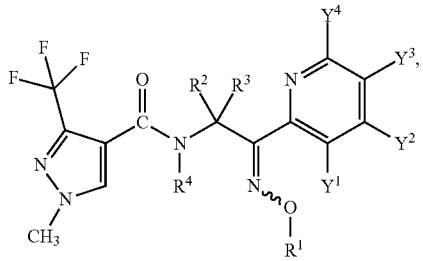
[I]-89

[I]-90

-continued

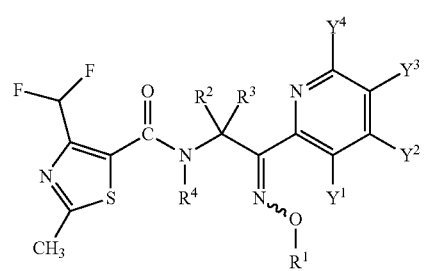
[I]-91

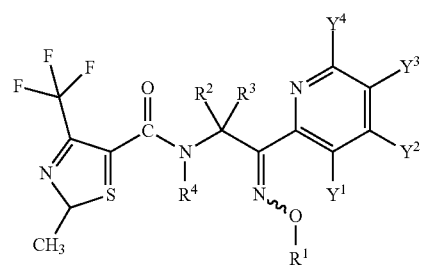
[I]-92 or

Combinations of substituents in the compounds of a second group are shown in Table 3.

TABLE 3

| $R^4$ | $R^2$ | $R^3$ | $Y^1$ | $Y^2$ | $Y^3$ | $Y^4$ | $R^1$ |
|---|---|---|---|---|---|---|---|
| $CH_3$ | H | H | Cl | H | Cl | H | $CH_3$ |
| Et | H | H | Cl | H | Cl | H | $CH_3$ |
| i-Pr | H | H | Cl | H | Cl | H | $CH_3$ |
| c-Pr | H | H | Cl | H | Cl | H | $CH_3$ |
| c-Bu | H | H | Cl | H | Cl | H | $CH_3$ |
| $CH_2CHF_2$ | H | H | Cl | H | Cl | H | $CH_3$ |
| $CH_2OCH_3$ | H | H | Cl | H | Cl | H | $CH_3$ |
| $CH_2OEt$ | H | H | Cl | H | Cl | H | $CH_3$ |
| $CH_2OC(O)CH_3$ | H | H | Cl | H | Cl | H | $CH_3$ |
| $CH_2OC(O)OCH_3$ | H | H | Cl | H | Cl | H | $CH_3$ |
| $CH_2SCH_3$ | H | H | Cl | H | Cl | H | $CH_3$ |
| $CH_2CN$ | H | H | Cl | H | Cl | H | $CH_3$ |
| $CH_2C(O)OCH_3$ | H | H | Cl | H | Cl | H | $CH_3$ |
| $CH_2C(O)NH_2$ | H | H | Cl | H | Cl | H | $CH_3$ |
| $CH_2C(S)NH_2$ | H | H | Cl | H | Cl | H | $CH_3$ |
| $CH_2CH=CH_2$ | H | H | Cl | H | Cl | H | $CH_3$ |
| $CH_2C\equiv CH$ | H | H | Cl | H | Cl | H | $CH_3$ |
| $C(O)CH_3$ | H | H | Cl | H | Cl | H | $CH_3$ |
| $C(O)Et$ | H | H | Cl | H | Cl | H | $CH_3$ |
| $C(O)Pr-n$ | H | H | Cl | H | Cl | H | $CH_3$ |
| $C(O)Pr-i$ | H | H | Cl | H | Cl | H | $CH_3$ |
| $C(O)Pr-c$ | H | H | Cl | H | Cl | H | $CH_3$ |
| $C(O)Bu-t$ | H | H | Cl | H | Cl | H | $CH_3$ |
| $C(O)CH_2OCH_3$ | H | H | Cl | H | Cl | H | $CH_3$ |
| $C(O)CH=CH_2$ | H | H | Cl | H | Cl | H | $CH_3$ |
| $C(O)OCH_3$ | H | H | Cl | H | Cl | H | $CH_3$ |
| $C(O)OEt$ | H | H | Cl | H | Cl | H | $CH_3$ |
| $C(O)OPr-i$ | H | H | Cl | H | Cl | H | $CH_3$ |
| $C(O)OCH_2CH_2OCH_3$ | H | H | Cl | H | Cl | H | $CH_3$ |
| $C(O)OCH_2CH=CH_2$ | H | H | Cl | H | Cl | H | $CH_3$ |
| $OCH_3$ | H | H | Cl | H | Cl | H | $CH_3$ |
| OEt | H | H | Cl | H | Cl | H | $CH_3$ |
| $SCCl_3$ | H | H | Cl | H | Cl | H | $CH_3$ |
| Et | H | H | Cl | H | Br | H | $CH_3$ |
| $CH_2OCH_3$ | H | H | Cl | H | Br | H | $CH_3$ |

TABLE 3-continued

| R⁴ | R² | R³ | Y¹ | Y² | Y³ | Y⁴ | R¹ |
|---|---|---|---|---|---|---|---|
| CH₂CN | H | H | Cl | H | Br | H | CH₃ |
| CH₂CH=CH₂ | H | H | Cl | H | Br | H | CH₃ |
| CH₂C≡CH | H | H | Cl | H | Br | H | CH₃ |
| C(O)CH₃ | H | H | Cl | H | Br | H | CH₃ |
| C(O)OCH₃ | H | H | Cl | H | Br | H | CH₃ |
| CH₃ | H | H | Cl | H | CF₃ | H | CH₃ |
| Et | H | H | Cl | H | CF₃ | H | CH₃ |
| i-Pr | H | H | Cl | H | CF₃ | H | CH₃ |
| c-Pr | H | H | Cl | H | CF₃ | H | CH₃ |
| c-Bu | H | H | Cl | H | CF₃ | H | CH₃ |
| CH₂CHF₂ | H | H | Cl | H | CF₃ | H | CH₃ |
| CH₂OCH₃ | H | H | Cl | H | CF₃ | H | CH₃ |
| CH₂OEt | H | H | Cl | H | CF₃ | H | CH₃ |
| CH₂OC(O)CH₃ | H | H | Cl | H | CF₃ | H | CH₃ |
| CH₂OC(O)OCH₃ | H | H | Cl | H | CF₃ | H | CH₃ |
| CH₂SCH₃ | H | H | Cl | H | CF₃ | H | CH₃ |
| CH₂CN | H | H | Cl | H | CF₃ | H | CH₃ |
| CH₂C(O)OCH₃ | H | H | Cl | H | CF₃ | H | CH₃ |
| CH₂C(O)NH₂ | H | H | Cl | H | CF₃ | H | CH₃ |
| CH₂C(S)NH₂ | H | H | Cl | H | CF₃ | H | CH₃ |
| CH₂CH=CH₂ | H | H | Cl | H | CF₃ | H | CH₃ |
| CH₂C≡CH | H | H | Cl | H | CF₃ | H | CH₃ |
| C(O)CH₃ | H | H | Cl | H | CF₃ | H | CH₃ |
| C(O)Et | H | H | Cl | H | CF₃ | H | CH₃ |
| C(O)Pr-n | H | H | Cl | H | CF₃ | H | CH₃ |
| C(O)Pr-i | H | H | Cl | H | CF₃ | H | CH₃ |
| C(O)Pr-c | H | H | Cl | H | CF₃ | H | CH₃ |
| C(O)Bu-t | H | H | Cl | H | CF₃ | H | CH₃ |
| C(O)CH₂OCH₃ | H | H | Cl | H | CF₃ | H | CH₃ |
| C(O)CH=CH₂ | H | H | Cl | H | CF₃ | H | CH₃ |
| C(O)OCH₃ | H | H | Cl | H | CF₃ | H | CH₃ |
| C(O)OEt | H | H | Cl | H | CF₃ | H | CH₃ |
| C(O)OPr-i | H | H | Cl | H | CF₃ | H | CH₃ |
| C(O)OCH₂CH₂OCH₃ | H | H | Cl | H | CF₃ | H | CH₃ |
| C(O)OCH₂CH=CH₂ | H | H | Cl | H | CF₃ | H | CH₃ |
| OCH₃ | H | H | Cl | H | CF₃ | H | CH₃ |
| OEt | H | H | Cl | H | CF₃ | H | CH₃ |
| SCCl₃ | H | H | Cl | H | CF₃ | H | CH₃ |
| Et | H | H | Cl | H | C≡CBu-t | H | CH₃ |
| CH₂OCH₃ | H | H | Cl | H | C≡CBu-t | H | CH₃ |
| CH₂CN | H | H | Cl | H | C≡CBu-t | H | CH₃ |
| CH₂CH=CH₂ | H | H | Cl | H | C≡CBu-t | H | CH₃ |
| CH₂C≡CH | H | H | Cl | H | C≡CBu-t | H | CH₃ |
| C(O)CH₃ | H | H | Cl | H | C≡CBu-t | H | CH₃ |
| C(O)OCH₃ | H | H | Cl | H | C≡CBu-t | H | CH₃ |
| Et | H | H | Cl | H | C≡CSi(CH₃)₃ | H | CH₃ |
| CH₂OCH₃ | H | H | Cl | H | C≡CSi(CH₃)₃ | H | CH₃ |
| CH₂CN | H | H | Cl | H | C≡CSi(CH₃)₃ | H | CH₃ |
| CH₂CH=CH₂ | H | H | Cl | H | C≡CSi(CH₃)₃ | H | CH₃ |
| CH₂C≡CH | H | H | Cl | H | C≡CSi(CH₃)₃ | H | CH₃ |
| C(O)CH₃ | H | H | Cl | H | C≡CSi(CH₃)₃ | H | CH₃ |
| C(O)OCH₃ | H | H | Cl | H | C≡CSi(CH₃)₃ | H | CH₃ |
| Et | H | H | Cl | H | C≡CPh | H | CH₃ |
| CH₂OCH₃ | H | H | Cl | H | C≡CPh | H | CH₃ |
| CH₂CN | H | H | Cl | H | C≡CPh | H | CH₃ |
| CH₂CH=CH₂ | H | H | Cl | H | C≡CPh | H | CH₃ |
| CH₂C≡CH | H | H | Cl | H | C≡CPh | H | CH₃ |
| C(O)CH₃ | H | H | Cl | H | C≡CPh | H | CH₃ |
| C(O)OCH₃ | H | H | Cl | H | C≡CPh | H | CH₃ |
| Et | H | H | Br | H | Br | H | CH₃ |
| CH₂OCH₃ | H | H | Br | H | Br | H | CH₃ |
| CH₂CN | H | H | Br | H | Br | H | CH₃ |
| CH₂CH=CH₂ | H | H | Br | H | Br | H | CH₃ |
| CH₂C≡CH | H | H | Br | H | Br | H | CH₃ |
| C(O)CH₃ | H | H | Br | H | Br | H | CH₃ |
| C(O)OCH₃ | H | H | Br | H | Br | H | CH₃ |
| Et | CH₃ | H | Cl | H | Cl | H | CH₃ |
| CH₂OCH₃ | CH₃ | H | Cl | H | Cl | H | CH₃ |
| CH₂CN | CH₃ | H | Cl | H | Cl | H | CH₃ |
| CH₂CH=CH₂ | CH₃ | H | Cl | H | Cl | H | CH₃ |
| CH₂C≡CH | CH₃ | H | Cl | H | Cl | H | CH₃ |
| C(O)CH₃ | CH₃ | H | Cl | H | Cl | H | CH₃ |
| C(O)OCH₃ | CH₃ | H | Cl | H | Cl | H | CH₃ |
| Et | CH₃ | H | Cl | H | CF₃ | H | CH₃ |
| CH₂OCH₃ | CH₃ | H | Cl | H | CF₃ | H | CH₃ |
| CH₂CN | CH₃ | H | Cl | H | CF₃ | H | CH₃ |
| CH₂CH=CH₂ | CH₃ | H | Cl | H | CF₃ | H | CH₃ |
| CH₂C≡CH | CH₃ | H | Cl | H | CF₃ | H | CH₃ |

TABLE 3-continued

| R⁴ | R² | R³ | Y¹ | Y² | Y³ | Y⁴ | R¹ |
|---|---|---|---|---|---|---|---|
| C(O)CH₃ | CH₃ | H | Cl | H | CF₃ | H | CH₃ |
| C(O)OCH₃ | CH₃ | H | Cl | H | CF₃ | H | CH₃ |
| H | CH₃ | CH₃ | Cl | H | Cl | H | CH₃ |
| H | CH₃ | CH₃ | Cl | H | Cl | H | CH₃(Z) |
| H | CH₃ | CH₃ | Cl | H | Br | H | CH₃ |
| H | CH₃ | CH₃ | Cl | H | Br | H | CH₃(Z) |
| H | CH₃ | CH₃ | Cl | H | CF₃ | H | CH₃ |
| H | CH₃ | CH₃ | Cl | H | CF₃ | H | CH₃(Z) |
| H | CH₃ | CH₃ | Cl | H | C≡CBu-t | H | CH₃ |
| H | CH₃ | CH₃ | Cl | H | C≡CBu-t | H | CH₃(Z) |
| H | CH₃ | CH₃ | Cl | H | C≡CSi(CH₃)₃ | H | CH₃ |
| H | CH₃ | CH₃ | Cl | H | C≡CSi(CH₃)₃ | H | CH₃(Z) |
| H | CH₃ | CH₃ | Cl | H | C≡CPh | H | CH₃ |
| H | CH₃ | CH₃ | Cl | H | C≡CPh | H | CH₃(Z) |
| H | CH₃ | CH₃ | Br | H | Br | H | CH₃ |
| H | CH₃ | CH₃ | Br | H | Br | H | CH₃(Z) |
| H | | —CH₂CH₂— | Cl | H | Cl | H | CH₃ |
| H | | —CH₂CH₂— | Cl | H | Cl | H | CH₃(Z) |
| H | | —CH₂CH₂— | Cl | H | Cl | F | CH₃ |
| H | | —CH₂CH₂— | Cl | H | Cl | F | CH₃(Z) |
| H | | —CH₂CH₂— | Cl | H | Br | H | CH₃ |
| H | | —CH₂CH₂— | Cl | H | Br | H | CH₃(Z) |
| H | | —CH₂CH₂— | Cl | H | CF₃ | H | CH₃ |
| H | | —CH₂CH₂— | Cl | H | CF₃ | H | CH₃(Z) |
| H | | —CH₂CH₂— | Cl | H | C≡CBu-t | H | CH₃ |
| H | | —CH₂CH₂— | Cl | H | C≡CBu-t | H | CH₃(Z) |
| H | | —CH₂CH₂— | Cl | H | C≡CSi(CH₃)₃ | H | CH₃ |
| H | | —CH₂CH₂— | Cl | H | C≡CSi(CH₃)₃ | H | CH₃(Z) |
| H | | —CH₂CH₂— | Cl | H | C≡CPh | H | CH₃ |
| H | | —CH₂CH₂— | Cl | H | C≡CPh | H | CH₃(Z) |
| H | | —CH₂CH₂— | Br | H | Br | H | CH₃ |
| H | | —CH₂CH₂— | Br | H | Br | H | CH₃(Z) |
| H | | —CH₂CH₂CH₂— | Cl | H | Cl | H | CH₃ |
| H | | —CH₂CH₂CH₂— | Cl | H | Cl | H | CH₃(Z) |
| H | | —CH₂CH₂CH₂— | Cl | H | Br | H | CH₃ |
| H | | —CH₂CH₂CH₂— | Cl | H | Br | H | CH₃(Z) |
| H | | —CH₂CH₂CH₂— | Cl | H | CF₃ | H | CH₃ |
| H | | —CH₂CH₂CH₂— | Cl | H | CF₃ | H | CH₃(Z) |
| H | | —CH₂CH₂CH₂— | Cl | H | C≡CBu-t | H | CH₃ |
| H | | —CH₂CH₂CH₂— | Cl | H | C≡CBu-t | H | CH₃(Z) |
| H | | —CH₂CH₂CH₂— | Cl | H | C≡CSi(CH₃)₃ | H | CH₃ |
| H | | —CH₂CH₂CH₂— | Cl | H | C≡CSi(CH₃)₃ | H | CH₃(Z) |
| H | | —CH₂CH₂CH₂— | Cl | H | C≡CPh | H | CH₃ |
| H | | —CH₂CH₂CH₂— | Cl | H | C≡CPh | H | CH₃(Z) |
| H | | —CH₂CH₂CH₂— | Br | H | Br | H | CH₃ |
| H | | —CH₂CH₂CH₂— | Br | H | Br | H | CH₃(Z) |
| H | | —CH₂OCH₂— | Cl | H | Cl | H | CH₃ |
| H | | —CH₂OCH₂— | Cl | H | Cl | H | CH₃(Z) |
| H | | —CH₂OCH₂— | Cl | H | Br | H | CH₃ |
| H | | —CH₂OCH₂— | Cl | H | Br | H | CH₃(Z) |
| H | | —CH₂OCH₂— | Cl | H | CF₃ | H | CH₃ |
| H | | —CH₂OCH₂— | Cl | H | CF₃ | H | CH₃(Z) |
| H | | —CH₂OCH₂— | Cl | H | C≡CBu-t | H | CH₃ |
| H | | —CH₂OCH₂— | Cl | H | C≡CBu-t | H | CH₃(Z) |
| H | | —CH₂OCH₂— | Cl | H | C≡CSi(CH₃)₃ | H | CH₃ |
| H | | —CH₂OCH₂— | Cl | H | C≡CSi(CH₃)₃ | H | CH₃(Z) |
| H | | —CH₂OCH₂— | Cl | H | C≡CPh | H | CH₃ |
| H | | —CH₂OCH₂— | Cl | H | C≡CPh | H | CH₃(Z) |
| H | | —CH₂OCH₂— | Br | H | Br | H | CH₃ |
| H | | —CH₂OCH₂— | Br | H | Br | H | CH₃(Z) |
| H | | —CH₂SCH₂— | Cl | H | Cl | H | CH₃ |
| H | | —CH₂SCH₂— | Cl | H | Cl | H | CH₃(Z) |
| H | | —CH₂SCH₂— | Cl | H | CF₃ | H | CH₃ |
| H | | —CH₂SCH₂— | Cl | H | CF₃ | H | CH₃(Z) |
| H | | —CH₂CH₂CH₂CH₂— | Cl | H | Cl | H | CH₃ |
| H | | —CH₂CH₂CH₂CH₂— | Cl | H | CF₃ | H | CH₃ |
| H | | —CH₂OCH₂CH₂— | Cl | H | Cl | H | CH₃ |
| H | | —CH₂OCH₂CH₂— | Cl | H | Cl | H | CH₃(Z) |
| H | | —CH₂OCH₂CH₂— | Cl | H | Br | H | CH₃ |
| H | | —CH₂OCH₂CH₂— | Cl | H | CF₃ | H | CH₃ |
| H | | —CH₂OCH₂CH₂— | Cl | H | CF₃ | H | CH₃(Z) |
| H | | —CH₂OCH₂CH₂— | Cl | H | C≡CBu-t | H | CH₃ |
| H | | —CH₂OCH₂CH₂— | Cl | H | C≡CSi(CH₃)₃ | H | CH₃ |
| H | | —CH₂OCH₂CH₂— | Cl | H | C≡CPh | H | CH₃ |
| H | | —CH₂OCH₂CH₂— | Br | H | Br | H | CH₃ |
| H | | —CH₂SCH₂CH₂— | Cl | H | Cl | H | CH₃ |
| H | | —CH₂SCH₂CH₂— | Cl | H | CF₃ | H | CH₃ |
| H | | —CH₂S(O)CH₂CH₂— | Cl | H | Cl | H | CH₃ |

TABLE 3-continued

| R⁴ | R² | R³ | Y¹ | Y² | Y³ | Y⁴ | R¹ |
|---|---|---|---|---|---|---|---|
| H | —CH₂S(O)CH₂CH₂— | | Cl | H | CF₃ | H | CH₃ |
| H | —CH₂SO₂CH₂CH₂— | | Cl | H | Cl | H | CH₃ |
| H | —CH₂SO₂CH₂CH₂— | | Cl | H | CF₃ | H | CH₃ |
| Et | H | H | Cl | H | Cl | H | Et |
| CH₂OCH₃ | H | H | Cl | H | Cl | H | Et |
| CH₂CN | H | H | Cl | H | Cl | H | Et |
| CH₂CH=CH₂ | H | H | Cl | H | Cl | H | Et |
| CH₂C≡CH | H | H | Cl | H | Cl | H | Et |
| C(O)CH₃ | H | H | Cl | H | Cl | H | Et |
| C(O)OCH₃ | H | H | Cl | H | Cl | H | Et |
| Et | H | H | Cl | H | CF₃ | H | Et |
| CH₂OCH₃ | H | H | Cl | H | CF₃ | H | Et |
| CH₂CN | H | H | Cl | H | CF₃ | H | Et |
| CH₂CH=CH₂ | H | H | Cl | H | CF₃ | H | Et |
| CH₂C≡CH | H | H | Cl | H | CF₃ | H | Et |
| C(O)CH₃ | H | H | Cl | H | CF₃ | H | Et |
| C(O)OCH₃ | H | H | Cl | H | CF₃ | H | Et |
| H | CH₃ | CH₃ | Cl | H | Cl | H | Et |
| H | CH₃ | CH₃ | Cl | H | Cl | H | Et(Z) |
| H | CH₃ | CH₃ | Cl | H | CF₃ | H | Et |
| H | CH₃ | CH₃ | Cl | H | CF₃ | H | Et(Z) |
| H | —CH₂CH₂— | | Cl | H | Cl | H | Et |
| H | —CH₂CH₂— | | Cl | H | Cl | H | Et(Z) |
| H | —CH₂CH₂— | | Cl | H | Cl | F | Et |
| H | —CH₂CH₂— | | Cl | H | Cl | F | Et(Z) |
| H | —CH₂CH₂— | | Cl | H | Br | H | Et |
| H | —CH₂CH₂— | | Cl | H | Br | H | Et(Z) |
| H | —CH₂CH₂— | | Cl | H | CF₃ | H | Et |
| H | —CH₂CH₂— | | Cl | H | CF₃ | H | Et(Z) |
| H | —CH₂CH₂— | | Cl | H | C≡CBu-t | H | Et |
| H | —CH₂CH₂— | | Cl | H | C≡CBu-t | H | Et(Z) |
| H | —CH₂CH₂— | | Cl | H | C≡CSi(CH₃)₃ | H | Et |
| H | —CH₂CH₂— | | Cl | H | C≡CSi(CH₃)₃ | H | Et(Z) |
| H | —CH₂CH₂— | | Cl | H | C≡CPh | H | Et |
| H | —CH₂CH₂— | | Cl | H | C≡CPh | H | Et(Z) |
| H | —CH₂CH₂— | | Br | H | Br | H | Et |
| H | —CH₂CH₂— | | Br | H | Br | H | Et(Z) |
| H | —CH₂CH₂CH₂— | | Cl | H | Cl | H | Et |
| H | —CH₂CH₂CH₂— | | Cl | H | Cl | H | Et(Z) |
| H | —CH₂CH₂CH₂— | | Cl | H | CF₃ | H | Et |
| H | —CH₂CH₂CH₂— | | Cl | H | CF₃ | H | Et(Z) |
| H | —CH₂OCH₂— | | Cl | H | Cl | H | Et |
| H | —CH₂OCH₂— | | Cl | H | Cl | H | Et(Z) |
| H | —CH₂OCH₂— | | Cl | H | Br | H | Et |
| H | —CH₂OCH₂— | | Cl | H | Br | H | Et(Z) |
| H | —CH₂OCH₂— | | Cl | H | CF₃ | H | Et |
| H | —CH₂OCH₂— | | Cl | H | CF₃ | H | Et(Z) |
| H | —CH₂OCH₂— | | Cl | H | C≡CBu-t | H | Et |
| H | —CH₂OCH₂— | | Cl | H | C≡CBu-t | H | Et(Z) |
| H | —CH₂OCH₂— | | Cl | H | C≡CSi(CH₃)₃ | H | Et |
| H | —CH₂OCH₂— | | Cl | H | C≡CSi(CH₃)₃ | H | Et(Z) |
| H | —CH₂OCH₂— | | Cl | H | C≡CPh | H | Et |
| H | —CH₂OCH₂— | | Cl | H | C≡CPh | H | Et(Z) |
| H | —CH₂OCH₂— | | Br | H | Br | H | Et |
| H | —CH₂OCH₂— | | Br | H | Br | H | Et(Z) |
| H | —CH₂SCH₂— | | Cl | H | Cl | H | Et |
| H | —CH₂SCH₂— | | Cl | H | CF₃ | H | Et |
| H | —CH₂OCH₂CH₂— | | Cl | H | Cl | H | Et |
| H | —CH₂OCH₂CH₂— | | Cl | H | CF₃ | H | Et |
| H | CH₃ | CH₃ | Cl | H | Cl | H | n-Pr |
| H | CH₃ | CH₃ | Cl | H | CF₃ | H | n-Pr |
| H | —CH₂CH₂— | | Cl | H | Cl | H | n-Pr |
| H | —CH₂CH₂— | | Cl | H | Cl | H | n-Pr(Z) |
| H | —CH₂CH₂— | | Cl | H | Br | H | n-Pr |
| H | —CH₂CH₂— | | Cl | H | CF₃ | H | n-Pr |
| H | —CH₂CH₂— | | Cl | H | CF₃ | H | n-Pr(Z) |
| H | —CH₂CH₂— | | Cl | H | C≡CBu-t | H | n-Pr |
| H | —CH₂CH₂— | | Cl | H | C≡CSi(CH₃)₃ | H | n-Pr |
| H | —CH₂CH₂— | | Cl | H | C≡CPh | H | n-Pr |
| H | —CH₂CH₂— | | Br | H | Br | H | n-Pr |
| H | —CH₂CH₂CH₂— | | Cl | H | Cl | H | n-Pr |
| H | —CH₂CH₂CH₂— | | Cl | H | CF₃ | H | n-Pr |
| H | —CH₂OCH₂— | | Cl | H | Cl | H | n-Pr(Z) |
| H | —CH₂OCH₂— | | Cl | H | CF₃ | H | n-Pr |
| H | —CH₂OCH₂— | | Cl | H | CF₃ | H | n-Pr(Z) |
| Et | H | H | Cl | H | Cl | H | i-Pr |
| CH₂OCH₃ | H | H | Cl | H | Cl | H | i-Pr |

TABLE 3-continued

| R⁴ | R² | R³ | Y¹ | Y² | Y³ | Y⁴ | R¹ |
|---|---|---|---|---|---|---|---|
| CH₂CN | H | H | Cl | H | Cl | H | i-Pr |
| CH₂CH═CH₂ | H | H | Cl | H | Cl | H | i-Pr |
| CH₂C≡CH | H | H | Cl | H | Cl | H | i-Pr |
| C(O)CH₃ | H | H | Cl | H | Cl | H | i-Pr |
| C(O)OCH₃ | H | H | Cl | H | Cl | H | i-Pr |
| Et | H | H | Cl | H | CF₃ | H | i-Pr |
| CH₂OCH₃ | H | H | Cl | H | CF₃ | H | i-Pr |
| CH₂CN | H | H | Cl | H | CF₃ | H | i-Pr |
| CH₂CH═CH₂ | H | H | Cl | H | CF₃ | H | i-Pr |
| CH₂C≡CH | H | H | Cl | H | CF₃ | H | i-Pr |
| C(O)CH₃ | H | H | Cl | H | CF₃ | H | i-Pr |
| C(O)OCH₃ | H | H | Cl | H | CF₃ | H | i-Pr |
| H | CH₃ | CH₃ | Cl | H | Cl | H | i-Pr |
| H | CH₃ | CH₃ | Cl | H | Cl | H | i-Pr(Z) |
| H | CH₃ | CH₃ | Cl | H | CF₃ | H | i-Pr |
| H | CH₃ | CH₃ | Cl | H | CF₃ | H | i-Pr(Z) |
| H | —CH₂CH₂— | | Cl | H | Cl | H | i-Pr |
| H | —CH₂CH₂— | | Cl | H | Cl | H | i-Pr(Z) |
| H | —CH₂CH₂— | | Cl | H | Cl | F | i-Pr |
| H | —CH₂CH₂— | | Cl | H | Cl | F | i-Pr(Z) |
| H | —CH₂CH₂— | | Cl | H | Br | H | i-Pr |
| H | —CH₂CH₂— | | Cl | H | Br | H | i-Pr(Z) |
| H | —CH₂CH₂— | | Cl | H | CF₃ | H | i-Pr |
| H | —CH₂CH₂— | | Cl | H | CF₃ | H | i-Pr(Z) |
| H | —CH₂CH₂— | | Cl | H | C≡CBu-t | H | i-Pr |
| H | —CH₂CH₂— | | Cl | H | C≡CBu-t | H | i-Pr(Z) |
| H | —CH₂CH₂— | | Cl | H | C≡CSi(CH₃)₃ | H | i-Pr |
| H | —CH₂CH₂— | | Cl | H | C≡CSi(CH₃)₃ | H | i-Pr(Z) |
| H | —CH₂CH₂— | | Cl | H | C≡CPh | H | i-Pr |
| H | —CH₂CH₂— | | Cl | H | C≡CPh | H | i-Pr(Z) |
| H | —CH₂CH₂— | | Br | H | Br | H | i-Pr |
| H | —CH₂CH₂— | | Br | H | Br | H | i-Pr(Z) |
| H | —CH₂CH₂CH₂— | | Cl | H | Cl | H | i-Pr |
| H | —CH₂CH₂CH₂— | | Cl | H | Cl | H | i-Pr(Z) |
| H | —CH₂CH₂CH₂— | | Cl | H | CF₃ | H | i-Pr |
| H | —CH₂CH₂CH₂— | | Cl | H | CF₃ | H | i-Pr(Z) |
| H | —CH₂OCH₂— | | Cl | H | Cl | H | i-Pr |
| H | —CH₂OCH₂— | | Cl | H | Cl | H | i-Pr(Z) |
| H | —CH₂OCH₂— | | Cl | H | Br | H | i-Pr |
| H | —CH₂OCH₂— | | Cl | H | Br | H | i-Pr(Z) |
| H | —CH₂OCH₂— | | Cl | H | CF₃ | H | i-Pr |
| H | —CH₂OCH₂— | | Cl | H | CF₃ | H | i-Pr(Z) |
| H | —CH₂OCH₂— | | Cl | H | C≡CBu-t | H | i-Pr |
| H | —CH₂OCH₂— | | Cl | H | C≡CBu-t | H | i-Pr(Z) |
| H | —CH₂OCH₂— | | Cl | H | C≡CSi(CH₃)₃ | H | i-Pr |
| H | —CH₂OCH₂— | | Cl | H | C≡CSi(CH₃)₃ | H | i-Pr(Z) |
| H | —CH₂OCH₂— | | Cl | H | C≡CPh | H | i-Pr |
| H | —CH₂OCH₂— | | Cl | H | C≡CPh | H | i-Pr(Z) |
| H | —CH₂OCH₂— | | Br | H | Br | H | i-Pr |
| H | —CH₂OCH₂— | | Br | H | Br | H | i-Pr(Z) |
| H | —CH₂SCH₂— | | Cl | H | Cl | H | i-Pr |
| H | —CH₂SCH₂— | | Cl | H | CF₃ | H | i-Pr |
| H | —CH₂OCH₂CH₂— | | Cl | H | Cl | H | i-Pr |
| H | —CH₂OCH₂CH₂— | | Cl | H | CF₃ | H | i-Pr |
| H | —CH₂CH₂— | | Cl | H | Cl | H | n-Bu |
| H | —CH₂CH₂— | | Cl | H | Cl | H | n-Bu(Z) |
| H | —CH₂CH₂— | | Cl | H | CF₃ | H | n-Bu |
| H | —CH₂CH₂— | | Cl | H | CF₃ | H | n-Bu(Z) |
| H | —CH₂OCH₂— | | Cl | H | Cl | H | n-Bu |
| H | —CH₂OCH₂— | | Cl | H | CF₃ | H | n-Bu |
| H | —CH₂CH₂— | | Cl | H | Cl | H | i-Bu |
| H | —CH₂CH₂— | | Cl | H | Cl | H | i-Bu(Z) |
| H | —CH₂CH₂— | | Cl | H | CF₃ | H | i-Bu |
| H | —CH₂CH₂— | | Cl | H | CF₃ | H | i-Bu(Z) |
| H | —CH₂OCH₂— | | Cl | H | Cl | H | i-Bu |
| H | —CH₂OCH₂— | | Cl | H | CF₃ | H | i-Bu |
| H | CH₃ | CH₃ | Cl | H | Cl | H | CH₂Pr-c |
| H | CH₃ | CH₃ | Cl | H | CF₃ | H | CH₂Pr-c |
| H | —CH₂CH₂— | | Cl | H | Cl | H | CH₂Pr-c |
| H | —CH₂CH₂— | | Cl | H | Cl | H | CH₂Pr-c(Z) |
| H | —CH₂CH₂— | | Cl | H | Br | H | CH₂Pr-c |
| H | —CH₂CH₂— | | Cl | H | CF₃ | H | CH₂Pr-c |
| H | —CH₂CH₂— | | Cl | H | CF₃ | H | CH₂Pr-c(Z) |
| H | —CH₂CH₂— | | Cl | H | C≡CBu-t | H | CH₂Pr-c |
| H | —CH₂CH₂— | | Cl | H | C≡CSi(CH₃)₃ | H | CH₂Pr-c |
| H | —CH₂CH₂— | | Cl | H | C≡CPh | H | CH₂Pr-c |
| H | —CH₂CH₂— | | Br | H | Br | H | CH₂Pr-c |
| H | —CH₂CH₂CH₂— | | Cl | H | Cl | H | CH₂Pr-c |

TABLE 3-continued

| R⁴ | R² | R³ | Y¹ | Y² | Y³ | Y⁴ | R¹ |
|---|---|---|---|---|---|---|---|
| H | | —CH₂CH₂CH₂— | Cl | H | CF₃ | H | CH₂Pr-c |
| H | | —CH₂OCH₂— | Cl | H | Cl | H | CH₂Pr-c |
| H | | —CH₂OCH₂— | Cl | H | Cl | H | CH₂Pr-c(Z) |
| H | | —CH₂OCH₂— | Cl | H | CF₃ | H | CH₂Pr-c |
| H | | —CH₂OCH₂— | Cl | H | CF₃ | H | CH₂Pr-c(Z) |
| H | CH₃ | CH₃ | Cl | H | Cl | H | s-Bu |
| H | CH₃ | CH₃ | Cl | H | CF₃ | H | s-Bu |
| H | | —CH₂CH₂— | Cl | H | Cl | H | s-Bu |
| H | | —CH₂CH₂— | Cl | H | Cl | H | s-Bu(Z) |
| H | | —CH₂CH₂— | Cl | H | Br | H | s-Bu |
| H | | —CH₂CH₂— | Cl | H | CF₃ | H | s-Bu |
| H | | —CH₂CH₂— | Cl | H | CF₃ | H | s-Bu(Z) |
| H | | —CH₂CH₂— | Cl | H | C≡CBu-t | H | s-Bu |
| H | | —CH₂CH₂— | Cl | H | C≡CSi(CH₃)₃ | H | s-Bu |
| H | | —CH₂CH₂— | Cl | H | C≡CPh | H | s-Bu |
| H | | —CH₂CH₂— | Br | H | Br | H | s-Bu |
| H | | —CH₂CH₂CH₂— | Cl | H | Cl | H | s-Bu |
| H | | —CH₂CH₂CH₂— | Cl | H | CF₃ | H | s-Bu |
| H | | —CH₂OCH₂— | Cl | H | Cl | H | s-Bu |
| H | | —CH₂OCH₂— | Cl | H | Cl | H | s-Bu(Z) |
| H | | —CH₂OCH₂— | Cl | H | CF₃ | H | s-Bu |
| H | | —CH₂OCH₂— | Cl | H | CF₃ | H | s-Bu(Z) |
| H | CH₃ | CH₃ | Cl | H | Cl | H | t-Bu |
| H | CH₃ | CH₃ | Cl | H | CF₃ | H | t-Bu |
| H | | —CH₂CH₂— | Cl | H | Cl | H | t-Bu |
| H | | —CH₂CH₂— | Cl | H | Cl | H | t-Bu(Z) |
| H | | —CH₂CH₂— | Cl | H | Br | H | t-Bu |
| H | | —CH₂CH₂— | Cl | H | CF₃ | H | t-Bu |
| H | | —CH₂CH₂— | Cl | H | CF₃ | H | t-Bu(Z) |
| H | | —CH₂CH₂— | Cl | H | C≡CBu-t | H | t-Bu |
| H | | —CH₂CH₂— | Cl | H | C≡CSi(CH₃)₃ | H | t-Bu |
| H | | —CH₂CH₂— | Cl | H | C≡CPh | H | t-Bu |
| H | | —CH₂CH₂— | Br | H | Br | H | t-Bu |
| H | | —CH₂CH₂CH₂— | Cl | H | Cl | H | t-Bu |
| H | | —CH₂CH₂CH₂— | Cl | H | CF₃ | H | t-Bu |
| H | | —CH₂OCH₂— | Cl | H | Cl | H | t-Bu |
| H | | —CH₂OCH₂— | Cl | H | Cl | H | t-Bu(Z) |
| H | | —CH₂OCH₂— | Cl | H | CF₃ | H | t-Bu |
| H | | —CH₂OCH₂— | Cl | H | CF₃ | H | t-Bu(Z) |
| H | | —CH₂CH₂— | Cl | H | Cl | H | CH(Et)₂ |
| H | | —CH₂CH₂— | Cl | H | Cl | H | CH(Et)₂(Z) |
| H | | —CH₂CH₂— | Cl | H | CF₃ | H | CH(Et)₂ |
| H | | —CH₂CH₂— | Cl | H | CF₃ | H | CH(Et)₂(Z) |
| H | | —CH₂OCH₂— | Cl | H | Cl | H | CH(Et)₂ |
| H | | —CH₂OCH₂— | Cl | H | CF₃ | H | CH(Et)₂ |
| H | | —CH₂CH₂— | Cl | H | Cl | H | c-Pen |
| H | | —CH₂CH₂— | Cl | H | Cl | H | c-Pen(Z) |
| H | | —CH₂CH₂— | Cl | H | CF₃ | H | c-Pen |
| H | | —CH₂CH₂— | Cl | H | CF₃ | H | c-Pen(Z) |
| H | | —CH₂OCH₂— | Cl | H | Cl | H | c-Pen |
| H | | —CH₂OCH₂— | Cl | H | CF₃ | H | c-Pen |
| H | CH₃ | CH₃ | Cl | H | Cl | H | CH₂CHF₂ |
| H | CH₃ | CH₃ | Cl | H | CF₃ | H | CH₂CHF₂ |
| H | | —CH₂CH₂— | Cl | H | Cl | H | CH₂CHF₂ |
| H | | —CH₂CH₂— | Cl | H | Cl | H | CH₂CHF₂(Z) |
| H | | —CH₂CH₂— | Cl | H | Br | H | CH₂CHF₂ |
| H | | —CH₂CH₂— | Cl | H | CF₃ | H | CH₂CHF₂ |
| H | | —CH₂CH₂— | Cl | H | CF₃ | H | CH₂CHF₂(Z) |
| H | | —CH₂CH₂— | Cl | H | C≡CBu-t | H | CH₂CHF₂ |
| H | | —CH₂CH₂— | Cl | H | C≡CSi(CH₃)₃ | H | CH₂CHF₂ |
| H | | —CH₂CH₂— | Cl | H | C≡CPh | H | CH₂CHF₂ |
| H | | —CH₂CH₂— | Br | H | Br | H | CH₂CHF₂ |
| H | | —CH₂CH₂CH₂— | Cl | H | Cl | H | CH₂CHF₂ |
| H | | —CH₂CH₂CH₂— | Cl | H | CF₃ | H | CH₂CHF₂ |
| H | | —CH₂OCH₂— | Cl | H | Cl | H | CH₂CHF₂ |
| H | | —CH₂OCH₂— | Cl | H | Cl | H | CH₂CHF₂(Z) |
| H | | —CH₂OCH₂— | Cl | H | CF₃ | H | CH₂CHF₂ |
| H | | —CH₂OCH₂— | Cl | H | CF₃ | H | CH₂CHF₂(Z) |
| H | CH₃ | CH₃ | Cl | H | Cl | H | CH₂CF₃ |
| H | CH₃ | CH₃ | Cl | H | CF₃ | H | CH₂CF₃ |
| H | | —CH₂CH₂— | Cl | H | Cl | H | CH₂CF₃ |
| H | | —CH₂CH₂— | Cl | H | Cl | H | CH₂CF₃(Z) |
| H | | —CH₂CH₂— | Cl | H | Br | H | CH₂CF₃ |
| H | | —CH₂CH₂— | Cl | H | CF₃ | H | CH₂CF₃ |
| H | | —CH₂CH₂— | Cl | H | CF₃ | H | CH₂CF₃(Z) |
| H | | —CH₂CH₂— | Cl | H | C≡CBu-t | H | CH₂CF₃ |
| H | | —CH₂CH₂— | Cl | H | C≡CSi(CH₃)₃ | H | CH₂CF₃ |
| H | | —CH₂CH₂— | Cl | H | C≡CPh | H | CH₂CF₃ |

TABLE 3-continued

| R⁴ | R² | R³ | Y¹ | Y² | Y³ | Y⁴ | R¹ |
|---|---|---|---|---|---|---|---|
| H | | —CH₂CH₂— | Br | H | Br | H | CH₂CF₃ |
| H | | —CH₂CH₂CH₂— | Cl | H | Cl | H | CH₂CF₃ |
| H | | —CH₂CH₂CH₂— | Cl | H | CF₃ | H | CH₂CF₃ |
| H | | —CH₂OCH₂— | Cl | H | Cl | H | CH₂CF₃ |
| H | | —CH₂OCH₂— | Cl | H | Cl | H | CH₂CF₃(Z) |
| H | | —CH₂OCH₂— | Cl | H | CF₃ | H | CH₂CF₃ |
| H | | —CH₂OCH₂— | Cl | H | CF₃ | H | CH₂CF₃(Z) |
| H | CH₃ | CH₃ | Cl | H | Cl | H | CH₂CH=CH₂ |
| H | CH₃ | CH₃ | Cl | H | CF₃ | H | CH₂CH=CH₂ |
| H | | —CH₂CH₂— | Cl | H | Cl | H | CH₂CH=CH₂ |
| H | | —CH₂CH₂— | Cl | H | Cl | H | CH₂CH=CH₂(Z) |
| H | | —CH₂CH₂— | Cl | H | Br | H | CH₂CH=CH₂ |
| H | | —CH₂CH₂— | Cl | H | CF₃ | H | CH₂CH=CH₂ |
| H | | —CH₂CH₂— | Cl | H | CF₃ | H | CH₂CH=CH₂(Z) |
| H | | —CH₂CH₂— | Cl | H | C≡CBu-t | H | CH₂CH=CH₂ |
| H | | —CH₂CH₂— | Cl | H | C≡CSi(CH₃)₃ | H | CH₂CH=CH₂ |
| H | | —CH₂CH₂— | Cl | H | C≡CPh | H | CH₂CH=CH₂ |
| H | | —CH₂CH₂— | Br | H | Br | H | CH₂CH=CH₂ |
| H | | —CH₂CH₂CH₂— | Cl | H | Cl | H | CH₂CH=CH₂ |
| H | | —CH₂CH₂CH₂— | Cl | H | CF₃ | H | CH₂CH=CH₂ |
| H | | —CH₂OCH₂— | Cl | H | Cl | H | CH₂CH=CH₂ |
| H | | —CH₂OCH₂— | Cl | H | Cl | H | CH₂CH=CH₂(Z) |
| H | | —CH₂OCH₂— | Cl | H | CF₃ | H | CH₂CH=CH₂ |
| H | | —CH₂OCH₂— | Cl | H | CF₃ | H | CH₂CH=CH₂(Z) |
| H | CH₃ | CH₃ | Cl | H | Cl | H | CH(CH₃)CH=CH₂ |
| H | CH₃ | CH₃ | Cl | H | CF₃ | H | CH(CH₃)CH=CH₂ |
| H | | —CH₂CH₂— | Cl | H | Cl | H | CH(CH₃)CH=CH₂ |
| H | | —CH₂CH₂— | Cl | H | Cl | H | CH(CH₃)CH=CH₂(Z) |
| H | | —CH₂CH₂— | Cl | H | Br | H | CH(CH₃)CH=CH₂ |
| H | | —CH₂CH₂— | Cl | H | CF₃ | H | CH(CH₃)CH=CH₂ |
| H | | —CH₂CH₂— | Cl | H | CF₃ | H | CH(CH₃)CH=CH₂(Z) |
| H | | —CH₂CH₂— | Cl | H | C≡CBu-t | H | CH(CH₃)CH=CH₂ |
| H | | —CH₂CH₂— | Cl | H | C≡CSi(CH₃)₃ | H | CH(CH₃)CH=CH₂ |
| H | | —CH₂CH₂— | Cl | H | C≡CPh | H | CH(CH₃)CH=CH₂ |
| H | | —CH₂CH₂— | Br | H | Br | H | CH(CH₃)CH=CH₂ |
| H | | —CH₂CH₂CH₂— | Cl | H | Cl | H | CH(CH₃)CH=CH₂ |
| H | | —CH₂CH₂CH₂— | Cl | H | CF₃ | H | CH(CH₃)CH=CH₂ |
| H | | —CH₂OCH₂— | Cl | H | Cl | H | CH(CH₃)CH=CH₂ |
| H | | —CH₂OCH₂— | Cl | H | Cl | H | CH(CH₃)CH=CH₂(Z) |
| H | | —CH₂OCH₂— | Cl | H | CF₃ | H | CH(CH₃)CH=CH₂ |
| H | | —CH₂OCH₂— | Cl | H | CF₃ | H | CH(CH₃)CH=CH₂(Z) |
| H | | —CH₂CH₂— | Cl | H | Cl | H | CH₂(Ph-4-F) |
| H | | —CH₂CH₂— | Cl | H | Cl | H | CH₂(Ph-4-F)(Z) |
| H | | —CH₂CH₂— | Cl | H | CF₃ | H | CH₂(Ph-4-F) |
| H | | —CH₂CH₂— | Cl | H | CF₃ | H | CH₂(Ph-4-F)(Z) |
| H | | —CH₂OCH₂— | Cl | H | Cl | H | CH₂(Ph-4-F) |
| H | | —CH₂OCH₂— | Cl | H | CF₃ | H | CH₂(Ph-4-F) |
| H | | —CH₂CH₂— | Cl | H | Cl | H | CH₂(Ph-4-Cl) |
| H | | —CH₂CH₂— | Cl | H | Cl | H | CH₂(Ph-4-Cl)(Z) |
| H | | —CH₂CH₂— | Cl | H | CF₃ | H | CH₂(Ph-4-Cl) |
| H | | —CH₂CH₂— | Cl | H | CF₃ | H | CH₂(Ph-4-Cl)(Z) |
| H | | —CH₂OCH₂— | Cl | H | Cl | H | CH₂(Ph-4-Cl) |
| H | | —CH₂OCH₂— | Cl | H | CF₃ | H | CH₂(Ph-4-Cl) |
| H | | —CH₂CH₂— | Cl | H | Cl | H | CH₂(Ph-4-CN) |
| H | | —CH₂CH₂— | Cl | H | Cl | H | CH₂(Ph-4-CN)(Z) |
| H | | —CH₂CH₂— | Cl | H | CF₃ | H | CH₂(Ph-4-CN) |
| H | | —CH₂CH₂— | Cl | H | CF₃ | H | CH₂(Ph-4-CN)(Z) |
| H | | —CH₂OCH₂— | Cl | H | Cl | H | CH₂(Ph-4-CN) |
| H | | —CH₂OCH₂— | Cl | H | CF₃ | H | CH₂(Ph-4-CN) |
| H | | —CH₂CH₂— | Cl | H | Cl | H | CH₂(Ph-3,4-F₂) |
| H | | —CH₂CH₂— | Cl | H | Cl | H | CH₂(Ph-3,4-F₂)(Z) |
| H | | —CH₂CH₂— | Cl | H | CF₃ | H | CH₂(Ph-3,4-F₂) |
| H | | —CH₂CH₂— | Cl | H | CF₃ | H | CH₂(Ph-3,4-F₂)(Z) |
| H | | —CH₂OCH₂— | Cl | H | Cl | H | CH₂(Ph-3,4-F₂) |
| H | | —CH₂OCH₂— | Cl | H | CF₃ | H | CH₂(Ph-3,4-F₂) |
| H | | —CH₂CH₂— | Cl | H | Cl | H | CH(CH₃)Ph |
| H | | —CH₂CH₂— | Cl | H | Cl | H | CH(CH₃)Ph(Z) |
| H | | —CH₂CH₂— | Cl | H | CF₃ | H | CH(CH₃)Ph |
| H | | —CH₂CH₂— | Cl | H | CF₃ | H | CH(CH₃)Ph(Z) |
| H | | —CH₂OCH₂— | Cl | H | Cl | H | CH(CH₃)Ph |
| H | | —CH₂OCH₂— | Cl | H | CF₃ | H | CH(CH₃)Ph |
| H | | —CH₂CH₂— | Cl | H | Cl | H | CH(CH₃)(Ph-4-F) |
| H | | —CH₂CH₂— | Cl | H | Cl | H | CH(CH₃)(Ph-4-F)(Z) |
| H | | —CH₂CH₂— | Cl | H | CF₃ | H | CH(CH₃)(Ph-4-F) |
| H | | —CH₂CH₂— | Cl | H | CF₃ | H | CH(CH₃)(Ph-4-F)(Z) |
| H | | —CH₂OCH₂— | Cl | H | Cl | H | CH(CH₃)(Ph-4-F) |
| H | | —CH₂OCH₂— | Cl | H | CF₃ | H | CH(CH₃)(Ph-4-F) |

The compounds of the present invention are capable of controlling pathogens causing plant diseases in Tracheophyta such as plants of the order Pinales, the group magnoliids, the group monocots and the group eudicots, and pathogens causing infections of Vertebrata such as animals of the class Mammalia, the class Aves, the class Reptilia and the class Actinopterygii, and pests such as plant-parasitic or animal-parasitic nematodes, Acanthocephala, Platyhelminthes and Protozoa.

Pests against plants may, for example, be fungi of the phylum Ascomycota, fungi of the phylum Basidiomycota, fungi of the phylum Chitridiomycota, fungi of the phylum Blastocladiomycota, fungi of the phylum Mucoromycotina, protists of the phylum Cercozoa, microorganisms of the phylum Heterokontophyta class Oomycetes, gram-positive bacteria of the phylum Actinobacteria, gram-positive bacteria of the phylum Tenericutes, gram-negative bacteria of the phylum Proteobacteria, nematodes of the order Aphelenchida and nematodes of the order Tylenchida. The compounds of the present invention have excellent controlling effect particularly on plant pathogenic fungi belonging to the phylum Ascomycota and the phylum Basidiomycota, and plant-parasitic nematodes belonging to the order Aphelenchida and the order Tylenchida at low doses.

Pests against animals may, for example, be fungi of the phylum Ascomycota, fungi of the phylum Basidiomycota, gram-positive bacteria of the phylum Actinobacteria, gram-positive bacteria of the phylum Firmicutes, gram-positive bacteria of the phylum Tenericutes, gram-negative bacteria of the phylum Proteobacteria, nematodes of the order Enoplida, nematodes of the order Rhabditida, nematodes of the order Strongylida, nematodes of the orderAscaridida, nematodes of the order Spirurida, microorganisms of the phylum Acanthocephala, cestodes of the order Pseudophyllidea, cestodes of the order Cyclophyllidea, trematodes of the order Strigeidida, trematodes of the order Echinostomida, trematodes of the order Plagiorchiida, trematodes of the order Opisthorchiida, amebas, Piroplasmida sporozoa, Haemosporida sporozoa, Eucoccidiorida sporozoa, *Vestibuliferida ciliata*, *Trichomonadida flagellata*, *Diplomonadida flagellata* and *Kinetoplastida flagellata*. Particularly, the compounds of the present invention have excellent effect to control internal parasites parasitizing animals of the class Mammalia belonging to the family Cebidae, the family Cercopithecidae, the family Hominidae, the family Leporidae, the family Chinchillidae, the family Caviidae, the family Cricetidae, the family Muridae, the family Sciuridae, the family Camelidae, the family Suidae, the family Cervidae, the family Bovidae, the family Felidae, the family Canidae, the family Mustelidae, the family Equidae, the family Macropodidae and the like, especially animal-parasitic nematodes belonging to the order Enoplida, the order Rhabditida, the order Strongylida, the order Aphelenchida, the order Tylenchida, the order Ascaridida and the order Spirurida, parasitizing mammals of the family Suidae, the family Bovidae, the family Felidae, the family Canidae and the family Equidae.

The compounds of the present invention are also effective on pests which have acquired resistance to conventional fungicides or nematicides, and the compounds of the present invention have very useful characteristics such that they have little harmful effect on non-target animals such as mammals, fishes, crustaceans, natural enemies and useful insects.

The compounds of the present invention may be used in any dosage form such as a soluble concentrate, an emulsifiable concentrate, a wettable powder, a water soluble powder, a water dispersible granule, a water soluble granule, a suspension concentrate, a concentrated emulsion, a suspoemulsion, a microemulsion, a dustable powder, a granule, a tablet or an emulsifiable gel usually after mixed with an appropriate solid carrier or a liquid carrier, and if necessary, with a surfactant, a penetrant, a spreader, a thickener, an anti-freezing agent, a binder, an anti-caking agent, a disintegrant, an antifoaming agent, a preservative, a stabilizer or the like. A formulation in an arbitrary dosage form may be sealed in water-soluble packaging such as a water-soluble capsule or a water-soluble film, for labor saving or improved safety.

As solid carriers, natural minerals such as quartz, calcite, meerschaum, dolomite, chalk, kaolinite, pyrophyllite, sericite, halloysite, methahalloysite, kibushi clay, gairome clay, pottery stone, zeeklite, allophone, Shirasu, mica, talc, bentonite, activated clay, acid clay, pumice, attapulgite, zeolite and diatomaceous earth, calcined natural minerals such as calcined clay, pearlite, Shirasu-balloons, vermiculite, attapulgus clay and calcined diatomaceous earth, inorganic salts such as magnesium carbonate, calcium carbonate, sodium carbonate, sodium hydrogen carbonate, ammonium sulfate, sodium sulfate, magnesium sulfate, diammonium hydrogen phosphate, ammonium dihydrogen phosphate and potassium chloride, saccharides such as glucose, fructose, sucrose and lactose, polysaccharides such as starch, cellulose powder and dextrin, organic substances such as urea, urea derivatives, benzoic acid and benzoic acid salts, plants such as wood flour, powdered cork, corncob, walnut shell and tobacco stems, fly ash, white carbon (such as hydrated synthetic silica, anhydrous synthetic silica and hydrous synthetic silicate), fertilizers and the like may be mentioned.

As liquid carriers, aromatic hydrocarbons such as xylene, alkyl ($C_9$ or $C_{10}$ etc.) benzene, phenylxylylethane and alkyl ($C_1$ or $C_3$ etc.) naphthalene, aliphatic hydrocarbons such as machine oil, normal paraffin, isoparaffin and naphthene, mixtures of aromatic hydrocarbons and aliphatic hydrocarbons such as kerosene, alcohols such as ethanol, isopropanol, cyclohexanol, phenoxyethanol and benzyl alcohol, polyhydric alcohols such as ethylene glycol, propylene glycol, diethylene glycol, hexylene glycol, polyethylene glycol and polypropylene glycol, ethers such as propyl cellosolve, butyl cellosolve, phenyl cellosolve, propylene glycol monomethyl ether, propylene glycol monoethyl ether, propylene glycol monopropyl ether, propylene glycol monobutyl ether and propylene glycol monophenyl ether, ketones such as acetophenone, cyclohexanone and γ-butyrolactone, esters such as fatty acid methyl esters, dialkyl succinates, dialkyl glutamate, dialkyl adipates and dialkyl phthalates, acid amides such as N-alkyl ($C_1$, $C_8$ or $C_{12}$ etc.) pyrrolidone, fats and oils such as soybean oil, linseed oil, rapeseed oil, coconut oil, cottonseed oil and castor oil, dimethyl sulfoxide, water and the like may be mentioned.

These solid and liquid carriers may be used alone or in combinations of two or more.

As surfactants, nonionic surfactants such as polyoxyethylene alkyl ether, polyoxyethylene alkyl(mono or di)phenyl ether, polyoxyethylene(mono, di or tri)styrylphenyl ether, polyoxyethylenepolyoxypropylene block copolymers, polyoxyethylene fatty acid (mono or di)ester, sorbitan fatty acid ester, polyoxyethylene sorbitan fatty acid ester, ethylene oxide adducts of castor oil, acetylene glycol, acetylene alcohol, ethylene oxide adducts of acetylene glycol, ethylene oxide adducts of acetylene alcohol and alkyl glycosides, anionic surfactants such as alkyl sulfate salts, alkylbenzenesulfonic acid salts, lignin sulfonate, alkylsulfosuccinic acid salts, naphthalenesulfonic acid salts, alkylnaphthalenesulfonic acid salts, salts of naphthalenesulfonic acid-formalin condensates, salts of alkylnaphthalenesulfonic acid-formalin condensates, polyoxyethylene alkyl ether sulfate or phosphate salts, polyoxyethylene(mono or di) alkylphenyl ether sulfate or phosphate salts, polyoxyethylene(mono, di or tri)styrylphenyl ether sulfate or phosphate salts, polycarboxylic acid salts (such as polyacrylates, polymaleates and copolymers of maleic acid and an olefin) and polystyrenesulfonic acid salts, cationic surfactants such as alkylamine salts and alkyl quaternary ammonium salts, amphoteric surfactants such as amino acid types and betaine types, silicone surfactants and fluorine surfactants may be mentioned.

The amount of these surfactants is usually preferred to be from 0.05 to 20 parts by weight per 100 parts by weight of the agent of the present invention, though there is no particular restrictions. These surfactants may be used alone or in combination of two or more.

The suitable application dose of the compounds of the present invention is generally about from 0.005 to 50 kg per hectare (ha) in terms of the active ingredient, though it varies depending on the application situation, the application season, the application method and the cultivated crop.

When the compounds of the present invention are used to control internal parasites in mammals and birds as farm animals/poultry and pet animals, the compounds of the present invention may be administered in an effective amount together with pharmaceutically acceptable additives orally, parenterally by injection (intramuscular, subcutaneously, intravenously or intraperitoneally); percutaneously by dipping, spraying, bathing, washing, pouring-on and spotting-on and dusting, or intranasally. The compounds of the present invention may be administered through molded articles such as chips, plates, bands, collars, ear marks, limb bands and ID tags. The compounds of the present invention are administered in an arbitrary dosage form suitable for the administration route.

The dosage form may be a solid preparation such as a dust, a granule, a wettable powder, a pellet, a tablet, a ball, a capsule and an molded article containing an active ingredient, a liquid preparation such as an injection fluid, an oral liquid, a liquid preparation applied to the skin or coelom, a pour-on preparation, a spot-on preparation, a flowable, an emulsion, and a semisolid preparation such as an ointment and a gel.

A solid preparation may generally be used by oral administration or by percutaneous or by environmental application after dilution with water or the like. A solid preparation can be prepared by mixing an active ingredient with an appropriate vehicle, and with an adjuvant if necessary, and formulating the mixture into a desired dosage form. As the vehicle, an inorganic vehicle such as a carbonate, a hydrogen carbonate, a phosphate, aluminum oxide, silica or clay or an organic vehicle such as a saccharide, cellulose, cereal flour or starch may, for example, be mentioned.

An injection fluid may be administered intravenously, intramuscularly or subcutaneously. An injection fluid can be prepared by dissolving an active ingredient in an appropriate solvent and, if necessary, adding additives such as a solubilizer, an acid, a base, a buffering salt, an antioxidant and a protectant. As appropriate solvents, water, ethanol, butanol, benzyl alcohol, glycerin, propylene glycol, polyethylene glycol, N-methylpyrrolidone and mixtures thereof, physiologically acceptable vegetable oils and synthetic oils suitable for injection may be mentioned. As solubilizers, polyvinylpyrrolidone, polyoxyethylated castor oil, polyoxyethylated sorbitan ester and the like may be mentioned. As protectants, benzyl alcohol, trichlorobutanol, p-hydroxybenzoic acid esters, n-butanol and the like may be mentioned.

An oral liquid may be administered directly or after dilution and can be prepared in the same manner as an injection fluid.

A flowable, an emulsion or the like may be administered directly or after dilution percutaneously or by environmental application.

A liquid preparation applied to the skin is administered by dripping, spreading, rubbing, spraying, sprinkling or dipping (soaking, bathing or washing) and can be prepared in the same manner as an injection fluid.

A pour-on preparation and a spot-on preparation are dripped or sprayed to a limited area of the skin so that they permeate through the skin and act systemically. A pour-on preparation and a spot-on preparation can be prepared by dissolving, suspending or emulsifying an active ingredient in an appropriate skin-friendly solvent or solvent mixture. If necessary, additives such as a surfactant, a colorant, an absorbefacient, an antioxidant, a light stabilizer and an adhesive may be added.

As appropriate solvents, water, alkanol, glycol, polyethylene glycol, polypropylene glycol, glycerin, benzyl alcohol, phenylethanol, phenoxyethanol, ethyl acetate, butyl acetate, benzyl benzoate, dipropylene glycol monomethyl ether, diethylene glycol monobutyl ether, acetone, methyl ethyl ketone, aromatic and/or aliphatic hydrocarbons, vegetable or synthetic oils, DMF, liquid paraffin, light liquid paraffin, silicone, dimethylacetamide, N-methylpyrrolidone or 2,2-dimethyl-4-oxy-methylene-1,3-dioxolane may be mentioned. As absorbefacients, DMSO, isopropyl myristate, pelargonic acid dipropylene glycol, silicone oil, fatty acid esters, triglycerides and aliphatic alcohols may be mentioned. As antioxidants, sulfites, metabisulfites, ascorbic acid, butylhydroxytoluene, butylhydroxyanisole and tocopherol may be mentioned.

An emulsion may be administered orally, percutaneously or by injection. An emulsion can be prepared by dissolving an active ingredient in a hydrophobic phase or a hydrophilic phase and homogenizing the resulting solution with another liquid phase together with an appropriate emulsifier, and further if necessary with additives such as a colorant, an absorbefacient, a protectant, an antioxidant, a light screen and a thickner.

As hydrophobic phases (oils), paraffin oil, silicone oil, sesame oil, almond oil, castor oil, synthetic triglycerides, ethyl stearate, di-n-butyryl adipate, hexyl laurate, pelargonic acid dipropylene glycol, esters of branched short-chain fatty acids with $C_{16}$-$C_{18}$ saturated fatty acids, isopropyl myristate, isopropyl palmitate, esters of $C_{12}$-$C_{18}$ saturated alcohols with caprylic/capric acid, isopropyl stearate, oleyl oleate, decyl oleate, ethyl oleate, ethyl lactate, fatty acid ester waxes, dibutyl phthalate, diisopropyl adipate, isotridecyl alcohol, 2-octyldodecanol, cetylstearyl alcohol and oleyl alcohol may be mentioned.

As hydrophilic phases, water, propylene glycol, glycerin and sorbitol may be mentioned.

As emulsifiers, nonionic surfactants such as polyoxyethylated castor oil, polyoxyethylated sorbitan monoolefinic acid, sorbitan monostearate, glycerin monostearate, polyoxyethyl stearate and alkyl phenol polyglycol ether; amphoteric surfactants such as disodium N-lauryl-β-iminodipropionate and lecithin; anionic surfactants such as sodium lauryl sulfate, aliphatic alcohol sulfate ether, mono/dialkylpolyglycol orthophosphate monoethanolamine salt; and cationic surfactants such as cetyltrimethylammonium chloride may, for example, be mentioned.

As other additives, carboxymethylcellulose, methylcellulose, polyacrylate, alginate, gelatin, gum arabic, polyvinylpyrrolidone, polyvinyl alcohol, methyl vinyl ether, maleic anhydride copolymers, polyethylene glycol, waxes and colloidal silica may be mentioned.

A semisolid preparation is administered by applying or spreading onto the skin or introducing into the coelom. A gel can be prepared by adding a thickener to a solution prepared in the same manner as an injection fluid sufficiently to give a transparent viscous substance like an ointment.

Formulation examples of preparations using the compounds of the present invention are given below. However, formulations of the present invention are by no means restricted thereto. In the following formulation examples, "parts" means parts by weight.

[Wettable Powder]

| | |
|---|---|
| Compound of the present invention | 0.1 to 80 parts |
| Solid carrier | 5 to 98.9 parts |
| Surfactant | 1 to 10 parts |
| Others | 0 to 5 parts |

As the others, an anti-caking agent, a stabilizer and the like may be mentioned.

[Emulsifiable Concentrate]

| | |
|---|---|
| Compound of the present invention | 0.1 to 30 parts |
| Organic solvent | 45 to 95 parts |
| Surfactant | 4.9 to 30 parts |
| Water | 0 to 50 parts |
| Others | 0 to 10 parts |

As the others, a spreader, a stabilizer and the like may be mentioned.

[Suspension Concentrate]

| | |
|---|---|
| Compound of the present invention | 0.1 to 70 parts |
| Liquid carrier | 15 to 98.89 parts |
| Surfactant | 1 to 12 parts |
| Others | 0.01 to 30 parts |

As the others, an anti-freezing agent, a thickener and the like may be mentioned.

[Water Dispersible Granule]

| | |
|---|---|
| Compound of the present invention | 0.1 to 90 parts |
| Solid carrier | 0 to 98.9 parts |
| Surfactant | 1 to 20 parts |
| Others | 0 to 10 parts |

As the others, a binder, a stabilizer and the like may be mentioned.

[Soluble Concentrate]

| | |
|---|---|
| Compound of the present invention | 0.01 to 70 parts |
| Liquid carrier | 20 to 99.99 parts |
| Others | 0 to 10 parts |

As the others, an anti-freezing agent, a spreader and the like may be mentioned.

[Granule]

| | |
|---|---|
| Compound of the present invention | 0.01 to 80 parts |
| Solid carrier | 10 to 99.99 parts |
| Others | 0 to 10 parts |

As the others, a binder, a stabilizer and the like may be mentioned.

[Dustable Powder]

| | |
|---|---|
| Compound of the present invention | 0.01 to 30 parts |
| Solid carrier | 65 to 99.99 parts |
| Others | 0 to 5 parts |

As the others, an anti-drift agent, a stabilizer and the like may be mentioned.

Next, more specific examples of preparations containing compounds of the present invention as an active ingredient are given below. However, the present invention is by no means restricted thereto.

In the following Formulation Examples, "parts" means parts by weight.

[Formulation Example 1] Wettable Powder

| | |
|---|---|
| Compound No. 2-132 of the present invention | 20 parts |
| Pyrophyllite | 74 parts |
| Sorpol 5039 | 4 parts |
| (tradename for a mixture of a nonionic surfactant and an anionic surfactant: manufactured by TOHO Chemical Industry Col., Ltd.) | |
| CARPLEX #80D | 2 parts |
| (hydrous synthetic silicic acid: tradename manufactured by Shionogi & Co., Ltd.) | |

The above ingredients are mixed and pulverized homogenously to obtain a wettable powder.

[Formulation Example 2] Emulsifiable Concentrate

| | |
|---|---|
| Compound No. 2-124 of the present invention | 5 parts |
| Xylene | 75 parts |
| N-methylpyrrolidone | 15 parts |
| Sorpol 2680 | 5 parts |
| (tradename for a mixture of a nonionic surfactant and an anionic surfactant: manufactured by TOHO Chemical Industry Co., Ltd.) | |

The above ingredients are mixed homogenously to obtain an emulsifiable concentrate.

[Formulation Example 3] Emulsifiable Concentrate

| | |
|---|---|
| Compound No. 2-117 of the present invention | 4 parts |
| DBE | 36 parts |
| (tradename for a mixture of dimethyl adipate, dimethyl glutarate and dimethyl succinate: manufactured by INVISTA) | |
| Diisobutyl adipate | 30 parts |
| N-methylpyrrolidone | 10 parts |
| Soprofol BSU | 14 parts |
| (tradename for a nonionic surfactant: manufactured by Rhodia Nicca. Ltd.) | |

-continued

| | |
|---|---|
| Rhodacal 70BC | 6 parts |
| (tradename for an anionic surfactant: manufactured by Rhodia Nicca. Ltd.) | |

The above ingredients are mixed homogenously to obtain an emulsifiable concentrate.

[Formulation Example 4] Emulsifiable Concentrate

| | |
|---|---|
| Compound No. 2-020 of the present invention | 4 parts |
| DBE | 11 parts |
| (tradename for a mixture of dimethyl adipate, dimethyl glutarate and dimethyl succinate: manufactured by INVISTA) | |
| Diisobutyl adipate | 30 parts |
| N-methylpyrrolidone | 5 parts |
| Soprofol BSU | 14 parts |
| (tradename for a nonionic surfactant: manufactured by Rhodia Nicca. Ltd.) | |
| Rhodacal 70BC | 6 parts |
| (tradename for an anionic surfactant: manufactured by Rhodia Nicca. Ltd.) | |
| Propylene glycol | 10 parts |
| Water | 20 parts |

The above ingredients are mixed homogenously to obtain an emulsifiable concentrate.

[Formulation Example 5] Suspension Concentrate

| | |
|---|---|
| Compound No. 2-136 of the present invention | 25 parts |
| AGRISOL S-710 | 10 parts |
| (tradename for a nonionic surfactant: manufactured by Kao Corporation) | |
| Lunox 1000C | 0.5 part |
| (tradename for an anionic surfactant: manufactured by TOHO Chemical Industry Co., Ltd.) | |
| Xanthan gum | 0.2 part |
| Water | 64.3 parts |

The above ingredients are mixed homogenously and wet-pulverized to obtain a suspension concentration.

[Formulation Example 6] Water Soluble Granule

| | |
|---|---|
| Compound No. 2-128 of the present invention | 75 parts |
| HITENOL NE-15 | 5 parts |
| (tradename for an anionic surfactant: manufactured by Dai-ichi Kogyo Seiyaku Co., Ltd.) | |
| VANILLEX N | 10 parts |
| (tradename for an anionic surfactant: manufactured by Nippon Paper Industries Co., LTD.) | |
| CARPLEX #80D | 10 parts |
| (tradename for hydrous synthetic silicic acid: manufactured by Shionogi & Co., Ltd.) | |

The above ingredients are mixed and pulverized homogenously, then kneaded with a small amount of water, granulated through an extrusion granulator and dried to obtain a water soluble granule.

[Formulation Example 7] Granule

| | |
|---|---|
| Compound No. 2-120 of the present invention | 5 parts |
| Bentonite | 50 parts |
| Talc | 45 parts |

The above ingredients are mixed and pulverized homogenously, then kneaded with a small amount of water, granulated through an extrusion granulator and dried to obtain a granule.

[Formulation Example 8] Dustable Powder

| | |
|---|---|
| Compound No. 2-140 of the present invention | 3 parts |
| CARPLEX #80D | 0.5 part |
| (tradename for a hydrous synthetic silicic acid: manufactured by Shionogi & Co., Ltd.) | |
| Kaolinite | 95 parts |
| Diisopropyl phosphate | 1.5 parts |

The above ingredients are mixed and pulverized homogeneously to obtain a dustable powder.

It is applied after diluted with water by a factor of from 1 to 20000 so as to achieve an active ingredient concentration of from 0.005 to 50 kg/ha.

[Formulation Example 9] Wettable Powder Preparation

| | |
|---|---|
| Compound No. 2-126 of the present invention | 25 parts |
| Sodium diisobutylnaphthalenesulfonate | 1 part |
| Calcium n-dodecylbenzenesulfonate | 10 parts |
| Alkyl aryl polyglycol ether | 12 parts |
| Naphthalenesulfonic acid-formalin condensate sodium salt | 3 parts |
| Silicone emulsion | 1 part |
| Silicon dioxide | 3 parts |
| Kaolin | 45 parts |

[Formulation Example 10] Water-Soluble Concentrate Preparation

| | |
|---|---|
| Compound No. 2-212 of the present invention | 20 parts |
| Polyoxyethylenelauryl ether | 3 parts |
| Sodium dioctylsulfosuccinate | 3.5 parts |
| Dimethyl sulfoxide | 37 parts |
| 2-Propanol | 36.5 parts |

[Formulation Example 11] Liquid Preparation for Spraying

| | |
|---|---|
| Compound No. 2-185 of the present invention | 2 parts |
| Dimethyl sulfoxide | 10 parts |
| 2-Propanol | 35 parts |
| Acetone | 53 parts |

[Formulation Example 12] Liquid Preparation for Percutaneous Administration

| | |
|---|---|
| Compound No. 2-151 of the present invention | 5 parts |
| Hexylene glycol | 50 parts |
| Isopropanol | 45 parts |

[Formulation Example 13] Liquid Preparation for Percutaneous Administration

| | |
|---|---|
| Compound No. 2-114 of the present invention | 5 parts |
| Propylene glycol monomethyl ether | 50 parts |
| Dipropylene glycol | 45 parts |

[Formulation Example 14] Liquid Preparation for Percutaneous Administration (by Dripping)

| | |
|---|---|
| Compound No. 2-174 of the present invention | 2 parts |
| Light liquid paraffin | 98 parts |

[Formulation Example 15] Liquid Preparation for Percutaneous Administration (by Dripping)

| | |
|---|---|
| Compound No. 2-240 of the present invention | 2 parts |
| Light liquid paraffin | 58 parts |
| Olive oil | 30 parts |
| ODO-H | 9 parts |
| Shin-etsu silicone | 1 part |

For use as agricultural fungicides or nematocides, if necessary, the compounds of the present invention may be mixed with other fungicides, other nematocides, insecticides, miticides, plant growth regulators, herbicides, synergists, fertilizers, soil conditioners and the like at the time of formulation or application.

Further, for use as internal parasiticides, the compounds of the present invention in effective amounts may be applied alone as active ingredients, or if necessary, they may be mixed with other antibiotics, other vermicides and the like at the time of formulation or application.

Particularly, the combined use with other fungicides, other nematocides, other antibiotics, other vermicides or the like is expected to broaden the pesticidal spectrum by the additive or synergistic effect of the other agrochemicals, to improve the pesticidal effect, to reduce the application cost by enabling control at lower doses, and further, to prolong the pesticidal effect for a long period of time. Particularly, the combined use with other fungicides, nematocides, antibiotics or vermicides differing in the mechanism of action is a very useful controlling method with a view to preventing the pests from acquiring resistance to pesticides. In such cases, they may be combined with a plurality of known fungicides, known nematocides, known insecticides, known miticides, known antibiotics or known vermicides simultaneously.

The fungicides, nematocides, insecticides, miticides, vermicides and antibiotics to be used in combination with the compounds of the present invention include, for example, the compounds disclosed in e.g. The Pesticidal Manual, 15th edition, 2009, having the generic names listed below, but are not necessarily restricted thereto.

Fungicides: such as acibenzolar-S-methyl, acypetacs, aldimorph, ametoctradin, amisulbrom, amobam, ampropylfos, anilazine, azaconazole, azoxystrobin, benalaxyl, benalaxyl-M, benodanil, benomyl, benthiavalicarb-isopropyl, benthiazole, benzovindiflupyr, biphenyl, bitertanol, bixafen, bordeaux mixture, boscalid, bromuconazole, bupirimate, calcium polysulfide, captan, carbendazim, carboxin, carpropamid, carvone, cheshunt mixture, chinomethionat, chloroneb, chloropicrin, chlorothalonil, chlozolinate, climbazole, copper carbonate, basic, copper hydroxide, copper naphthenate, copper oleate, copper oxychloride, copper sulfate, copper sulfate, basic, coumoxystrobin, cresol, cufraneb, cyazofamid, cyflufenamid, cymoxanil, cyproconazole, cyprodinil, dazomet, dichlofluanid, dichlorophen, diclobutrazol, diclocymet, diclomezine, dicloran, diethofencarb, difenoconazole, diflumetorim, dimethomorph, dimoxystrobin, diniconazole, diniconazole-M, dinobuton, dinocap, dinocap-4, dinocap-6, diphenylamine, dithianon, DNOC, dodemorph-acetate, dodine, drazoxolon, edifenphos, enestrobin, enoxastrobin, epoxiconazole, etaconazole, ethaboxam, ethirimol, ethoxyquin, etridiazole, famoxadone, fenamidone, fenaminstrobin, fenarimol, fenbuconazole, fenfuram, fenhexamid, fenitropan, fenoxanil, fenpiclonil, fenpropidin, fenpropimorph, fenpyrazamine, fentin, ferbam, ferimzone, fluazinam, fludioxonil, flufenoxystrobin, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetyl-aluminium, fuberidazole, furalaxyl, furametpyr, furconazole, furmecyclox, guazatine, hexachlorobenzene, hexaconazole, hymexazol, imazalil, imibenconazole, iminoctadine-albesilate, iminoctadine-triacetate, ipconazole, iprobenfos, iprodione, iprovalicarb, isofetamid, isoprothiolane, isopyrazam, isotianil, kasugamycin, kresoxim-methyl, laminarin, mancopper, mancozeb, mandestrobin, mandipropamid, maneb, mepanipyrim, mepronil, metalaxyl, metalaxyl-M, metam, metconazole, methfuroxam, metiram, metominostrobin, metrafenone, metsulfovax, milneb, myclobutanil, nabam, natamycin, nickel bis(dimethyldithiocarbamate), nitrothal-isopropy, nuarimol, ofurace, orysastrobin, oxadixyl, oxathiapiprolin, oxine copper, oxpoconazole fumarate, oxycarboxin, pefurazoate, penconazole, pencycuron, penflufen, pentachlorophenol (PCP), penthiopyrad, 2-phenylphenol, phthalide, picoxystrobin, piperalin, polycarbamate, polyoxins, polyoxorim, potassium azide, potassium hydrogen carbonate, probenazole, prochloraz, procymidone, propamocarb hydrochloride, propiconazole, propineb, proquinazid, prothioconazole, pyraclostrobin, pyrametostrobin, pyraoxystrobin, pyrazophos, pyribencarb-methyl, pyrifenox, pyrimethanil, pyriminostrobin, pyriofenone, pyrisoxazole, pyroquilon, quinacetol-sulfate, quinoxyfen, quintozene, sedaxane, silthiofam, simeconazole, sodium hydrogen carbonate, sodium hypochlorite, spiroxamine, sulfur, tebuconazole, tebufloquin, tecoram, tetraconazole, thiabendazole, thifluzamide, thiophanate-methyl, thiram, tiadinil, tolclofos-methyl, tolprocarb, tolylfluanid, triadimefon, triadimenol, triazoxide, tributyltin oxide, triclopyricab, tricyclazole, tridemorph, trifloxystrobin, triflumizole, triforine, triticonazole, validamycin, valifenalate, vinclozolin, zinc naphthenate, zinc sulfate, ziram, zoxamide, shiitake mushroom mycelium extracts, shiitake mushroom fruiting body extracts, BCF-082 (experimental name), NNF-0721 (experimental name) and ZF-9646 (experimental name).

Insecticides: such as abamectin, acephate, acetamiprid, afidopyropen, afoxolaner, alanycarb, aldicarb, allethrin, azamethiphos, azinphos-ethyl, azinphos-methyl, *bacillus thuringiensis*, bendiocarb, benfluthrin, benfuracarb, bensultap, bifenthrin, bioallethrin, bioresmethrin, bistrifluron, buprofezin, butocarboxim, carbaryl, carbofuran, carbosulfan, cartap, chlorantraniliprole, chlorethoxyfos, chlorfenapyr, chlorfenvinphos, chlorfluazuron, chlormephos, chlorpyrifos, chlorpyrifos-methyl, chromafenozide, clothianidin, cyanophos, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, beta-cypermethrin, zeta-cypermethrin, cyphenothrin, cyromazine, deltamethrin, diafenthiuron, diazinon, dichlorvos, diflubenzuron, dimethoate, dimethylvinphos, dinotefuran, diofenolan, disulfoton, emamectin-benzoate, empenthrin, endosulfan, alpha-endosulfan, EPN, esfenvalerate, ethiofencarb, ethiprole, etofenprox, etrimfos, fenitrothion, fenobucarb, fenoxycarb, fenthion, fenvalerate, fipronil, flometoquin, flonicamid, fluazuron, flubendiamide, flucycloxuron, flucythrinate, flufenerim, flufenoxuron, flufiprole, flumethrin, flupyradifurone, fluralaner, fluvalinate, tau-fluvalinate, fonofos, furathiocarb, halofenozide, heptafluthrin, hexaflumuron, hydramethylnon, imidacloprid, imiprothrin, indoxacarb, indoxacarb-MP, isoprocarb, isoxathion, lepimectin, lufenuron, malathion, meperfluthrin, metaflumizone, metaldehyde, methacrifos, methamidophos, methidathion, methomyl, methoprene, methoxychlor, methoxyfenozide, metofluthrin, muscalure, nitenpyram, novaluron, noviflumuron, omethoate, oxydemeton-methyl, parathion-methyl, permethrin, phenothrin, phenthoate, phorate, phosalone, phosmet, phoxim, pirimicarb, pirimiphos-methyl, profenofos, prothiofos, pymetrozine, pyraclofos, pyrethrins, pyridalyl, pyrifluquinazon, pyriprole, pyriproxyfen, resmethrin, rotenone, silafluofen, spinetoram, spinosad, spirotetramat, sulfotep, sulfoxaflor, tebufenozide, teflubenzuron, tefluthrin, terbufos, tetrachlorvinphos, tetramethrin, d-T-80-phthalthrin (d-tetramethrin), tetramethylfluthrin, thiacloprid, thiamethoxam, thiocyclam, thiodicarb, thiofanox, thiometon, tolfenpyrad, tralomethrin, transfluthrin, triazamate, trichlorfon, triflumuron, ME5382 (experimental name), NC-515 (experimental name) and ZD12501 (experimental name).

Miticides: such as acequinocyl, acrinathrin, amidoflumet, amitraz, azocyclotin, benzoximate, bifenazate, bromopropylate, clofentezine, cyenopyrafen, cyflumetofen, dicofol, dienochlor, etoxazole, fenazaquin, fenbutatin oxide, fenothiocarb, fenpropathrin, fenpyroximate, fluacrypyrim, formetanate, halfenprox, hexythiazox, milbemectin, propargite, pyflubumide, pyridaben, pyrimidifen, spirodiclofen, spiromesifen, tebufenpyrad and NA-89 (experimental name).

Nematicides: such as cadusafos, dichlofenthion, ethoprophos, fenamiphos, fluensulfone, fosthiazate, fosthietan, imicyafos, isamidofos, isazofos, methyl bromide, methyl isothiocyanate, oxamyl, sodium azide, BYI-1921 (experimental name) and MAI-08015 (experimental name).

Vermicides: such as acriflavine, albendazole, atovaguone, azithromycin, bithionol, bromofenofos, cambendazole, carnidazole, chloroquine, clazuril, clindamycin hydrochloride, clorsulon, closantel, coumaphos, cymiazol, dichlorophen, diethylcarbamazine, diminazene, disophenol, dithiazanine iodide, doxycycline hydrochloride, doramectin, emodepside, eprinomectin, febantel, fenbendazole, flubendazole, furazolidone, glycalpyramide, imidocarb, ivermectin, levamisole, mebendazole, mefloquine, melarsamine hydrochloride, metronidazole, metyridine, milbemycin oxime, monepantel, morantel tartrate, moxidectin, nicarbazin, niclosamide, nitroscanate, nitroxynil, omphalotin, oxantel pamoate, oxantel tartrate, oxfendazolee, oxibendazole, oxyclozanide, pamaquine, phenothiazine, piperazine adipate, piperazine citrate, piperazine phosphate, PNU-97333 (para-herquamide A), PNU-141962 (2-deoxyparaherquamide), praziquantel, primaquine, propetamphos, propoxur, pyrantel pamoate, pyrimethamine, santonin, selamectin, sulfadimethoxine, sulfadoxine, sulfamerazine, sulfamonomethoxine, sulfamoildapsone, thiabendazole, tinidazole, toltrazuril, tribromsalan and triclabendazole.

Antifungal agents: such as ketoconazole and miconazole nitrate.

Antibiotics: such as amoxicillin, ampicillin, bethoxazin, bithionol, bronopol, cefapirin, cefazolin, cefquinome, ceftiofur, chlortetracycline, clavulanic acid, danofloxacin, difloxacin, dinitolmide, enrofloxacin, florfenicol, lincomycin, lomefloxacin, marbofloxacin, miloxacin, mirosamycin, nitrapyrin, norfloxacin, octhilinone, ofloxacin, orbifloxacin, oxolinic acid, oxytetracycline, penicillin, streptomycin, thiamphenicol, tiamulin fumarate, tilmicosin phosphate, acetylisovaleryltylosin, tylosin phosphate, tulathromycin, valnemulin, calcinated shell calcium (calcium oxide), *Talaromyces, Trichoderma* and *Coniothyrium*.

EXAMPLES

The present invention will be described in further detail by referring to the following specific Examples of synthesis of and tests on the compounds of the present invention. However, the present invention is by no means restricted thereto.

Synthetic Examples

Synthetic Example 1

(Z)—N-[2-(2,4-dichlorophenyl)-2-(methoxyimino) ethyl]-2-(trifluoromethyl)benzamide (Compound No. 1-004 of the present invention)

Step 1: Preparation of 2-bromo-1-(2,4-dichlorophenyl)ethanone-O-methyloxime

To 4.00 g of 2-bromo-1-(2,4-dichlorophenyl)ethanone in 20 ml of ethanol, 1.25 g of methoxyamine hydrochloride was added, and the mixture was stirred at room temperature for 12 hours. After completion of the reaction, the solvent was evaporated under reduced pressure, and the resulting residue was mixed with 20 ml of water and extracted with ethyl acetate (20 ml×2). The resulting organic layers were combined, washed with water (20 ml×1) and then dried over saturated aqueous sodium chloride and then anhydrous sodium sulfate, and the solvent was evaporated under reduced pressure to obtain 3.85 g of the desired crude product as a pale yellow oil. The oil was used in the next step without further purification.

$^1$H NMR (CDCl$_3$, Me$_4$ Si, 300 MHz) δ7.2-7.55 (m, 3H), 4.56 and 4.35 (s, 2H), 4.06 and 4.04 (s, 3H).

Step 2: Preparation of N-[2-(2,4-dichlorophenyl)-2-(methoxyimino)ethyl]phthalimide To 2.17 g of 2-bromo-1-(2,4-dichlorophenyl)ethanone-O-methyloxime in 20 ml of N,N-dimethylformamide, 3.03 g of potassium phthalimide and 1.61 g of potassium carbonate were added, and the mixture was stirred at room temperature for 18 hours. After completion of the reaction, the reaction mixture was mixed with 40 ml of water and extracted with ethyl acetate (50 ml×1), the resulting organic layer was washed with water (20 ml×1) and then dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 2.10 g of the desired product as pale yellow crystals.

m.p.: 82.0-85.0° C.

$^1$H NMR (CDCl$_3$, Me$_4$Si, 300 MHz) δ7.65-7.8 (m, 4H), 7.15-7.35 (m, 3H), 4.92 (s, 2H), 4.01 (s, 3H).

Step 3: Preparation of 2-amino-1-(2,4-dichlorophenyl)ethanone-O-methyloxime

To 316 mg of N-[2-(2,4-dichlorophenyl)-2-(methoxyimino)ethyl]phthalimide in 10 ml of ethanol, 108 mg of hydrazine monohydrate was added, and the mixture was stirred at 60° C. for 2 hours. After completion of the reaction, the reaction mixture was allowed to cool to room temperature, mixed with 30 ml of water and extracted with ethyl acetate (40 ml×1). The resulting organic layer was dried over saturated aqueous sodium chloride and then anhydrous sodium sulfate, and the solvent was evaporated under reduced pressure to obtain 170 mg of the desired crude product as a colorless oil. The oil was used in the next step without further purification.

$^1$H NMR (CDCl$_3$, Me$_4$Si, 300 MHz) δ7.25-7.45 (m, 3H), 3.99 (s, 3H), 3.82 (s, 2H).

Step 4: Preparation of (Z)—N-[2-(2,4-dichlorophenyl)-2-(methoxyimino)ethyl]-2-(trifluoromethyl)benzamide To a solution of 170 mg of 2-amino-1-(2,4-dichlorophenyl)ethanone-O-methyloxime and 74 mg of triethylamine in 5 ml of dichloromethane, 122 mg of 2-(trifluoromethyl)benzoyl chloride was added dropwise, and the mixture was stirred at room temperature for 1 hour. After completion of the reaction, the reaction mixture was mixed with 10 ml of water and extracted with chloroform (20 ml×1), the resulting organic layer was dried over saturated aqueous sodium chloride and then anhydrous sodium sulfate, and the solvent was evaporated under reduced pressure. The resulting residue was mixed with 3 ml of diisopropyl ether and crystallized to obtain 110 mg of the desired product as white crystals.

m.p.: 146.0-148.0° C.

$^1$H NMR (CDCl$_3$, Me$_4$Si, 300 MHz) δ7.25-7.7 (m, 6H), 7.05-7.15 (m, 1H), 6.31 (bs, 1H), 4.62 (d, J=6.3 Hz, 2H), 4.02 (s, 3H).

Synthetic Example 2

(Z)—N-[2-(3,5-dichloropyridin-2-yl)-2-(ethoxyimino)ethyl]-2-(trifluoromethyl)benzamide (Compound No. 2-120 of the present invention)

Step 1: Preparation of 1-(3,5-dichloropyridin-2-yl)ethanone

To 20 g of 3,5-dichloropyridine-2-carbonitrile in 150 ml of tetrahydrofuran, 139 ml of a 1M tetrahydrofuran solution of methylmagnesium bromide was added dropwise with stirring under cooling with ice, and the mixture was stirred at the same temperature for 1 hour. After completion of the reaction, the reaction mixture was mixed with 15 ml of concentrated hydrochloric acid and 100 ml of water and extracted with ethyl acetate (100 ml×2), the resulting organic layers were combined, washed with water (100 ml×1) and dried over saturated aqueous solution chloride and then anhydrous sodium sulfate, and the solvent was evaporated under reduced pressure. The resulting residue was dissolved in 40 ml of ethyl acetate and 10 ml of hexane, 20 g of silica gel was added, the mixture was stirred at room temperature for 1 hour and then subjected to filtration, and the solvent was evaporated under reduced pressure. The precipitated solid was washed with 50 ml of hexane to obtain 17.16 g of the desired product as pale yellow crystals.

$^1$H NMR (CDCl$_3$, Me$_4$Si, 300 MHz) δ8.50 (d, J=2.1 Hz, 1H), 7.82 (d, J=2.1 Hz, 1H), 2.68 (s, 3H).

Step 2: Preparation of 2-bromo-1-(3,5-dichloropyridin-2-yl)ethanone

To 5.00 g of 1-(3,5-dichloropyridin-2-yl)ethanone in 75 ml of tetrahydrofuran, 9.94 g of trimethylphenylammonium tribromide was added, and the mixture was stirred at room temperature for 16 hours. After completion of the reaction, the precipitated solid was filtered off through celite, and the solvent was evaporated under reduced pressure. The resulting residue was purified by silica gel column chromatography using ethyl acetate-hexane (with a gradient of from 5:95 to 15:85) as the eluent to obtain 6.64 g of the desired product as a brown oil.

$^1$H NMR (CDCl$_3$, Me$_4$Si, 300 MHz) δ8.51 (d, J=1.9 Hz, 1H), 7.88 (d, J=1.9 Hz, 1H), 4.67 (s, 2H).

Step 3: Preparation of 2-bromo-1-(3,5-dichloropyridin-2-yl)ethanone-O-ethyloxime To 3.00 g of 2-bromo-1-(3,5-dichloropyridin-2-yl)ethanone in 25 ml of ethanol, 1.09 g of ethoxyamine hydrochloride was added, and the mixture was stirred at room temperature for 16 hours. After completion of the reaction, the solvent was evaporated under reduced pressure, the resulting residue was mixed with 50 ml of water and extracted with ethyl acetate (50 ml×2), the resulting organic layers were combined, washed with water (50 ml×1) and dried over saturated aqueous sodium chloride and then anhydrous sodium sulfate, and the solvent was evaporated under reduced pressure. The resulting residue was purified by silica gel column chromatograph using ethyl acetate-hexane (with a gradient of from 5:95 to 15:85) as the eluent to obtain 3.03 g of the desired product as a colorless oil.

$^1$H NMR (CDCl$_3$, Me$_4$Si, 300 MHz) δ8.50 (d, J=2.1 Hz, 1H), 7.81 (d, J=2.1 Hz, 1H), 4.67 and 4.52 (s, 2H), 4.35 and 4.32 (q, J=7.2 Hz, 2H), 1.37 and 1.36 (t, J=7.2 Hz, 3H).

Step 4: Preparation of N-[2-(3,5-dichloropyridin-2-yl)-2-(ethoxyimino)ethyl]phthalimide To 3.00 g of 2-bromo-1-(3,5-dichloropyridin-2-yl)ethanone-O-ethyloxime in 20 ml of N,N-dimethylformamide, 2.32 g of potassium phthalimide was added, and the mixture was stirred at room temperature for 12 hours. After completion of the reaction, the reaction mixture was mixed with 50 ml of water and extracted with ethyl acetate (100 ml×1), the resulting organic layer was washed with water (50 ml×1) and dried over saturated aqueous sodium chloride and then anhydrous sodium sulfate, and the solvent was evaporated under reduced pressure. The resulting residue was washed with 10 ml of diisopropyl ether to obtain 3.08 g of the desired product as white crystals.

m.p.: 99.0 to 101.00° C.
$^1$H NMR (CDCl$_3$, Me$_4$Si, 300 MHz) δ8.29 (d, J=2.1 Hz, 1H), 7.65-7.85 (m, 5H), 4.99 (s, 2H), 4.27 (q, J=7.2 Hz, 2H), 1.29 (t, J=7.2 Hz, 3H).

Step 5: Preparation of 2-amino-1-(3,5-dichloropyridin-2-yl)ethanone-O-ethyloxime To 3.00 g of N-[2-(3,5-dichloropyridin-2-yl)-2-(ethoxyimino)ethyl]phthalimide in 30 ml of ethanol, 793 mg of hydrazine monohydrate was added, and the mixture was stirred at 70° C. for 3 hours. After completion of the reaction, the reaction mixture was allowed to cool to room temperature, mixed with 100 ml of water and extracted with ethyl acetate (100 ml×2). The resulting organic layers were combined, washed with water (100 ml×1) and dried over saturated aqueous sodium chloride and then anhydrous sodium sulfate, and the solvent was evaporated under reduced pressure to obtain 1.62 g of the desired crude product as a brown oil. The oil was used in the next step without further purification.

$^1$H NMR (CDCl$_3$, Me$_4$Si, 300 MHz) δ8.51 and 8.48 (d, J=2.0 Hz, 1H), 7.79 and 7.77 (d, J=2.0 Hz, 1H), 4.27 and 4.13 (q, J=6.9 Hz, 2H), 3.90 and 3.74 (s, 2H), 1.34 and 1.21 (t, J=6.9 Hz, 3H).

Step 6: Preparation of N-[2-(3,5-dichloropyridin-2-yl)-2-(ethoxyimino)ethyl]-2-(trifluoromethyl)benzamide (Compound No. 2-003 of the present invention)

To a solution of 200 mg of 2-amino-1-(3,5-dichloropyridin-2-yl)ethanone-O-ethyloxime and 90 mg of triethylamine in 3 ml of dichloromethane, 169 mg of 2-(trifluoromethyl)benzoyl chloride was added dropwise with stirring under cooling with ice, and after the addition, the mixture was stirred at room temperature for another 30 minutes. After completion of the reaction, the reaction mixture was mixed with 10 ml of water and extracted with ethyl acetate (15 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 190 mg of the desired product as a pale yellow resinous substance.

$^1$H NMR (CDCl$_3$, Me$_4$Si, 300 MHz) δ8.45 and 8.29 (d, J=2.1 Hz, 1H), 7.80 and 7.78 (d, J=2.1 Hz, 1H), 7.35-7.75 (m, 4H), 6.52 (bs, 1H), 4.75 and 4.52 (d, J=6.0 Hz, 2H), 4.30 and 4.13 (q, J=7.2 Hz, 2H), 1.35 and 1.21 (t, J=7.2 Hz, 3H).

Step 7: Preparation of (Z)—N-[2-(3,5-dichloropyridin-2-yl)-2-(ethoxyimino)ethyl]-2-(trifluoromethyl)benzamide 190 mg of N-[2-(3,5-dichloropyridin-2-yl)-2-(ethoxyimino)ethyl]-2-(trifluoromethyl)benzamide was dissolved in 4 ml of acetonitrile, and the solution was irradiated with light for 2.5 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 3:7) as the eluent to obtain 41.3 mg of the desired product as white crystals.

m.p.: 84.0 to 86.0° C.
$^1$H NMR (CDCl$_3$, Me$_4$Si, 300 MHz) δ8.51 (d, J=2.1 Hz, 1H), 7.79 (d, J=2.1 Hz, 1H), 7.5-7.75 (m, 4H), 6.50 (bs, 1H), 4.53 (d, J=4.8 Hz, 2H), 4.13 (q, J=7.2 Hz, 2H), 1.21 (t, J=7.2 Hz, 3H).

Synthetic Example 3

N-[2-(3,5-dichloropyridin-2-yl)-2-(ethoxyimino)ethyl]-3-difluoromethyl-1-methyl-1H-pyrazole-4-carboxamide (Compound No. 17-004 of the present invention)

To 176 mg of 3-difluoromethyl-1-methyl-1H-pyrazole-4-carboxylic acid in 1 ml of dichloromethane, 10 mg of N,N-dimethylformamide and 381 mg of oxalyl chloride were added, and the mixture was stirred at room temperature for 1 hour. After completion of the reaction, the solvent was evaporated under reduced pressure, and the resulting residue was dissolved in 2 ml of dichloromethane, and to the solution, 190 mg of the 2-amino-1-(3,5-dichloropyridin-2-yl)ethanone-O-ethyloxime prepared in Step 5 in Synthetic Example 2 in 2 ml of dichloromethane and then 91 mg of pyridine were added dropwise with stirring under cooling with ice, and after the addition, the mixture was stirred at room temperature for another 2 hours. After completion of the reaction, the reaction mixture was mixed with 10 ml of water and extracted with chloroform (20 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:4 to 1:1) as the eluent to obtain 165.3 mg of a pale yellow resinous substance. The resinous substance was dissolved in 5 ml of acetic acid and stirred at 70° C. for 2 hours, the solvent was evaporated under reduced pressure, and the resulting residue was purified by silica gel column chromatography using ethyl acetate-hexane (with a gradient of from 1:4 to 1:1) as the eluent to obtain 130.6 mg of the desired product as a colorless resinous substance (E/Z=1/1).

$^1$H NMR (CDCl$_3$, Me$_4$Si, 300 MHz) δ8.50 and 8.47 (d, J=2.1 Hz, 1H), 7.90 and 7.86 (s, 1H), 7.76 and 7.75 (d, J=2.1 Hz, 1H), 6.9-7.1 (m, 1H), 6.84 and 6.73 (t, J=54.3 Hz, 1H), 4.71 and 4.49 (d, J=6.0 Hz, 2H), 4.31 and 4.14 (q, J=7.2 Hz, 2H), 3.92 and 3.89 (s, 3H), 1.36 and 1.23 (t, J=7.2 Hz, 3H).

Synthetic Example 4

N-[2-(3,5-dichloropyridin-2-yl)-2-(tert-butoxyimino)ethyl]-3-(trifluoromethyl)pyrazine-2-carboxamide (Compounds Nos. 9-005 and 9-006 of the present invention)

Step 1: Preparation of 2-bromo-1-(3,5-dichloropyridin-2-yl)ethanoneoxime

To 2.00 g of the 2-bromo-1-(3,5-dichloropyridin-2-yl)ethanone prepared in Step 2 in Synthetic Example 2 in 15 ml of ethanol, 517 mg of hydroxylamine hydrochloride was added, and the mixture was stirred at room temperature for 12 hours. After completion of the reaction, the reaction mixture was mixed with 100 ml of water and extracted with ethyl acetate (50 ml×2), the resulting organic layers were combined, washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 1.31 g of the desired product as a pale orange oil.

$^1$H NMR (CDCl$_3$, Me$_4$Si, 300 MHz) δ8.53 and 8.50 (d, J=2.1 Hz, 1H), 7.82 and 7.81 (d, J=2.1 Hz, 1H), 4.75 and 4.58 (s, 2H).

Step 2: Preparation of 2-bromo-1-(3,5-dichloropyridin-2-yl)ethanone-O-(tert-butyl)oxime To a solution of 1.31 g of 2-bromo-1-(3,5-dichloropyridin-2-yl)ethanoneoxime and 1.71 g of tert-butanol in 20 ml of dichloromethane, 3.27 g of boron trifluoride diethyl ether complex was added, and the mixture was stirred at room temperature for 48 hours. After completion of the reaction, the solvent was evaporated under reduced pressure, and the resulting residue was purified by silica gel column chromatography using ethyl acetate-hexane (with a gradient of from 0:100 to 15:85) as the eluent to obtain 140 mg of the desired product as a colorless oil.

$^1$H NMR (CDCl$_3$, Me$_4$Si, 300 MHz) δ8.50 and 8.48 (d, J=2.1 Hz, 1H), 7.81 and 7.77 (d, J=2.1 Hz, 1H), 4.70 and 4.53 (s, 2H), 1.39 and 1.38 (s, 9H).

Step 3: Preparation of N-[2-(3,5-dichloropyridin-2-yl)-2-(tert-butoxyimino)ethyl]phthalimide To 140 mg of 2-bromo-1-(3,5-dichloropyridin-2-yl)ethanone-O-(tert-butyl)oxime in 2 ml of N,N-dimethylformamide, 91 mg of potassium phthalimide was added, and the mixture was stirred at room temperature for 5 hours. After completion of the reaction, the reaction mixture was mixed with 10 ml of water and extracted with ethyl acetate (15 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 2:8 to 4:6) as the eluent to obtain 162 mg of the desired product as a colorless resinous substance.

$^1$H NMR (CDCl$_3$, Me$_4$Si, 300 MHz) δ8.30 (d, J=2.1 Hz, 1H), 7.7-7.85 (m, 2H), 7.74 (d, J=2.1 Hz, 1H), 7.6-7.7 (m, 2H), 4.97 (s, 2H), 1.27 (s, 9H).

Step 4: Preparation of 2-amino-1-(3,5-dichloropyridin-2-yl)ethanone-O-(tert-butyl)oxime To 162 mg of N-[2-(3,5-dichloropyridin-2-yl)-2-(tert-butoxyimino)ethyl]phthalimide in 10 ml of ethanol, 40 mg of hydrazine monohydrate was added, and the mixture was stirred at 80° C. for 1 hour. After completion of the reaction, the solvent was evaporated under reduced pressure, and the reaction mixture was mixed with 30 ml of water and extracted with ethyl acetate (25 ml×2). The resulting organic layers were combined, washed with water (20 ml×1) and dried over saturated aqueous sodium chloride and then anhydrous sodium sulfate, and the solvent was evaporated under reduced pressure to obtain 89 mg of the desired crude product as a colorless oil. The oil was used in the next step without further purification.

$^1$H NMR (CDCl$_3$, Me$_4$Si, 300 MHz) δ8.47 (d, J=2.4 Hz, 1H), 7.79 (d, J=2.4 Hz, 1H), 3.88 (bs, 2H), 1.36 (s, 9H).

Step 5: Preparation of N-[2-(3,5-dichloropyridin-2-yl)-2-(tert-butoxyimino)ethyl]-3-(trifluoromethyl)pyrazine-2-carboxamide To 74 mg of 3-(trifluoromethyl)pyrazine-2-carboxylic acid in 3 ml of dichloromethane, 10 mg of N,N-dimethylformamide and 57 mg of oxalyl chloride were added, and the mixture was stirred at room temperature for 1 hour. After completion of the reaction, the solvent was evaporated under reduced pressure, and the resulting residue was dissolved in 10 ml of dichloromethane. To the solution, 89 mg of 2-amino-1-(3,5-dichloropyridin-2-yl)ethanone-O-(tert-butyl)oxime and 39 mg of triethylamine were added with stirring under cooling with ice, and the mixture was stirred at room temperature for another 1 hour. After completion of the reaction, the reaction mixture was mixed with 10 ml of water and extracted with chloroform (10 ml×1), the resulting organic layer was dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 22 mg of geometrical isomer A and 111 mg of geometrical isomer B of the desired product as colorless resinous substances.

Isomer A:
$^1$H NMR (CDCl$_3$, Me$_4$Si, 300 MHz) δ8.77 (d, J=2.4 Hz, 1H), 8.69 (d, J=2.4 Hz, 1H), 8.46 (d, J=2.1 Hz, 1H), 8.14 (bs, 1H), 7.78 (d, J=2.1 Hz, 1H), 4.77 (d, J=6.0 Hz, 2H), 1.42 (s, 9H).

Isomer B:
$^1$H NMR (CDCl$_3$, Me$_4$Si, 300 MHz) δ8.77 (d, J=2.4 Hz, 1H), 8.70 (d, J=2.4 Hz, 1H), 8.46 (d, J=2.1 Hz, 1H), 8.17 (bs, 1H), 7.78 (d, J=2.1 Hz, 1H), 4.79 (d, J=6.0 Hz, 2H), 1.39 (s, 9H).

Synthetic Example 5

(Z)—N-[2-(3,5-dichloropyridin-2-yl)-2-(propoxyimino)ethyl]-2-(trifluoromethyl)benzamide (Compound No. 2-126 of the present invention)

Step 1: Preparation of N-[2-(3,5-dichloropyridin-2-yl)-2-oxoethyl]phthalimide To 3.00 g of the 2-bromo-1-(3,5-dichloropyridin-2-yl)ethanone prepared in Step 2 in Synthetic Example 2 in 30 ml of N,N-dimethylformamide, 4.13 g of potassium phthalimide was added, and the mixture was stirred at 80° C. for 3 hours and then at room temperature for 18 hours. After completion of the reaction, the reaction mixture was mixed with 150 ml of water and extracted with ethyl acetate (50 ml×2), the resulting organic layers were combined, washed with water (50 ml×1) and dried over saturated aqueous sodium chloride and then anhydrous sodium sulfate, and the solvent was evaporated under reduced pressure. The resulting residue was mixed with 40 ml of a mixture of diisopropyl ether and hexane (1:1), the insolubles were filtered off, and the solvent was evaporated under reduced pressure. The resulting residue was purified by silica gel column chromatography using ethyl acetate-hexane (with a gradient of from 15:85 to 25:75) as the eluent to obtain 0.32 g of the desired product as a dark brown resinous substance.

$^1$H NMR (CDCl$_3$, Me$_4$Si, 300 MHz) δ8.58 (d, J=2.0 Hz, 1H), 7.65-7.8 (m, 5H), 5.30 (s, 2H).

Step 2: Preparation of N-[2-(3,5-dichloropyridin-2-yl)-2-(hydroxyimino)ethyl]phthalimide To 0.32 g of N-[2-(3,5-dichloropyridin-2-yl)-2-oxoethyl]phthalimide in 15 ml of ethanol, 0.66 g of hydroxylamine hydrochloride was added and refluxed with heating for 4 hours with stirring. After completion of the reaction, the solvent was evaporated under reduced pressure, and the reaction mixture was mixed with 30 ml of water and 50 ml of ethyl acetate, and the resulting organic layer was collected. The organic layer was washed with water (30 ml×1) and dried over saturated aqueous sodium chloride and then anhydrous sodium sulfate, the solvent was evaporated under reduced pressure, and the resulting residue was washed with 10 ml of hexane to obtain 265 mg of the desired product as yellow crystals.

m.p.: 138.0 to 141.0° C.

$^1$H NMR (CDCl$_3$, Me$_4$Si, 300 MHz) δ8.47 and 8.30 (d, J=2.0 Hz, 1H), 8.13 and 7.52 (s, 1H), 7.65-7.9 (m, 5H), 5.05 and 4.78 (s, 2H).

Step 3: Preparation of N-[2-(3,5-dichloropyridin-2-yl)-2-(propoxyimino)ethyl]phthalimide To 265 mg of N-[2-(3,5-dichloropyridin-2-yl)-2-(hydroxyimino)ethyl]phthalimide in 2 ml of N,N-dimethylformamide, 310 mg of potassium carbonate and 387 mg of 1-iodopropane were added, and the mixture was stirred at room temperature for 18 hours. After completion of the reaction, the reaction mixture was mixed with 30 ml of water and extracted with ethyl acetate (50 ml×1), the resulting organic layer was washed with water (50 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 15:85 to 25:75) as the eluent to obtain 235 mg of the desired product as a yellow resinous substance.

$^1$H NMR (CDCl$_3$, Me$_4$Si, 300 MHz) δ8.42 and 8.29 (d, J=2.0 Hz, 1H), 7.65-7.9 (m, 5H), 4.99 and 4.76 (s, 2H), 4.18 and 4.00 (t, J=6.7 Hz, 2H), 1.5-1.75 (m, 2H), 0.93 and 0.81 (t, J=7.5 Hz, 3H).

Step 4: Preparation of 2-amino-1-(3,5-dichloropyridin-2-yl)ethanone-O-propyloxime To 235 mg of N-[2-(3,5-dichloropyridin-2-yl)-2-(propoxyimino)ethyl]phthalimide in 5 ml of ethanol, 90 mg of hydrazine monohydrate was added and refluxed with heating for 3 hours with stirring. After completion of the reaction, the reaction mixture was allowed to cool to room temperature, mixed with 20 ml of water and extracted with ethyl acetate (35 ml×2). The resulting organic layers were combined, washed with water (20 ml×1) and dried over saturated aqueous sodium chloride and then anhydrous sodium sulfate, and the solvent was evaporated under reduced pressure to obtain 151 mg of the desired crude product as a brown oil. The oil was used in the next step without further purification.

$^1$H NMR (CDCl$_3$, Me$_4$Si, 300 MHz) δ8.49 and 8.48 (d, J=2.0 Hz, 1H), 7.78 and 7.76 (d, J=2.0 Hz, 1H), 4.17 and 4.01 (t, J=6.6 Hz, 2H), 3.89 and 3.73 (s, 2H), 1.5-1.85 (m, 2H), 0.98 and 0.86 (t, J=7.4 Hz, 3H).

Step 5: Preparation of N-[2-(3,5-dichloropyridin-2-yl)-2-(propoxyimino)ethyl]-2-(trifluoromethyl)benzamide (Compound No. 2-004 of the present invention)

In a solution of 151 mg of 2-amino-1-(3,5-dichloropyridin-2-yl)ethanone-O-propyloxime and 86 mg of triethylamine in 4 ml of dichloromethane, 154 mg of 2-(trifluoromethyl)benzoyl chloride was added dropwise with stirring under cooling with ice, and after the addition, the mixture was stirred at room temperature for another 2 hours. After completion of the reaction, the reaction mixture was mixed with 10 ml of water and extracted with chloroform (30 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 2:8 to 3:7) as the eluent to obtain 218 mg of the desired product as a pale yellow resinous substance.

$^1$H NMR (CDCl$_3$, Me$_4$Si, 300 MHz) δ8.49 and 8.44 (d, J=2.1 Hz, 1H), 7.80 and 7.78 (d, J=2.1 Hz, 1H), 7.35-7.7 (m, 4H), 6.53 and 6.49 (bs, 1H), 4.75 and 4.52 (d, J=6.3 Hz, 2H), 4.21 and 4.03 (t, J=6.9 Hz, 2H), 1.7-1.8 and 1.55-4.65 (m, 2H), 0.96 and 0.86 (t, J=7.5 Hz, 3H).

Step 6: Preparation of (Z)—N-[2-(3,5-dichloropyridin-2-yl)-2-(propoxyimino)ethyl]-2-(trifluoromethyl)benzamide To 218 mg of N-[2-(3,5-dichloropyridin-2-yl)-2-(propoxyimino)ethyl]-2-(trifluoromethyl)benzamide in 3 ml of acetonitrile, 5 mg of benzophenone was added, and the mixture was irradiated with light for 48 hours in a quartz cell (manufactured by Fine, 4 clear windows for spectroscopy) using a 100 W high-pressure mercury lamp (manufactured by USHIO INC., lamp: UM-102, power supply UM-103B-B). After completion of the reaction, the solvent was evaporated under reduced pressure, and the resulting residue was purified by silica gel column chromatography using ethyl acetate-hexane (with a gradient of from 25:75 to 35:65) as the eluent to obtain 83 mg of the desired product as white crystals.

m.p.: 80.0 to 83.0° C.

$^1$H NMR (CDCl$_3$, Me$_4$Si, 300 MHz) δ8.51 (d, J=1.9 Hz, 1H), 7.79 (d, J=1.9 Hz, 1H), 7.5-7.75 (m, 4H), 6.50 (bs, 1H), 4.53 (d, J=5.2 Hz, 2H), 4.04 (t, J=6.6 Hz, 2H), 1.5-1.7 (m, 2H), 0.86 (t, J=7.4 Hz, 3H)

Synthetic Example 6

(Z)—N-[2-[3-chloro-5-(trifluoromethyl)pyridin-2-yl]-2-(cyclopropylmethoxyimino)ethyl]-2-(trifluoromethyl)benzamide (Compound No. 2-024 of the present invention)

Step 1: Preparation of 2-bromo-1-[3-chloro-5-(trifluoromethyl)pyridin-2-yl]ethanone To 0.82 g of 1-[3-chloro-5-(trifluoromethyl)pyridin-2-yl]ethanone in 10 ml of tetrahydrofuran, 1.38 g of trimethylphenylammonium tribromide was added, and the mixture was stirred at room temperature for 16 hours. After completion of the reaction, the precipitated solid was filtered off through celite, and the solvent was evaporated under reduced pressure. The resulting residue was purified by silica gel column chromatography using diethyl ether as the eluent to obtain 1.43 g of the desired product as a brown oil. The oil was used in the next step without further purification.

Step 2: Preparation of N-[2-[3-chloro-5-(trifluoromethyl)pyridin-2-yl]-2-oxoethyl]phthalimide To 1.43 g of 2-bromo-1-[3-chloro-5-(trifluoromethyl)pyridin-2-yl]ethanone in 10 ml of N,N-dimethylformamide, 0.68 g of potassium phthalimide and 0.01 g of potassium iodide were added, and the mixture was stirred at 85° C. for 1 hour. After completion of the reaction, the reaction mixture was allowed to cool to room temperature, mixed with 10 ml of water and extracted with ethyl acetate (10 ml×3), the resulting organic layers were combined, washed with water and dried over saturated aqueous sodium chloride and then anhydrous sodium sulfate, and the solvent was evaporated under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 5:95 to 46:60) as the eluent to obtain 0.47 g of the desired product as a pale yellow resinous substance.
$^1$H NMR (CDCl$_3$, Me$_4$Si, 300 MHz) δ8.87 (d, J=1.8 Hz, 1H), 8.10 (d, J=1.8 Hz, 1H), 7.85-7.95 (m, 2H), 7.7-7.8 (m, 2H), 5.32 (s, 2H).

Step 3: Preparation of N-[2-[3-chloro-5-(trifluoromethyl)pyridin-2-yl]-2-(hydroxyimino)ethyl]phthalimide To a solution of 0.47 g of N-[2-[3-chloro-5-(trifluoromethyl)pyridin-2-yl]-2-oxoethyl]phthalimide and 0.54 g of hydroxylamine hydrochloride in 5 ml of ethanol, 0.94 g of pyridine was added, and the mixture was stirred at room temperature for 24 hours. After completion of the reaction, the reaction mixture was mixed with 5 ml of water and extracted with ethyl acetate (5 ml×3), the resulting organic layers were combined, dried over saturated aqueous sodium chloride and then anhydrous sodium sulfate, and the solvent was distilled off under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 1:3 to 2:2) as the eluent to obtain 325 mg of the desired product as white crystals.
$^1$H NMR (CDCl$_3$, Me$_4$Si, 300 MHz) δ10.57 and 9.75 (s, 1H), 8.7-8.8 (m, 1H), 7.9-7.95 (m, 1H), 7.6-7.85 (m, 4H), 5.07 and 4.80 (s, 2H)

Step 4: Preparation of (E)-N-[2-[3-chloro-5-(trifluoromethyl)pyridin-2-yl]-2-(cyclopropylmethoxyimino)ethyl]phthalimide To 300 mg of N-[2-[3-chloro-5-(trifluoromethyl)pyridin-2-yl]-2-(hydroxyimino)ethyl]phthalimide in 5 ml of N,N-dimethylformamide, 324 mg of potassium carbonate and 158 mg of cyclopropylmethyl bromide were added, and the mixture was stirred at room temperature for 18 hours. After completion of the reaction, the reaction mixture was mixed with 5 ml of water and extracted with ethyl acetate (5 ml×3), the resulting organic layers were combined, washed with water and dried over saturated aqueous sodium chloride and then anhydrous sodium sulfate, and the solvent was evaporated under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 1:19 to 4:16) as the eluent to obtain 98 mg of the desired product as a pale yellow resinous substance.
$^1$H NMR (CDCl$_3$, Me$_4$Si, 300 MHz) δ8.61 (d, J=1.5 Hz, 1H), 7.97 (d, J=1.5 Hz, 1H), 7.75-7.85 (m, 2H), 7.65-7.75 (m, 2H), 5.03 (s, 2H), 4.03 (d, J=7.5 Hz, 2H), 1.05-1.25 (m, 1H), 0.4-0.5 (m, 2H), 0.15-0.25 (m, 2H).

Step 5: Preparation of (E)-2-amino-1-[3-chloro-5-(trifluoromethyl)pyridin-2-yl]ethanone-O-(cyclopropylmethyl)oxime To 98 mg of (E)-N-[2-[3-chloro-5-(trifluoromethyl)pyridin-2-yl]-2-(cyclopropylmethoxyimino)ethyl]phthalimide in 3 ml of ethanol, 76 mg of hydrazine monohydrate was added, and the mixture was stirred at 80° C. for 1 hour. After completion of the reaction, the reaction mixture was allowed to cool to room temperature, mixed with 5 ml of water and extracted with ethyl acetate (5 ml×3). The resulting organic layers were combined, dried over saturated aqueous sodium chloride and then anhydrous sodium sulfate, and the solvent was evaporated under reduced pressure. The resulting residue was purified by silica gel column chromatography using methanol-chloroform (1:10) as the eluent to obtain 65 mg of the desired product as a pale yellow oil. The oil was used in the next step without further purification.
$^1$H NMR (CDCl$_3$, Me$_4$Si, 300 MHz) δ8.78 (d, J=1.5 Hz, 1H), 8.00 (d, J=1.5 Hz, 1H), 4.05 (d, J=7.2 Hz, 2H), 3.96 (s, 2H), 1.66 (bs, 2H), 1.15-1.35 (m, 1H), 0.55-0.65 (m, 2H), 0.3-0.4 (m, 2H).

Step 6: Preparation of (E)-N-[2-[3-chloro-5-(trifluoromethyl)pyridin-2-yl]-2-(cyclopropylmethoxyimino)ethyl]-2-(trifluoromethyl)benzamide (Compound No. 2-023 of the present invention)

In a solution of 65 mg of (E)-2-amino-1-[3-chloro-5-(trifluoromethyl)pyridin-2-yl]ethanone-O-(cyclopropylmethyl)oxime and 32 mg of triethylamine in 2 ml of dichloromethane, 39 mg of 2-(trifluoromethyl)benzoyl chloride was added dropwise with stirring under cooling with ice, and after the addition, the mixture was stirred at room temperature for another 1 hour. After completion of the reaction, the reaction mixture was mixed with 2 ml of water and extracted with dichloromethane (2 ml×1), the resulting organic layer was dried over saturated aqueous sodium chloride and then anhydrous sodium sulfate, and the solvent was evaporated under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 2:18 to 5:15) as the eluent to obtain 85 mg of the desired product as white crystals.
m.p.: 98.0 to 101.0° C.
$^1$H NMR (CDCl$_3$, Me$_4$Si, 300 MHz) δ8.75 (d, J=1.5 Hz, 1H), 8.02 (d, J=1.5 Hz, 1H), 7.6-7.7 (m, 1H), 7.45-7.6 (m, 2H), 7.35-7.45 (m, 1H), 6.55 (bs, 1H), 4.81 (d, J=6.0 Hz, 2H), 4.19 (d, J=7.2 Hz, 2H), 1.15-1.3 (m, 1H), 0.3-0.4 (m, 2H), 0.5-0.6 (m, 2H).

Step 7: Preparation of (Z)—N-[2-[3-chloro-5-(trifluoromethyl)pyridin-2-yl]-2-(cyclopropylmethoxyimino)ethyl]-2-(trifluoromethyl)benzamide To 85 mg of (E)-N-[2-[3-chloro-5-(trifluoromethyl)pyridin-2-yl]-2-(cyclopropylmethoxyimino)ethyl]-2-(trifluoromethyl)benzamide in 3 ml of acetonitrile, 1 mg of benzophenone was added, and the mixture was irradiated with light for 5 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) as the eluent to obtain 47 mg of the desired product as white crystals.
m.p.: 73.0 to 74.0° C.
$^1$H NMR (CDCl$_3$, Me$_4$Si, 300 MHz) δ8.80 (d, J=1.5 Hz, 1H), 8.01 (d, J=1.5 Hz, 1H), 7.65-7.75 (m, 1H), 7.5-7.65 (m, 3H), 6.52 (bs, 1H), 4.58 (d, J=6.0 Hz, 2H), 3.91 (d, J=7.2 Hz, 2H), 1.0-1.15 (m, 1H), 0.45-0.55 (m, 2H), 0.2-0.3 (m, 2H).

Synthetic Example 7

(Z)—N-[2-(3,5-dichloropyridin-2-yl)-2-methoxyimino-1-methylethyl]-2-(trifluoromethyl)benzamide
(Compound No. 2-117 of the present invention)

Step 1: Preparation of 1-(3,5-dichloropyridin-2-yl)-1-propanone

To 5.0 g of 3,5-dichloropyridin-2-carbonitrile in 50 ml of tetrahydrofuran, 38 ml of 13% ethylmagnesium bromide in tetrahydrofuran was added dropwise with stirring under cooling with ice, and after the addition, the mixture was stirred at room temperature for 1 hour. After completion of the reaction, the reaction mixture was added dropwise to 55 ml of 1N aqueous hydrochloric acid with stirring under cooling with ice, and extracted with ethyl acetate (50 ml×2). The resulting organic layers were combined, washed with water (50 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of 5:95 to 15:85) as the eluent to obtain 4.4 g of the desired product as pale yellow crystals.
$^1$H NMR (CDCl$_3$, Me$_4$Si, 300 MHz) δ8.48 (d, J=2.1 Hz, 1H), 7.81 (d, J=2.1 Hz, 1H), 3.10 (q, J=7.2 Hz, 2H), 1.20 (t, J=7.2 Hz, 3H).

Step 2: Preparation of 2-bromo-1-(3,5-dichloropyridin-2-yl)-1-propanone

To 4.40 g of 1-(3,5-dichloropyridin-2-yl)-1-propanone in 20 ml of ethyl acetate-chloroform (1:1), 10.12 g of copper(I) bromide was added, and the mixture was stirred at room temperature for 12 hours. After completion of the reaction, the reaction mixture was mixed with 30 ml of saturated aqueous sodium hydrogencarbonate, and the precipitated solid was filtered off through celite and washed with 20 ml of ethyl acetate. The filtrate was mixed with 100 ml of ethyl acetate, the resulting organic layer was collected, washed with water (30 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 15:85) as the eluent to obtain 5.00 g of the desired product as a pale orange oil.
$^1$H NMR (CDCl$_3$, Me$_4$Si, 300 MHz) δ8.49 (d, J=2.1 Hz, 1H), 7.86 (d, J=2.1 Hz, 1H), 5.76 (q, J=6.9 Hz, 1H), 1.89 (d, J=6.9 Hz, 3H).

Step 3: Preparation of N-[2-(3,5-dichloropyridin-2-yl)-1-methyl-2-oxoethyl]phthalimide To 5.00 g of 2-bromo-1-(3,5-dichloropyridin-2-yl)-1-propanone in 20 ml of N,N-dimethylformamide, 3.27 g of potassium phthalimide was added, and the mixture was stirred at room temperature for 2 hours. After completion of the reaction, the reaction mixture was mixed with 50 ml of water and extracted with ethyl acetate (50 ml×2), and the resulting organic layers were combined, washed with water (30 ml×1) and dried over saturated aqueous sodium chloride and then anhydrous sodium sulfate, and the solvent was evaporated under reduced pressure to obtain 2.02 g of the desired crude product as brown crystals. The crystals were used in the next step without further purification.
$^1$H NMR (CDCl$_3$, Me$_4$Si, 300 MHz) δ8.34 (d, J=2.1 Hz, 1H), 7.65-7.9 (m, 5H), 5.57 (q, J=6.9 Hz, 1H), 1.68 (d, J=6.9 Hz, 3H).

Step 4: Preparation of N-[2-(3,5-dichloropyridin-2-yl)-2-methoxyimino-1-methylethyl]phthalimide To 1.00 g of N-[2-(3,5-dichloropyridin-2-yl)-1-methyl-2-oxoethyl]phthalimide in 10 ml of ethanol, 2.39 g of methoxyamine hydrochloride and 3.40 g of pyridine were added and refluxed with heating for 18 hours with stirring. After completion of the reaction, the reaction mixture was allowed to cool to room temperature, mixed with 30 ml of 1N aqueous hydrochloric acid and extracted with ethyl acetate (40 ml×2). The resulting organic layers were combined, washed with 30 ml of 1N aqueous hydrochloric acid and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 0.81 g of the desired product as a colorless resinous substance.
$^1$H NMR (CDCl$_3$, Me$_4$Si, 300 MHz) δ8.34 and 8.20 (bs, 1H), 7.65-7.85 (m, 5H), 5.95-6.05 and 5.3-5.65 (m, 1H), 4.01 and 3.86 (bs, 3H), 1.75-1.85 (m, 3H).

Step 5: Preparation of 2-amino-1-(3,5-dichloropyridin-2-yl)-1-propanone-O-methyloxime To 810 mg of N-[2-(3,5-dichloropyridin-2-yl)-2-methoxyimino-1-methylethyl]phthalimide in 30 ml of ethanol, 161 mg of hydrazine monohydrate was added and refluxed with heating for 1 hour with stirring. After completion of the reaction, the solvent was evaporated under reduced pressure, and the resulting residue was mixed with 20 ml of water and extracted with ethyl acetate (30 ml×1). The resulting organic layer was washed with water (20 ml×1) and dried over saturated aqueous sodium chloride and then anhydrous sodium sulfate, and the solvent was evaporated under reduced pressure to obtain 430 mg of the desired crude product as a pale yellow oil. The oil was used in the next step without further purification.

$^1$H NMR (CDCl$_3$, Me$_4$Si, 300 MHz) δ8.51 and 8.48 (d, J=2.1 Hz, 1H), 7.79 and 7.77 (d, J=2.1 Hz, 1H), 4.4-4.5 and 3.9-3.05 (m, 1H), 3.99 and 3.84 (s, 3H), 1.32 and 1.27 (d, J=6.9 Hz, 3H).

Step 6: Preparation of N-[2-(3,5-dichloropyridin-2-yl)-2-methoxyimino-1-methylethyl]-2-(trifluoromethyl)benzamide (Compound No. 2-115 of the present invention)

To a solution of 430 mg of 2-amino-1-(3,5-dichloropyridin-2-yl)-1-propanone-O-methyloxime and 210 mg of triethylamine in 20 ml of dichloromethane, 361 mg of 2-(trifluoromethyl)benzoyl chloride was added dropwise with stirring under cooling with ice, and after the addition, the mixture was stirred at room temperature for another 1 hour. After completion of the reaction, the reaction mixture was mixed with 30 ml of water and extracted with chloroform (20 ml×1), the resulting organic layer was washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 296 mg of the desired product as a colorless resinous substance.

$^1$H NMR (CDCl$_3$, Me$_4$Si, 300 MHz) δ8.50 and 8.41 (d, J=1.8 Hz, 1H), 7.82 and 7.79 (d, J=1.8 Hz, 1H), 7.4-7.75 (m, 4H), 6.65-7.0 (m, 1H), 5.7-5.85 and 5.2-5.3 (m, 1H), 4.05 and 3.87 (s, 3H), 1.56 and 1.45 (d, J=6.6 Hz, 3H).

Step 7: Preparation of (Z)—N-[2-(3,5-dichloropyridin-2-yl)-2-methoxyimino-1-methylethyl]-2-(trifluoromethyl)benzamide 160 mg of N-[2-(3,5-dichloropyridin-2-yl)-2-methoxyimino-1-methylethyl]-2-(trifluoromethyl)benzamide in 4 ml of acetonitrile was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the precipitated solid was washed with 5 ml of diisopropyl ether to obtain 33 mg of the desired product as white crystals. m.p.: 104.0 to 105.0° C.

$^1$H NMR (CDCl$_3$, Me$_4$Si, 300 MHz) δ8.50 (d, J=2.1 Hz, 1H), 7.80 (d, J=2.1 Hz, 1H), 7.5-7.75 (m, 4H), 6.78 (bs, 1H), 5.2-5.35 (m, 1H), 3.87 (s, 3H), 1.45 (d, J=6.6 Hz, 3H).

Synthetic Example 8

(Z)—N-[2-[3-chloro-5-(trifluoromethyl)pyridin-2-yl]-2-(ethoxyimino)ethyl]-2-(trifluoromethyl)benzamide (Compound No. 2-185 of the present invention)

Step 1: Preparation of N-[2-[3-chloro-5-(trifluoromethyl)pyridin-2-yl]-2-(ethoxyimino)ethyl]phthalimide To 214 mg of the N-[2-[3-chloro-5-(trifluoromethyl)pyridin-2-yl]-2-oxoethyl]phthalimide prepared in Step 2 in Synthetic Example 6 in 3 ml of ethanol, 84 mg of ethoxyamine hydrochloride was added, and the mixture was stirred at room temperature for 18 hours. After completion of the reaction, the reaction mixture was mixed with 5 ml of water and extracted with ethyl acetate (5 ml×3), and the resulting organic layers were combined, dried over saturated aqueous sodium chloride and then anhydrous sodium sulfate, and the solvent was evaporated under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 2:18 to 5:15) as the eluent to obtain 111 mg of the desired product as a brown resinous substance.

$^1$H NMR (CDCl$_3$, Me$_4$Si, 300 MHz) δ8.60 (d, J=1.5 Hz, 1H), 7.97 (d, J=1.5 Hz, 1H), 7.8-7.9 (m, 2H), 7.65-7.75 (m, 2H), 5.02 and 4.80 (s, 2H), 4.29 and 4.11 (q, J=7.2 Hz, 2H), 1.30 and 1.17 (t, J=7.2 Hz, 3H).

Step 2: Preparation of 2-amino-1-[3-chloro-5-(trifluoromethyl)pyridin-2-yl]ethanone-O-ethyloxime To 111 mg of N-[2-[3-chloro-5-(trifluoromethyl)pyridin-2-yl]-2-(ethoxyimino)ethyl]phthalimide in 3 ml of ethanol, 86 mg of hydrazine monohydrate was added, and the mixture was stirred at 80° C. for 1 hour. After completion of the reaction, the reaction mixture was allowed to cool to room temperature, mixed with 5 ml of water and extracted with ethyl acetate (5 ml×3). The resulting organic layers were combined, dried over saturated aqueous sodium chloride and then anhydrous sodium sulfate, the solvent was evaporated under reduced pressure, and the resulting residue was purified by silica gel column chromatography using methanol-chloroform (1:10) as the eluent to obtain 47 mg of the desired product as a yellow oil. The oil was used in the next step without further purification.

$^1$H NMR (CDCl$_3$, Me$_4$Si, 300 MHz) δ8.80 and 8.77 (d, J=1.5 Hz, 1H), 8.00 and 7.97 (d, J=1.5 Hz, 1H), 4.29 and 4.13 (q, J=7.2 Hz, 2H), 3.93 and 3.77 (s, 2H), 1.70 (bs, 2H), 1.35 and 1.22 (t, J=7.2z, 3H).

Step 3: Preparation of N-[2-[3-chloro-5-(trifluoromethyl)pyridin-2-yl]-2-(ethoxyimino)ethyl]-2-(trifluoromethyl)benzamide (Compound No. 2-016 of the present invention)

To a solution of 47 mg of 2-amino-1-[3-chloro-5-(trifluoromethyl)pyridin-2-yl]ethanone-O-ethyloxime and 25 mg of triethylamine in 2 ml of dichloromethane, 31 mg of 2-(trifluoromethyl)benzoyl chloride was added dropwise with stirring under cooling with ice, and after the addition, the mixture was stirred at room temperature for another 1 hour. After completion of the reaction, the reaction mixture was mixed with 2 ml of water and extracted with dichloromethane (2 ml×1), the resulting organic layer was dried over saturated aqueous sodium chloride and then anhydrous sodium sulfate, and the solvent was evaporated under reduced pressure. The resulting residue was purified by preparative medium pressure liquid chromatography (preparative medium pressure chromatograph: YFLC-Wprep manufactured by Yamazen Science, Inc.) using ethyl acetate-hexane (with a gradient of from 2:18 to 5:15) as the eluent to obtain 48 mg of the desired product as a colorless resinous substance.

$^1$H NMR (CDCl$_3$, Me$_4$Si, 300 MHz) δ8.81 and 8.75 (d, J=1.5 Hz, 1H), 8.03 and 8.00 (d, J=1.5 Hz, 1H), 7.35-7.55

(m, 4H), 6.51 (bs, 1H), 4.79 and 4.58 (d, J=5.4 Hz, 2H), 4.34 and 4.16 (q, J=7.2 Hz, 2H), 1.38 and 1.24 (t, J=7.2 Hz, 3H).

Step 4: Preparation of (Z)—N-[2-[3-chloro-5-(trifluoromethyl)pyridin-2-yl]-2-(ethoxyimino)ethyl]-2-(trifluoromethyl)benzamide To 48 mg of N-[2-[3-chloro-5-(trifluoromethyl)pyridin-2-yl]-2-(ethoxyimino)ethyl]-2-(trifluoromethyl)benzamide in 3 ml of acetonitrile, 1 mg of benzophenone was added, and the mixture was irradiated with light for 4 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) as the eluent to obtain 42 mg of the desired product as white crystals.

m.p.: 60.0 to 62.0° C.

$^1$H NMR (CDCl$_3$, Me$_4$Si, 300 MHz) δ8.81 (d, J=1.5 Hz, 1H), 8.00 (d, J=1.5 Hz, 1H), 7.5-7.55 (m, 4H), 6.51 (bs, 1H), 4.79 (d, J=5.4 Hz, 2H), 4.16 (q, J=7.2 Hz, 2H), 1.24 (t, J=7.2 Hz, 3H).

Synthetic Example 9

N-[2-(3-chloro-5-methoxypyridin-2-yl)-2-(methoxyimino)ethyl]-2-(trifluoromethyl)benzamide (compound No. 2-083 of the present invention)

Step 1: Preparation of 2-bromo-1-(3-chloro-5-methoxypyridin-2-yl)ethanone

To 0.90 g of 1-(3-chloro-5-methoxypyridin-2-yl)ethanone in 10 ml of tetrahydrofuran, 1.82 g of trimethylphenylammonium tribromide was added, and the mixture was stirred at room temperature for 16 hours. After completion of the reaction, the precipitated solid was filtered off, and the solvent was evaporated under reduced pressure. The resulting residue was purified by silica gel column chromatography using ethyl acetate-hexane (with a gradient of from 1:9 to 3:7) as the eluent to obtain 0.57 g of the desired product as pale yellow crystals.

$^1$H NMR (CDCl$_3$, Me$_4$Si, 300 MHz) δ8.23 (d, J=2.4 Hz, 1H), 7.28 (d, J=2.4 Hz, 1H), 4.74 (s, 2H), 3.95 (s, 3H).

Step 2: Preparation of N-[2-(3-chloro-5-methoxypyridin-2-yl)-2-oxoethyl]phthalimide To 570 mg of 2-bromo-1-(3-chloro-5-methoxypyridin-2-yl)ethanone in 10 ml of N,N-dimethylformamide, 800 mg of potassium phthalimide and 36 mg of potassium iodide were added, and the mixture was stirred at 80° C. for 5 hours. After completion of the reaction, the reaction mixture was allowed to cool to room temperature, mixed with 20 ml of water and extracted with ethyl acetate (40 ml×1), the resulting organic layer was dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 0.12 g of the desired product as white crystals.

$^1$H NMR (CDCl$_3$, Me$_4$Si, 300 MHz) δ8.30 (d, J=2.4 Hz, 1H), 7.85-7.95 (m, 2H), 7.7-7.8 (m, 2H), 7.27 (d, J=2.4 Hz, 2H), 5.31 (s, 2H), 3.96 (s, 3H).

Step 3: Preparation of N-[2-(3-chloro-5-methoxypyridin-2-yl)-2-(methoxyimino)ethyl]phthalimide To a solution of 120 mg of N-[2-(3-chloro-5-methoxypyridin-2-yl)-2-oxoethyl]phthalimide and 60 mg of methoxyamine hydrochloride in 5 ml of ethanol, 85 mg of pyridine was added, and the mixture was stirred at 80° C. for 6 hours. After completion of the reaction, the solvent was evaporated under reduced pressure, and the resulting residue was purified by silica gel column chromatography using ethyl acetate-hexane (with a gradient of from 1:9 to 3:7) as the eluent to obtain 101 mg of the desired product as a pale yellow oil.

$^1$H NMR (CDCl$_3$, Me$_4$Si, 300 MHz) δ8.17 and 8.01 (d, J=2.7 Hz, 1H), 7.65-7.9 (m, 4H), 7.20 and 7.19 (d, J=2.7 Hz, 1H), 4.99 and 4.77 (s, 2H), 4.04 and 3.84 (s, 3H), 3.84 and 3.78 (s, 3H).

Step 4: Preparation of N-[2-(3-chloro-5-methoxypyridin-2-yl)-2-(methoxyimino)ethyl]-2-(trifluoromethyl)benzamide To 101 mg of N-[2-(3-chloro-5-methoxypyridin-2-yl)-2-(methoxyimino)ethyl]phthalimide in 5 ml of ethanol, 42 mg of hydrazine monohydrate was added, and the mixture was stirred at room temperature for 12 hours. After completion of the reaction, the reaction mixture was mixed with 15 ml of water and extracted with ethyl acetate (30 ml×1), the resulting organic layer was washed with water (20 ml×1) and dried over saturated aqueous sodium chloride and then anhydrous sodium sulfate, and the solvent was evaporated under reduced pressure. The resulting residue was dissolved in 5 ml of dichloromethane, and to the solution, 46 mg of 2-(trifluoromethyl)benzoyl chloride and then 33 mg of triethylamine were added, and the mixture was stirred at room temperature for one hour. After completion of the reaction, the reaction mixture was mixed with 5 ml of water and extracted with ethyl acetate (15 ml×1), the resulting organic layer was washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 87 mg of a pale yellow resinous substance. The resinous substance was dissolved in 5 ml of ethanol, and 0.5 ml of a 1,4-dioxane solution (4 mol/L) of hydrogen chloride, and the mixture was stirred at 70° C. for 2 hours. The solvent was evaporated under reduced pressure, and the resulting residue was purified by silica gel column chromatography using ethyl acetate-hexane (with a gradient of from 1:9 to 3:7) as the eluent to obtain 80 mg of the desired product as a colorless resinous substance (E/Z=55/45).

$^1$H NMR (CDCl$_3$, Me$_4$Si, 300 MHz) δ8.23 and 8.19 (d, J=2.7 Hz, 1H), 7.35-7.75 (m, 4H), 7.28 and 7.27 (d, J=2.7 Hz, 1H), 6.57 and 6.50 (bs, 1H), 4.74 and 4.52 (d, J=6.0 Hz, 2H), 4.05 and 3.87 (s, 3H), 3.84 (bs, 3H).

Synthetic Example 10

(Z)—N-[2-(3,5-dichloropyridin-2-yl)-2-(isopropoxyimino)ethyl]-2-(trifluoromethyl)benzamide (Compound No. 2-128 of the present invention)

Step 1: Preparation of 1-[2-(3,5-dichloropyridin-2-yl)-2-oxoethyl]-1,3,5,7-tetraazatricyclo[3,3,1,1$^{3,7}$]decan-1-ium bromide 5.00 g of the 2-bromo-1-(3,5-dichloropyridin-2-yl)ethanone prepared in Step 2 in Synthetic Example 2 in 30 ml of chloroform was added dropwise to 2.61 g of 1,3,5,7-tetraazatricyclo[3,3,1,1$^{3,7}$]decane in 50 ml of chloroform with stirring at room temperature, and the mixture was stirred at the same temperature for 2 hours. After completion of the reaction, the precipitated crystals were collected by filtration and washed with 30 ml of chloroform to obtain 7.40 g of the desired product as white crystals.
m.p.>177.0° C. (decomposition)

Step 2: Preparation of 2-amino-1-(3,5-dichloropyridin-2-yl)ethanone hydrochloride To a suspension of 7.0 g of 1-[2-(3,5-dichloropyridin-2-yl)-2-oxoethyl]-1,3,5,7-tetraazatricyclo[3,3,1,1$^{3,7}$]decan-1-ium bromide in 70 ml of ethanol, 7 ml of concentrated hydrochloric acid was added, and the mixture was stirred at room temperature for 14 hours. After completion of the reaction, the solid was collected by filtration and washed with 15 ml of ethanol to obtain 3.7 g of the desired product as white crystals.
m.p.>207.0° C. (decomposition)
$^1$H NMR (CDCl$_3$, Me$_4$Si-DMSO-d$_6$, 300 MHz) δ8.83 (bs, 1H), 8.51 (bs, 1H), 4.54 (bs, 2H).

Step 3: Preparation of N-[2-(3,5-dichloropyridin-2-yl)-2-oxoethyl]-2-(trifluoromethyl)benzamide To a suspension of 3.7 g of 2-amino-1-(3,5-dichloropyridin-2-yl)ethanone hydrochloride in 50 ml of ethyl acetate, 30 ml of water and 3.5 g of 2-(trifluoromethyl)benzoyl chloride were added, and 6.1 g of potassium carbonate in 30 ml of water was added dropwise with stirring under cooling with ice, and the mixture was stirred at the same temperature for 30 minutes. After completion of the reaction, the reaction mixture was mixed with 20 ml of ethyl acetate, the resulting organic layer was collected, washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 2:8 to 6:4) as the eluent to obtain 3.8 g of the desired product as pale yellow crystals.
m.p.: 123.0 to 125.0° C.
$^1$H NMR (CDCl$_3$, Me$_4$Si, 300 MHz) δ8.55 (d, J=2.1 Hz, 1H), 7.88 (d, J=2.1 Hz, 1H), 7.5-7.75 (m, 4H), 6.69 (bs, 1H), 5.10 (d, J=4.8 Hz, 2H).

Step 4: Preparation of N-[2-(3,5-dichloropyridin-2-yl)-2-(hydroxyimino)ethyl]-2-(trifluoromethyl)benzamide To a solution of 3.38 g of N-[2-(3,5-dichloropyridin-2-yl)-2-oxoethyl]-2-(trifluoromethyl)benzamide and 0.934 g of hydroxylamine hydrochloride in 20 ml of ethanol, 1.10 g of sodium acetate was added, and the mixture was stirred at room temperature for 12 hours. After completion of the reaction, the solvent was evaporated under reduced pressure, the resulting residue was mixed with 40 ml of water and extracted with ethyl acetate (20 ml×2), the resulting organic layers were combined, washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 2:8 to 4:6) as the eluent to obtain 1.90 g of the desired product as white crystals.
m.p.: 134.0 to 136.0° C.
$^1$H NMR (CDCl$_3$, Me$_4$Si, 300 MHz) δ8.52 and 8.45 (d, J=2.4 Hz, 1H), 7.81 and 7.80 (d, J=2.4 Hz, 1H), 7.35-7.75 (m, 4H), 6.53 (bs, 1H), 4.80 and 4.55 (d, J=6.3 Hz, 2H).

Step 5: Preparation of (E)-N-[2-(3,5-dichloropyridin-2-yl)-2-(isopropoxyimino)ethyl]-2-(trifluoromethyl)benzamide (Compound No. 2-239 of the present invention)

To a suspension of 300 mg of N-[2-(3,5-dichloropyridin-2-yl)-2-(hydroxyimino)ethyl]-2-(trifluoromethyl)benzamide and 315 mg of potassium carbonate in 3 ml of N,N-dimethylformamide, 195 mg of 2-iodopropane was added, and the mixture was stirred at room temperature for 6 hours. After completion of the reaction, the reaction mixture was mixed with 20 ml of water and extracted with ethyl acetate (10 ml×2), the resulting organic layers were combined, washed with water (10 ml×2), the resulting organic layer was dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 258 mg of the desired product as white crystals.
m.p.: 54.0 to 57.0° C.
$^1$H NMR (CDCl$_3$, Me$_4$Si, 300 MHz) δ8.45 (d, J=2.1 Hz, 1H), 7.81 (d, J=2.1 Hz, 1H), 7.35-7.7 (m, 4H), 6.49 (bs, 1H), 4.76 (d, J=6.3 Hz, 2H), 4.45-4.6 (m, 1H), 1.33 (d, J=6.0 Hz, 6H).

Step 6: Preparation of (Z)—N-[2-(3,5-dichloropyridin-2-yl)-2-(isopropoxyimino)ethyl]-2-(trifluoromethyl)benzamide To 258 mg of (E)-N-[2-(3,5-dichloropyridin-2-yl)-2-(isopropoxyimino)ethyl]-2-(trifluoromethyl)benzamide in 4 ml of acetonitrile, 2 mg of benzophenone was added, and the mixture was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 3:7) as the eluent to obtain 231 mg of the desired product as white crystals.
m.p.: 107.0 to 108.0° C.
$^1$H NMR (CDCl$_3$, Me$_4$Si, 300 MHz) δ8.50 (d, J=2.1 Hz, 1H), 7.78 (d, J=2.1 Hz, 1H), 7.5-7.8 (m, 4H), 6.54 (bs, 1H), 4.53 (d, J=5.1 Hz, 2H), 4.3-4.45 (m, 1H), 1.18 (d, J=6.3 Hz, 6H).

Synthetic Example 11

(Z)—N-[2-(3,5-dichloropyridin-2-yl)-2-(tert-butoxyimino)ethyl]-2-(trifluoromethyl)benzamide (compound No. 2-140 of the present invention)

Step 1: Preparation of N-[2-(3,5-dichloropyridin-2-yl)-2-(tert-butoxyimino)ethyl]-2-(trifluoromethyl) benzamide (compound No. 2-139 of the present invention)

To a solution of 200 mg of the N-[2-(3,5-dichloropyridin-2-yl)-2-oxoethyl]-2-(trifluoromethyl)benzamide prepared in Step 3 in Synthetic Example 10 and 199 mg of O-(tert-butyl)hydroxylamine hydrochloride in 2.6 ml of ethanol, 167 mg of pyridine was added, and the mixture was stirred at 70° C. for 18 hours. After completion of the reaction, the solvent was evaporated under reduced pressure, the resulting residue was mixed with 2 ml of water and extracted with ethyl acetate (2 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 207 mg of the desired product as a colorless resinous substance.

$^1$H NMR (CDCl$_3$, Me$_4$Si, 300 MHz) δ8.50 and 8.44 (d, J=2.4 Hz, 1H), 7.25-7.85 (m, 5H), 6.54 (bs, 1H), 4.77 and 4.54 (d, J=5.7 Hz, 2H), 1.37 and 1.24 (s, 9H).

Step 2: Preparation of (Z)—N-[2-(3,5-dichloropyridin-2-yl)-2-(tert-butoxyimino)ethyl]-2-(trifluoromethyl)benzamide 207 mg of N-[2-(3,5-dichloropyridin-2-yl)-2-(tert-butoxyimino)ethyl]-2-(trifluoromethyl)benzamide in 4 ml of acetonitrile was irradiated with light for 8 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) to obtain 190 mg of the desired product as a colorless resinous substance.

$^1$H NMR (CDCl$_3$, Me$_4$Si, 300 MHz) δ8.50 (d, J=2.0 Hz, 1H), 7.77 (d, J=2.0 Hz, 1H), 7.5-7.75 (m, 4H), 6.56 (bs, 1H), 4.53 (d, J=5.1 Hz, 2H), 1.24 (s, 9H).

Synthetic Example 12

(Z)—N-[2-(3,5-dichloropyridin-2-yl)-2-(2,2,2-trifluoroethoxyimino)ethyl]-2-(trifluoromethyl)benzamide (compound No. 2-212 of the present invention)

Step 1: Preparation of tert-butyl N-[2-(3,5-dichloropyridin-2-yl)-2-oxoethyl]carbamate To 35.1 g of 2-bromo-3,5-dichloropyridine in 10 ml of tetrahydrofuran, 116.3 ml of a 1.3 M tetrahydrofuran solution of isopropylmagnesium chloride-lithium chloride complex was added dropwise with stirring at −20° C., and after the addition, the mixture was stirred at the same temperature for 15 minutes. Then, to the reaction mixture, 15.0 g of N-methoxy-N-methyl-2-(tert-butoxycarbonylamino)acetamide in 114 ml of tetrahydrofuran was added dropwise, and after the addition, the mixture was stirred at the same temperature for another 2 hours. After completion of the reaction, the reaction mixture was mixed with 100 ml of saturated aqueous ammonium chloride and 100 ml of water and extracted with ethyl acetate (200 ml×2), the resulting organic layers were combined, washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 0:10 to 3:7) as the eluent to obtain 12.5 g of the desired product as pale yellow crystals.

m.p.: 82.0 to 84.0° C.

$^1$H NMR (CDCl$_3$, Me$_4$Si, 300 MHz) δ8.51 (d, J=2.1 Hz, 1H), 7.85 (d, J=2.1 Hz, 1H), 5.31 (bs, 1H), 4.76 (bs, 2H), 1.47 (s, 9H).

Step 2: Preparation of tert-butyl N-[2-(3,5-dichloropyridin-2-yl)-2-(hydroxyimino)ethyl]carbamate To a solution of 10.6 g of tert-butyl N-[2-(3,5-dichloropyridin-2-yl)-2-oxoethyl]carbamate and 4.8 g of hydroxylamine hydrochloride in 87 ml of ethanol, 6.1 g of pyridine was added, and the mixture was stirred at room temperature for 24 hours. After completion of the reaction, the solvent was evaporated under reduced pressure, the resulting residue was mixed with 50 ml of water and extracted with ethyl acetate (100 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 40:60) as the eluent to obtain 10.1 g of the desired product as a pale yellow resinous substance.

$^1$H NMR (CDCl$_3$, Me$_4$Si, 300 MHz) δ8.52 and 8.47 (d, J=2.4 Hz, 1H), 7.82 and 7.79 (d, J=2.4 Hz, 1H), 5.65 and 5.16 (bs, 1H), 4.46 and 4.24 (d, J=5.4 Hz, 2H), 1.39 and 1.34 (s, 9H).

Step 3: Preparation of tert-butyl N-[2-(3,5-dichloropyridin-2-yl)-2-(2,2,2-trifluoroethoxyimino)ethyl] carbamate To 5.0 g of tert-butyl N-[2-(3,5-dichloropyridin-2-yl)-2-(hydroxyimino)ethyl]carbamate in 16.0 ml of N,N-dimethylformamide, 4.3 g of potassium carbonate and 5.4 g of 2,2,2-trifluoroethyl trifluoromethanesulfonate were added, and the mixture was stirred at room temperature for 18 hours. After completion of the reaction, the reaction mixture was mixed with 100 ml of water and extracted with ethyl acetate (100 ml×2), the resulting organic layers were combined, washed with water (50 ml×2) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 0:10 to 3:7) as the eluent to obtain 4.8 g of the desired product as a pale yellow oil.

$^1$H NMR (CDCl$_3$, Me$_4$Si, 300 MHz) δ8.51 and 8.49 (d, J=1.8 Hz, 1H), 7.80 and 7.78 (d, J=1.8 Hz, 1H), 4.94 (bs, 1H), 4.0-4.65 (m, 4H), 1.39 and 1.34 (s, 9H).

Step 4: Preparation of 2-aminol-(3,5-dichloropyridin-2-yl)ethanone-O-(2,2,2-trifluoroethyl)oxime hydrochloride To 4.9 g of tert-butyl N-[2-(3,5-dichloropyridin-2-yl)-2-(2,2,2-trifluoroethoxyimino)ethyl]carbamate in 5 ml of 1,4-dioxane, 25 ml of a 1,4-dioxane solution (4 mol/L) of hydrogen chloride was added, and the mixture was stirred at room temperature for 3 hours. After completion of the reaction, the solvent was evaporated under reduced pressure, and the resulting residue was washed with 20 ml of hexane to obtain 3.1 g of the desired product as pale brown crystals.
m.p.: 141.0 to 143.0° C.
$^1$H NMR (CDCl$_3$, Me$_4$Si, 300 MHz) δ8.98 (bs, 3H), 8.56 and 8.52 (d, J=2.1 Hz, 1H), 7.83 and 7.80 (d, J=2.1 Hz, 1H), 4.72 and 4.54 (q, J=8.7 Hz, 2H), 4.28 and 4.10 (bs, 2H).

Step 5: Preparation of N-[2-(3,5-dichloropyridin-2-yl)-2-(2,2,2-trifluoroethoxyimino)ethyl]-2-(trifluoromethyl)benzamide (compound No. 2-011 of the present invention)

To 2.0 g of 2-aminol-(3,5-dichloropyridin-2-yl)ethanone-O-(2,2,2-trifluoroethyl)oxime hydrochloride in 12.0 ml of water, 1.4 g of 2-(trifluoromethyl)benzoyl chloride in 12.0 ml of dichloromethane and 2.4 g of potassium carbonate were added at room temperature with stirring, and the mixture was stirred at the same temperature for 2 hours. After completion of the reaction, the resulting organic layer was collected and dried over anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 2.6 g of the desired product as a pale yellow resinous substance.
$^1$H NMR (CDCl$_3$, Me$_4$Si, 300 MHz) δ8.51 and 8.46 (d, J=2.1 Hz, 1H), 7.82 and 7.81 (d, J=2.1 Hz, 1H), 7.35-7.75 (m, 4H), 6.39 (bs, 1H), 4.80 and 4.57 (d, J=6.0 Hz, 2H), 4.61 and 4.42 (q, J=8.4 Hz, 2H).

Step 6: Preparation of (Z)—N-[2-(3,5-dichloropyridin-2-yl)-2-(2,2,2-trifluoroethoxyimino)ethyl]-2-(trifluoromethyl)benzamide 2.6 g of N-[2-(3,5-dichloropyridin-2-yl)-2-(2,2,2-trifluoroethoxyimino)ethyl]-2-(trifluoromethyl)benzamide was dissolved in 12.0 ml of acetonitrile, and the solution was irradiated with light for 48 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was washed with 20 ml of hexane to obtain 2.1 g of the desired product as white crystals.
m.p.: 100.0 to 102.0° C.
$^1$H NMR (CDCl$_3$, Me$_4$Si, 300 MHz) δ8.52 (d, J=2.1 Hz, 1H), 7.45-7.85 (m, 5H), 6.39 (bs, 1H), 4.57 (d, J=5.4 Hz, 2H), 4.42 (q, J=8.7 Hz, 2H).

Synthetic Example 13

(S)—N-[2-(3,5-dichloropyridin-2-yl)-2-(Z)-(isopropoxyimino)-1-methylethyl]-2-(trifluoromethyl)benzamide (compound No. 2-132 of the present invention)

Step 1: Preparation of (S)—N-methoxy-N-methyl-2-(tert-butoxycarbonylamino)propionamide To 20.0 g of N-(tert-butoxycarbonyl)-L-alanine in 352 ml of dichloromethane, 12.4 g of N,O-dimethylhydroxylamine hydrochloride, 15.7 g of 1-hydroxybenzotriazole monohydrate, 24.3 g of 1-(3-dimethylaminopropyl)-3-ethylcarbodiimide hydrochloride and 42.7 g of triethylamine were added, and the mixture was stirred at room temperature for 1.5 hours. After completion of the reaction, the reaction mixture was washed with 500 ml of saturated aqueous sodium hydrogen carbonate, 500 ml of 1N aqueous hydrochloric acid and 500 ml of water in this order, the resulting organic layer was dried over saturated aqueous sodium chloride and then anhydrous sodium sulfate, and the solvent was evaporated under reduced pressure. The resulting residue was washed with 200 ml of hexane to obtain 13.1 g of the desired product as white crystals.
m.p.: 144.0 to 145.0° C.
$^1$H NMR (CDCl$_3$, Me$_4$Si, 300 MHz) δ5.22 (bs, 1H), 4.68 (bs, 1H), 3.77 (s, 3H), 3.21 (s, 3H), 1.44 (s, 9H), 1.31 (d, J=6.9 Hz, 3H).

Step 2: Preparation of tert-butyl (S)—N-[2-(3,5-dichloropyridin-2-yl)-1-methyl-2-oxoethyl]carbamate To 11.0 g of 2-bromo-3,5-dichloropyridine in 5 ml of tetrahydrofuran, 36.4 ml of a 1.3 M tetrahydrofuran solution of isopropylmagnesium chloride-lithium chloride complex was added dropwise with stirring at −20° C., and after the addition, the mixture was stirred at the same temperature for 15 minutes. Then, to the reaction mixture, 5.0 g of (S)—N-methoxy-N-methyl-2-(tert-butoxycarbonylamino)propionamide in 36 ml of tetrahydrofuran was added dropwise, and after the addition, the mixture was stirred at the same temperature for another 2 hours. After completion of the reaction, the reaction mixture was mixed with 30 ml of saturated aqueous ammonium chloride and 10 ml of water and extracted with ethyl acetate (40 ml×2), the resulting organic layers were combined, washed with water (40 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 10:0 to 3:7) to obtain 4.5 g of the desired product as a pale yellow oil.
$^1$H NMR (CDCl$_3$, Me$_4$Si, 300 MHz) δ8.51 (d, J=2.1 Hz, 1H), 7.84 (d, J=2.1 Hz, 1H), 5.50 (bs, 1H), 5.32 (bs, 1H), 1.46 (s, 9H), 1.36 (d, J=7.2 Hz, 3H).
Optical purity: 95% e.e.
Optical rotation: $[α]_D^{17.5}$−20.20° (CHCl$_3$, c=0.10)

Step 3: Preparation of tert-butyl (S)—N-[2-(3,5-dichloropyridin-2-yl)-2-hydroxyimino-1-methylethyl]carbamate To a solution of 1.0 g of tert-butyl (S)—N-[2-(3,5-dichloropyridin-2-yl)-1-methyl-2-oxoethyl]carbamate and 239 mg of hydroxylamine hydrochloride in 5 ml of ethanol, 272 mg of pyridine was added, and the mixture was stirred at room temperature for 18 hours. After completion of the reaction, the solvent was evaporated under reduced pressure, the resulting residue was mixed with 10 ml of water and extracted with ethyl acetate (10 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 40:60)

as the eluent to obtain 740 mg of the desired product as pale yellow crystals.

m.p.: 51.0 to 53.0° C.
$^1$H NMR (CDCl$_3$, Me$_4$Si, 300 MHz) δ8.53 (d, J=2.1 Hz, 1H), 7.78 (d, J=2.1 Hz, 1H), 5.15 (bs, 1H), 4.81 (bs, 1H), 1.3-1.65 (m, 12H).
Optical purity: 95% e.e.
Optical rotation: $[α]_D^{17.8}$ −27.40° (CHCl$_3$, c=0.10)

Step 4: Preparation of tert-butyl (S)—N-[2-(3,5-dichloropyridin-2-yl)-2-(isopropoxyimino)-1-methylethyl]carbamate To 655 mg of tert-butyl (S)—N-[2-(3,5-dichloropyridin-2-yl)-2-hydroxyimino-1-methylethyl]carbamate in 1.6 ml of N,N-dimethylformamide, 445 mg of potassium carbonate and 789 mg of 2-iodopropane were added, and the mixture was stirred at room temperature for 18 hours. After completion of the reaction, the reaction mixture was mixed with 5 ml of water and extracted with ethyl acetate (10 ml×2), the resulting organic layers were combined, washed with water (10 ml×2) and dried over saturated aqueous sodium chloride and then aqueous sodium sulfate, and the solvent was evaporated under reduced pressure. The resulting residue was purified by silica gel column chromatography using ethyl acetate-hexane (with a gradient of from 0:10 to 3:7) as the eluent to obtain 411 mg of the desired product as a colorless oil.

$^1$H NMR (CDCl$_3$, Me$_4$Si, 300 MHz) δ8.49 and 8.44 (d, J=2.1 Hz, 1H), 7.77 and 7.73 (d, J=2.1 Hz, 1H), 5.20 (bs, 1H), 4.74 (bs, 1H), 4.25-4.5 (m, 1H), 1.1-1.6 (m, 18H).
Optical purity: 95% e.e.
Optical rotation: $[α]_D^{18.0}$ −29.90° (CHCl$_3$, c=0.14)

Step 5: Preparation of (S)-2-amino-1-(3,5-dichloropyridin-2-yl)propanone-O-isopropyloxime hydrochloride To 350 mg of tert-butyl (S)—N-[2-(3,5-dichloropyridin-2-yl)-2-(isopropoxyimino)-1-methylethyl]carbamate in 3 ml of 1,4-dioxane, 5 ml of a 1,4-dioxane solution (4 mol/L) of hydrogen chloride was added, and the mixture was stirred at room temperature for 6 hours. After completion of the reaction, the solvent was evaporated under reduced pressure, and the resulting residue was washed with 20 ml of hexane to obtain 253 mg of the desired product as white crystals.

m.p.: 215.0 to 216.0° C.
$^1$H NMR (CDCl$_3$, Me$_4$Si, 300 MHz) δ9.00 (bs, 3H), 8.51 (d, J=2.1 Hz, 1H), 7.76 (d, J=2.1 Hz, 1H), 4.35-4.6 (m, 2H), 1.73 and 1.57 (d, J=6.9 Hz, 3H), 1.15-1.4 (m, 6H).
Optical purity: 95% e.e.
Optical rotation: $[α]_D^{18.6}$ −15.50° (CHCl$_3$, c=0.10)

Step 6: Preparation of (S)—N-[2-(3,5-dichloropyridin-2-yl)-2-(isopropoxyimino)-1-methylethyl]-2-(trifluoromethyl)benzamide (compound No. 2-130 of the present invention)

To 210 mg of (S)-2-amino-1-(3,5-dichloropyridin-2-yl)propanone-O-isopropyloxime hydrochloride in 1.3 ml of water, 151 mg of 2-(trifluoromethyl)benzoyl chloride in 1.3 ml of dichloromethane and 278 mg of potassium carbonate were added with stirring at room temperature, and the mixture was stirred at the same temperature for 2 hours. After completion of the reaction, the resulting organic layer was collected and dried over anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 221 mg of the desired product as a colorless resinous substance.

$^1$H NMR (CDCl$_3$, Me$_4$Si, 300 MHz) δ8.48 and 8.40 (d, J=1.8 Hz, 1H), 7.4-7.85 (m, 5H), 7.00 and 6.85 (bs, 1H), 5.7-5.85 and 5.15-5.3 (m, 1H), 4.25-4.55 (m, 1H), 1.15-1.6 (m, 9H).
Optical purity: 95% e.e.
Optical rotation: $[α]_D^{19.0}$ −13.20° (EtOH, c=0.10)

Step 7: Preparation of (S)—N-[2-(3,5-dichloropyridin-2-yl)-2-[(Z)-isopropoxyimino]-1-methylethyl]-2-(trifluoromethyl)benzamide 240 mg of (S)—N-[2-(3,5-dichloropyridin-2-yl)-2-(isopropoxyimino)-1-methylethyl]-2-(trifluoromethyl)benzamide was dissolved in 4 ml of acetonitrile, and the solution was irradiated with light for 8 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) as the eluent to obtain 153 mg of the desired product as a colorless resinous substance.

$^1$H NMR (CDCl$_3$, Me$_4$Si, 300 MHz) δ8.48 (d, J=2.1 Hz, 1H), 7.78 (d, J=2.1 Hz, 1H), 7.45-7.75 (m, 4H), 6.84 (bs, 1H), 5.15-5.3 (m, 1H), 4.25-4.45 (m, 1H), 1.44 (d, J=6.6 Hz, 3H), 1.18 (d, J=6.0 Hz, 6H).
Optical purity: 95% e.e.
Optical rotation: $[α]_D^{21.8}$ −8.60° (EtOH, c=0.10)

Synthetic Example 14

(S)—N-[2-(3, 5-dichloropyridin-2-yl)-2-[(Z)-ethoxyimino]-1-methylethyl]-2-(trifluoromethyl) benzamide (compound No. 2-124 of the present invention)

Step 1: Preparation of tert-butyl (S)—N-[2-(3,5-dichloropyridin-2-yl)-2-ethoxyimino-1-methylethyl] carbamate To a solution of 1.0 g of the tert-butyl (S)—N-[2-(3,5-dichloropyridin-2-yl)-1-methyl-2-oxoethyl]carbamate prepared in Step 2 in Synthetic Example 13 and 336 mg of ethoxyamine hydrochloride in 6.3 ml of ethanol, 272 mg of pyridine was added, and the mixture was stirred at room temperature for 18 hours. After completion of the reaction, the solvent was distilled off under reduced pressure, the resulting residue was mixed with 10 ml of water and extracted with ethyl acetate (10 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 40:60) as the eluent to obtain 824 mg of the desired produced as a pale yellow oil.

$^1$H NMR (CDCl$_3$, Me$_4$Si, 300 MHz) δ8.50 (d, J=2.1 Hz, 1H), 7.74 (d, J=2.1 Hz, 1H), 5.19 (bs, 1H), 4.75 (bs, 1H), 4.26 and 4.11 (q, J=7.2 Hz, 2H), 1.1-1.55 (m, 15H).
Optical purity: 95% e.e.
Optical rotation: $[α]_D^{17.9}$ −30.00° (CHCl$_3$, c=0.10)

Step 2: Preparation of (S)-2-amino-1-(3,5-dichloro-pyridin-2-yl)propanone-O-ethyloxime hydrochloride To 780 mg of tert-butyl (S)—N-[2-(3,5-dichloropyridin-2-yl)-2-ethoxyimino-1-methylethyl]carbamate in 3 ml of 1,4-dioxane, 5 ml of a 1,4-dioxane solution (4 mol/L) of hydrogen chloride was added, and the mixture was stirred at room temperature for 6 hours. After completion of the reaction, the solvent was evaporated under reduced pressure, and the resulting residue was washed with 20 ml of hexane to obtain 643 mg of the desired product as beige crystals.
m.p.: 209.0 to 210.0° C.
$^1$H NMR (CDCl$_3$, Me$_4$Si, 300 MHz) δ8.98 (bs, 3H), 8.52 (d, J=2.1 Hz, 1H), 7.77 (d, J=2.1 Hz, 1H), 4.51 (bs, 1H), 4.35 and 4.20 (q, J=7.2 Hz, 2H), 1.73 and 1.59 (d, J=7.2 Hz, 3H), 1.38 and 1.25 (t, J=7.2 Hz, 3H).
Optical purity: 95% e.e.
Optical rotation: $[α]_D^{18.5}$ −10.90° (CHCl$_3$, c=0.10)

Step 3: Preparation of (S)—N-[2-(3,5-dichloropyri-din-2-yl)-2-ethoxyimino-1-methylethyl]-2-(trifluo-romethyl)benzamide (compound No. 2-122 of the present invention)

To 550 mg of (S)-2-amino-1-(3,5-dichloropyridin-2-yl)propanone-O-ethyloxime hydrochloride in 3.7 ml of water, 423 mg of 2-(trifluoromethyl)benzoyl chloride in 3.7 ml of dichloromethane and 763 mg of potassium carbonate were added with stirring at room temperature, and the mixture was stirred at the same temperature for 2 hours. After completion of the reaction, the organic layer was collected and dried over anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 800 mg of the desired product as a colorless resinous substance.
$^1$H NMR (CDCl$_3$, Me$_4$Si, 300 MHz) δ8.49 (d, J=2.1 Hz, 1H), 7.4-7.85 (m, 5H), 6.98 and 6.81 (bs, 1H), 5.75-5.85 and 5.15-5.35 (m, 1H), 4.29 and 4.12 (q, J=7.2 Hz, 2H), 1.15-1.65 (m, 6H).
Optical purity: 95% e.e.
Optical rotation: $[α]_D^{19.0}$ −13.10° (EtOH, c=0.10)

Step 4: Preparation of (S)—N-[2-(3,5-dichloropyri-din-2-yl)-2-[(Z)-ethoxyimino]-1-methylethyl]-2-(trifluoromethyl)benzamide 580 mg of (S)—N-[2-(3,5-dichloropyridin-2-yl)-2-ethoxyimino-1-methylethyl]-2-(trifluoromethyl)benzamide was dissolved in 3 ml of acetonitrile, and the solution was irradiated with light for 8 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) as the eluent to obtain 557 mg of the desired product as a colorless resinous substance.

$^1$H NMR (CDCl$_3$, Me$_4$Si, 300 MHz) δ8.49 (d, J=2.1 Hz, 1H), 7.4-7.85 (m, 5H), 6.81 (bs, 1H), 5.15-5.35 (m, 1H), 4.12 (q, J=7.2 Hz, 2H), 1.45 (d, J=6.9 Hz, 3H), 1.20 (t, J=7.2 Hz, 3H).
Optical purity: 95% e.e.
Optical rotation: $[α]_D^{21.7}$ −11.40° (EtOH, c=0.10)

Synthetic Example 15

(Z)—N-[2-(3,5-dichloropyridin-2-yl)-2-(sec-butoxy-imino)ethyl]-2-(trifluoromethyl)benzamide (compound No. 2-136 of the present invention)

Step 1: Preparation of N-[2-(3,5-dichloropyridin-2-yl)-2-oxoethyl]-2-(trifluoromethyl)benzamide To 5.0 g of the tert-butyl N-[2-(3,5-dichloropyridin-2-yl)-2-oxoethyl]carbamate prepared in Step 1 in Synthetic Example 12 in 2 ml of 1,4-dioxane, 25 ml of a 1,4-dioxane solution (4 mol/L) of hydrogen chloride was added, and the mixture was stirred at room temperature for 1.5 hours. After completion of the reaction, the solvent was evaporated under reduced pressure, the resulting residue was dissolved in 33 ml of water and 33 ml of dichloromethane, and to the resulting solution, 4.5 g of potassium carbonate was added and further, 3.8 g of 2-(trifluoromethyl)benzoyl chloride was added with stirring under cooling with ice, and the mixture was stirred at room temperature for 2 hours. After completion of the reaction, the resulting organic layer was collected and dried over anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 2.8 g of the desired product as pale yellow crystals.
m.p.: 123.0 to 125.0° C.
$^1$H NMR (CDCl$_3$, Me$_4$Si, 300 MHz) δ8.56 (d, J=2.1 Hz, 1H), 7.88 (d, J=2.1 Hz, 1H), 7.5-7.8 (m, 4H), 6.69 (bs, 1H), 5.10 (d, J=5.1 Hz, 2H).

Step 2: Preparation of N-[2-(3,5-dichloropyridin-2-yl)-2-(hydroxyimino)ethyl]-2-(trifluoromethyl)benz-amide To 2.8 g of N-[2-(3,5-dichloropyridin-2-yl)-2-oxoethyl]-2-(trifluoromethyl)benzamide in 19 ml of ethanol, 1.0 g of hydroxylamine hydrochloride was added, and the mixture was stirred at room temperature for 96 hours. After completion of the reaction, the solvent was evaporated under reduced pressure, the resulting residue was mixed with 50 ml of water and extracted with ethyl acetate (50 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 2.8 g of the desired product as pale yellow crystals.
m.p.: 134.0 to 136.0° C.
$^1$H NMR (CDCl$_3$, Me$_4$Si, 300 MHz) δ8.52 and 8.45 (d, J=2.4 Hz, 1H), 7.81 and 7.80 (d, J=2.4 Hz, 1H), 7.35-7.75 (m, 4H), 6.53 (bs, 1H), 4.80 and 4.55 (d, J=6.3 Hz, 2H).

Step 3: Preparation of N-[2-(3,5-dichloropyridin-2-yl)-2-(sec-butoxyimino)ethyl]-2-(trifluoromethyl) benzamide (Compound No. 2-009 of the present invention)

To a suspension of 500 mg of N-[2-(3,5-dichloropyridin-2-yl)-2-(hydroxyimino)ethyl]-2-(trifluoromethyl)benzamide and 352 mg of potassium carbonate in 1.3 ml of N,N-dimethylformamide, 704 mg of 2-iodobutane was added, and the mixture was stirred at room temperature for 12 hours. After completion the reaction, the reaction mixture was mixed with 3 ml of water and extracted with ethyl acetate (3 ml×2), the resulting organic layers were combined, washed with water (3 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 522 mg of the desired product as a pale yellow resinous substance.

$^1$H NMR (CDCl$_3$, Me$_4$Si, 300 MHz) δ8.50 and 8.44 (d, J=2.1 Hz, 1H), 7.81 and 7.78 (d, J=2.1 Hz, 1H), 7.35-7.75 (m, 4H), 6.53 (bs, 1H), 4.76 and 4.52 (d, J=5.7 Hz, 2H), 4.25-4.35 and 4.1-4.2 (m, 1H), 1.35-1.85 (m, 2H), 1.30 and 1.17 (d, J=6.3 Hz, 3H), 0.94 and 0.83 (t, J=7.2 Hz, 3H).

Step 4: Preparation of (Z)—N-[2-(3,5-dichloropyridin-2-yl)-2-(sec-butoxyimino)ethyl]-2-(trifluoromethyl)benzamide To 522 mg of N-[2-(3,5-dichloropyridin-2-yl)-2-(sec-butoxyimino)ethyl]-2-(trifluoromethyl)benzamide in 3 ml of acetonitrile, 1 mg of benzophenone was added, and the mixture was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 5:95 to 50:50) as the eluent to obtain 416 mg of the desired product as white crystals.

m.p.: 68.0 to 70.0° C.

$^1$H NMR (CDCl$_3$, Me$_4$Si, 300 MHz) δ8.50 (d, J=2.1 Hz, 1H), 7.45-7.8 (m, 5H), 6.53 (bs, 1H), 4.53 (d, J=4.8 Hz, 2H), 4.05-4.2 (m, 1H), 1.35-1.7 (m, 2H), 1.18 (d, J=6.3 Hz, 3H), 0.84 (t, J=7.5 Hz, 3H).

Synthetic Example 16

(Z)—N-[2-(3,5-dichloropyridin-2-yl)-2-(methoxyimino)ethyl]-2-(trifluoromethyl)benzamide (Compound No. 2-114 of the present invention)

Step 1: Preparation of N-[2-(3,5-dichloropyridin-2-yl)-2-(methoxyimino)ethyl]-2-(trifluoromethyl)benzamide (Compound No. 2-002 of the present invention)

To a solution of 200 mg of the N-[2-(3,5-dichloropyridin-2-yl)-2-oxoethyl]-2-(trifluoromethyl)benzamide prepared in Step 1 in Synthetic Example 15 and 133 mg of methoxyamine hydrochloride in 2.7 ml of ethanol, 168 mg of pyridine was added, and the mixture was stirred at 80° C. for 6 hours. After completion of the reaction, the reaction mixture was mixed with 10 ml of water and extracted with ethyl acetate (10 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 191 mg of the desired product as a pale yellow resinous substance.

$^1$H NMR (CDCl$_3$, Me$_4$Si, 300 MHz) δ8.50 and 8.45 (d, J=2.1 Hz, 1H), 7.80 and 7.78 (d, J=2.1 Hz, 1H), 7.35-7.75 (m, 4H), 6.48 and 6.43 (bs, 1H), 4.73 and 4.53 (d, J=6.3 Hz, 2H), 4.06 and 4.02 (s, 3H).

Step 2: Preparation of (Z)—N-[2-(3,5-dichloropyridin-2-yl)-2-(methoxyimino)ethyl]-2-(trifluoromethyl)benzamide 191 mg of N-[2-(3,5-dichloropyridin-2-yl)-2-(methoxyimino)ethyl]-2-(trifluoromethyl)benzamide in 4 ml of acetonitrile was irradiated with light for 11 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 3:7) as the eluent to obtain 149 mg of the desired product as white crystals.

m.p.: 88.0 to 89.0° C.

$^1$H NMR (CDCl$_3$, Me$_4$Si, 300 MHz) δ8.50 (d, J=2.0 Hz, 1H), 7.78 (d, J=2.0 Hz, 1H), 7.35-7.75 (m, 4H), 6.45 (bs, 1H), 4.53 (d, J=4.8 Hz, 2H), 4.02 (s, 3H).

Synthetic Example 17

(Z)—N-[2-(3, 5-dichloropyridin-2-yl)-2-[1-(4-fluorophenyl)ethoxyimino]ethyl]-2-(trifluoromethyl)benzamide (Compound No. 2-174 of the present invention)

Step 1: Preparation of N-[2-methoxy(methyl)amino-2-oxoethyl]-2-(trifluoromethyl)benzamide To 45.2 g of 2-[2-(trifluoromethyl)benzoylamino]acetic acid in 609 ml of dichloromethane, 21.4 g of N,O-dimethylhydroxylamine hydrochloride, 42.0 g of 1-(3-dimethylaminopropyl)-3-ethylcarbodiimide hydrochloride, 73.8 g of triethylamine and 2.2 g of 4-(dimethylamino)pyridine were added, and the mixture was stirred at room temperature for 18 hours. After completion of the reaction, the reaction mixture was washed with 500 ml of saturated anhydrous sodium hydrogen carbonate, 500 ml of 1N aqueous hydrochloric acid twice and 500 ml of water in this order, the resulting organic layer was dried over saturated aqueous sodium chloride and then anhydrous sodium sulfate, and the solvent was evaporated under reduced pressure. The resulting residue was washed with 200 ml of hexane to obtain 31.4 g of the desired product as white crystals.

m.p.: 106.0 to 107.0° C.

$^1$H NMR (CDCl$_3$, Me$_4$Si, 300 MHz) δ7.5-7.75 (m, 4H), 6.70 (bs, 1H), 4.40 (d, J=3.9 Hz, 2H), 3.77 (s, 3H), 3.25 (s, 3H).

Step 2: Preparation of N-[2-(3,5-dichloropyridin-2-yl)-2-oxoethyl]-2-(trifluoromethyl)benzamide To 17.6 g of 2-bromo-3,5-dichloropyridin in 5 ml of tetrahydrofuran, 58.3 ml of a 1.3M tetrahydrofuran solution of isopropylmagnesium chloride-lithium chloride complex was added dropwise with stirring at −20° C., and after the addition, the mixture was stirred at the same temperature for 30 minutes. Then, to the reaction mixture, 10.0 g of N-[2- methoxy(methyl)amino-2-oxoethyl]-2-(trifluoromethyl) benzamide in 57.4 ml of tetrahydrofuran was added dropwise, and after the addition, the mixture was stirred at room temperature for another 3 hours. After completion of the reaction, the reaction mixture was mixed with 100 ml of saturated aqueous ammonium chloride and 100 ml of water and extracted with ethyl acetate (150 ml×2), the resulting organic layers were combined, washed with water (100 ml×1) and dried over saturated aqueous sodium chloride and then anhydrous sodium sulfate, and the solvent was distilled off under reduced pressure. The residue was purified by silica gel column chromatography using ethyl acetate-hexane (with a gradient of from 5:95 to 50:50) as the eluent to obtain 3.0 g of the desired product as pale yellow crystals.

m.p.: 123.0 to 125.0° C.

$^1$H NMR (CDCl$_3$, Me$_4$Si, 300 MHz) δ8.56 (d, J=2.1 Hz, 1H), 7.88 (d, J=2.1 Hz, 1H), 7.5-7.8 (m, 4H), 6.69 (bs, 1H), 5.10 (d, J=5.1 Hz, 2H).

Step 3: Preparation of N-[2-(3,5-dichloropyridin-2-yl)-2-(hydroxyimino)ethyl]-2-(trifluoromethyl)benzamide To 2.8 g of N-[2-(3,5-dichloropyridin-2-yl)-2-oxoethyl]-2-(trifluoromethyl)benzamide in 19 ml of ethanol, 1.0 g of hydroxylamine hydrochloride was added, and the mixture was stirred at room temperature for 96 hours. After completion of the reaction, the solvent was evaporated under reduced pressure, the resulting residue was mixed with 50 ml of water and extracted with ethyl acetate (50 ml×2), the resulting organic layers were combined, dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 2.8 g of the desired product as white crystals.

m.p.: 134.0 to 136.0° C.

$^1$H NMR (CDCl$_3$, Me$_4$Si, 300 MHz) δ8.52 and 8.45 (d, J=2.4 Hz, 1H), 7.81 and 7.80 (d, J=2.4 Hz, 1H), 7.35-7.75 (m, 4H), 6.53 (bs, 1H), 4.80 and 4.55 (d, J=6.3 Hz, 2H).

Step. 4: Preparation of N-[2-(3,5-dichloropyridin-2-yl)-2-[1-(4-fluorophenyl)ethoxyimino]ethyl]-2-(trifluoromethyl)benzamide (Compound No. 2-173 of the present invention)

To a suspension of 200 mg of N-[2-(3,5-dichloropyridin-2-yl)-2-(hydroxyimino)ethyl]-2-(trifluoromethyl)benzamide and 211 mg of potassium carbonate in 2 ml of N,N-dimethylformamide, 155 mg of 1-(1-bromoethyl)-4-fluorobenzene was added, and the mixture was stirred at room temperature for 18 hours. After completion of the reaction, the reaction mixture was mixed with 3 ml of water and extracted with ethyl acetate (3 ml×2), the resulting organic layers were combined, washed with water (3 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 171 mg of the desired product as a pale yellow resinous substance.

$^1$H NMR (CDCl$_3$, Me$_4$Si, 300 MHz) δ8.52 and 8.42 (d, J=2.1 Hz, 1H), 7.80 and 7.77 (d, J=2.1 Hz, 1H), 6.0-7.75 (m, 8H), 6.40 (bs, 1H), 5.38 and 5.21 (q, J=6.9 Hz, 1H), 4.81 and 4.49 (d, J=5.7 Hz, 2H), 1.64 and 1.45 (d, J=6.9 Hz, 3H).

Step 5: Preparation of (Z)—N-[2-(3,5-dichloropyridin-2-yl)-2-[1-(4-fluorophenyl)ethoxyimino]ethyl]-2-(trifluoromethyl)benzamide To 171 mg of N-[2-(3,5-dichloropyridin-2-yl)-2-[1-(4-fluorophenyl)ethoxyimino]ethyl]-2-(trifluoromethyl)benzamide in 3 ml of acetonitrile, 1 mg of benzophenone was added, and the mixture was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 5:95 to 50:50) as the eluent to obtain 98 mg of the desired product as a pale yellow resinous substance.

$^1$H NMR (CDCl$_3$, Me$_4$Si, 300 MHz) δ8.52 (d, J=2.0 Hz, 1H), 7.80 (d, J=2.0 Hz, 1H), 6.85-7.75 (m, 8H), 6.38 (bs, 1H), 5.22 (q, J=6.6 Hz, 1H), 4.50 (d, J=5.5 Hz, 2H), 1.45 (d, J=6.6 Hz, 3H).

Synthetic Example 18

(Z)—N-[2-(3,5-dibromopyridin-2-yl)-2-(ethoxyimino)ethyl]-2-(trifluoromethyl)benzamide (Compound No. 2-236 of the present invention)

Step 1: Preparation of N-[2-(3,5-dibromopyridin-2-yl)-2-oxoethyl]-2-(trifluoromethyl)benzamide To 5.5 g of 3,5-dibromopyridine in 1 ml of tetrahydrofuran, 22.7 ml of a 1.0M tetrahydrofuran-toluene solution of 2,2,6,6-tetramethylpiperidinylmagnesium chloride-lithium chloride complex was added dropwise with stirring at −20° C., and after the addition, the mixture was stirred at the same temperature for 30 minutes. Then, to the reaction mixture, 3.0 g of the N-[2-methoxy(methyl)amino-2-oxoethyl]-2-(trifluoromethyl)benzamide prepared in Step 1 in Synthetic Example 17 in 17 ml of tetrahydrofuran was added dropwise, and after the addition, the mixture was stirred at the same temperature for another 1 hour. After completion of the reaction, the reaction mixture was mixed with 30 ml of saturated aqueous ammonium chloride and 20 ml of water and extracted with ethyl acetate (50 ml×2), the resulting organic layers were combined, washed with water (50 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 659 mg of the desired product as a pale yellow oil.

$^1$H NMR (CDCl$_3$, Me$_4$Si, 300 MHz) δ8.69 (d, J=2.1 Hz, 1H), 8.25 (d, J=2.1 Hz, 1H), 7.1-7.8 (m, 4H), 6.68 (bs, 1H), 5.10 (d, J=4.8 Hz, 2H).

Step 2: Preparation of N-[2-(3,5-dibromopyridin-2-yl)-2-(ethoxyimino)ethyl]-2-(trifluoromethyl)benzamide (Compound No. 2-235 of the present invention)

To 200 mg of N-[2-(3,5-dibromopyridin-2-yl)-2-oxoethyl]-2-(trifluoromethyl)benzamide in 1.4 ml of ethanol, 63 mg of ethoxyamine hydrochloride was added, and the mixture was stirred at room temperature for 18 hours. After completion of the reaction, the solvent was evaporated under reduced pressure, the resulting residue was mixed with 4 ml of water and extracted with ethyl acetate (4 ml×2), the resulting organic layers were combined, dried over saturated aqueous sodium chloride and then anhydrous sodium sulfate, and the solvent was evaporated under reduced pressure. The residue was purified by silica gel column chromatography using ethyl acetate-hexane (with a gradient of from 5:95 to 50:50) as the eluent to obtain 195 mg of the desired product as a pale yellow resinous substance.

$^1$H NMR (CDCl$_3$, Me$_4$Si, 300 MHz) δ8.63 and 8.58 (d, J=2.1 Hz, 1H), 8.14 and 8.10 (d, J=2.1 Hz, 1H), 7.1-7.75 (m, 4H), 6.43 (bs, 1H), 4.75 and 4.53 (d, J=5.7 Hz, 2H), 4.30 and 4.13 (q, J=7.2 Hz, 2H), 1.36 and 1.22 (t, J=7.2 Hz, 3H).

Step 3: Preparation of (Z)—N-[2-(3,5-dibromopyridin-2-yl)-2-(ethoxyimino)ethyl]-2-(trifluoromethyl)benzamide 195 mg of N-[2-(3,5-dibromopyridin-2-yl)-2-(ethoxyimino)ethyl]-2-(trifluoromethyl)benzamide was dissolved in 3 ml of acetonitrile, and the solution was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was purified by silica gel column chromatography using ethyl acetate-hexane (with a gradient of from 1:9 to 5:5) as the eluent to obtain 125 mg of the desired product as a pale yellow resinous substance.

$^1$H NMR (CDCl$_3$, Me$_4$Si, 300 MHz) δ8.63 (d, J=2.1 Hz, 1H), 8.10 (d, J=2.1 Hz, 1H), 7.1-7.75 (m, 4H), 6.52 (bs, 1H), 4.53 (d, J=5.7 Hz, 2H), 4.13 (q, J=7.2 Hz, 2H), 1.22 (t, J=7.2 Hz, 3H).

Synthetic Example 19

N-[2-(3,5-dichloropyridin-2-yl)-2-(isopropoxyimino)ethyl]-2-(trifluoromethyl)benzamide (Compound No. 2-005 of the present invention)

Step 1: Preparation of 3,5-dichloro-2-(nitromethyl)pyridine

To 30.74 g of potassium tert-butoxide in 100 ml of dimethylsulfoxide, 16.72 g of nitromethane was added dropwise with stirring under cooling with ice, and after the addition, the mixture was stirred at room temperature for another 1 hour. Then, the reaction mixture was cooled with ice again, and to the reaction mixture, 25.00 g of 2,3,5-trichloropyridine in 100 ml of dimethylsulfoxide was added dropwise with stirring, and after the addition, the mixture was stirred at 70° C. for another 6 hours. After completion of the reaction, the reaction mixture was allowed to cool to room temperature, poured into 200 ml of 10% aqueous hydrochloric acid with stirring under cooling with ice and extracted with ethyl acetate (200 ml×1). The resulting organic layer was washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 10:90) as the eluent to obtain 10.10 g of the desired product as a pale yellow oil.

$^1$H NMR (CDCl$_3$, Me$_4$Si, 300 MHz) δ8.53 (d, J=2.4 Hz, 1H), 7.84 (d, J=2.4 Hz, 1H), 5.76 (s, 2H).

Step 2: Preparation of N-chloromethyl-2-(trifluoromethyl)benzamide

To 15.50 g of N-hydroxymethyl-2-(trifluoromethyl)benzamide in 200 ml of dichloromethane, 16.83 g of thionyl chloride was added dropwise with stirring under cooling with ice, and after the addition, the mixture was stirred at room temperature for another 3 hours. After completion of the reaction, the solvent was evaporated under reduced pressure, and the precipitated solid was washed with 50 ml of hexane to obtain 16.90 g of the desired product as white crystals.

$^1$H NMR (CDCl$_3$, Me$_4$Si, 300 MHz) δ7.5-7.75 (m, 4H), 6.40 (bs, 1H), 5.32 (d, J=7.5 Hz, 2H).

Step 3: Preparation of N-[2-(3,5-dichloropyridin-2-yl)-2-nitroethyl]-2-(trifluoromethyl)benzamide To 6.57 g of potassium tert-butoxide in 100 ml of N,N-dimethylformamide, 10.10 g of 3,5-dichloro-2-(nitromethyl)pyridine was added dropwise with stirring under cooling with ice, and after the addition, the mixture was stirred at the same temperature for another 30 minutes. Then, to the reaction mixture, 11.59 g of N-chloromethyl-2-(trifluoromethyl)benzamide in 50 ml of N,N-dimethylformamide was added dropwise with stirring under cooing with ice, and after the addition, the mixture was stirred at room temperature for another 2 hours. After completion of the reaction, the reaction mixture was carefully poured into 100 ml of ice-water, acidified with 10% aqueous hydrochloric acid and extracted with ethyl acetate (100 ml×2). The resulting organic layers were combined, washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 14.00 g of the desired product as a pale yellow resinous substance.

$^1$H NMR (CDCl$_3$, Me$_4$Si, 300 MHz) δ8.48 (d, J=2.1 Hz, 1H), 7.87 (d, J=2.1 Hz, 1H), 7.45-7.75 (m, 4H), 6.49 (bs, 1H), 6.35 (dd, J=7.2, 4.5 Hz, 1H), 4.3-4.5 (m, 2H).

Step 4: Preparation of N-[2-(3,5-dichloropyridin-2-yl)-2-(hydroxyimino)ethyl]-2-(trifluoromethyl)benzamide To 14.00 g of N-[2-(3,5-dichloropyridin-2-yl)-2-nitroethyl]-2-(trifluoromethyl)benzamide in 70 ml of a mixture of N,N-dimethylformamide-water (7:1), 16.62 g of sodium nitrite was added, and the mixture was stirred at 60° C. for 18 hours. After completion of the reaction, the reaction mixture was allowed to cool to room temperature, poured into 100 ml of water and extracted with ethyl acetate (100 ml×2). The resulting organic layers were combined, washed with water (50 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 3:7 to 1:1) as the eluent to obtain 5.90 g of the desired product as pale yellow crystals.

¹H NMR (CDCl₃, Me₄Si, 300 MHz) δ8.52 and 8.45 (d, J=2.4 Hz, 1H), 7.81 and 7.80 (d, J=2.4 Hz, 1H), 7.35-7.75 (m, 4H), 6.53 (bs, 1H), 4.80 and 4.55 (d, J=6.3 Hz, 2H).

Step 5: Preparation of N-[2-(3,5-dichloropyridin-2-yl)-2-(isopropoxyimino)ethyl]-2-(trifluoromethyl)benzamide To a suspension of 450 mg of N-[2-(3,5-dichloropyridin-2-yl)-2-(hydroxyimino)ethyl]-2-(trifluoromethyl)benzamide and 476 mg of potassium carbonate in 5 ml of N,N-dimethylformamide, 313 mg of 2-iodopropane was added, and the mixture was stirred at room temperature for 12 hours. After completion of the reaction, the reaction mixture was mixed with 20 ml of water and extracted with ethyl acetate (25 ml×2), the resulting organic layers were combined, washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 121 mg of a colorless resinous substance. The resinous substance was dissolved in 10 ml of ethanol, the solution was mixed with 1 ml of a 1,4-dioxane solution (4 mol/L) of hydrogen chloride and stirred at 70° C. for 5 hours, and the solvent was evaporated under reduced pressure. The resulting residue was purified by silica gel column chromatography using ethyl acetate-hexane (with a gradient of from 1:9 to 3:7) as the eluent to obtain 99 mg of the desired product as a colorless resinous substance (E/Z=50/50).

¹H NMR (CDCl₃, Me₄Si, 300 MHz) δ8.50 and 8.45 (d, J=2.1 Hz, 1H), 7.81 and 7.78 (d, J=2.1 Hz, 1H), 7.35-7.75 (m, 4H), 6.53 and 6.49 (bs, 1H), 4.76 and 4.53 (d, J=6.0 Hz, 2H), 4.45-4.55 and 4.3-4.45 (m, 1H), 1.33 and 1.18 (d, J=6.3 Hz, 6H).

Synthetic Example 20

(Z)—N-[2-(5-bromo-3-chloropyridin-2-yl)-2-(methoxyimino)ethyl]-2-(trifluoromethyl)benzamide (Compound No. 2-216 of the present invention)

Step 1: Preparation of 5-bromo-3-chloro-2-(nitromethyl)pyridine

To 12.4 g of potassium tert-butoxide in 79 ml of dimethylsulfoxide, 6.7 g of nitromethane was added dropwise with stirring under cooling with ice, and after the addition, the mixture was stirred at room temperature for another 1 hour. Then, the reaction mixture was added dropwise to 25.0 g of 5-bromo-2,3-dichloropyridine in 20 ml of dimethylsulfoxide with stirring under cooling with ice, and after the addition, the mixture was stirred at room temperature for 23 hours and at 50° C. for 6 hours. After completion of the reaction, the reaction mixture was allowed to cool to room temperature, mixed with 100 ml of water and 100 ml of saturated aqueous ammonium chloride and extracted with ethyl acetate (200 ml×2). The resulting organic layers were combined, washed with water (100 ml×3) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 30:70) as the eluent to obtain 7.8 g of the desired product as a pale yellow oil.

¹H NMR (CDCl₃, Me₄Si, 300 MHz) δ8.62 (d, J=2.1 Hz, 1H), 7.98 (d, J=2.1 Hz, 1H), 5.74 (s, 2H).

Step 2: Preparation of N-[2-(5-bromo-3-chloropyridin-2-yl)-2-nitroethyl]-2-(trifluoromethyl)benzamide To 4.2 g of potassium tert-butoxide in 72 ml of N,N-dimethylformamide, 7.8 g of 5-bromo-3-chloro-2-(nitromethyl)pyridine was added dropwise with stirring under cooling with ice, and after the addition, the mixture was stirred at the same temperature for another 1 hour. Then, to the reaction mixture, 4.7 g of the N-chloromethyl-2-(trifluoromethyl)benzamide prepared in Step 2 in Synthetic Example 19 in 30 ml of N,N-dimethylformamide was added dropwise with stirring under cooling with ice, and after the addition, the mixture was stirred at room temperature for another 2 hours. After completion of the reaction, the reaction mixture was carefully poured into 100 ml of ice-water, acidified with 10% aqueous hydrochloric acid and extracted with ethyl acetate (100 ml×2). The resulting organic layers were combined, washed with water (100 ml×2) and dried over saturated aqueous sodium chloride and then anhydrous sodium sulfate, and the solvent was distilled off under reduced pressure. The resulting residue was purified by silica gel column chromatography using ethyl acetate-hexane (with a gradient of from 5:95 to 50:50) as the eluent to obtain 6.0 g of the desired product as a pale yellow oil.

¹H NMR (CDCl₃, Me₄Si, 300 MHz) δ8.57 (d, J=1.8 Hz, 1H), 8.01 (d, J=1.8 Hz, 1H), 7.4-7.75 (m, 4H), 6.48 (bs, 1H), 6.25-6.4 (m, 1H), 4.25-4.5 (m, 2H).

Step 3: Preparation of N-[2-(5-bromo-3-chloropyridin-2-yl)-2-(hydroxyimino)ethyl]-2-(trifluoromethyl)benzamide To 6.0 g of N-[2-(5-bromo-3-chloropyridin-2-yl)-2-nitroethyl]-2-(trifluoromethyl)benzamide in 65 ml of a mixture of N,N-dimethylformamide-water (7:1), 6.4 g of sodium nitrite was added, and the mixture was stirred at 60° C. for 18 hours. After completion of the reaction, the reaction mixture was allowed to cool to room temperature, poured into 100 ml of water, mixed with 20 ml of saturated aqueous ammonium chloride and extracted with ethyl acetate (100 ml×2). The resulting organic layers were combined, washed with water (50 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 2:8 to 6:4) as the eluent to obtain 3.1 g of the desired product as a pale yellow resinous substance.

¹H NMR (CDCl₃, Me₄Si, 300 MHz) δ8.6-8.65 and 8.5-8.6 (m, 1H), 7.9-8.0 (m, 1H), 7.35-7.75 (m, 4H), 6.51 (bs, 1H), 4.75-4.85 and 4.5-4.6 (m, 2H).

Step 4: Preparation of N-[2-(5-bromo-3-chloropyridin-2-yl)-2-(methoxyimino)ethyl]-2-(trifluoromethyl)benzamide To a suspension of 200 mg of N-[2-(5-bromo-3-chloropyridin-2-yl)-2-(hydroxyimino)ethyl]-2-(trifluoromethyl)benzamide and 189 mg of potassium carbonate in 1 ml of N,N-dimethylformamide, 97 mg of iodomethane was added, and the mixture was stirred at room temperature for 23 hours. After completion of the reaction, the reaction mixture was mixed with 10 ml of water and extracted with ethyl acetate (20 ml×2), the resulting organic layers were combined, washed with water (10 ml×2) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 5:95 to 50:50) as the eluent to obtain 143 mg of the desired product as a pale yellow resinous substance.

$^1$H NMR (CDCl$_3$, Me$_4$Si, 300 MHz) δ8.61 and 8.56 (d, J=1.8 Hz, 1H), 7.96 and 7.94 (d, J=1.8 Hz, 1H), 7.35-7.75 (m, 4H), 6.48 (bs, 1H), 4.74 and 4.54 (d, J=5.4 Hz, 2H), 4.07 and 3.88 (s, 3H).

Step 5: Preparation of (Z)—N-[2-(5-bromo-3-chloropyridin-2-yl)-2-(methoxyimino)ethyl]-2-(trifluoromethyl)benzamide 143 mg of N-[2-(5-bromo-3-chloropyridin-2-yl)-2-(methoxyimino)ethyl]-2-(trifluoromethyl)benzamide was dissolved in 3 ml of acetonitrile, and the solution was irradiated with light for 12 hours in a quartz cell (manufactured by Fine, 4 clear windows for spectroscopy) using a 100 W high-pressure mercury lamp (manufactured by USHIO INC., lamp: UM-102, power supply: UM-103B-B). After completion of the reaction, the solvent was evaporated under reduced pressure, and the resulting residue was washed with 10 ml of hexane to obtain 63 mg of the desired product as pale yellow crystals.

m.p.: 85.0 to 86.0° C.

$^1$H NMR (CDCl$_3$, Me$_4$Si, 300 MHz) δ8.61 (d, J=1.8 Hz, 1H), 7.94 (d, J=1.8 Hz, 1H), 7.5-7.75 (m, 4H), 6.48 (bs, 1H), 4.54 (d, J=5.4 Hz, 2H), 3.88 (s, 3H).

Synthetic Example 21

(Z)—N-[2-[3-chloro-5-(trifluoromethyl)pyridin-2-yl]-2-(isopropoxyimino)ethyl]-2-(trifluoromethyl) benzamide (Compound No. 2-020 of the present invention)

Step 1: Preparation of N-[2-[3-chloro-5-(trifluoromethyl)pyridin-2-yl]-2-nitroethyl]-2-(trifluoromethyl) benzamide To 10.26 g of potassium tert-butoxide in 80 ml of N,N-dimethylformamide, 20.00 g of 3-chloro-2-nitromethyl-5-(trifluoromethyl)pyridine was added dropwise with stirring under cooling with ice, and after the addition, the mixture was stirred at the same temperature for another 30 minutes. Then, to the reaction mixture, 18.77 g of the N-chloromethyl-2-(trifluoromethyl)benzamide prepared in Step 2 in Synthetic Example 19 in 20 ml of N,N-dimethylformamide was added dropwise with stirring under cooling with ice, and after the addition, the mixture was stirred at room temperature for another 3 hours. After completion of the reaction, the reaction mixture was carefully poured into 150 ml of 5% aqueous hydrochloric acid under cooling with ice and extracted with ethyl acetate (100 ml×2). The resulting organic layers were combined, washed with water (100 ml×2) and dried over saturated aqueous sodium chloride and then anhydrous sodium sulfate, and the solvent was evaporated under reduced pressure. The precipitated solid was purified with 30 ml of diisopropyl ether to obtain 19.80 g of the desired product as white crystals.

m.p.: 100.0 to 102.0° C.

$^1$H NMR (CDCl$_3$, Me$_4$Si, 300 MHz) δ8.78 (s, 1H), 8.09 (s, 1H), 7.45-7.75 (m, 4H), 6.50 (bs, 1H), 6.4-6.5 (m, 1H), 4.35-4.5 (m, 2H).

Step 2: Preparation of N-[2-[3-chloro-5-(trifluoromethyl)pyridin-2-yl]-2-(hydroxyimino)ethyl]-2-(trifluoromethyl)benzamide To 19.80 g of N-[2-[3-chloro-5-(trifluoromethyl)pyridin-2-yl]-2-nitroethyl]-2-(trifluoromethyl)benzamide in 100 ml of a mixture of N,N-dimethylformamide-water (7:1), 21.65 g of sodium nitrite was added, and the mixture was stirred at from 45 to 50° C. for 12 hours. After completion of the reaction, the reaction mixture was allowed to cool to room temperature, poured into 150 ml of water and extracted with ethyl acetate (100 ml×2). The resulting organic layers were combined, washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 3:7 to 1:1) as the eluent to obtain 11.10 g of the desired product as white crystals.

m.p.: 110.0 to 113.0° C.

$^1$H NMR (CDCl$_3$, Me$_4$Si, 300 MHz) δ8.82 and 8.75 (s, 1H), 8.04 (s, 1H), 7.35-7.7 (m, 4H), 6.52 (bs, 1H), 4.83 and 4.59 (d, J=6.3 Hz, 2H).

Step 3: Preparation of (E)-N-[2-[3-chloro-5-(trifluoromethyl)pyridin-2-yl]-2-(isopropoxyimino)ethyl]-2-(trifluoromethyl)benzamide (Compound No. 2-019 of the present invention)

To a suspension of 20.00 g of N-[2-[3-chloro-5-(trifluoromethyl)pyridin-2-yl]-2-(hydroxyimino)ethyl]-2-(trifluoromethyl)benzamide and 19.48 g of potassium carbonate in 105 ml of N,N-dimethylformamide, 10.38 g of 2-iodopropane was added, and the mixture was stirred at room temperature for 12 hours. After completion of the reaction, the reaction mixture was mixed with 200 ml of water and extracted with ethyl acetate (100 ml×3), the resulting organic layers were combined, washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 11.00 g of the desired product as white crystals.

m.p.: 81.0 to 83.0° C.

$^1$H NMR (CDCl$_3$, Me$_4$Si, 300 MHz) δ8.73 (s, 1H), 8.01 (s, 1H), 7.35-7.75 (m, 4H), 6.48 (bs, 1H), 4.78 (d, J=5.1 Hz, 2H), 4.45-4.6 (m, 1H), 1.34 (d, J=6.0 Hz, 6H).

Step 4: Preparation of (Z)—N-[2-[3-chloro-5-(trifluoromethyl)pyridin-2-yl]-2-(isopropoxyimino) ethyl]-2-(trifluoromethyl)benzamide 11.00 g of (E)-N-[2-[3-chloro-5-(trifluoromethyl)pyridin-2-yl]-2-(isopropoxyimino)ethyl]-2-(trifluoromethyl)benzamide was dissolved in 30 ml of acetic acid and stirred at 70° C. for 1 hour. After completion of the reaction, the solvent was evaporated under reduced pressure, and the resulting residue was purified by silica gel column chromatography using ethyl acetate-chloroform (with a gradient of from 0:100 to 5:95) as the eluent to obtain 5.63 g of the desired product as white crystals.

m.p.: 97.0 to 98.0° C.

$^1$H NMR (CDCl$_3$, Me$_4$Si, 300 MHz) δ8.79 (s, 1H), 7.99 (s, 1H), 7.5-7.75 (m, 4H), 6.49 (bs, 1H), 4.56 (d, J=5.1 Hz, 2H), 4.3-4.45 (m, 1H), 1.19 (d, J=6.0 Hz, 6H).

Synthetic Example 22

N-[2-[3-chloro-5-(3,3-dimethyl-1-butynyl)pyridin-2-yl]-2-(isopropoxyimino)ethyl]-2-(trifluoromethyl) benzamide (Compound No. 2-248 of the present invention)

Step 1: Preparation of N-[2-(5-bromo-3-chloropyridin-2-yl)-2-(isopropoxyimino)ethyl]-2-(trifluoromethyl)benzamide (Compound No. 2-181 of the present invention)

To a suspension of 1.80 g of the N-[2-(5-bromo-3-chloropyridin-2-yl)-2-(hydroxyimino)ethyl]-2-(trifluoromethyl) benzamide prepared in Step 3 in Synthetic Example 20 and 0.86 g of potassium carbonate in 10 ml of N,N-dimethylformamide, 1.30 g of 2-iodopropane was added, and the mixture was stirred at room temperature for 13 hours. After completion of the reaction, the reaction mixture was mixed with 100 ml of water and extracted with ethyl acetate (50 ml×2), the resulting organic layers were combined, washed with water (100 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:4 to 2:2) as the eluent to obtain 1.26 g of the desired product as a pale yellow resinous substance.

$^1$H NMR (CDCl$_3$, Me$_4$Si, 300 MHz) δ8.60 and 8.54 (d, J=1.9 Hz, 1H), 7.96 and 7.93 (d, J=1.9 Hz, 1H), 7.35-7.75 (m, 4H), 6.53 and 6.49 (bs, 1H), 4.75 and 4.53 (d, J=6.1 and 5.0 Hz, 2H), 4.51 and 4.37 (sep, J=6.3 Hz, 1H), 1.33 and 1.19 (d, J=6.3 Hz, 6H).

Step 2: Preparation of N-[2-[3-chloro-5-(3,3-dimethyl-1-butynyl)pyridin-2-yl]-2-(isopropoxyimino) ethyl]-2-(trifluoromethyl)benzamide To a solution of 0.15 g of N-[2-(5-bromo-3-chloropyridin-2-yl)-2-(isopropoxyimino)ethyl]-2-(trifluoromethyl)benzamide and 0.05 g of 3,3-dimethyl-1-butyne in 3 ml of triethylamine, 0.04 g of copper(I) iodide and 0.02 g of dichlorobistriphenylphosphine palladium(II) were added, and the mixture was stirred at 80° C. for 3 hours. After completion of the reaction, the reaction mixture was allowed to cool to room temperature, mixed with 10 ml of water and extracted with ethyl acetate (20 ml×1). The resulting organic layer was washed with water (10 ml×1) and dried over saturated aqueous sodium chloride and then anhydrous sodium sulfate, and the solvent was evaporated under reduced pressure. The residue was purified by silica gel column chromatography using ethyl acetate-hexane (with a gradient of from 1:5 to 2:4) as the eluent to obtain 0.15 g of the desired product as a yellow resinous substance.

$^1$H NMR (CDCl$_3$, Me$_4$Si, 300 MHz) δ8.49 and 8.43 (d, J=1.7 Hz, 1H), 7.76 and 7.73 (d, J=1.7 Hz, 1H), 7.45-7.8 (m, 4H), 6.60 (bs, 1H), 4.77 and 4.52 (d, J=5.8 and 4.8 Hz, 2H), 4.50 and 4.35 (sep, J=6.3 Hz, 1H), 1.32 (s, 9H), 1.31 and 1.17 (d, J=6.3 Hz, 6H).

Synthetic Example 23

N-[2-(5-bromo-3-chloropyridin-2-yl)-2-(methoxyimino)ethyl]-2-(trifluoromethyl)benzthioamide (Compound No. 5-001 of the present invention)

To 222 mg of the N-[2-(5-bromo-3-chloropyridin-2-yl)-2-(methoxyimino)ethyl]-2-(trifluoromethyl)benzamide prepared in Step 4 in Synthetic Example 20 in 5 ml of 1,4-dioxane, 200 mg of Lawesson's Reagent (2,4-bis(4-methoxyphenyl)-1,3-dithia-2,4-diphosphetane-2,4-disulfide) was added, and the mixture was stirred at 80° C. for 3 hours and then at room temperature for 12 hours. After completion of the reaction, the reaction mixture was mixed with 40 ml of 0.05M aqueous sodium hydroxide and extracted with a mixture of ethyl acetate-diethyl ether (2:1) (30 ml×1), the resulting organic layer was washed with 40 ml of 0.2M aqueous sodium hydroxide and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 2:8) as the eluent to obtain 133 mg of the desired product as a brown resinous substance.

$^1$H NMR (CDCl$_3$, Me$_4$Si, 300 MHz) δ8.61 and 8.53 (d, J=2.0 Hz, 1H), 8.33 and 8.08 (bs, 1H), 7.98 and 7.96 (d, J=2.0 Hz, 1H), 7.35-7.7 (m, 4H), 5.10 and 4.80 (d, J=5.1 and 4.4 Hz, 2H), 4.09 and 3.89 (s, 3H).

Synthetic Example 24

N-[2-(3,5-dichloropyridin-2-yl)-2-(methoxyimino) ethyl]-N-methyl-2-(trifluoromethyl)benzamide (Compound No. 4-005 of the present invention)

To 33 mg of 60% sodium hydride in oil in 5 ml of tetrahydrofuran, 300 mg of the N-[2-(3,5-dichloropyridin-2-yl)-2-(methoxyimino)ethyl]-2-(trifluoromethyl)benzamide prepared in Step 1 in Synthetic Example 16 in 3 ml of tetrahydrofuran was added dropwise with stirring and cooling with ice, and the mixture was stirred at the same temperature for 30 minutes. Then, the reaction mixture was mixed with 157 mg of methyl iodide, warmed to room temperature and stirred for another 1 hour. After completion of the reaction, the reaction mixture was poured into 20 ml of ice-water and extracted with ethyl acetate (50 ml×1), the organic layer was washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 2:8) as the eluent to obtain 203 mg of the desired product as a pale yellow resinous substance.

$^1$H NMR (CDCl$_3$, Me$_4$Si, 300 MHz) δ8.51 and 8.40 (d, J=2.0 Hz, 1H), 7.81 and 7.80 (d, J=2.0 Hz, 1H), 7.4-7.75 (m, 3H), 6.9-7.15 (m, 1H), 5.00 and 4.53 (d, J=15.0 Hz, 1H), 4.75 and 4.34 (d, J=15.0 Hz, 1H), 4.06 and 3.96 (s, 3H), 3.02 and 2.82 (s, 3H).

Synthetic Example 25

N-cyclopropyl-N-[2-(3, 5-dichloropyridin-2-yl)-2-(methoxyimino)ethyl]-5-fluoro-1-methyl-3-trifluoromethyl-1H-pyrazole-4-carboxamide (Compound No. 17-009 of the present invention)

Step 1: Preparation of 2-cyclopropylamino-1-(3,5-dichloropyridin-2-yl)ethanone-O-methyloxime To 700 mg of 2-bromo-1-(3,5-dichloropyridin-2-yl)ethanone-O-methyloxime prepared in the same manner as in Steps 1 to 3 in Synthetic Example 2 in 10 ml of acetonitrile, 402 mg of cyclopropylamine in 5 ml of acetonitrile was added, and the mixture was stirred at room temperature for 18 hours. After completion of the reaction, the reaction mixture was mixed with 30 ml of water and extracted with ethyl acetate (40 ml×2, the resulting organic layers were combined, washed with water (30 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 3:7 to 5:5) as the eluent to obtain 450 mg of the desired product as a colorless resinous substance.

$^1$H NMR (CDCl$_3$, Me$_4$Si, 300 MHz) δ8.48 (bs, 1H), 7.78 (bs, 1H), 3.8-4.05 (m, 5H), 1.95-2.1 (m, 1H), 0.15-0.4 (m, 4H).

Step 2: Preparation of N-cyclopropyl-N-[2-(3,5-dichloropyridin-2-yl)-2-(methoxyimino)ethyl]-5-fluoro-1-methyl-3-trifluoromethyl-1H-pyrazole-4-carboxamide To 204 mg of 5-fluoro-1-methyl-3-trifluoromethyl-1H-pyrazole-4-carboxylic acid in 3 ml of dichloromethane, 16 mg of N,N-dimethylformamide and 161 mg of oxalyl chloride were added, and the mixture was stirred at room temperature for 1 hour. After completion of the reaction, the solvent was evaporated under reduced pressure, the resulting residue was dissolved in 5 ml of dichloromethane, and added dropwise to a solution of 220 mg of 2-cyclopropylamino-1-(3,5-dichloropyridin-2-yl)ethanone-O-methyloxime and 162 mg of triethylamine in 10 ml of dichloromethane with stirring under cooling with ice, and after the addition, the mixture was stirred at room temperature for another 1 hour. After completion of the reaction, the reaction mixture was mixed with 20 ml of water and extracted with chloroform (20 ml×1), the resulting organic layer was washed with water (20 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:4 to 2:3) as the eluent to obtain 252 mg of the desired product as white crystals.

m.p.: 95.0 to 97.0° C.
$^1$H NMR (CDCl$_3$, Me$_4$Si, 300 MHz) δ8.43 (d, J=2.1 Hz, 1H), 7.77 (d, J=2.1 Hz, 1H), 4.81 (bs, 2H), 4.04 (s, 3H), 3.78 (s, 3H), 2.7-2.8 (m, 1H), 0.55-0.7 (m, 4H).

Synthetic Example 26

N-[2-[3-chloro-5-(2,2,2-trifluoroethoxy)pyridin-2-yl]-2-(methoxyimino)ethyl]-2-(trifluoromethyl)benzamide (Compound No. 2-223 of the present invention)

Step 1: Preparation of 1-(3-chloro-5-hydroxypyridin-2-yl)ethanone

To a solution of 3.8 g of the 1-(3,5-dichloropyridin-2-yl)ethanone prepared in Step 1 in Synthetic Example 2 and 13.8 g of potassium carbonate in 20 ml of dimethylsulfoxide, 5.9 g of acetaldoxime was added, and the mixture was stirred at 80° C. for 4 hours. After completion of the reaction, the reaction mixture was allowed to cool to room temperature, mixed with 50 ml of water and washed with diethyl ether (30 ml×1), the resulting aqueous layer was acidified with 6N aqueous hydrochloric acid and extracted with ethyl acetate (25 ml×2). The resulting organic layers were combined, dried over saturated aqueous sodium chloride and then anhydrous sodium sulfate, and the solvent was evaporated under reduced pressure to obtain 1.0 g of desired crude product as brown crystals. The crystals were used in the next step without further purification.

m.p.: 143.0 to 145.0° C.
$^1$H NMR (CDCl$_3$, Me$_4$Si, 300 MHz) δ8.20 (d, J=2.4 Hz, 1H), 7.30 (d, J=2.4 Hz, 1H), 2.68 (s, 3H).

Step 2: Preparation of 1-[3-chloro-5-(2,2,2-trifluoroethoxy)pyridin-2-yl]ethanone To 1.0 g of 1-(3-chloro-5-hydroxypyridin-2-yl)ethanone in 15 ml of N,N-dimethylformamide, 1.2 g of potassium carbonate and 1.6 g of 2,2,2-trifluoroethyl trifluoromethanesulfonate were added, and the mixture was stirred at room temperature for 12 hours. After completion of the reaction, the reaction mixture was mixed with 40 ml of water and extracted with ethyl acetate (50 ml×1), the resulting organic layer was washed with water (20 ml×1) and dried over saturated aqueous sodium chloride and then anhydrous sodium sulfate, and the solvent was evaporated under reduced pressure. The residue was purified by silica gel column chromatography using ethyl acetate-hexane (with a gradient of from 1:9 to 3:7) as the eluent to obtain 1.2 g of the desired product as white crystals.

m.p.: 52.0 to 55.0° C.
$^1$H NMR (CDCl$_3$, Me$_4$Si, 300 MHz) δ8.30 (d, J=2.7 Hz, 1H), 7.33 (d, J=2.7 Hz, 1H), 4.47 (q, J=7.8 Hz, 2H), 2.68 (s, 3H).

Step 3: Preparation of 2-bromo-1-[3-chloro-5-(2,2,2-trifluoroethoxy)pyridin-2-yl]ethanone To 1.1 g of 1-[3-chloro-5-(2,2,2-trifluoroethoxy)pyridin-2-yl]ethanone in 20 ml of tetrahydrofuran, 1.6 g of trimethylphenylammonium tribromide was added, and the mixture was stirred at room temperature for 12 hours. After completion of the reaction, the precipitated solid was filtered off through celite, and the solvent was evaporated under reduced pressure to obtain 1.3 g of the desired crude product as a pale yellow oil. The oil was used in the next step without further purification.

$^1$H NMR (CDCl$_3$, Me$_4$Si, 300 MHz) δ8.32 (d, J=2.7 Hz, 1H), 7.37 (d, J=2.7 Hz, 1H), 4.72 (s, 2H), 4.50 (q, J=7.8 Hz, 2H).

Step 4: Preparation of 2-bromo-1-[3-chloro-5-(2,2,2-trifluoroethoxy)pyridin-2-yl]ethanone-O-methyloxime To 1.3 g of 2-bromo-1-[3-chloro-5-(2,2,2-trifluoroethoxy)pyridin-2-yl]ethanone in 10 ml of ethanol, 362 mg of methoxyamine hydrochloride was added, and the mixture was stirred at room temperature for 13 hours. After completion of the reaction, the solvent was evaporated under reduced pressure, and the resulting residue was purified by silica gel column chromatography using ethyl acetate-hexane (with a gradient of from 0:100 to 5:95) to obtain 1.2 g of the desired product as a colorless oil.

$^1$H NMR (CDCl$_3$, Me$_4$Si, 300 MHz) δ8.30 (d, J=2.4 Hz, 1H), 7.37 (d, J=2.4 Hz, 1H), 4.51 (s, 2H), 4.44 (q, J=7.5 Hz, 2H), 4.10 (s, 3H).

Step 5: Preparation of N-[2-[3-chloro-5-(2,2,2-trifluoroethoxy)pyridin-2-yl]-2-(methoxyimino)ethyl]phthalimide To 1.0 g of 2-bromo-1-[3-chloro-5-(2,2,2-trifluoroethoxy)pyridin-2-yl]ethanone-O-methyloxime in 10 ml of N,N-dimethylformamide, 615 mg of potassium phthalimide was added, and the mixture was stirred at room temperature for 13 hours. After completion of the reaction, the reaction mixture was mixed with 30 ml of water and extracted with ethyl acetate (20 ml×1), the resulting organic layer was washed with water (20 ml×1) and dried over saturated aqueous sodium chloride and then anhydrous sodium sulfate, and the solvent was evaporated under reduced pressure. The resulting residue was washed with 10 ml of diisopropyl ether to obtain 790 mg of the desired product as pale orange crystals.

$^1$H NMR (CDCl$_3$, Me$_4$Si, 300 MHz) δ8.08 (d, J=2.4 Hz, 1H), 7.55-7.9 (m, 4H), 7.28 (d, J=2.4 Hz, 1H), 4.98 (s, 2H), 4.33 (q, J=7.8 Hz, 2H), 4.04 (s, 3H).

Step 6: Preparation of 2-amino-1-[3-chloro-5-(2,2,2-trifluoroethoxy)pyridin-2-yl]ethanone-O-methyloxime To 790 mg of N-[2-[3-chloro-5-(2,2,2-trifluoroethoxy)pyridin-2-yl]-2-(methoxyimino)ethyl]phthalimide in 10 ml of ethanol, 187 mg of hydrazine monohydrate was added and refluxed with heating for 1 hour with stirring. After completion of the reaction, the reaction mixture was allowed to cool to room temperature, mixed with 30 ml of water and extracted with ethyl acetate (25 ml×2). The resulting organic layers were combined, washed with water (20 ml×1) and dried over saturated aqueous sodium chloride and then anhydrous sodium sulfate, and the solvent was evaporated under reduced pressure to obtain 446 mg of the desired crude product as a brown oil. The oil was used in the next step without further purification.

$^1$H NMR (CDCl$_3$, Me$_4$Si, 300 MHz) δ8.32 and 8.31 (d, J=2.4 Hz, 1H), 7.38 and 7.37 (d, J=2.4 Hz, 1H), 4.4-4.5 (m, 2H), 4.03 and 3.91 (s, 2H), 3.88 and 3.75 (s, 3H).

Step 7: Preparation of N-[2-[3-chloro-5-(2,2,2-trifluoroethoxy)pyridin-2-yl]-2-(methoxyimino)ethyl]-2-(trifluoromethyl)benzamide To a solution of 227 mg of 2-amino-1-[3-chloro-5-(2,2,2-trifluoroethoxy)pyridin-2-yl]ethanone-O-methyloxime and 92 mg of triethylamine in 5 ml of dichloromethane, 175 mg of 2-(trifluoromethyl)benzoyl chloride was added dropwise with stirring under cooling with ice, and after the addition, the mixture was stirred at room temperature for another 1 hour. After completion of the reaction, the reaction mixture was mixed with 10 ml of water and extracted with chloroform (10 ml×1), the resulting organic layer was washed with water (10 ml×1) and dried over saturated aqueous sodium chloride and then anhydrous sodium sulfate, and the solvent was evaporated under reduced pressure. The resulting residue was purified by silica gel column chromatography using ethyl acetate-hexane (with a gradient of from 1:9 to 3:7) as the eluent to obtain 249 mg of the desired product as a colorless resinous substance.

$^1$H NMR (CDCl$_3$, Me$_4$Si, 300 MHz) δ8.31 and 8.27 (d, J=3.0 Hz, 1H), 7.35-7.75 (m, 5H), 6.52 and 6.45 (bs, 1H), 4.75 and 4.53 (d, J=6.0 Hz, 2H), 4.43 (q, J=7.8 Hz, 2H), 4.06 and 3.88 (s, 3H).

The compounds of the present invention can be produced in accordance with the processes and Examples previously described. Examples of the oxime-substituted amide compounds of the present invention produced in the same manners as in Synthetic Examples 1 to 26 are shown in Tables 4 to 32, and examples of their intermediates are shown in Tables 33 to 45. However, the oxime-substituted amide compounds of the present invention and their intermediates are by no means restricted thereto.

In the Tables, Et denotes ethyl group, n-Pr denotes normal propyl group, i-Pr and Pr-i denote isopropyl group, c-Pr and Pr-c denote cyclopropyl group, n-Bu denotes normal butyl group, i-Bu denotes isobutyl group, s-Bu denotes sec-butyl group, c-Bu and Bu-c denote cyclobutyl group, t-Bu and Bu-t denote tert-butyl group, Pen denotes pentyl group, c-Pen and Pen-c denote cyclopentyl group, Hex denotes hexyl group, c-Hex and Hex-c denote cyclohexyl group, Ph denotes phenyl group, and Naph denotes naphthyl group.

In the Tables, aromatic heterocyclic rings represented by D-1-1b to D-32-3b have the following structures, respectively.

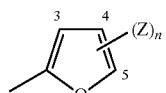

D-1-1b

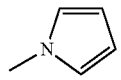

D-3-a

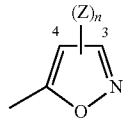

D-5-3b

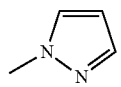

D-7-a

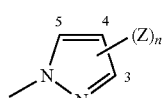

D-7-b

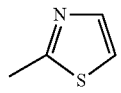

D-10-1a

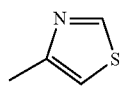

D-10-2a

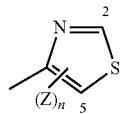

D-10-2b

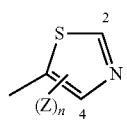

D-10-3b

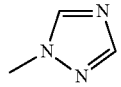

D-22-a

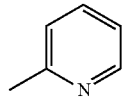

D-32-1a

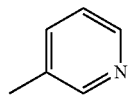

D-32-2a

-continued

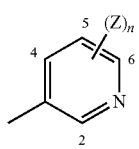
D-32-2b

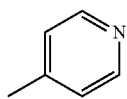
D-32-3a

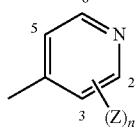
D-32-3b

The numbers indicating the positions of the substituent $(Z)_n$ correspond to the numbers in the above structural formulae, and in the Tables, the aliphatic heterocyclic rings represented by E-2-2a to E-14-1a have the following structures, respectively.

E-2-2a

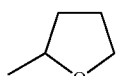
E-5-1a

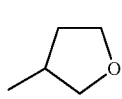
E-5-2a

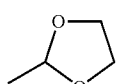
E-9-1a

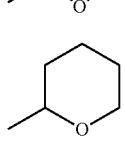
E-14-1a

In the Tables, partial saturated heterocyclic rings represented by M-4-2a and M-7-b have the following structures, respectively.

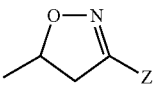
M-4-2a

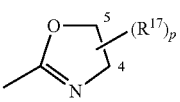
M-7-b

In the Tables, T-3 to T-6 have the following structures, respectively.

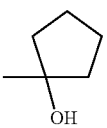
T-3

T-4

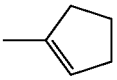
T-5

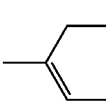
T-6

Further, in the Tables, the expression (R) or (S) in the column substituent $R^2$ means that the proportion of the R-isomer or the S-isomer is at least 90% in a mixture ratio of optical isomers due to the carbon atom attached to $R^2$, and the expression (E) or (Z) in the column substituent $R^1$ means that the proportion of the E-isomer or the Z-isomer is at least 90% in a mixture ratio of oxime geometrical isomers attached to the substituent $R^1$. In the column m.p., "*1" means that the compound was oily or resinous.

TABLE 4

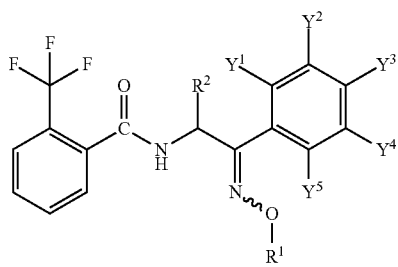

| No. | $R^2$ | $Y^1$ | $Y^2$ | $Y^3$ | $Y^4$ | $Y^5$ | $R^1$ | m.p.(° C.) |
|---|---|---|---|---|---|---|---|---|
| 1-001 | $CH_3$ | H | H | F | H | H | $CH_3$ | 69.0-71.0 |
| 1-002 | $CH_3$ | H | H | F | H | H | $CH_2$(Ph-4-Cl) | *1 |
| 1-003 | H | Cl | H | Cl | H | H | $CH_3$ | *1 |
| 1-004 | H | Cl | H | Cl | H | H | $CH_3$(Z) | 146.0-148.0 |

TABLE 4-continued

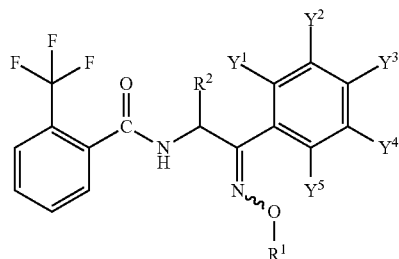

| No. | R² | Y¹ | Y² | Y³ | Y⁴ | Y⁵ | R¹ | m.p.(° C.) |
|---|---|---|---|---|---|---|---|---|
| 1-005 | CH₃ | Cl | H | Cl | H | H | CH₃ | *1 |
| 1-006 | CH₃ | Cl | H | Cl | H | H | i-Pr | *1 |
| 1-007 | CH₃ | Cl | H | Cl | H | H | CH₂CF₃ | *1 |
| 1-008 | CH₃ | Cl | H | Cl | H | H | CH₂(Ph-4-Cl) | *1 |
| 1-009 | CH₃ | CH₃ | H | OPr-i | H | H | i-Pr | *1 |
| 1-010 | CH₃ | CH₃ | H | OPr-i | H | H | CH₂(Ph-4-Cl) | *1 |
| 1-011 | CH₃ | H | H | Br | H | H | Et | 95.0-96.0 |
| 1-012 | CH₃ | H | H | I | H | H | Et | 89.0-90.0 |
| 1-013 | CH₃ | H | H | t-Bu | H | H | Et | *1 |
| 1-014 | CH₃ | H | H | CF₃ | H | H | Et | 90.0-92.0 |
| 1-015 | CH₃ | H | H | CF₃ | H | H | CH₂Pr-c | 91.0-93.0 |
| 1-016 | CH₃ | H | H | CF₃ | H | H | CH₂CF₃ | 79.0-81.0 |
| 1-017 | CH₃ | H | H | CF₃ | H | H | CH₂(D-32-2b)-6-Cl | 110.0-115.0 |
| 1-018 | CH₃ | H | H | OCF₃ | H | H | Et | 83.0-85.0 |
| 1-019 | CH₃ | H | H | OCF₃ | H | H | CH₂Pr-c | 59.0-610 |
| 1-020 | CH₃ | H | H | OPh | H | H | Et | *1 |
| 1-021 | CH₃ | H | H | OPh | H | H | CH₂CF₃ | 70.0-72.0 |
| 1-022 | CH₃ | H | H | OPh | H | H | CH₂(D-32-2b)-6-Cl | *1 |
| 1-023 | CH₃ | H | H | Ph | H | H | Et | *1 |
| 1-024 | CH₃ | H | H | Ph | H | H | i-Pr | *1 |
| 1-025 | CH₃ | H | H | Ph | H | H | CH₂Pr-c | *1 |
| 1-026 | CH₃ | H | H | Ph | H | H | CH₂CF₃ | 78.0-80.0 |
| 1-027 | CH₃ | H | H | Ph | H | H | CH₂(D-32-2b)-6-Cl | *1 |
| 1-028 | CH₃ | H | F | F | F | H | Et | 83.0-86.0 |
| 1-029 | CH₃ | H | F | F | F | H | CH₂Pr-c | 69.0-71.0 |
| 1-030 | CH₃ | H | F | F | F | H | CH₂CF₃ | 86.0-88.0 |
| 1-031 | CH₃ | H | F | F | F | H | CH₂(D-32-2b)-6-Cl | 69.0-72.0 |
| 1-032 | CH₃ | H | Cl | Cl | H | H | Et | 73.0-75.0 |
| 1-033 | CH₃ | H | Cl | Cl | H | H | CH₂Pr-c | 86.0-88.0 |
| 1-034 | CH₃ | H | Cl | Cl | H | H | CH(CH₃)Ph | *1 |
| 1-035 | CH₃ | H | Br | H | CF₃ | H | Et | *1 |
| 1-036 | CH₃ | H | OPr-i | H | H | H | Et | *1 |
| 1-037 | CH₃ | H | —CH=CHCH=CH— | | H | H | Et | *1 |
| 1-038 | CH₃ | H | —CH=CHCH=CH— | | H | H | CH₂CF₃ | *1 |
| 1-039 | CH₃ | H | —CH=CHCH=CH— | | H | H | CH₂(D-32-2b)-6-Cl | *1 |
| 1-040 | CH₃ | F | H | F | H | H | Et | 74.0-76.0 |
| 1-041 | CH₃ | F | H | F | H | H | CH₂Pr-c | *1 |
| 1-042 | CH₃ | F | H | F | H | F | CH₂Pr-c | *1 |
| 1-043 | CH₃ | F | H | Cl | H | H | Et | *1 |
| 1-044 | CH₃ | F | H | Cl | H | H | i-Pr | *1 |
| 1-045 | CH₃ | F | H | Br | H | H | Et | *1 |
| 1-046 | CH₃ | F | H | Br | H | H | i-Pr | *1 |
| 1-047 | CH₃ | F | H | Br | H | H | CH₂Pr-c | *1 |
| 1-048 | CH₃ | F | H | Br | H | H | CH₂CF₃ | *1 |
| 1-049 | CH₃ | F | H | Br | F | H | Et | *1 |
| 1-050 | CH₃ | F | H | CF₃ | H | H | Et | *1 |
| 1-051 | CH₃ | F | F | F | H | H | CH₃ | *1 |
| 1-052 | CH₃ | F | F | F | H | H | Et | *1 |
| 1-053 | CH₃ | Cl | H | H | F | H | Et | *1 |
| 1-054 | CH₃ | Cl | H | H | Cl | H | Et | *1 |
| 1-055 | CH₃ | Cl | H | H | Cl | H | CH(CH₃)Ph | *1 |
| 1-056 | CH₃ | Cl | H | H | CF₃ | H | Et | 64.0-66.0 |
| 1-057 | CH₃ | Cl | H | F | H | H | Et | *1 |
| 1-058 | CH₃ | Cl | H | Cl | H | H | Et | *1 |
| 1-059 | H | Cl | H | Cl | H | H | i-Pr | 71.0-73.0 |
| 1-060 | CH₃ | Cl | H | Cl | H | H | CH₂CH₂OCH₃ | *1 |
| 1-061 | CH₃ | Cl | H | Cl | H | H | CH₂(Ph-4-CN) | *1 |
| 1-062 | CH₃ | Cl | H | Cl | H | H | CH₂(D-1-1b)-5-CF₃ | *1 |
| 1-063 | CH₃ | Cl | H | Cl | H | H | CH₂(D-32-2b)-6-Cl | *1 |
| 1-064 | CH₃ | Cl | H | Cl | H | H | CH₂(D-32-3b)-2-Cl | *1 |
| 1-065 | CH₃ | Cl | H | Br | H | H | Et | *1 |
| 1-066 | CH₃ | Cl | H | Br | H | H | i-Pr | *1 |
| 1-067 | CH₃ | Cl | H | Br | H | H | CH₂Pr-c | *1 |
| 1-068 | CH₃ | Cl | H | Br | H | H | CH₂CF₃ | *1 |
| 1-069 | CH₃ | Cl | H | Br | H | H | CH₂(D-32-2b)-6-Cl | *1 |

TABLE 4-continued

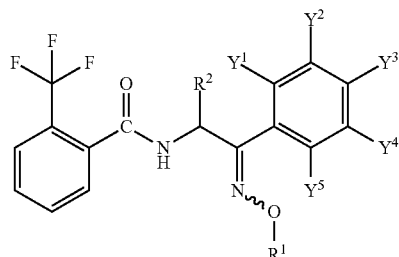

| No. | R² | Y¹ | Y² | Y³ | Y⁴ | Y⁵ | R¹ | m.p.(° C.) |
|---|---|---|---|---|---|---|---|---|
| 1-070 | CH₃ | Cl | H | CH₃ | H | H | CH₃ | *1 |
| 1-071 | CH₃ | Cl | H | CH₃ | H | H | Et | *1 |
| 1-072 | CH₃ | Cl | H | CF₃ | H | H | Et | *1 |
| 1-073 | CH₃ | Cl | H | OCH₃ | H | H | CH₃ | *1 |
| 1-074 | CH₃ | Cl | H | OCH₃ | H | H | Et | *1 |
| 1-075 | CH₃ | Cl | H | SCH₃ | H | H | Et | *1 |
| 1-076 | CH₃ | Cl | H | S(O)CH₃ | H | H | Et | *1 |
| 1-077 | CH₃ | Cl | H | SO₂CH₃ | H | H | Et | *1 |
| 1-078 | CH₃ | Cl | H | C(O)CH₃ | H | H | Et | *1 |
| 1-079 | CH₃ | Cl | H | C(CH₃)=NOCH₃ | H | H | Et | *1 |
| 1-080 | CH₃ | Cl | H | CN | H | H | CH₃ | *1 |
| 1-081 | CH₃ | Cl | H | CN | H | H | Et | *1 |
| 1-082 | CH₃ | Cl | H | (M-7-b)-4,4-(CH₃)₂ | H | H | Et | 50.0-80.0 |
| 1-083 | CH₃ | Cl | H | CH=CH₂ | H | H | CH₃ | *1 |
| 1-084 | CH₃ | Cl | H | CH=CH₂ | H | H | Et | *1 |
| 1-085 | CH₃ | Cl | H | Ph | H | H | CH₃ | *1 |
| 1-086 | CH₃ | Cl | H | Ph | H | H | Et | *1 |
| 1-087 | CH₃ | Cl | H | Ph-4-OCF₃ | H | H | CH₃ | *1 |
| 1-088 | CH₃ | Cl | H | Ph-4-OCF₃ | H | H | Et | *1 |
| 1-089 | CH₃ | Cl | H | D-3-a | H | H | Et | *1 |
| 1-090 | CH₃ | Cl | H | D-7-a | H | H | Et | *1 |
| 1-091 | CH₃ | Cl | H | (D-7-b)-3-CF₃ | H | H | Et | *1 |
| 1-092 | CH₃ | Cl | F | H | H | H | Et | *1 |
| 1-093 | CH₃ | Br | H | F | H | H | Et | *1 |
| 1-094 | CH₃ | Br | H | F | H | H | CH₂CH₂OCH₃ | *1 |
| 1-095 | CH₃ | Br | H | F | F | H | Et | *1 |
| 1-096 | CH₃ | CH₃ | H | Cl | H | H | Et | *1 |
| 1-097 | CH₃ | CH₃ | H | CH₃ | H | H | Et | *1 |
| 1-098 | CH₃ | CF₃ | H | Cl | H | H | Et | *1 |
| 1-099 | CH₃ | OCH₃ | H | Cl | H | H | Et | *1 |
| 1-100 | CH₃ | CH=NOEt | H | Cl | H | H | Et | *1 |
| 1-101 | CH₃ | E-9-1a | H | Cl | H | H | Et | *1 |
| 1-102 | CH₃ | —CH=CHCH=CH— | | Br | H | H | Et | *1 |

TABLE 5

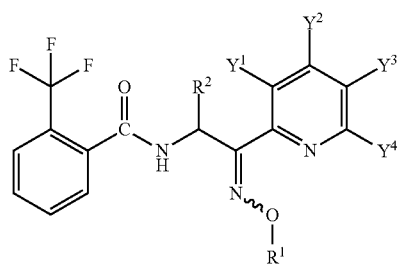

| No. | R² | Y¹ | Y² | Y³ | Y⁴ | R¹ | m.p.(° C.) |
|---|---|---|---|---|---|---|---|
| 2-001 | H | H | H | CF₃ | H | CH₃ | 128.0-130.0 |
| 2-002 | H | Cl | H | Cl | H | CH₃ | *1 |
| 2-003 | H | Cl | H | Cl | H | Et | *1 |
| 2-004 | H | Cl | H | Cl | H | n-Pr | *1 |
| 2-005 | H | Cl | H | Cl | H | i-Pr | *1 |
| 2-006 | H | Cl | H | Cl | H | n-Bu | *1 |
| 2-007 | H | Cl | H | Cl | H | i-Bu | *1 |
| 2-008 | H | Cl | H | Cl | H | CH₂Pr-c | *1 |
| 2-009 | H | Cl | H | Cl | H | s-Bu | *1 |
| 2-010 | H | Cl | H | Cl | H | c-Bu | *1 |
| 2-011 | H | Cl | H | Cl | H | CH₂CF₃ | *1 |

TABLE 5-continued

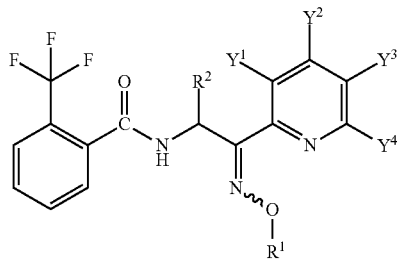

| No. | R² | Y¹ | Y² | Y³ | Y⁴ | R¹ | m.p.(° C.) |
|---|---|---|---|---|---|---|---|
| 2-012 | H | Cl | H | Cl | H | CH₂CH=CH₂ | *1 |
| 2-013 | H | Cl | H | Cl | H | CH₂(Ph-4-Cl) | *1 |
| 2-014 | H | Cl | H | CF₃ | H | CH₃ | *1 |
| 2-015 | CH₃ | Cl | H | CF₃ | H | CH₃ | *1 |
| 2-016 | H | Cl | H | CF₃ | H | Et | *1 |
| 2-017 | H | Cl | H | CF₃ | H | n-Pr | *1 |
| 2-018 | H | Cl | H | CF₃ | H | i-Pr | 67.0-68.0 |
| 2-019 | H | Cl | H | CF₃ | H | i-Pr(E) | 81.0-83.0 |
| 2-020 | H | Cl | H | CF₃ | H | i-Pr(Z) | 97.0-98.0 |
| 2-021 | H | Cl | H | CF₃ | H | i-Bu | *1 |
| 2-022 | H | Cl | H | CF₃ | H | CH₂Pr-c | *1 |
| 2-023 | H | Cl | H | CF₃ | H | CH₂Pr-c(E) | 98.0-101.0 |
| 2-024 | H | Cl | H | CF₃ | H | CH₂Pr-c(Z) | 73.0-74.0 |
| 2-025 | H | Cl | H | CF₃ | H | s-Bu | *1 |
| 2-026 | H | Cl | H | CF₃ | H | c-Bu | *1 |
| 2-027 | H | Cl | H | CF₃ | H | CH(Et)₂ | *1 |
| 2-028 | H | Cl | H | CF₃ | H | CH(CH₃)Pr-c | *1 |
| 2-029 | H | Cl | H | CF₃ | H | c-Pen | *1 |
| 2-030 | H | Cl | H | CF₃ | H | CH₂CHF₂ | *1 |
| 2-031 | H | Cl | H | CF₃ | H | CH₂CHF₂(E) | *1 |
| 2-032 | H | Cl | H | CF₃ | H | CH₂CF₃ | *1 |
| 2-033 | CH₃ | Cl | H | CF₃ | H | CH₂CF₃ | *1 |
| 2-034 | H | Cl | H | CF₃ | H | CH₂CH₂SCH₃ | *1 |
| 2-035 | H | Cl | H | CF₃ | H | CH₂(M-4-2a)CH₃ | *1 |
| 2-036 | H | Cl | H | CF₃ | H | CH₂CN | *1 |
| 2-037 | H | Cl | H | CF₃ | H | CH(CH₃)CN | *1 |
| 2-038 | H | Cl | H | CF₃ | H | CH₂CH₂CN | *1 |
| 2-039 | H | Cl | H | CF₃ | H | CH₂C(O)NHCH₂CF₃ | *1 |
| 2-040 | H | Cl | H | CF₃ | H | CH₂CH=CH₂ | *1 |
| 2-041 | H | Cl | H | CF₃ | H | CH₂C(CH₃)=CH₂ | *1 |
| 2-042 | H | Cl | H | CF₃ | H | CH(CH₃)CH=CH₂ | *1 |
| 2-043 | H | Cl | H | CF₃ | H | CH₂CH=C(CH₃)₂ | 62.0-64.0 |
| 2-044 | H | Cl | H | CF₃ | H | CH₂C≡CH | *1 |
| 2-045 | H | Cl | H | CF₃ | H | CH₂Ph | 93.0-95.0 |
| 2-046 | H | Cl | H | CF₃ | H | CH₂(Ph-2-F) | *1 |
| 2-047 | H | Cl | H | CF₃ | H | CH₂(Ph-3-F) | 65.0-70.0 |
| 2-048 | H | Cl | H | CF₃ | H | CH₂(Ph-4-F) | *1 |
| 2-049 | H | Cl | H | CF₃ | H | CH₂(Ph-2-Cl) | 83.0-84.0 |
| 2-050 | H | Cl | H | CF₃ | H | CH₂(Ph-3-Cl) | *1 |
| 2-051 | H | Cl | H | CF₃ | H | CH₂(Ph-4-Cl) | *1 |
| 2-052 | H | Cl | H | CF₃ | H | CH₂(Ph-2-CH₃) | 104.0-106.0 |
| 2-053 | H | Cl | H | CF₃ | H | CH₂(Ph-3-CH₃) | *1 |
| 2-054 | H | Cl | H | CF₃ | H | CH₂(Ph-4-CH₃) | *1 |
| 2-055 | H | Cl | H | CF₃ | H | CH₂(Ph-4-Bu-t) | *1 |
| 2-056 | H | Cl | H | CF₃ | H | CH₂(Ph-2-CF₃) | *1 |
| 2-057 | H | Cl | H | CF₃ | H | CH₂(Ph-3-CF₃) | *1 |
| 2-058 | H | Cl | H | CF₃ | H | CH₂(Ph-4-CF₃) | *1 |
| 2-059 | H | Cl | H | CF₃ | H | CH₂(Ph-3-OCH₃) | *1 |
| 2-060 | H | Cl | H | CF₃ | H | CH₂(Ph-4-OCH₃) | *1 |
| 2-061 | H | Cl | H | CF₃ | H | CH₂(Ph-2-OCF₃) | *1 |
| 2-062 | H | Cl | H | CF₃ | H | CH₂(Ph-3-OCF₃) | *1 |
| 2-063 | H | Cl | H | CF₃ | H | CH₂(Ph-4-OCF₃) | *1 |
| 2-064 | H | Cl | H | CF₃ | H | CH₂(Ph-4-NO₂) | *1 |
| 2-065 | H | Cl | H | CF₃ | H | CH₂(Ph-2-CN) | *1 |
| 2-066 | H | Cl | H | CF₃ | H | CH₂(Ph-3-CN) | *1 |
| 2-067 | H | Cl | H | CF₃ | H | CH₂(Ph-4-CN) | *1 |
| 2-068 | H | Cl | H | CF₃ | H | CH₂(Ph-4-Ph) | *1 |
| 2-069 | H | Cl | H | CF₃ | H | CH₂(Ph-2,4-F₂) | *1 |
| 2-070 | H | Cl | H | CF₃ | H | CH₂(Ph-2,6-F₂) | 86.0-88.0 |
| 2-071 | H | Cl | H | CF₃ | H | CH₂(Ph-3,4-F₂) | *1 |
| 2-072 | H | Cl | H | CF₃ | H | CH₂(Ph-3,5-F₂) | *1 |
| 2-073 | H | Cl | H | CF₃ | H | CH₂(Ph-3,4-Cl₂) | *1 |
| 2-074 | H | Cl | H | CF₃ | H | CH₂(Ph-3,4,5-F₃) | *1 |
| 2-075 | H | Cl | H | CF₃ | H | CH₂(2-Naph) | *1 |
| 2-076 | H | Cl | H | CF₃ | H | CH₂(D-5-3b)-3-CH₃ | 95.0-97.0 |

TABLE 5-continued

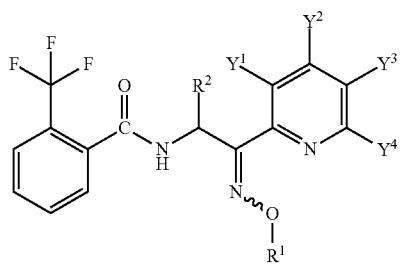

| No. | R² | Y¹ | Y² | Y³ | Y⁴ | R¹ | m.p.(° C.) |
|---|---|---|---|---|---|---|---|
| 2-077 | H | Cl | H | CF₃ | H | CH₂(D-32-1a) | *1 |
| 2-078 | H | Cl | H | CF₃ | H | CH₂(D-32-2a) | *1 |
| 2-079 | H | Cl | H | CF₃ | H | CH₂(D-32-2b)-6-Cl | *1 |
| 2-080 | H | Cl | H | CF₃ | H | CH₂(D-32-3a) | *1 |
| 2-081 | H | Cl | H | CF₃ | H | CH(CH₃)Ph | *1 |
| 2-082 | H | Cl | H | CF₃ | H | CH₂CH₂Ph | 106.0-108.0 |
| 2-083 | H | Cl | H | OCH₃ | H | CH₃ | *1 |
| 2-084 | H | OCH₃ | H | Cl | H | CH₃ | *1 |
| 2-085 | H | F | H | Cl | H | i-Pr | *1 |
| 2-086 | H | Cl | H | Cl | H | c-Pen | *1 |
| 2-087 | H | Cl | H | Cl | H | CH₂CH₂Cl | *1 |
| 2-088 | H | Cl | H | Cl | H | CH(CH₃)OEt | *1 |
| 2-089 | H | Cl | H | Cl | H | E-14-1a | *1 |
| 2-090 | H | Cl | H | Cl | H | CH₂(E-9-1a) | *1 |
| 2-091 | H | Cl | H | Cl | H | CH₂CH₂SCH₃ | *1 |
| 2-092 | H | Cl | H | Cl | H | CH₂Si(CH₃)₃ | *1 |
| 2-093 | H | Cl | H | Cl | H | CH₂C(CH₃)=NOCH₃ | *1 |
| 2-094 | H | Cl | H | Cl | H | CH₂CN | *1 |
| 2-095 | H | Cl | H | Cl | H | CH₂C(O)OCH₃ | *1 |
| 2-096 | H | Cl | H | Cl | H | CH(CH₃)CH=CH₂ | *1 |
| 2-097 | H | Cl | H | Cl | H | CH₂CCl=CHCl | *1 |
| 2-098 | H | Cl | H | Cl | H | CH₂(Ph-2-F) | *1 |
| 2-099 | H | Cl | H | Cl | H | CH₂(Ph-3-F) | *1 |
| 2-100 | H | Cl | H | Cl | H | CH₂(Ph-4-F) | *1 |
| 2-101 | H | Cl | H | Cl | H | CH₂(Ph-2-Cl) | *1 |
| 2-102 | H | Cl | H | Cl | H | CH₂(Ph-3-Cl) | *1 |
| 2-103 | H | Cl | H | Cl | H | CH₂(Ph-4-SCF₃) | *1 |
| 2-104 | H | Cl | H | Cl | H | CH₂(Ph-4-CN) | *1 |
| 2-105 | H | Cl | H | Cl | H | CH₂(Ph-3,4-F₂) | *1 |
| 2-106 | H | Cl | H | Cl | Cl | Et | *1 |
| 2-107 | H | Cl | H | Cl | Cl | i-Pr | *1 |
| 2-108 | H | Cl | H | Cl | Cl | CH₂Pr-c | *1 |
| 2-109 | H | Cl | H | Cl | Cl | CH₂CH=CH₂ | *1 |
| 2-110 | H | Cl | H | Cl | Cl | CH₂(Ph-4-F) | *1 |
| 2-111 | H | Cl | H | CH₂OCH₃ | H | i-Pr | *1 |
| 2-112 | H | F | H | F | H | i-Pr | *1 |
| 2-113 | H | F | H | Cl | H | Et | *1 |
| 2-114 | H | Cl | H | Cl | H | CH₃(Z) | 88.0-89.0 |
| 2-115 | CH₃ | Cl | H | Cl | H | CH₃ | *1 |
| 2-116 | CH₃(S) | Cl | H | Cl | H | CH₃ 95% e.e. $[\alpha]_D^{19.0}$ −13.70° (EtOH, c = 0.10) | *1 |
| 2-117 | CH₃ | Cl | H | Cl | H | CH₃(Z) | 104.0-105.0 |
| 2-118 | CH₃(S) | Cl | H | Cl | H | CH₃(Z) 95% e.e. $[\alpha]_D^{21.7}$ −12.50° (EtOH, c = 0.10) | *1 |
| 2-119 | Et | Cl | H | Cl | H | CH₃ | *1 |
| 2-120 | H | Cl | H | Cl | H | Et(Z) | 84.0-86.0 |
| 2-121 | CH₃ | Cl | H | Cl | H | Et | *1 |
| 2-122 | CH₃(S) | Cl | H | Cl | H | Et 95% e.e. $[\alpha]_D^{19.0}$ −13.10° (EtOH, c = 0.10) | *1 |
| 2-123 | CH₃ | Cl | H | Cl | H | Et(Z) | *1 |
| 2-124 | CH₃(S) | Cl | H | Cl | H | Et(Z) 95% e.e. $[\alpha]_D^{21.7}$ −11.40° (EtOH, c = 0.10) | *1 |
| 2-125 | t-Bu | Cl | H | Cl | H | Et | *1 |
| 2-126 | H | Cl | H | Cl | H | n-Pr(Z) | 80.0-83.0 |
| 2-127 | CH₃ | Cl | H | Cl | H | n-Pr(Z) | *1 |
| 2-128 | H | Cl | H | Cl | H | i-Pr(Z) | 107.0-108.0 |
| 2-129 | CH₃ | Cl | H | Cl | H | i-Pr | *1 |
| 2-130 | CH₃(S) | Cl | H | Cl | H | i-Pr 95% e.e. $[\alpha]_D^{19.0}$ −11.40° (EtOH, c = 0.10) | *1 |
| 2-131 | CH₃ | Cl | H | Cl | H | i-Pr(Z) | *1 |
| 2-132 | CH₃(S) | Cl | H | Cl | H | i-Pr(Z) 95% e.e. $[\alpha]_D^{21.8}$ −11.40° (EtOH, c = 0.10) | *1 |
| 2-133 | H | Cl | H | Cl | H | n-Bu(Z) | 80.0-84.0 |
| 2-134 | H | Cl | H | Cl | H | i-Bu(Z) | 91.0-93.0 |
| 2-135 | H | Cl | H | Cl | H | CH₂Pr-c(Z) | 119.0-121.0 |

TABLE 5-continued

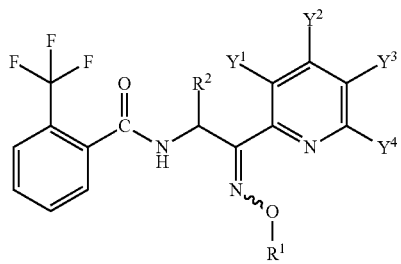

| No. | R² | Y¹ | Y² | Y³ | Y⁴ | R¹ | m.p.(° C.) |
|---|---|---|---|---|---|---|---|
| 2-136 | H | Cl | H | Cl | H | s-Bu(Z) | 68.0-70.0 |
| 2-137 | CH₃ | Cl | H | Cl | H | s-Bu(Z) | *1 |
| 2-138 | H | Cl | H | Cl | H | c-Bu(Z) | 100.0-102.0 |
| 2-139 | H | Cl | H | Cl | H | t-Bu | *1 |
| 2-140 | H | Cl | H | Cl | H | t-Bu(Z) | *1 |
| 2-141 | H | Cl | H | Cl | H | Pen | *1 |
| 2-142 | H | Cl | H | Cl | H | Pen(Z) | 79.0-80.0 |
| 2-143 | H | Cl | H | Cl | H | CH₂Bu-c | 72.0-75.0 |
| 2-144 | H | Cl | H | Cl | H | CH(Et)₂ | *1 |
| 2-145 | H | Cl | H | Cl | H | c-Pen(Z) | 99.0-100.0 |
| 2-146 | H | Cl | H | Cl | H | Hex | *1 |
| 2-147 | H | Cl | H | Cl | H | CH₂Pen-c | 75.0-78.0 |
| 2-148 | H | Cl | H | Cl | H | c-Hex | 73.0-76.0 |
| 2-149 | H | Cl | H | Cl | H | CH₂Hex-c | *1 |
| 2-150 | H | Cl | H | Cl | H | CH₂CHF₂ | *1 |
| 2-151 | CH₃ | Cl | H | Cl | H | CH₂CF₃(Z) | *1 |
| 2-152 | H | Cl | H | Cl | H | CH₂CH₂OCH₃ | *1 |
| 2-153 | H | Cl | H | Cl | H | E-2-2a | *1 |
| 2-154 | H | Cl | H | Cl | H | CH₂(E-5-1a) | 74.0-77.0 |
| 2-155 | H | Cl | H | Cl | H | CH₂(E-5-2a) | *1 |
| 2-156 | H | Cl | H | Cl | H | CH₂C(O)OEt | *1 |
| 2-157 | H | Cl | H | Cl | H | CH₂CH=CH₂(Z) | 78.0-82.0 |
| 2-158 | CH₃ | Cl | H | Cl | H | CH₂CH=CH₂(Z) | *1 |
| 2-159 | H | Cl | H | Cl | H | CH₂CCl=CH₂ | *1 |
| 2-160 | H | Cl | H | Cl | H | CH₂C≡CH | *1 |
| 2-161 | H | Cl | H | Cl | H | CH₂Ph | *1 |
| 2-162 | H | Cl | H | Cl | H | CH₂(Ph-4-OCH₃) | *1 |
| 2-163 | H | Cl | H | Cl | H | CH₂(Ph-2-CN) | *1 |
| 2-164 | H | Cl | H | Cl | H | CH₂(D-10-1a) | *1 |
| 2-165 | H | Cl | H | Cl | H | CH₂(D-10-2a) | *1 |
| 2-166 | H | Cl | H | Cl | H | CH₂(D-10-2b)-2-Cl | *1 |
| 2-167 | H | Cl | H | Cl | H | CH₂(D-10-3b)-2-Cl | *1 |
| 2-168 | H | Cl | H | Cl | H | CH₂(D-32-2b)-6-Cl | *1 |
| 2-169 | H | Cl | H | Cl | H | CH₂(D-32-3b)-2-Cl | *1 |
| 2-170 | H | Cl | H | Cl | H | CH₂(D-32-3b)-2,6-Cl₂ | 155.0-165.0 |
| 2-171 | H | Cl | H | Cl | H | CH(CH₃)Ph | *1 |
| 2-172 | H | Cl | H | Cl | H | CH(CH₃)Ph(Z) | *1 |
| 2-173 | H | Cl | H | Cl | H | CH(CH₃)(Ph-4-F) | *1 |
| 2-174 | H | Cl | H | Cl | H | CH(CH₃)(Ph-4-F)(Z) | *1 |
| 2-175 | H | Cl | H | Cl | H | C(CH₃)₂Ph | *1 |
| 2-176 | H | Cl | H | Cl | H | CH₂CH₂Ph | *1 |
| 2-177 | H | Cl | H | Cl | H | Ph | *1 |
| 2-178 | H | Cl | H | Cl | F | Et | *1 |
| 2-179 | H | Cl | H | Cl | F | i-Pr | *1 |
| 2-180 | H | Cl | H | Cl | OCH₃ | i-Pr | *1 |
| 2-181 | H | Cl | H | Br | H | i-Pr | *1 |
| 2-182 | H | Cl | H | Br | H | i-Pr(Z) | 109.0-111.0 |
| 2-183 | H | Cl | H | CF₃ | H | CH₃(Z) | 113.0-117.0 |
| 2-184 | CH₃ | Cl | H | CF₃ | H | CH₃(Z) | *1 |
| 2-185 | H | Cl | H | CF₃ | H | Et(Z) | 60.0-62.0 |
| 2-186 | CH₃ | Cl | H | CF₃ | H | Et(Z) | *1 |
| 2-187 | H | Cl | H | CF₃ | H | n-Pr(Z) | 71.0-72.0 |
| 2-188 | CH₃ | Cl | H | CF₃ | H | i-Pr(Z) | *1 |
| 2-189 | H | Cl | H | CF₃ | H | n-Bu(Z) | 88.0-89.0 |
| 2-190 | H | Cl | H | CF₃ | H | i-Bu(Z) | 84.0-85.0 |
| 2-191 | H | Cl | H | CF₃ | H | s-Bu(Z) | 79.0-82.0 |
| 2-192 | H | Cl | H | CF₃ | H | Pen(Z) | 87.0-89.0 |
| 2-193 | H | Cl | H | CF₃ | H | c-Pen(Z) | 106.0-108.0 |
| 2-194 | H | Cl | H | CF₃ | H | CH₂CH=CH₂(Z) | 49.0-50.0 |
| 2-195 | H | Cl | H | CF₃ | H | CH(CH₃)Ph(Z) | *1 |
| 2-196 | H | Cl | H | CF₃ | H | CH(CH₃)(Ph-4-F)(Z) | *1 |
| 2-197 | H | Cl | H | OCH₃ | H | i-Pr | *1 |
| 2-198 | H | Cl | H | C(CH₃)=NOCH₃ | H | i-Pr | *1 |
| 2-199 | H | Cl | H | CN | H | Et | *1 |
| 2-200 | H | Cl | H | CN | H | i-Pr | *1 |

TABLE 5-continued

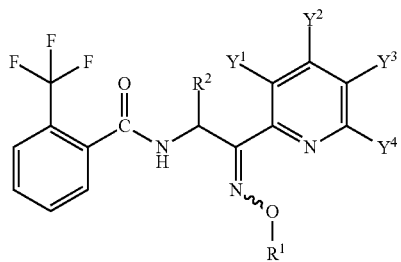

| No. | R² | Y¹ | Y² | Y³ | Y⁴ | R¹ | m.p.(° C.) |
|---|---|---|---|---|---|---|---|
| 2-201 | H | Cl | H | CN | H | CH₂Pr-c | *1 |
| 2-202 | H | Cl | H | CN | H | CH(CH₃)Ph | *1 |
| 2-203 | H | CF₃ | H | CF₃ | H | i-Pr | 60.0-65.0 |
| 2-204 | H | Cl | H | F | H | n-Pr | *1 |
| 2-205 | H | Cl | H | F | H | i-Pr(Z) | 99.0-101.0 |
| 2-206 | Ph | Cl | H | Cl | H | CH₃(Z) | *1 |
| 2-207 | CH₃ | Cl | H | Cl | H | n-Bu(Z) | *1 |
| 2-208 | CH₃ | Cl | H | Cl | H | i-Bu(Z) | *1 |
| 2-209 | CH₃ | Cl | H | Cl | H | CH₂Pr-c(Z) | *1 |
| 2-210 | CH₃ | Cl | H | Cl | H | t-Bu(Z) | *1 |
| 2-211 | H | Cl | H | Cl | H | CH(Et)₂(2) | *1 |
| 2-212 | H | Cl | H | Cl | H | CH₂CF₃(Z) | 100.0-102.0 |
| 2-213 | H | Cl | H | Cl | H | CH(CH₃)CH=CH₂(Z) | *1 |
| 2-214 | H | Cl | H | Cl | F | Et(Z) | *1 |
| 2-215 | H | Cl | H | Cl | F | i-Pr(Z) | 122.0-125.0 |
| 2-216 | H | Cl | H | Br | H | CH₃(Z) | 85.0-86.0 |
| 2-217 | H | Cl | H | Br | H | Et(Z) | 101.0-102.0 |
| 2-218 | H | Cl | H | CH₃ | H | i-Pr(Z) | 117.0-119.0 |
| 2-219 | H | Cl | H | CF₃ | H | CH(Et)₂(Z) | *1 |
| 2-220 | H | Cl | H | CF₃ | H | CH(CH₃)CH=CH₂(Z) | *1 |
| 2-221 | H | Cl | H | CF₃ | H | CH₂(Ph-4-CN)(Z) | 139.0-141.0 |
| 2-222 | H | Cl | H | OCHF₂ | H | CH₃ | *1 |
| 2-223 | H | Cl | H | OCH₂CF₃ | H | CH₃ | *1 |
| 2-224 | H | Cl | H | CH=CH₂ | H | i-Pr | *1 |
| 2-225 | H | Cl | H | C≡CH | H | i-Pr(Z) | 104.0-105.0 |
| 2-226 | H | Cl | H | C≡CSi(CH₃)₃ | H | i-Pr(Z) | *1 |
| 2-227 | H | Cl | H | D-3-a | H | i-Pr | *1 |
| 2-228 | H | Cl | H | D-7-a | H | i-Pr | *1 |
| 2-229 | H | Cl | H | D-22-a | H | i-Pr | *1 |
| 2-230 | H | Cl | Cl | Cl | H | CH₃(Z) | 129.0-130.0 |
| 2-231 | H | Cl | Cl | Cl | H | Et(Z) | 100.0-101.0 |
| 2-232 | H | Cl | CN | Cl | H | i-Pr | *1 |
| 2-233 | H | Br | H | Br | H | CH₃ | 65.0-75.0 |
| 2-234 | CH₃ | Br | H | Br | H | CH₃(Z) | *1 |
| 2-235 | H | Br | H | Br | H | Et | *1 |
| 2-236 | H | Br | H | Br | H | Et(Z) | *1 |
| 2-237 | CH₃ | Br | H | Br | H | Et(Z) | *1 |
| 2-238 | H | Br | H | Br | H | n-Pr | *1 |
| 2-239 | H | Cl | H | Cl | H | i-Pr(E) | 54.0-570 |
| 2-240 | H | Cl | H | Cl | H | CH₂CHF₂(Z) | 58.0-62.0 |
| 2-241 | H | Cl | H | Cl | H | CH₂(Ph-4-F)(Z) | 105.0-109.0 |
| 2-242 | H | Cl | H | Cl | H | CH₂(Ph-4-Cl)(Z) | *1 |
| 2-243 | H | Cl | H | Cl | H | CH₂(Ph-3,4-F₂)(Z) | *1 |
| 2-244 | H | Cl | H | Br | H | CH(CH₃)Ph(Z) | *1 |
| 2-245 | H | Cl | H | CF₃ | H | CH₂(Ph-3,4-F₂)(Z) | 96.0-98.0 |
| 2-246 | H | Cl | H | CF₃ | H | CH₂(Ph-3,4,5-F₃)(Z) | 100.0-103.0 |
| 2-247 | H | Cl | H | O(Ph-4-Cl) | H | CH₃ | *1 |
| 2-248 | H | Cl | H | C≡CBu-t | H | i-Pr | *1 |
| 2-249 | H | Cl | H | C≡CPh | H | i-Pr | *1 |
| 2-250 | H | Br | H | Br | H | i-Pr(Z) | 113.0-115.0 |
| 2-251 | H | Br | H | Br | H | CH₂CF₃ | *1 |
| 2-252 | H | Cl | H | H | H | CH₃(Z) | 95.0-98.0 |
| 2-253 | H | Cl | H | H | H | i-Pr(Z) | 99.0-102.0 |
| 2-254 | CH₃(S) | Cl | H | Cl | H | n-Pr(Z) | *1 |
| | | | | | | 83% e.e. [α]$_D^{26.1}$ −9.42° (EtOH, c = 0.10) | |
| 2-255 | H | Cl | H | O(Ph-4-Cl) | H | i-Pr | *1 |
| 2-256 | H | Cl | H | C≡CCH₃ | H | i-Pr | *1 |
| 2-257 | H | Cl | H | C≡CPr-c | H | i-Pr(Z) | *1 |
| 2-258 | H | Cl | H | C≡CPen-c | H | i-Pr | *1 |
| 2-259 | H | Cl | H | C≡CCl | H | i-Pr | *1 |
| 2-260 | H | Cl | H | C≡CBr | H | i-Pr | *1 |
| 2-261 | H | Cl | H | C≡CI | H | i-Pr | *1 |
| 2-262 | H | Cl | H | C≡CC(CH₃)₂OH | H | i-Pr | *1 |
| 2-263 | H | Cl | H | C≡C(T-3) | H | i-Pr | *1 |
| 2-264 | H | Cl | H | C≡C(T-4) | H | i-Pr | *1 |

TABLE 5-continued

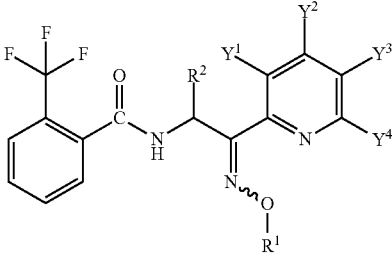

| No. | $R^2$ | $Y^1$ | $Y^2$ | $Y^3$ | $Y^4$ | $R^1$ | m.p.(° C.) |
|---|---|---|---|---|---|---|---|
| 2-265 | H | Cl | H | C≡C(T-5) | H | i-Pr | *1 |
| 2-266 | H | Cl | H | C≡C(T-6) | H | i-Pr | *1 |
| 2-267 | H | Cl | H | C≡C(Ph-4-Bu-t) | H | i-Pr | *1 |
| 2-268 | H | Cl | H | C≡C(D-32-1a) | H | i-Pr | *1 |
| 2-269 | H | Cl | H | C≡C(D-32-2a) | H | i-Pr | *1 |
| 2-270 | H | Cl | H | C≡C(D-32-3a) | H | i-Pr | *1 |
| 2-271 | H | Cl | H | Ph-4-F | H | i-Pr | *1 |

TABLE 6

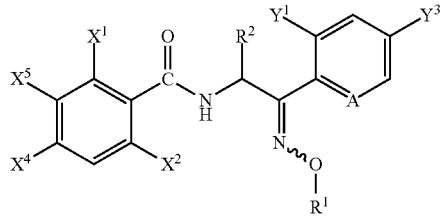

| No. | $X^1$ | $X^2$ | $X^4$ | $X^5$ | $R^2$ | $Y^1$ | $Y^3$ | A | $R^1$ | m.p.(° C.) |
|---|---|---|---|---|---|---|---|---|---|---|
| 3-001 | F | F | H | H | $CH_3$ | H | F | CH | $CH_3$ | 58.0-61.0 |
| 3-002 | F | F | H | H | $CH_3$ | H | F | CH | $CH_2$(Ph-4-Cl) | *1 |
| 3-003 | $CH_3$ | H | H | H | $CH_3$ | Cl | Cl | CH | $CH_3$ | *1 |
| 3-004 | F | H | H | H | H | Cl | Cl | N | Et | *1 |
| 3-005 | F | F | H | H | H | Cl | Cl | N | Et | *1 |
| 3-006 | Cl | H | H | H | H | Cl | Cl | N | Et | *1 |
| 3-007 | Cl | H | H | H | H | Cl | Cl | N | n-Pr(Z) | *1 |
| 3-008 | Cl | F | H | H | H | Cl | Cl | N | Et | *1 |
| 3-009 | Cl | Cl | H | H | H | Cl | Cl | N | Et | *1 |
| 3-010 | Br | H | H | H | H | Cl | Cl | N | Et | *1 |
| 3-011 | Br | H | H | H | H | Cl | Cl | N | n-Pr(Z) | *1 |
| 3-012 | I | H | H | H | $CH_3$ | H | Br | CH | Et | 106.0-109.0 |
| 3-013 | I | H | H | H | $CH_3$ | Cl | Cl | CH | Et | *1 |
| 3-014 | I | H | H | H | H | Cl | Cl | N | Et | *1 |
| 3-015 | I | H | H | H | H | Cl | Cl | N | n-Pr(Z) | *1 |
| 3-016 | I | H | H | H | H | Cl | Cl | N | i-Pr(Z) | *1 |
| 3-017 | I | H | H | H | H | Cl | Cl | N | $CH_2$Pr-c | *1 |
| 3-018 | I | H | H | H | H | Cl | Cl | N | CH($CH_3$)Ph | *1 |
| 3-019 | $CH_3$ | H | H | H | H | Cl | Cl | N | n-Pr(Z) | *1 |
| 3-020 | $CH_3$ | H | H | H | H | Cl | Cl | N | i-Pr(Z) | *1 |
| 3-021 | $CH_3$ | H | H | F | H | Cl | Cl | N | Et | *1 |
| 3-022 | $CHF_2$ | H | H | H | H | Cl | Cl | N | Et | 93.0-95.0 |
| 3-023 | $CHF_2$ | H | H | H | H | Cl | Cl | N | i-Pr(Z) | *1 |
| 3-024 | $CF_3$ | H | F | H | H | Cl | Cl | N | i-Pr(Z) | *1 |
| 3-025 | $CF_3$ | F | H | H | H | Cl | Cl | N | Et | *1 |
| 3-026 | $OCH_3$ | H | H | H | H | Cl | Cl | N | Et | *1 |
| 3-027 | $OCHF_2$ | H | H | H | H | Cl | Cl | N | Et | *1 |
| 3-028 | $OCF_3$ | H | H | H | H | Cl | Cl | N | Et | *1 |
| 3-029 | $SCH_3$ | H | H | H | H | Cl | Cl | N | Et | *1 |
| 3-030 | $NO_2$ | H | H | H | H | Cl | Cl | N | Et | *1 |
| 3-031 | CN | H | H | H | H | Cl | Cl | N | Et | *1 |
| 3-032 | Ph | H | H | H | H | Cl | Cl | N | Et | *1 |
| 3-033 | Cl | H | H | H | H | Cl | Cl | N | $CH_3$ | *1 |
| 3-034 | Cl | H | H | H | H | Cl | Cl | N | s-Bu(Z) | 74.0-79.0 |
| 3-035 | Cl | H | H | H | H | Cl | Cl | N | t-Bu(Z) | *1 |
| 3-036 | Cl | H | H | H | H | Cl | Cl | N | $CH_2CF_3$(Z) | 93.0-94.0 |
| 3-037 | Br | H | H | H | H | Cl | Cl | N | $CH_3$(Z) | *1 |
| 3-038 | Br | H | H | H | H | Cl | Cl | N | s-Bu(Z) | *1 |
| 3-039 | Br | H | H | H | H | Cl | Cl | N | t-Bu(Z) | *1 |

TABLE 6-continued

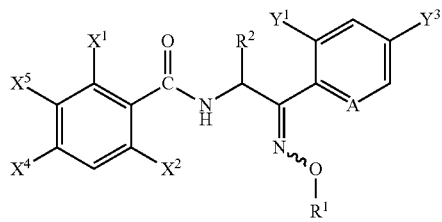

| No. | $X^1$ | $X^2$ | $X^4$ | $X^5$ | $R^2$ | $Y^1$ | $Y^3$ | A | $R^1$ | m.p.(° C.) |
|---|---|---|---|---|---|---|---|---|---|---|
| 3-040 | Br | H | H | H | H | Cl | Cl | N | $CH_2CF_3$(Z) | *1 |
| 3-041 | Br | H | H | H | H | Cl | Cl | N | $CH(CH_3)$(Ph-4-F)(Z) | 68.0-72.0 |
| 3-042 | I | H | H | H | H | Cl | Cl | N | $CH_3$ | *1 |
| 3-043 | I | H | H | H | H | Cl | Cl | N | s-Bu(Z) | *1 |
| 3-044 | I | H | H | H | H | Cl | Cl | N | t-Bu | *1 |
| 3-045 | I | H | H | H | H | Cl | Cl | N | $CH_2CF_3$ | *1 |
| 3-046 | $CH_3$ | H | H | H | H | Cl | Cl | N | $CH_3$ | *1 |
| 3-047 | $CH_3$ | H | H | H | H | Cl | Cl | N | s-Bu(Z) | 76.0-79.0 |
| 3-048 | $CH_3$ | H | H | H | H | Cl | Cl | N | t-Bu(Z) | *1 |
| 3-049 | $CH_3$ | H | H | H | H | Cl | Cl | N | $CH_2CF_3$ | 86.0-87.0 |
| 3-050 | $CH_3$ | H | H | H | H | Cl | Cl | N | $CH(CH_3)$(Ph-4-F)(Z) | 95.0-100.0 |
| 3-051 | $CH_3$ | H | H | H | H | Br | Br | N | $CH_2CF_3$ | *1 |

TABLE 7

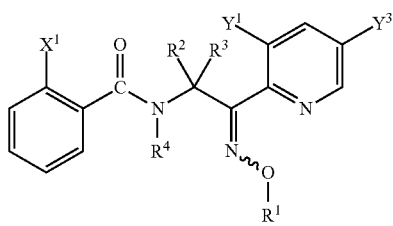

| No. | $X^1$ | $R^4$ | $R^2$ | $R^3$ | $Y^1$ | $Y^3$ | $R^1$ | m.p.(° C.) |
|---|---|---|---|---|---|---|---|---|
| 4-001 | I | H | $CH_3$ | $CH_3$ | Cl | Cl | $CH_3$ | *1 |
| 4-002 | $CF_3$ | H | $CH_3$ | $CH_3$ | Cl | Cl | Et(Z) | *1 |
| 4-003 | $CF_3$ | H | —$CH_2CH_2$— | | Cl | Cl | Et(Z) | 104.0-105.0 |
| 4-004 | $CF_3$ | H | —$CH_2CH_2CH_2$— | | Cl | Cl | Et | *1 |
| 4-005 | $CF_3$ | $CH_3$ | H | H | Cl | Cl | $CH_3$ | *1 |
| 4-006 | $CF_3$ | Et | H | H | Cl | Cl | $CH_3$ | *1 |
| 4-007 | $CF_3$ | c-Pr | H | H | Cl | Cl | $CH_3$ | 75.0-77.0 |
| 4-008 | $CF_3$ | $CH_2OCH_3$ | H | H | Cl | Cl | $CH_3$ | *1 |
| 4-009 | $CF_3$ | $CH_2CH=CH_2$ | H | H | Cl | Cl | $CH_3$ | *1 |
| 4-010 | $CF_3$ | $CH_2C\equiv CH$ | H | H | Cl | Cl | $CH_3$ | *1 |
| 4-011 | $CF_3$ | c-Pr | H | H | Cl | $CF_3$ | $CH_3$ | *1 |
| 4-012 | $CF_3$ | $CH_2CN$ | H | H | Cl | Cl | $CH_3$ | *1 |
| 4-013 | $CF_3$ | $C(O)CH_3$ | H | H | Cl | Cl | $CH_3$ | *1 |
| 4-014 | $CF_3$ | $C(O)OCH_3$ | H | H | Cl | Cl | $CH_3$ | *1 |
| 4-015 | $CF_3$ | $SCCl_3$ | H | H | Cl | Cl | $CH_3$ | *1 |

TABLE 8

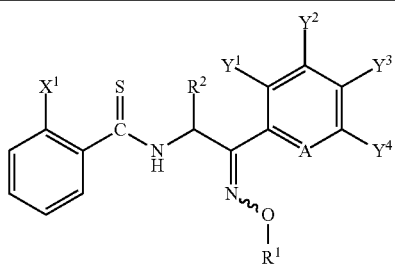

| No. | $X^1$ | $R^2$ | $Y^1$ | $Y^2$ | $Y^3$ | $Y^4$ | A | $R^1$ | m.p.(° C) |
|---|---|---|---|---|---|---|---|---|---|
| 5-001 | $CF_3$ | H | Cl | H | Br | H | N | $CH_3$ | *1 |

TABLE 9

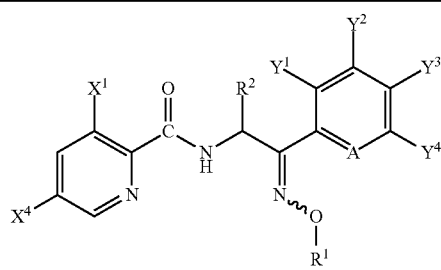

| No. | $X^1$ | $X^4$ | $R^2$ | $Y^1$ | $Y^2$ | $Y^3$ | $Y^4$ | A | $R^1$ | m.p.(° C.) |
|---|---|---|---|---|---|---|---|---|---|---|
| 6-001 | Cl | H | H | Cl | H | Cl | H | N | Et | *1 |
| 6-002 | Cl | $CF_3$ | H | Cl | H | Cl | H | N | Et | 49.0-55.0 |
| 6-003 | Br | H | H | Cl | H | Cl | H | N | Et | *1 |
| 6-004 | $CH_3$ | H | H | Cl | H | Cl | H | N | Et | *1 |
| 6-005 | $CF_3$ | H | H | Cl | H | Cl | H | N | Et(Z) | *1 |
| 6-006 | Cl | H | H | Cl | H | Cl | H | N | i-Pr(Z) | *1 |
| 6-007 | Br | H | H | Cl | H | Cl | H | N | i-Pr(Z) | *1 |
| 6-008 | $CF_3$ | H | H | Cl | H | Cl | H | N | i-Pr(Z) | *1 |

TABLE 10

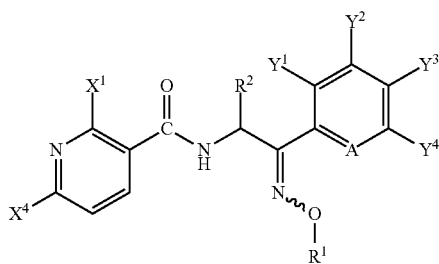

| No. | $X^1$ | $X^4$ | $R^2$ | $Y^1$ | $Y^2$ | $Y^3$ | $Y^4$ | A | $R^1$ | m.p.(° C.) |
|---|---|---|---|---|---|---|---|---|---|---|
| 7-001 | Cl | H | H | Cl | H | Cl | H | CH | $CH_3$ | *1 |
| 7-002 | Cl | H | H | Cl | H | Cl | H | N | Et | *1 |
| 7-003 | Br | $CF_3$ | H | Cl | H | Cl | H | N | Et | *1 |
| 7-004 | $CF_3$ | H | $CH_3$ | Cl | H | Cl | H | CH | Et | *1 |
| 7-005 | $CF_3$ | H | H | Cl | H | Cl | H | N | Et | 97.0-99.0 |
| 7-006 | Cl | H | H | Cl | H | Cl | H | N | $CH_3$(Z) | *1 |
| 7-007 | Cl | H | H | Cl | H | Cl | H | N | n-Pr(Z) | *1 |
| 7-008 | Cl | H | H | Cl | H | Cl | H | N | t-Bu(Z) | *1 |
| 7-009 | Cl | H | H | Cl | H | Cl | H | N | $CH_2CF_3$(Z) | *1 |

TABLE 11

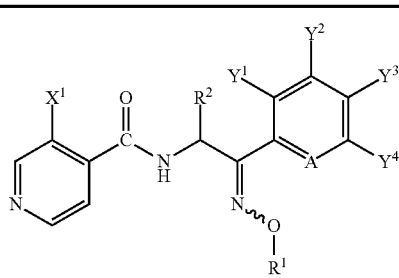

| No. | $X^1$ | $R^2$ | $Y^1$ | $Y^2$ | $Y^3$ | $Y^4$ | A | $R^1$ | m.p.(° C.) |
|---|---|---|---|---|---|---|---|---|---|
| 8-001 | $CF_3$ | H | Cl | H | Cl | H | N | Et(Z) | *1 |

TABLE 12

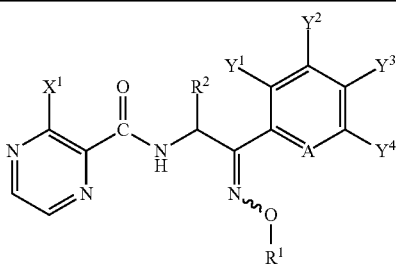

| No. | $X^1$ | $R^2$ | $Y^1$ | $Y^2$ | $Y^3$ | $Y^4$ | A | $R^1$ | m.p.(° C.) |
|---|---|---|---|---|---|---|---|---|---|
| 9-001 | $CF_3$ | H | Cl | H | Cl | H | N | $CH_3$(Z) | *1 |
| 9-002 | $CF_3$ | $CH_3$ | Cl | H | Cl | H | CH | Et(Z) | *1 |
| 9-003 | $CF_3$ | H | Cl | H | Cl | H | N | Et | 90.0-92.0 |
| 9-004 | $CF_3$ | H | Cl | H | Cl | H | N | $CH_2$Pr-c | *1 |
| 9-005 | $CF_3$ | H | Cl | H | Cl | H | N | t-Bu(isomer A) | *1 |
| 9-006 | $CF_3$ | H | Cl | H | Cl | H | N | t-Bu(isomer B) | *1 |
| 9-007 | $CF_3$ | H | Cl | H | Cl | H | N | i-Pr(Z) | *1 |

TABLE 13

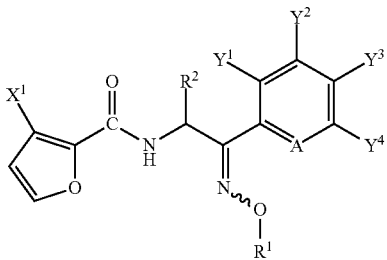

| No. | X¹ | R² | Y¹ | Y² | Y³ | Y⁴ | A | R¹ | m.p.(° C.) |
|---|---|---|---|---|---|---|---|---|---|
| 10-001 | Br | H | Cl | H | Cl | H | N | Et | *1 |
| 10-002 | $CH_3$ | H | Cl | H | Cl | H | N | Et(Z) | *1 |

TABLE 14

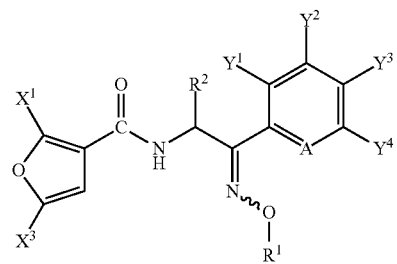

| No. | X¹ | X³ | R² | Y¹ | Y² | Y³ | Y⁴ | A | R¹ | m.p.(° C.) |
|---|---|---|---|---|---|---|---|---|---|---|
| 11-001 | $CH_3$ | $CH_3$ | H | Cl | H | Cl | H | N | Et | *1 |
| 11-002 | $CF_3$ | $CH_3$ | H | Cl | H | Cl | H | N | Et | *1 |
| 11-003 | $CF_3$ | Ph | H | Cl | H | Cl | H | N | Et | *1 |

TABLE 15

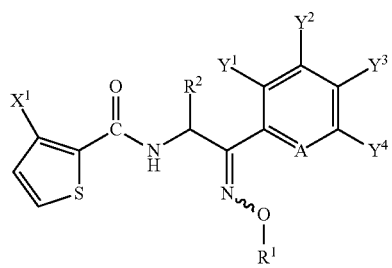

| No. | X¹ | R² | Y¹ | Y² | Y³ | Y⁴ | A | R¹ | m.p.(° C) |
|---|---|---|---|---|---|---|---|---|---|
| 12-001 | $CH_3$ | $CH_3$ | H | H | F | H | CH | $CH_3$ | *1 |
| 12-002 | $CH_3$ | $CH_3$ | H | H | F | H | CH | $CH_2$(Ph-4-Cl) | *1 |
| 12-003 | $CH_3$ | H | Cl | H | Cl | H | CH | $CH_3$ | *1 |
| 12-004 | $CH_3$ | $CH_3$ | Cl | H | Cl | H | CH | $CH_3$ | 75.0-77.0 |
| 12-005 | $CH_3$ | $CH_3$ | Cl | H | Cl | H | CH | i-Pr | *1 |
| 12-006 | $CH_3$ | $CH_3$ | Cl | H | Cl | H | CH | $CH_2$(Ph-4-Cl) | *1 |
| 12-007 | $CH_3$ | H | Cl | H | $CF_3$ | H | N | i-Pr | *1 |
| 12-008 | Br | H | Cl | H | Cl | H | N | Et | *1 |
| 12-009 | I | H | Cl | H | Cl | H | N | Et | *1 |
| 12-010 | $CH_3$ | H | Cl | H | Cl | H | N | Et | *1 |
| 12-011 | $CF_3$ | H | Cl | H | Cl | H | N | Et | *1 |
| 12-012 | $CH_3$ | H | Cl | H | Cl | H | N | $CH_3$ | *1 |
| 12-013 | $CH_3$ | H | Cl | H | Cl | H | N | n-Pr | *1 |
| 12-014 | $CH_3$ | H | Cl | H | Cl | H | N | s-Bu(E) | *1 |
| 12-015 | $CH_3$ | H | Cl | H | Cl | H | N | s-Bu(Z) | 56.0-61.0 |
| 12-016 | $CH_3$ | H | Cl | H | Cl | H | N | t-Bu(Z) | *1 |
| 12-017 | $CH_3$ | H | Cl | H | Cl | H | N | $CH_2CF_3$ | *1 |
| 12-018 | $CF_3$ | $CH_3$(S) | Cl | H | Cl | H | N | n-Pr(Z) | *1 83% e.e. $[\alpha]_D^{25.6}$ −7.32° (EtOH, c = 0.10) |
| 12-019 | $CF_3$ | H | Cl | H | Cl | H | N | i-Pr | 46.0-50.0 |
| 12-020 | $CF_3$ | H | Cl | H | $CF_3$ | H | N | n-Pr(Z) | *1 |

TABLE 16

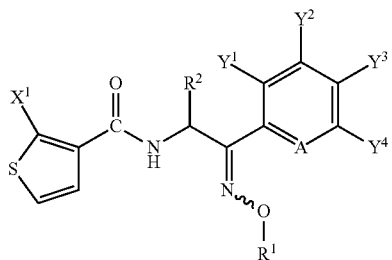

| No. | X¹ | R² | Y¹ | Y² | Y³ | Y⁴ | A | R¹ | m.p. (° C.) |
|---|---|---|---|---|---|---|---|---|---|
| 13-001 | I | H | Cl | H | Cl | H | N | Et | *1 |
| 13-002 | $CF_3$ | H | Cl | H | Cl | H | N | Et | *1 |
| 13-003 | I | $CH_3$(S) | Cl | H | Cl | H | N | n-Pr(Z) | *1 |

83% e.e. $[\alpha]_D^{25.9}$ −25.10° (EtOH, c = 0.10)

TABLE 17

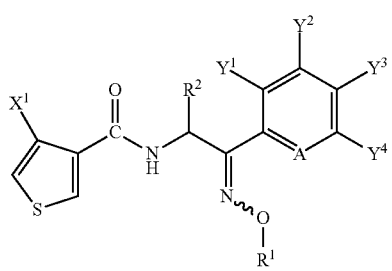

| No. | X¹ | R² | Y¹ | Y² | Y³ | Y⁴ | A | R¹ | m.p. (° C.) |
|---|---|---|---|---|---|---|---|---|---|
| 14-001 | I | H | Cl | H | Cl | H | N | Et | *1 |

TABLE 18

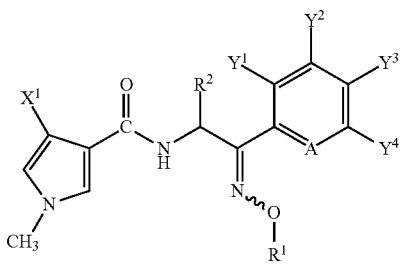

| No. | X¹ | R² | Y¹ | Y² | Y³ | Y⁴ | A | R¹ | m.p. (° C.) |
|---|---|---|---|---|---|---|---|---|---|
| 15-001 | $CF_3$ | H | Cl | H | Cl | H | N | Et(Z) | *1 |
| 15-002 | $CF_3$ | H | Cl | H | Cl | H | N | i-Pr(Z) | *1 |

TABLE 19

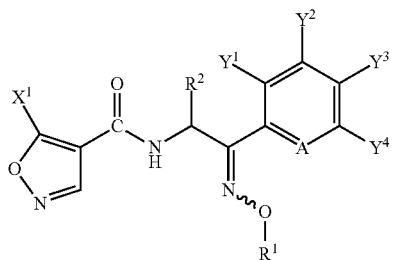

| No. | X¹ | R² | Y¹ | Y² | Y³ | Y⁴ | A | R¹ | m.p. (° C.) |
|---|---|---|---|---|---|---|---|---|---|
| 16-001 | $CF_3$ | H | Cl | H | Cl | H | N | Et(Z) | 112.0-113.0 |

TABLE 20

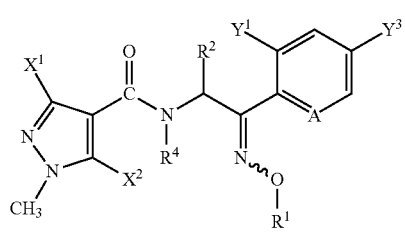

| No. | X¹ | X² | R⁴ | R² | Y¹ | Y³ | A | R¹ | m.p. (° C.) |
|---|---|---|---|---|---|---|---|---|---|
| 17-001 | Cl | Cl | H | H | Cl | Cl | N | Et | *1 |
| 17-002 | $CHF_2$ | H | H | H | Cl | Cl | CH | $CH_3$ | *1 |
| 17-003 | $CHF_2$ | H | H | $CH_3$ | Cl | Cl | CH | $CH_3$ | *1 |
| 17-004 | $CHF_2$ | H | H | H | Cl | Cl | N | Et | *1 |
| 17-005 | $CF_3$ | H | H | H | Cl | Cl | CH | $CH_3$ | *1 |
| 17-006 | $CF_3$ | H | H | H | Cl | Cl | N | Et | *1 |
| 17-007 | $CF_3$ | H | H | H | Cl | $CF_3$ | N | $CH_3$ | 105.0-110.0 |
| 17-008 | $CF_3$ | F | H | H | Cl | Cl | N | $CH_3$(Z) | *1 |
| 17-009 | $CF_3$ | F | c-Pr | H | Cl | Cl | N | $CH_3$ | 95.0-97.0 |
| 17-010 | $CF_3$ | F | H | H | Cl | Cl | N | Et(Z) | 88.0-90.0 |
| 17-011 | $CHF_2$ | H | H | H | Cl | Cl | N | i-Pr(Z) | *1 |
| 17-012 | $CHF_2$ | H | H | H | Cl | $CF_3$ | N | n-Pr(Z) | *1 |

TABLE 21

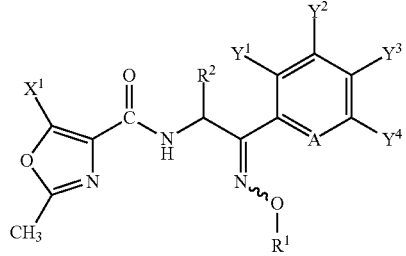

| No. | X¹ | R² | Y¹ | Y² | Y³ | Y⁴ | A | R¹ | m.p. (° C.) |
|---|---|---|---|---|---|---|---|---|---|
| 18-001 | $CF_3$ | H | Cl | H | Cl | H | N | Et(Z) | *1 |

TABLE 22

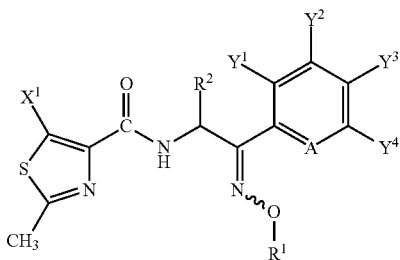

| No. | X¹ | R² | Y¹ | Y² | Y³ | Y⁴ | A | R¹ | m.p. (° C.) |
|---|---|---|---|---|---|---|---|---|---|
| 19-001 | CH₃ | H | Cl | H | Cl | H | N | Et | *1 |

TABLE 23

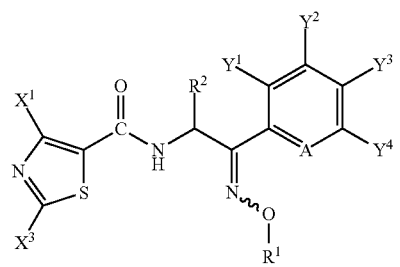

| No. | X¹ | X³ | R² | Y¹ | Y² | Y³ | Y⁴ | A | R¹ | m.p. (° C.) |
|---|---|---|---|---|---|---|---|---|---|---|
| 20-001 | CHF₂ | CH₃ | H | Cl | H | Cl | H | N | Et | *1 |
| 20-002 | CF₃ | CH₃ | CH₃ | Cl | H | Cl | H | CH | Et | *1 |
| 20-003 | CF₃ | CH₃ | H | Cl | H | Cl | H | N | Et | *1 |
| 20-004 | CF₃ | CH₃ | H | Cl | H | Cl | H | N | CH₂Pr-c(Z) | *1 |
| 20-005 | CF₃ | CH₃ | H | Cl | H | Cl | H | N | CH(CH₃)Ph | *1 |
| 20-006 | CF₃ | CH₃ | H | Cl | H | Cl | H | N | CH₂CF₃(Z) | 127.0-128.0 |
| 20-007 | CF₃ | CF₃ | H | Cl | H | Cl | H | N | Et | 98.0-103.0 |

TABLE 24

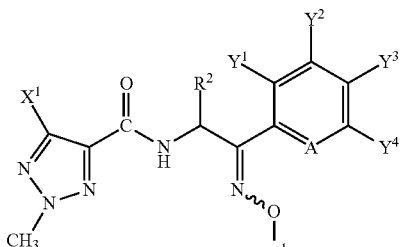

| No. | X¹ | R² | Y¹ | Y² | Y³ | Y⁴ | A | R¹ | m.p. (° C.) |
|---|---|---|---|---|---|---|---|---|---|
| 21-001 | CF₃ | H | Cl | H | Cl | H | N | Et(Z) | *1 |

TABLE 25

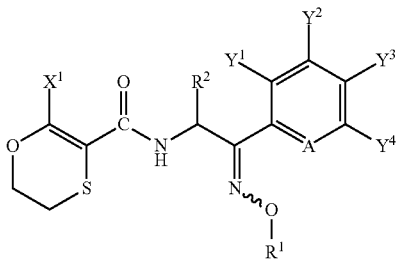

| No. | X¹ | R² | Y¹ | Y² | Y³ | Y⁴ | A | R¹ | m.p. (° C.) |
|---|---|---|---|---|---|---|---|---|---|
| 22-001 | CF₃ | CH₃ | Cl | H | Cl | H | CH | Et | *1 |
| 22-002 | CF₃ | H | Cl | H | Cl | H | N | Et | *1 |
| 22-003 | CF₃ | H | Cl | H | Cl | H | N | i-Pr | *1 |

TABLE 26

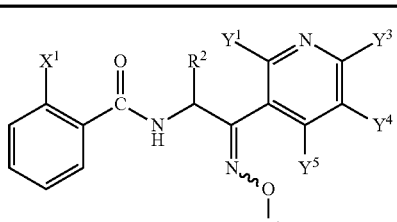

| No. | X¹ | R² | Y¹ | Y³ | Y⁴ | Y⁵ | R¹ | m.p. (° C.) |
|---|---|---|---|---|---|---|---|---|
| 23-001 | CF₃ | H | Cl | H | Cl | H | Et | 84.0-86.0 |
| 23-002 | CF₃ | H | Cl | H | Cl | H | i-Pr | 75.0-77.0 |
| 23-003 | CF₃ | H | Cl | H | Cl | H | c-Pen | 89.0-91.0 |
| 23-004 | CF₃ | H | Cl | H | Cl | H | CH₂(Ph-4-F) | *1 |
| 23-005 | CF₃ | H | Cl | Cl | H | H | CH₃ | 124.0-126.0 |

TABLE 27

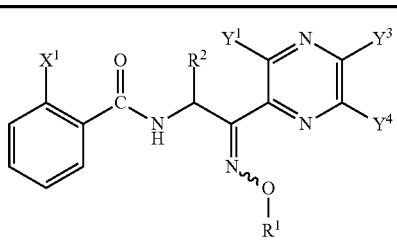

| No. | X¹ | R² | Y¹ | Y³ | Y⁴ | R¹ | m.p. (° C.) |
|---|---|---|---|---|---|---|---|
| 24-001 | CF₃ | H | Cl | Cl | H | i-Pr | *1 |

TABLE 28

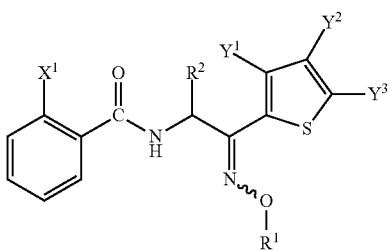

| No. | $X^1$ | $R^2$ | $Y^1$ | $Y^2$ | $Y^3$ | $R^1$ | m.p. (° C.) |
|---|---|---|---|---|---|---|---|
| 25-001 | $CF_3$ | H | Cl | Cl | Cl | $CH_3$ | 95.0-100.0 |
| 25-002 | $CF_3$ | H | Cl | Cl | Cl | Et | 95.0-100.0 |
| 25-003 | $CF_3$ | H | Cl | Cl | Cl | n-Pr | 75.0-78.0 |
| 25-004 | $CF_3$ | H | Cl | Cl | Cl | i-Pr | 98.0-102.0 |

TABLE 29

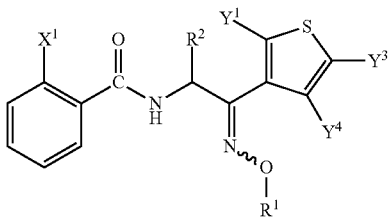

| No. | $X^1$ | $R^2$ | $Y^1$ | $Y^3$ | $Y^4$ | $R^1$ | m.p. (° C.) |
|---|---|---|---|---|---|---|---|
| 26-001 | $CF_3$ | $CH_3$ | Cl | H | H | Et | *1 |
| 26-002 | $CF_3$ | $CH_3$ | Cl | H | H | $CH(CH_3)Ph$ | *1 |
| 26-003 | $CF_3$ | $CH_3$ | Cl | Cl | H | Et | *1 |

TABLE 30

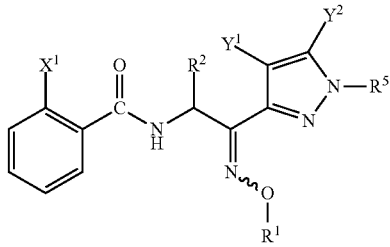

| No. | $X^1$ | $R^2$ | $Y^1$ | $Y^2$ | $R^5$ | $R^1$ | m.p. (° C.) |
|---|---|---|---|---|---|---|---|
| 27-001 | $CF_3$ | $CH_3$ | Cl | OPr-i | $CH_3$ | $CH_3$(E) | *1 |
| 27-002 | $CF_3$ | $CH_3$ | Cl | OPr-i | $CH_3$ | $CH_3$(Z) | *1 |

TABLE 31

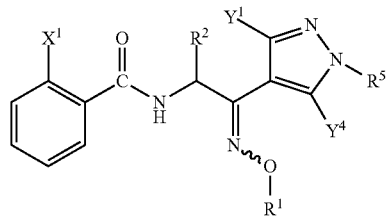

| No. | $X^1$ | $R^2$ | $Y^1$ | $R^5$ | $Y^4$ | $R^1$ | m.p. (° C.) |
|---|---|---|---|---|---|---|---|
| 28-001 | $CF_3$ | $CH_3$ | $CF_3$ | $CH_3$ | H | Et | 129.0-131.0 |

TABLE 32

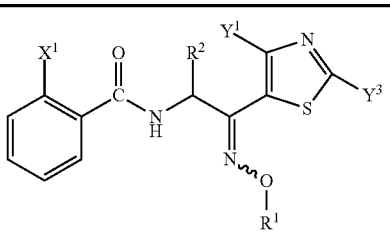

| No. | $X^1$ | $R^2$ | $Y^1$ | $Y^3$ | $R^1$ | m.p. (° C.) |
|---|---|---|---|---|---|---|
| 29-001 | $CF_3$ | H | Cl | Cl | $CH_3$ | *1 |
| 29-002 | $CF_3$ | H | Cl | Cl | Et | *1 |

TABLE 33

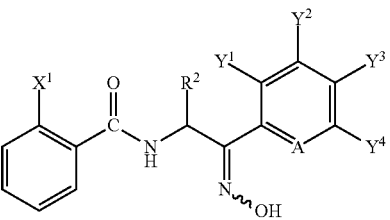

| No. | $X^1$ | $R^2$ | $Y^1$ | $Y^2$ | $Y^3$ | $Y^4$ | A | m.p. (° C.) |
|---|---|---|---|---|---|---|---|---|
| 30-001 | $CF_3$ | $CH_3$ | H | H | $CF_3$ | H | CH | 174.0-175.0 |
| 30-002 | $CF_3$ | $CH_3$ | H | H | $OCF_3$ | H | CH | 111.0-113.0 |
| 30-003 | $CF_3$ | $CH_3$ | H | H | OPh | H | CH | 118.0-120.0 |
| 30-004 | $CF_3$ | $CH_3$ | H | H | Ph | H | CH | 151.0-153.0 |
| 30-005 | $CF_3$ | $CH_3$ | H | F | F | F | CH | 174.0-175.0 |
| 30-006 | $CF_3$ | $CH_3$ | H | Cl | Cl | H | CH | 157.0-160.0 |
| 30-007 | $CF_3$ | $CH_3$ | H | —CH=CHCH=CH— | | H | CH | *1 |
| 30-008 | $CF_3$ | $CH_3$ | F | H | F | H | CH | 132.0-134.0 |
| 30-009 | $CF_3$ | $CH_3$ | F | H | F | H | CF | *1 |
| 30-010 | $CF_3$ | H | F | H | F | H | N | *1 |
| 30-011 | $CF_3$ | $CH_3$ | F | H | Cl | H | CH | 144.0-145.0 |
| 30-012 | $CF_3$ | H | F | H | Cl | H | N | *1 |
| 30-013 | $CF_3$ | $CH_3$ | F | H | Br | H | CH | *1 |
| 30-014 | $CF_3$ | $CH_3$ | F | H | Br | H | CF | *1 |
| 30-015 | $CF_3$ | $CH_3$ | Cl | H | H | Cl | CH | 158.0-160.0 |
| 30-016 | $CF_3$ | $CH_3$ | Cl | H | Cl | H | CH | *1 |
| 30-017 | $CF_3$ | H | Cl | H | Cl | H | N | 134.0-136.0 |
| 30-018 | $CF_3$ | $CH_3$ | Cl | H | Cl | H | N | *1 |
| 30-019 | $CF_3$ | H | Cl | H | Cl | F | N | *1 |
| 30-020 | $CF_3$ | H | Cl | H | Cl | $OCH_3$ | N | *1 |
| 30-021 | $CF_3$ | $CH_3$ | Cl | H | Br | H | CH | *1 |
| 30-022 | $CF_3$ | H | Cl | H | Br | H | N | *1 |

TABLE 33-continued

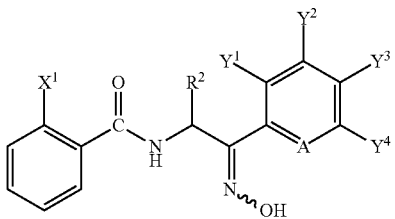

| No. | X¹ | R² | Y¹ | Y² | Y³ | Y⁴ | A | m.p. (° C.) |
|---|---|---|---|---|---|---|---|---|
| 30-023 | CF₃ | H | Cl | H | CF₃ | H | N | 110.0-113.0 |
| 30-024 | CF₃ | H | Cl | H | C(CH₃)=NOCH₃ | H | N | *1 |
| 30-025 | CF₃ | H | Cl | H | CN | H | N | *1 |
| 30-026 | CF₃ | CH₃ | Br | H | F | H | CN | 48.0-50.0 |
| 30-027 | CF₃ | CH₃ | CH₃ | H | Cl | H | CN | 132.0-133.0 |
| 30-028 | CF₃ | H | CF₃ | H | CF₃ | H | N | *1 |

TABLE 34

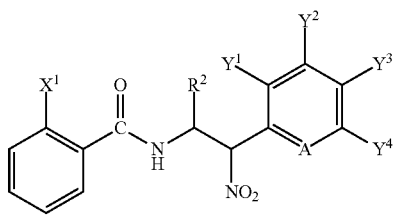

| No. | X¹ | R² | Y¹ | Y² | Y³ | Y⁴ | A | m.p. (° C.) |
|---|---|---|---|---|---|---|---|---|
| 31-001 | CF₃ | H | F | H | F | H | N | *1 |
| 31-002 | CF₃ | H | F | H | Cl | H | N | *1 |
| 31-003 | CF₃ | H | Cl | H | Cl | H | N | *1 |
| 31-004 | CF₃ | H | Cl | H | Cl | F | N | *1 |
| 31-005 | CF₃ | H | Cl | H | Cl | OCH₃ | N | *1 |
| 31-006 | CF₃ | H | Cl | H | Br | H | N | *1 |
| 31-007 | CF₃ | H | Cl | H | CF₃ | H | N | 100.0-102.0 |
| 31-008 | CF₃ | H | Cl | H | C(CH₃)=NOCH₃ | H | N | *1 |
| 31-009 | CF₃ | H | Cl | H | CN | H | N | *1 |
| 31-010 | CF₃ | H | CF₃ | H | CF₃ | H | N | *1 |

TABLE 35

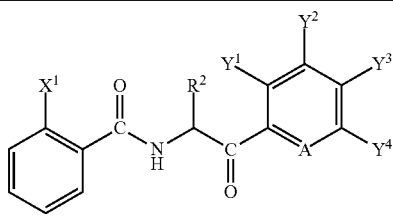

| No. | X¹ | R² | Y¹ | Y² | Y³ | Y⁴ | A | m.p. (° C.) |
|---|---|---|---|---|---|---|---|---|
| 32-001 | I | CH₃ | H | H | Br | H | CH | 140.0-144.0 |
| 32-002 | I | H | Cl | H | Cl | H | N | 109.0-110.0 |
| 32-003 | CF₃ | CH₃ | H | H | I | H | CH | 127.0-128.0 |
| 32-004 | CF₃ | CH₃ | H | H | t-Bu | H | CH | *1 |
| 32-005 | CF₃ | CH₃ | H | H | CF₃ | H | CH | 107.0-108.0 |
| 32-006 | CF₃ | CH₃ | H | H | OCF₃ | H | CH | 88.0-89.0 |
| 32-007 | CF₃ | CH₃ | H | H | OPh | H | CH | 103.0-105.0 |
| 32-008 | CF₃ | CH₃ | H | H | Ph | H | CH | 167.0-168.0 |
| 32-009 | CF₃ | CH₃ | H | F | F | F | CH | 128.0-129.0 |
| 32-010 | CF₃ | CH₃ | H | Cl | Cl | H | CH | 128.0-129.0 |
| 32-011 | CF₃ | CH₃ | H | Br | H | CF₃ | CH | *1 |
| 32-012 | CF₃ | CH₃ | H | OPr-i | H | H | CH | *1 |
| 32-013 | CF₃ | CH₃ | H | —CH=CHCH=CH— | | H | CH | *1 |
| 32-014 | CF₃ | CH₃ | F | H | F | H | CH | 67.0-69.0 |
| 32-015 | CF₃ | CH₃ | F | H | F | H | CF | *1 |
| 32-016 | CF₃ | CH₃ | F | H | Cl | H | CH | 73.0-74.0 |
| 32-017 | CF₃ | CH₃ | F | H | Br | H | CH | 89.0-90.0 |
| 32-018 | CF₃ | CH₃ | F | H | Br | H | CF | *1 |
| 32-019 | CF₃ | CH₃ | F | H | Br | F | CH | *1 |
| 32-020 | CF₃ | CH₃ | F | H | CF₃ | H | CH | 80.0-81.0 |
| 32-021 | CF₃ | CH₃ | F | F | F | H | CH | 107.0-108.0 |
| 32-022 | CF₃ | CH₃ | Cl | H | H | F | CH | 67.0-69.0 |
| 32-023 | CF₃ | CH₃ | Cl | H | H | Cl | CH | 88.0-90.0 |
| 32-024 | CF₃ | CH₃ | Cl | H | H | CF₃ | CH | *1 |
| 32-025 | CF₃ | CH₃ | Cl | H | F | H | CH | *1 |
| 32-026 | CF₃ | CH₃ | Cl | H | Cl | H | CH | 52.0-53.0 |
| 32-027 | CF₃ | H | Cl | H | Cl | H | N | 123.0-125.0 |
| 32-028 | CF₃ | CH₃ | Cl | H | Cl | H | N | 85.0-89.0 |
| 32-029 | CF₃ | CH₃ | Cl | H | Br | H | CH | *1 |
| 32-030 | CF₃ | CH₃ | Cl | H | CH₃ | H | CH | *1 |
| 32-031 | CF₃ | CH₃ | Cl | H | CF₃ | H | CH | *1 |
| 32-032 | CF₃ | H | Cl | H | CF₃ | H | N | *1 |
| 32-033 | CF₃ | CH₃ | Cl | H | OCH₃ | H | CH | *1 |
| 32-034 | CF₃ | CH₃ | Cl | H | SCH₃ | H | CH | *1 |
| 32-035 | CF₃ | CH₃ | Cl | H | CN | H | CH | *1 |

TABLE 35-continued

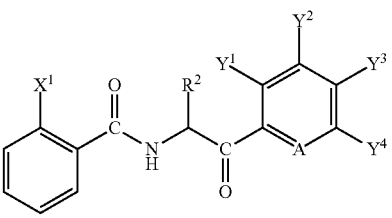

| No. | $X^1$ | $R^2$ | $Y^1$ | $Y^2$ | $Y^3$ | $Y^4$ | A | m.p. (° C.) |
|---|---|---|---|---|---|---|---|---|
| 32-036 | $CF_3$ | $CH_3$ | Cl | H | $C(O)OCH_2C(CH_3)_2NH_2 \cdot HCl$ | H | CH | 135.0-137.0 |
| 32-037 | $CF_3$ | $CH_3$ | Cl | H | (M-7-b)-4,4-$(CH_3)_2$ | H | CH | *1 |
| 32-038 | $CF_3$ | $CH_3$ | Cl | H | $CH=CH_2$ | H | CH | *1 |
| 32-039 | $CF_3$ | $CH_3$ | Cl | H | $C\equiv CSi(CH_3)_3$ | H | CH | *1 |
| 32-040 | $CF_3$ | $CH_3$ | Cl | H | Ph | H | CH | *1 |
| 32-041 | $CF_3$ | $CH_3$ | Cl | H | Ph-4-$OCF_3$ | H | CH | *1 |
| 32-042 | $CF_3$ | $CH_3$ | Cl | H | D-3-a | H | CH | *1 |
| 32-043 | $CF_3$ | $CH_3$ | Cl | H | D-7-a | H | CH | *1 |
| 32-044 | $CF_3$ | $CH_3$ | Cl | H | (D-7-b)-3-$CF_3$ | H | CH | *1 |
| 32-045 | $CF_3$ | $CH_3$ | Cl | F | H | H | CH | 50.0-51.0 |
| 32-046 | $CF_3$ | $CH_3$ | Br | H | F | H | CH | *1 |
| 32-047 | $CF_3$ | $CH_3$ | Br | H | F | F | CH | *1 |
| 32-048 | $CF_3$ | $CH_3$ | $CH_3$ | H | Cl | H | CH | *1 |
| 32-049 | $CF_3$ | $CH_3$ | $CF_3$ | H | Cl | H | CH | *1 |
| 32-050 | $CF_3$ | $CH_3$ | $OCH_3$ | H | Cl | H | CH | 90.0-92.0 |
| 32-051 | $CF_3$ | $CH_3$ | E-9-1a | H | Cl | H | CH | *1 |
| 32-052 | $CF_3$ | $CH_3$ | —CH=CHCH=CH— | | Br | H | CH | *1 |
| 32-053 | $CF_3$ | Ph | Cl | H | Cl | H | N | 164.0-166.0 |
| 32-054 | $CF_3$ | H | Cl | Cl | Cl | H | N | 124.0-125.0 |
| 32-055 | $CF_3$ | H | Cl | CN | Cl | H | N | *1 |
| 32-056 | $CF_3$ | H | Br | H | Br | H | N | *1 |
| 32-057 | $CF_3$ | $CH_3$ | Br | H | Br | H | N | *1 |

TABLE 36

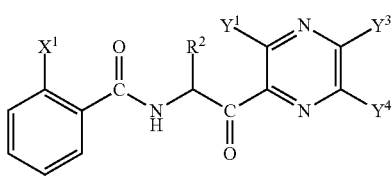

| No. | $X^1$ | $R^2$ | $Y^1$ | $Y^3$ | $Y^4$ | m.p. (° C.) |
|---|---|---|---|---|---|---|
| 33-001 | $CF_3$ | H | Cl | Cl | H | *1 |

TABLE 37

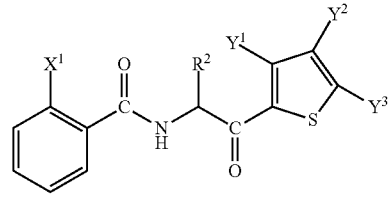

| No. | $X^1$ | $R^2$ | $Y^1$ | $Y^2$ | $Y^3$ | m.p. (° C.) |
|---|---|---|---|---|---|---|
| 34-001 | $CF_3$ | H | Cl | Cl | Cl | 173.0-174.0 |

TABLE 38

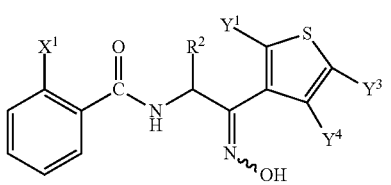

| No. | $X^1$ | $R^2$ | $Y^1$ | $Y^3$ | $Y^4$ | m.p. (° C.) |
|---|---|---|---|---|---|---|
| 35-001 | $CF_3$ | $CH_3$ | Cl | H | H | *1 |

TABLE 39

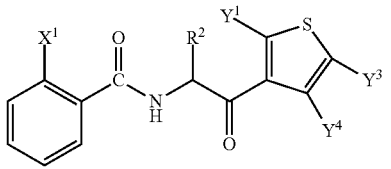

| No. | $X^1$ | $R^2$ | $Y^1$ | $Y^3$ | $Y^4$ | m.p. (° C.) |
|---|---|---|---|---|---|---|
| 36-001 | $CF_3$ | $CH_3$ | Cl | H | H | 109.0-110.0 |
| 36-002 | $CF_3$ | $CH_3$ | Cl | Cl | H | *1 |

TABLE 40

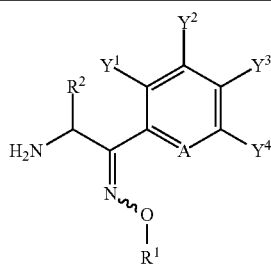

In the Tables, the expression "(HCl)" in the column substituent R¹ means the compound being a hydrochloride

| No. | R² | Y¹ | Y² | Y³ | Y⁴ | A | R¹ | m.p. (° C.) |
|---|---|---|---|---|---|---|---|---|
| 37-001 | CH₃ | Cl | H | Cl | H | CH | Et | *1 |
| 37-002 | H | Cl | H | Cl | H | N | CH₃(HCl) | 167.0-168.0 |
| 37-003 | CH₃ | Cl | H | Cl | H | N | CH₃ | *1 |
| 37-004 | CH₃(S) | Cl | H | Cl | H | N | CH₃(HCl) | 203.0-204.0 |
|  |  |  |  |  |  |  | 95% e.e. $[\alpha]_D^{18.1}$ −5.50° (CHCl₃, c = 0.10) |  |
| 37-005 | H | Cl | H | Cl | H | N | Et | *1 |
| 37-006 | CH₃(S) | Cl | H | Cl | H | N | Et(HCl) | 209.0-210.0 |
|  |  |  |  |  |  |  | 95% e.e. $[\alpha]_D^{18.5}$ −10.90° (CHCl₃, c = 0.10) |  |
| 32-007 | H | Cl | H | Cl | H | N | n-Pr(HCl) | 140.0-141.0 |
| 37-008 | H | Cl | H | Cl | H | N | i-Pr | *1 |
| 37-009 | CH₃ | Cl | H | Cl | H | N | i-Pr(HCl) | *1 |
| 37-010 | CH₃(S) | Cl | H | Cl | H | N | i-Pr(HCl) | 215.0-216.0 |
|  |  |  |  |  |  |  | 95% e.e. $[\alpha]_D^{18.8}$ −15.50° (CHCl₃, c = 0.10) |  |
| 37-011 | H | Cl | H | Cl | H | N | CH₂Pr-c | *1 |
| 37-012 | H | Cl | H | Cl | H | N | s-Bu(HCl) | 165.0-166.0 |
| 37-013 | H | Cl | H | Cl | H | N | t-Bu(HCl) | 178.0-179.0 |
| 37-014 | H | Cl | H | Cl | H | N | CH₂CF₃(HCl) | 141.0-143.0 |
| 37-015 | H | Cl | H | Cl | H | N | CH(CH₃)Ph | *1 |
| 37-016 | H | Cl | H | Cl | H | N | CH(CH₃)(Ph-4-F)(HCl) | *1 |
| 37-017 | H | Cl | H | CF₃ | H | N | Et | *1 |
| 37-018 | H | Cl | H | CF₃ | H | N | CH₂Pr-c(E) | *1 |
| 37-019 | H | Cl | H | CH₂OCH₃ | H | N | i-Pr | *1 |
| 37-020 | H | Cl | H | OCH₃ | H | N | i-Pr | *1 |
| 37-021 | H | Cl | H | OCH₂CF₃ | H | N | CH₃ | *1 |
| 37-022 | H | Br | H | Br | H | N | i-Pr(HCl) | 160.0-180.0 |
| 37-023 | H | Br | H | Br | H | N | CH₂CF₃(HCl) | 165.0-175.0 |
| 37-024 | CH₃(S) | Cl | H | Cl | H | N | n-Pr(HCl) | *1 |
|  |  |  |  |  |  |  | 83% e.e. $[\alpha]_D^{25.4}$ −6.66° (CHCl₃, c = 0.10) |  |
| 37-025 | H | Cl | H | CF₃ | H | N | CH₃ | *1 |
| 37-026 | H | Cl | H | CF₃ | H | N | n-Pr | *1 |
| 37-027 | H | Cl | H | CF₃ | H | N | i-Pr | *1 |

TABLE 41

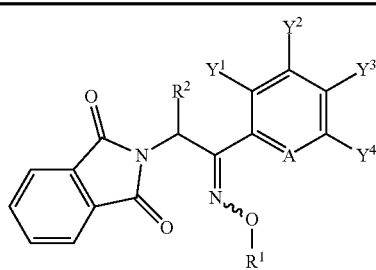

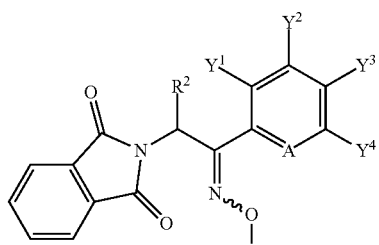

| No. | R² | Y¹ | Y² | Y³ | Y⁴ | A | R¹ | m.p. (° C.) |
|---|---|---|---|---|---|---|---|---|
| 38-001 | H | Cl | H | Cl | H | CH | CH₃ | 82.0-85.0 |
| 38-002 | H | Cl | H | Cl | H | N | H | 138.0-141.0 |
| 38-003 | CH₃ | Cl | H | Cl | H | N | CH₃ | *1 |
| 38-004 | Et | Cl | H | Cl | H | N | CH₃ | *1 |
| 38-005 | H | Cl | H | Cl | H | N | Et | 99.0-101.0 |
| 38-006 | H | Cl | H | Cl | H | N | n-Pr | *1 |
| 38-007 | H | Cl | H | Cl | H | N | t-Bu | *1 |
| 38-008 | H | Cl | H | CF₃ | H | N | H | *1 |
| 38-009 | CH₃ | Cl | H | CF₃ | H | N | H | *1 |
| 38-010 | H | Cl | H | CF₃ | H | N | Et | *1 |
| 38-011 | H | Cl | H | CF₃ | H | N | CH₂Pr-c(E) | *1 |
| 38-012 | H | Cl | H | CH₂OCH₃ | H | N | H | *1 |
| 38-013 | H | Cl | H | CH₂OCH₃ | H | N | i-Pr | *1 |
| 38-014 | H | Cl | H | OCH₃ | H | N | H | *1 |
| 38-015 | H | Cl | H | OCH₃ | H | N | CH₃ | *1 |
| 38-016 | H | Cl | H | OCH₃ | H | N | i-Pr | *1 |

TABLE 42

| No. | R² | Y¹ | Y² | Y³ | Y⁴ | A | m.p. (° C.) |
|---|---|---|---|---|---|---|---|
| 39-001 | CH₃ | F | H | H | H | CF | 111.0-112.0 |
| 39-002 | CH₃ | F | H | H | F | CH | 104.0-105.0 |
| 39-003 | CH₃ | F | H | F | H | CH | 116.0-117.0 |
| 39-004 | CH₃ | F | H | Cl | H | CH | 73.0-74.0 |
| 39-005 | CH₃ | F | H | CF₃ | H | CH | 108.0-109.0 |
| 39-006 | CH₃ | Cl | H | Cl | H | CH | 120.0-121.0 |
| 39-007 | H | Cl | H | Cl | H | N | *1 |
| 39-008 | CH₃ | Cl | H | Cl | H | N | *1 |
| 39-009 | H | Cl | H | CF₃ | H | N | *1 |
| 39-010 | CH₃ | Cl | H | CF₃ | H | N | *1 |
| 39-011 | H | Cl | H | CH₂OCH₃ | H | N | *1 |
| 39-012 | H | Cl | H | OCH₃ | H | N | *1 |

TABLE 43

| No. | R² | Y¹ | Y² | Y³ | Y⁴ | A | m.p. (° C.) |
|---|---|---|---|---|---|---|---|
| 40-001 | CH₃ | Cl | H | Cl | H | N | *1 |
| 40-002 | CH₃ | Cl | H | CF₃ | H | N | *1 |

TABLE 44

| No. | R² | Y¹ | Y² | Y³ | Y⁴ | A | R¹ | m.p. (° C.) |
|---|---|---|---|---|---|---|---|---|
| 41-001 | CH₃ | Cl | H | Cl | H | CH | H | *1 |
| 41-002 | H | Cl | H | Cl | H | N | H | *1 |
| 41-003 | CH₃(S) | Cl | H | Cl | H | N | H | 51.0-53.0 95% e.e. [α]$_D^{17.8}$ −27.40° (CHCl₃, c = 0.10) |
| 41-004 | H | Cl | H | Cl | H | N | CH₃ | *1 |
| 41-005 | CH₃(S) | Cl | H | Cl | H | N | CH₃ | *1 |

TABLE 44-continued

| No. | R² | Y¹ | Y² | Y³ | Y⁴ | A | R¹ | m.p. (° C.) |
|---|---|---|---|---|---|---|---|---|
| 41-006 | CH₃ | Cl | H | Cl | H | CH | Et | 90.0-92.0 95% e.e. [α]$_D^{17.8}$ −33.00° (CHCl₃, c = 0.10) |
| 41-007 | CH₃(S) | Cl | H | Cl | H | N | Et | *1 |
| 41-008 | t-Bu | Cl | H | Cl | H | N | Et | *1 95% e.e. [α]$_D^{17.8}$ −30.00° (CHCl₃, c = 0.10) |
| 41-009 | H | Cl | H | Cl | H | N | n-Pr | *1 |
| 41-010 | H | Cl | H | Cl | H | N | i-Pr | *1 |
| 41-011 | CH₃ | Cl | H | Cl | H | N | i-Pr | *1 |
| 41-012 | CH₃(S) | Cl | H | Cl | H | N | i-Pr | *1 95% e.e. [α]$_D^{18.0}$ −29.90° (CHCl₃, c = 0.14) |
| 41-013 | H | Cl | H | Cl | H | N | CH₂Pr-c | *1 |
| 41-014 | H | Cl | H | Cl | H | N | s-Bu | *1 |
| 41-015 | H | Cl | H | Cl | H | N | t-Bu | *1 |
| 41-016 | H | Cl | H | Cl | H | N | CH₂CF₃ | *1 |
| 41-017 | H | Cl | H | Cl | H | N | CH(CH₃)Ph | *1 |
| 41-018 | H | Cl | H | Cl | H | N | CH(CH₃)(Ph-4-F) | *1 |
| 41-019 | CH₃(S) | Cl | H | Cl | H | N | n-Pr | *1 83% e.e. [α]$_D^{28.3}$ −23.50° (CHCl₃, c = 0.10) |

TABLE 45

| No. | R² | Y¹ | Y² | Y³ | Y⁴ | A | m.p. (° C.) |
|---|---|---|---|---|---|---|---|
| 42-001 | CH₃ | Cl | H | Cl | H | CH | *1 |
| 42-002 | H | Cl | H | Cl | H | N | 82.0-84.0 |
| 42-003 | CH₃ | Cl | H | Cl | H | N | 111.0-112.0 |
| 42-004 | CH₃(S) | Cl | H | Cl | H | N | 95% e.e. [α]$_D^{17.5}$ −20.20° (CHCl₃, c = 0.10) |
| 42-005 | t-Bu | Cl | H | Cl | H | N | *1 |
| 42-006 | H | Br | H | Br | H | N | *1 |

Among the compounds shown in Tables 4 to 45, ¹H NMR data of compounds of which melting points are not disclosed in the Tables are shown in Table 46.

TABLE 46

| No. | ¹H NMR (CDCl$_3$, Me$_4$Si, 300 MHz) |
|---|---|
| 1-002 | δ 7.05-7.75 (m, 13H), 5.45-5.55 and 5.1-5.2 (m, 1H), 5.13 and 5.02 (s, 2H), 1.53 and 1.36 (d, J = 7.2 Hz, 3H). |
| 1-003 | δ 7.05-7.75 (m, 7H), 6.48 and 6.34 (bs, 1H), 4.61 and 4.43 (d, J = 6.3 Hz, 2H), 4.02 and 3.85 (s, 3H). |
| 1-005 | δ 7.1-7.9 (m, 7H), 6.72 and 6.64 (d, J = 6.9 Hz, 1H), 5.31 and 5.05 (dq, J = 6.9 and 6.6 Hz, 1H), 3.96 and 3.83 (s, 3H), 1.59 and 1.45 (d, J = 6.6 Hz, 3H). |
| 1-006 | δ 7.1-7.75 (m, 7H), 6.84 and 6.69 (d, J = 7.2 Hz, 1H), 5.2-5.35 and 4.95-5.1 (m, 1H), 4.35-4.5 and 4.25-4.35 (m, 1H), 1.58 and 1.43 (d, J = 6.9 Hz, 3H), 1.1-1.5 (m, 6H). |
| 1-007 | δ 7.15-7.75 (m, 7H), 6.48 and 6.45 (bs, 1H), 5.3-5.45 and 5.0-5.25 (m, 1H), 4.54 and 4.38 (q, J = 8.4 Hz, 2H), 1.63 and 1.46 (d, J = 6.9 Hz, 3H). |
| 1-008 | δ 7.1-7.75 (m, 11H), 6.60 and 6.50 (d, J = 7.5 Hz, 1H), 5.25-5.4 and 4.95-5.1 (m, 1H), 5.16 and 5.01 (s, 2H), 1.56 and 1.42 (d, J = 6.9 Hz, 3H). |
| 1-009 | δ 7.45-7.75 (m, 4H), 7.7-7.1 (m, 1H), 6.96 (bs, 1H), 6.7-6.8 (m, 2H), 5.25-5.4 and 4.85-5.0 (m, 1H), 4.45-4.65 (m, 1H), 4.35-4.45 and 4.2-4.35 (m, 1H), 2.36 and 2.19 (s, 3H), 1.1-1.4 (m, 15H). |
| 1-010 | δ 6.6-7.75 (m, 12H), 5.3-5.4 and 4.9-5.05 (m, 1H), 5.12 and 4.99 (s, 2H), 4.5-4.65 (m, 1H), 2.25 and 2.15 (s, 3H), 1.25-1.55 (m, 9H). |
| 1-013 | δ 6.8-7.75 (m, 9H), 5.5-5.65 and 5.15-5.25 (m, 1H), 4.0-4.25 (m, 2H), 1.58 and 1.39 (d, J = 7.2 Hz, 3H), 1.34 and 1.33 (s, 9H), 1.1-1.3 (m, 3H). |
| 1-020 | δ 6.8-7.75 (m, 14H), 5.45-5.6 and 5.1-5.25 (m, 1H), 4.15-4.25 and 4.05-4.15 (m, 2H), 1.58 and 1.40 (d, J = 7.2 Hz, 3H), 1.28 and 1.23 (t, J = 7.2 Hz, 3H). |
| 1-022 | δ 8.36 and 8.30 (d, J = 2.1 Hz, 1H), 6.5-7.75 (m, 16H), 5.0-5.6 (m, 3H), 1.54 and 1.38 (d, J = 7.2 Hz, 3H). |
| 1-023 | δ 6.8-7.8 (m, 14H), 5.55-5.7 and 5.15-5.3 (m, 1H), 4.2-4.3 and 4.05-4.2 (m, 2H), 1.61 and 1.43 (d, J = 7.2 Hz, 3H), 1.30 and 1.25 (t, J = 7.2 Hz, 3H). |
| 1-024 | δ 6.85-7.85 (m, 14H), 5.55-5.7 and 5.2-5.35 (m, 1H), 4.4-4.5 and 4.25-4.4 (m, 1H), 1.15-1.65 (m, 9H). |
| 1-025 | δ 3.6-7.85 (m, 14H), 5.55-5.7 and 5.2-5.3 (m, 1H), 3.8-4.05 (m, 2H), 1.63 and 1.43 (d, J = 6.9 Hz, 3H), 1.0-1.25 (m, 1H), 0.4-0.55 (m, 2H), 0.15-0.3 (m, 2H). |
| 1-027 | δ 8.38 and 8.32 (d, J = 2.1 Hz, 1H), 7.2-7.8 (m, 15H), 6.58 and 6.19 (bs, 1H), 5.05-5.7 (m, 3H), 1.57 and 1.40 (d, J = 6.9 Hz, 3H). |
| 1-034 | δ 6.4-7.8 (m, 13H), 4.85-5.55 (m, 2H), 1.2-1.7 (m, 6H). |
| 1-035 | δ 7.45-8.1 (m, 7H), 6.70 and 6.64 (bs, 1H), 5.35-5.55 and 5.1-5.25 (m, 1H), 4.2-4.3 and 4.05-4.2 (m, 2H), 1.59 and 1.41 (d, J = 6.9 Hz, 3H), 1.30 and 1.22 (t, J = 7.2 Hz, 3H). |
| 1-036 | δ 6.8-7.75 (m, 9H), 5.45-5.6 and 5.1-5.2 (m, 1H), 4.5-4.7 (m, 1H), 4.0-4.3 (m, 2H), 1.1-1.6 (m, 12H). |
| 1-037 | δ 6.85-8.25 (m, 12H), 4.8-5.65 (m, 1H), 3.95-4.35 (m, 2H), 1.1-1.65 (m, 6H). |
| 1-038 | δ 6.4-8.25 (m, 12H), 4.85-5.85 (m, 1H), 4.3-4.65 (m, 2H), 1.15-1.7 (m, 3H). |
| 1-039 | δ 6.6-8.45 (m, 15H), 4.8-5.8 (m, 3H), 1.5-1.65 (m, 3H). |
| 1-041 | δ 6.6-7.75 (m, 8H), 5.35-5.5 and 5.0-5.15 (m, 1H), 3.95-4.05 and 3.8-3.9 (m, 2H), 1.6-1.65 and 1.4-1.45 (m, 3H), 0.95-1.3 (m, 1H), 0.45-0.55 (m, 2H), 0.15-0.3 (m, 2H). |
| 1-042 | δ 6.4-7.75 (m, 7H), 5.3-5.45 and 5.0-5.15 (m, 1H), 4.00 and 3.87 (d, J = 6.9 Hz, 2H), 1.75 and 1.43 (d, J = 6.9 Hz, 3H), 1.0-1.3 (m, 1H), 0.45-0.6 (m, 2H), 0.15-0.3 (m, 2H). |
| 1-043 | δ 7.1-7.75 (m, 7H), 6.66 and 6.55 (bs, 1H), 5.35-5.5 and 5.0-5.15 (m, 1H), 4.25 and 4.10 (q, J = 7.2 Hz, 2H), 1.60 and 1.21 (d, J = 6.6 Hz, 3H), 1.32 and 1.19 (t, J = 7.2 Hz, 3H). |
| 1-044 | δ 7.1-7.75 (m, 7H), 6.69 and 6.61 (bs, 1H), 5.35-5.5 and 5.0-5.15 (m, 1H), 4.25-4.5 (m, 1H), 1.1-1.65 (m, 9H). |
| 1-045 | δ 7.1-7.75 (m, 7H), 6.64 and 6.53 (bs, 1H), 5.35-5.5 and 5.0-5.15 (m, 1H), 4.25 and 4.10 (q, J = 7.2 Hz, 2H), 1.55-1.65 and 1.35-1.45 (m, 3H), 1.31 and 1.19 (t, J = 7.2 Hz, 3H). |
| 1-046 | δ 7.1-7.75 (m, 7H), 6.67 and 6.59 (bs, 1H), 5.3-5.5 and 5.0-5.15 (m, 1H), 4.25-4.5 (m, 1H), 1.1-1.65 (m, 9H). |
| 1-047 | δ 7.15-7.75 (m, 7H), 6.71 and 6.64 (bs, 1H), 5.35-5.5 and 5.0-5.15 (m, 1H), 3.95-4.05 and 3.8-3.9 (m, 2H), 1.6-1.65 and 1.4-1.45 (m, 3H), 0.95-1.3 (m, 1H), 0.4-0.55 (m, 2H), 0.15-0.3 (m, 2H). |

TABLE 46-continued

| No. | $^1$H NMR (CDCl$_3$, Me$_4$Si, 300 MHz) |
|---|---|
| 1-048 | δ 7.05-7.75 (m, 7H), 6.42 and 6.28 (bs, 1H), 5.35-5.5 and 5.05-5.2 (m, 1H), 4.5-4.65 and 4.3-4.45 (m, 2H), 1.6-1.65 and 1.4-1.45 (m, 3H). |
| 1-049 | δ 6.95-7.75 (m, 6H), 6.55 (bs, 1H), 5.3-5.45 and 5.0-5.1 (m, 1H), 4.2-4.3 and 4.05-4.2 (m, 2H), 1.15-1.65 (m, 6H). |
| 1-050 | δ 7.0-7.75 (m, 7H), 6.47 and 6.59 (bs, 1H), 5.35-5.5 and 5.05-5.15 (m, 1H), 4.05-4.35 (m, 2H), 1.6-1.65 and 1.4-1.45 (m, 3H), 1.33 and 1.19 (t, J = 7.2 Hz, 3H). |
| 1-051 | δ 6.95-7.75 (m, 6H), 6.56 and 6.47 (bs, 1H), 5.3-5.45 and 5.0-5.15 (m, 1H), 4.01 and 3.85 (s, 3H), 1.55-1.65 and 1.4-1.45 (m, 3H). |
| 1-052 | δ 6.95-7.75 (m, 6H), 6.5-6.7 (m, 1H), 5.3-5.45 and 5.0-5.15 (m, 1H), 4.2-4.35 and 4.05-4.2 (m, 2H), 1.6-1.65 and 1.4-1.5 (m, 3H), 1.33 and 1.21 (t, J = 7.2 Hz, 3H). |
| 1-053 | δ 6.6-7.75 (m, 8H), 5.25-5.4 and 5.0-5.15 (m, 1H), 4.05-4.3 (m, 2H), 1.61 and 1.46 (d, J = 6.9 Hz, 3H), 1.31 and 1.19 (t, J = 7.2 Hz, 3H). |
| 1-054 | δ 7.2-7.75 (m, 7H), 6.77 and 6.64 (bs, 1H), 5.25-5.4 and 5.0-5.1 (m, 1H), 4.24 and 4.09 (q, J = 7.2 Hz, 2H), 1.59 and 1.46 (d, J = 6.9 Hz, 3H), 1.31 and 1.19 (t, J = 7.2 Hz, 3H). |
| 1-055 | δ 7.1-7.75 (m, 12H), 6.49 (bs, 1H), 4.85-5.45 (m, 2H), 1.35-1.7 (m, 6H). |
| 1-057 | δ 6.95-7.75 (m, 7H), 6.80 and 6.69 (bs, 1H), 5.25-5.4 and 4.95-5.1 (m, 1H), 4.0-4.3 (m, 2H), 1.60 and 1.45 (d, J = 7.2 Hz, 3H), 1.15-1.35 (m, 3H). |
| 1-058 | δ 7.15-7.75 (m, 7H), 6.78 and 6.66 (bs, 1H), 5.25-5.35 and 4.95-5.1 (m, 1H), 4.0-4.3 (m, 2H), 1.55-1.65 and 1.4-1.5 (m, 3H), 1.15-1.35 (m, 3H). |
| 1-060 | δ 7.15-7.8 (m, 7H), 6.62 (bs, 1H), 5.15-5.3 and 4.95-5.15 (m, 1H), 4.05-4.35 (m, 2H), 3.45-3.65 (m, 2H), 3.28 and 2.96 (s, 3H), 1.61 and 1.45 (d, J = 6.9 Hz, 3H). |
| 1-061 | δ 7.15-7.75 (m, 11H), 6.41 (bs, 1H), 5.0-5.5 (m, 3H), 1.60 and 1.43 (d, J = 6.9 Hz, 3H). |
| 1-062 | δ 7.1-7.75 (m, 7H), 6.3-6.75 (m, 3H), 4.95-5.35 (m, 3H), 1.56 and 1.43 (d, J = 6.9 Hz, 3H). |
| 1-063 | δ 8.38 and 8.28 (d, J = 2.1 Hz, 1H), 7.15-7.75 (m, 9H), 6.41 (bs, 1H), 5.0-5.45 (m, 3H), 1.57 and 1.42 (d, J = 7.2 Hz, 3H). |
| 1-064 | δ 8.25-8.45 (m, 1H), 7.05-7.75 (m, 9H), 6.3-6.45 (m, 1H), 5.0-5.55 (m, 3H), 1.64 and 1.44 (d, J = 6.9 Hz, 3H). |
| 1-065 | δ 7.05-7.75 (m, 7H), 6.78 and 6.66 (bs, 1H), 5.2-5.45 and 4.95-5.1 (m, 1H), 4.0-4.3 (m, 2H), 1.4-1.65 (m, 3H), 1.15-1.35 (m, 3H). |
| 1-066 | δ 7.05-7.75 (m, 7H), 6.82 and 6.68 (bs, 1H), 5.2-5.45 and 4.95-5.1 (m, 1H), 4.2-4.5 (m, 1H), 1.1-1.65 (m, 9H). |
| 1-067 | δ 7.05-7.8 (m, 7H), 6.68 and 6.67 (bs, 1H), 4.95-5.45 (m, 1H), 3.98 and 3.85 (d, J = 7.2 Hz, 2H), 1.61 and 1.45 (d, J = 7.2 Hz, 3H), 0.95-1.2 (m, 1H), 0.4-0.55 (m, 2H), 0.15-0.25 (m, 2H). |
| 1-068 | δ 7.1-7.8 (m, 7H), 6.46 (bs, 1H), 5.3-5.45 and 5.0-5.2 (m, 1H), 4.45-4.6 and 4.3-4.45 (m, 2H), 1.63 and 1.46 (d, J = 6.9 Hz, 3H). |
| 1-069 | δ 8.25-8.4 (m, 1H), 6.4-7.75 (m, 10H), 5.0-5.45 (m, 3H), 1.56 and 1.42 (d, J = 6.9 Hz, 3H). |
| 1-070 | δ 7.05-7.75 (m, 7H), 6.72 (bs, 1H), 5.3-5.45 and 4.95-5.1 (m, 1H), 3.97 and 3.83 (s, 3H), 2.36 and 2.35 (s, 3H), 1.4-1.6 (m, 3H). |
| 1-071 | δ 7.05-7.75 (m, 7H), 6.7-6.85 (m, 1H), 5.3-5.45 and 4.95-5.1 (m, 1H), 4.0-4.3 (m, 2H), 2.36 and 2.35 (s, 3H), 1.58 and 1.44 (d, J = 6.9 Hz, 3H), 1.15-1.35 (m, 3H). |
| 1-072 | δ 6.5-8.0 (m, 8H), 5.25-5.4 and 5.0-5.15 (m, 1H), 4.2-4.3 and 4.0-4.2 (m, 2H), 1.63 and 1.47 (d, J = 6.9 Hz, 3H), 1.15-1.35 (m, 3H). |
| 1-073 | δ 6.65-7.75 (m, 8H), 5.25-5.4 and 5.0-5.1 (m, 1H), 3.75-4.0 (m, 6H), 1.57 and 1.43 (d, J = 6.9 Hz, 3H). |
| 1-074 | δ 6.7-7.75 (m, 8H), 5.25-5.4 and 4.95-5.1 (m, 1H), 4.0-4.3 (m, 2H), 3.82 and 3.81 (s, 3H), 1.58 and 1.43 (d, J = 6.9 Hz, 3H), 1.15-1.35 (m, 3H). |
| 1-075 | δ 7.0-7.75 (m, 7H), 6.6-6.9 (m, 1H), 5.25-5.4 and 4.95-5.1 (m, 1H), 4.15-4.3 and 4.0-4.15 (m, 2H), 2.50 and 2.48 (s, 3H), 1.4-1.65 (m, 3H), 1.15-1.35 (m, 3H). |
| 1-076 | δ 7.3-7.8 (m, 7H), 6.59 (bs, 1H), 5.2-5.4 and 5.0-5.2 (m, 1H), 4.05-4.3 (m, 2H), 2.7-2.8 (m, 3H), 1.45-1.7 (m, 3H), 1.15-1.35 (m, 3H). |
| 1-077 | δ 7.3-8.05 (m, 7H), 6.72 and 6.55 (bs, 1H), 5.25-5.35 and 5.0-5.15 (m, 1H), 4.26 and 4.10 (q, J = 7.2 Hz, 2H), 3.11 and 3.06 (s, 3H), 1.65 and 1.48 (d, J = 6.9 Hz, 3H), 1.32 and 1.19 (t, J = 7.2 Hz, 3H). |
| 1-078 | δ 7.3-8.05 (m, 7H), 6.65 (bs, 1H), 5.25-5.4 and 5.0-5.2 (m, 1H), 4.25 and 4.09 (q, J = 7.2 Hz, 2H), 2.62 and 2.61 (s, 3H), 1.63 and 1.47 (d, J = 6.9 Hz, 3H), 1.32 and 1.18 (t, J = 7.2 Hz, 3H). |
| 1-079 | δ 7.2-7.8 (m, 7H), 6.65-6.85 (m, 1H), 5.3-5.45 and 5.0-5.15 (m, 1H), 3.95-4.3 (m, 5H), 2.15-2.25 (m, 3H), 1.60 and 1.45 (d, J = 6.9 Hz, 3H), 1.15-1.35 (m, 3H). |

TABLE 46-continued

| No. | $^{1}$H NMR (CDCl$_3$, Me$_4$Si, 300 MHz) |
|---|---|
| 1-080 | δ 7.2-7.75 (m, 7H), 6.45-6.75 (m, 1H), 5.2-5.35 and 5.0-5.15 (m, 1H), 4.01 and 3.84 (s, 3H), 1.63 and 1.47 (d, J = 6.9 Hz, 3H). |
| 1-081 | δ 7.2-7.75 (m, 7H), 6.75 and 6.55 (bs, 1H), 5.2-5.35 and 5.0-5.15 (m, 1H), 4.05-4.3 (m, 2H), 1.63 and 1.47 (d, J = 6.9 Hz, 3H), 1.15-1.35 (m, 3H). |
| 1-083 | δ 7.15-7.75 (m, 7H), 6.6-6.8 (m, 2H), 5.7-5.85 (m, 1H), 5.0-5.4 (m, 2H), 3.99 and 3.84 (s, 3H), 1.59 and 1.45 (d, J = 7.2 Hz, 3H). |
| 1-084 | δ 7.15-7.75 (m, 7H), 6.55-6.85 (m, 2H), 5.7-5.85 (m, 1H), 5.0-5.4 (m, 2H), 4.15-4.3 and 4.0-4.15 (m, 2H), 1.60 and 1.45 (d, J = 6.9 Hz, 3H), 1.15-1.35 (m, 3H). |
| 1-085 | δ 7.25-7.75 (m, 12H), 6.72 (bs, 1H), 5.35-5.45 and 5.05-5.2 (m, 1H), 4.00 and 3.87 (s, 3H), 1.63 and 1.49 (d, J = 6.9 Hz, 3H). |
| 1-086 | δ 7.25-7.75 (m, 12H), 6.7-6.85 (m, 1H), 5.35-5.5 and 5.05-5.2 (m, 1H), 4.0-4.3 (m, 2H), 1.64 and 1.49 (d, J = 6.9 Hz, 3H), 1.15-1.35 (m, 3H). |
| 1-087 | δ 7.25-7.75 (m, 11H), 6.65-6.8 (m, 1H), 5.35-5.45 and 5.05-5.2 (m, 1H), 4.01 and 3.87 (s, 3H), 1.63 and 1.49 (d, J = 6.9 Hz, 3H). |
| 1-088 | δ 7.25-7.75 (m, 11H), 6.73 (bs, 1H), 5.3-5.45 and 5.05-5.2 (m, 1H), 4.0-4.3 (m, 2H), 1.64 and 1.49 (d, J = 6.9 Hz, 3H), 1.15-1.35 (m, 3H). |
| 1-089 | δ 7.2-7.75 (m, 7H), 7.1-7.65 (m, 2H), 6.6-6.9 (m, 1H), 6.3-6.4 (m, 2H), 5.3-5.45 and 5.0-5.15 (m, 1H), 4.0-4.3 (m, 2H), 1.62 and 1.48 (d, J = 6.9 Hz, 3H), 1.15-1.35 (m, 3H). |
| 1-090 | δ 7.25-7.95 (m, 10H), 6.4-6.8 (m, 1H), 5.25-5.45 and 5.0-5.2 (m, 1H), 4.05-4.3 (m, 2H), 1.62 and 1.47 (d, J = 6.9 Hz, 3H), 1.15-1.35 (m, 3H). |
| 1-091 | δ 7.2-8.0 (m, 8H), 6.6-6.85 (m, 2H), 5.25-5.4 and 5.0-5.2 (m, 1H), 4.05-4.3 (m, 2H), 1.63 and 1.48 (d, J = 6.9 Hz, 3H), 1.15-1.35 (m, 3H). |
| 1-092 | δ 7.0-7.75 (m, 7H), 6.70 (bs, 1H), 5.25-5.4 and 5.0-5.15 (m, 1H), 4.05-4.3 (m, 2H), 1.61 and 1.45 (d, J = 6.9 Hz, 3H), 1.15-1.35 (m, 3H). |
| 1-093 | δ 6.6-7.75 (m, 8H), 5.25-5.4 and 5.0-5.15 (m, 1H), 4.05-4.3 (m, 2H), 1.15-1.65 (m, 6H). |
| 1-094 | δ 6.9-7.75 (m, 7H), 6.61 (bs, 1H), 5.0-5.3 (m, 1H), 4.15-4.35 (m, 2H), 3.5-3.6 (m, 2H), 3.29 and 2.96 (s, 3H), 1.4-1.85 (m, 3H). |
| 1-095 | δ 6.4-7.75 (m, 7H), 5.3-5.5 and 5.0-5.1 (m, 1H), 4.2-4.35 and 4.05-4.2 (m, 2H), 1.4-1.65 (m, 3H), 1.15-1.4 (m, 3H). |
| 1-096 | δ 7.15-7.8 (m, 7H), 7.10 and 6.81 (bs, 1H), 5.2-5.4 and 4.9-5.05 (m, 1H), 4.20 and 4.07 (q, J = 6.9 Hz, 2H), 3.38 and 2.23 (s, 3H), 1.35-1.6 (m, 3H), 1.29 and 1.18 (t, J = 6.9 Hz, 3H). |
| 1-097 | δ 7.0-8.05 (m, 7H), 6.91 (bs, 1H), 5.2-5.4 and 4.85-5.05 (m, 1H), 4.19 and 4.06 (q, J = 7.0 Hz, 2H), 2.35 and 2.34 (s, 3H), 2.32 and 2.21 (s, 3H), 1.52 and 1.38 (d, J = 7.2 Hz, 3H), 1.28 and 1.18 (t, J = 7.0 Hz, 3H). |
| 1-098 | δ 7.4-7.8 (m, 7H), 6.54 (bs, 1H), 5.0-5.2 (m, 1H), 4.0-4.3 (m, 2H), 1.1-1.65 (m, 6H). |
| 1-099 | δ 6.7-7.8 (m, 8H), 5.35-5.5 and 5.0-5.15 (m, 1H), 4.0-4.25 (m, 2H), 3.75-3.85 (m, 3H), 1.15-1.6 (m, 6H). |
| 1-100 | δ 6.7-8.25 (m, 9H), 4.95-5.4 (m, 1H), 4.0-4.3 (m, 4H), 1.0-1.6 (m, 9H). |
| 1-101 | δ 6.7-8.0 (m, 8H), 5.0-5.85 (m, 2H), 3.45-4.35 (m, 6H), 1.15-1.7 (m, 6H). |
| 1-102 | δ 6.65-8.35 (m, 11H), 5.5-5.65 and 5.05-5.2 (m, 1H), 4.0-4.35 (m, 2H), 1.05-1.65 (m, 6H). |
| 2-006 | δ 8.49 and 8.44 (d, J = 2.1 Hz, 1H), 7.80 and 7.78 (d, J = 2.1 Hz, 1H), 7.35-7.75 (m, 4H), 6.48 (bs, 1H), 4.75 and 4.52 (d, J = 6.0 Hz, 2H), 4.26 and 4.07 (t, J = 6.9 Hz, 2H), 1.65-1.8 and 1.5-1.65 (m, 2H), 1.35-1.5 and 1.2-1.35 (m, 2H), 0.93 and 0.89 (t, J = 7.2 Hz, 3H). |
| 2-007 | δ 8.50 and 8.45 (d, J = 2.1 Hz, 1H), 7.80 and 7.78 (d, J = 2.1 Hz, 1H), 7.35-7.75 (m, 4H), 6.48 (bs, 1H), 4.77 and 4.53 (d, J = 5.7 Hz, 2H), 4.02 and 3.85 (d, J = 6.9 Hz, 2H), 1.85-2.15 (m, 1H), 0.96 and 0.83 (d, J = 6.9 Hz, 6H). |
| 2-008 | δ 8.50 and 8.45 (bs, 1H), 7.75-7.85 (m, 1H), 7.35-7.7 (m, 4H), 6.59 (bs, 1H), 4.78 and 4.53 (d, J = 6.0 Hz, 2H), 4.07 and 3.89 (d, J = 7.2 Hz, 2H), 1.0-1.25 (m, 1H), 0.4-0.6 (m, 2H), 0.15-0.35 (m, 2H). |
| 2-010 | δ 8.51 and 8.44 (d, J = 2.1 Hz, 1H), 7.80 and 7.79 (d, J = 2.1 Hz, 1H), 7.35-7.75 (m, 4H), 6.49 (bs, 1H), 4.75-4.9 and 4.6-4.75 (m, 1H), 4.77 and 4.53 (d, J = 6.0 Hz, 2H), 1.95-2.4 (m, 4H), 1.5-1.85 (m, 2H). |
| 2-012 | δ 8.49 and 8.44 (d, J = 2.1 Hz, 1H), 7.80 and 7.79 (d, J = 2.1 Hz, 1H), 7.3-7.75 (m, 4H), 6.45-6.6 (m, 1H), 5.8-6.1 (m, 1H), 5.1-5.4 (m, 2H), 4.7-4.8 (m, 2H), 4.5-4.6 (m, 2H). |
| 2-013 | δ 8.50 and 8.43 (d, J = 2.1 Hz, 1H), 7.79 and 7.77 (d, J = 2.1 Hz, 1H), 7.15-7.75 (m, 8H), 6.39 (bs, 1H), 5.24 and 5.06 (s, 2H), 4.77 and 4.52 (d, J = 6.3 Hz, 2H). |
| 2-014 | δ 8.80 and 8.75 (s, 1H), 8.03 and 8.01 (s, 1H), 7.35-7.75 (m, 4H), 6.44 (bs, 1H), 4.77 and 4.57 (d, J = 5.1 Hz, 2H), 4.09 and 3.89 (s, 3H). |
| 2-015 | δ 8.79 and 8.70 (s, 1H), 8.02 and 8.00 (s, 1H), 7.35-7.75 (m, 4H), 6.85 and 6.70 (bs, 1H), 5.78 and 5.29 (m, 1H), 4.07 and 3.88 (s, 3H), 1.59 and 1.48 (d, J = 6.9 Hz, 3H). |
| 2-017 | δ 8.80 and 8.75 (s, 1H), 8.03 and 8.00 (s, 1H), 7.3-7.75 (m, 4H), 6.46 (bs, 1H), 4.79 and 4.57 (d, J = 6.0 Hz, 2H), 4.24 and 4.05 (t, J = 6.9 Hz, 2H), 1.7-1.85 and 1.55-1.7 (m, 2H), 0.99 and 0.86 (t, J = 7.5 Hz, 3H). |

TABLE 46-continued

| No. | $^1$H NMR (CDCl$_3$, Me$_4$Si, 300 MHz) |
|---|---|
| 2-021 | δ 8.79 and 8.74 (s, 1H), 8.02 and 7.99 (s, 1H), 7.35-7.7 (m, 4H), 6.47 (bs, 1H), 4.80 and 4.56 (d, J = 5.1 Hz, 2H), 4.05 and 3.86 (d, J = 6.9 Hz, 2H), 2.09 and 1.93 (m, 1H), 0.96 and 0.83 (d, J = 6.9 Hz, 6H). |
| 2-022 | δ 8.81 and 8.75 (s, 1H), 8.02 and 8.01 (s, 1H), 7.35-7.75 (m, 4H), 6.51 (bs, 1H), 4.81 and 4.57 (d, J = 6.3 Hz, 2H), 4.09 and 3.91 (d, J = 7.2 Hz, 2H), 1.15-1.3 and 1.0-1.15 (m, 1H), 0.5-0.6 and 0.4-0.5 (m, 2H), 0.25-0.35 and 0.15-0.25 (m, 2H). |
| 2-025 | δ 8.80 and 8.74 (s, 1H), 8.03 and 7.99 (s, 1H), 7.35-7.75 (m, 4H), 6.49 (bs, 1H), 4.79 and 4.56 (d, J = 6.0 Hz, 2H), 4.33 and 4.17 (m, 1H), 1.45-1.8 (m, 2H), 1.32 and 1.18 (d, J = 6.3 Hz, 3H), 0.95 and 0.83 (t, J = 7.5 Hz, 3H). |
| 2-026 | δ 8.80 and 8.73 (s, 1H), 8.03 and 8.00 (s, 1H), 7.35-7.75 (m, 4H), 6.45 (bs, 1H), 4.8-4.9 and 4.6-4.75 (m, 1H), 4.79 and 4.56 (d, J = 6.0 Hz, 2H), 1.6-2.4 (m, 6H). |
| 2-027 | δ 8.78 and 8.73 (s, 1H), 8.02 and 7.98 (s, 1H), 7.35-7.75 (m, 4H), 6.48 (bs, 1H), 4.80 and 4.55 (d, J = 6.3 Hz, 2H), 4.1-4.2 and 3.9-4.05 (m, 1H), 1.5-1.5 (m, 4H), 0.95 and 0.83 (t, J = 7.5 Hz, 6H). |
| 2-028 | δ 8.81 and 8.75 (s, 1H), 8.02 and 8.00 (s, 1H), 7.4-7.75 (m, 4H), 6.45-6.6 (m, 1H), 4.7-4.85 and 4.5-4.6 (m, 2H), 3.7-3.8 and 3.55-3.65 (m, 1H), 2.40 and 1.26 (d, J = 6.3 Hz, 3H), 0.8-1.15 (m, 1H), 0.2-0.55 (m, 4H). |
| 2-029 | δ 8.79 and 8.74 (s, 1H), 8.03 and 7.99 (s, 1H), 7.3-7.7 (m, 4H), 6.4-6.55 (m, 1H), 4.85-4.9 and 4.7-4.75 (m, 1H), 4.77 and 4.56 (d, J = 6.3 Hz, 2H), 1.5-1.95 (m, 8H). |
| 2-030 | δ 8.80 and 8.76 (s, 1H), 8.40 and 8.02 (s, 1H), 7.3-7.75 (m, 4H), 6.39 (bs, 1H), 6.06 and 5.95 (tt, J = 55.8 and 4.2 Hz, 1H), 4.81 and 4.60 (d, J = 5.7 Hz, 2H), 4.44 and 4.25 (td, J = 13.5, 4.2 Hz, 2H). |
| 2-031 | δ 8.76 (s, 1H), 8.05 (s, 1H), 7.35-7.7 (m, 4H), 6.39 (bs, 1H), 6.77 (tt, J = 55.2 and 4.2 Hz, 1H), 4.81 (d, J = 6.3 Hz, 2H), 4.44 (td, J = 13.2, 4.2 Hz, 2H). |
| 2-032 | δ 8.81 and 8.76 (s, 1H), 8.04 and 8.03 (s, 1H), 7.3-7.75 (m, 4H), 6.34 (bs, 1H), 4.82 and 4.61 (d, J = 6.3 Hz, 2H), 4.63 and 4.43 (q, J = 8.7 Hz, 2H). |
| 2-033 | δ 8.82 and 8.73 (s, 1H), 8.06 and 8.03 (s, 1H), 7.25-7.75 (m, 4H), 6.62 (bs, 1H), 5.82 and 5.36 (m, 1H), 4.62 and 4.43 (q, J = 8.7 Hz, 2H), 1.65 and 1.49 (d, J = 6.9 Hz, 3H). |
| 2-034 | δ 8.80 and 8.77 (s, 1H), 8.03 and 8.01 (s, 1H), 7.35-7.75 (m, 4H), 6.44 and 6.80 (bs, 1H), 4.78 and 4.58 (d, J = 6.0 Hz, 2H), 4.42 and 4.24 (t, J = 6.6 Hz, 2H), 2.85 and 2.72 (t, J = 6.6 Hz, 2H), 2.06 and 2.05 (s, 3H). |
| 2-035 | δ 8.80 and 8.75 (s, 1H), 8.03 and 8.00 (s, 1H), 7.3-7.75 (m, 4H), 6.44 and 6.54 (bs, 1H), 4.05-5.0 (m, 5H), 2.7-3.15 (m, 2H), 1.99 and 1.90 (s, 3H). |
| 2-036 | δ 8.82 and 8.76 (s, 1H), 8.07 and 8.03 (s, 1H), 7.3-7.75 (m, 4H), 6.39 (bs, 1H), 4.93 and 4.72 (s, 2H), 4.81 and 4.64 (d, J = 6.0 Hz, 2H). |
| 2-037 | δ 8.83 and 8.75 (s, 1H), 8.07 and 8.03 (s, 1H), 7.35-7.75 (m, 4H), 6.41 (bs, 1H), 5.10 and 4.94 (q, J = 6.9 Hz, 1H), 4.78 and 4.63 (d, J = 6.0 Hz, 2H), 1.77 and 1.58 (d, J = 6.9 Hz, 3H). |
| 2-038 | δ 8.81 and 8.77 (s, 1H), 8.05 and 8.03 (s, 1H), 7.35-7.75 (m, 4H), 6.44 (bs, 1H), 4.81 and 4.60 (d, J = 6.0 Hz, 2H), 4.48 and 4.30 (t, J = 6.3 Hz, 2H), 2.84 and 2.71 (t, J = 6.3 Hz, 2H). |
| 2-039 | δ 8.83 and 8.72 (s, 1H), 8.10 and 8.06 (s, 1H), 7.35-7.75 (m, 5H), 6.44 and 6.32 (bs, 1H), 4.91 and 4.89 (bs, 2H), 4.66 and 4.64 (bs, 2H), 3.9-4.05 (m, 2H). |
| 2-040 | δ 8.79 and 8.73 (s, 1H), 8.01 and 7.99 (s, 1H), 7.3-7.7 (m, 4H), 6.45-6.55 (m, 1H), 5.8-6.2 (m, 1H), 5.15-5.4 (m, 2H), 4.80 and 4.57 (d, J = 6.3 Hz, 2H), 4.75-4.8 and 4.55-4.6 (m, 2H). |
| 2-041 | δ 8.80 and 8.74 (s, 1H), 8.01 (bs, 1H), 7.3-7.75 (m, 4H), 6.43 (bs, 1H), 4.85-5.05 (m, 2H), 4.82 and 4.57 (d, J = 6.0 Hz, 2H), 4.70 and 4.50 (s, 2H), 1.80 and 1.69 (s, 3H). |
| 2-042 | δ 8.81 and 8.74 (s, 1H), 8.02 and 8.00 (s, 1H), 7.35-7.75 (m, 4H), 6.45 (bs, 1H), 5.75-6.05 (m, 1H), 5.05-5.35 (m, 2H), 4.8-4.9 and 4.65-4.75 (m, 1H), 4.81 and 4.57 (d, J = 6.3 Hz, 2H), 1.44 and 1.27 (d, J = 6.6 Hz, 3H). |
| 2-044 | δ 8.81 and 8.75 (s, 1H), 8.04 and 8.02 (s, 1H), 7.35-7.75 (m, 4H), 6.41 (bs, 1H), 4.87 and 4.68 (d, J = 2.7 Hz, 2H), 4.81 and 4.61 (d, J = 6.0 Hz, 2H), 2.51 and 2.46 (t, J = 2.7 Hz, 1H). |
| 2-046 | δ 8.77 and 8.72 (s, 1H), 7.99 and 7.97 (s, 1H), 7.2-7.7 (m, 6H), 6.85-7.15 (m, 2H), 6.48 (bs, 1H), 5.37 and 5.18 (s, 2H), 4.78 and 4.55 (d, J = 6.0 Hz, 2H). |
| 2-048 | δ 8.77 and 8.71 (s, 1H), 8.00 and 7.97 (s, 1H), 7.2-7.7 (m, 6H), 6.95-7.1 (m, 2H), 6.45 (bs, 1H), 5.26 and 5.06 (s, 2H), 4.78 and 4.55 (d, J = 6.0 Hz, 2H). |
| 2-050 | δ 8.80 and 8.72 (s, 1H), 8.00 (bs, 1H), 7.1-7.7 (m, 8H), 6.41 (bs, 1H), 5.26 and 5.07 (s, 2H), 4.80 and 4.56 (d, J = 6.0 Hz, 2H). |

TABLE 46-continued

| No. | ¹H NMR (CDCl₃, Me₄Si, 300 MHz) |
|---|---|
| 2-051 | δ 8.79 and 8.73 (s, 1H), 8.01 and 7.99 (s, 1H), 7.2-7.7 (m, 8H), 6.41 (bs, 1H), 5.26 and 5.07 (s, 2H), 4.80 and 4.56 (d, J = 6.0 Hz, 2H). |
| 2-053 | δ 8.77 and 8.72 (s, 1H), 8.00 and 7.97 (s, 1H), 7.05-7.7 (m, 8H), 6.4-6.5 (m, 1H), 5.26 and 5.08 (s, 2H), 4.78 and 4.55 (d, J = 6.3 Hz, 2H), 2.33 and 2.31 (s, 3H). |
| 2-054 | δ 8.76 and 8.71 (s, 1H), 7.99 and 7.96 (s, 1H), 7.05-7.7 (m, 8H), 6.4-6.5 (m, 1H), 5.25 and 5.07 (s, 2H), 4.77 and 4.54 (d, J = 6.3 Hz, 2H), 2.34 and 2.32 (s, 3H). |
| 2-055 | δ 8.78 and 8.73 (s, 1H), 8.00 and 7.98 (s, 1H), 7.15-7.75 (m, 8H), 6.4-6.5 (m, 1H), 5.27 and 5.10 (s, 2H), 4.79 and 4.57 (d, J = 6.0 Hz, 2H), 1.32 and 1.30 (s, 9H). |
| 2-056 | δ 8.81 and 8.73 (s, 1H), 8.00 (bs, 1H), 7.25-7.7 (m, 8H), 6.45 (bs, 1H), 5.51 and 5.33 (s, 2H), 4.83 and 4.57 (d, J = 6.0 Hz, 2H). |
| 2-057 | δ 8.79 and 8.72 (s, 1H), 8.00 and 7.99 (s, 1H), 7.25-7.7 (m, 8H), 6.43 (bs, 1H), 5.34 and 5.15 (s, 2H), 4.81 and 4.55 (d, J = 6.0 Hz, 2H). |
| 2-058 | δ 8.80 and 8.72 (s, 1H), 8.00 (bs, 1H), 7.25-7.7 (m, 8H), 6.40 (bs, 1H), 5.35 and 5.16 (s, 2H), 4.83 and 4.56 (d, J = 6.0 Hz, 2H). |
| 2-059 | δ 8.78 and 8.72 (s, 1H), 8.00 and 7.98 (s, 1H), 7.2-7.7 (m, 5H), 6.75-7.0 (m, 3H), 6.44 (bs, 1H), 5.28 and 5.09 (s, 2H), 4.80 and 4.56 (d, J = 6.0 Hz, 2H), 3.79 and 3.76 (s, 3H). |
| 2-060 | δ 8.78 and 8.74 (s, 1H), 8.01 and 7.97 (s, 1H), 7.2-7.75 (m, 6H), 6.8-6.95 (m, 2H), 6.4-6.5 (m, 1H), 5.24 and 5.05 (s, 2H), 4.77 and 4.56 (d, J = 6.0 Hz, 2H), 3.81 and 3.79 (s, 3H). |
| 2-061 | δ 8.79 and 8.73 (s, 1H), 7.99 (bs, 1H), 7.15-7.7 (m, 8H), 6.45 (bs, 1H), 5.39 and 5.21 (s, 2H), 4.80 and 4.56 (d, J = 6.3 Hz, 2H). |
| 2-062 | δ 8.81 and 8.73 (s, 1H), 8.00 (bs, 1H), 7.1-7.7 (m, 8H), 6.39 (bs, 1H), 5.30 and 5.11 (s, 2H), 4.82 and 4.57 (d, J = 6.3 Hz, 2H). |
| 2-063 | δ 8.79 and 8.72 (s, 1H), 8.01 and 7.99 (s, 1H), 7.1-7.7 (m, 8H), 6.40 (bs, 1H), 5.29 and 5.10 (s, 2H), 4.81 and 4.56 (d, J = 6.0 Hz, 2H). |
| 2-064 | δ 8.82 and 8.72 (s, 1H), 7.25-8.25 (m, 9H), 6.3-6.5 (m, 1H), 5.40 and 5.20 (s, 2H), 4.86 and 4.57 (d, J = 6.3 Hz, 2H). |
| 2-065 | δ 8.79 and 8.72 (s, 1H), 8.00 and 7.97 (s, 1H), 7.3-7.7 (m, 8H), 6.63 and 6.56 (bs, 1H), 5.47 and 5.29 (s, 2H), 4.84 and 4.55 (d, J = 5.7 Hz, 2H). |
| 2-066 | δ 8.81 and 8.72 (s, 1H), 8.01 (bs, 1H), 7.25-7.75 (m, 8H), 6.39 (bs, 1H), 5.31 and 5.12 (s, 2H), 4.82 and 4.56 (d, J = 6.3 Hz, 2H). |
| 2-067 | δ 8.81 and 8.72 (s, 1H), 8.00 (bs, 1H), 7.25-7.7 (m, 8H), 6.43 (bs, 1H), 5.36 and 5.15 (s, 2H), 4.84 and 4.56 (d, J = 6.0 Hz, 2H). |
| 2-068 | δ 8.80 and 8.74 (s, 1H), 8.01 and 7.99 (s, 1H), 7.25-7.7 (m, 13H), 6.41 (bs, 1H), 5.35 and 5.16 (s, 2H), 4.82 and 4.58 (d, J = 6.3 Hz, 2H). |
| 2-069 | δ 8.78 and 8.72 (s, 1H), 8.00 and 7.98 (s, 1H), 7.25-7.75 (m, 5H), 6.6-6.9 (m, 2H), 6.43 (bs, 1H), 5.31 and 5.12 (s, 2H), 4.78 and 4.55 (d, J = 6.3 Hz, 2H). |
| 2-071 | δ 8.80 and 8.73 (s, 1H), 8.01 and 8.00 (s, 1H), 6.95-7.75 (m, 7H), 6.38 (bs, 1H), 5.23 and 5.04 (s, 2H), 4.80 and 4.56 (d, J = 6.0 Hz, 2H). |
| 2-072 | δ 8.82 and 8.73 (s, 1H), 8.02 (bs, 1H), 7.3-7.7 (m, 4H), 6.65-7.0 (m, 3H), 6.3-6.45 (m, 1H), 5.26 and 5.06 (s, 2H), 4.83 and 4.57 (d, J = 6.0 Hz, 2H). |
| 2-073 | δ 8.80 and 8.72 (s, 1H), 8.00 (bs, 1H), 7.05-7.7 (m, 7H), 6.3-6.5 (m, 1H), 5.23 and 5.04 (s, 2H), 4.80 and 4.56 (d, J = 6.3 Hz, 2H). |
| 2-074 | δ 8.80 and 8.72 (s, 1H), 8.01 (bs, 1H), 7.25-7.7 (m, 4H), 6.85-7.1 (m, 2H), 6.35-6.5 (m, 1H), 5.20 and 5.00 (s, 2H), 4.81 and 4.56 (d, J = 6.0 Hz, 2H). |
| 2-075 | δ 8.79 and 8.73 (s, 1H), 7.98 (bs, 1H), 7.35-7.9 (m, 11H), 6.40 (bs, 1H), 5.46 and 5.27 (s, 2H), 4.81 and 4.56 (d, J = 6.0 Hz, 2H). |
| 2-077 | δ 8.83 and 8.76 (s, 1H), 8.52 and 8.01 (d, J = 4.5 Hz, 1H), 8.00 and 7.99 (s, 1H), 7.05-7.7 (m, 7H), 6.45 (bs, 1H), 5.44 and 5.25 (s, 2H), 4.85 and 4.59 (d, J = 5.4 Hz, 2H). |
| 2-078 | δ 8.81 and 8.74 (s, 1H), 8.5-8.7 (m, 2H), 8.02 and 8.00 (s, 1H), 7.80 and 7.78 (t, J = 2.1 Hz, 1H), 7.25-7.75 (m, 5H), 6.40 (bs, 1H), 5.32 and 5.13 (s, 2H), 4.81 and 4.57 (d, J = 6.3 Hz, 2H). |
| 2-079 | δ 8.80 and 8.72 (s, 1H), 8.41 and 8.31 (s, 1H), 8.01 and 7.99 (s, 1H), 7.77 and 7.75 (d, J = 2.4 Hz, 1H), 7.25-7.7 (m, 5H), 6.39 (bs, 1H), 5.28 and 5.09 (s, 2H), 4.80 and 4.55 (d, J = 6.3 Hz, 2H). |
| 2-080 | δ 8.84 and 8.74 (s, 1H), 8.5-8.6 (m, 2H), 8.03 and 8.01 (s, 1H), 7.15-7.7 (m, 6H), 6.47 (bs, 1H), 5.33 and 5.12 (s, 2H), 4.88 and 4.58 (d, J = 6.0 Hz, 2H). |
| 2-081 | δ 8.81 and 8.70 (s, 1H), 8.00 and 7.97 (s, 1H), 7.0-7.7 (m, 9H), 6.42 and 6.36 (bs, 1H), 5.41 and 5.25 (q, J = 6.9 Hz, 1H), 4.8-4.9 (m, 1H), 4.5-4.55 (m, 1H), 1.67 and 1.47 (d, J = 6.9 Hz, 3H). |
| 2-084 | δ 8.21 and 8.19 (d, J = 2.1 Hz, 1H), 7.35-7.75 (m, 4H), 7.28 and 7.27 (d, J = 2.1 Hz, 1H), 6.54 and 6.47 (bs, 1H), 4.71 and 4.51 (d, J = 6.0 Hz, 2H), 4.06 and 3.89 (s, 3H), 3.88 and 3.85 (s, 3H). |
| 2-085 | δ 8.44 and 8.39 (d, J = 2.1 Hz, 1H), 7.4-7.8 (m, 5H), 6.63 and 6.58 (bs, 1H), 4.83 and 4.60 (d, J = 5.7 Hz, 2H), 4.45-4.65 and 4.35-4.55 (m, 1H), 1.33 and 1.20 (d, J = 6.3 Hz, 6H). |

TABLE 46-continued

| No. | $^1$H NMR (CDCl$_3$, Me$_4$Si, 300 MHz) |
|---|---|
| 2-086 | δ 8.48 and 8.43 (d, J = 2.1 Hz, 1H), 7.80 and 7.77 (d, J = 2.1 Hz, 1H), 7.35-7.75 (m, 4H), 6.53 and 6.46 (bs, 1H), 4.5-4.9 (m, 3H), 1.4-2.0 (m, 8H). |
| 2-087 | δ 8.45-8.55 (m, 1H), 7.75-7.85 (m, 1H), 7.35-7.75 (m, 4H), 6.59 and 6.46 (bs, 1H), 4.78 and 4.55 (d, J = 5.7 Hz, 2H), 4.47 and 4.29 (t, J = 6.0 Hz, 2H), 3.79 and 3.67 (t, J = 6.0 Hz, 2H). |
| 2-088 | δ 8.50 and 8.45 (d, J = 2.1 Hz, 1H), 7.81 and 7.79 (d, J = 2.1 Hz, 1H), 7.35-7.75 (m, 4H), 6.52 (bs, 1H), 5.41 and 5.24 (q, J = 5.1 Hz, 1H), 4.5-4.9 (m, 2H), 3.45-3.95 (m, 2H), 1.49 and 1.35 (d, J = 5.1 Hz, 3H), 1.19 and 1.16 (t, J = 7.2 Hz, 3H). |
| 2-089 | δ 8.51 and 8.43 (d, J = 2.4 Hz, 1H), 7.81 and 7.79 (d, J = 2.4 Hz, 1H), 7.3-7.7 (m, 4H), 6.54 and 6.48 (bs, 1H), 5.44 and 5.32 (t, J = 3.6 Hz, 1H), 4.8-4.9 and 4.55-4.65 (m, 2H), 3.55-4.0 (m, 2H), 1.4-2.0 (m, 6H). |
| 2-090 | δ 8.45-8.55 (m, 1H), 7.75-7.85 (m, 1H), 7.4-7.75 (m, 4H), 6.84 and 6.49 (bs, 1H), 5.18 and 5.12 (t, J = 4.2 Hz, 1H), 4.76 and 4.55 (d, J = 5.7 Hz, 2H), 4.29 and 4.14 (d, J = 4.2 Hz, 2H), 3.7-3.95 (m, 4H). |
| 2-091 | δ 8.50 and 8.47 (d, J = 2.1 Hz, 1H), 7.81 and 7.79 (d, J = 2.1 Hz, 1H), 7.35-7.75 (m, 4H), 6.81 and 6.47 (bs, 1H), 4.75 and 4.54 (d, J = 5.7 Hz, 2H), 4.39 and 4.22 (t, J = 6.9 Hz, 2H), 2.83 and 2.71 (t, J = 6.9 Hz, 2H), 2.05 and 2.04 (s, 3H). |
| 2-092 | δ 8.49 and 8.45 (d, J = 2.1 Hz, 1H), 7.80 and 7.78 (d, J = 2.1 Hz, 1H), 7.35-7.75 (m, 4H), 6.50 and 6.43 (bs, 1H), 4.74 and 4.52 (d, J = 5.7 Hz, 2H), 4.06 and 3.88 (s, 2H), 0.10 and −0.05 (s, 9H). |
| 2-093 | δ 8.50 and 8.45 (d, J = 2.1 Hz, 1H), 7.90 and 7.80 (d, J = 2.1 Hz, 1H), 7.35-7.75 (m, 4H), 6.58 and 6.45 (bs, 1H), 4.75-5.2 (m, 2H), 4.5-4.6 (m, 2H), 3.83, 3.78 and 3.76 (s, 3H), 1.99, 1.92, 1.82 and 1.81 (s, 3H). |
| 2-094 | δ 8.52 and 8.46 (d, J = 2.1 Hz, 1H), 7.84 and 7.81 (d, J = 2.1 Hz, 1H), 7.3-7.75 (m, 4H), 6.41 (bs, 1H), 4.90 and 4.71 (s, 2H), 4.79 and 4.60 (d, J = 5.7 Hz, 2H). |
| 2-095 | δ 8.52 and 8.48 (d, J = 2.1 Hz, 1H), 7.80 (d, J = 2.1 Hz, 1H), 7.4-7.75 (m, 4H), 6.96 and 6.47 (bs, 1H), 4.82 and 4.60 (s, 2H), 4.80 and 4.56 (d, J = 5.7 Hz, 2H), 3.74 and 3.68 (s, 3H). |
| 2-096 | δ 8.49 and 8.44 (d, J = 2.1 Hz, 1H), 7.80 and 7.77 (d, J = 2.1 Hz, 1H), 7.35-7.75 (m, 4H), 6.48 (bs, 1H), 5.98 and 5.84 (ddd, J = 17.1, 1.8, 6.6 Hz, 1H), 5.27 and 5.14 (dt, J = 17.1, 1.5 Hz, 1H), 5.17 and 5.09 (dt, J = 10.8, 1.5 Hz, 1H), 4.75-4.9 and 4.6-4.75 (m, 1H), 4.79 and 4.53 (d, J = 5.1 Hz, 2H), 1.43 and 1.26 (d, J = 6.6 Hz, 3H). |
| 2-097 | δ 8.50 and 8.45 (d, J = 2.1 Hz, 1H), 7.75-7.85 (m, 1H), 7.35-7.75 (m, 4H), 6.3-6.6 (m, 2H), 4.5-5.05 (m, 4H). |
| 2-098 | δ 8.49 and 8.44 (d, J = 2.1 Hz, 1H), 7.78 and 7.77 (d, J = 2.1 Hz, 1H), 6.95-7.75 (m, 8H), 6.46 (bs, 1H), 5.35 and 5.17 (s, 2H), 4.76 and 4.53 (d, J = 5.7 Hz, 2H). |
| 2-099 | δ 8.51 and 8.44 (d, J = 2.1 Hz, 1H), 7.79 and 7.78 (d, J = 2.1 Hz, 1H), 6.95-7.75 (m, 8H), 6.41 (bs, 1H), 5.27 and 5.09 (s, 2H), 4.79 and 4.53 (d, J = 5.7 Hz, 2H). |
| 2-100 | δ 8.50 and 8.44 (d, J = 2.1 Hz, 1H), 7.80 and 7.77 (d, J = 2.1 Hz, 1H), 6.9-7.75 (m, 8H), 6.43 (bs, 1H), 5.24 and 5.06 (s, 2H), 4.77 and 4.53 (d, J = 5.7 Hz, 2H). |
| 2-101 | δ 8.51 and 8.45 (d, J = 2.1 Hz, 1H), 7.79 and 7.78 (d, J = 2.1 Hz, 1H), 7.15-7.75 (m, 8H), 6.52 and 6.45 (bs, 1H), 5.39 and 5.23 (s, 2H), 4.79 and 4.54 (d, J = 5.7 Hz, 2H). |
| 2-102 | δ 8.51 and 8.44 (d, J = 2.1 Hz, 1H), 7.79 and 7.78 (d, J = 2.1 Hz, 1H), 7.1-7.75 (m, 8H), 6.41 (bs, 1H), 5.24 and 5.01 (s, 2H), 4.78 and 4.53 (d, J = 5.7 Hz, 2H). |
| 2-103 | δ 8.50 and 8.42 (d, J = 2.1 Hz, 1H), 7.79 and 7.78 (d, J = 2.1 Hz, 1H), 7.25-7.7 (m, 8H), 6.44 (bs, 1H), 5.31 and 5.13 (s, 2H), 4.76 and 4.53 (d, J = 5.1 Hz, 2H). |
| 2-104 | δ 8.53 and 8.44 (d, J = 1.8 Hz, 1H), 7.81 and 7.80 (d, J = 1.8 Hz, 1H), 7.3-7.75 (m, 8H), 6.38 (bs, 1H), 5.34 and 5.15 (s, 2H), 4.83 and 4.54 (d, J = 5.7 Hz, 2H). |
| 2-105 | δ 8.50 and 8.43 (d, J = 2.1 Hz, 1H), 7.79 and 7.78 (d, J = 2.1 Hz, 1H), 6.95-7.75 (m, 7H), 6.41 (bs, 1H), 5.21 and 5.03 (s, 2H), 4.78 and 4.52 (d, J = 5.7 Hz, 2H). |
| 2-106 | δ 7.89 and 7.87 (s, 1H), 7.4-7.75 (m, 4H), 6.44 (bs, 1H), 4.72 and 4.52 (d, J = 6.0 Hz, 2H), 4.31 and 4.14 (q, J = 7.2 Hz, 2H), 1.35 and 1.22 (t, J = 7.2 Hz, 3H). |
| 2-107 | δ 7.88 and 7.85 (s, 1H), 7.4-7.75 (m, 4H), 6.42 (bs, 1H), 4.71 and 4.52 (d, J = 6.3 Hz, 2H), 4.45-4.55 and 4.3-4.45 (m, 1H), 1.32 and 1.19 (d, J = 6.3 Hz, 6H). |
| 2-108 | δ 7.88 and 7.87 (s, 1H), 7.4-7.75 (m, 4H), 6.44 (bs, 1H), 4.74 and 4.52 (d, J = 5.7 Hz, 2H), 4.06 and 3.89 (d, J = 7.2 Hz, 2H), 1.0-1.3 (m, 1H), 0.45-0.65 (m, 2H), 0.15-0.35 (m, 2H). |

TABLE 46-continued

| No. | ¹H NMR (CDCl₃, Me₄Si, 300 MHz) |
|---|---|
| 2-109 | δ 7.89 and 7.87 (s, 1H), 7.4-7.75 (m, 4H), 6.41 and 6.40 (bs, 1H), 5.85-6.1 (m, 1H), 5.15-5.4 (m, 2H), 4.75 and 4.74 (d, J = 6.0 Hz, 2H), 4.58 and 4.34 (d, J = 5.1 Hz, 2H). |
| 2-110 | δ 7.87 and 7.85 (s, 1H), 7.2-7.75 (m, 6H), 6.95-7.1 (m, 2H), 6.38 and 6.36 (bs, 1H), 5.24 and 5.06 (s, 2H), 4.72 and 4.52 (d, J = 6.0 Hz, 2H). |
| 2-111 | δ 8.47 and 8.42 (d, J = 1.5 Hz, 1H), 7.79 and 7.76 (d, J = 1.5 Hz, 1H), 7.3-7.75 (m, 4H), 6.62 (bs, 1H), 4.78 and 4.53 (d, J = 5.4 Hz, 2H), 4.45-4.6 and 4.25-4.45 (m, 1H), 4.50 and 4.48 (s, 2H), 3.46 and 3.41 (s, 3H), 1.33 and 1.18 (d, J = 6.3 Hz, 6H). |
| 2-112 | δ 8.08 and 8.06 (dd, J = 3.0, 1.9 Hz, 1H), 7.82 and 7.63 (td, J = 7.3, 3.0 Hz, 1H), 7.25-7.75 (m, 4H), 6.25-6.45 (m, 1H), 4.63 and 4.51 (d, J = 6.3 Hz, 2H), 4.51 and 4.40 (sep, J = 6.3 Hz, 1H), 1.33 and 1.21 (d, J = 6.3 Hz, 6H). |
| 2-113 | δ 8.55 and 8.39 (d, J = 1.9 Hz, 1H), 7.4-7.8 (m, 5H), 7.1-7.2 and 6.6-6.7 (m, 1H), 6.85-6.9 and 4.8-4.9 (m, 2H), 3.85-4.4 (m, 2H), 1.33 and 1.20 (d, J = 6.9 Hz, 3H). |
| 2-118 | δ 8.49 (d, J = 2.1 Hz, 1H), 7.4-7.85 (m, 5H), 6.78 (bs, 1H), 5.2-5.3 (m, 1H), 3.86 (s, 3H), 1.45 (d, J = 6.6 Hz, 3H). |
| 2-119 | δ 8.49 and 8.40 (d, J = 1.8 Hz, 1H), 7.82 and 7.78 (d, J = 1.8 Hz, 1H), 7.5-7.7 (m, 4H), 5.15-5.25 (m, 1H), 4.05 and 3.88 (s, 3H), 1.85-2.05 (m, 1H), 1.6-1.75 (m, 1H), 1.04 (t, J = 7.5 Hz, 3H). |
| 2-121 | δ 8.50 and 8.41 (d, J = 1.8 Hz, 1H), 7.82 and 7.79 (d, J = 1.8 Hz, 1H), 7.4-7.75 (m, 4H), 6.65-7.05 (m, 1H), 5.75-5.85 and 5.2-5.35 (m, 1H), 4.29 and 4.12 (q, J = 6.9 Hz, 2H), 1.56 and 1.44 (d, J = 6.9 Hz, 3H), 1.26 and 1.21 (t, J = 6.9 Hz, 3H). |
| 2-123 | δ 8.50 (d, J = 2.0 Hz, 1H), 7.79 (d, J = 2.0 Hz, 1H), 7.4-7.75 (m, 4H), 6.80 (bs, 1H), 5.25 (dq, J = 7.4, 6.8 Hz, 1H), 4.12 (q, J = 7.0 Hz, 2H), 1.45 (d, J = 6.8 Hz, 3H), 1.20 (t, J = 7.0 Hz, 3H). |
| 2-125 | δ 7.25-8.7 (m, 6H), 5.0-6.8 (m, 1H), 4.1-4.35 (m, 2H), 1.15-1.35 (m, 3H), 1.00 and 0.94 (s, 9H). |
| 2-127 | δ 8.50 (d, J = 1.9 Hz, 1H), 7.79 (d, J = 1.9 Hz, 1H), 7.45-7.75 (m, 4H), 6.81 (bs, 1H), 5.15-5.35 (m, 1H), 4.02 (t, J = 6.7 Hz, 2H), 1.5-1.7 (m, 2H), 1.45 (d, J = 6.9 Hz, 3H), 0.85 (t, J = 7.4 Hz, 3H). |
| 2-129 | δ 8.49 and 8.40 (d, J = 1.8 Hz, 1H), 7.81 and 7.78 (d, J = 1.8 Hz, 1H), 7.4-7.75 (m, 4H), 6.7-7.05 (m, 1H), 5.7-5.85 and 5.15-5.3 (m, 1H), 4.4-4.55 and 4.3-4.4 (m, 1H), 1.56 and 1.43 (d, J = 6.6 Hz, 3H), 1.05-1.35 (m, 6H). |
| 2-131 | δ 8.49 (d, J = 2.0 Hz, 1H), 7.78 (d, J = 2.0 Hz, 1H), 7.45-7.75 (m, 4H), 6.84 (bs, 1H), 5.24 (dq, J = 7.8, 6.8 Hz, 1H), 4.35 (sep, J = 6.3 Hz, 1H), 1.44 (d, J = 6.8 Hz, 3H), 1.18 (d, J = 6.3 Hz, 6H). |
| 2-137 | δ 8.49 (d, J = 2.0 Hz, 1H), 7.78 (d, J = 2.0 Hz, 1H), 7.45-7.75 (m, 4H), 6.83 (bs, 1H), 5.15-5.3 (m, 1H), 4.05-4.2 (m, 1H), 1.35-1.7 (m, 2H), 1.44 (d, J = 6.8 Hz, 3H), 1.16 (d, J = 6.5 Hz, 3H), 0.82 (t, J = 7.4 Hz, 3H). |
| 2-141 | δ 8.50 and 8.45 (d, J = 2.1 Hz, 1H), 7.80 and 7.78 (d, J = 2.1 Hz, 1H), 7.35-7.75 (m, 4H), 6.49 (bs, 1H), 4.75 and 4.53 (d, J = 5.4 Hz, 2H), 4.24 and 4.06 (t, J = 6.6 Hz, 2H), 1.15-1.8 (m, 6H), 0.8-0.95 (m, 3H). |
| 2-144 | δ 8.50 and 8.45 (d, J = 2.1 Hz, 1H), 7.75-7.85 (m, 1H), 7.35-7.75 (m, 4H), 6.54 (bs, 1H), 4.78 and 4.52 (d, J = 5.7 Hz, 2H), 4.0-4.2 and 3.9-4.0 (m, 1H), 1.4-1.8 (m, 4H), 0.94 and 0.83 (t, J = 7.5 Hz, 6H). |
| 2-146 | δ 8.50 and 8.45 (d, J = 2.1 Hz, 1H), 7.80 and 7.78 (d, J = 2.1 Hz, 1H), 7.35-7.75 (m, 4H), 6.49 (bs, 1H), 4.75 and 4.53 (d, J = 5.7 Hz, 2H), 4.24 and 4.06 (t, J = 6.9 Hz, 2H), 1.15-1.8 (m, 8H), 0.8-0.95 (m, 3H). |
| 2-149 | δ 8.50 and 8.45 (d, J = 2.1 Hz, 1H), 7.80 and 7.78 (d, J = 2.1 Hz, 1H), 7.35-7.75 (m, 4H), 6.47 (bs, 1H), 4.75 and 4.52 (d, J = 5.7 Hz, 2H), 4.06 and 3.88 (d, J = 6.6 Hz, 2H), 0.75-1.85 (m, 11H). |
| 2-150 | δ 8.51 and 8.46 (d, J = 2.1 Hz, 1H), 7.82 and 7.80 (d, J = 2.1 Hz, 1H), 7.35-7.75 (m, 4H), 6.39 (bs, 1H), 6.06 and 5.95 (tt, J = 55.5 and 4.5 Hz, 1H), 4.78 and 4.56 (d, J = 5.7 Hz, 2H), 4.41 and 4.24 (td, J = 13.2, 4.5 Hz, 2H). |
| 2-151 | δ 8.52 (d, J = 2.0 Hz, 1H), 7.82 (d, J = 2.0 Hz, 1H), 7.45-7.8 (m, 4H), 6.60 (bs, 1H), 5.32 (dq, J = 7.8, 6.8 Hz, 1H), 4.41 (q, J = 8.5 Hz, 2H), 1.47 (d, J = 6.8 Hz, 3H). |
| 2-152 | δ 8.50 and 8.48 (d, J = 2.1 Hz, 1H), 7.81 and 7.79 (d, J = 2.1 Hz, 1H), 7.4-7.75 (m, 4H), 6.90 and 6.52 (bs, 1H), 4.75 and 4.54 (d, J = 5.7 Hz, 2H), 4.38 and 4.23 (t, J = 5.1 Hz, 2H), 3.64 and 3.58 (t, J = 5.1 Hz, 2H), 3.30 and 3.13 (s, 3H). |
| 2-153 | δ 8.50 and 8.43 (d, J = 2.1 Hz, 1H), 7.75-7.85 (m, 1H), 7.3-7.75 (m, 4H), 6.63 and 6.53 (bs, 1H), 5.3-5.45 and 5.2-5.3 (m, 1H), 4.5-4.95 (m, 6H). |
| 2-155 | δ 8.51 and 8.45 (bs, 1H), 7.82 and 7.80 (bs, 1H), 7.35-7.75 (m, 4H), 6.56 (bs, 1H), 4.76 and 4.53 (d, J = 5.1 Hz, 2H), 3.4-4.3 (m, 6H), 2.5-2.8 (m, 1H), 1.45-2.1 (m, 2H). |
| 2-156 | δ 8.52 and 8.49 (d, J = 2.1 Hz, 1H), 7.80 (d, J = 2.1 Hz, 1H), 7.45-7.75 (m, 4H), 7.02 and 6.47 (bs, 1H), 4.80 and 4.59 (s, 2H), 4.80 and 4.57 (d, J = 5.7 Hz, 2H), 4.20 and 4.15 (q, J = 7.2 Hz, 2H), 1.26 and 1.21 (t, J = 7.2 Hz, 3H). |

TABLE 46-continued

| No. | ¹H NMR (CDCl₃, Me₄Si, 300 MHz) |
|---|---|
| 2-158 | δ 8.50 (d, J = 2.0 Hz, 1H), 7.79 (d, J = 2.0 Hz, 1H), 7.45-7.75 (m, 4H), 6.78 (bs, 1H), 5.8-6.0 (m, 1H). 5.1-5.35 (m, 3H), 4.57 (d, J = 5.8 Hz, 2H), 1.45 (d, J = 6.8 Hz, 3H). |
| 2-159 | δ 8.51 and 8.46 (d, J = 2.1 Hz, 1H), 7.75-7.85 (m, 1H), 7.35-7.75 (m, 4H), 6.47 and 6.42 (bs, 1H), 5.3-5.55 (m, 2H), 4.80 and 4.56 (d, J = 5.7 Hz, 2H), 4.79 and 4.59 (s, 2H). |
| 2-160 | δ 8.50 and 8.45 (d, J = 1.8 Hz, 1H), 7.81 and 7.79 (d, J = 1.8 Hz, 1H), 7.35-7.75 (m, 4H), 6.49 and 6.43 (bs, 1H), 4.85 and 4.66 (d, J = 2.1 Hz, 2H), 4.78 and 4.57 (d, J = 5.7 Hz, 2H), 2.50 and 2.45 (t, J = 2.1 Hz, 1H). |
| 2-161 | δ 8.50 and 8.45 (d, J = 2.1 Hz, 1H), 7.80 and 7.78 (d, J = 2.1 Hz, 1H), 7.25-7.75 (m, 9H), 6.45 (bs, 1H), 5.29 and 5.11 (s, 2H), 4.78 and 4.53 (d, J = 6.0 Hz, 2H). |
| 2-162 | δ 8.49 and 8.45 (d, J = 2.1 Hz, 1H), 7.80 and 7.76 (d, J = 2.1 Hz, 1H), 7.15-7.75 (m, 6H), 6.87 (t, J = 8.7 Hz, 2H), 6.46 and 6.42 (bs, 1H), 5.21 and 5.04 (s, 2H), 4.75 and 4.53 (d, J = 5.7 Hz, 2H), 3.80 and 3.79 (s, 3H). |
| 2-163 | δ 8.52 and 8.45 (d, J = 2.1 Hz, 1H), 7.80 and 7.78 (d, J = 2.1 Hz, 1H), 7.3-7.75 (m, 8H), 6.57 and 6.51 (bs, 1H), 5.47 and 5.29 (s, 2H), 4.83 and 4.54 (d, J = 5.7 Hz, 2H). |
| 2-164 | δ 8.52 and 8.47 (d, J = 2.1 Hz, 1H), 7.80 and 7.73 (d, J = 2.1 Hz, 1H), 7.3-7.75 (m, 6H), 6.91 and 6.49 (bs, 1H), 5.57 and 4.39 (s, 2H), 4.82 and 4.58 (d, J = 5.7 Hz, 2H). |
| 2-165 | δ 8.45-8.8 (m, 2H), 7.79 (t, J = 2.1 Hz, 1H), 7.2-7.75 (m, 5H), 6.98 and 6.48 (bs, 1H), 5.46 and 5.31 (bs, 2H), 4.79 and 4.56 (d, J = 6.0 Hz, 2H). |
| 2-166 | δ 8.51 and 8.45 (d, J = 2.1 Hz, 1H), 7.80 and 7.79 (d, J = 2.1 Hz, 1H), 7.35-7.75 (m, 4H), 7.30 and 7.08 (s, 1H), 6.57 and 6.42 (bs, 1H), 5.32 and 5.16 (bs, 2H), 4.80 and 4.55 (d, J = 5.7 Hz, 2H). |
| 2-167 | δ 8.51 and 8.46 (d, J = 2.4 Hz, 1H), 7.83 and 7.79 (d, J = 2.4 Hz, 1H), 7.3-7.75 (m, 5H), 6.40 (bs, 1H), 5.34 and 5.16 (bs, 2H), 4.76 and 4.57 (d, J = 6.0 Hz, 2H). |
| 2-168 | δ 8.51 and 8.44 (d, J = 2.1 Hz, 1H), 8.42 and 8.31 (d, J = 2.1 Hz, 1H), 7.25-7.85 (m, 7H), 6.37 (bs, 1H), 5.27 and 5.09 (s, 2H), 4.78 and 4.53 (d, J = 5.7 Hz, 2H). |
| 2-169 | δ 8.54 and 8.43 (d, J = 2.1 Hz, 1H), 8.25-8.4 (m, 1H), 7.83 and 7.80 (d, J = 2.1 Hz, 1H), 7.05-7.75 (m, 6H), 6.51 (bs, 1H), 5.28 and 5.08 (s, 2H), 4.84 and 4.54 (d, J = 5.7 Hz, 2H). |
| 2-171 | δ 8.52 and 8.42 (d, J = 2.1 Hz, 1H), 7.81 and 7.77 (d, J = 2.1 Hz, 1H), 7.2-7.7 (m, 9H), 6.45 and 6.40 (bs, 1H), 5.41 and 5.25 (q, J = 6.6 Hz, 1H), 4.75-7.85 and 4.45-4.55 (m, 2H), 1.66 and 1.47 (d, J = 6.6 Hz, 3H). |
| 2-172 | δ 8.52 (d, J = 2.0 Hz, 1H), 7.80 (d, J = 2.0 Hz, 1H), 7.15-7.75 (m, 9H), 6.40 (bs, 1H), 5.25 (q, J = 6.6 Hz, 1H), 4.50 (dd, J = 5.1, 1.7 Hz, 2H), 1.47 (d, J = 6.6 Hz, 3H). |
| 2-175 | δ 8.54 and 8.39 (d, J = 2.1 Hz, 1H), 7.82 and 7.74 (d, J = 2.1 Hz, 1H), 7.2-7.7 (m, 9H), 6.55 and 6.35 (bs, 1H), 4.87 and 4.49 (d, J = 6.3 Hz, 2H), 1.74 and 1.62 (s, 6H). |
| 2-176 | δ 8.50 and 8.47 (d, J = 2.1 Hz, 1H), 7.82 and 7.76 (d, J = 2.1 Hz, 1H), 7.0-7.75 (m, 9H), 6.44 and 6.27 (bs, 1H), 4.69 and 4.54 (d, J = 5.7 Hz, 2H), 4.47 and 4.28 (t, J = 7.2 Hz, 2H), 3.06 and 2.92 (t, J = 7.2 Hz, 2H). |
| 2-177 | δ 8.54 and 8.48 (dd, J = 2.1, 0.9 Hz, 1H), 7.0-7.9 (m, 10H), 6.61 (bs, 1H), 4.99 and 4.70 (d, J = 5.7 Hz, 2H). |
| 2-178 | δ 7.92 and 7.90 (d, J = 7.7 Hz, 1H), 7.4-7.75 (m, 4H), 6.39 (bs, 1H), 4.70 and 4.51 (d, J = 6.3 and 5.2 Hz, 2H), 4.32 and 4.14 (q, J = 7.0 Hz, 2H), 1.35 and 1.22 (t, J = 7.0 Hz, 3H). |
| 2-179 | δ 7.92 and 8.89 (d, J = 8.3 Hz, 1H), 7.4-7.75 (m, 4H), 6.39 (bs, 1H), 4.70 and 4.51 (d, J = 6.3 and 5.6 Hz, 2H), 4.52 and 4.38 (sep, J = 6.3 Hz, 1H), 1.33 and 1.19 (d, J = 6.3 Hz, 6H). |
| 2-180 | δ 7.4-7.75 (m, 5H), 6.53 and 6.43 (s, 1H), 4.75-4.8 and 4.5-4.6 (m, 2H), 4.3-4.4 and 3.6-3.7 (m, 1H), 4.00 and 3.99 (bs, 3H), 1.33 and 1.21 (d, J = 6.3 Hz, 6H). |
| 2-184 | δ 8.79 (bs, 1H), 8.00 (bs, 1H), 7.5-7.7 (m, 4H), 6.72 (bs, 1H), 5.25-5.35 (m, 1H), 3.88 (s, 3H), 1.47 (d, J = 6.9 Hz, 3H). |
| 2-186 | δ 8.79 (bs, 1H), 7.99 (bs, 1H), 7.5-7.7 (m, 4H), 6.74 (bs, 1H), 5.2-5.35 (m, 1H), 4.12 (q, J = 7.2 Hz, 2H), 1.47 (d, J = 6.9 Hz, 3H), 1.21 (t, J = 7.2 Hz, 3H). |
| 2-188 | δ 8.78 (bs, 1H), 7.98 (bs, 1H), 7.5-7.7 (m, 4H), 6.78 (bs, 1H), 5.2-5.35 (m, 1H), 4.3-4.45 (m, 1H), 1.46 (d, J = 6.9 Hz, 3H), 1.18 (d, J = 6.3 Hz, 6H). |
| 2-195 | δ 8.82 (d, J = 1.9 Hz, 1H), 8.02 (d, J = 1.9 Hz, 1H), 7.15-7.8 (m, 9H), 6.37 (bs, 1H), 5.26 (q, J = 6.4 Hz, 1H), 4.54 (dd, J = 5.5, 1.8 Hz, 2H), 1.48 (d, J = 6.4 Hz, 3H). |
| 2-196 | δ 8.82 (d, J = 2.0 Hz, 1H), 8.02 (d, J = 2.0 Hz, 1H), 6.85-7.75 (m, 8H), 6.35 (bs, 1H), 5.24 (q, J = 6.5 Hz, 1H), 4.53 (d, J = 5.5 Hz, 2H), 1.46 (d, J = 6.5 Hz, 3H). |

TABLE 46-continued

| No. | $^1$H NMR (CDCl$_3$, Me$_4$Si, 300 MHz) |
|---|---|
| 2-197 | δ 8.23 and 8.20 (d, J = 2.8 Hz, 1H), 7.35-7.75 (m, 4H), 7.29 and 7.27 (d, J = 2.8 Hz, 1H), 6.64 and 6.59 (bs, 1H), 4.76 and 4.52 (d, J = 5.8 and 5.0 Hz, 2H), 4.50 and 4.36 (sep, J = 6.2 Hz, 1H), 3.89 and 3.88 (s, 3H), 1.33 and 1.19 (d, J = 6.2 Hz, 6H). |
| 2-198 | δ 8.75 and 8.72 (d, J = 1.8 Hz, 1H), 8.06 and 8.04 (d, J = 1.8 Hz, 1H), 7.35-7.75 (m, 4H), 6.62 (bs, 1H), 4.79 and 4.54 (d, J = 6.0 and 4.9 Hz, 2H), 4.55 and 4.37 (sep, J = 6.3 Hz, 1H), 4.04 and 4.03 (s, 3H), 2.24 and 2.21 (s, 3H), 1.34 and 1.18 (d, J = 6.3 Hz, 6H). |
| 2-199 | δ 8.80 and 8.74 (d, J = 1.7 Hz, 1H), 8.05 and 8.03 (d, J = 1.7 Hz, 1H), 7.35-7.75 (m, 4H), 6.42 (bs, 1H), 4.77 and 4.56 (d, J = 6.1 and 5.1 Hz, 2H), 4.34 and 4.15 (q, J = 7.0 Hz, 2H), 1.37 and 1.22 (t, J = 7.0 Hz, 3H). |
| 2-200 | δ 8.80 and 8.74 (d, J = 2.1 Hz, 1H), 8.05 and 8.02 (d, J = 2.1 Hz, 1H), 7.35-7.8 (m, 4H), 6.44 (bs, 1H), 4.77 and 4.56 (d, J = 6.0 Hz, 2H), 4.54 and 4.39 (sep, J = 6.3 Hz, 1H), 1.35 and 1.19 (d, J = 6.3 Hz, 6H). |
| 2-201 | δ 8.80 and 8.75 (d, J = 2.0 and 1.7 Hz, 1H), 8.05 and 8.04 (d, J = 2.0 and 1.7 Hz, 1H), 7.4-7.75 (m, 4H), 6.49 and 6.42 (bs, 1H), 4.79 and 4.57 (d, J = 6.1 and 5.5 Hz, 2H), 4.34 and 4.15 (d, J = 7.2 Hz, 2H), 1.0-1.3 (m, 1H), 0.45-0.65 (m, 2H), 0.15-0.35 (m, 2H). |
| 2-202 | δ 8.81 and 8.70 (d, J = 2.0 Hz, 1H), 8.04 and 8.00 (d, J = 2.0 Hz, 1H), 7.15-7.55 (m, 9H), 6.40 and 6.32 (bs, 1H), 5.43 and 5.26 (q, J = 6.6 Hz, 1H), 4.5-4.85 (m, 2H), 1.68 and 1.47 (d, J = 6.6 Hz, 3H). |
| 2-204 | δ 8.44 and 8.39 (d, J = 2.4 Hz, 1H), 7.45-7.75 (m, 5H), 6.52 (bs, 1H), 4.77 and 4.53 (d, J = 6.1 and 5.1 Hz, 2H), 4.21 and 4.03 (t, J = 6.8 Hz, 2H), 1.7-1.85 and 1.55-1.7 (m, 2H), 0.97 and 0.86 (t, J = 7.3 Hz, 3H). |
| 2-206 | δ 7.2-8.5 (m, 12H), 6.28 (d, J = 7.2 Hz, 1H), 3.92 (s, 3H). |
| 2-207 | δ 8.49 (d, J = 2.1 Hz, 1H), 7.45-7.8 (m, 5H), 6.78 (bs, 1H), 5.15-5.3 (m, 1H), 4.06 (t, J = 6.9 Hz, 2H), 1.5-1.65 (m, 2H), 1.44 (d, J = 6.9 Hz, 3H), 1.2-1.4 (m, 2H), 0.87 (t, J = 6.9 Hz, 3H). |
| 2-208 | δ 8.49 (d, J = 2.1 Hz, 1H), 7.45-7.8 (m, 5H), 6.75 (bs, 1H), 5.15-5.3 (m, 1H), 3.84 (d, J = 6.6 Hz, 2H), 1.8-2.0 (m, 1H), 1.45 (d, J = 6.6 Hz, 3H), 0.83 (d, J = 6.6 Hz, 6H). |
| 2-209 | δ 8.50 (d, J = 2.1 Hz, 1H), 7.45-7.85 (m, 5H), 6.81 (bs, 1H), 5.15-5.35 (m, 1H), 3.88 (d, J = 7.2 Hz, 2H), 1.44 (d, J = 6.9 Hz, 3H), 1.0-1.15 (m, 1H), 0.45-0.55 (m, 2H), 0.15-0.25 (m, 2H). |
| 2-210 | δ 8.49 (d, J = 2.1 Hz, 1H), 7.78 (d, J = 2.1 Hz, 1H), 7.5-7.65 (m, 4H), 6.87 (bs, 1H), 5.2-5.3 (m, 1H), 1.44 (d, J = 6.6 Hz, 3H), 1.23 (s, 9H). |
| 2-211 | δ 8.49 (d, J = 2.1 Hz, 1H), 7.45-7.8 (m, 5H), 6.52 (bs, 1H), 4.51 (d, J = 5.1 Hz, 2H), 3.85-4.0 (m, 1H), 1.4-1.65 (m, 4H), 0.83 (t, J = 7.5 Hz, 6H). |
| 2-213 | δ 8.49 (d, J = 2.1 Hz, 1H), 7.45-7.8 (m, 5H), 6.49 (bs, 1H), 5.75-5.9 (m, 1H), 5.05-5.2 (m, 2H), 4.6-4.75 (m, 1H), 4.53 (d, J = 5.1 Hz, 2H), 1.26 (d, J = 6.6 Hz, 3H). |
| 2-214 | δ 7.90 (d, J = 7.8 Hz, 1H), 7.45-7.75 (m, 4H), 6.3-6.45 (m, 1H), 4.52 (d, J = 4.9 Hz, 2H), 4.14 (q, J = 7.1 Hz, 2H), 1.22 (t, J = 7.1 Hz, 3H). |
| 2-219 | δ 8.80 (d, J = 2.0 Hz, 1H), 8.00 (d, J = 2.0 Hz, 1H), 7.45-7.75 (m, 4H), 6.49 (bs, 1H), 4.56 (d, J = 5.5 Hz, 2H), 3.97 (qui, J = 6.1 Hz, 1H), 1.45-1.65 (m, 4H), 0.83 (t, J = 7.3 Hz, 6H). |
| 2-220 | δ 8.80 (d, J = 2.0 Hz, 1H), 8.00 (d, J = 2.0 Hz, 1H), 7.45-7.75 (m, 4H), 6.47 (bs, 1H), 5.85 (ddd, J = 17.3, 10.7, 6.2 Hz, 1H), 5.05-5.2 (m, 2H), 4.71 (qd, J = 6.8, 6.2 Hz, 1H), 4.58 (d, J = 5.1 Hz, 2H), 1.27 (d, J = 6.8 Hz, 3H). |
| 2-222 | δ 8.43 and 8.39 (d, J = 2.4 Hz, 1H), 7.3-7.75 (m, 5H), 6.59 and 6.57 (t, J = 72.0 Hz, 1H), 6.49 and 6.42 (bs, 1H), 4.75 and 4.54 (d, J = 6.3 Hz, 2H), 4.07 and 3.89 (s, 3H). |
| 2-224 | δ 8.51 and 8.40 (d, J = 2.1 Hz, 1H), 7.35-7.85 (m, 5H), 6.55-6.75 (m, 2H), 5.75-5.95 (m, 1H), 5.35-5.55 (m, 1H), 4.3-4.8 (m, 3H), 1.33 and 1.19 (d, J = 6.0 Hz, 6H). |
| 2-226 | δ 8.56 (d, J = 1.7 Hz, 1H), 7.80 (d, J = 1.7 Hz, 1H), 7.5-7.75 (m, 4H), 6.57 (bs, 1H), 4.53 (d, J = 5.1 Hz, 2H), 4.36 (sep, J = 6.3 Hz, 1H), 1.17 (d, J = 6.3 Hz, 6H), 0.27 (s, 9H). |
| 2-227 | δ 8.45-8.65 (m, 1H), 6.35-7.8 (m, 10H), 4.3-4.85 (m, 3H), 1.15-1.4 (m, 6H). |
| 2-228 | δ 8.85-8.95 (m, 1H), 6.35-8.2 (m, 9H), 4.3-4.85 (m, 3H), 1.15-1.4 (m, 6H). |
| 2-229 | δ 8.91 (d, J = 2.1 Hz, 1H), 8.65 (bs, 1H), 8.15-8.2 (m, 2H), 7.5-7.75 (m, 4H), 6.55 (bs, 1H), 4.58 (d, J = 6.6 Hz, 2H), 4.3-4.45 (m, 1H), 1.20 (d, J = 6.6 Hz, 6H). |
| 2-232 | δ 8.70 and 8.64 (s, 1H), 7.4-7.8 (m, 4H), 6.40 (bs, 1H), 4.3-4.75 (m, 3H), 1.33 and 1.20 (d, J = 6.6 Hz, 6H). |
| 2-234 | δ 8.63 (d, J = 2.1 Hz, 1H), 8.11 (d, J = 2.1 Hz, 1H), 7.5-7.75 (m, 4H), 6.5-7.0 (m, 1H), 5.15-5.35 (m, 1H), 3.87 (s, 3H), 1.47 (d, J = 6.6 Hz, 3H). |

TABLE 46-continued

| No. | ¹H NMR (CDCl₃, Me₄Si, 300 MHz) |
|---|---|
| 2-237 | δ 8.63 (bs, 1H), 8.1-8.15 (m, 1H), 7.5-7.75 (m, 4H), 6.5-7.0 (m, 1H), 5.15-5.35 (m, 1H), 4.13 (q, J = 7.2 Hz, 2H), 1.46 (d, J = 6.9 Hz, 3H), 1.21 (t, J = 7.2 Hz, 3H). |
| 2-238 | δ 8.63 and 8.58 (d, J = 2.1 Hz, 1H), 8.14 and 8.10 (d, J = 2.1 Hz, 1H), 7.1-7.75 (m, 4H), 6.43 (bs, 1H), 4.75 and 4.52 (d, J = 5.7 Hz, 2H), 4.21 and 4.03 (t, J = 6.9 Hz, 2H), 1.3-1.85 (m, 2H), 0.97 and 0.86 (t, J = 7.5 Hz, 3H). |
| 2-242 | δ 8.51 (d, J = 2.1 Hz, 1H), 7.15-7.8 (m, 9H), 6.41 (bs, 1H), 5.06 (s, 2H), 4.53 (d, J = 5.1 Hz, 2H). |
| 2-243 | δ 8.51 (d, J = 2.1 Hz, 1H), 6.9-7.85 (m, 8H), 6.39 (bs, 1H), 5.03 (s, 2H), 4.54 (d, J = 5.4 Hz, 2H). |
| 2-244 | δ 8.59 (d, J = 2.0 Hz, 1H), 7.94 (d, J = 2.0 Hz, 1H), 7.15-7.7 (m, 9H), 6.41 (bs, 1H), 5.24 (q, J = 6.5 Hz, 1H), 4.99 (dd, J = 5.1, 1.7 Hz, 2H), 1.47 (d, J = 6.5 Hz, 3H). |
| 2-247 | δ 8.31 and 8.27 (d, J = 2.7 Hz, 1H), 7.25-7.75 (m, 7H), 6.95-7.1 (m, 2H), 6.52 (bs, 1H), 4.76 and 4.54 (d, J = 5.8 and 5.1 Hz, 2H), 4.06 and 3.89 (s, 3H). |
| 2-249 | δ 8.65 and 8.59 (d, J = 1.7 Hz, 1H), 7.91 and 7.87 (d, J = 1.7 Hz, 1H), 7.35-7.75 (m, 9H), 6.59 (bs, 1H), 4.80 and 4.56 (d, J = 5.8 and 5.1 Hz, 2H), 4.54 and 4.38 (sep, J = 6.3 Hz, 1H), 1.34 and 1.19 (d, J = 6.3 Hz, 6H). |
| 2-251 | δ 8.63 and 8.58 (d, J = 1.5 Hz, 1H), 8.15 and 8.12 (d, J = 1.5 Hz, 1H), 7.45-7.9 (m, 4H), 6.48 (bs, 1H), 4.78 and 4.55 (d, J = 5.4 Hz, 2H), 4.61 and 4.41 (q, J = 8.4 Hz, 2H). |
| 2-254 | δ 8.50 (d, J = 2.1 Hz, 1H), 7.79 (d, J = 2.1 Hz, 1H), 7.5-7.75 (m, 4H), 6.80 (bs, 1H), 5.15-5.35 (m, 1H), 4.02 (t, J = 6.9 Hz, 2H), 1.5-1.7 (m, 2H), 1.45 (d, J = 6.9 Hz, 3H), 0.86 (t, J = 7.5 Hz, 3H). |
| 2-255 | δ 8.30 and 8.26 (d, J = 2.4 Hz, 1H), 7.3-7.75 (m, 6H), 7.33 and 7.30 (d, J = 2.4 Hz, 1H), 6.95-7.1 (m, 2H), 6.58 (bs, 1H), 4.77 and 4.53 (d, J = 5.8 and 4.8 Hz, 2H), 4.51 and 4.37 (sep, J = 6.3 Hz, 1H), 1.33 and 1.20 (d, J = 6.3 Hz, 6H). |
| 2-256 | δ 8.50 and 8.44 (d, J = 1.7 Hz, 1H), 7.75 and 7.72 (d, J = 1.7 Hz, 1H), 7.35-7.75 (m, 4H), 6.55 (bs, 1H), 4.77 and 4.52 (d, J = 6.1 and 5.1 Hz, 2H), 4.51 and 4.36 (sep, J = 6.5 Hz, 1H), 2.09 and 2.08 (s, 3H), 1.33 and 1.18 (d, J = 6.5 Hz, 6H). |
| 2-257 | δ 8.43 (d, J = 1.7 Hz, 1H), 7.35-7.75 (m, 4H), 7.74 (d, J = 1.7 Hz, 1H), 6.59 (bs, 1H), 4.77 (d, J = 5.1 Hz, 2H), 4.36 (sep, J = 4.4 Hz, 1H), 1.45-1.55 (m, 1H), 1.20 (d, J = 4.4 Hz, 6H), 0.85-0.95 (m, 4H). |
| 2-258 | δ 8.49 and 8.44 (d, J = 1.7 Hz, 1H), 7.76 and 7.73 (d, J = 1.7 Hz, 1H), 7.3-7.7 (m, 4H), 6.62 (bs, 1H), 4.78 and 4.53 (d, J = 5.8 and 4.8 Hz, 2H), 4.52 and 4.36 (sep, J = 6.5 Hz, 1H), 2.75-2.95 (m, 1H), 1.9-2.15 (m, 2H), 1.5-1.9 (m, 6H), 1.34 and 1.18 (d, J = 6.5 Hz, 6H). |
| 2-259 | δ 8.57 and 8.51 (d, J = 1.7 Hz, 1H), 7.82 and 7.79 (d, J = 1.7 Hz, 1H), 7.3-7.75 (m, 4H), 6.52 (bs, 1H), 4.77 and 4.53 (d, J = 5.8 and 5.1 Hz, 2H), 4.52 and 4.38 (sep, J = 6.5 Hz, 1H), 1.33 and 1.18 (d, J = 6.5 Hz, 6H). |
| 2-260 | δ 8.57 and 8.52 (d, J = 2.0 Hz, 1H), 7.83 and 7.79 (d, J = 2.0 Hz, 1H), 7.25-7.75 (m, 4H), 6.52 (bs, 1H), 4.77 and 4.53 (d, J = 5.8 and 4.8 Hz, 2H), 4.50 and 4.36 (sep, J = 6.1 Hz, 1H), 1.33 and 1.18 (d, J = 6.1 Hz, 6H). |
| 2-261 | δ 8.56 and 8.50 (d, J = 1.7 Hz, 1H), 7.81 and 7.77 (d, J = 1.7 Hz, 1H), 7.3-7.75 (m, 4H), 6.52 (bs, 1H), 4.77 and 4.53 (d, J = 6.1 and 5.1 Hz, 2H), 4.52 and 4.36 (sep, J = 6.3 Hz, 1H), 1.33 and 1.18 (d, J = 6.3 Hz, 6H). |
| 2-262 | δ 8.54 and 8.48 (d, J = 1.7 Hz, 1H), 7.80 and 7.77 (d, J = 1.7 Hz, 1H), 7.35-7.75 (m, 4H), 6.55 (bs, 1H), 4.78 and 4.54 (d, J = 5.1 Hz, 2H), 4.53 and 4.36 (sep, J = 6.5 Hz, 1H), 2.07 (bs, 1H), 1.64 and 1.57 (s, 6H), 1.34 and 1.19 (d, J = 6.5 Hz, 6H). |
| 2-263 | δ 8.53 and 8.47 (d, J = 1.7 Hz, 1H), 7.79 and 7.76 (d, J = 1.7 Hz, 1H), 7.3-7.75 (m, 4H), 6.54 (bs, 1H), 4.77 and 4.53 (d, J = 6.1 and 4.8 Hz, 2H), 4.51 and 4.36 (sep, J = 6.3 Hz, 1H), 1.7-2.15 (m, 8H), 1.33 and 1.18 (d, J = 6.3 Hz, 6H). |
| 2-264 | δ 8.55 and 8.49 (d, J = 1.7 Hz, 1H), 7.81 and 7.78 (d, J = 1.7 Hz, 1H), 7.45-7.75 (m, 4H), 6.57 (bs, 1H), 4.77 and 4.53 (d, J = 6.1 and 5.1 Hz, 2H), 4.50 and 4.36 (sep, J = 6.3 Hz, 1H), 1.55-2.05 (m, 10H), 1.33 and 1.18 (d, J = 6.3 Hz, 6H). |
| 2-265 | δ 8.54 and 8.49 (d, J = 1.7 Hz, 1H), 7.81 and 7.77 (d, J = 1.7 Hz, 1H), 7.35-7.75 (m, 4H), 6.59 (bs, 1H), 6.24 (bs, 1H), 4.78 and 4.53 (d, J = 6.1 and 4.8 Hz, 2H), 4.52 and 4.36 (sep, J = 6.1 Hz, 1H), 2.45-2.65 (m, 4H), 1.9-2.05 (m, 2H), 1.33 and 1.18 (d, J = 6.1 Hz, 6H). |

TABLE 46-continued

| No. | $^1$H NMR (CDCl$_3$, Me$_4$Si, 300 MHz) |
|---|---|
| 2-266 | δ 8.52 and 8.46 (d, J = 1.7 Hz, 1H), 7.78 and 7.75 (d, J = 1.7 Hz, 1H), 7.3-7.75 (m, 4H), 6.56 (bs, 1H), 6.30 (bs, 1H), 4.78 and 4.53 (d, J = 5.8 and 4.8 Hz, 2H), 4.52 and 4.36 (sep, J = 6.5 Hz, 1H), 2.1-2.3 (m, 4H), 1.55-1.75 (m, 4H), 1.33 and 1.18 (d, J = 6.5 Hz, 6H). |
| 2-267 | δ 8.63 and 8.58 (d, J = 1.7 Hz, 1H), 7.90 and 7.86 (d, J = 1.7 Hz, 1H), 7.35-7.75 (m, 8H), 6.63 (bs, 1H), 4.80 and 4.56 (d, J = 5.8 and 5.1 Hz, 2H), 4.55 and 4.38 (sep, J = 6.5 Hz, 1H), 1.35 and 1.20 (d, J = 6.5 Hz, 6H), 1.34 (s, 9H). |
| 2-268 | δ 8.72 and 8.66 (d, J = 1.7 Hz, 1H), 8.6-8.65 (m, 1H), 7.98 and 7.94 (d, J = 1.7 Hz, 1H), 7.3-7.75 (m, 7H), 6.59 (bs, 1H), 4.81 and 4.57 (d, J = 5.1 Hz, 2H), 4.54 and 4.38 (sep, J = 6.1 Hz, 1H), 1.36 and 1.21 (d, J = 6.1 Hz, 6H). |
| 2-269 | δ 8.78 and 8.77 (d, J = 1.0 Hz, 1H), 8.67 and 8.62 (d, J = 1.7 Hz, 1H), 8.55-8.6 (m, 1H), 7.93 and 7.90 (d, J = 1.7 Hz, 1H), 7.85 and 7.82 (t, J = 2.0 Hz, 1H), 7.3-7.8 (m, 5H), 6.70 (bs, 1H), 4.81 and 4.57 (d, J = 5.1 Hz, 2H), 4.53 and 4.35 (sep, J = 6.5 Hz, 1H), 1.36 and 1.21 (d, J = 6.5 Hz, 6H). |
| 2-270 | δ 8.55-8.7 (m, 3H), 7.94 and 7.91 (d, J = 2.0 Hz, 1H), 7.45-7.75 (m, 4H), 7.40 (d, J = 6.3 Hz, 2H), 6.72 (bs, 1H), 4.81 and 4.57 (d, J = 5.8 Hz, 2H), 4.52 and 4.39 (sep, J = 6.1 Hz, 1H), 1.36 and 1.21 (d, J = 6.1 Hz, 6H). |
| 2-271 | δ 8.72 and 8.71 (d, J = 2.0 Hz, 1H), 7.89 and 7.83 (d, J = 2.0 Hz, 1H), 7.05-7.75 (m, 8H), 6.81 and 6.64 (bs, 1H), 4.75 and 4.58 (d, J = 6.1 and 5.1 Hz, 2H), 4.39 and 4.06 (sep, J = 6.3 Hz, 1H), 1.21 and 0.98 (d, J = 6.3 Hz, 6H). |
| 3-002 | δ 6.75-7.75 (m, 12H), 5.45-5.6 and 5.1-5.2 (m, 1H), 5.17 and 5.04 (ds, 2H), 1.54 and 1.37 (d, J = 7.2 Hz, 3H). |
| 3-003 | δ 7.1-7.5 (m, 7H), 6.51 (bs, 1H), 5.25-5.4 and 5.0-5.15 (m, 1H), 4.00 and 3.85 (s, 3H), 2.44 and 2.35 (s, 3H), 1.60 and 1.45 (d, J = 6.9 Hz, 3H). |
| 3-004 | δ 8.51 and 8.49 (d, J = 2.0 Hz, 1H), 7.95-8.15 (m, 1H), 7.78 and 7.77 (d, J = 2.0 Hz, 1H), 7.0-7.65 (m, 3H), 7.53 (bs, 1H), 4.79 and 4.57 (dd, J = 6.1, 1.5 Hz and 4.8, 1.5 Hz, 2H), 4.34 and 4.17 (q, J = 7.0 Hz, 2H), 1.38 and 1.25 (t, J = 7.0 Hz, 3H). |
| 3-005 | δ 8.51 and 8.47 (d, J = 2.0 Hz, 1H), 7.80 and 7.78 (d, J = 2.0 Hz, 1H), 7.25-7.45 (m, 1H), 6.85-7.0 (m, 2H), 6.66 and 6.61 (bs, 1H), 4.76 and 4.56 (d, J = 6.1 and 5.1 Hz, 2H), 4.32 and 4.15 (q, J = 7.2 Hz, 2H), 1.36 and 1.22 (t, J = 7.2 Hz, 3H). |
| 3-006 | δ 8.51 and 8.47 (d, J = 2.0 Hz, 1H), 7.79 and 7.78 (d, J = 2.0 Hz, 1H), 7.25-7.7 (m, 4H), 6.97 and 6.89 (bs, 1H), 4.77 and 4.56 (d, J = 6.1 and 5.1 Hz, 2H), 4.32 and 4.15 (q, J = 7.0 Hz, 2H), 1.37 and 1.23 (t, J = 7.0 Hz, 3H). |
| 3-007 | δ 8.50 (d, J = 2.1 Hz, 1H), 7.77 (d, J = 2.1 Hz, 1H), 7.6-7.7 (m, 1H), 7.25-7.45 (m, 3H), 6.96 (bs, 1H), 4.55 (d, J = 5.1 Hz, 2H), 4.05 (t, J = 6.9 Hz, 2H), 1.55-1.7 (m, 2H), 0.87 (t, J = 7.5 Hz, 3H). |
| 3-008 | δ 8.51 and 8.46 (d, J = 2.0 Hz, 1H), 7.80 and 7.78 (d, J = 2.0 Hz, 1H), 7.1-7.35 (m, 2H), 6.9-7.1 (m, 1H), 6.48 and 6.40 (bs, 1H), 4.79 and 4.58 (d, J = 6.1 and 5.1 Hz, 2H), 4.31 and 4.14 (q, J = 7.0 Hz, 2H), 1.36 and 1.22 (t, J = 7.0 Hz, 3H). |
| 3-009 | δ 8.51 and 8.46 (d, J = 2.0 Hz, 1H), 7.80 and 7.78 (d, J = 2.0 Hz, 1H), 7.15-7.35 (m, 3H), 6.40 and 6.34 (bs, 1H), 4.81 and 4.60 (d, J = 6.1 and 5.1 Hz, 2H), 4.31 and 4.14 (q, J = 7.0 Hz, 2H), 1.36 and 1.22 (t, J = 6.3 Hz, 3H). |
| 3-010 | δ 8.51 and 8.47 (d, J = 2.0 Hz, 1H), 7.80 and 7.78 (d, J = 2.0 Hz, 1H), 7.2-7.65 (m, 4H), 6.71 and 6.66 (bs, 1H), 4.77 and 4.55 (d, J = 6.1 and 5.1 Hz, 2H), 4.32 and 4.15 (q, J = 7.0 Hz, 2H), 1.37 and 1.23 (t, J = 7.0 Hz, 3H). |
| 3-011 | δ 8.51 (d, J = 2.1 Hz, 1H), 7.78 (d, J = 2.1 Hz, 1H), 7.2-7.65 (m, 4H), 6.71 (bs, 1H), 4.55 (d, J = 5.1 Hz, 2H), 4.04 (t, J = 6.9 Hz, 2H), 1.55-1.7 (m, 2H), 0.86 (t, J = 7.5 Hz, 3H). |
| 3-013 | δ 7.8-7.9 (m, 1H), 7.05-7.5 (m, 6H), 6.59 (bs, 1H), 5.25-5.4 and 5.0-5.1 (m, 1H), 4.26 and 4.11 (q, J = 7.2 Hz, 2H), 1.45-1.65 (m, 3H), 1.34 and 1.20 (t, J = 7.2 Hz, 3H). |
| 3-014 | δ 8.52 and 8.47 (d, J = 2.0 Hz, 1H), 7.8-7.9 (m, 1H), 7.80 and 7.78 (d, J = 2.0 Hz, 1H), 7.2-7.45 (m, 2H), 7.0-7.15 (m, 1H), 6.48 (bs, 1H), 4.77 and 4.54 (d, J = 6.1 and 5.1 Hz, 2H), 4.32 and 4.15 (q, J = 7.0 Hz, 2H), 1.37 and 1.22 (t, J = 7.0 Hz, 3H). |
| 3-015 | δ 8.51 (d, J = 2.1 Hz, 1H), 7.87 (d, J = 7.8 Hz, 1H), 7.78 (d, J = 2.1 Hz, 1H), 7.05-7.45 (m, 3H), 6.47 (bs, 1H), 4.54 (d, J = 5.4 Hz, 2H), 4.04 (t, J = 6.6 Hz, 2H), 1.5-1.7 (m, 2H), 0.86 (t, J = 7.5 Hz, 3H). |
| 3-016 | δ 8.51 and 8.47 (d, J = 2.0 Hz, 1H), 7.7-8.1 (m, 1H), 7.80 and 7.78 (d, J = 2.0 Hz, 1H), 7.05-7.45 (m, 3H), 6.52 and 6.48 (bs, 1H), 4.77 and 4.54 (d, J = 6.1 and 5.1 Hz, 2H), 4.53 and 4.48 (sep, J = 6.3 Hz, 1H), 1.34 and 1.19 (d, J = 6.3 Hz, 6H). |
| 3-017 | δ 8.52 and 8.48 (d, J = 2.0 Hz, 1H), 7.8-7.9 (m, 1H), |

TABLE 46-continued

| No. | ¹H NMR (CDCl₃, Me₄Si, 300 MHz) |
|---|---|
|  | 7.80 and 7.79 (d, J = 2.0 Hz, 1H), 7.2-7.45 (m, 2H), 7.0-7.15 (m, 1H), 6.48 (bs, 1H), 4.79 and 4.55 (d, J = 6.1 and 5.1 Hz, 2H), 4.08 and 3.91 (d, J = 7.2 Hz, 2H), 1.0-1.3 (m, 1H), 0.4-0.65 (m, 2H), 0.15-0.35 (m, 2H). |
| 3-018 | δ 8.52 and 8.43 (d, J = 2.0 Hz, 1H), 7.7-7.9 (m, 1H), 7.80 and 7.75 (d, J = 2.0 Hz, 1H), 7.0-7.45 (m, 8H), 6.45 (bs, 1H), 5.42 and 5.27 (q, J = 6.6 Hz, 1H), 4.45-4.85 (m, 2H), 1.68 and 1.47 (d, J = 6.6 Hz, 3H). |
| 3-019 | δ 8.50 (d, J = 2.1 Hz, 1H), 7.78 (d, J = 2.1 Hz, 1H), 7.15-7.45 (m, 4H), 6.41 (bs, 1H), 4.52 (d, J = 5.4 Hz, 2H), 4.03 (t, J = 6.9 Hz, 2H), 2.41 (s, 3H), 1.55-1.7 (m, 2H), 0.86 (t, J = 7.8 Hz, 3H). |
| 3-020 | δ 8.51 and 8.47 (d, J = 2.0 Hz, 1H), 7.81 and 7.77 (d, J = 2.0 Hz, 1H), 7.1-7.5 (m, 4H), 6.52 (bs, 1H), 4.73 and 4.53 (d, J = 6.0 and 5.5 Hz, 2H), 4.52 and 4.38 (sep, J = 6.3 Hz, 1H), 2.41 and 2.32 (s, 3H), 1.34 and 1.19 (d, J = 6.3 Hz, 6H). |
| 3-021 | δ 8.51 and 8.48 (d, J = 2.0 Hz, 1H), 7.81 and 7.79 (d, J = 2.0 Hz, 1H), 6.95-7.3 (m, 3H), 6.42 (bs, 1H), 4.72 and 4.52 (d, J = 6.1 and 5.1 Hz, 2H), 4.31 and 4.14 (q, J = 7.0 Hz, 2H), 2.30 and 2.21 (d, J = 2.4 Hz, 3H), 1.36 and 1.22 (t, J = 7.0 Hz, 3H). |
| 3-023 | δ 8.50 and 8.47 (d, J = 2.0 Hz, 1H), 7.81 and 7.79 (d, J = 2.0 Hz, 1H), 7.3-8.1 (m, 4H), 7.23 and 7.12 (t, J = 55.6 Hz, 1H), 6.64 (bs, 1H), 4.74 and 4.52 (d, J = 6.2 and 4.8 Hz, 2H), 4.3-4.65 (m, 1H), 1.34 and 1.20 (d, J = 6.3 Hz, 6H). |
| 3-024 | δ 8.50 and 8.45 (d, J = 2.0 Hz, 1H), 7.81 and 7.78 (d, J = 2.0 Hz, 1H), 7.25-7.65 (m, 3H), 6.53 (bs, 1H), 4.74 and 4.51 (d, J = 6.1 and 4.9 Hz, 2H), 4.51 and 4.37 (sep, J = 6.1 Hz, 1H), 1.33 and 1.19 (d, J = 6.1 Hz, 6H). |
| 3-025 | δ 8.50 and 8.45 (d, J = 2.0 Hz, 1H), 7.81 and 7.79 (d, J = 2.0 Hz, 1H), 7.4-7.6 (m, 2H), 7.25-7.4 (m, 1H), 6.52 and 6.45 (bs, 1H), 4.79 and 4.57 (d, J = 6.1 and 5.1 Hz, 2H), 4.31 and 4.14 (q, J = 7.0 Hz, 2H), 1.35 and 1.21 (t, J = 7.0 Hz, 3H). |
| 3-026 | δ 8.60 and 8.31 (bs, 1H). 8.50 and 8.48 (d, J = 2.0 Hz, 1H), 8.17 and 8.12 (dd, J = 8.0, 1.8 Hz, 1H), 7.76 (d, J = 2.0 Hz, 1H), 7.35-7.5 (m, 1H), 6.85-7.1 (m, 2H), 4.79 and 4.57 (d, J = 5.8 and 4.8 Hz, 2H), 4.33 and 4.18 (q, J = 7.0 Hz, 2H), 3.99 and 3.89 (s, 3H), 1.38 and 1.26 (t, J = 7.0 Hz, 3H). |
| 3-027 | δ 8.51 and 8.48 (d, J = 2.0 Hz, 1H), 8.09 and 8.02 (dd, J = 7.8, 1.9 Hz, 1H), 7.78 and 7.77 (d, J = 2.0 Hz, 1H), 7.62 (bs, 1H), 7.05-7.7 (m, 3H), 6.63 and 6.53 (d, J = 73.1 Hz, 1H), 4.77 and 4.55 (d, J = 6.1 and 4.8 Hz, 2H), 4.33 and 4.17 (q, J = 7.0 Hz, 2H), 1.37 and 1.24 (t, J = 7.0 Hz, 3H). |
| 3-028 | δ 8.51 and 8.47 (d, J = 2.0 and 2.4 Hz, 1H), 8.02 and 7.94 (dd, J = 7.9, 2.1 Hz, 1H), 7.79 and 7.78 (d, J = 2.0 and 2.4 Hz, 1H), 7.2-7.6 (m, 3H), 7.44 (bs, 1H), 4.77 and 4.54 (d, J = 6.1 and 4.8 Hz, 2H), 4.33 and 4.16 (q, J = 7.0 Hz, 2H), 1.37 and 1.22 (t, J = 7.0 Hz, 3H). |
| 3-029 | δ 8.50 and 8.47 (d, J = 2.0 Hz, 1H), 7.79 and 7.77 (d, J = 2.0 Hz, 1H), 7.1-7.6 (m, 4H), 7.01 (bs, 1H), 4.77 and 4.56 (d, J = 6.1 and 5.1 Hz, 2H), 4.32 and 4.15 (q, J = 7.0 Hz, 2H), 2.44 and 2.39 (s, 3H), 1.37 and 1.23 (t, J = 7.0 Hz, 3H). |
| 3-030 | δ 8.51 and 8.45 (d, J = 2.0 Hz, 1H), 8.05 and 8.00 (dd, J = 7.8, 1.2 Hz, 1H), 7.83 and 7.80 (d, J = 2.0 Hz, 1H), 7.35-7.75 (m, 3H), 6.50 (bs, 1H), 4.78 and 4.56 (d, J = 5.8 and 5.5 Hz, 2H), 4.32 and 4.15 (q, J = 7.0 Hz, 2H), 1.36 and 1.22 (t, J = 7.0 Hz, 3H). |
| 3-031 | δ 8.51 and 8.48 (d, J = 2.0 Hz, 1H), 7.81 and 7.79 (d, J = 2.0 Hz, 1H), 7.35-7.85 (m, 4H), 7.07 and 6.99 (bs, 1H), 4.80 and 4.57 (d, J = 5.8 and 5.1 Hz, 2H), 4.34 and 4.17 (q, J = 7.0 Hz, 2H), 1.37 and 1.23 (t, J = 7.0 Hz, 3H). |
| 3-032 | δ 8.42 and 8.31 (d, J = 2.0 Hz, 1H), 7.72 and 7.71 (d, J = 2.0 Hz, 1H), 7.25-7.7 (m, 9H), 6.05 and 6.03 (bs, 1H), 4.50 and 4.25 (d, J = 6.1 and 5.1 Hz, 2H), 4.18 and 4.01 (q, J = 7.0 Hz, 2H), 1.27 and 1.14 (t, J = 7.0 Hz, 3H). |
| 3-033 | δ 8.45-8.55 (m, 1H), 7.2-7.8 (m, 5H), 6.95 (bs, 1H), 4.75 and 4.55 (d, J = 5.7 Hz, 2H), 4.07 and 3.89 (s, 3H). |
| 3-035 | δ 8.50 (d, J = 2.1 Hz, 1H), 7.7-7.8 (m, 2H), 7.3-7.45 (m, 3H), 7.17 (bs, 1H), 4.56 (d, J = 4.8 Hz, 2H), 1.26 (s, 9H). |
| 3-037 | δ 8.45-8.55 (m, 1H), 7.2-7.85 (m, 5H), 6.73 (bs, 1H), 4.5-4.6 (m, 2H), 3.88 (s, 3H). |
| 3-038 | δ 8.51 (d, J = 2.1 Hz, 1H), 7.77 (d, J = 2.1 Hz, 1H), 7.5-7.65 (m, 2H), 7.2-7.4 (m, 2H), 6.75 (bs, 1H), 4.55 (d, J = 5.1 Hz, 2H), 4.05-4.25 (m, 1H), 1.15-1.7 (m, 5H), 0.84 (t, J = 7.8 Hz, 3H). |
| 3-039 | δ 8.50 (d, J = 2.1 Hz, 1H), 7.77 (d, J = 2.1 Hz, 1H), 7.55-7.65 (m, 2H), 7.2-7.4 (m, 2H), 6.83 (bs, 1H), 4.55 (d, J = 5.4 Hz, 2H), 1.26 (s, 9H). |
| 3-040 | δ 8.52 (d, J = 2.1 Hz, 1H), 7.81 (d, J = 2.1 Hz, 1H), 7.25-7.7 (m, 4H), 6.68 (bs, 1H), 4.58 (d, J = 5.4 Hz, 2H), 4.44 (q, J = 8.4 Hz, 2H). |
| 3-042 | δ 8.4-8.55 (m, 1H), 7.0-7.9 (m, 5H), 6.54 (bs, 1H), 4.7-4.8 and 4.5-4.6 (m, 2H), 3.85-4.1 (m, 3H). |

TABLE 46-continued

| No. | $^1$H NMR (CDCl$_3$, Me$_4$Si, 300 MHz) |
|---|---|
| 3-043 | δ 8.51 (d, J = 2.1 Hz, 1H), 7.87 (d, J = 8.1 Hz, 1H), 7.77 (d, J = 2.1 Hz, 1H), 7.3-7.45 (m, 2H), 7.05-7.15 (m, 1H), 6.49 (bs, 1H), 4.54 (d, J = 5.1 Hz, 2H), 4.05-4.25 (m, 1H), 1.15-1.7 (m, 5H), 0.84 (t, J = 7.5 Hz, 3H). |
| 3-044 | δ 8.51 and 8.46 (d, J = 2.1 Hz, 1H), 7.75-7.9 (m, 2H), 7.0-7.45 (m, 3H), 6.52 (bs, 1H), 4.78 and 4.54 (d, J = 5.4 Hz, 2H), 1.39 and 1.26 (s, 9H). |
| 3-045 | δ 8.53 and 8.49 (d, J = 2.1 Hz, 1H), 7.8-7.95 (m, 2H), 7.0-7.45 (m, 3H), 6.37 (bs, 1H), 4.35-4.85 (m, 4H). |
| 3-046 | δ 8.50 and 8.47 (d, J = 2.1 Hz, 1H), 7.79 and 7.78 (d, J = 2.1 Hz, 1H), 7.1-7.5 (m, 4H), 6.48 and 6.40 (bs, 1H), 4.71 and 4.53 (d, J = 6.0 Hz, 2H), 4.06 and 3.88 (s, 3H), 2.40 and 2.30 (s, 3H). |
| 3-048 | δ 8.50 (d, J = 2.1 Hz, 1H), 7.77 (d, J = 2.1 Hz, 1H), 7.15-7.45 (m, 4H), 6.45 (bs, 1H), 4.53 (d, J = 5.1 Hz, 2H), 2.43 (s, 3H), 1.26 (s, 9H). |
| 3-051 | δ 8.64 and 8.60 (d, J = 1.5 Hz, 1H), 8.14 and 8.11 (d, J = 1.5 Hz, 1H), 7.1-7.4 (m, 4H), 6.35 and 6.27 (bs, 1H), 4.76 and 4.56 (d, J = 5.4 Hz, 2H), 4.61 and 4.41 (q, J = 8.4 Hz, 2H), 2.40 (s, 3H). |
| 4-001 | δ 8.43 and 8.36 (d, J = 2.1 Hz, 1H), 7.82 (d, J = 2.1 Hz, 1H), 7.75 (d, J = 7.8 Hz, 1H), 7.2-7.35 (m, 1H), 6.95-7.1 (m, 1H), 6.59 (d, J = 7.8 Hz, 1H), 5.83 and 4.14 (s, 1H), 3.79 and 3.62 (s, 3H), 1.84 and 1.55 (s, 6H). |
| 4-002 | δ 8.47 (d, J = 2.4 Hz, 1H), 7.79 (d, J = 2.4 Hz, 1H), 7.45-7.75 (m, 4H), 7.21 (bs, 1H), 4.0-4.2 (m, 2H), 1.82 (s, 3H), 1.75 (s, 3H), 1.17 (t, J = 7.2 Hz, 3H). |
| 4-004 | δ 8.45-8.55 (m, 1H), 7.35-7.75 (m, 5H), 6.59 and 6.43 (bs, 1H), 4.05-4.3 (m, 2H), 2.5-3.0 (m, 4H), 1.75-2.15 (m, 2H), 1.2-1.35 (m, 3H). |
| 4-006 | δ 8.50 and 8.40 (d, J = 2.0 Hz, 1H), 7.80 (d, J = 2.0 Hz, 1H), 7.35-7.7 (m, 3H), 6.9-7.15 (m, 1H), 4.88 and 4.62, 4.25 (d, J = 3.1, 15.3, 15.3 Hz, 2H), 4.07 and 3.96 (s, 3H), 2.95-3.30 (m, 2H), 1.22 and 1.09 (t, J = 7.2 Hz, 3H). |
| 4-008 | δ 8.47 and 8.38 (d, J = 2.4 and 2.0 Hz, 1H), 7.80 and 7.78 (d, J = 2.4 and 2.0 Hz, 1H), 7.4-7.75 (m, 3H), 7.15-7.25 (m, 1H), 4.25-5.3 (m, 4H), 4.08 and 3.91 (s, 3H), 3.38 and 3.15 (s, 3H). |
| 4-009 | δ 8.50 and 8.40 (d, J = 2.4 Hz, 1H), 7.80 (d, J = 2.4 Hz, 1H), 7.35-7.7 (m, 3H), 6.95-7.2 (m, 1H), 5.5-6.0 (m, 1H), 5.0-5.35 (m, 2H), 4.89 and 4.57 (d, J = 15.0 Hz, 1H), 4.76 and 4.28 (d, J = 15.0 Hz, 1H), 4.06 and 3.93 (s, 3H), 3.4-3.9 (m, 2H). |
| 4-010 | δ 8.47 and 8.38 (d, J = 2.4 Hz, 1H), 7.81 and 7.79 (d, J = 2.4 Hz, 1H), 7.4-7.75 (m, 3H), 7.1-7.25 (m, 1H), 5.09 and 4.73 (d, J = 9.6 Hz, 1H), 4.80 and 4.42 (d, J = 9.6 Hz, 1H), 3.7-4.3 (m, 2H), 4.08 and 3.95 (s, 3H), 2.28 and 2.22 (t, J = 2.6 Hz, 1H). |
| 4-011 | δ 8.81 and 8.79 (s, 1H), 8.00 and 7.98 (s, 1H), 7.35-7.7 (m, 4H), 4.6-5.4 (m, 2H), 4.09 and 3.92 (s, 3H), 2.75-2.85 and 2.6-2.7 (m, 1H), 0.35-0.9 (m, 4H). |
| 4-012 | δ 8.52 and 8.40 (d, J = 2.0 Hz, 1H), 7.3-7.85 (m, 4H), 7.09 and 7.02 (d, J = 6.8 Hz, 1H), 3.95-5.1 (m, 4H), 4.27 and 3.94 (s, 3H). |
| 4-013 | δ 8.47 and 8.44 (d, J = 2.0 Hz, 1H), 7.81 and 7.75 (d, J = 2.0 Hz, 1H), 7.45-7.75 (m, 4H), 4.82 and 4.73 (s, 2H), 3.94 and 3.87 (s, 3H), 2.42 and 2.28 (s, 3H). |
| 4-014 | δ 8.53 and 8.44 (d, J = 2.0 Hz, 1H), 7.82 and 7.79 (d, J = 2.0 Hz, 1H), 7.35-7.75 (m, 4H), 4.98 (bs, 2H), 4.06 and 3.90 (s, 3H), 3.63 and 3.59 (s, 3H). |
| 4-015 | δ 8.52 (bs, 1H), 7.4-7.9 (m, 5H), 5.67 (bs, 1H), 4.82 (bs, 1H), 3.94 (s, 3H). |
| 6-001 | δ 8.25-8.5 (m, 3H), 7.7-7.85 (m, 2H), 7.3-7.4 (m, 1H), 4.76 and 4.54 (d, J = 6.0 Hz, 2H), 4.34 and 4.16 (m, J = 7.2 Hz, 2H), 1.38 and 1.23 (t, J = 7.2 Hz, 3H). |
| 6-003 | δ 8.25-8.55 (m, 3H), 7.7-7.85 (m, 2H), 7.2-7.3 (m, 1H), 4.76 and 4.54 (d, J = 5.7 Hz, 2H), 4.33 and 4.16 (q, J = 7.2 Hz, 2H), 1.38 and 1.23 (t, J = 7.2 Hz, 3H). |
| 6-004 | δ 8.3-8.7 (m, 3H), 7.7-7.8 (m, 1H), 7.5-7.6 (m, 1H). 7.2-7.35 (m, 1H), 4.74 and 4.52 (d, J = 5.7 Hz, 2H), 4.33 and 4.16 (q, J = 7.2 Hz, 2H), 2.67 and 2.66 (s, 3H), 1.38 and 1.23 (t, J = 7.2 Hz, 3H). |
| 6-005 | δ 8.75 (dd, J = 4.8, 1.0 Hz, 1H), 8.49 (d, J = 2.0 Hz, 1H), 8.23 (bs, 1H), 8.15 (dd, J = 8.2, 1.0 Hz, 1H), 7.75 (d, J = 2.0 Hz, 1H), 7.56 (dd, J = 8.2, 4.8 Hz, 1H), 4.55 (d, J = 5.5 Hz, 2H), 4.16 (q, J = 7.0 Hz, 2H), 1.23 (t, J = 7.0 Hz, 3H). |
| 6-006 | δ 8.45-8.5 (m, 2H), 8.32 (bs, 1H), 7.79 (dd, J = 8.1, 1.5 Hz, 1H), 7.73 (d, J = 1.8 Hz, 1H), 7.35 (dd, J = 8.1, 4.5 Hz, 1H), 4.52 (d, J = 5.7 Hz, 2H), 4.35-4.45 (m, 1H), 1.20 (d, J = 6.0 Hz, 6H). |
| 6-007 | δ 8.51 (dd, J = 4.5, 1.5 Hz, 1H), 8.48 (d, J = 2.1 Hz, 1H), 8.32 (bs, 1H), 8.00 (dd, J = 8.1, 1.5 Hz, 1H), 7.73 (d, J = 2.1 Hz, 1H), 7.26 (dd, J = 8.1, 4.5 Hz, 1H), 4.52 (d, J = 5.7 Hz, 2H), 4.35-4.45 (m, 1H), 1.20 (d, J = 6.0 Hz, 6H). |

TABLE 46-continued

| No. | $^1$H NMR (CDCl$_3$, Me$_4$Si, 300 MHz) |
|---|---|
| 6-008 | δ 8.75 (dd, J = 4.8, 1.5 Hz, 1H), 8.48 (d, J = 2.1 Hz, 1H), 8.25 (bs, 1H), 8.15 (d, J = 7.8 Hz, 1H), 7.74 (d, J = 2.1 Hz, 1H), 7.56 (dd, J = 7.8, 4.8 Hz, 1H), 4.55 (d, J = 5.4 Hz, 2H), 4.35-4.45 (m, 1H), 1.20 (d, J = 6.3 Hz, 6H). |
| 7-001 | δ 8.4-8.5 and 8.3-8.4 (m, 1H), 8.0-8.1 and 7.8-7.85 (m, 1H), 7.15-7.5 (m, 5H), 4.65 and 4.60 (d, J = 6.3 Hz, 2H), 4.04 and 3.87 (s, 3H). |
| 7-002 | δ 8.50 and 8.47 (d, J = 2.1 Hz, 1H), 8.4-8.5 (m, 1H), 8.05-8.2 (m, 1H), 7.80 and 7.78 (d, J = 2.1 Hz, 1H), 7.25-7.4 (m, 1H), 6.44 and 6.27 (bs, 1H), 4.78 and 4.56 (d, J = 6.0 Hz, 2H), 4.33 and 4.16 (q, J = 7.2 Hz, 2H), 1.38 and 1.24 (t, J = 7.2 Hz, 3H). |
| 7-003 | δ 8.51 and 8.48 (d, J = 2.1 Hz, 1H), 8.08 and 8.00 (d, J = 7.8 Hz, 1H), 7.81 and 7.79 (d, J = 2.1 Hz, 1H), 7.72 and 7.69 (d, J = 7.8 Hz, 1H), 7.07 and 7.01 (bs, 1H), 4.78 and 4.56 (d, J = 6.3 Hz, 2H), 4.34 and 4.16 (q, J = 7.2 Hz, 2H), 1.38 and 1.23 (t, J = 7.2 Hz, 3H). |
| 7-004 | δ 8.7-8.8 (m, 1H), 7.89 and 7.73 (d, J = 7.8 Hz, 1H), 7.1-7.6 (m, 4H), 6.95 and 6.81 (bs, 1H), 5.2-5.35 and 4.95-5.1 (m, 1H), 4.36 and 4.09 (q, J = 7.2 Hz, 2H), 1.60 and 1.45 (d, J = 7.2 Hz, 3H), 1.31 and 1.18 (t, J = 7.2 Hz, 3H). |
| 7-006 | δ 8.4-8.55 (m, 2H), 8.05-8.15 (m, 1H), 7.78 (d, J = 1.8 Hz, 1H), 7.25-7.4 (m, 2H), 4.55 (d, J = 5.1 Hz, 2H), 3.89 (s, 3H). |
| 7-007 | δ 8.51 (d, J = 2.1 Hz, 1H), 8.45-8.5 (m, 1H), 8.1-8.2 (m, 1H), 7.78 (d, J = 2.1 Hz, 1H), 7.3-7.4 (m, 2H), 4.56 (d, J = 4.8 Hz, 2H), 4.06 (t, J = 6.9 Hz, 2H), 1.55-1.75 (m, 2H), 0.87 (t, J = 7.5 Hz, 3H). |
| 7-008 | δ 8.4-8.55 (m, 2H), 8.15-8.25 (m, 1H), 7.78 (d, J = 2.4 Hz, 1H), 7.58 (bs, 1H), 7.3-7.4 (m, 1H), 4.56 (d, J = 4.8 Hz, 2H), 1.27 (s, 9H). |
| 7-009 | δ 8.5-8.55 (m, 1H), 8.45-8.5 (m, 1H), 8.05-8.15 (m, 1H), 7.8-7.85 (m, 1H), 7.25-7.4 (m, 2H), 4.60 (d, J = 5.4 Hz, 2H), 4.45 (q, J = 8.7 Hz, 2H). |
| 8-001 | δ 8.98 (s, 1H), 8.89 (d, J = 4.8 Hz, 1H), 8.51 (d, J = 2.0 Hz, 1H), 7.80 (d, J = 2.0 Hz, 1H), 7.48 (d, J = 4.8 Hz, 1H), 6.62 (bs, 1H), 4.53 (d, J = 5.1 Hz, 2H), 4.14 (q, J = 7.0 Hz, 2H), 1.22 (t, J = 7.0 Hz, 3H). |
| 9-001 | δ 8.81 (d, J = 2.1 Hz, 1H), 8.76 (d, J = 2.1 Hz, 1H), 8.48 (d, J = 2.1 Hz, 1H), 8.03 (bs, 1H), 7.77 (d, J = 2.1 Hz, 1H), 4.56 (d, J = 5.8 Hz, 2H), 3.90 (s, 3H). |
| 9-002 | δ 8.81 (d, J = 2.4 Hz, 1H), 8.77 (d, J = 2.4 Hz, 1H), 8.10 (bs, 1H), 7.44 (d, J = 2.1 Hz, 1H), 7.30 (dd, J = 8.1, 2.1 Hz, 1H), 7.16 (d, J = 8.1 Hz, 1H), 5.0-5.15 (m, 1H), 4.12 (q, J = 7.2 Hz, 2H), 1.48 (d, J = 6.9 Hz, 3H), 1.21 (t, J = 7.2 Hz, 3H). |
| 9-004 | δ 8.82 and 8.79 (d, J = 2.4 Hz, 1H), 8.77 and 8.71 (d, J = 2.4 Hz, 1H), 8.50 and 8.48 (d, J = 2.0 Hz, 1H), 8.08 (bs, 1H), 7.78 and 7.77 (d, J = 2.0 Hz, 1H), 4.82 and 4.57 (d, J = 6.1 and 5.5 Hz, 2H), 4.01 and 3.92 (d, J = 7.0 Hz, 2H), 1.0-1.2 (m, 1H), 0.45-0.65 (m, 2H), 0.15-0.4 (m, 2H). |
| 9-007 | δ 8.82 (d, J = 2.7 Hz, 1H), 8.76 (d, J = 2.7 Hz, 1H), 8.49 (d, J = 1.8 Hz, 1H), 8.05 (bs, 1H), 7.76 (d, J = 1.8 Hz, 1H), 4.56 (d, J = 5.1 Hz, 2H), 4.35-4.45 (m, 1H), 1.20 (d, J = 6.3 Hz, 6H). |
| 10-001 | δ 8.50 and 8.48 (d, J = 2.1 Hz, 1H), 7.78 and 7.76 (d, J = 2.1 Hz, 1H), 7.44 and 7.40 (d, J = 2.1 Hz, 1H), 7.16 (bs, 1H), 6.57 and 6.54 (d, J = 2.1 Hz, 1H), 4.74 and 4.51 (d, J = 5.4 Hz, 2H), 4.25-4.4 and 4.05-4.25 (m, 2H), 1.38 and 1.24 (t, J = 7.2 Hz, 3H). |
| 10-002 | δ 8.50 (d, J = 2.0 Hz, 1H), 7.76 (d, J = 2.0 Hz, 1H), 7.31 (d, J = 1.4 Hz, 1H), 6.91 (s, 1H), 6.32 (d, J = 1.4 Hz, 1H), 4.48 (d, J = 5.1 Hz, 2H), 4.16 (q, J = 7.0 Hz, 2H), 2.36 (s, 3H), 1.23 (t, J = 7.0 Hz, 3H). |
| 11-001 | δ 8.49 and 8.46 (d, J = 2.0 Hz, 1H), 7.77 and 7.75 (d, J = 2.0 Hz, 1H), 6.33 (bs, 1H), 6.00 and 5.86 (s, 1H), 4.66 and 4.44 (d, J = 6.1 and 5.1 Hz, 2H), 4.31 and 4.14 (q, J = 7.0 Hz, 2H), 2.50 and 2.45 (s, 3H), 2.24 and 2.22 (s, 3H), 1.36 and 1.23 (t, J = 7.0 Hz, 3H). |
| 11-002 | δ 8.50 and 8.46 (d, J = 2.0 Hz, 1H), 7.79 and 7.77 (d, J = 2.0 Hz, 1H), 6.69 (bs, 1H), 6.34 and 6.27 (s, 1H), 4.69 and 4.47 (d, J = 5.5 and 4.8 Hz, 2H), 4.31 and 4.15 (q, J = 7.0 Hz, 2H), 2.36 and 2.33 (s, 3H), 1.36 and 1.23 (t, J = 7.0 Hz, 3H). |
| 11-003 | δ 8.51 and 8.48 (d, J = 2.4 and 2.0 Hz, 1H), 7.81 and 7.79 (d, J = 2.4 and 2.0 Hz, 1H), 7.65-7.75 (m, 2H), 7.3-7.5 (m, 3H), 6.95 and 6.88 (s, 1H), 6.82 and 6.80 (bs, 1H), 4.74 and 4.51 (d, J = 5.8 and 4.8 Hz, 2H), 4.33 and 4.16 (q, J = 7.0 Hz, 2H), 1.37 and 1.24 (t, J = 7.0 Hz, 3H). |
| 12-001 | δ 6.85-7.8 (m, 7H), 5.4-5.55 and 5.05-5.15 (m, 1H), 4.03 and 3.88 (s, 3H), 2.55 and 2.51 (s, 3H), 1.54 and 1.35 (d, J = 6.9 Hz, 3H). |
| 12-002 | δ 6.85-7.75 (m, 11H), 5.4-5.55 and 5.05-5.15 (m, 1H), 5.20 and 5.07 (s, 2H), 2.47 and 2.37 (s, 3H), 1.54 and 1.34 (d, J = 6.9 Hz, 3H). |
| 12-003 | δ 7.1-7.45 (m, 4H), 6.88 and 6.82 (d, J = 2.1 Hz, 1H), 6.54 and 6.32 (bs, 1H), 4.59 and 4.40 (d, J = 6.3 Hz, 2H), 4.03 and 3.88 (s, 3H), 2.51 and 2.35 (s, 3H). |

TABLE 46-continued

| No. | $^1$H NMR (CDCl$_3$, Me$_4$Si, 300 MHz) |
|---|---|
| 12-005 | δ 6.85-7.55 (m, 6H), 5.15-5.3 and 4.9-5.05 (m, 1H), 4.4-4.55 and 4.3-4.4 (m, 1H), 2.54 and 2.48 (s, 3H), 1.56 and 1.42 (d, J = 6.9 Hz, 3H), 1.15-1.4 (m, 6H). |
| 12-006 | δ 7.1-7.45 (m, 8H), 6.87 and 6.83 (d, J = 5.1 Hz, 1H), 6.63 and 6.56 (d, J = 7.5 Hz, 1H), 5.25-5.35 and 4.95-5.05 (m, 1H), 5.19 and 5.03 (s, 2H), 2.44 and 2.36 (s, 3H), 1.55 and 1.40 (d, J = 6.9 Hz, 3H). |
| 12-007 | δ 8.77 (s, 1H), 8.00 (s, 1H), 7.24 (d, J = 5.1 Hz, 1H), 6.85 (d, J = 5.1 Hz, 1H), 6.66 (bs, 1H), 4.73 (d, J = 6.0 Hz, 2H), 4.45-4.6 (m, 1H), 2.44 (s, 3H), 1.36 (t, J = 6.3 Hz, 6H). |
| 12-008 | δ 8.51 and 8.48 (d, J = 2.0 Hz, 1H), 7.78 and 7.77 (d, J = 2.0 Hz, 1H), 7.83 and 7.70 (bs, 1H), 7.45 and 7.42 (d, J = 5.3 Hz, 1H), 7.04 and 6.99 (d, J = 5.3 Hz, 1H), 4.78 and 4.55 (d, J = 6.1 and 4.9 Hz, 2H), 4.34 and 4.17 (q, J = 7.0 Hz, 2H), 1.38 and 1.25 (t, J = 7.0 Hz, 3H). |
| 12-009 | δ 8.50 and 8.48 (d, J = 2.0 Hz, 1H), 7.78 and 7.77 (d, J = 2.0 Hz, 1H), 7.58 and 7.44 (bs, 1H), 7.39 and 7.36 (d, J = 5.1 Hz, 1H), 7.14 and 7.10 (d, J = 5.1 Hz, 1H), 4.78 and 4.55 (d, J = 5.8 and 5.1 Hz, 2H), 4.34 and 4.17 (q, J = 7.0 Hz, 2H), 1.38 and 1.25 (t, J = 7.0 Hz, 3H). |
| 12-010 | δ 8.50 and 8.47 (d, J = 2.4 Hz, 1H), 7.78 and 7.76 (d, J = 2.4 Hz, 1H), 7.27 and 7.24 (d, J = 5.1 Hz, 1H), 6.87 and 6.84 (d, J = 5.1 Hz, 1H), 6.60 (bs, 1H), 4.70 and 4.49 (d, J = 6.3 Hz, 2H), 4.32 and 4.15 (q, J = 7.2 Hz, 2H), 2.51 and 2.46 (s, 3H), 1.37 and 1.24 (t, J = 7.2 Hz, 3H). |
| 12-011 | δ 8.50 and 8.46 (d, J = 2.0 Hz, 1H), 7.79 and 7.77 (d, J = 2.0 Hz, 1H), 7.46 (d, J = 5.1 Hz, 1H), 7.26 (d, J = 5.1 Hz, 1H), 7.04 (bs, 1H), 4.74 and 4.51 (d, J = 6.1 and 4.8 Hz, 2H), 4.32 and 4.16 (q, J = 7.2 Hz, 2H), 1.37 and 1.24 (t, J = 7.2 Hz, 3H). |
| 12-012 | δ 8.49 and 8.47 (d, J = 2.1 Hz, 1H), 7.78 and 7.76 (d, J = 2.1 Hz, 1H), 7.27 and 7.23 (d, J = 4.8 Hz, 1H), 6.87 and 6.84 (d, J = 4.8 Hz, 1H), 6.58 (bs, 1H), 4.70 and 4.50 (d, J = 5.7 Hz, 2H), 4.07 and 3.90 (s, 3H), 2.50 and 2.41 (s, 3H). |
| 12-013 | δ 8.50 and 8.48 (d, J = 2.1 Hz, 1H), 7.79 and 7.77 (d, J = 2.1 Hz, 1H), 7.2-7.3 (m, 1H), 6.8-6.9 (m, 1H), 6.61 (bs, 1H), 4.72 and 4.50 (d, J = 5.4 Hz, 2H), 4.23 and 4.06 (t, J = 6.9 Hz, 2H), 2.53 and 2.43 (s, 3H), 1.55-1.9 (m, 2H), 1.00 and 0.88 (t, J = 7.2 Hz, 3H). |
| 12-014 | δ 8.48 (d, J = 2.1 Hz, 1H), 7.79 (d, J = 2.1 Hz, 1H), 7.24 (d, J = 5.1 Hz, 1H), 6.85 (d, J = 5.1 Hz, 1H), 6.66 (bs, 1H), 4.65-4.75 (m, 2H), 4.25-4.4 (m, 1H), 2.44 (s, 3H), 1.5-1.9 (m, 2H), 1.33 (d, J = 4.8 Hz, 3H), 0.98 (t, J = 7.5 Hz, 3H). |
| 12-016 | δ 8.50 (d, J = 2.1 Hz, 1H), 7.76 (d, J = 2.1 Hz, 1H), 7.29 (d, J = 5.1 Hz, 1H), 6.89 (d, J = 5.1 Hz, 1H), 6.76 (bs, 1H), 4.90 (d, J = 4.8 Hz, 2H), 2.54 (s, 3H), 1.27 (s, 9H). |
| 12-017 | δ 8.51 and 8.49 (d, J = 2.1 Hz, 1H), 7.75-7.85 (m, 1H), 7.2-7.35 (m, 1H), 6.8-6.95 (m, 1H), 6.47 (bs, 1H), 4.35-4.8 (m, 4H), 2.50 and 2.42 (s, 3H). |
| 12-018 | δ 8.51 (d, J = 2.1 Hz, 1H), 7.78 (d, J = 2.1 Hz, 1H), 7.45 (d, J = 5.7 Hz, 1H), 7.36 (bs, 1H), 7.26 (d, J = 5.7 Hz, 1H), 5.1-5.3 (m, 1H), 4.05 (t, J = 6.6 Hz, 2H), 1.5-1.75 (m, 2H), 1.43 (d, J = 6.6 Hz, 3H), 0.87 (t, J = 7.2 Hz, 3H). |
| 12-020 | δ 8.79 (bs, 1H), 7.99 (bs, 1H), 7.45 (d, J = 5.4 Hz, 1H), 7.26 (d, J = 5.4 Hz, 1H), 7.01 (bs, 1H), 4.54 (d, J = 4.8 Hz, 2H), 4.07 (t, J = 6.9 Hz, 2H), 1.55-1.75 (m, 2H), 0.87 (t, J = 7.5 Hz, 3H). |
| 13-001 | δ 8.51 and 8.48 (d, J = 2.1 Hz, 1H), 7.79 and 7.78 (d, J = 2.1 Hz, 1H), 7.35-7.45 (m, 1H), 7.05-7.2 (m, 1H), 6.94 and 6.88 (bs, 1H), 4.75 and 4.52 (d, J = 5.4 Hz, 2H), 4.33 and 4.15 (q, J = 7.2 Hz, 2H), 1.38 and 1.24 (t, J = 7.2 Hz, 3H). |
| 13-002 | δ 8.45-8.55 (m, 1H), 7.75-7.9 (m, 1H), 7.2-7.5 (m, 2H), 6.74 (bs, 1H), 4.7-4.8 and 4.45-4.55 (m, 2H), 4.25-4.4 and 4.05-4.2 (m, 2H), 1.15-1.4 (m, 3H). |
| 13-003 | δ 8.51 (d, J = 2.1 Hz, 1H), 7.78 (d, J = 2.1 Hz, 1H), 7.43 (d, J = 5.7 Hz, 1H), 7.1-7.25 (m, 2H), 5.15-5.3 (m, 1H), 4.05 (t, J = 6.9 Hz, 2H), 1.55-1.75 (m, 2H), 4.47 (d, J = 6.9 Hz, 3H), 0.87 (t, J = 7.5 Hz, 3H). |
| 14-001 | δ 8.50 and 8.47 (d, J = 1.5 Hz, 1H), 7.65-7.8 (m, 2H), 7.48 and 7.44 (d, J = 3.6 Hz, 1H), 6.96 and 6.91 (bs, 1H), 4.29 and 4.13 (d, J = 6.0 Hz, 2H), 4.33 and 4.16 (q, J = 7.2 Hz, 2H), 1.37 and 1.23 (t, J = 7.2 Hz, 3H). |
| 15-001 | δ 8.50 (d, J = 2.0 Hz, 1H), 7.76 (d, J = 2.0 Hz, 1H), 7.24 (d, J = 2.7 Hz, 1H), 6.93 (d, J = 2.7 Hz, 1H), 6.78 (bs, 1H), 4.49 (d, J = 4.8 Hz, 2H), 4.17 (d, J = 7.0 Hz, 2H), 3.68 (s, 3H), 1.23 (t, J = 7.0 Hz, 3H). |
| 15-002 | δ 8.48 (d, J = 2.1 Hz, 1H), 7.74 (d, J = 2.1 Hz, 1H), 7.24 (bs, 1H), 6.92 (bs, 1H), 6.82 (bs, 1H), 4.47 (d, J = 4.8 Hz, 2H), 4.3-4.45 (m, 1H), 3.67 (s, 3H), 1.20 (d, J = 6.0 Hz, 6H). |
| 17-001 | δ 8.50 and 8.47 (d, J = 2.0 and 2.4 Hz, 1H), 7.78 and 7.77 (d, J = 2.4 and 2.0 Hz, 1H), 7.21 and 7.12 (bs, 1H), 4.73 and 4.50 (d, J = 6.1 and 4.8 Hz, 2H), 4.32 and 4.15 (q, J = 7.0 Hz, 2H), 3.84 and 3.81 (s, 3H), 1.37 and 1.24 (t, J = 7.0 Hz, 3H). |

TABLE 46-continued

| No. | $^1$H NMR (CDCl$_3$, Me$_4$Si, 300 MHz) |
|---|---|
| 17-002 | δ 7.98 and 7.80 (s, 1H), 7.1-7.45 (m, 3H), 7.00 and 6.90 (bs, 1H), 6.86 and 6.72 (t, J = 54.0 Hz, 1H), 4.59 and 4.40 (d, J = 6.0 Hz, 2H), 4.02 and 3.87 (s, 3H), 3.91 and 3.87 (s, 3H). |
| 17-003 | δ 7.90 and 7.88 (s, 1H), 7.44 and 7.41 (d, J = 1.9 Hz, 1H), 7.1-7.35 (m, 2H), 7.10 (bs, 1H), 6.87 and 6.75 (t, J = 54.2 Hz, 1H), 5.2-5.4 and 4.9-5.1 (m, 1H), 4.01 and 3.86 (s, 3H), 3.93 and 3.90 (s, 3H), 1.56 and 1.41 (d, J = 7.2 Hz, 3H). |
| 17-005 | δ 7.92 and 7.82 (s, 1H), 7.2-7.45 (m, 3H), 6.88 and 6.68 (bs, 1H), 4.57 and 4.38 (d, J = 6.3 Hz, 2H), 4.03 and 3.87 (s, 3H), 3.95 and 3.91 (s, 3H). |
| 17-006 | δ 8.50 and 8.47 (d, J = 2.2 Hz, 1H), 7.94 and 7.89 (s, 1H), 7.78 and 7.77 (d, J = 2.2 Hz, 1H), 6.9-6.95 and 6.8-6.85 (m, 1H), 4.71 and 4.48 (d, J = 5.8 Hz, 2H), 4.32 and 4.16 (q, J = 7.2 Hz, 2H), 3.96 and 3.93 (s, 3H), 1.36 and 1.24 (t, J = 7.2 Hz, 3H). |
| 17-008 | δ 8.49 (d, J = 2.1 Hz, 1H), 7.77 (d, J = 2.1 Hz, 1H), 6.71 (bs, 1H), 4.47 (d, J = 4.8 Hz, 2H), 3.89 (s, 3H), 3.84 (s, 3H). |
| 17-011 | δ 8.48 (d, J = 1.8 Hz, 1H), 7.89 (s, 1H), 7.74 (d, J = 1.8 Hz, 1H), 7.05 (bs, 1H), 6.83 (t, J = 54.6 Hz, 1H), 4.48 (d, J = 5.1 Hz, 2H), 4.3-4.45 (m, 1H), 3.92 (s, 3H), 1.20 (d, J = 6.3 Hz, 6H). |
| 17-012 | δ 8.79 (bs, 1H), 7.97 (bs, 1H), 7.90 (s, 1H), 7.00 (bs, 1H), 6.82 (t, J = 54.3 Hz, 1H), 4.52 (d, J = 5.1 Hz, 2H), 4.07 (t, J = 6.6 Hz, 2H), 3.92 (s, 3H), 1.55-1.75 (m, 2H), 0.87 (t, J = 7.5 Hz, 3H). |
| 18-001 | δ 8.49 (d, J = 2.0 Hz, 1H), 7.76 (d, J = 2.0 Hz, 1H), 7.61 (bs, 1H), 4.48 (d, J = 5.5 Hz, 2H), 4.16 (q, J = 7.0 Hz, 2H), 2.55 (s, 3H), 1.23 (t, J = 7.0 Hz, 3H). |
| 19-001 | δ 8.50 and 8.48 (d, J = 2.1 Hz, 1H), 7.80 and 7.78 (d, J = 2.1 Hz, 1H), 6.55 (bs, 1H), 4.69 and 4.47 (d, J = 6.3 Hz, 2H), 4.32 and 4.15 (q, J = 7.2 Hz, 2H), 2.68 and 2.65 (s, 3H), 2.65 and 2.57 (s, 3H), 1.37 and 1.24 (t, J = 7.2 Hz, 3H). |
| 20-001 | δ 8.50 and 8.47 (d, J = 2.1 Hz, 1H), 7.79 and 7.77 (d, J = 2.1 Hz, 1H), 7.17 and 7.08 (t, J = 54.6 Hz, 1H), 6.8-7.05 (m, 1H), 4.70 and 4.47 (d, J = 6.3 Hz, 2H), 4.32 and 4.16 (q, J = 7.2 Hz, 2H), 2.75 and 2.72 (s, 3H), 1.37 and 1.24 (t, J = 7.2 Hz, 3H). |
| 20-002 | δ 7.1-7.5 (m, 4H), 5.1-5.25 and 4.85-5.0 (m, 1H), 4.26 and 4.11 (q, J = 7.2 Hz, 2H), 2.74 and 2.73 (s, 3H), 1.4-1.6 (m, 3H), 1.34 and 1.21 (t, J = 7.2 Hz, 3H). |
| 20-003 | δ 8.50 and 8.46 (d, J = 2.1 Hz, 1H), 7.80 and 7.78 (d, J = 2.1 Hz, 1H), 6.95-7.1 (m, 1H), 4.72 and 4.48 (d, J = 5.7 Hz, 2H), 4.32 and 4.15 (q, J = 7.2 Hz, 2H), 2.73 and 2.71 (s, 3H), 1.36 and 1.24 (t, J = 7.2 Hz, 3H). |
| 20-004 | δ 8.47 (d, J = 2.0 Hz, 1H), 7.81 (d, J = 2.0 Hz, 1H), 7.04 (bs, 1H), 4.75 (d, J = 5.8 Hz, 2H), 4.09 (d, J = 7.2 Hz, 2H), 2.71 (s, 3H), 1.0-1.3 (m, 1H), 0.4-0.65 (m, 2H), 0.15-0.4 (m, 2H). |
| 20-005 | δ 8.50 and 8.43 (d, J = 2.0 Hz, 1H), 7.80 and 7.76 (d, J = 2.0 Hz, 1H), 7.15-7.45 (m, 5H), 6.95 (bs, 1H), 5.41 and 5.26 (q, J = 6.8 Hz, 1H), 4.45 and 4.33 (d, J = 4.9 and 5.8 Hz, 2H), 2.73 and 2.71 (s, 3H), 1.67 and 1.48 (d, J = 6.8 Hz, 3H). |
| 21-001 | δ 8.49 (d, J = 2.0 Hz, 1H), 7.76 (d, J = 2.0 Hz, 1H), 7.35 (bs, 1H), 4.51 (d, J = 5.1 Hz, 2H), 4.28 (s, 3H), 4.17 (q, J = 7.0 Hz, 2H), 1.23 (t, J = 7.0 Hz, 3H). |
| 22-001 | δ 7.43 and 7.42 (d, J = 1.8 Hz, 1H), 7.25-7.35 (m, 1H), 7.12 and 7.10 (s, 1H), 6.74 and 6.65 (bs, 1H), 5.05-5.15 and 4.8-4.9 (m, 1H), 4.05-4.45 (m, 4H), 3.05-3.15 (m, 2H), 1.15-1.65 (m, 6H). |
| 22-002 | δ 8.50 and 8.47 (d, J = 2.1 Hz, 1H), 7.79 and 7.77 (d, J = 2.1 Hz, 1H), 6.49 (bs, 1H), 4.1-4.65 (m, 6H), 3.0-3.15 (m, 2H), 1.35 and 1.23 (t, J = 7.2 Hz, 3H). |
| 22-003 | δ 8.49 and 8.46 (d, J = 2.1 Hz, 1H), 7.79 and 7.76 (d, J = 2.1 Hz, 1H), 6.49 (bs, 1H), 4.3-4.65 (m, 5H), 3.0-3.15 (m, 2H), 1.33 and 1.20 (d, J = 6.3 Hz, 6H). |
| 23-004 | δ 8.35-8.4 (m, 1H), 7.0-7.85 (m, 9H), 6.31 (bs, 1H), 5.22 and 5.06 (s, 2H), 4.65 and 4.76 (d, J = 6.0 Hz, 2H). |
| 24-001 | δ 8.55 and 8.50 (s, 1H), 7.4-7.75 (m, 4H), 6.42 (bs, 1H), 4.35-4.8 (m, 3H), 1.35 and 1.21 (d, J = 6.3 Hz, 6H). |
| 26-001 | δ 6.65-7.75 (m, 7H), 5.35-5.5 and 5.05-5.2 (m, 1H), 4.23 and 4.12 (q, J = 7.2 Hz, 2H), 1.59 and 1.41 (d, J = 7.2 Hz, 3H), 1.30 and 1.22 (t, J = 7.2 Hz, 3H). |
| 26-002 | δ 6.5-7.75 (m, 12H), 4.8-5.55 (m, 2H), 1.3-1.7 (m, 6H). |
| 26-003 | δ 6.55-7.75 (m, 6H), 5.2-5.45 and 5.0-5.15 (m, 1H), 4.05-4.35 (m, 2H), 1.2-1.65 (m, 6H). |
| 27-001 | δ 7.45-7.7 (m, 5H), 5.95-6.1 (m, 1H), 4.8-4.9 (m, 1H), 4.02 (s, 3H), 3.60 (s, 3H), 1.51 (d, J = 6.9 Hz, 3H), 1.35 (d, J = 6.0 Hz, 6H). |
| 27-002 | δ 7.5-7.75 (m, 4H), 6.97 (d, J = 7.8 Hz, 1H), 5.15-5.25 (m, 1H), 4.75-4.9 (m, 1H), 3.90 (s, 3H), 3.64 (s, 3H), 1.40 (d, J = 7.2 Hz, 3H), 1.37 (d, J = 6.6 Hz, 6H). |
| 29-001 | δ 7.4-7.85 (m, 4H), 6.58 and 6.41 (bs, 1H), 4.85 and 4.73 (d, J = 5.7 Hz, 2H), 4.05 and 4.03 (s, 3H). |

TABLE 46-continued

| No. | $^1$H NMR (CDCl$_3$, Me$_4$Si, 300 MHz) |
|---|---|
| 29-002 | δ 7.4-7.8 (m, 4H), 6.61 and 6.42 (bs, 1H), 4.87 and 4.74 (d, J = 5.4 Hz, 2H), 4.2-4.4 (m, 2H), 1.25-1.4 (m, 3H). |
| 30-007 | δ 6.5-8.65 (m, 13H), 4.85-5.85 (m, 1H), 1.4-1.7 (m, 3H). |
| 30-009 | δ 6.95-7.75 (m, 6H), 6.3-6.7 (m, 1H), 5.0-5.3 (m, 1H), 1.4-1.65 (m, 3H). |
| 30-010 | δ 8.18 and 8.08 (d, J = 2.4 Hz, 1H), 8.32 (bs, 1H), 7.3-7.75 (m, 5H), 6.45 (bs, 1H), 4.69 and 4.54 (d, J = 6.3 and 5.3 Hz, 2H). |
| 30-012 | δ 8.47 and 8.42 (d, J = 2.0 Hz, 1H), 8.20 (bs, 1H), 7.4-7.75 (m, 5H), 6.64 (bs, 1H), 4.90 and 4.65 (d, J = 6.3 and 5.3 Hz, 2H). |
| 30-013 | δ 7.15-7.75 (m, 7H), 6.55 (bs, 1H), 5.35-5.5 and 5.05-5.2 (m, 1H), 1.4-1.7 (m, 3H). |
| 30-014 | δ 7.1-7.75 (m, 6H), 6.44 (bs, 1H), 5.05-5.25 (m, 1H), 1.4-1.5 (m, 3H). |
| 30-016 | δ 7.15-8.05 (m, 8H), 6.90 and 6.59 (bs, 1H), 5.25-5.4 and 5.0-5.1 (m, 1H), 1.63 and 1.46 (d, J = 6.9 Hz, 3H). |
| 30-018 | δ 8.51 and 8.41 (d, J = 2.4 Hz, 1H), 7.92 and 7.81 (bs, 1H), 7.4-7.75 (m, 4H), 7.00 and 6.77 (d, J = 7.8 Hz, 1H), 5.75-5.9 and 5.2-5.35 (m, 1H), 1.59 and 1.44 (d, J = 6.9 Hz, 3H). |
| 30-019 | δ 7.94 and 7.91 (s, 1H), 7.4-7.75 (m, 4H), 6.45 and 6.39 (bs, 1H), 4.75 and 4.54 (d, J = 6.3 Hz, 2H). |
| 30-020 | δ 7.4-7.85 (m, 5H), 6.47 (bs, 1H), 4.83 and 4.56 (d, J = 6.0 Hz, 2H), 4.02 and 3.99 (s, 3H). |
| 30-021 | δ 7.1-7.75 (m, 8H), 6.85 and 6.55 (bs, 1H), 5.2-5.4 and 5.0-5.2 (m, 1H), 1.64 and 1.47 (d, J = 6.9 Hz, 3H). |
| 30-024 | δ 8.80 and 8.75 (d, J = 1.7 Hz, 1H), 8.09 (d, J = 1.7 Hz, 1H), 7.45-7.75 (m, 4H), 6.61 (bs, 1H), 5.78 (bs, 1H), 4.86 and 4.59 (d, J = 6.3 and 5.1 Hz, 2H), 4.04 and 4.03 (s, 3H), 2.23 and 2.22 (s, 3H). |
| 30-025 | δ 8.81 and 8.74 (d, J = 1.8 Hz, 1H), 8.06 and 8.05 (d, J = 1.8 Hz, 1H), 7.35-7.8 (m, 4H), 6.47 and 6.39 (bs, 1H), 4.83 (d, J = 6.0 Hz, 1H), 4.59 (d, J = 6.0 Hz, 1H). |
| 30-028 | δ 9.04 (d, J = 1.7 Hz, 1H), 8.31 (d, J = 1.7 Hz, 1H), 7.35-7.75 (m, 4H), 6.48 (bs, 1H), 4.48 (d, J = 6.1 Hz, 2H). |
| 31-001 | δ 8.43 (d, J = 2.4 Hz, 1H), 7.4-7.8 (m, 5H), 6.37 (bs, 1H), 5.99 (dd, J = 8.5, 4.6 Hz, 1H), 4.1-4.35 (m, 2H). |
| 31-002 | δ 8.43 (d, J = 1.2 Hz, 1H), 7.4-7.75 (m, 5H), 6.55 (bs, 1H), 6.21 (t, J = 6.3 Hz, 1H), 4.40 (t, J = 6.3 Hz, 2H). |
| 31-004 | δ 7.99 (d, J = 7.2 Hz, 1H), 7.4-7.75 (m, 4H), 6.46 (bs, 1H), 6.30 (dd, J = 6.6, 5.8 Hz, 1H), 4.3-4.4 (m, 2H). |
| 31-005 | δ 7.77 (s, 1H), 7.45-7.75 (m, 4H), 6.48 (bs, 1H), 6.2-6.3 (m, 1H), 4.2-4.45 (m, 2H), 3.96 (s, 3H). |
| 31-008 | δ 8.75 (d, J = 1.8 Hz, 1H), 8.09 (d, J = 1.8 Hz, 1H), 7.45-7.75 (m, 4H), 6.57 (bs, 1H), 6.38 (dd, J = 7.4, 5.0 Hz, 1H), 4.3-4.6 (m, 2H), 4.04 (s, 3H), 2.22 (s, 3H). |
| 31-009 | δ 8.77 (d, J = 1.8 Hz, 1H), 8.12 (d, J = 1.8 Hz, 1H), 7.45-7.75 (m, 4H), 6.49 (t, J = 6.3 Hz, 1H), 6.43 (t, J = 6.3 Hz, 1H), 4.40 (t, J = 6.3 Hz, 2H). |
| 31-010 | δ 9.07 (d, J = 1.4 Hz, 1H), 8.35 (d, J = 1.4 Hz, 1H), 7.4-7.8 (m, 4H), 6.54 (dd, J = 6.9, 5.8 Hz, 1H), 6.29 (dd, J = 7.2, 4.7 Hz, 1H), 4.45 (ddd, J = 14.9, 6.9, 4.7 Hz, 1H), 4.38 (ddd, J = 14.9, 7.2, 5.8 Hz, 1H). |
| 32-004 | δ 7.9-8.0 (m, 1H), 7.5-7.75 (m, 7H), 7.00 (bs, 1H), 5.65-5.8 (m, 1H), 1.56 (d, J = 7.2 Hz, 3H), 1.36 (s, 9H). |
| 32-011 | δ 8.33 (s, 1H), 8.19 (s, 1H), 8.02 (s, 1H), 7.5-7.8 (m, 4H), 6.77 (bs, 1H), 5.65-5.8 (m, 1H), 1.56 (d, J = 7.2 Hz, 3H). |
| 32-012 | δ 7.1-7.75 (m, 8H), 6.96 (bs, 1H), 5.65-5.8 (m, 1H), 4.55-4.7 (m, 1H), 1.56 (d, J = 7.2 Hz, 3H), 1.37 (d, J = 6.0 Hz, 6H). |
| 32-013 | δ 7.5-8.6 (m, 11H), 6.6-7.1 (m, 1H), 4.9-6.0 (m, 1H), 1.45-1.65 (m, 3H). |
| 32-015 | δ 7.0-7.9 (m, 6H), 6.81 (bs, 1H), 5.5-5.65 (m, 1H), 1.5-1.6 (m, 3H). |
| 32-018 | δ 7.15-7.75 (m, 6H), 6.68 (bs, 1H), 5.25-5.4 (m, 1H), 1.50 (d, J = 7.2 Hz, 3H). |
| 32-019 | δ 7.45-7.75 (m, 6H), 6.7-6.9 (m, 1H), 5.45-5.6 (m, 1H), 1.5-1.6 (m, 3H). |
| 32-024 | δ 7.85-7.9 (m, 1H), 7.5-7.75 (m, 6H), 6.88 (bs, 1H), 5.5-5.65 (m, 1H), 1.49 (d, J = 7.2 Hz, 3H). |
| 32-025 | δ 7.5-7.75 (m, 5H), 7.2-7.3 (m, 1H), 7.05-7.15 (m, 1H), 6.35 (bs, 1H), 5.5-5.65 (m, 1H), 1.46 (d, J = 7.2 Hz, 3H). |
| 32-029 | δ 7.5-7.8 (m, 7H), 6.71 (bs, 1H), 5.45-5.6 (m, 1H), 1.46 (d, J = 7.5 Hz, 3H). |
| 32-030 | δ 7.65-7.75 (m, 1H), 7.5-7.65 (m, 4H), 7.25-7.35 (m, 1H), 7.15-7.2 (m, 1H), 6.82 (bs, 1H), 5.55-5.7 (m, 1H), 2.40 (s, 3H), 1.45 (d, J = 7.2 Hz, 3H). |
| 32-031 | δ 7.45-7.8 (m, 7H), 6.65 (bs, 1H), 5.45-5.6 (m, 1H), 1.49 (d, J = 7.8 Hz, 3H). |
| 32-032 | δ 8.86 (s, 1H), 8.11 (s, 1H), 7.45-7.8 (m, 4H), 5.13 (bs, 1H), 5.12 (d, J = 4.8 Hz, 2H). |
| 32-033 | δ 7.65-7.75 (m, 2H), 7.5-7.65 (m, 3H), 7.00 (d, J = 2.4 Hz, 1H), 6.75-6.95 (m, 2H), 5.6-5.75 (m, 1H), 3.87 (s, 3H), 1.46 (d, J = 7.2 Hz, 3H). |
| 32-034 | δ 6.7-7.85 (m, 8H), 5.5-5.7 (m, 1H), 2.52 (s, 3H), 1.45 (d, J = 7.2 Hz, 3H). |
| 32-035 | δ 7.45-7.8 (m, 7H), 6.59 (bs, 1H). 5.35-5.5 (m, 1H), 1.49 (d, J = 7.2 Hz, 3H). |

TABLE 46-continued

| No. | $^1$H NMR (CDCl$_3$, Me$_4$Si, 300 MHz) |
|---|---|
| 32-037 | δ 8.07 (d, J = 1.5 Hz, 1H), 7.9-7.95 (m, 1H), 7.7-7.75 (m, 1H), 7.5-7.65 (m, 4H), 6.73 (bs, 1H), 5.5-5.65 (m, 1H), 4.15 (s, 2H), 1.46 (d, J = 7.2 Hz, 3H), 1.40 (s, 6H). |
| 32-038 | δ 7.65-7.75 (m, 1H), 7.45-7.65 (m, 5H), 7.35-7.45 (m, 1H), 6.78 (bs, 1H), 6.69 (dd, J = 17.7, 11.1 Hz, 1H), 5.88 (d, J = 17.7 Hz, 1H), 5.55-5.7 (m, 1H), 5.50 (d, J = 11.1 Hz, 1H), 1.47 (d, J = 7.2 Hz, 3H). |
| 32-039 | δ 7.4-7.75 (m, 7H), 6.72 (bs, 1H), 5.5-5.65 (m, 1H), 1.45 (d, J = 7.2 Hz, 3H), 0.27 (s, 9H). |
| 32-040 | δ 7.35-7.8 (m, 12H), 6.83 (bs, 1H), 5.6-5.75 (m, 1H), 1.51 (d, J = 7.2 Hz, 3H). |
| 32-041 | δ 7.3-7.8 (m, 11H), 6.80 (bs, 1H), 5.6-5.75 (m, 1H), 1.51 (d, J = 7.2 Hz, 3H). |
| 32-042 | δ 7.78 (d, J = 8.7 Hz, 1H), 7.5-7.75 (m, 5H), 7.39 (dd, J = 8.7, 2.1 Hz, 1H), 7.13 (t, J = 2.1 Hz, 2H), 6.79 (bs, 1H), 6.40 (t, J = 2.1 Hz, 2H), 5.6-5.75 (m, 1H), 1.50 (d, J = 7.2 Hz, 3H). |
| 32-043 | δ 7.25-8.05 (m, 8H), 6.87 (bs, 1H), 6.5-6.55 (m, 1H), 6.35-6.4 (m, 1H), 5.55-5.7 (m, 1H), 1.48 (d, J = 6.9 Hz, 3H). |
| 32-044 | δ 8.0-8.1 (m, 1H), 8.95 (d, J = 2.1 Hz, 1H), 7.5-7.85 (m, 6H), 6.79 (d, J = 2.1 Hz, 1H), 6.74 (bs, 1H), 5.55-5.7 (m, 1H), 1.49 (d, J = 6.9 Hz, 3H). |
| 32-046 | δ 7.05-7.75 (m, 7H), 6.70 (bs, 1H), 5.45-5.65 (m, 1H), 1.48 (d, J = 6.9 Hz, 3H). |
| 32-047 | δ 7.5-7.85 (m, 6H), 6.73 (bs, 1H), 5.45-5.6 (m, 1H), 1.5-1.6 (m, 3H). |
| 32-048 | δ 7.7-7.75 (m, 2H), 7.5-7.65 (m, 3H), 7.3-7.35 (m, 2H), 6.86 (d, J = 7.2 Hz, 1H), 5.5-5.65 (m, 1H), 2.49 (s, 3H), 1.44 (d, J = 7.2 Hz, 3H). |
| 32-049 | δ 7.45-7.95 (m, 7H), 6.60 (bs, 1H), 5.4-5.55 (m, 1H), 1.50 (d, J = 7.2 Hz, 3H). |
| 32-051 | δ 7.65-7.75 (m, 2H), 7.4-7.65 (m, 5H), 6.77 (bs, 1H), 6.23 (s, 1H), 5.45-5.6 (m, 1H), 3.9-4.05 (m, 4H), 1.45 (d, J = 7.2 Hz, 3H). |
| 32-052 | δ 8.3-8.5 (m, 2H), 7.8-7.95 (m, 2H), 7.5-7.75 (m, 6H), 6.93 (bs, 1H), 5.65-5.8 (m, 1H), 1.48 (d, J = 7.2 Hz, 3H). |
| 32-055 | δ 8.76 (s, 1H), 7.5-7.8 (m, 4H), 6.83 (bs, 1H), 5.08 (d, J = 5.1 Hz, 2H). |
| 32-057 | δ 8.69 (d, J = 2.1 Hz, 1H), 8.2-8.25 (m, 1H), 7.45-7.75 (m, 4H), 6.69 (bs, 1H), 5.9-6.1 (m, 1H), 1.51 (d, J = 7.2 Hz, 3H). |
| 33-001 | δ 8.61 (s, 1H), 7.5-7.8 (m, 4H), 6.65 (bs, 1H), 5.05-5.15 (m, 2H). |
| 35-001 | δ 6.55-7.75 (m, 7H), 5.35-5.5 and 5.1-5.25 (m, 1H), 1.63 and 1.43 (d, J = 7.2 Hz, 3H). |
| 36-002 | δ 7.5-7.75 (m, 5H), 6.78 (bs, 1H), 5.75-5.95 and 5.45-5.65 (m, 1H), 1.45-1.65 (m, 3H). |
| 37-001 | δ 8.94 (bs, 2H), 7.45 (d, J = 1.8 Hz, 1H), 7.34 (dd, J = 8.1, 1.8 Hz, 1H), 7.23 (d, J = 8.1 Hz, 1H), 4.52 (q, J = 6.9 Hz, 1H), 4.16 (q, J = 6.9 Hz, 2H), 1.60 (d, J = 6.9 Hz, 3H), 1.23 (t, J = 6.9 Hz, 3H). |
| 37-008 | δ 8.50 (d, J = 2.1 Hz, 1H), 7.76 (d, J = 2.1 Hz, 1H), 4.35 (sep, J = 6.1 Hz, 1H), 3.73 (s, 2H), 1.18 (d, J = 6.1 Hz, 6H). |
| 37-009 | δ 8.98 (bs, 1H), 8.5-8.6 (m, 1H), 7.75-7.85 (m, 1H), 4.35-4.6 (m, 2H), 1.2-1.75 (m, 9H). |
| 37-011 | δ 8.51 and 8.48 (d, J = 2.0 Hz, 1H), 7.79 and 7.77 (d, J = 2.0 Hz, 1H), 4.04 and 3.89 (d, J = 7.2 Hz, 2H), 3.95 and 3.76 (s, 2H), 2.33 (bs, 2H), 0.95-1.3 (m, 1H), 0.4-0.65 (m, 2H), 0.05-0.4 (m, 2H). |
| 37-015 | δ 8.51 and 8.44 (d, J = 2.0 Hz, 1H), 7.77 and 7.74 (d, J = 2.0 Hz, 1H), 7.1-7.4 (m, 5H), 5.37 and 5.24 (q, J = 6.8 Hz, 1H), 3.96 and 3.70 (s, 2H), 2.15 (bs, 2H), 1.64 and 1.46 (d, J = 6.8 Hz, 3H). |
| 37-016 | δ 8.87 (bs, 3H), 8.45-8.5 (m, 1H), 7.7-7.75 (m, 1H), 6.9-7.45 (m, 4H), 5.42 and 5.32 (q, J = 6.9 Hz, 1H), 4.25 and 4.02 (bs, 2H), 1.70 and 1.53 (d, J = 6.9 Hz, 3H). |
| 37-019 | δ 8.47 and 8.46 (d, J = 1.7 Hz, 1H), 7.77 and 7.74 (d, J = 1.7 Hz, 1H), 4.48 (s, 2H), 4.48 and 4.35 (sep, J = 6.3 Hz, 1H), 3.89 and 3.73 (s, 2H), 3.43 and 3.33 (s, 3H), 1.32 and 1.18 (d, J = 6.3 Hz, 6H). |
| 37-020 | δ 8.24 and 8.23 (d, J = 2.5 Hz, 1H), 7.27 and 7.26 (d, J = 2.5 Hz, 1H), 4.46 and 4.34 (sep, J = 6.3 Hz, 1H), 3.89 and 3.88 (s, 3H), 3.87 and 3.72 (s, 2H), 1.31 and 1.19 (d, J = 6.3 Hz, 6H). |
| 37-024 | δ 8.97 (bs, 3H), 8.53 (d, J = 2.1 Hz, 1H), 7.77 (d, J = 2.1 Hz, 1H), 4.52 (bs, 1H), 4.11 (t, J = 6.9 Hz, 2H), 1.55-1.75 (m, 5H), 0.86 (t, J = 7.5 Hz, 3H). |
| 37-025 | δ 8.79 (d, J = 1.5 Hz, 1H), 8.01 (d, J = 1.5 Hz, 1H), 4.06 (s, 3H), 3.94 (s, 2H), 1.61 (bs, 2H). |
| 37-026 | δ 8.77 (d, J = 1.5 Hz, 1H), 8.00 (d, J = 1.5 Hz, 1H), 4.19 (t, J = 6.9 Hz, 2H), 3.94 (s, 2H), 1.75 (sxt, J = 6.9 Hz, 2H), 1.64 (bs, 2H), 0.99 (t, J = 6.9 Hz, 3H). |
| 37-027 | δ 8.77 (d, J = 1.5 Hz, 1H), 8.01 (d, J = 1.5Hz, 1H), 4.49 (sep, J = 6.3 Hz, 1H), 3.92 (s, 2H), 1.73 (bs, 2H), 1.33 (d, J = 6.9 Hz, 6H). |
| 38-004 | δ 8.35 and 8.20 (bs, 1H), 7.6-7.85 (m, 5H), 5.75-5.9 and 5.1-5.35 (m, 1H), 4.02 and 3.85 (bs, 3H), 2.05-2.6 (m, 2H), 0.85-1.05 (m, 3H). |
| 38-009 | δ 8.70 and 8.49 (bs, 1H), 7.94 and 7.92 (bs, 1H), 7.65-7.85 (m, 4H), 6.10 and 5.53 (q, J = 7.2 Hz, 1H), 1.85 and 1.80 (d, J = 7.2 Hz, 3H). |

TABLE 46-continued

| No. | $^1$H NMR (CDCl$_3$, Me$_4$Si, 300 MHz) |
|---|---|
| 38-012 | δ 8.63 and 8.45 (d, J = 1.7 Hz, 1H), 8.61 and 8.29 (d, J = 1.7 Hz, 1H), 7.6-7.9 (m, 4H), 5.08 and 4.81 (s, 2H), 4.48 and 4.40 (s, 2H), 3.45 and 3.35 (s, 3H). |
| 38-013 | δ 8.41 and 8.28 (d, J = 1.8 Hz, 1H), 7.6-7.9 (m, 5H), 5.00 and 4.78 (s, 2H), 4.46 and 4.39 (s, 2H), 4.46 and 4.32 (sep, J = 6.3 Hz, 1H), 3.43 and 3.33 (s, 3H), 1.25 and 1.12 (d, J = 6.3 Hz, 6H). |
| 38-014 | δ 8.22 and 8.04 (d, J = 2.4 Hz, 1H), 7.6-7.9 (m, 4H), 7.23 and 7.20 (d, J = 2.4 Hz, 1H), 5.07 and 4.79 (s, 2H), 3.86 and 3.80 (s, 3H). |
| 38-016 | δ 8.18 and 8.03 (d, J = 2.5 Hz, 1H), 7.6-7.9 (m, 4H), 7.21 and 7.18 (d, J = 2.5 Hz, 1H), 4.97 and 4.76 (s, 2H), 4.45 and 4.32 (sep, J = 6.3 Hz, 1H), 3.85 and 3.79 (s, 3H), 1.25 and 1.12 (d, J = 6.3 Hz, 6H). |
| 39-010 | δ 8.66 (bs, 1H), 8.03 (bs, 1H), 7.8-7.85 (m, 2H), 7.65-7.75 (m, 2H), 5.89 (m, J = 7.2 Hz, 1H), 1.70 (d, J = 7.2 Hz, 3H). |
| 39-011 | δ 8.55 (d, J = 1.2 Hz, 1H), 7.85-7.95 (m, 2H), 7.83 (d, J = 1.2 Hz, 1H), 7.7-7.8 (m, 2H), 5.34 (s, 2H), 4.56 (s, 2H). 3.48 (s, 3H). |
| 40-001 | δ 8.75 (bs, 2H), 8.39 (d, J = 2.1 Hz, 1H), 7.83 (d, J = 2.1 Hz, 1H), 5.83 (q, J = 7.5 Hz, 1H), 1.57 (d, J = 7.5 Hz, 3H). |
| 40-002 | δ 8.75 (bs, 2H), 8.69 (s, 1H), 8.05 (s, 1H), 5.75-5.9 (m, 1H), 1.59 (d, J = 6.9 Hz, 3H). |
| 41-001 | δ 7.1-7.5 (m, 3H), 5.03 (bs, 1H), 4.64 (bs, 1H), 1.41 (s, 9H), 1.3-1.4 (m, 3H). |
| 41-004 | δ 8.49 and 8.47 (d, J = 2.1 Hz, 1H), 7.77 and 7.75 (d, J = 2.1 Hz, 1H), 5.01 (bs, 1H), 4.39 and 4.20 (d, J = 5.4 Hz, 2H), 4.03 and 3.86 (s, 3H), 1.38 and 1.34 (s, 9H). |
| 41-005 | δ 8.50 (d, J = 2.1 Hz, 1H), 7.75 (d, J = 2.1 Hz, 1H), 5.14 (bs, 1H), 4.76 (bs, 1H), 4.01 and 3.86 (s, 3H), 1.3-1.55 (m, 12H). |
| 41-008 | δ 8.45-8.65 (m, 1H), 7.7-7.9 (m, 1H), 4.05-4.3 (m, 2H), 0.85-1.5 (m, 21H). |
| 41-009 | δ 8.50 and 8.47 (d, J = 2.1 Hz, 1H), 7.78 and 7.75 (d, J = 2.1 Hz, 1H), 5.02 (bs, 1H), 3.95-4.45 (m, 4H), 1.4-1.85 (m, 2H), 1.39 and 1.35 (s, 9H), 0.98 and 0.86 (t, J = 7.5 Hz, 3H). |
| 41-010 | δ 8.49 and 8.46 (d, J = 2.4 Hz, 1H), 7.77 and 7.74 (d, J = 2.4 Hz, 1H), 5.01 (bs, 1H), 4.1-4.55 (m, 3H), 1.39 and 1.35 (s, 9H), 1.31 and 1.17 (d, J = 6.3 Hz, 6H). |
| 41-011 | δ 8.45-8.6 (m, 1H), 7.7-7.8 (m, 1H), 4.25-5.3 (m, 3H), 1.1-1.6 (m, 18H). |
| 41-013 | δ 8.49 and 8.46 (d, J = 2.1 Hz, 1H), 7.77 and 7.75 (d, J = 2.1 Hz, 1H), 5.05 (bs, 1H), 4.42 and 4.19 (d, J = 6.3 Hz, 2H), 4.03 and 3.88 (d, J = 7.2 Hz, 2H), 1.39 and 1.35 (s, 9H), 1.1-1.3 (m, 1H), 0.55-0.65 and 0.45-0.55 (m, 2H), 0.3-0.35 and 0.2-0.25 (m, 2H). |
| 41-014 | δ 8.48 and 8.46 (d, J = 2.1 Hz, 1H), 7.77 and 7.73 (d, J = 2.1 Hz, 1H), 5.03 (bs, 1H), 4.05-4.45 (m, 3H), 0.8-1.85 (m, 17H). |
| 41-015 | δ 8.4-8.5 (m, 1H), 7.7-7.8 (m, 1H), 5.05 (bs, 1H), 4.35-4.45 (m, 2H), 1.3-1.4 (m, 18H). |
| 41-017 | δ 8.50 and 8.43 (d, J = 2.1 Hz, 1H), 7.76 and 7.72 (d, J = 2.1 Hz, 1H), 7.2-7.4 (m, 5H), 5.36 and 5.24 (q, J = 6.6 Hz, 1H), 4.8-5.05 (m, 1H), 4.45 and 4.15 (d, J = 5.4 Hz, 2H), 1.63 and 1.45 (d, J = 6.6 Hz, 3H), 1.36 and 1.35 (s, 9H). |
| 41-018 | δ 8.50 and 8.44 (d, J = 2.1 Hz, 1H), 7.76 and 7.73 (d, J = 2.1 Hz, 1H), 6.9-7.4 (m, 4H), 5.34 and 5.22 (q, J = 6.9 Hz, 1H), 4.97 (bs, 1H), 4.4-4.5 and 4.1-4.2 (m, 2H), 1.3-1.65 (m, 12H). |
| 41-019 | δ 8.50 (d, J = 2.1 Hz, 1H), 7.75 (d, J = 2.1 Hz, 1H), 5.21 (bs, 1H), 4.75 (bs, 1H), 4.02 (t, J = 6.9 Hz, 2H), 1.5-1.7 (m, 2H), 1.41 (s, 9H), 1.36 (d, J = 6.9 Hz, 3H), 0.86 (t, J = 7.5 Hz, 3H). |
| 42-001 | δ 7.54 (d, J = 7.5 Hz, 1H), 7.45-7.5 (m, 1H), 7.3-7.4 (m, 1H), 5.30 (bs, 1H), 4.95-5.1 (m, 1H), 1.43 (s, 9H), 1.33 (d, J = 7.2 Hz, 3H). |
| 42-005 | δ 8.55 (d, J = 1.8 Hz, 1H), 7.83 (d, J = 1.8 Hz, 1H), 5.65 (bs, 1H), 5.37 (bs, 1H), 1.44 (s, 9H), 0.91 (s, 9H). |
| 42-006 | δ 8.64 (d, J = 2.1 Hz, 1H), 8.21 (d, J = 2.1 Hz, 1H), 5.31 (bs, 1H), 4.75 (d, J = 4.5 Hz, 2H), 1.47 (s, 9H). |

Test Example

Now, usefulness of the compounds of the present invention as pesticides will be described in detail by referring to the following Test Examples, but the present invention is by no restricted thereto.

Preparation of Test Solutions A:

Compounds of the present invention were dissolved in a solvent for emulsion (a mixture of Sorpol (registered trademark) 3005XL (manufactured by Toho Chemical Industry Co., Ltd.): N-methylpyrrolidone:Solvesso (registered trademark) 200 (manufactured by ExxonMobil Chemical) in a ratio of 1:5:2) to prepare 20% emulsifiable concentrates. Then, distilled water was added to dilute the emulsifiable concentrates to the predetermined concentration (500 ppm), and the obtained solutions were used in the following Test Examples 1 to 7.

Preparation of Test Solutions B:

Compounds of the present invention were dissolved in dimethylsulfoxide to prepare 1% solutions. Then, distilled water was added to dilute the solutions to the predetermined concentration (100 ppm), and the obtained solutions were used in the following Test Examples 8 to 12.

Test Example 1: Test on the Preventive Effect Against Cucumber Powdery Mildew Cucumber (cultivar: Sagami Hanjiro) was planted in 90 cm$^3$ plastic pots, and in the seed leaf stage, 5 ml per pot of test solutions A of the compounds of the present invention were spray-inoculated. After drying in air, the pots were placed in an air-conditioned greenhouse (20° C.), and a suspension of conidium of *Erysiphe polygoni* (synonym: *Erysiphe betae*) was sprayed. After the pots were placed at the same temperature for 9 days, the proportion of the formed lesion in the inoculated leaves was measured to calculate the control value in accordance with the following formula. Here, the test was carried out in duplicate.

Control value=[1−(lesion area ratio in treated plot/lesion area ratio in non-treated plot)]×100

As a result, among the compounds tested, the following compounds showed a control value of at least 70%. Compounds Nos. 1-001 to 1-015, 1-018 to 1-021, 1-023 to 1-025, 1-028 to 1-030, 1-032 to 1-034, 1-036 to 1-038, 1-040 to 1-076, 1-078 to 1-102, 2-002 to 2-019, 2-020, 2-021 to 2-081, 2-083 to 2-089, 2-090*, 2-091, 2-092, 2-093*, 2-095 to 2-111, 2-113, 2-115, 2-117 to 2-121, 2-123, 2-124, 2-126, 2-127, 2-128, 2-129, 2-131 to 2-139, 2-141 to 2-205, 2-207 to 2-214, 2-215, 2-216 to 2-228, 2-230, 2-231, 2-233 to 2-235, 2-237, 2-238, 2-240 to 2-251, 3-001, 3-003, 3-004, 3-006, 3-007, 3-010 to 3-030, 3-033 to 3-051, 4-002 to 4-006, 4-008 to 4-011, 5-001, 6-001 to 6-005, 7-001 to 7-009, 9-001 to 9-006, 10-001, 11-001, 11-002, 12-001, 12-003 to 12-017, 13-001, 13-002, 15-001, 17-001, 17-002, 17-003 to 17-006, 17-007, 17-008 to 17-010, 19-001, 20-001 to 20-003, 20-004*, 20-005 to 20-007, 21-001, 22-001 to 22-003, 23-001, 23-002, 23-004, 25-001 to 25-004, 26-001 to 26-003, 27-002, 28-001, 30-017, 31-007, 32-026, 32-028 and 32-032 of the present invention.

The symbol * means that the test was carried out using a 100 ppm solution.

Test Example 2: Test on the Preventive Effect Against Cucumber Gray Mold (Spore Inoculation)

Cucumber (cultivar: Sagami Hanjiro) was planted in 90 cm$^3$ plastic pots, and in the seed leaf stage, 5 ml per pot of test solutions A of the compounds of the present invention were applied. After drying in air, the treated leaves were cut and put in plastic containers. 30 μl of a mixture of a suspension of conidium of *Botrytis cinerea* and a dissolved PDA medium in a ratio of 1:1 was dropped on each treated leaf and inoculated. After the inoculation, the plastic containers were placed at 20° C. in humid conditions for 3 days, and the proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%. Compounds Nos. 1-001, 1-005 to 1-007, 1-009, 1-024, 1-040 to 1-044, 1-046, 1-049 to 1-054, 1-057 to 1-060, 1-063, 1-065 to 1-067, 1-070 to 1-075, 1-079, 1-082, 1-083, 1-085, 1-090, 1-092, 1-093, 1-096, 1-097, 1-099, 1-100, 1-102, 2-002 to 2-019, 2-020, 2-021 to 2-030, 2-032 to 2-034, 2-040 to 2-051, 2-053 to 2-069, 2-071 to 2-086, 2-088, 2-089, 2-091, 2-092, 2-096 to 2-101, 2-104, 2-105, 2-107, 2-111, 2-114, 2-115, 2-117, 2-118, 2-120, 2-121, 2-123, 2-124, 2-126 to 2-129, 2-131 to 2-144, 2-146 to 2-150, 2-152 to 2-162, 2-164 to 2-166, 2-169, 2-171 to 2-175, 2-177 to 2-179, 2-181 to 2-202, 2-204, 2-205, 2-207 to 2-214, 2-215*, 2-216 to 2-228, 2-230 to 2-235, 2-237, 2-238, 2-240 to 2-251, 3-003 to 3-007, 3-010 to 3-020, 3-022 to 3-024, 3-026, 3-027, 3-029, 3-030, 3-033 to 3-051, 4-013, 4-015, 5-001, 6-001, 6-003 to 6-005, 7-001, 7-002, 7-004 to 7-009, 9-001 to 9-006, 10-001, 10-002, 11-001, 11-002, 12-001, 12-003 to 12-006, 12-008 to 12-013, 12-015 to 12-017, 13-001, 13-002, 15-001, 17-001 to 17-007, 17-009, 17-010, 18-001, 19-001, 20-001 to 20-003, 20-005, 20-006, 21-001, 22-001 to 22-003, 23-001 to 23-004, 24-001, 25-001, 25-002, 26-001, 26-003, 27-002 and 32-028 of the present invention.

The symbol * means that the test was carried out using a 100 ppm solution.

Test Example 3: Test on the Preventive Effect Against Cucumber Gray Mold (Mycelium Inoculation)

Cucumber (cultivar: Sagami Hanjiro) was planted in 90 cm$^3$ plastic pots, and in the seed leaf stage, 5 ml per pot of test solutions A of the compounds of the present invention were applied. On the next day, the pots were put in a plastic container, and agar blocks (diameter: 5 mm) containing *Botrytis cinerea* preliminarily cultivated in a PDA medium were inoculated to the seed leaves of the cucumber treated with the solutions. After the inoculation, the plastic container was covered with a plastic sheet and humidified, and placed at 20° C. for 2 days, whereupon the proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%. Compounds Nos. 1-005, 1-040, 1-041, 1-043, 1-050 to 1-052, 1-057, 1-058, 1-065, 1-070, 1-072 to 1-075, 1-080, 1-083, 1-090, 1-093, 1-094, 1-099, 1-100, 2-002 to 2-018, 2-020*, 2-021, 2-022, 2-024 to 2-027, 2-029, 2-032, 2-040, 2-042, 2-044, 2-045, 2-047, 2-048, 2-051 to 2-054, 2-060, 2-065, 2-069, 2-071, 2-074, 2-075, 2-081, 2-083, 2-085, 2-092, 2-096, 2-098, 2-113, 2-114, 2-115, 2-117, 2-118, 2-120, 2-121, 2-123, 2-124, 2-126 to 2-129, 2-131 to 2-143, 2-146, 2-149, 2-152, 2-154, 2-156 to 2-158, 2-160 to 2-162, 2-166 to 2-169, 2-171 to 2-174, 2-176, 2-178, 2-179, 2-181 to 2-196, 2-200 to 2-202, 2-204, 2-205, 2-207 to 2-214, 2-215, 2-216 to 2-220, 2-222, 2-223, 2-225 to 2-228, 2-230 to 2-235, 2-237, 2-238, 2-244 to 2-251, 3-004, 3-006, 3-007, 3-010, 3-011, 3-014, 3-015, 3-018 to 3-020, 3-022, 3-023, 3-026, 3-027, 3-029, 3-033 to 3-048, 3-051, 4-013, 4-015, 5-001, 6-001, 6-003, 6-005, 7-002, 7-004 to 7-009, 9-001 to 9-004, 9-006, 10-001, 11-001, 11-002, 12-004, 12-008 to 12-013, 12-015 to 12-017, 13-001, 13-002, 15-001, 17-002 to 17-004, 17-006, 17-007, 17-010, 19-001, 20-001, 20-003, 20-005, 20-006, 21-001, 22-001 to 22-003, 23-001, 24-001 and 32-028 of the present invention.

The symbol * means that the test was carried out using a 100 ppm solution.

Test Example 4: Test on the Preventive Effect Against Cucumber Stem Rot

Cucumber (cultivar: Sagami Hanjiro) was planted in 90 cm$^3$ plastic pots, and in the seed leaf stage, 5 ml per pot of test solutions A of the compounds of the present invention were applied. After drying in air, the pots were put in a plastic container, and agar blocks (diameter: 5 mm) containing *Sclerotinia sclerotiorum* preliminarily cultivated in a PDA medium were inoculated to the seed leaves of the cucumber treated with the solutions. After the inoculation, the plastic container was covered with a plastic sheet and humidified, and placed at 20° C. for 2 days, whereupon the proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%.
Compounds Nos. 1-001, 1-003, 1-005, 1-006, 1-036 to 1-038, 1-040, 1-041, 1-043 to 1-045, 1-051, 1-053, 1-054, 1-057, 1-058, 1-060, 1-065, 1-070, 1-071, 1-073 to 1-075, 1-079, 1-080, 1-092, 1-093, 1-096, 1-099, 2-002 to 2-019, 2-020*, 2-021, 2-022, 2-024 to 2-030, 2-032 to 2-034, 2-040 to 2-048, 2-050, 2-051, 2-053, 2-054, 2-056, 2-059, 2-060, 2-064 to 2-067, 2-069, 2-071, 2-072, 2-076, 2-079, 2-081, 2-083 to 2-089, 2-091, 2-092, 2-093*, 2-096 to 2-102, 2-104 to 2-111, 2-113, 2-114*, 2-115, 2-117 to 2-121, 2-123, 2-124, 2-126 to 2-129, 2-131 to 2-144, 2-146 to 2-169, 2-171 to 2-174, 2-176 to 2-179, 2-181 to 2-205, 2-207 to 2-214, 2-215, 2-216 to 2-228, 2-230 to 2-235, 2-237, 2-238, 2-240 to 2-251, 3-003, 3-005 to 3-007, 3-010, 3-011, 3-014 to 3-020, 3-022 to 3-024, 3-026, 3-027, 3-029, 3-030, 3-033 to 3-049, 3-051, 4-002 to 4-004, 4-013, 4-015, 5-001, 6-001, 6-003 to 6-005, 7-002, 7-004 to 7-009, 9-001 to 9-004, 9-006, 10-001, 10-002, 11-001, 11-002, 12-001, 12-004, 12-005, 12-009 to 12-013, 12-015 to 12-017, 13-001, 13-002, 15-001, 17-002 to 17-004, 17-006, 17-007, 17-009, 17-010, 19-001, 20-001 to 20-003, 20-005 to 20-007, 21-001, 22-001 to 22-003, 24-001, 25-001, 26-001, 27-002 and 32-028 of the present invention.

The symbol * means that the test was carried out using a 100 ppm solution.

Test Example 5: Test on the Preventive Effect Against Wheat Powdery Mildew

To wheat (cultivar: Norin-61-go) in 1.3-leaf stage planted in 90 cm³ plastic pots, 5 ml per pot of test solutions A of the compounds of the present invention were applied. On the next day, the pots were placed in an air-conditioned greenhouse (20° C.), and conidium of *Blumeria graminis* f. sp. *tritici* was inoculated to the wheat. 7 Days after, the proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%.
Compounds Nos. 1-001, 1-003, 1-005 to 1-011, 1-014, 1-040 to 1-046, 1-048 to 1-060, 1-062, 1-063, 1-065 to 1-068, 1-070 to 1-075, 1-078 to 1-088, 1-090 to 1-093, 1-095 to 1-102, 2-002 to 2-019, 2-020*, 2-021 to 2-034, 2-036 to 2-038, 2-040 to 2-051, 2-053 to 2-075, 2-077, 2-079, 2-081, 2-083 to 2-089, 2-090, 2-091, 2-092, 2-095 to 2-111, 2-113, 2-115, 2-117 to 2-121, 2-123, 2-124, 2-126 to 2-129, 2-131 to 2-134, 2-136 to 2-139, 2-141 to 2-155, 2-157 to 2-192, 2-194 to 2-205, 2-207 to 2-214, 2-215, 2-216 to 2-223, 2-225 to 2-228, 2-230 to 2-235, 2-237, 2-238, 2-240 to 2-251, 3-001, 3-003, 3-006, 3-007, 3-010 to 3-020, 3-022 to 3-025, 3-027, 3-028, 3-030, 3-033 to 3-051, 4-002 to 4-006, 4-008 to 4-011, 5-001, 6-001, 6-003, 6-005, 7-001, 7-002, 7-004 to 7-009, 9-001 to 9-006, 11-002, 12-001, 12-003 to 12-006, 12-008 to 12-013, 12-015 to 12-017, 13-001, 13-002, 15-001, 17-002 to 17-010, 18-001, 19-001, 20-001 to 20-003, 20-005 to 20-007, 21-001, 22-001 to 22-003, 23-001, 23-002, 23-004, 24-001, 25-001 to 25-004, 26-001, 26-003 and 31-007 of the present invention.

The symbol * means that the test was carried out using a 100 ppm solution.

Test Example 6: Test on the Preventive Effective Against Wheat Glume Blotch

To wheat (cultivar: Haruyutaka) in 1.3-leaf stage planted in 90 cm³ plastic pots, 5 ml per pot of test solutions A of the compounds of the present invention were applied. On the next day, a suspension of conidium of *Phaeosphaeria nodorum* synonym: *Septoria nodorum*) was spray-inoculated to the wheat, and the pots were placed in an inoculation chamber at 20° C. under a humidity of 100% for 2 days. Then, the pots were placed in an air-conditioned greenhouse (20° C.) for 6 days. The proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%.
Compounds Nos. 1-041, 1-044, 1-045, 1-058, 1-067, 1-075, 1-079, 1-082 to 1-084, 1-101, 1-102, 2-002 to 2-006, 2-008 to 2-010, 2-012 to 2-018, 2-020, 2-021, 2-022, 2-024 to 2-029, 2-037, 2-040 to 2-042, 2-044, 2-047, 2-048, 2-063, 2-064, 2-066, 2-067, 2-071, 2-072, 2-074, 2-081, 2-086, 2-087, 2-092, 2-096 to 2-099, 2-101, 2-102, 2-105, 2-012 to 2-018, 2-115, 2-118, 2-120, 2-121, 2-123, 2-124, 2-127 to 2-129, 2-131, 2-132, 2-134 to 2-136, 2-139, 2-141 to 2-146, 2-148, 2-158, 2-159, 2-162, 2-167, 2-168, 2-171 to 2-179, 2-181, 2-183 to 2-187, 2-190 to 2-196, 2-198, 2-202, 2-204, 2-205, 2-207 to 2-211, 2-214, 2-215*, 2-216, 2-217, 2-219, 2-220, 2-225 to 2-227, 2-231 to 2-235, 2-237, 2-238, 2-244 to 2-251, 3-007, 3-015, 3-016, 3-018, 3-020, 3-023, 3-034, 3-035, 3-038 to 3-041, 3-043, 3-047, 3-050, 4-003, 5-001, 6-003, 6-005, 7-007 to 7-009, 9-002, 9-003, 10-001, 12-008, 12-009, 12-011, 12-013, 12-015, 13-001, 15-001, 17-004, 17-009, 20-001 to 20-003, 20-006, 22-001, 22-003 and 25-001 to 25-004 of the present invention.

The symbol * means that the test was carried out using a 100 ppm solution.

Test Example 7: Test on the Preventive Effect Against Wheat Brown Leaf Rust

To wheat (cultivar: Norin-61-go) in 1.3-leaf stage planted in 90 cm³ plastic pots, 5 ml per pot of test solutions A of the compounds of the present invention were applied. On the next day, a suspension of spore of *Puccinia recondita* was spray-inoculated to the wheat, and the pots were placed in an inoculation chamber at 20° C. under a humidity of 100% for 1 day. Then, the pots were placed in an air-conditioned greenhouse (20° C.) for 8 days. The proportion of the formed lesion in the inoculated leaves was measured to calculate the control value in accordance with the same formula as in Test Example 1. Here, the test was carried out in duplicate.

As a result, among the compounds tested, the following compounds showed a control value of at least 70%.
Compounds Nos. 1-013, 1-046, 1-049, 1-053, 1-054, 1-057, 1-065 to 1-068, 1-071, 1-075, 1-079, 1-084 to 1-086, 1-090 to 1-092, 1-095, 2-005, 2-033, 2-075, 2-102, 2-106 to 2-110, 2-115, 2-117, 2-118, 2-120, 2-121, 2-123, 2-124, 2-126, 2-127, 2-129, 2-131 to 2-133, 2-136, 2-137, 2-141, 2-142, 2-158, 2-172, 2-174, 2-178, 2-179, 2-184, 2-186 to 2-188, 2-207 to 2-210, 2-214, 2-226, 2-232, 2-234, 2-237, 2-238, 2-248, 2-249, 3-016 to 3-018, 3-038, 3-039, 3-043, 3-044, 4-004, 5-001, 6-003, 7-004, 9-002, 12-009, 12-013, 12-016, 13-001, 17-010, 22-003, 25-001, 26-003, 30-011, 31-007 and 32-012 of the present invention.

Test Example 8: Test on the Antibacterial Activity on *Aspergillus niger*

60 µl of a potato dextrose 1% agar medium was added to each well of a 96 well plate, and 30 µl of sterilized water containing spores of *Aspergillus niger* (10 spores/3 µl) was added to each well. Further, 10 µl per well of test solutions B of the compounds of the present invention were added, and the plate was left at rest at 25° C. under dark conditions. 2 Days after addition of the solutions, the flora area ratio (%) was determined to calculate the efficacy (%) relative to the non-treated plot in accordance with the following formula.

Efficacy (%)=[1−(flora area ratio in treated plot/flora area ratio in non-treated plot)]×100

As a result, among the compounds tested, the following compounds showed an efficacy of at least 50%.
Compounds Nos. 1-001, 1-003, 1-005 to 1-008, 1-020, 1-036 to 1-038, 1-040, 1-041, 1-043 to 1-054, 1-056 to 1-070, 1-072 to 1-074, 1-080, 1-081, 1-083 to 1-087, 1-089, 1-090, 1-092 to 1-094, 1-096, 1-097, 1-099 to 1-102, 2-002 to 2-005, 2-007 to 2-019, 2-021, 2-024, 2-026 to 2-030, 2-032 to 2-034, 2-037, 2-040 to 2-042, 2-044 to 2-051, 2-053, 2-054, 2-056 to 2-061, 2-064 to 2-076, 2-079 to 2-081, 2-084, 2-086 to 2-089, 2-091 to 2-111, 2-114, 2-115, 2-117 to 2-124, 2-126 to 2-129, 2-132 to 2-137, 2-139 to 2-152, 2-154, 2-156 to 2-164, 2-166 to 2-169, 2-171 to 2-176, 2-181 to 2-197, 2-199 to 2-205, 2-207 to 2-212, 2-216 to 2-221, 2-223 to 2-227, 2-230 to 2-238, 2-245, 2-246, 3-003, 3-006, 3-007, 3-010 to 3-025, 3-029, 3-030, 3-036, 3-040, 4-002, 4-003, 7-001, 7-002, 7-004, 7-005, 7-007, 7-009, 9-001, 9-002, 9-004, 10-002, 12-001, 12-005, 12-006, 12-008, 12-010, 12-011, 13-001, 15-001, 17-001 to 17-010, 19-001, 20-001 to 20-003, 21-001, 22-001 to 22-003, 23-001 to 23-004, 26-001, 26-003 and 28-001 of the present invention.

Test Example 9: Insecticidal Test on *Meloidogyne incognita*

60 µl of a potato dextrose 1% agar medium was added to each well of a 96 well plate, and 30 µl of sterilized water containing eggs of *Meloidogyne incognita* (10 eggs/3 µl) was added to each well. Further, 10 µl per well of test solutions B of the compounds of the present invention were added, and the plate was left at rest at 25° C. under dark conditions. 4 Days after addition of the solutions, unhatched eggs and inactive larvae were counted, to calculate the efficacy (%) relative to the non-treated plot in accordance with the following formula.

Efficacy (%)=[(number of unhatched eggs+inactive larvae in treated plot)/number of active larvae in non-treated plot]×100

As a result, among the compounds tested, the following compounds showed an efficacy of at least 50%.
Compounds Nos. 1-001, 1-003, 1-005 to 1-007, 1-009, 1-020, 1-021, 1-023, 1-025, 1-040, 1-043, 1-047 to 1-053, 1-058 to 1-061, 1-063 to 1-069, 1-072 to 1-078, 1-081, 1-083, 1-092 to 1-096, 1-099 to 1-102, 2-002 to 2-019, 2-022, 2-024, 2-027 to 2-030, 2-032, 2-033, 2-036 to 2-040, 2-042, 2-044 to 2-048, 2-050, 2-051, 2-053 to 2-061, 2-064 to 2-067, 2-069, 2-071 to 2-075, 2-079 to 2-081, 2-083 to 2-085, 2-087, 2-088, 2-091 to 2-094, 2-096 to 2-111, 2-114, 2-115, 2-117 to 2-124, 2-126 to 2-133, 2-135 to 2-142, 2-146, 2-150 to 2-152, 2-157 to 2-164, 2-166 to 2-174, 2-176, 2-178, 2-180 to 2-189, 2-192, 2-194 to 2-197, 2-199 to 2-202, 2-204, 2-205, 2-207 to 2-210, 2-212, 2-216, 2-217, 2-220, 2-221, 2-223, 2-226, 2-227, 2-230 to 2-238, 2-245, 2-246, 2-248, 2-249, 2-251, 3-001, 3-002, 3-004 to 3-008, 3-010, 3-011, 3-014 to 3-025, 3-029, 3-030, 3-036, 3-040, 3-045, 3-049, 3-051, 4-002, 4-003, 7-002, 7-004, 7-005, 7-007, 7-009, 9-001 to 9-004, 12-001, 12-002, 12-005, 12-008, 12-010, 12-011, 12-013, 12-017, 13-001, 17-002, 23-001, 26-001 and 26-003 of the present invention.

Test Example 10: Test on the Preventive Effect on *Meloidogyne incognita*

1 ml per seedling of test solutions B of the compounds of the present invention were treated to the bases of garden balsam seedlings (about 2 weeks after budding) planted in a cell tray of which each cell was filled with 10 g of soil. 1 Hour after the application, 1 ml per cell of water containing *Meloidogyne incognita* 2 L larvae (100 2 L larvae/1 ml) was applied to the bases. The tray was placed in a greenhouse for 3 weeks, and the root knot level formed on the root was determined in accordance with the following damage index and the damage degree to calculate the efficacy (%) relative to the non-treated plot in accordance with the following formula.
<Damage Index>
0: No knot observed.
1: Knot observed on a part of the root system.
2: Knot observed on the entire root system.
3: Large knot observed.
4: Large knot observed on the entire root system.

[Damage degree]=[Σ(damage index×number of seedlings at each index)/(4×number of seedlings investigated)]×100

Efficacy (%)=[1−(damage degree in treated plot/damage degree in non-treated plot)]×100

As a result, among the compounds tested, the following compounds showed an efficacy of at least 50%.
Compounds Nos. 1-006, 1-061, 1-063, 1-099, 2-002 to 2-006, 2-008, 2-009, 2-011 to 2-013, 2-022, 2-024, 2-030, 2-032, 2-033, 2-044, 2-048, 2-051, 2-057, 2-058, 2-060, 2-061, 2-064, 2-066, 2-067, 2-069, 2-071 to 2-074, 2-079, 2-087, 2-088, 2-097 to 2-100, 2-102 to 2-105, 2-114, 2-115, 2-117, 2-120, 2-121, 2-126, 2-128, 2-129, 2-133, 2-135, 2-141, 2-142, 2-150, 2-151, 2-160 to 2-163, 2-166 to 2-171, 2-173, 2-174, 2-176, 2-178, 2-181, 2-182, 2-196, 2-199, 2-201, 2-202, 2-205, 2-209, 2-212, 2-216, 2-217, 2-237, 3-006, 3-010, 3-014, 3-016 to 3-018, 3-020, 3-021, 3-029, 3-030, 7-002, 7-005 and 12-010 of the present invention.

Test Example 11: Insecticidal Test on *Pratylenchus coffeae*

60 µl of a potato dextrose 1% agar medium was added to each well of a 96 well plate, and 30 µl of sterilized water containing *Pratylenchus coffeae* 2 L larvae cultured in callus was added to each well. Further, 10 µl per well of test solutions B of the compounds of the present invention were added, and the plate was left at rest at 25° C. under dark conditions. 4 Days after addition of the solutions, inactive larvae were counted to calculate the efficacy (%) relative to the non-treated plot in accordance with the following formula.

Efficacy (%)=(number of inactive larvae in treated plot/number of active larvae in non-treated plot)×100

As a result, among the compounds tested, the following compounds showed an efficacy of at least 50%.
Compounds Nos. 1-001, 1-003, 1-005 to 1-007, 1-058 to 1-061, 1-063, 1-064, 1-099, 2-002 to 2-018, 2-022, 2-024, 2-027, 2-029, 2-030, 2-032 to 2-034, 2-036 to 2-040, 2-042, 2-044, 2-046 to 2-048, 2-050, 2-051, 2-053 to 2-058, 2-060, 2-061, 2-064 to 2-067, 2-069, 2-071 to 2-075, 2-079 to 2-081, 2-083 to 2-085, 2-087, 2-088, 2-091, 2-093, 2-094, 2-096 to 2-108, 2-110, 2-115, 2-117, 2-120, 2-121, 2-129, 2-139, 2-141, 2-146, 2-150, 2-159 to 2-164, 2-166 to 2-171, 2-173, 2-176, 2-178, 2-181, 2-197, 2-199 to 2-202, 3-002, 3-005, 3-006, 3-008, 3-010, 3-014, 3-016 to 3-018, 3-020 to 3-023, 3-025, 3-030, 3-031, 7-002, 7-005, 12-002, 12-005, 12-008, 12-010 and 17-002 of the present invention.

Test Example 12: Insecticidal Test on *Haemonchus contortus*

60 µl of a potato dextrose 1% agar medium was added to each plate of a 96 well plate, and 30 µl of sterilized water containing eggs of *Haemonchus contortus* (10 eggs/3 µl) was added to each well. Further, 10 µl per well of test solutions B of the compounds of the present invention were added, and the plate was left at rest at 25° C. under dark conditions. 4 Days after addition of the solutions, unhatched eggs and inactive larvae were counted to calculate the efficacy (%) relative to the non-treated plot in accordance with the same formula as in Test Example 9.

As a result, among the compounds tested, the following compounds showed an efficacy of at least 50%.
Compounds Nos. 1-001 to 1-013, 1-017 to 1-021, 1-023, 1-024, 1-026, 1-028, 1-029, 1-031, 1-032, 1-034, 1-036 to 1-074, 1-080, 1-081, 1-083 to 1-094, 1-096, 1-097, 1-099 to 1-102, 2-001 to 2-019, 2-021 to 2-027, 2-029, 2-030, 2-032 to 2-051, 2-053 to 2-061, 2-064 to 2-089, 2-091 to 2-115, 2-117 to 2-129, 2-132 to 2-137, 2-139 to 2-164, 2-166 to 2-178, 2-180 to 2-197, 2-199 to 2-212, 2-216 to 2-221, 2-223 to 2-227, 2-230 to 2-238, 2-245, 2-246, 3-001 to 3-008, 3-010, 3-011, 3-013 to 3-030, 3-036, 3-040, 3-049, 4-002, 4-003, 7-001, 7-002, 7-004, 7-005, 7-007, 7-009, 8-001, 9-002, 9-004, 10-002, 12-001 to 12-008, 12-010, 12-011, 13-001, 15-001, 17-001, 17-003, 17-004, 17-006, 20-002, 20-003, 22-001, 22-002, 23-001 to 23-004, 26-001 to 26-003, 29-001 and 29-002 of the present invention.

INDUSTRIAL APPLICABILITY

The oxime-substituted amide compounds of the present invention are very useful compounds which are excellent in pesticidal activities, especially in fungicidal and nematocidal activities, and have little harmful effect on non-target organisms such as mammals, fishes and useful insects.

The entire disclosures of Japanese Patent Application No. 2012-156398 filed on Jul. 12, 2012, Japanese Patent Application No. 2013-019666 filed on Feb. 4, 2013 and Japanese Patent Application No. 2013-103989 filed on May 16, 2013 including specifications, claims and summaries are incorporated herein by reference in their entireties.

The invention claimed is:
1. A compound, which is represented by formula (IVa):

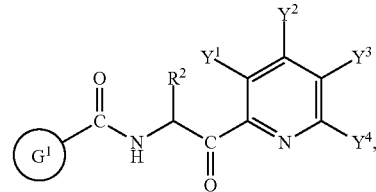

wherein:
$G^1$ is a structure represented by any one of $G^1$-1, $G^1$-2 and $G^1$-3:

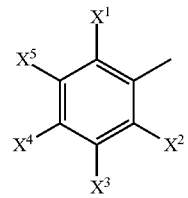

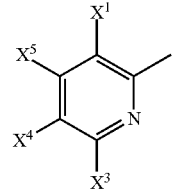

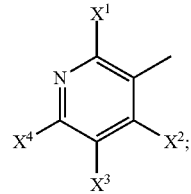

$X^1$ is a halogen atom, nitro, methyl, difluoromethyl or trifluoromethyl;
$X^2$, $X^3$ and $X^5$ are hydrogen atoms;
$X^4$ is a hydrogen atom, and when $G^1$ is $G^1$-1, $X^4$ is optionally a halogen atom;
$Y^1$ is a halogen atom;
$Y^2$ is a hydrogen atom, a halogen atom or cyano;
$Y^3$ is a halogen atom, cyano, methyl, trifluoromethyl, $C_1$-$C_4$ alkoxy, $C_1$-$C_4$ haloalkoxy, -C($R^{10}$)=NOR$^{11}$, $C_2$-$C_4$ alkenyl, $C_2$-$C_6$ alkynyl, ($C_2$-$C_6$)alkynyl substituted with $R^6$, D-3 or D-7;

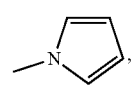

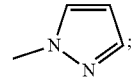

$Y^4$ is a hydrogen atom or a halogen atom;
$R^2$ is a hydrogen atom or methyl;
$R^6$ is a halogen atom, $C_3$-$C_6$ cycloalkyl, —OH, trimethylsilyl or phenyl;
$R^{10}$ is methyl; and
$R^{11}$ is methyl or ethyl.

2. The compound according to claim 1, wherein $G^1$ is $G^1$-1.

3. The compound according to claim 1, wherein $G^1$ is $G^1$-2.

4. The compound according to claim 1, wherein $G^1$ is $G^1$-3.

5. The compound according to claim 1, wherein the compound is:

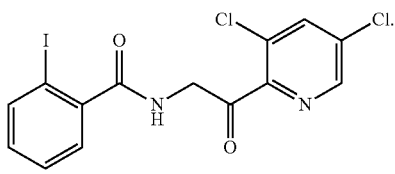

6. The compound according to claim 1, wherein the compound is:

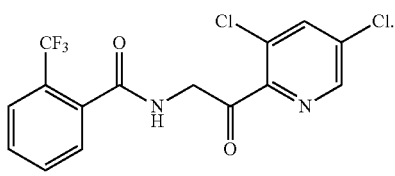 [SMILES: O=C(NCC(=O)c1ncc(Cl)cc1Cl)c1ccccc1C(F)(F)F]

7. The compound according to claim 1, wherein the compound is:

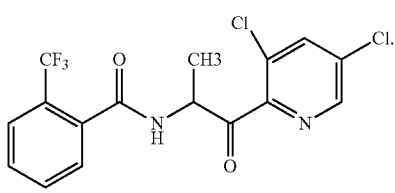 [SMILES: CC(NC(=O)c1ccccc1C(F)(F)F)C(=O)c1ncc(Cl)cc1Cl]

8. The compound according to claim 1, wherein the compound is:

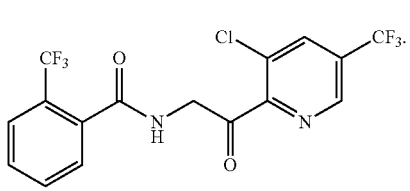 [SMILES: O=C(NCC(=O)c1ncc(C(F)(F)F)cc1Cl)c1ccccc1C(F)(F)F]

9. The compound according to claim 1, wherein the compound is:

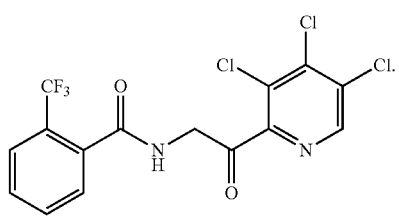

10. The compound according to claim 1, wherein the compound is:

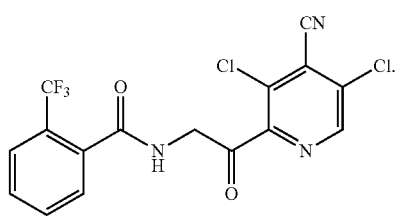 [SMILES: N#Cc1c(Cl)cnc(C(=O)CNC(=O)c2ccccc2C(F)(F)F)c1Cl]

11. The compound according to claim 1, wherein the compound is:

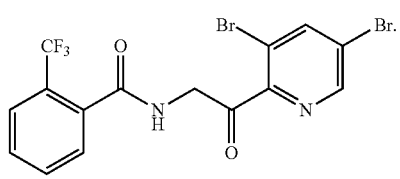 [SMILES: O=C(NCC(=O)c1ncc(Br)cc1Br)c1ccccc1C(F)(F)F]

12. The compound according to claim 1, wherein the compound is:

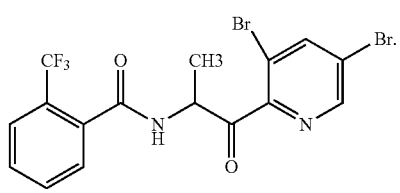 [SMILES: CC(NC(=O)c1ccccc1C(F)(F)F)C(=O)c1ncc(Br)cc1Br]

* * * * *